(12) United States Patent
Romero et al.

(10) Patent No.: US 10,206,931 B2
(45) Date of Patent: Feb. 19, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: F. Anthony Romero, South San Francisco, CA (US); Steven R. Magnuson, South San Francisco, CA (US); Richard Pastor, South San Francisco, CA (US); Vickie Hsiao-Wei Tsui, South San Francisco, CA (US); Jeremy Murray, South San Francisco, CA (US); Terry Crawford, South San Francisco, CA (US); Daniel J. Burdick, South San Francisco, CA (US); Brian K. Albrecht, Cambridge, MA (US); Alexandre Cote, Cambridge, MA (US); Alexander M. Taylor, Cambridge, MA (US); Christopher G. Nasveschuck, Stoneham, MA (US); Yves LeBlanc, Kirkland (CA); Michael Charles Hewitt, Brookline, MA (US); Kwong Wah Lai, Shanghai (CN); Kevin Chen, Shanghai (CN)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/482,581

(22) Filed: Apr. 7, 2017

(65) Prior Publication Data
US 2017/0312292 A1 Nov. 2, 2017

Related U.S. Application Data

(63) Continuation of application No. PCT/CN2015/091614, filed on Oct. 10, 2015.

(30) Foreign Application Priority Data

Oct. 10, 2014 (WO) ................ PCT/CN2014/088315

(51) Int. Cl.
| | | |
|---|---|---|
| *A61K 31/551* | (2006.01) |
| *C07D 243/12* | (2006.01) |
| *C07D 403/04* | (2006.01) |
| *C07D 403/14* | (2006.01) |
| *A61K 31/55* | (2006.01) |
| *C07D 223/16* | (2006.01) |

(Continued)

(52) U.S. Cl.
CPC ............ *A61K 31/55* (2013.01); *A61K 31/337* (2013.01); *A61K 31/5513* (2013.01); *A61K 45/06* (2013.01); *C07D 223/16* (2013.01); *C07D 243/12* (2013.01); *C07D 243/24* (2013.01); *C07D 267/14* (2013.01); *C07D 401/06* (2013.01); *C07D 401/12* (2013.01); *C07D 401/14* (2013.01); *C07D 403/04* (2013.01); *C07D 403/06* (2013.01); *C07D 403/14* (2013.01); *C07D 405/04* (2013.01); *C07D 405/12* (2013.01); *C07D 413/04* (2013.01); *C07D 413/10* (2013.01); *C07D 471/04* (2013.01); *C07D 495/04* (2013.01)

(58) Field of Classification Search
CPC .. A61K 31/551; C07D 243/12; C07D 403/04; C07D 403/14
USPC ........................................... 514/221; 540/517
See application file for complete search history.

(56) References Cited

U.S. PATENT DOCUMENTS

| | | | |
|---|---|---|---|
| 3,203,952 A | 8/1965 | Paquette | |
| 4,948,886 A | 8/1990 | Mais | |
| 2008/0076760 A1* | 3/2008 | Ohtake | ................ C07D 243/12 514/221 |

FOREIGN PATENT DOCUMENTS

| | | |
|---|---|---|
| WO | 2006051851 A1 | 5/2006 |
| WO | 2012151512 A2 | 11/2012 |

OTHER PUBLICATIONS

Khan et al., Circular Dichroism Studies on Chiral 1,3,4,5-Tetrahydro-2H-1,5-benzodiazepin-2-ones, Zeitschrift fuer Naturforschung, B: Chemical Sciences, vol. 50, No. 12, pp. 1869-1882. (Year: 1995).*

(Continued)

*Primary Examiner* — Brenda L Coleman
(74) *Attorney, Agent, or Firm* — Viksnins Harris Padys Malen LLP

(57) ABSTRACT

The present invention relates to compounds of formula (I):

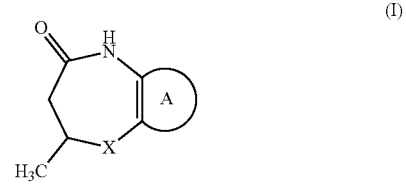

(I)

and to salts thereof, wherein A has any of the values defined in the specification, and compositions and uses thereof. The compounds are useful as inhibitors of CBP and/or EP300. Also included are pharmaceutical compositions comprising a compound of formula (I) or a pharmaceutically acceptable (Continued)

salt thereof, and methods of using such compounds and salts in the treatment of various CBP and/or EP300-mediated disorders.

17 Claims, No Drawings

(51) Int. Cl.

| | |
|---|---|
| *C07D 267/14* | (2006.01) |
| *C07D 401/14* | (2006.01) |
| *C07D 401/06* | (2006.01) |
| *C07D 401/12* | (2006.01) |
| *C07D 403/06* | (2006.01) |
| *C07D 405/04* | (2006.01) |
| *C07D 405/12* | (2006.01) |
| *C07D 413/04* | (2006.01) |
| *C07D 413/10* | (2006.01) |
| *C07D 243/24* | (2006.01) |
| *C07D 471/04* | (2006.01) |
| *C07D 495/04* | (2006.01) |
| *A61K 45/06* | (2006.01) |
| *A61K 31/337* | (2006.01) |
| *A61K 31/5513* | (2006.01) |

(56) References Cited

OTHER PUBLICATIONS

Jeanmougin, "The bromodomain revisited", Trends Biochem Sci 22(5), 151-153 (1997).
Kalsoom, et al., "In vitro and in silico exploration of IL-2 inhibition by small drug-like molecules", Med Chem Res 22, 5739-5751 (2013).
Muller, et al., "Bromodomains as therapeutic targets", Expert Rev Mol Med 13 (29), 1-21 (2011).
Patent Cooperation Treaty, International Searching Authority, Search Report and Written Opinion for PCT/CN2015/091614, 15 pages, dated Jan. 20, 2016.
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila* homeotic genes structurally related to the yeast transcriptional activator SNF2/SWI2", Cell 68, 561-572 (1992).
Sajid, et al., "Absolute configuration of 1,5-diazepin-2-ones: A critical test case for density functional theory", Computational and Theoretical Chemistry 1044, 15-23 (2014).

* cited by examiner

THERAPEUTIC COMPOUNDS AND USES THEREOF

CROSS-REFERENCE TO RELATED APPLICATION(S)

This patent application is a continuation of International application serial no. PCT/CN2015/091614, filed Oct. 10, 2015, which application is herein incorporated by reference herein, and this application claims the benefit of International application serial No. PCT/CN2014/088315, filed Oct. 10, 2014.

TECHNICAL FIELD OF THE INVENTION

The present invention relates to compounds useful as inhibitors of CBP/EP300 and methods of treating cancer using such inhibitors.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., Genes Dev., 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., Trends Biochem. Sci., 1997, 22, 5, 151-153; and Tamkun J. W., et al., Cell, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., Trends Pharm. Sci., 33(3): 146-153 (2012) and Muller et al., Expert Rev., 13(29): 1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Hence, the selective inhibition of bromodomains across a specific family, such as the selective inhibition of a bromodomain of CBP/EP300, creates varied opportunities as novel therapeutic agents in human dysfunction.

There is a need for treatments for cancer, immunological disorders, and other CBP/EP300 bromodomain related diseases.

SUMMARY OF THE INVENTION

One aspect includes a compound of formula (I):

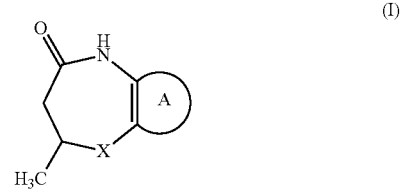

or a salt thereof, wherein:

X is NH, O, S, or —C($R^a$)$_2$—;

each $R^a$ is independently selected from the group consisting of H, $C_{1-6}$alkyl, $C_{2-6}$alkenyl, $C_{2-6}$alkynyl, and $C_{3-6}$carbocyclyl;

ring A is a 6 membered heteroaryl ring or a benzo ring, wherein ring A is optionally substituted with one or more groups $R^b$ that are independently selected from the group consisting of $R^c$, —F, —Cl, —Br, —I, —NO$_2$, —N($R^d$)$_2$, —CN, —C(O)—N($R^d$)$_2$, —S(O)—N($R^d$)$_2$, —S(O)$_2$—N($R^d$)$_2$, —O—$R^d$, —S—$R^d$, —O—C(O)—$R^d$, —O—C(O)—O—$R^d$, —C(O)—$R^d$, —C(O)—O—$R^d$, —S(O)—$R^d$, —S(O)$_2$—$R^d$, —O—C(O)—N($R^d$)$_2$, —N($R^d$)—C(O)—O$R^d$, —N($R^d$)—C(O)—N($R^d$)$_2$, —N($R^d$)—C(O)—$R^d$, —N($R^d$)—S(O)—$R^d$, —N($R^d$)—S(O)$_2$—$R^d$, —N($R^d$)—S(O)—N($R^d$)$_2$, —CH=C($R^c$)$_2$, and —N($R^d$)—S(O)$_2$—N($R^d$)$_2$;

each $R^c$ is independently selected from the group consisting of hydrogen, $C_{1-6}$alkyl, $C_{2-6}$alkenyl, $C_{2-6}$alkynyl, 3-20 membered carbocyclyl, 3-20 membered heterocyclyl, wherein any $C_{1-6}$alkyl, $C_{2-6}$alkenyl, $C_{2-6}$alkynyl, 3-20 membered carbocyclyl, and 3-20 membered heterocyclyl is optionally substituted with one or more groups $R^f$;

each $R^f$ is independently selected from the group consisting of oxo, 3-20 membered carbocyclyl, 3-20 membered heterocyclyl, halo, —NO$_2$, —N($R^g$)$_2$, —CN, —C(O)—N($R^g$)$_2$, —S(O)—N($R^g$)$_2$, —S(O)—N($R^g$), —O—$R^g$, —S—$R^g$, —O—C(O)—$R^g$, —C(O)—$R^g$, —C(O)—O—$R^g$, —S(O)—$R^g$, —S(O)$_2$—$R^g$, —C(O)—N($R^g$)$_2$, —N($R^g$)—C(O)—$R^g$, —Si($R^h$)$_3$, —N($R^g$)—C(O)—O—$R^g$, —N($R^g$)—

S(O)—$R^g$, N($R^g$)—S(O)$_2$—$R^g$, and $C_{1-6}$alkyl, which 3-20 membered carbocyclyl, 3-20 membered heterocyclyl, and $C_{1-6}$alkyl are optionally substituted with one or more groups $R^j$;

each $R^g$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^j$, or two $R^g$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from the group consisting of oxo and halo;

each $R^h$ is independently selected from the group consisting of H, $C_{1-6}$alkyl, $C_{2-6}$alkenyl, $C_{2-6}$alkynyl, and $C_{3-6}$carbocyclyl;

each $R^j$ is independently selected from the group consisting of oxo, halo, amino, hydroxyl, —Si($R^k$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^k$ is independently selected from the group consisting of H, $C_{1-6}$alkyl, $C_{2-6}$alkenyl, $C_{2-6}$alkynyl, and $C_{3-6}$carbocyclyl;

each $R^l$ is independently selected from the group consisting of oxo, halo, $C_{1-6}$alkyl, cyano, —N($R^l$)$_2$, —O—$R^l$, —S(O)—$R^l$, —S(O)$_2$—$R^l$, —S(O)—N($R^l$)$_2$, —S(O)$_2$—N($R^l$)$_2$, —N($R^l$)—S(O)—$R^l$, —N($R^l$)—C(O)—$R^l$, —N($R^l$)—C(O)—O—$R^l$, —N($R^l$)—S(O)$_2$—$R^l$, 3-20 membered heterocyclyl, and 3-20 membered carbocyclyl that is optionally substituted with one or more groups independently selected from the group consisting of halo, and $C_{1-6}$alkyl;

each $R^l$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^m$; or two $R^l$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from the group consisting of oxo and halo; and each $R^m$ is independently selected from the group consisting of oxo, halo, amino, hydroxyl, —Si($R^n$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^n$ is independently selected from the group consisting of H, $C_{1-6}$alkyl, $C_{2-6}$alkenyl, $C_{2-6}$alkynyl, and $C_{3-6}$carbocyclyl;

each $R^d$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^o$, or two $R^d$ are taken together with the nitrogen to which they are attached to form a 3-20 membered heterocyclyl that is optionally substituted with one or more groups independently selected from the group consisting of oxo, halo and $C_{1-3}$alkyl that is optionally substituted with one or more groups independently selected from oxo and halo;

each $R^o$ is independently selected from the group consisting of oxo, halo, amino, hydroxyl, cyano, —O—$R^p$, 3-20 membered carbocyclyl, 3-20 membered heterocyclyl, and $C_1$-$C_6$ alkyl, wherein any $C_1$-$C_6$ alkyl, 3-20 membered carbocyclyl and 3-20 membered heterocyclyl is optionally substituted with one or more groups independently selected from the group consisting of oxo, $C_1$-$C_4$alkyl, —O—$R^q$, and halo;

each $R^p$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^r$, each $R^r$ is independently selected from the group consisting of oxo, halo, amino, hydroxyl, —Si($R^s$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^s$ is independently selected from the group consisting of H, $C_{1-6}$alkyl, $C_{2-6}$alkenyl, $C_{2-6}$alkynyl, and $C_{3-6}$carbocyclyl;

each $R^q$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more groups $R^t$, each $R^t$ is independently selected from the group consisting of oxo, halo, amino, hydroxyl, —Si($R^u$)$_3$, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^u$ is independently selected from the group consisting of H, $C_{1-6}$alkyl, $C_{2-6}$alkenyl, $C_{2-6}$alkynyl, and $C_{3-6}$carbocyclyl; and two $R^e$ groups taken together with the carbon to which they are attached form a 3-20 membered carbocyclyl; or a salt thereof.

Another aspect includes a composition comprising a compound of formula (I) or a pharmaceutically acceptable salt thereof, and a pharmaceutically acceptable adjuvant, carrier, or vehicle.

Another aspect includes a method for treating a CBP and/or EP300-mediated disorder in an animal comprising administering a compound of formula (I) or a pharmaceutically acceptable salt thereof to the animal.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a CBP and/or EP300-mediated disorder.

Another aspect includes the use of a compound of formula (I) or a pharmaceutically acceptable salt thereof to prepare a medicament for treating a CBP and/or EP300-mediated disorder in an animal (e.g. a mammal such as a human).

Another aspect includes compounds for the study of CBP and/or EP300.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center. Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C— or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5][5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$.

Examples include, but are not limited to, ethenyl or vinyl (—C=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, dihydrophenanthryl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono-, bi- or tri-cyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S), In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, SO$_2$), and any nitrogen heteroatom may optionally be quaternized (e.g. [NR$_4$]$^+$Cl$^-$, [NR$_4$]$^+$OH$^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyco[2.2.2]octanyl, 7-oxabicyclo[2.2.1]heptane, azaspiro[3.5]nonanyl, azaspiro[2.5]octanyl, azaspiro[4.5]

decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "inhibitor" refers to a compound that binds to and inhibits the bromodomain of CBP and/or EP300 with measurable affinity and activity. In certain embodiments, an inhibitor has an $IC_{50}$ or binding constant of less about 20 µM, less than about 1 µM, less than about 500 nM, less than about 100 nM, or less than about 10 nM.

The terms "measurable affinity" and "measurably inhibit," as used herein, refer to a measurable reduction in activity (e.g., reduction in recognition of lysine acetyl recognition of chromatin) of the bromodomain of CBP and/or EP300 between: (i) a sample comprising a compound of formula I or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein).

"CBP/EP300 bromodomain inhibitor" or "CBP and/or EP300 bromodomain inhibitor" refers to a compound that binds to the CBP bromodomain and/or EP300 bromodomain and inhibits and/or reduces a biological activity of CBP and/or EP300. In some embodiments, CBP/EP300 bromodomain inhibitor binds to the CBP and/or EP300 primarily (e.g., solely) through contacts and/or interactions with the CBP bromodomain and/or EP300 bromodomain. In some embodiments, CBP/EP300 bromodomain inhibitor binds to the CBP and/or EP300 through contacts and/or interactions with the CBP bromodomain and/or EP300 bromodomain as well as additional CBP and/or EP300 residues and/or domains. In some embodiments, CBP/EP300 bromodomain inhibitor substantially or completely inhibits the biological activity of the CBP and/or EP300. In some embodiments, the biological activity is binding of the bromodomain of CBP and/or EP300 to chromatin (e.g., histones associated with DNA) and/or another acetylated protein. In certain embodiments, the CBP/EP300 bromodomain inhibitor blocks CBP/EP300 activity so as to restore a functional reponse by T-cells (e.g., proliferation, cytokine production, target cell killing) from a dysfunctional state to antigen stimulation. In some embodiments, the CBP/EP300 bromodomain inhibitor binds to and inhibits CBP bromodomain. In some embodiments, the CBP/EP300 bromodomain inhibitor binds to and inhibits EP300 bromodomain.

As used herein, "a" or "an" means one or more, unless clearly indicated otherwise. As used herein, "another" means at least a second or more.

Exemplary Values

In certain embodiments X is NH.
In certain embodiments X is O.
In certain embodiments X is S.
In certain embodiments X is $CH_2$.
In certain embodiments ring A is a 6-membered heteroaryl ring that is optionally substituted with one or more groups $R^b$ that are independently selected from the group consisting of $R^c$, —F, —Cl, —Br, —I, —$NO_2$, —$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —O—C(O)—O—$R^d$, —C(O)—$R^d$, —C(O)—O—$R^d$, —S(O)—$R^d$, —S(O)$_2$—$R^d$, —O—C(O)—$N(R^d)_2$, —$N(R^d)$—C(O)—$OR^d$, —$N(R^d)$—C(O)—$N(R^d)_2$, —$N(R^d)$—C(O)—$R^d$, —$N(R^d)$—S(O)—$R^d$, —$N(R^d)$—S(O)$_2$—$R^d$, —$N(R^d)$—S(O)—$N(R^d)_2$, —CH=C($R^e$)$_2$, and —$N(R^d)$—S(O)$_2$—$N(R^d)_2$; or a salt thereof.

In certain embodiments ring A is a 6-membered heteroaryl ring that is optionally substituted with one or more groups $R^b$ that are independently selected from the group consisting of $R^c$, —F, —Cl, —Br, —I, —C(O)—$N(R^d)_2$, —O—$R^d$, and —CH=C($R^e$)$_2$; or a salt thereof.

In certain embodiments ring A is a benzo ring that is optionally substituted with one or more groups $R^b$ that are independently selected from the group consisting of $R^c$, —F, —Cl, —Br, —I, —$NO_2$, —$N(R^d)_2$, —CN, —C(O)—$N(R^d)_2$, —S(O)—$N(R^d)$, —S(O)$_2$—$N(R^d)_2$, —O—$R^d$, —S—$R^d$, —O—C(O)—$R^d$, —O—C(O)—O—$R^d$, —C(O)—$R^d$, —C(O)—O—$R^d$, —S(O)—$R^d$, —S(O)$_2$—$R^d$, —O—C(O)—$N(R^d)_2$, —$N(R^d)$—C(O)—$OR^d$, —$N(R^d)$—C(O)—$N(R^d)_2$, —$N(R^d)$—C(O)—$R^d$, —$N(R^d)$—S(O)—$R^d$, —$N(R^d)$—S(O)$_2$—$R^d$, —$N(R^d)$—S(O)—$N(R^d)_2$, —CH=C($R^e$)$_2$, and —$N(R^d)$—S(O)$_2$—$N(R^d)_2$; or a salt thereof.

In certain embodiments ring A is a benzo ring that is optionally substituted with one or more groups $R^b$ that are independently selected from the group consisting of $R^c$, —F, —Cl, —Br, —I, —C(O)—$N(R^d)_2$, —O—$R^d$, and —CH=C($R^e$)$_2$ or a salt thereof.

In certain embodiments the compound is a compound of formula (Ia):

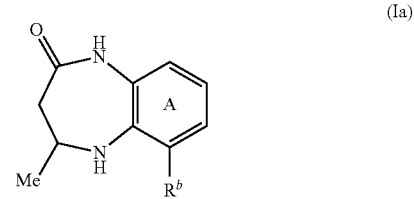

(Ia)

wherein ring A is optionally substituted with one or more additional groups $R^b$ that are independently selected from the group consisting of $R^c$, —F, —Cl, —Br, —I, —$NO_2$, —$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —O—C(O)—O—$R^d$, —C(O)—$R^d$, —C(O)—O—$R^d$, —S(O)—$R^d$, —S(O)$_2$—$R^d$, —O—C(O)—$N(R^d)_2$, —$N(R^d)$—C(O)—$OR^d$, —$N(R^d)$—C(O)—$N(R^d)_2$, —$N(R^d)$—C(O)—$R^d$, —$N(R^d)$—S(O)—$R^d$, —$N(R^d)$—S(O)$_2$—$R^d$, —$N(R^d)$—S(O)—$N(R^d)_2$, —CH=C($R^e$)$_2$, and —$N(R^d)$—(O)$_2$—$N(R^d)_2$; or a salt thereof.

In certain embodiments the compound is a compound of formula (Ia), wherein ring A is optionally substituted with one or more additional groups $R^b$ that are independently selected from the group consisting of $R^c$, —F, —Cl, —Br, —I, —C(O)—$N(R^d)_2$, —O—$R^d$, and —CH=C($R^e$)$_2$ or a salt thereof.

In certain embodiments $R^b$ is H, methyl ethyl, ethenyl, ethynyl,

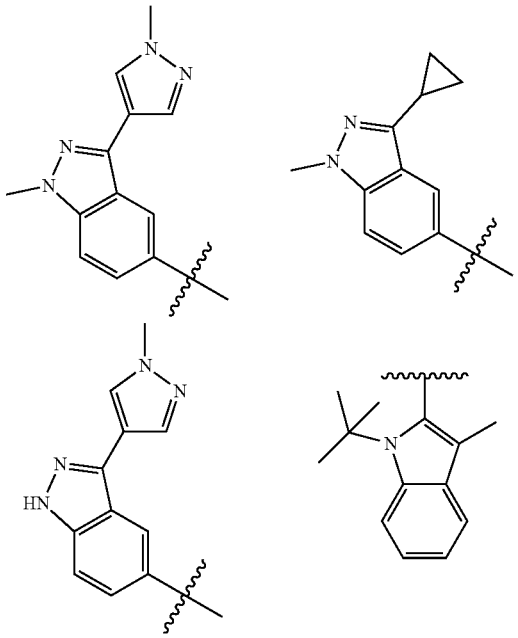

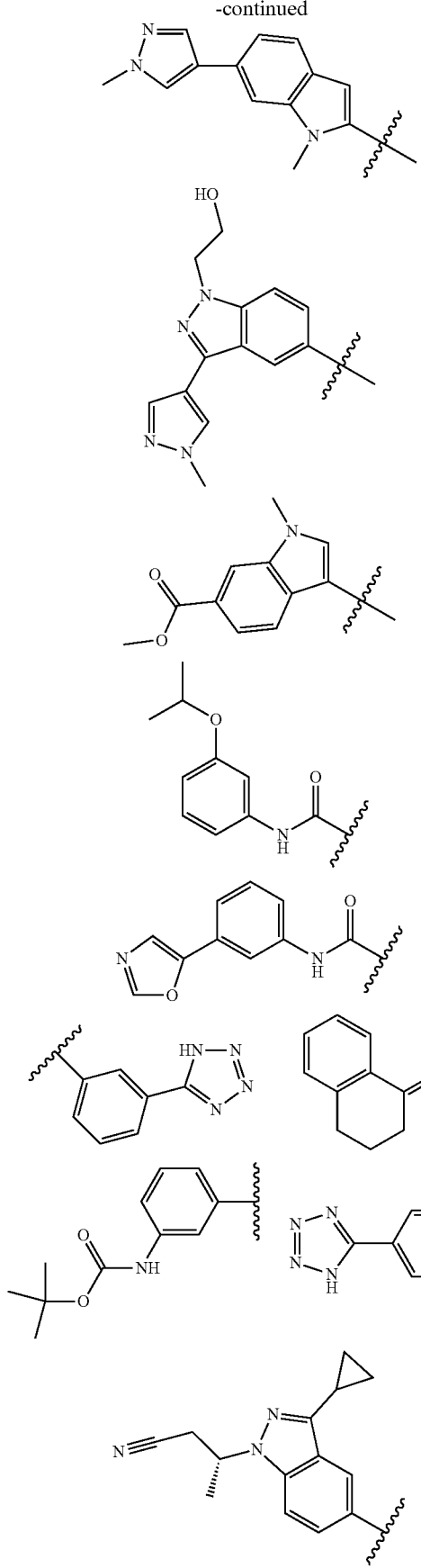
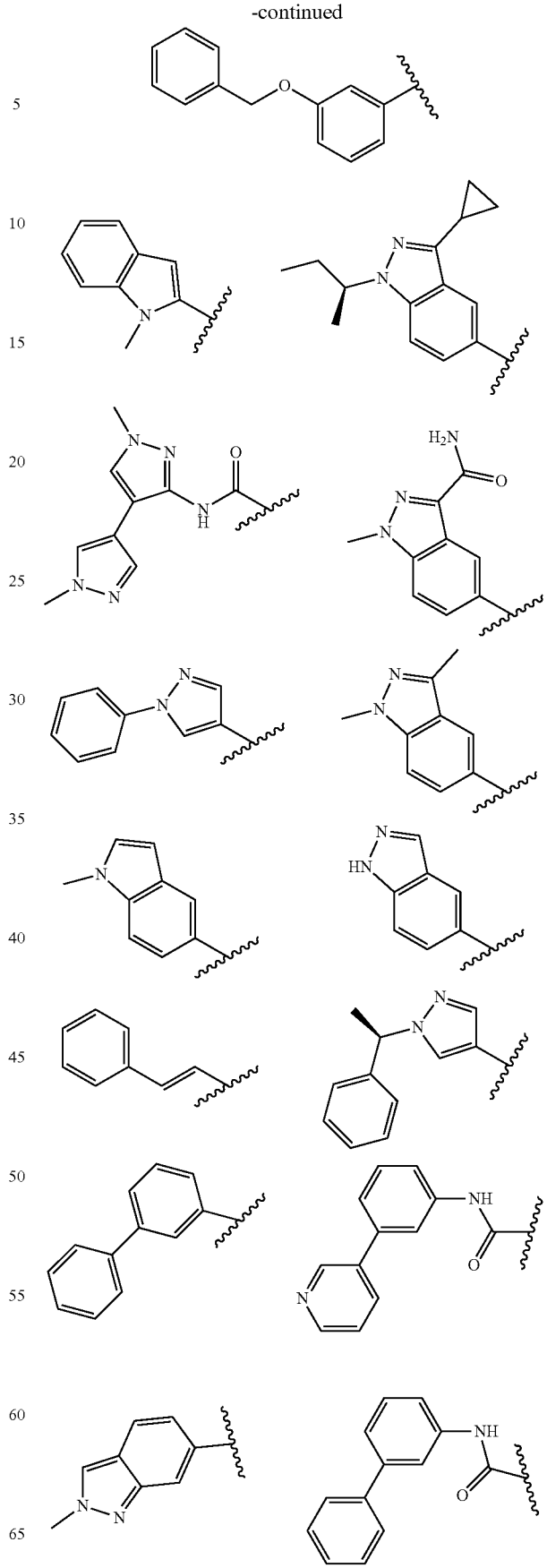

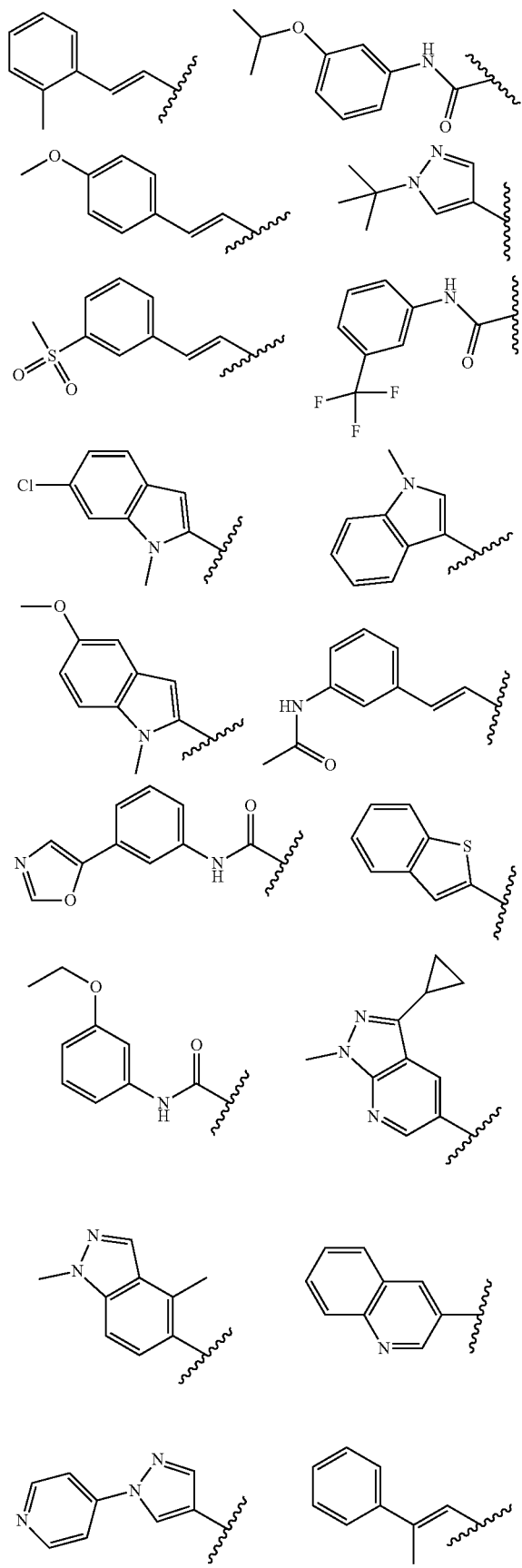
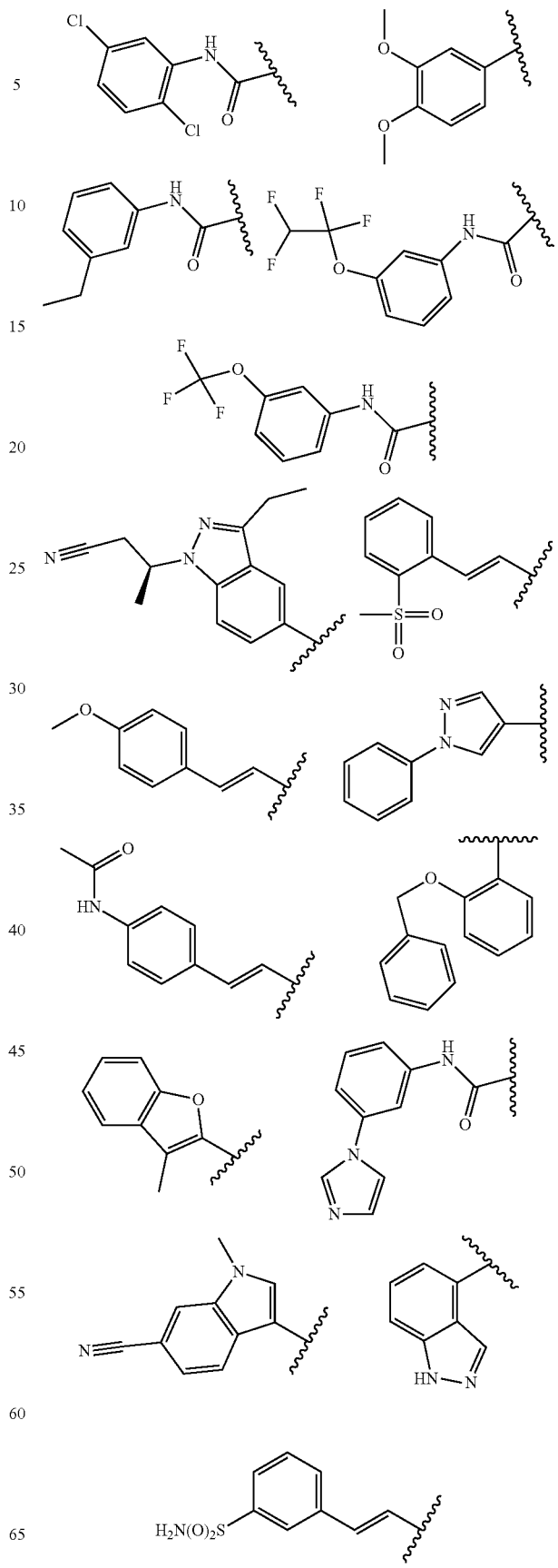

17
-continued
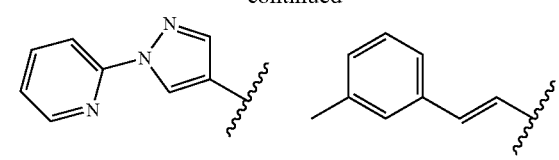
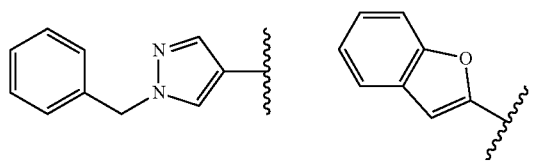
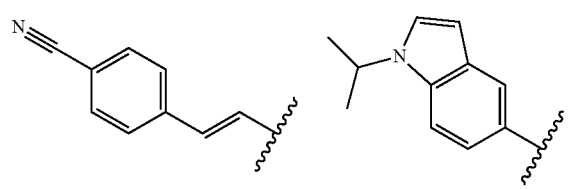
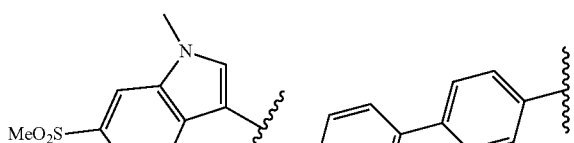
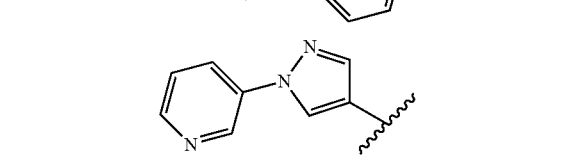
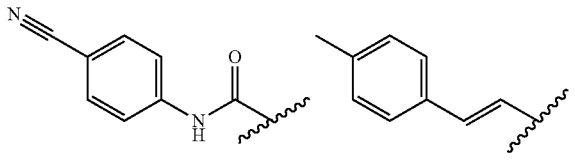
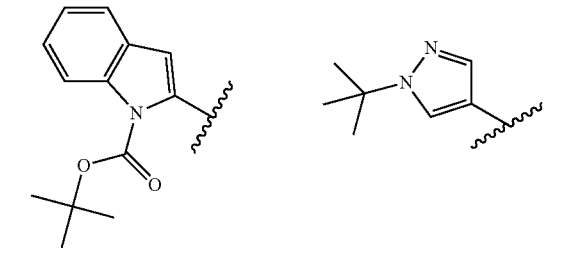
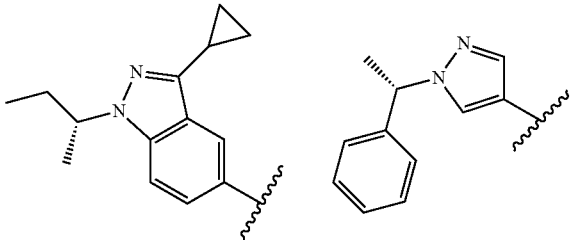
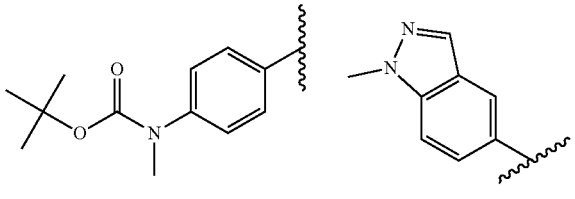
18
-continued
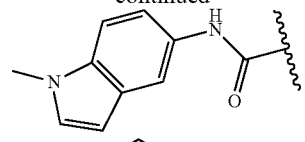
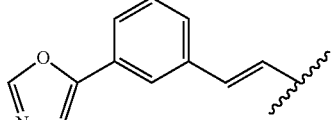
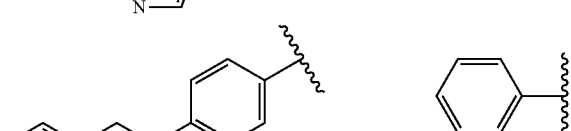
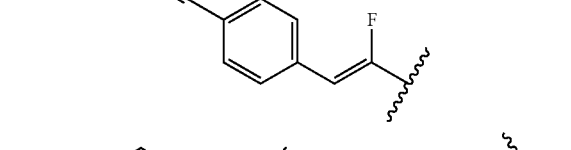
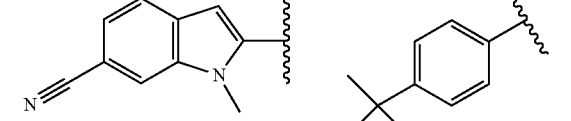
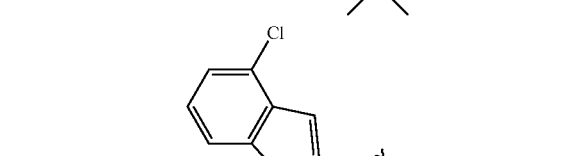
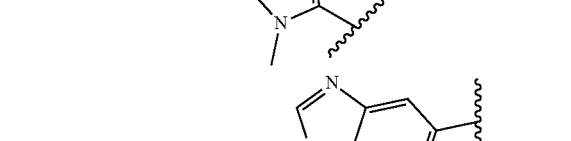
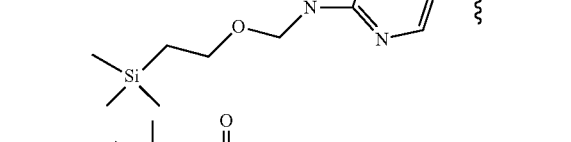
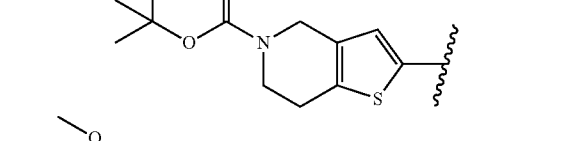
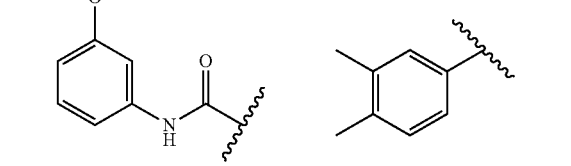
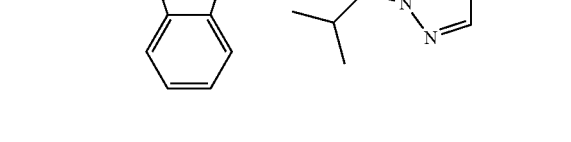

-continued
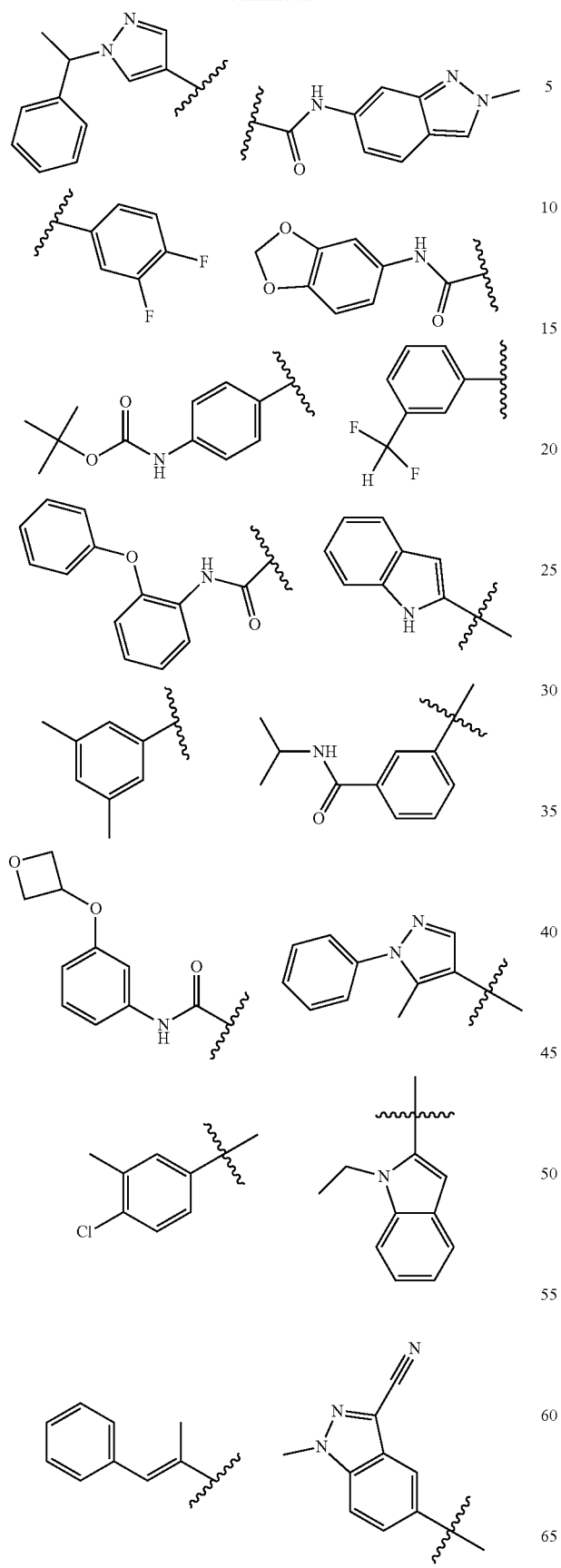
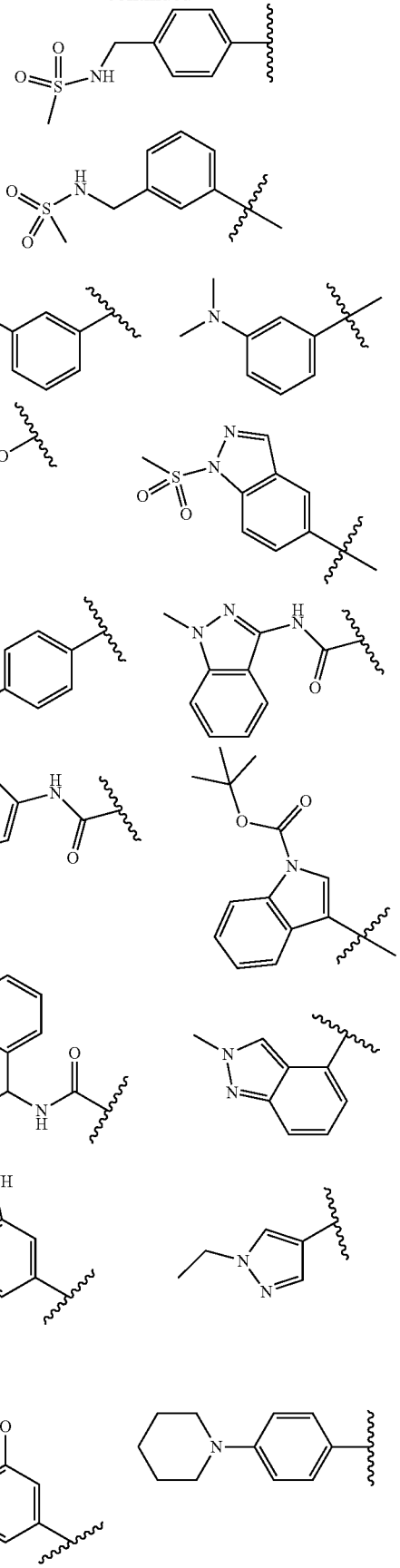

-continued
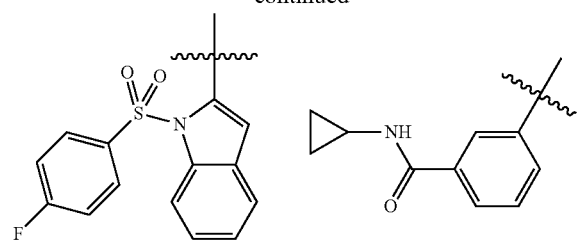
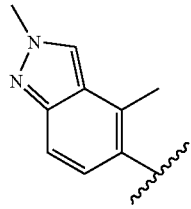
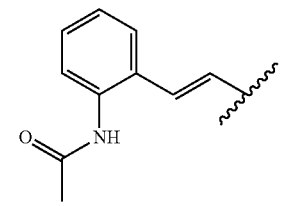
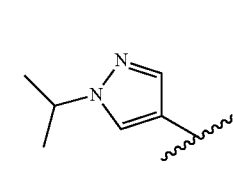
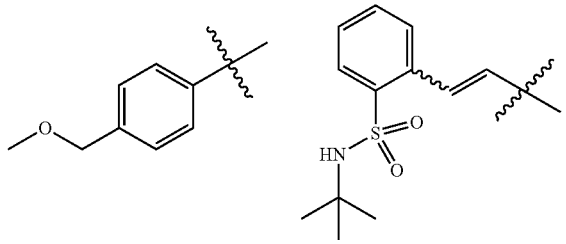
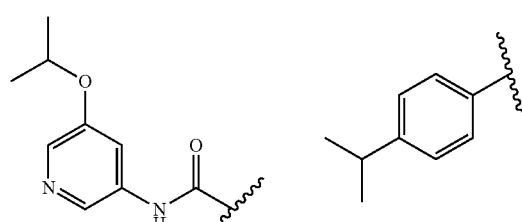
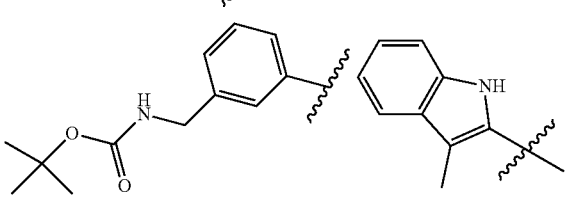
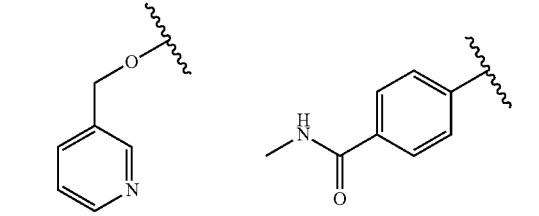
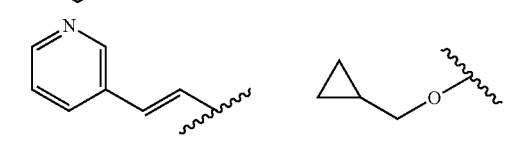
-continued
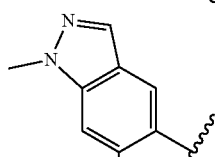
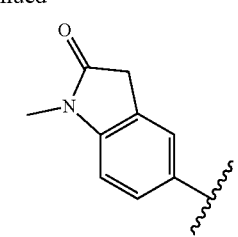
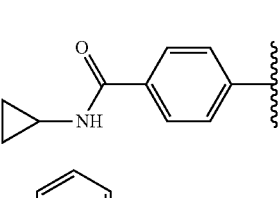
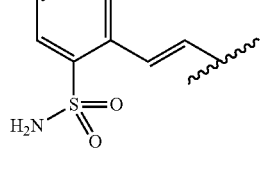
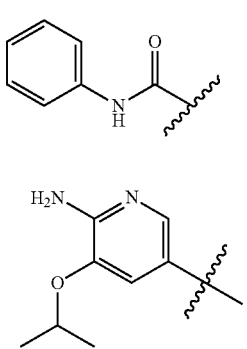
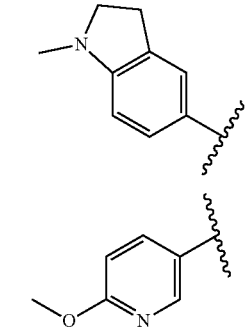
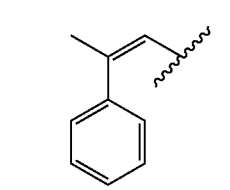
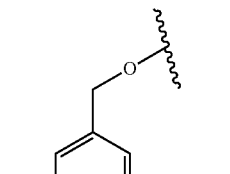
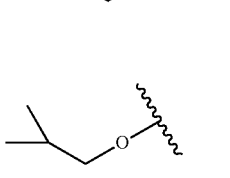
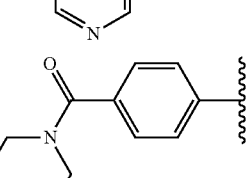
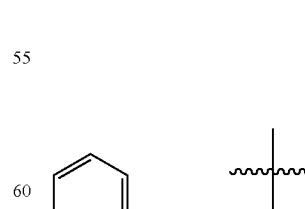
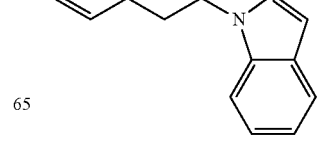
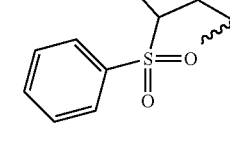

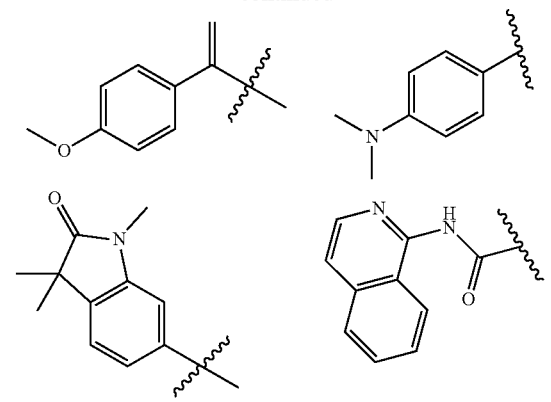
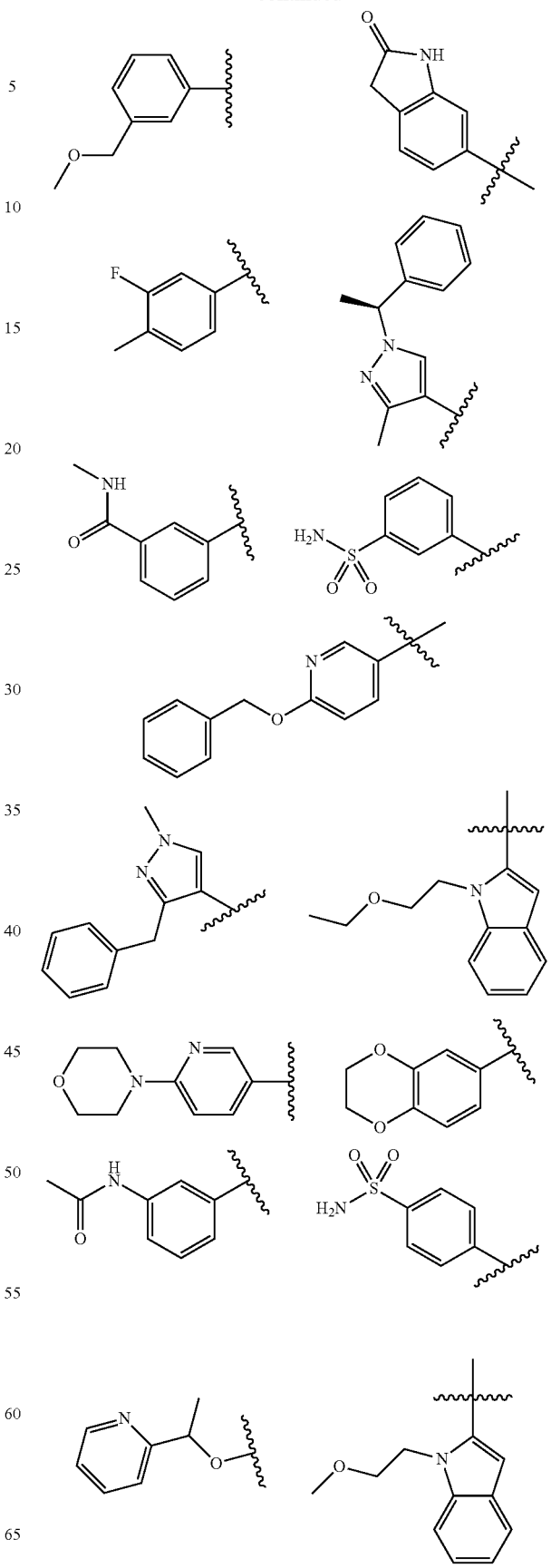

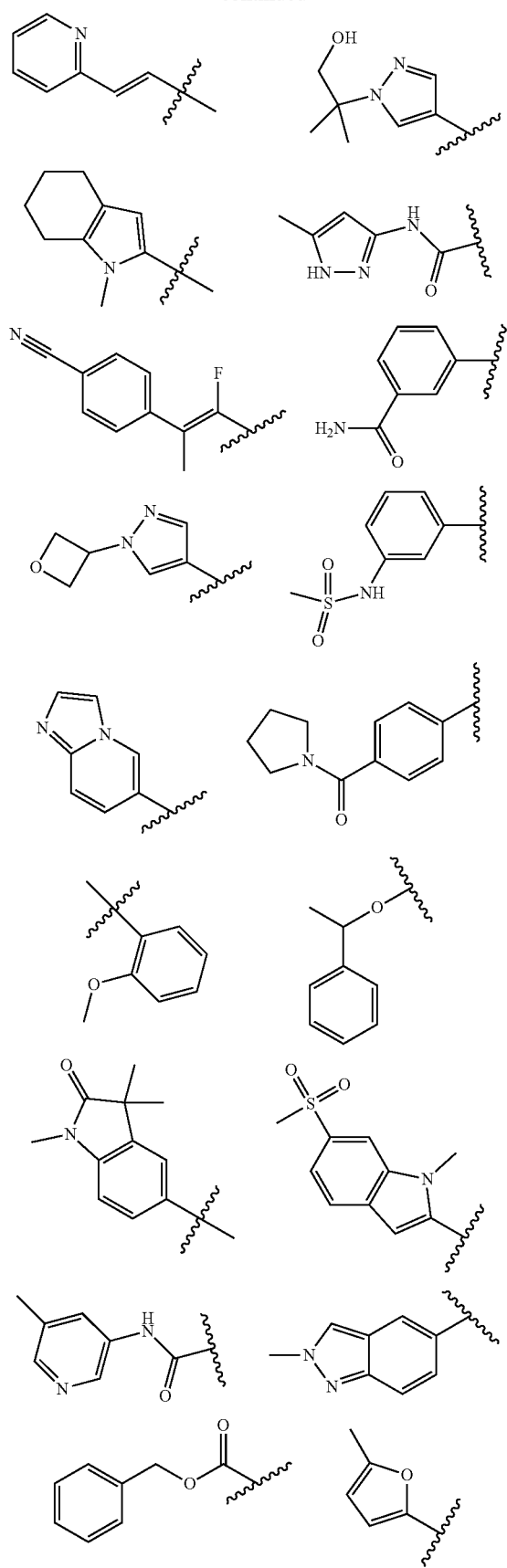
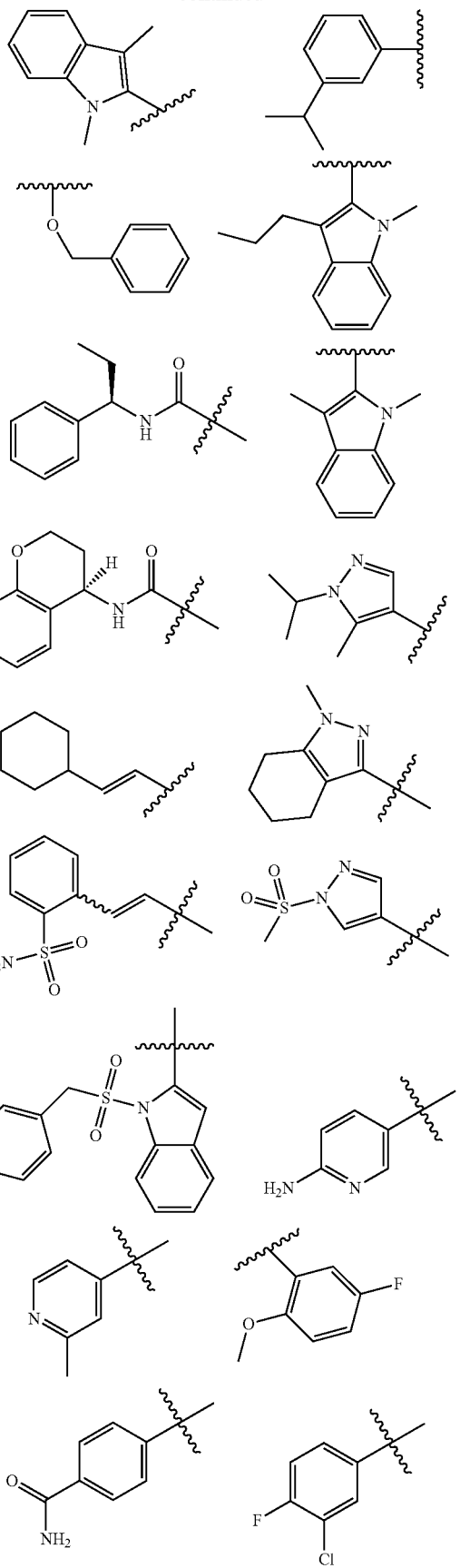

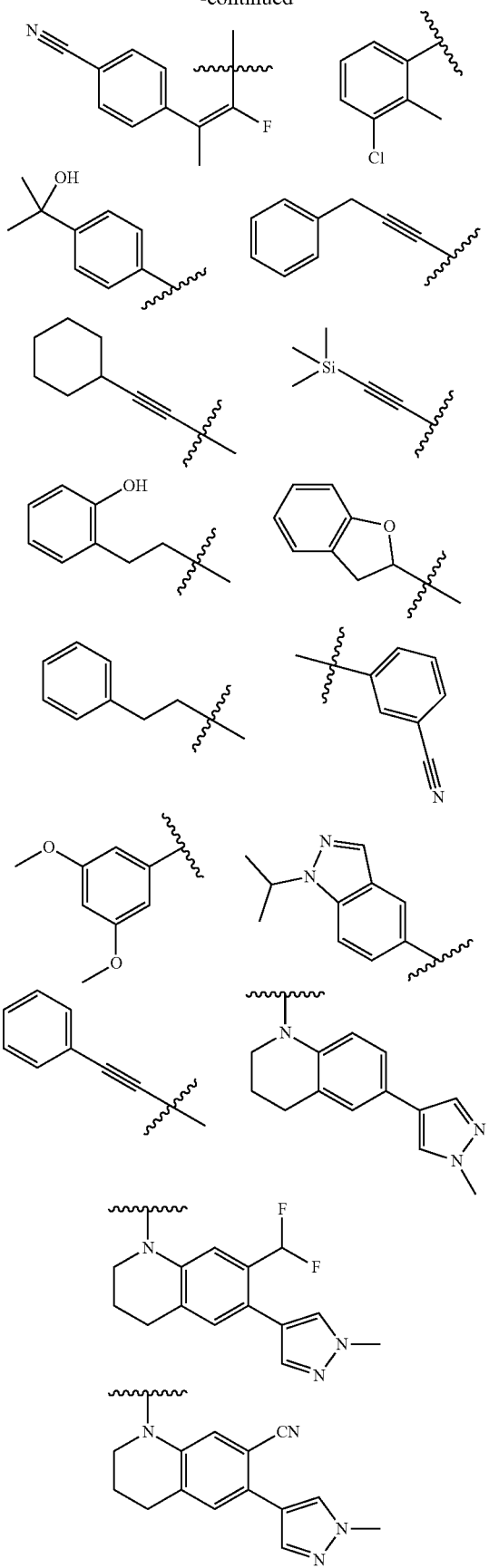
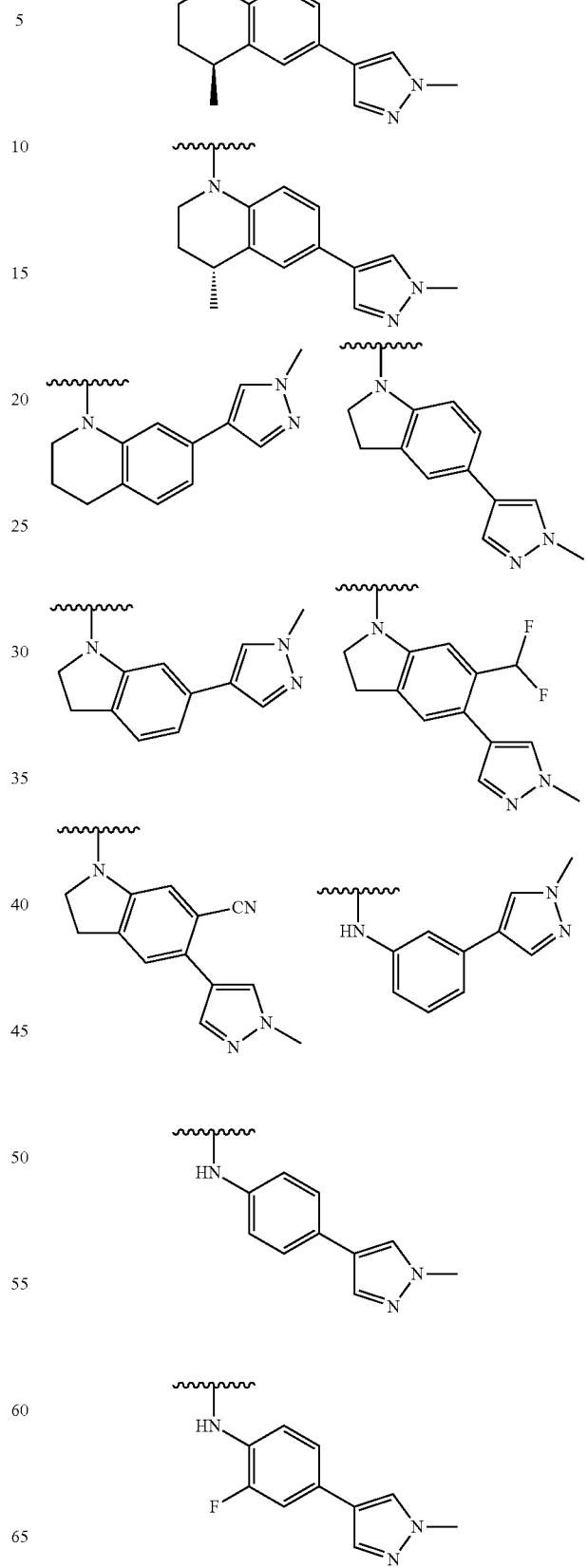

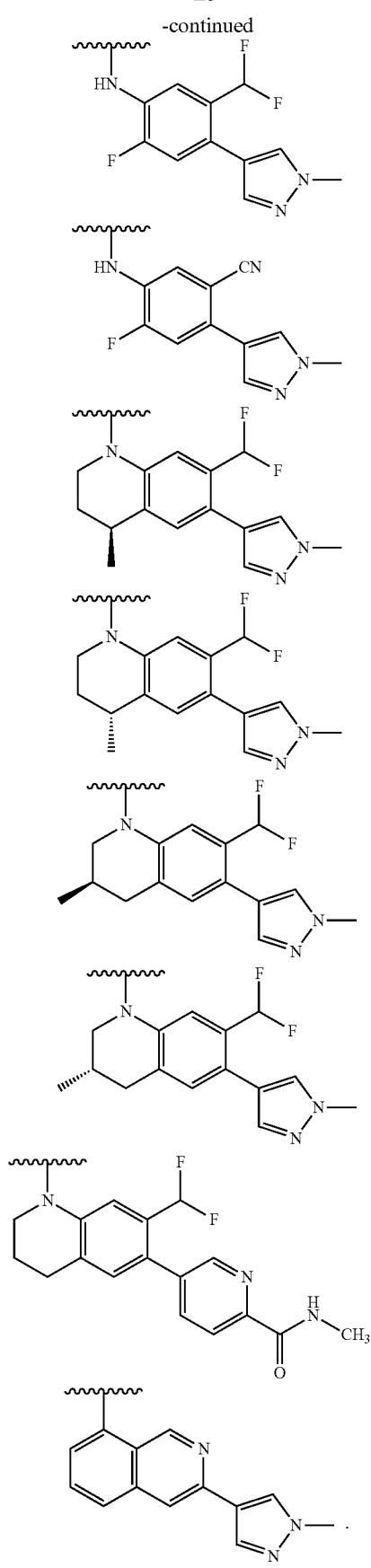
In certain embodiments $R^b$ is H, methyl ethyl, ethenyl, ethynyl,
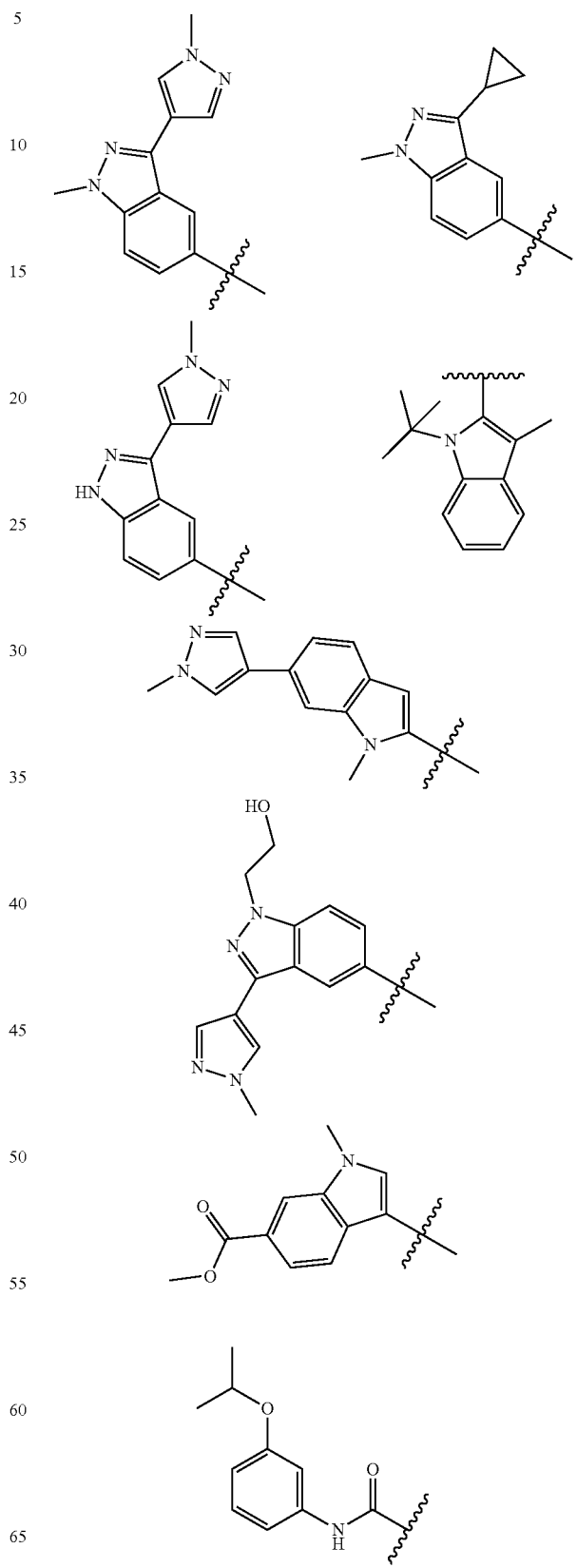
or

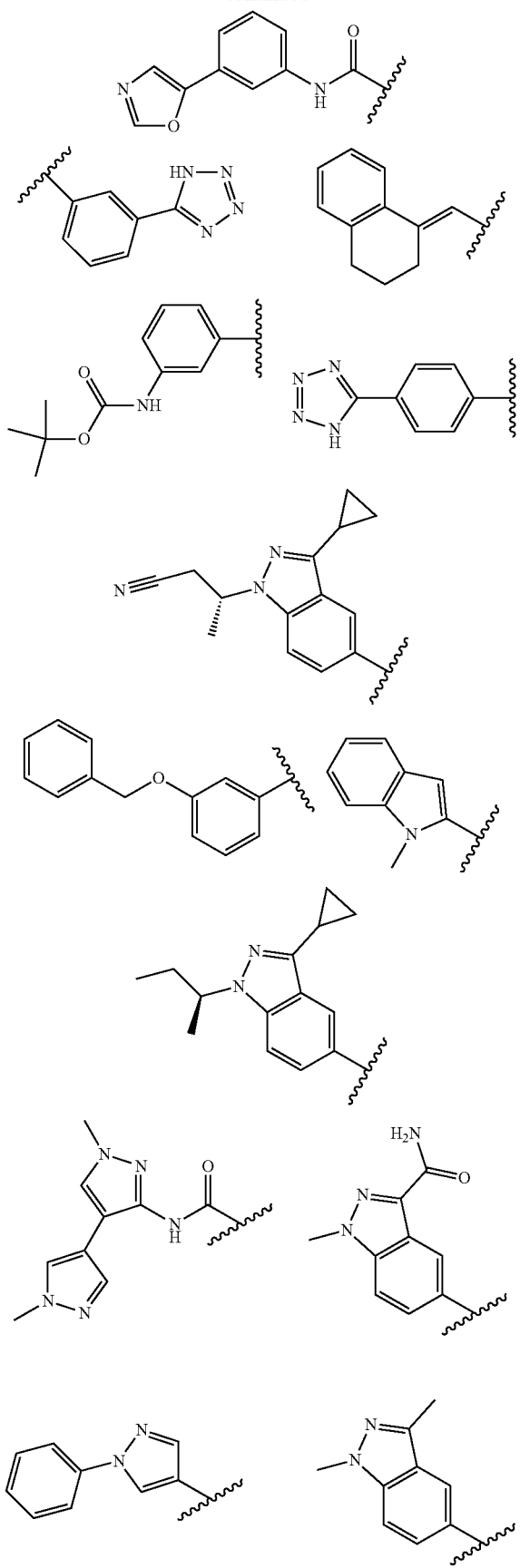
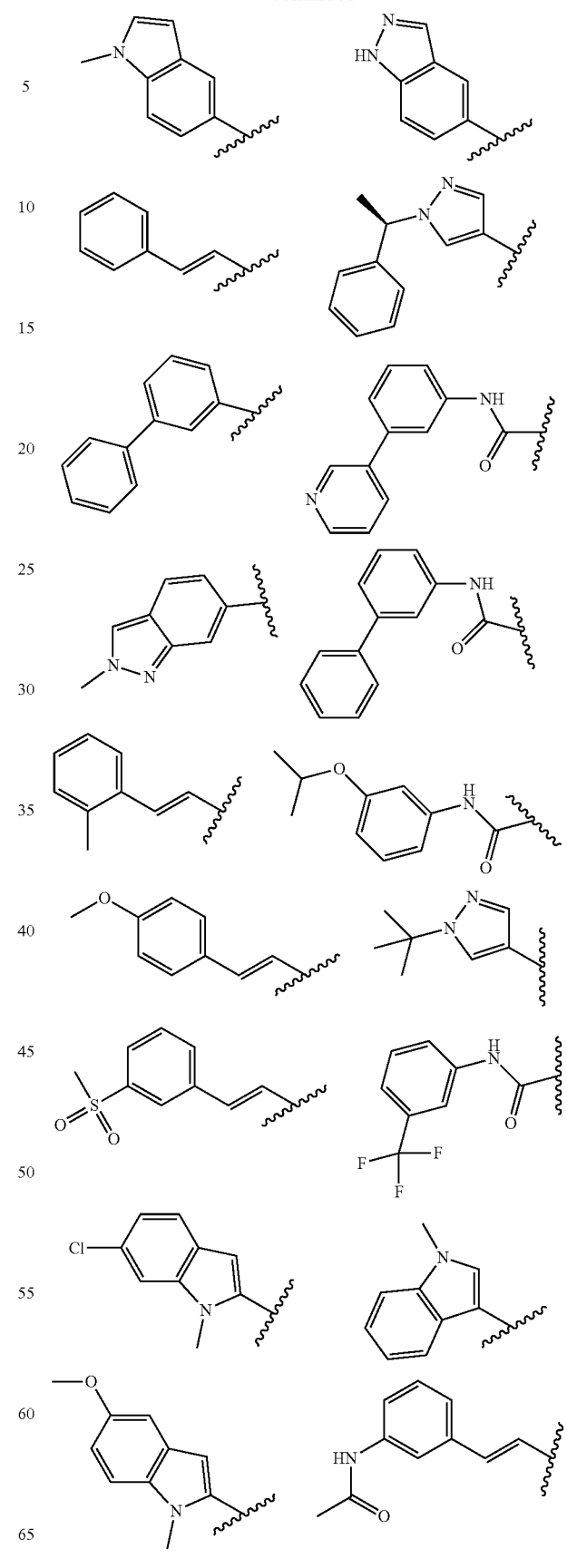

33
-continued
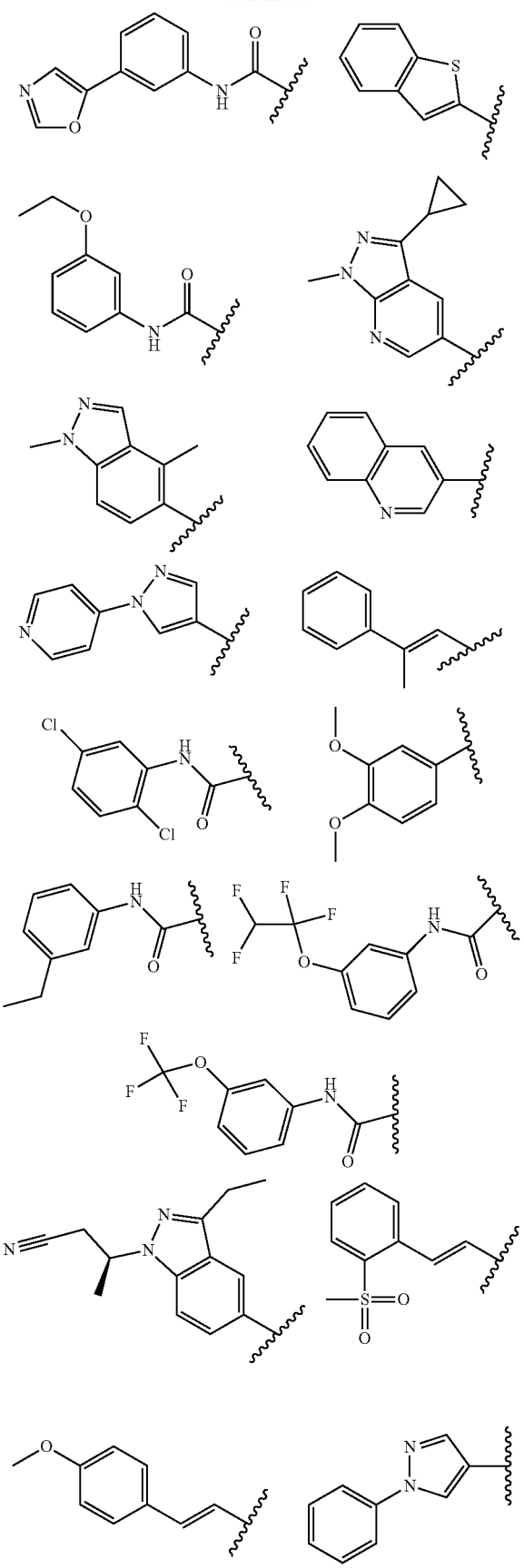
34
-continued
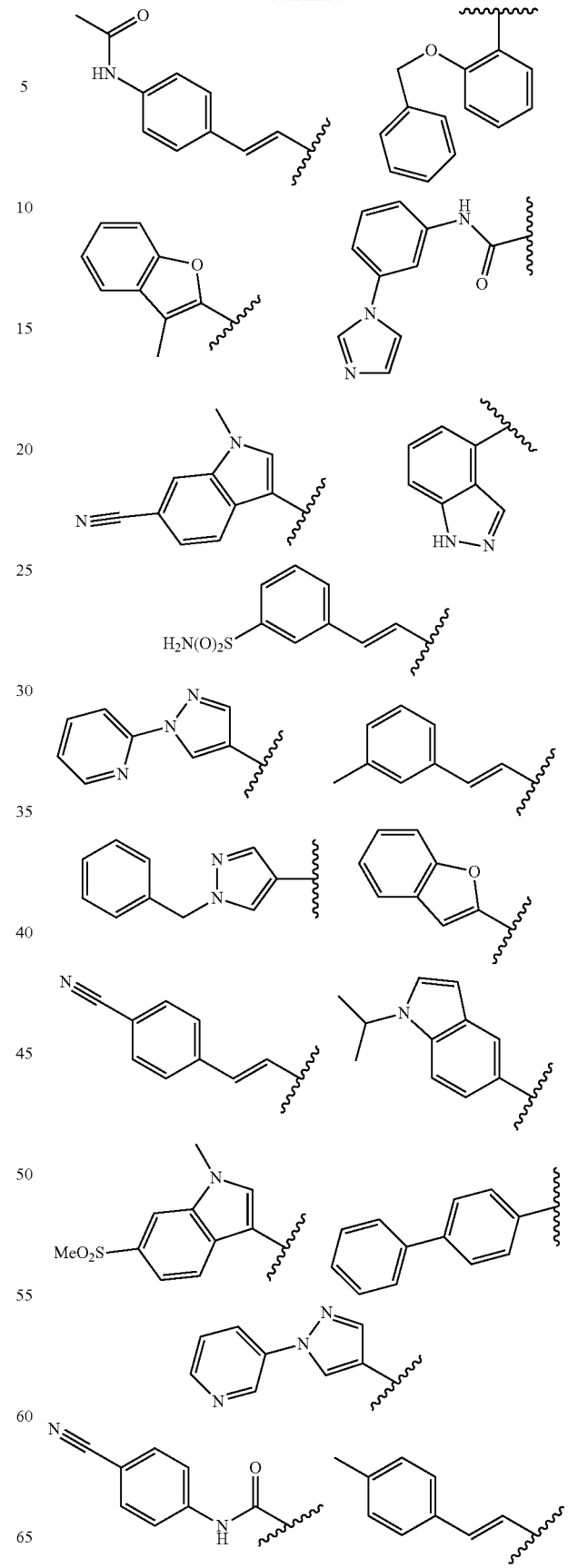

35
-continued
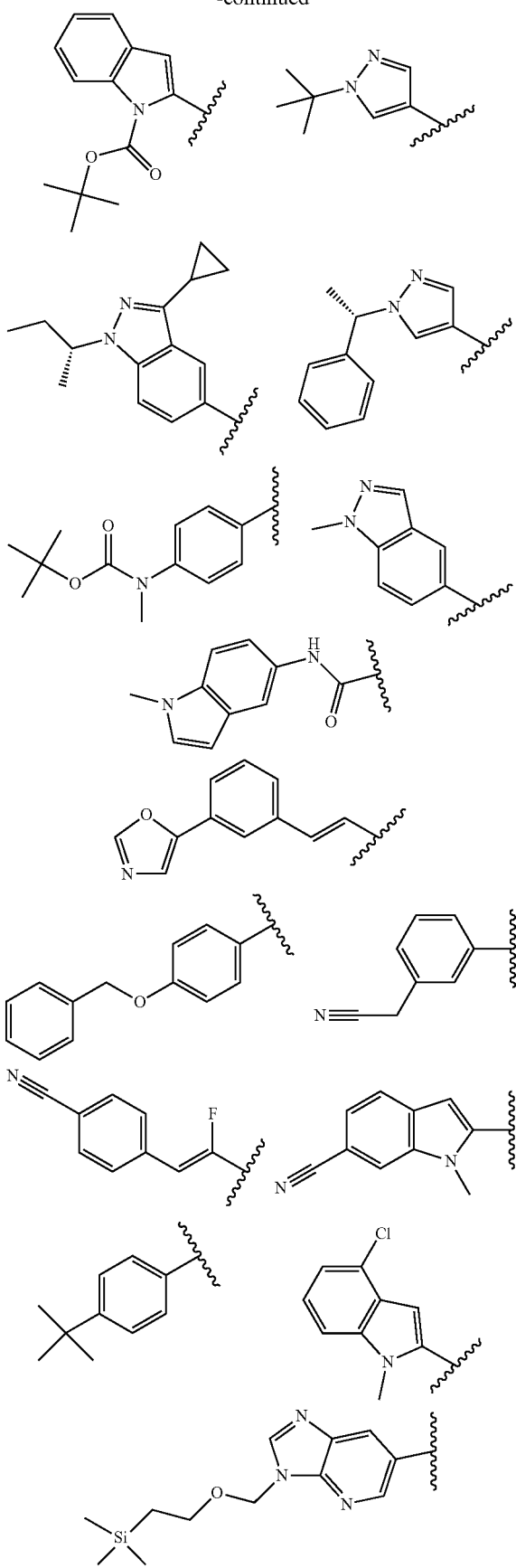
36
-continued
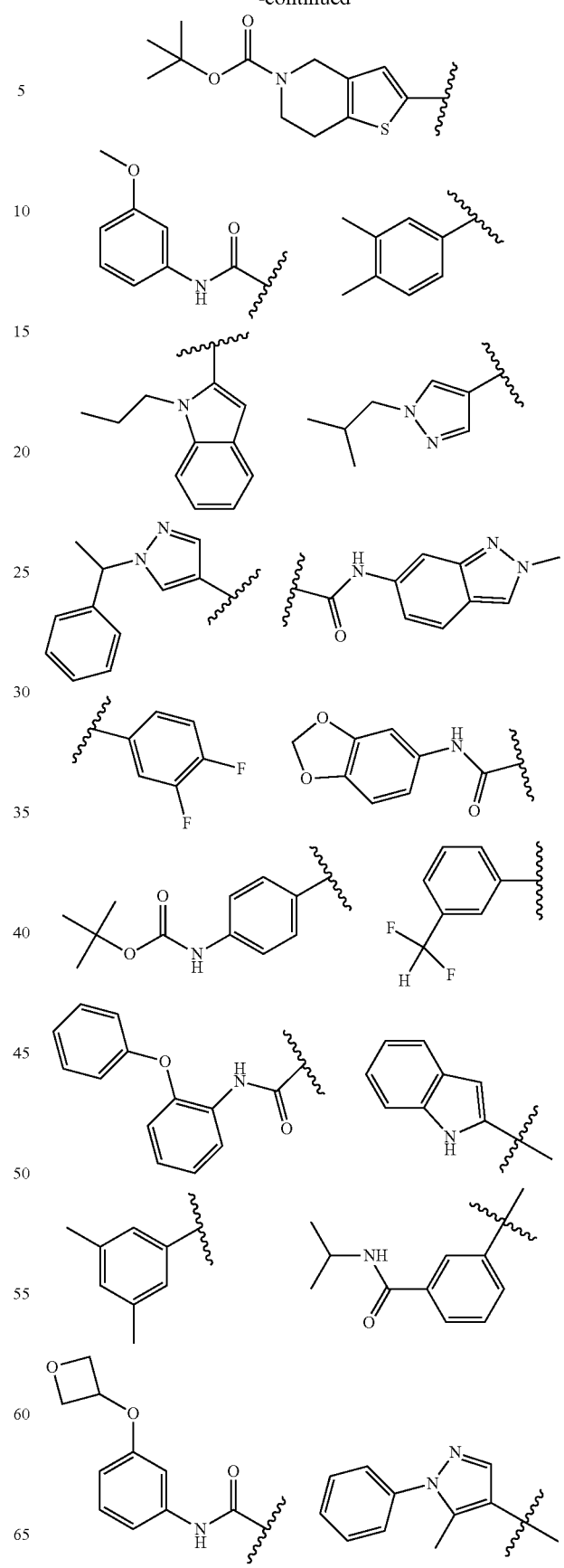

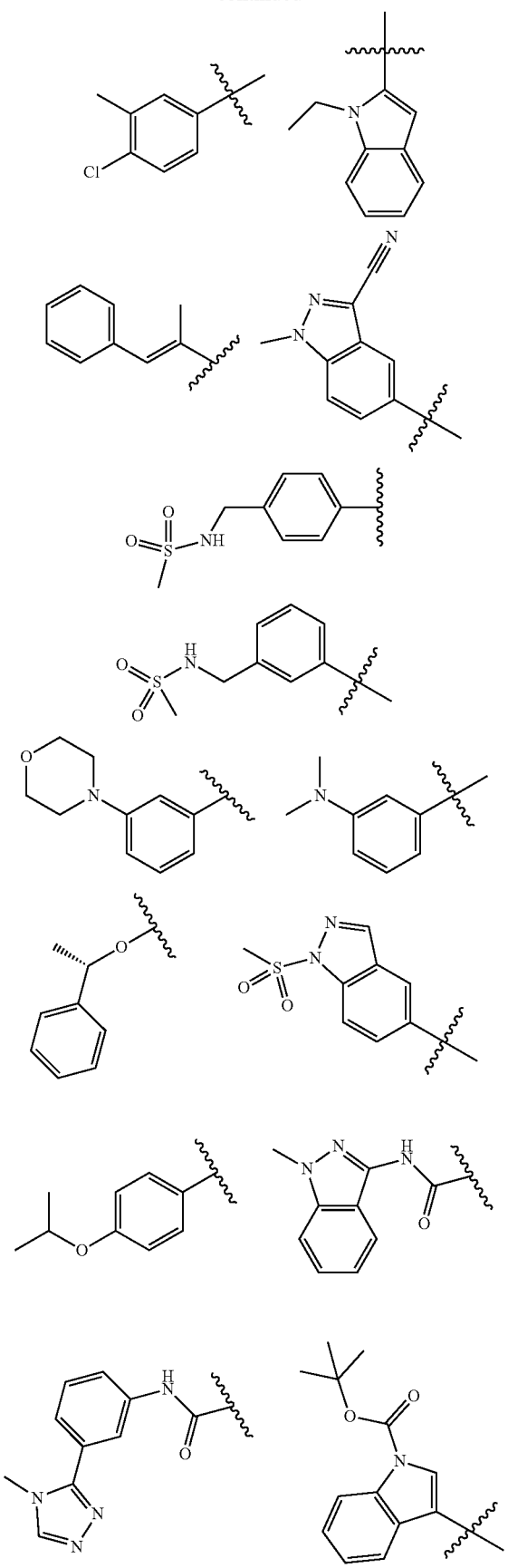
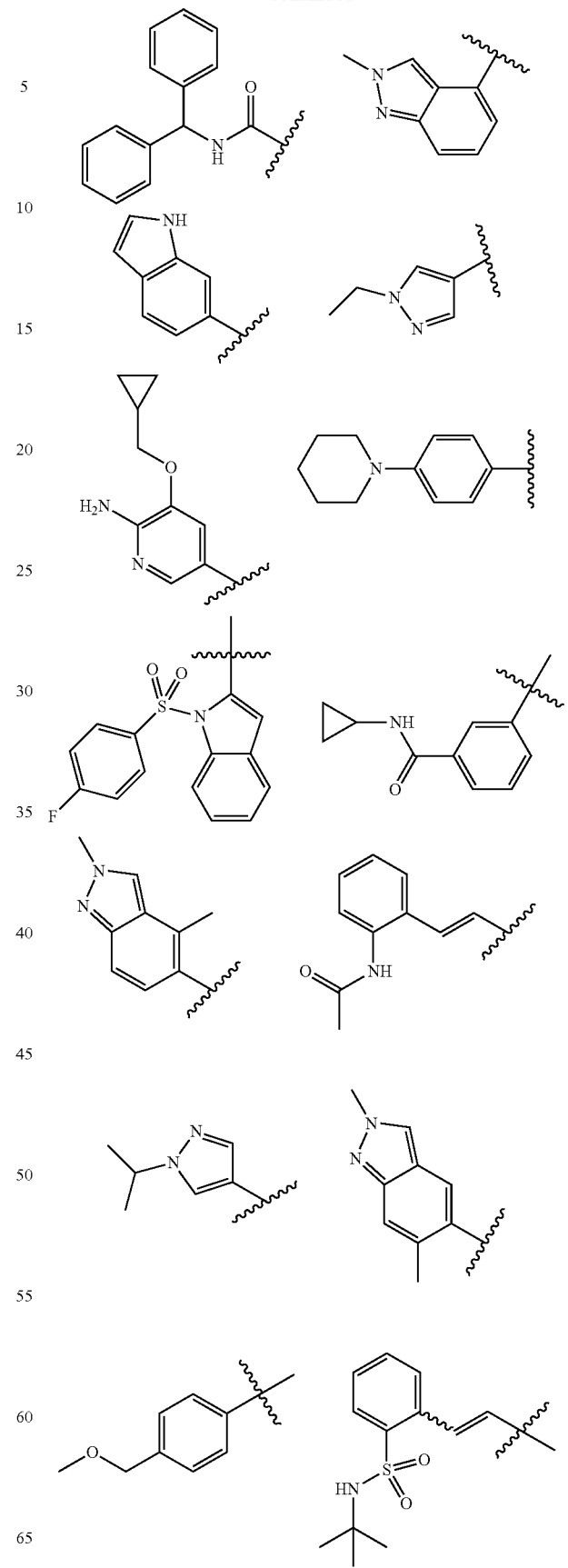

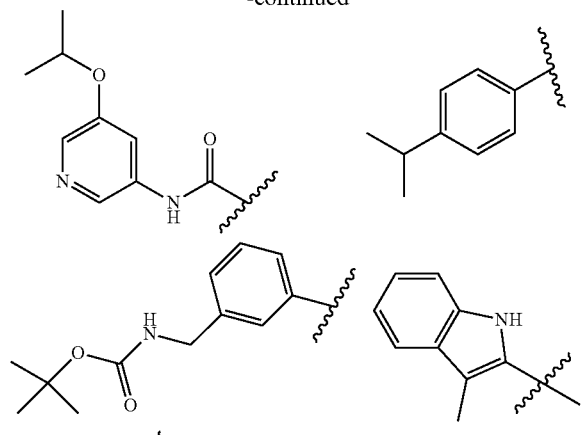
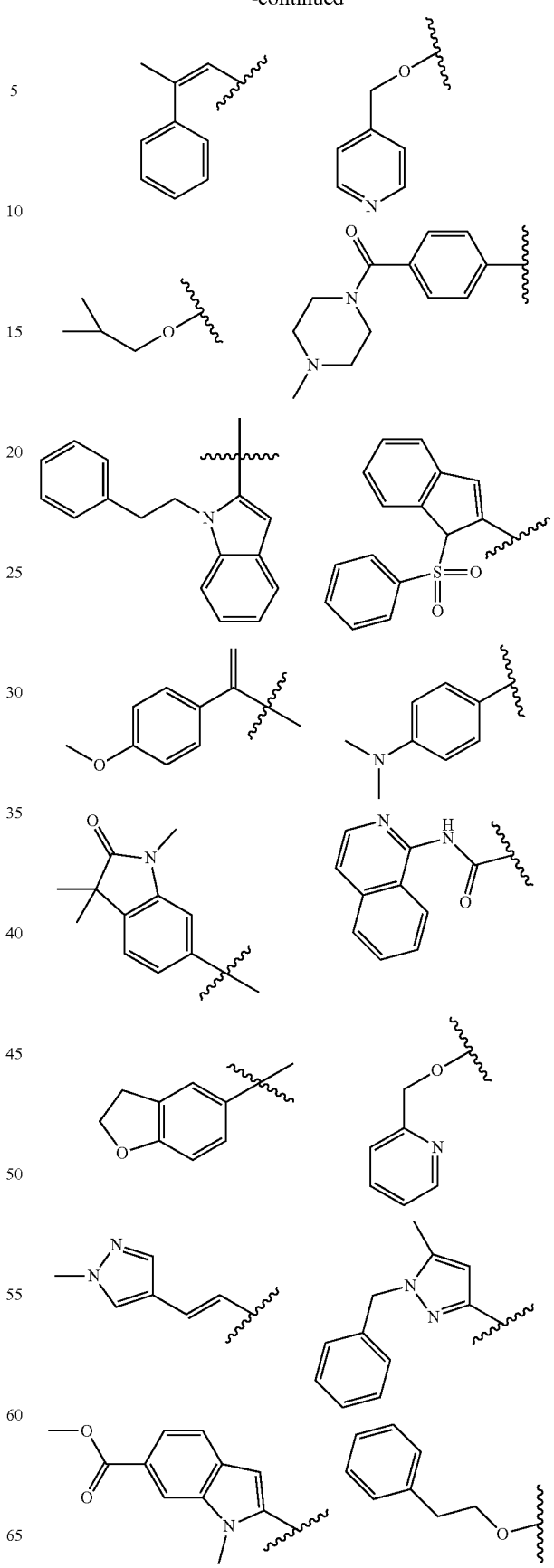

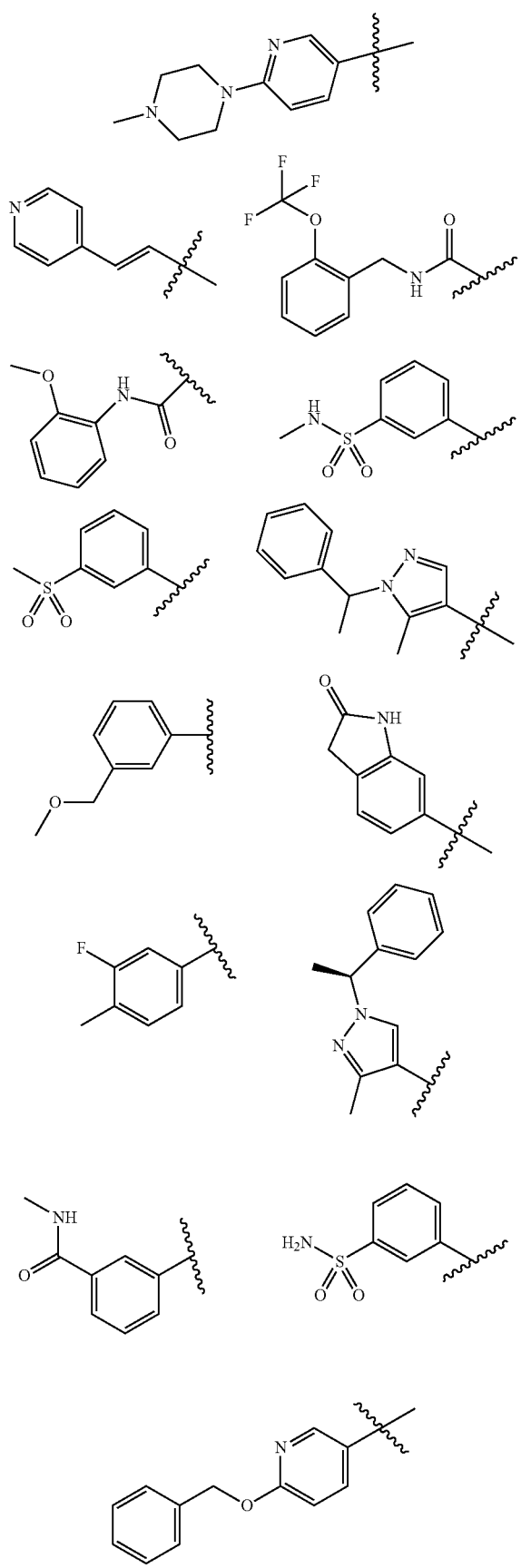
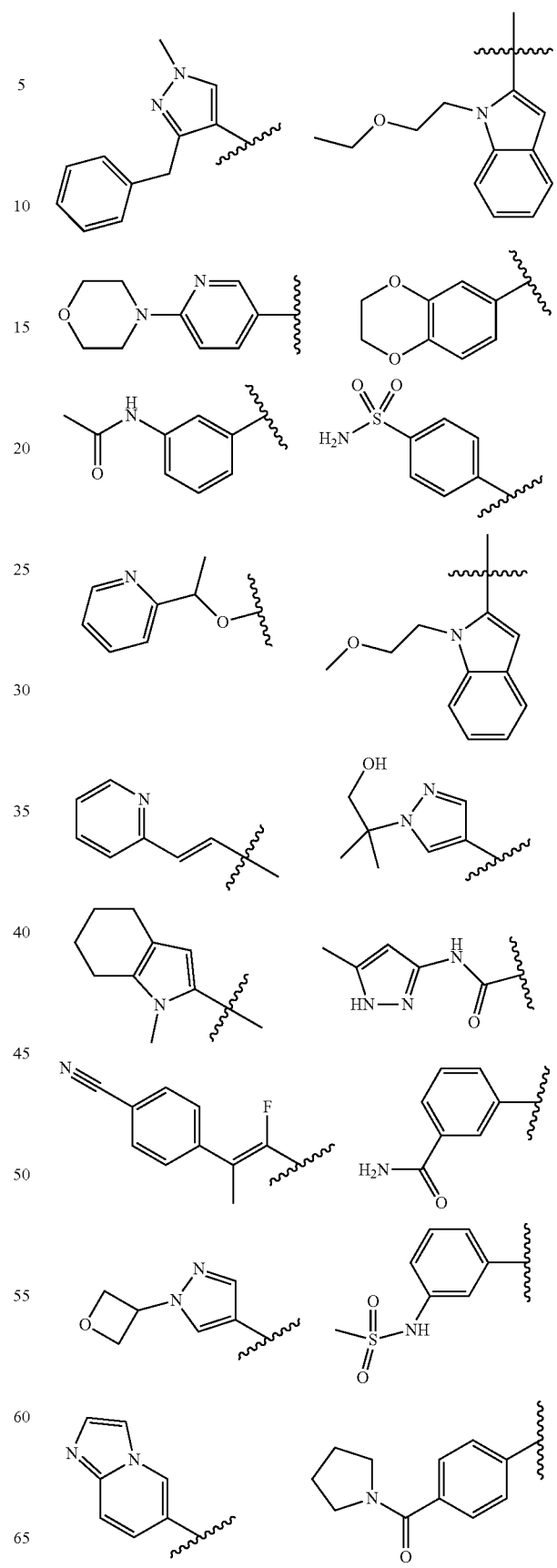

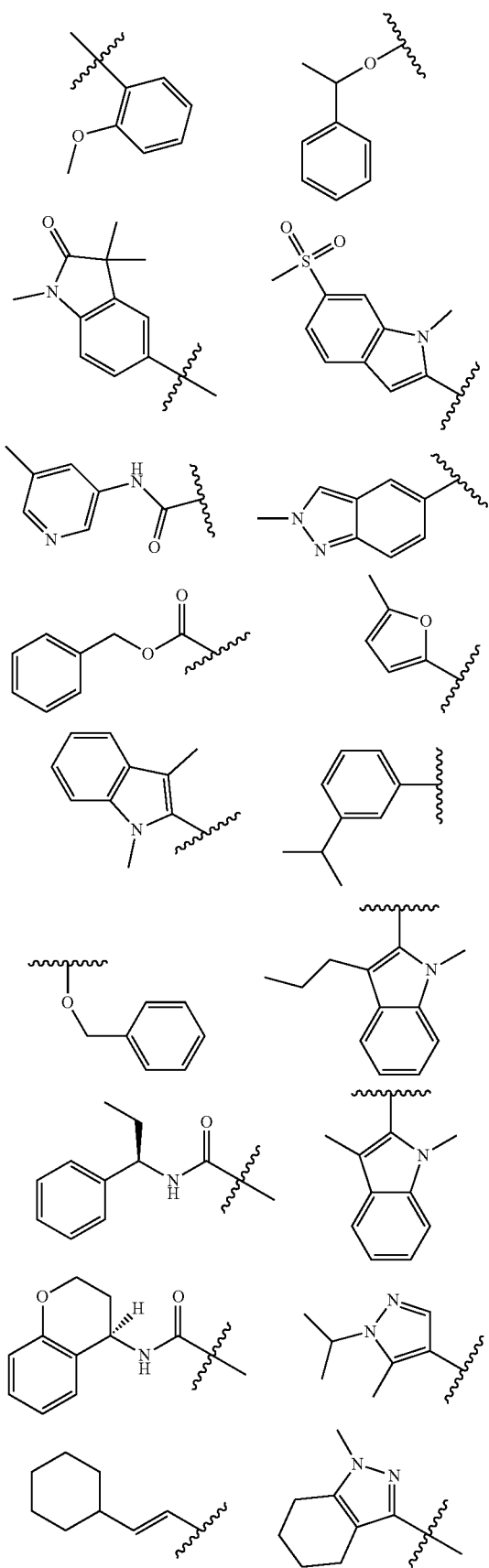
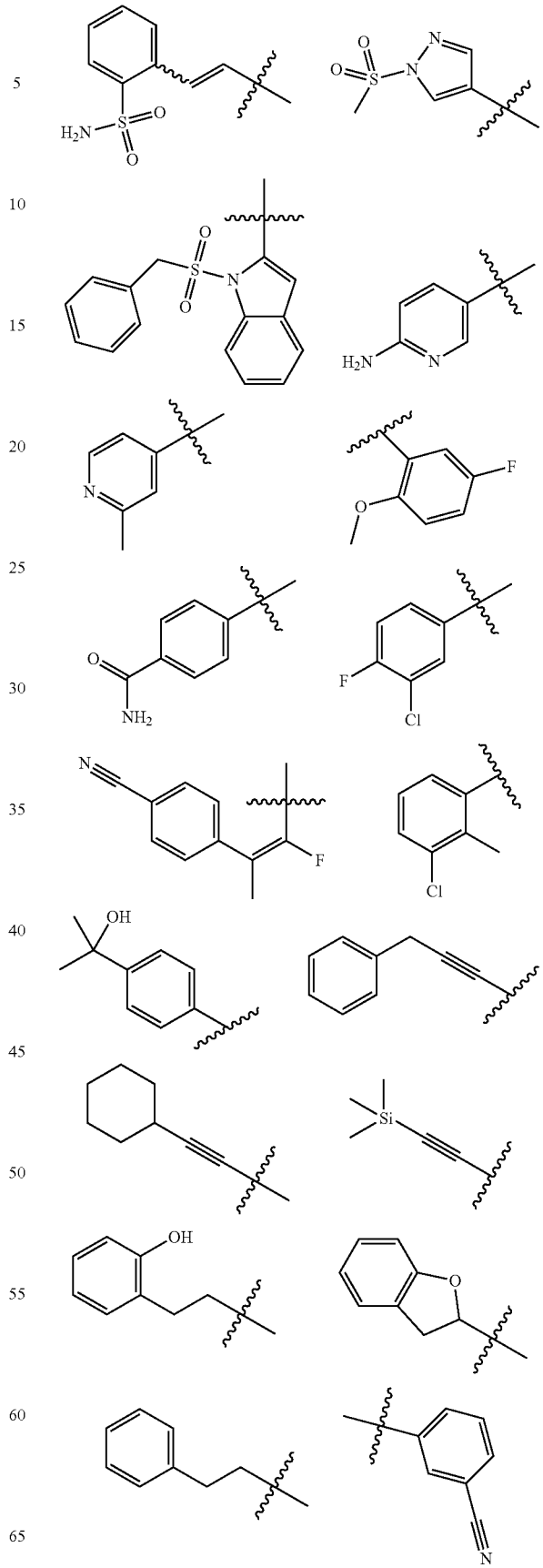

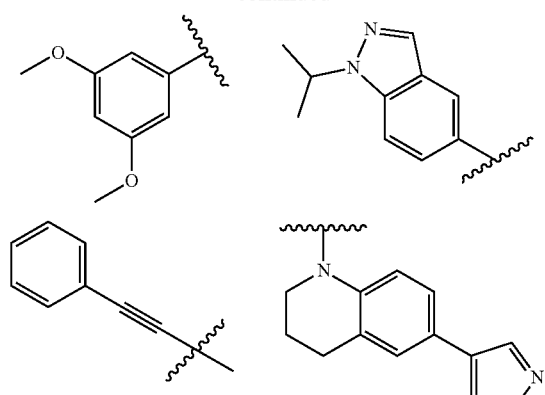
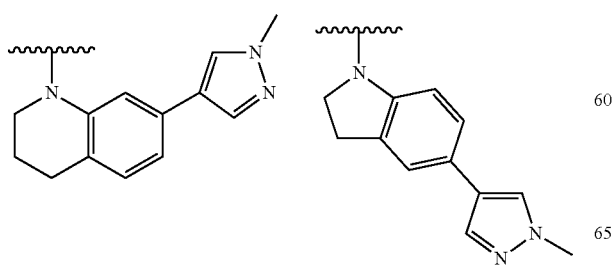
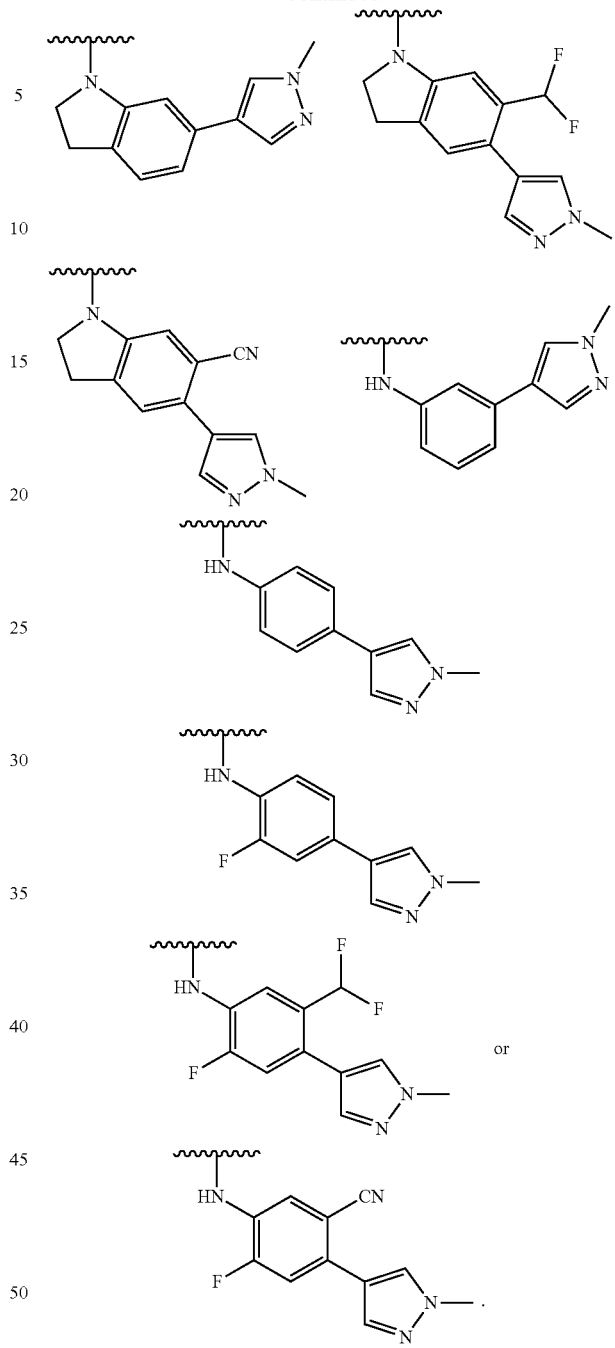
In certain embodiments the compound is a compound of formula (Ib):
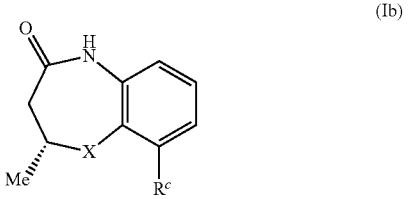

wherein:

X is NH, O, or —CH$_2$—;

R$^c$ is C$_{2-6}$alkenyl, C$_{2-6}$alkynyl, 6-10 membered aryl, and 5-14 membered heteroaryl, wherein any C$_{2-6}$alkenyl, C$_{2-6}$alkynyl, 6-10 membered aryl, and 5-14 membered heteroaryl is optionally substituted with one or more groups R$^f$ independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R$^g$, —N(R$^g$)—S(O)—R$^g$, N(R$^g$)—S(O)$_2$—R$^g$, and C$_{1-6}$alkyl, which 3-20 membered carbocyclyl, 3-20 membered heterocyclyl, and C$_{1-6}$alkyl are optionally substituted with one or more groups R$^i$ independently selected from the group consisting of oxo, halo, C$_{1-6}$alkyl, cyano, —N(R$^i$)$_2$, —O—R$^i$, —S(O)—R$^i$, —S(O)$_2$—R$^i$, —S(O)—N(R$^i$)$_2$, —S(O)$_2$—N(R$^i$)$_2$, —N(R$^i$)—S(O)—R$^i$, —N(R$^i$)—C(O)—R$^i$, —N(R$^i$)—C(O)—O—R$^i$, —N(R$^i$)—S(O)$_2$—R$^i$, 3-20 membered heterocyclyl, and 3-20 membered carbocyclyl that is optionally substituted with one or more groups R$^m$ independently selected from the group consisting of halo, and C$_{1-6}$alkyl; and R$^h$ is independently selected from the group consisting of H, C$_{1-6}$alkyl, C$_{2-6}$alkenyl, C$_{2-6}$alkynyl, and C$_{3-6}$carbocyclyl; or a salt thereof.

In certain embodiments the compound is a compound of formula (Ib) wherein R$^c$ is:

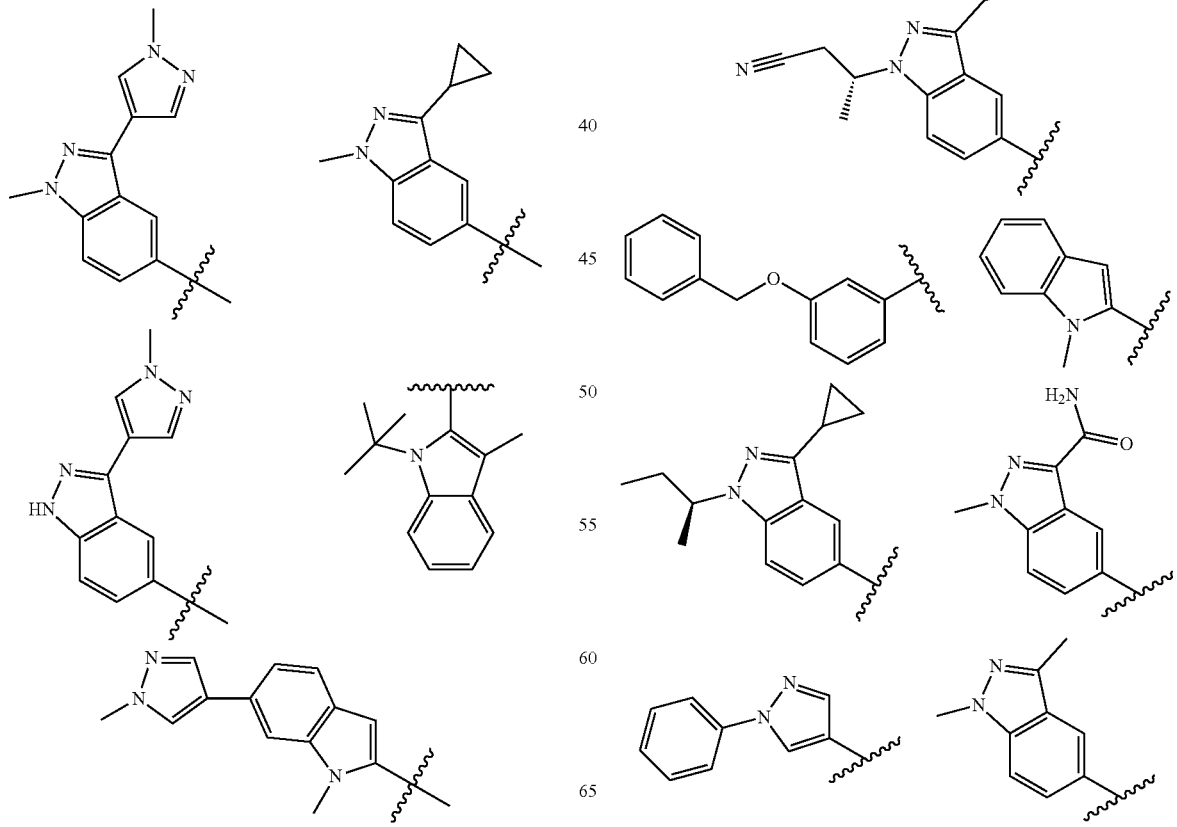

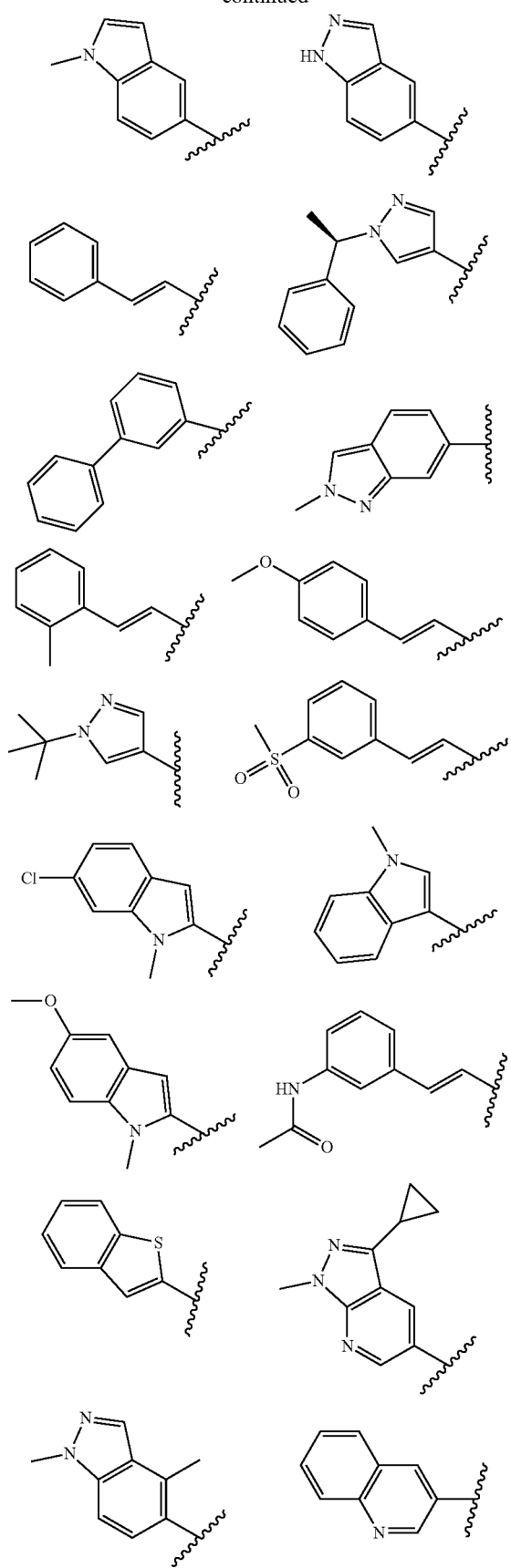
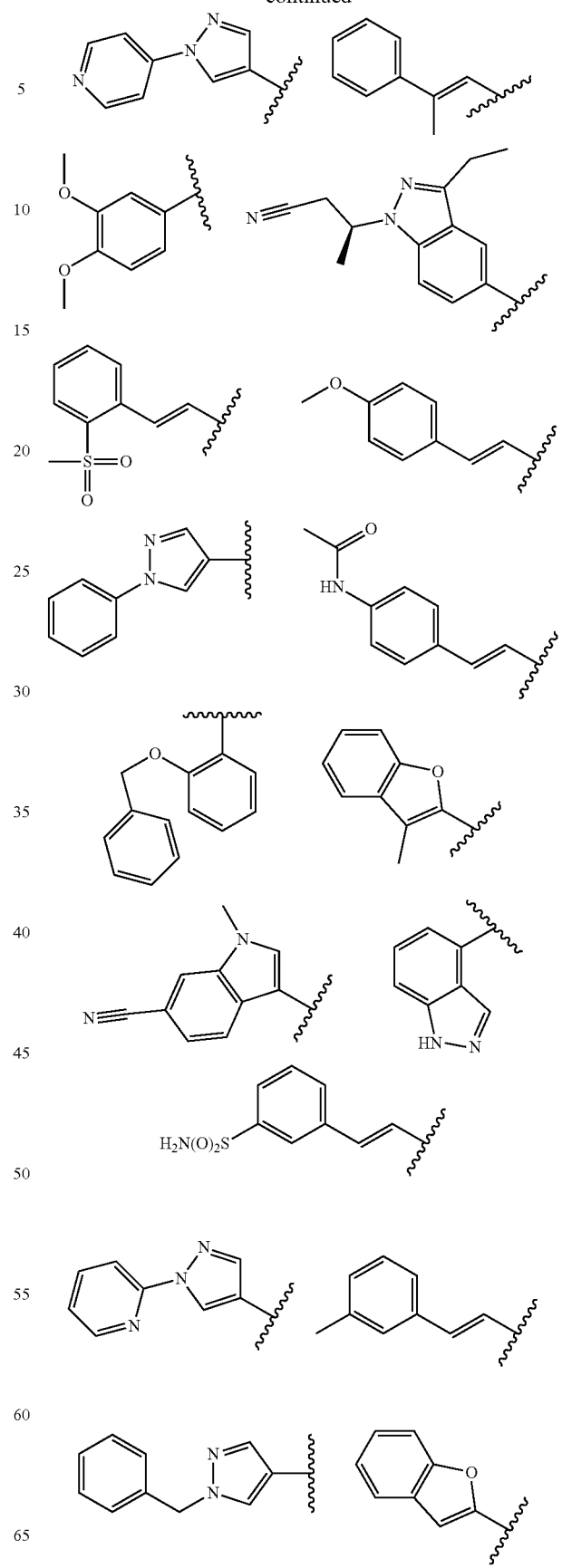

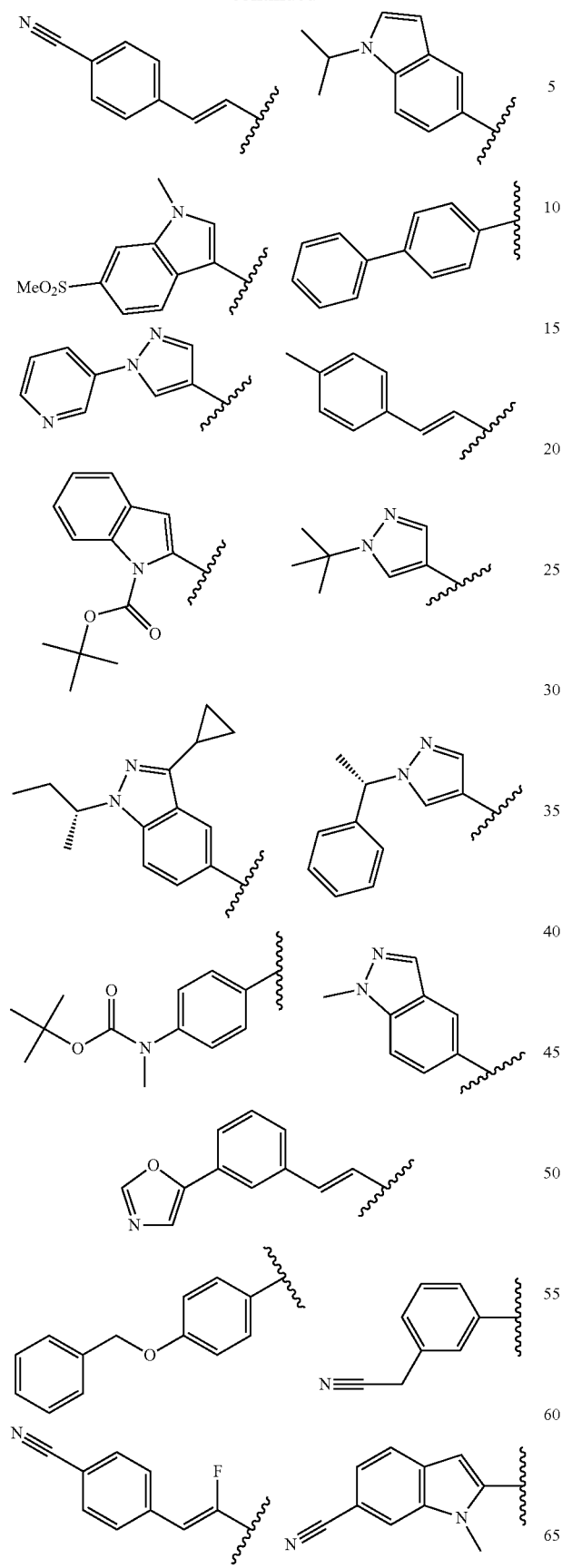
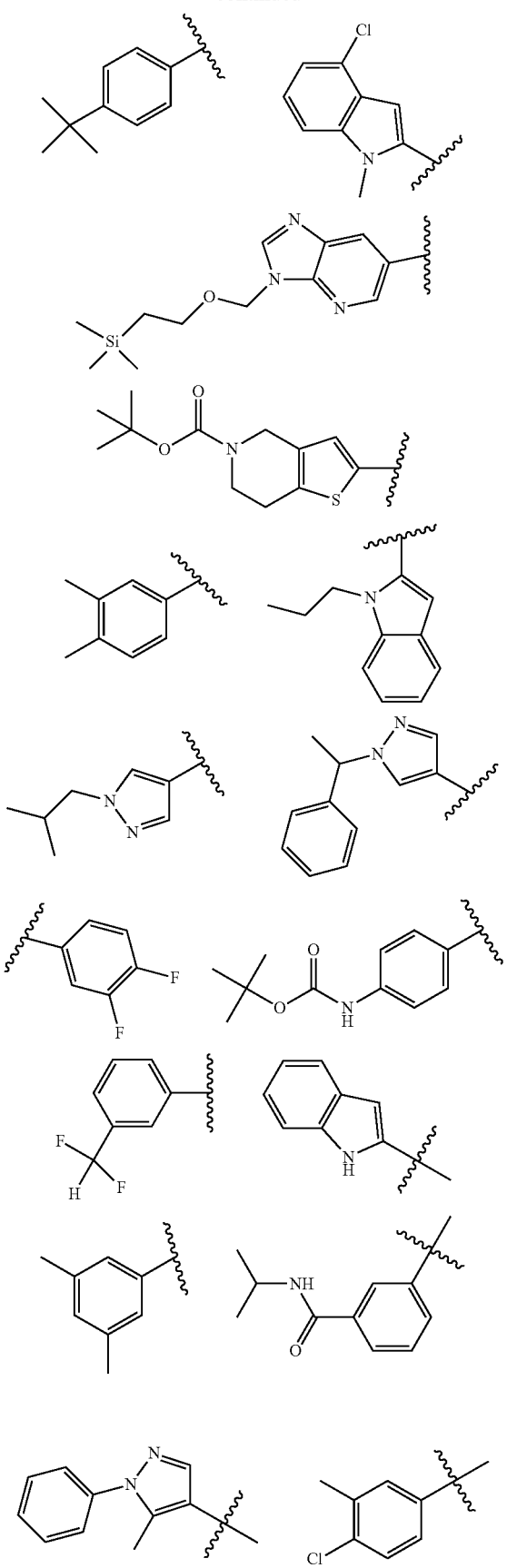

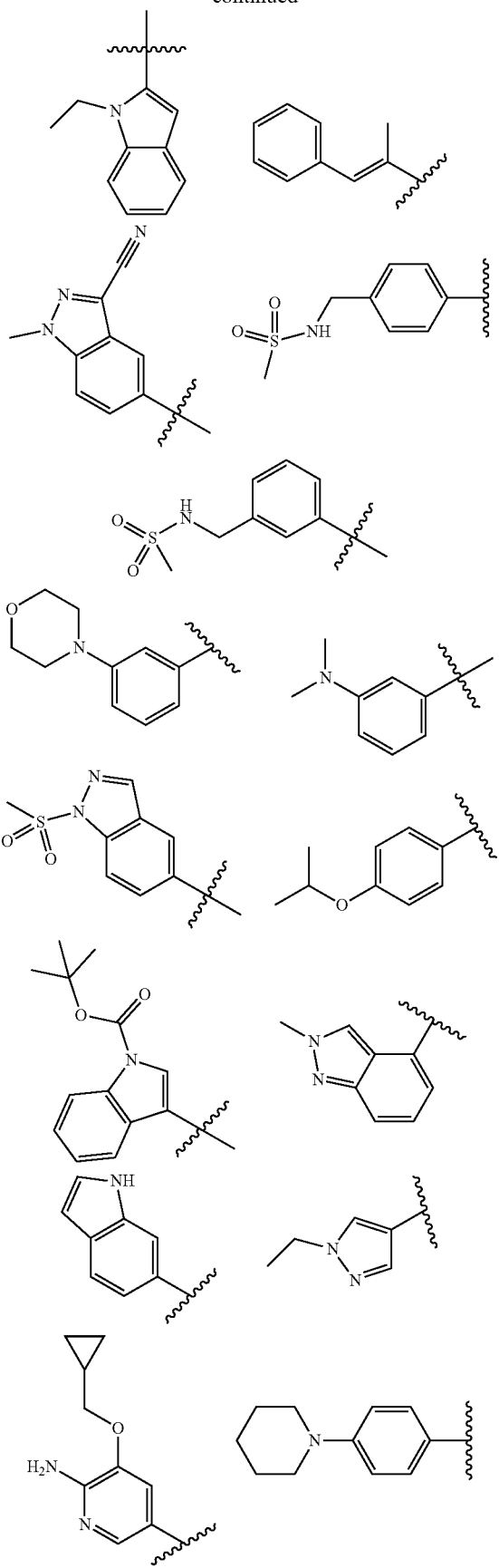
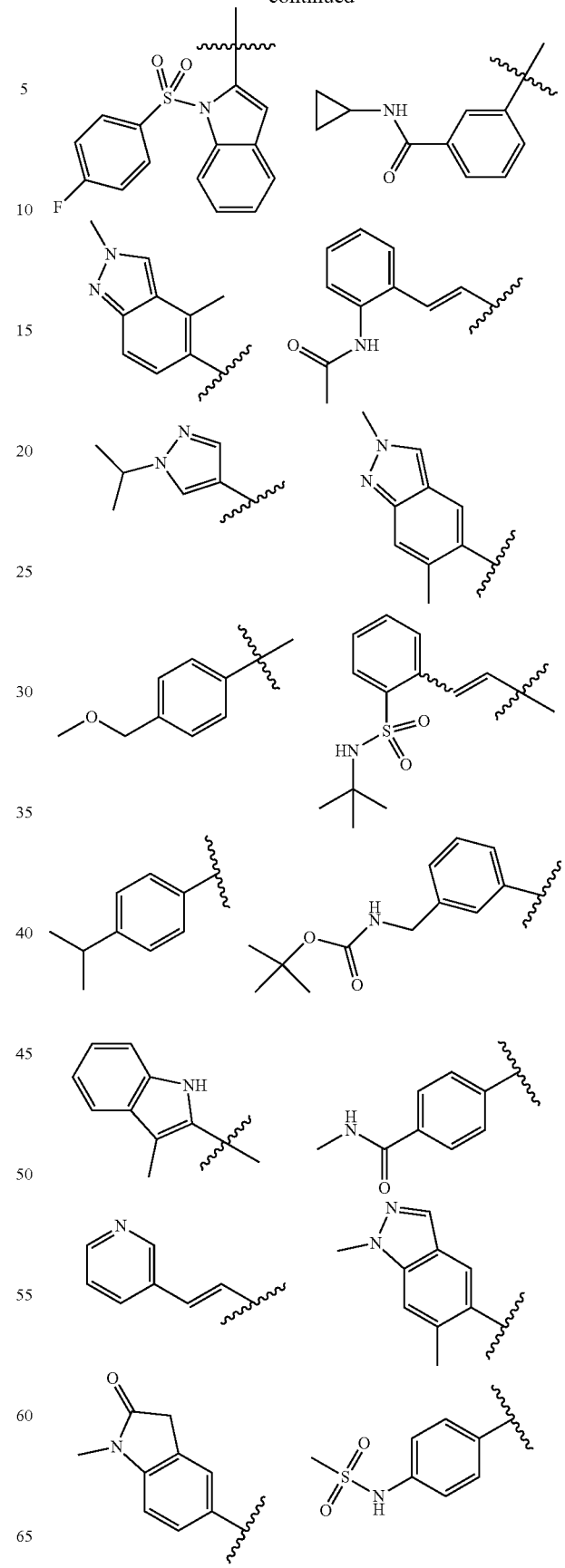

55
-continued
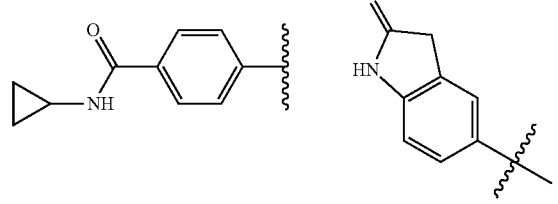
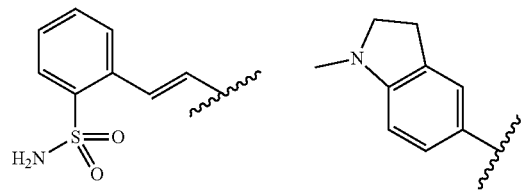
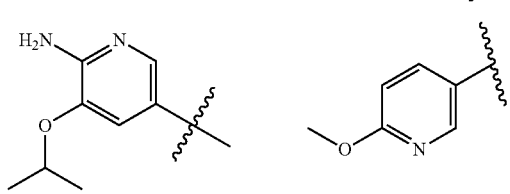
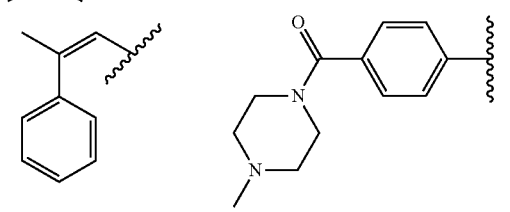
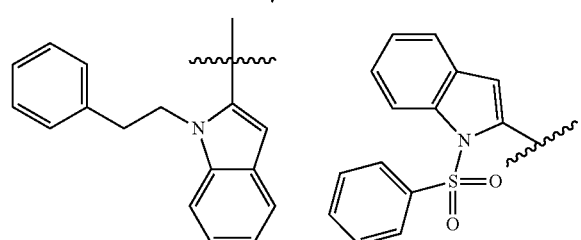
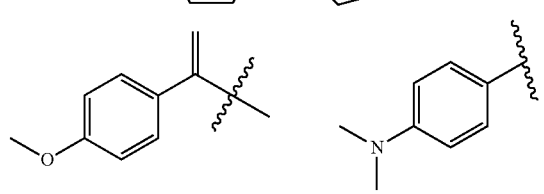
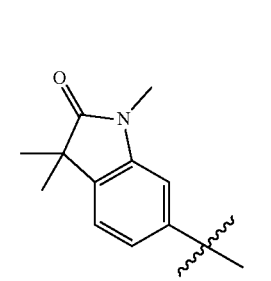
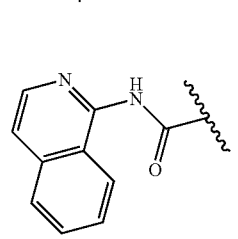
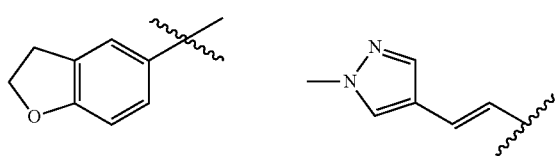
56
-continued
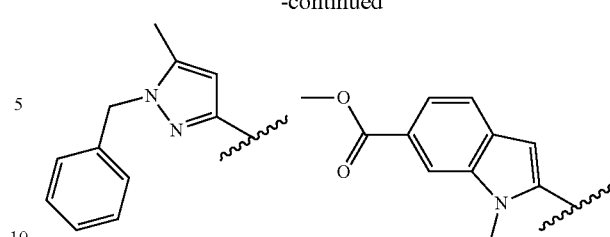
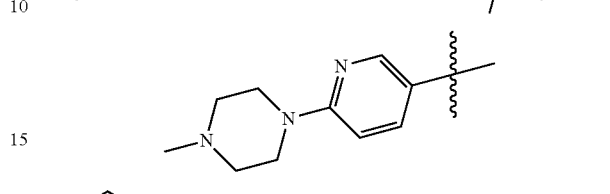
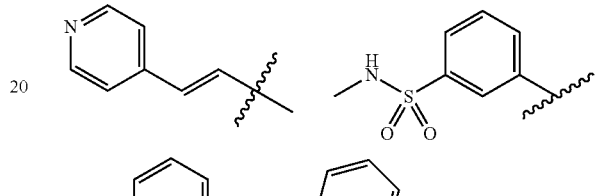
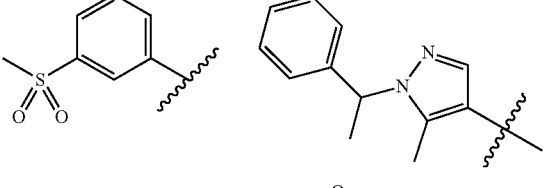
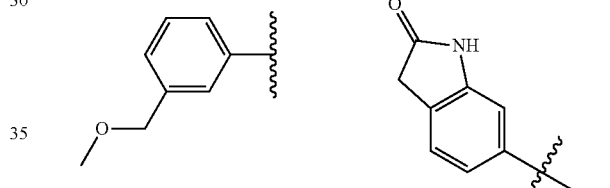
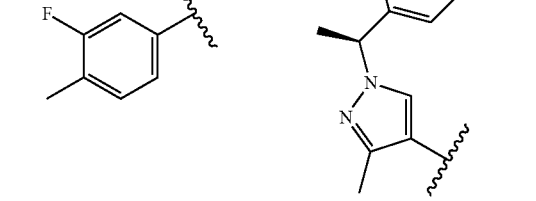
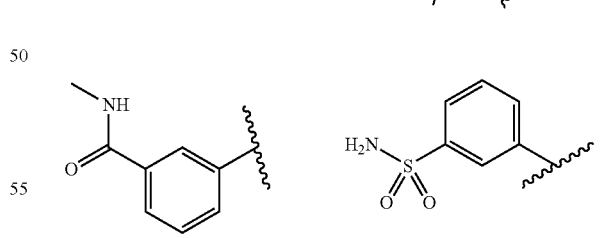
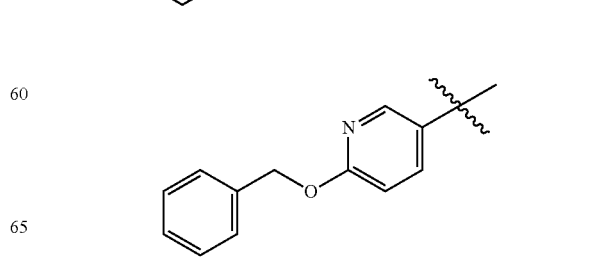

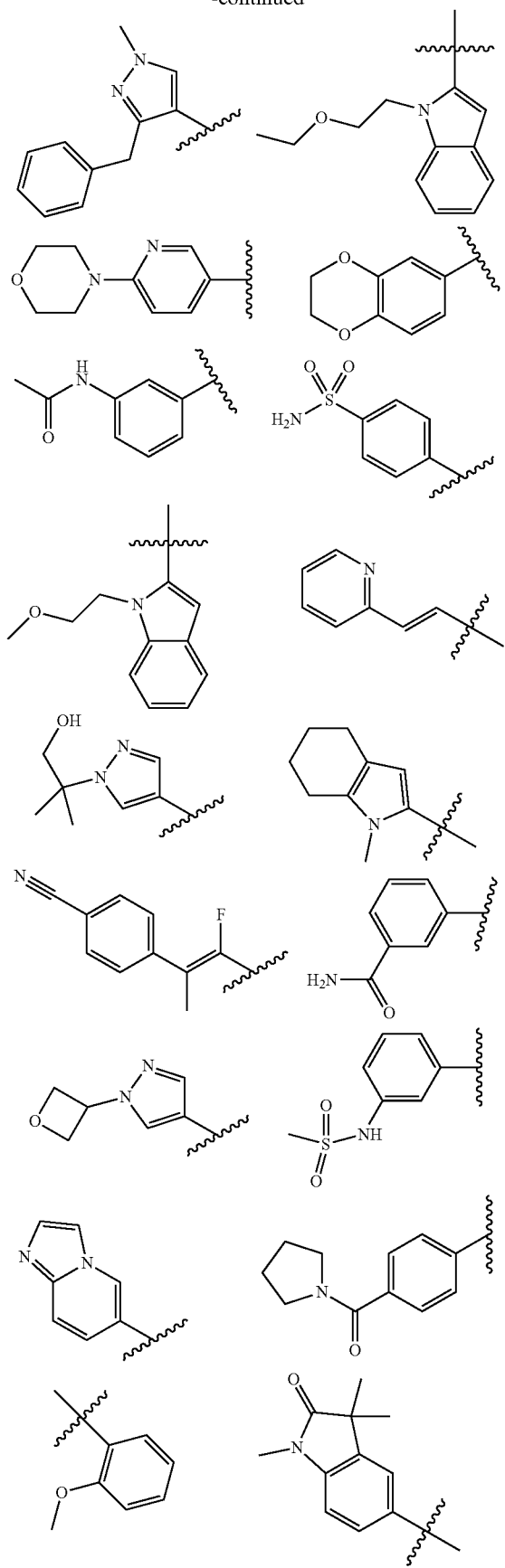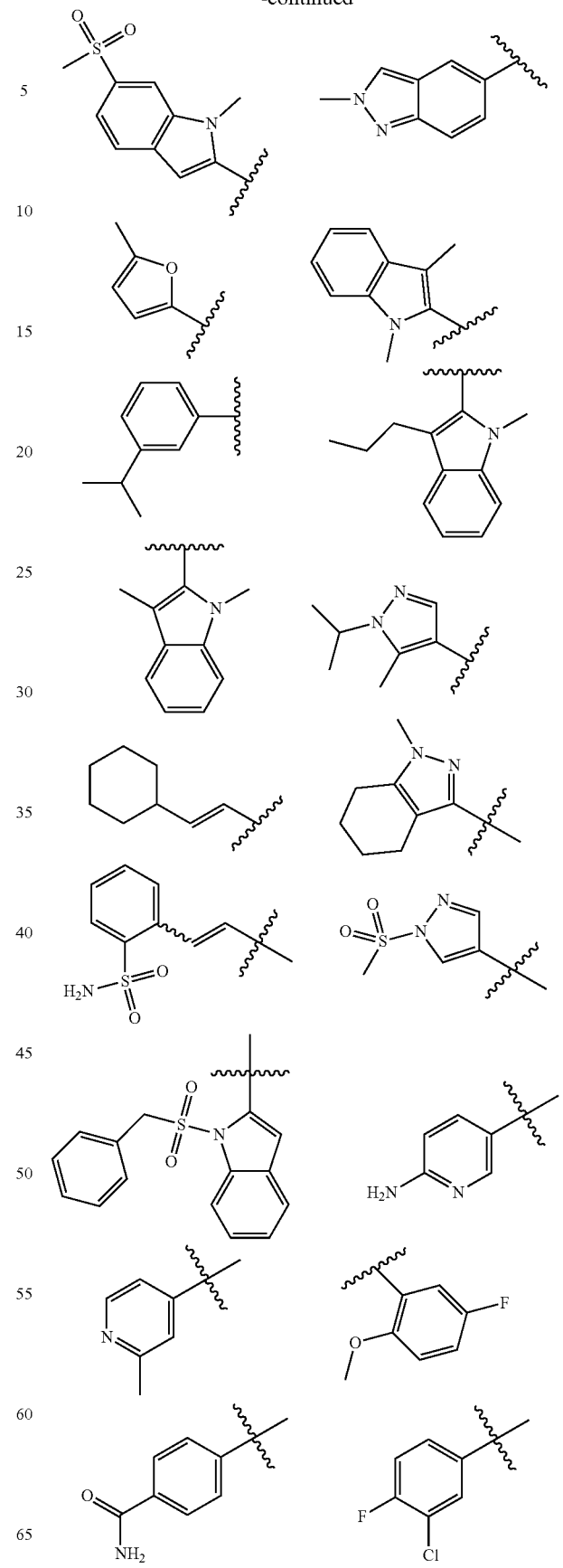

-continued

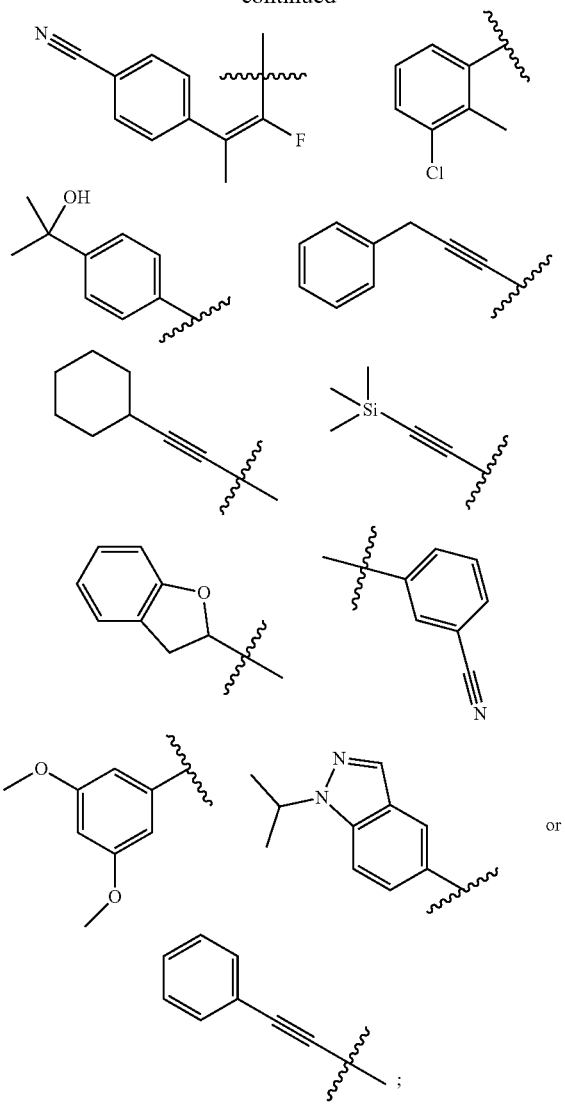

or a salt thereof.

In certain embodiments the compound is a compound of formula (Ic):

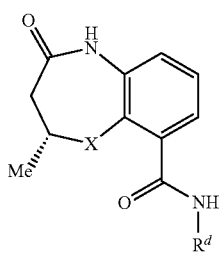

(Ic)

wherein:

X is NH or O;

$R^d$ is $C_{1-6}$alkyl, 6-10 membered aryl, or 5-10 membered heteroaryl, wherein each $C_{1-6}$alkyl, 6-10 membered aryl, or 5-10 membered heteroaryl is optionally substituted with one or more groups $R^o$ independently selected from the group consisting of oxo, halo, amino, hydroxyl, cyano, —O—$R^p$, 3-20 membered carbocyclyl, 3-20 membered heterocyclyl, and $C_1$-$C_6$ alkyl, wherein any $C_1$-$C_6$ alkyl, 3-20 membered carbocyclyl and 3-20 membered heterocyclyl is optionally substituted with one or more groups independently selected from the group consisting of oxo, $C_1$-$C_4$alkyl, —O—$R^q$, and halo;

$R^p$ is independently selected from the group consisting of hydrogen, $C_{1-6}$alkyl, $C_{2-6}$alkenyl, $C_{2-6}$alkynyl, 3-20 membered carbocyclyl, and 3-20 membered heterocyclyl, wherein each $C_{1-6}$alkyl, $C_{2-6}$alkenyl, $C_{2-6}$alkynyl, $C_{1-6}$alkoxy, 3-20 membered carbocyclyl, and 3-20 membered heterocyclyl is optionally substituted with one or more halo;

$R^q$ is $C_{1-6}$alkyl is optionally substituted with one or more halo;

or a salt thereof.

In certain embodiments the compound is a compound of formula (Ic), wherein $R^d$ is:

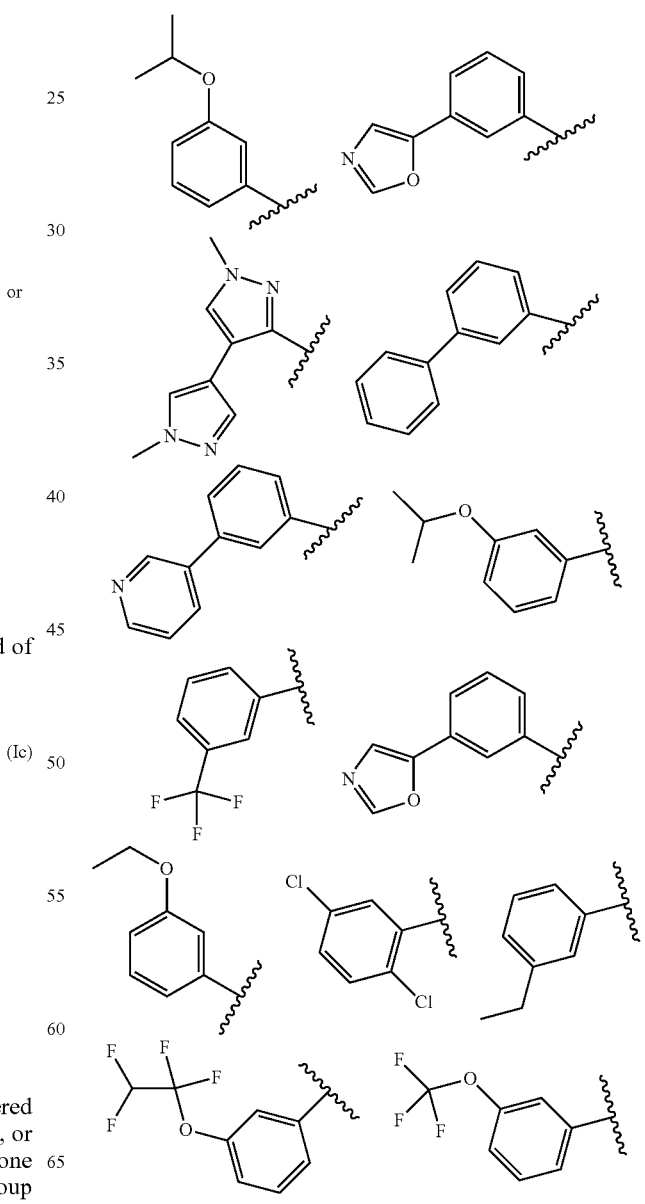

-continued

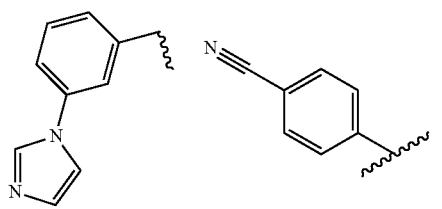
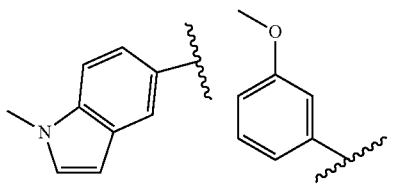
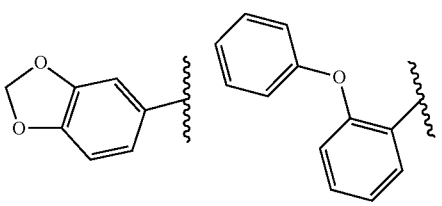
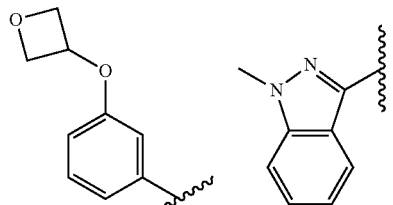
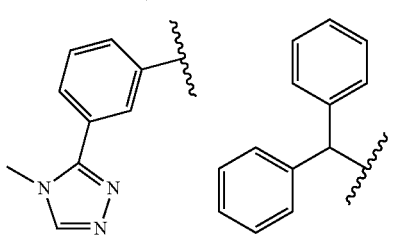
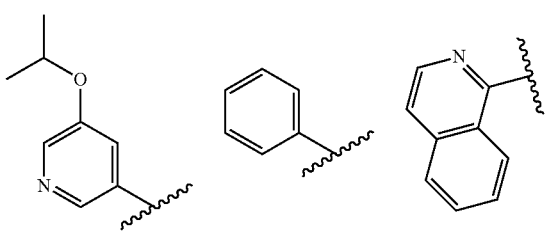
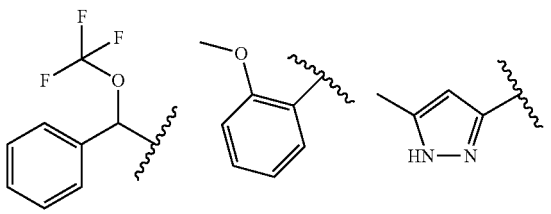
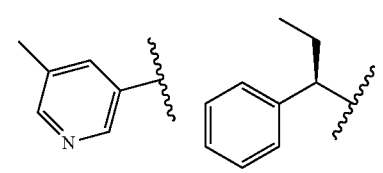

-continued

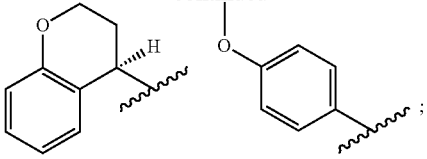

or a salt thereof.

In certain embodiments the compound is a compound of formula (Id):

(Id)

$$\text{[structure of formula Id with A ring, Me, and } R^c \text{ substituent]}$$

wherein:

$R^c$ is -(6-10 membered aryl)-Y, -(6-10 membered aryl)-Y, or 5-14 membered heteroaryl, wherein any 6-10 membered aryl and 5-14 membered heteroaryl is optionally substituted with one or more groups independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R$^g$, —N(R$^g$)—S(O)—R$^g$, N(R$^g$)—S(O)$_2$—R$^g$, and C$_{1-6}$alkyl, which 3-20 membered carbocyclyl, 3-20 membered heterocyclyl, and C$_{1-6}$alkyl are optionally substituted with one or more groups R$^i$;

Y is (6-10 membered aryl) or (5-14 membered heteroaryl) optionally substituted with one or more groups R$^i$;

each R$^i$ is independently selected from the group consisting of oxo, halo, C$_{1-6}$alkyl, cyano, —N(R$^j$)$_2$, —O—R$^j$, —S(O)—R$^j$, —S(O)$_2$—R$^j$, —S(O)—N(R$^j$)$_2$, —S(O)$_2$—N(R$^j$)$_2$, —N(R$^j$)—S(O)—R$^j$, —N(R$^j$)—C(O)—R$^j$, —N(R$^j$)—C(O)—O—R$^j$, —N(R$^j$)—S(O)$^2$—R$^j$, 3-20 membered heterocyclyl, and 3-20 membered carbocyclyl that is optionally substituted with one or more groups independently selected from the group consisting of halo, and C$_{1-6}$alkyl;

each R$^j$ is independently selected from the group consisting of hydrogen, C$_{1-6}$alkyl, C$_{2-6}$alkenyl, C$_{2-6}$alkynyl, 3-20 membered carbocyclyl, and 3-20 membered heterocyclyl, wherein each C$_{1-6}$alkyl, C$_{2-6}$alkenyl, C$_{2-6}$alkynyl, C$_{1-6}$alkoxy, 3-20 membered carbocyclyl, and 3-20 membered heterocyclyl is optionally substituted with one or more groups R$^m$;

each R$^m$ is independently selected from the group consisting of oxo, halo, amino, hydroxyl, —Si(R$^n$)$_3$, 3-20 membered carbocyclyl, 3-20 membered heterocyclyl, and C$_1$-C$_6$ alkyl, wherein any 3-20 membered carbocyclyl, 3-20 membered heterocyclyl, and C$_1$-C$_6$ alkyl is optionally substituted with one or more groups independently selected from the group consisting of oxo, C$_1$-C$_4$alkyl, and halo; and each R$^n$ is independently selected from the group consisting of H, C$_{1-6}$alkyl, C$_{2-6}$alkenyl, C$_{2-6}$alkynyl, and C$_{3-6}$carbocyclyl;

or a salt thereof.

In certain embodiments the compound is a compound of formula (Id), wherein $R^c$ is:
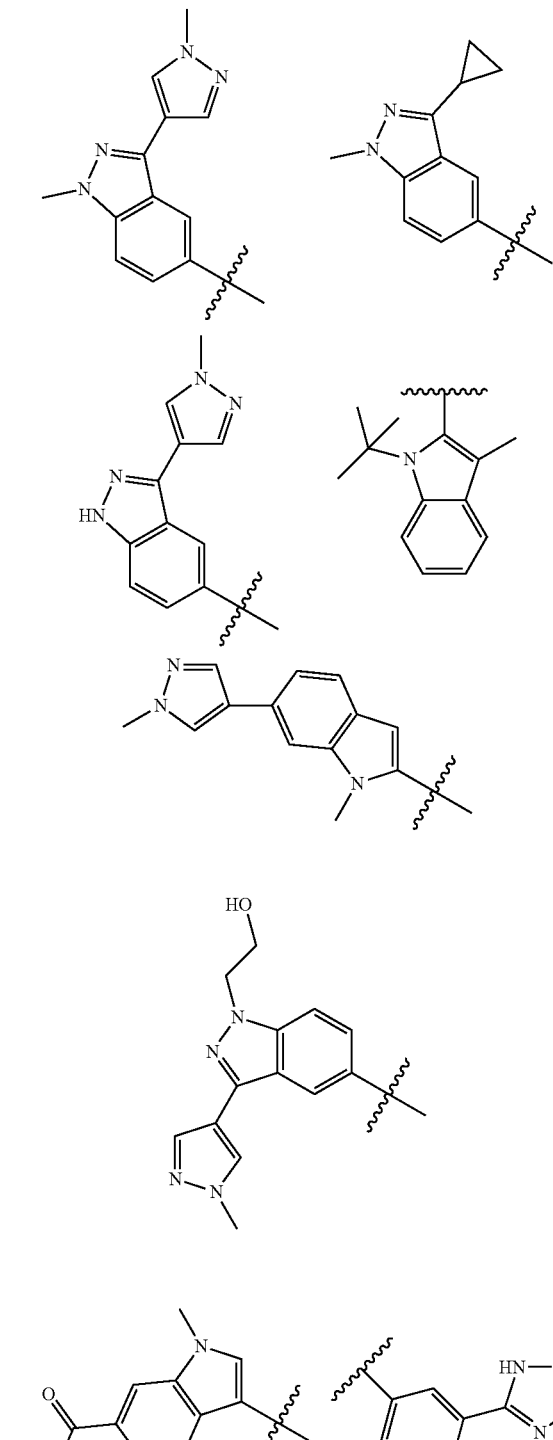
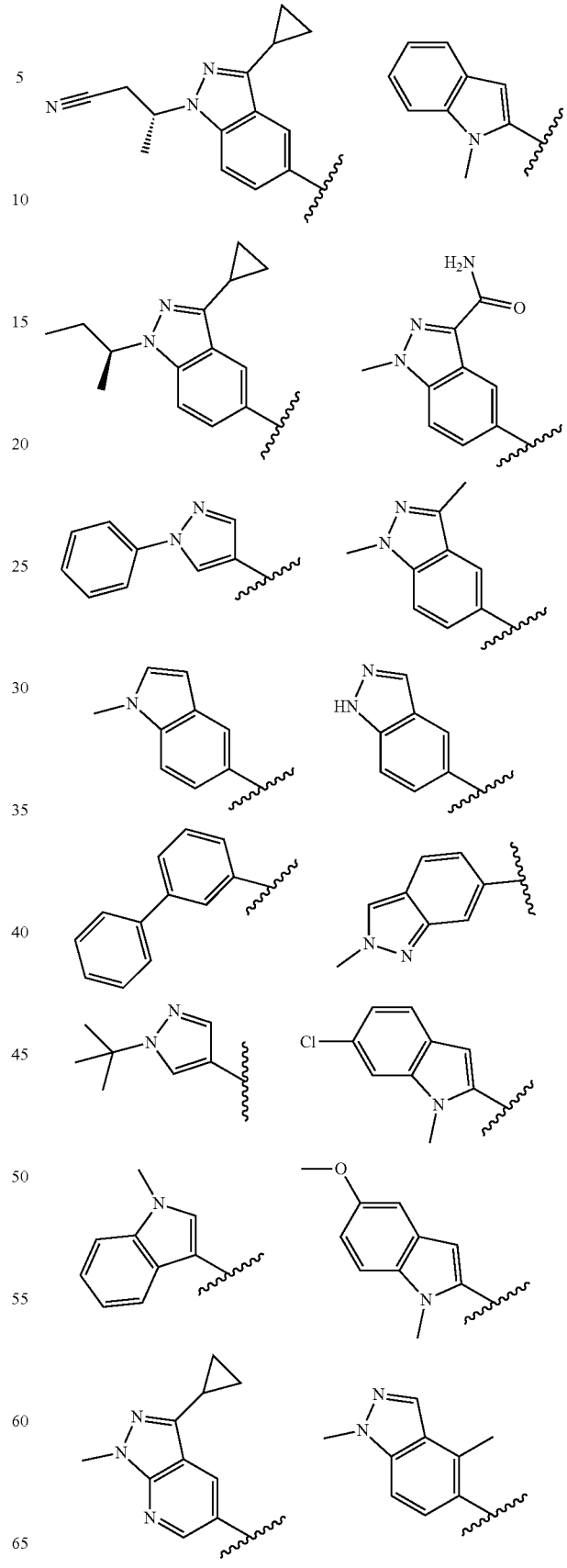

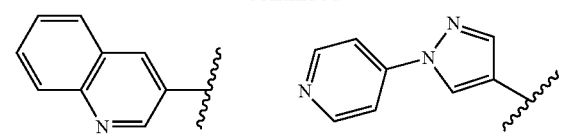
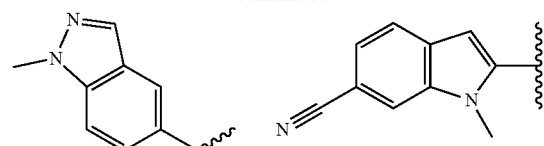
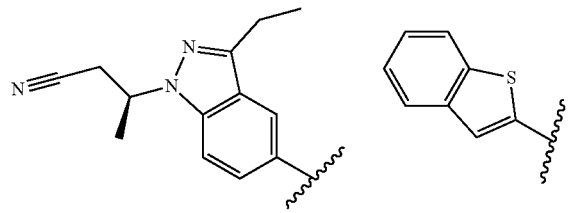
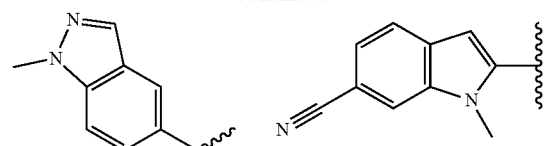
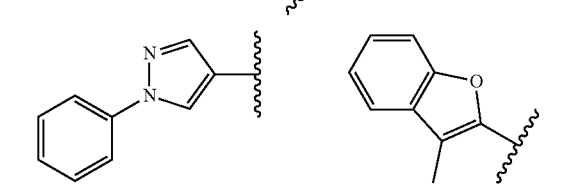
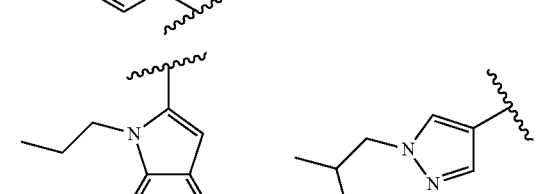
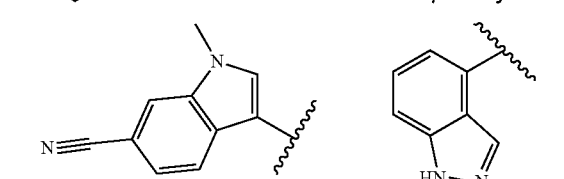
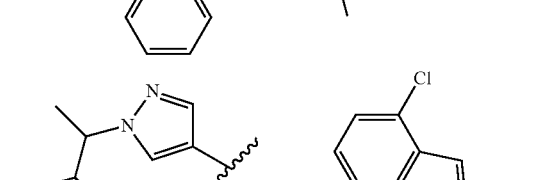
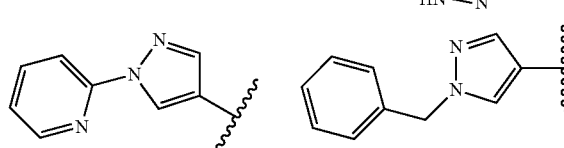
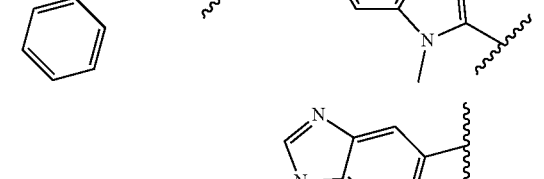
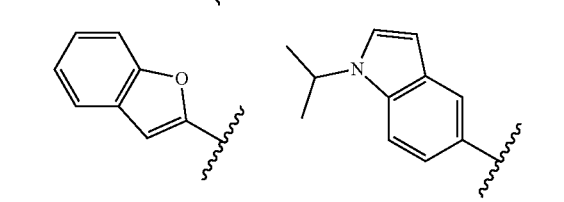
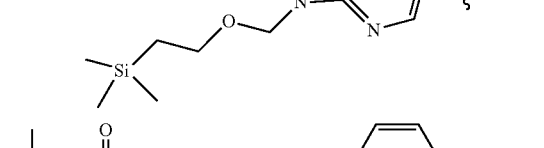
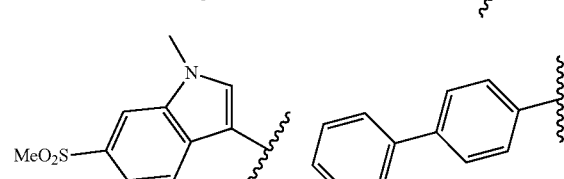
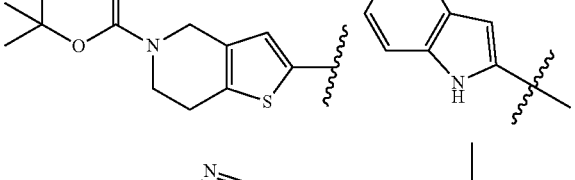
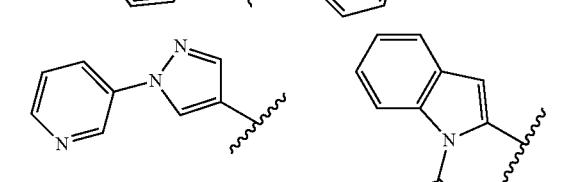
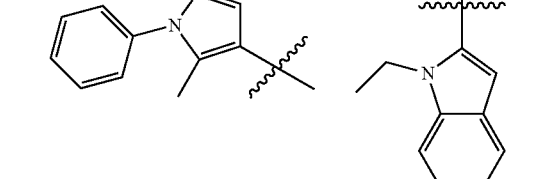
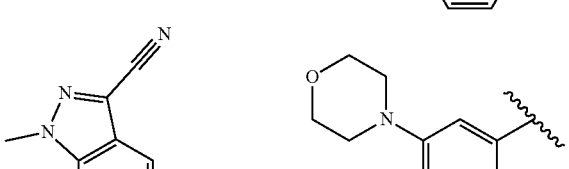
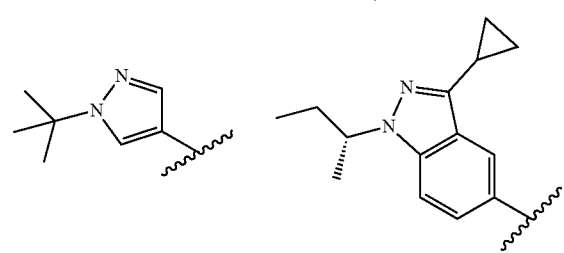
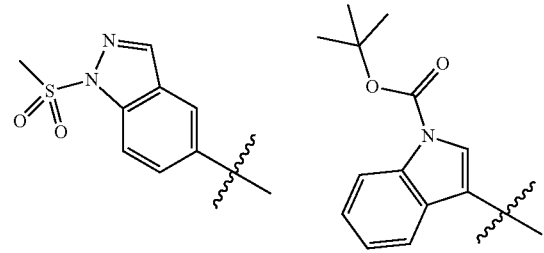

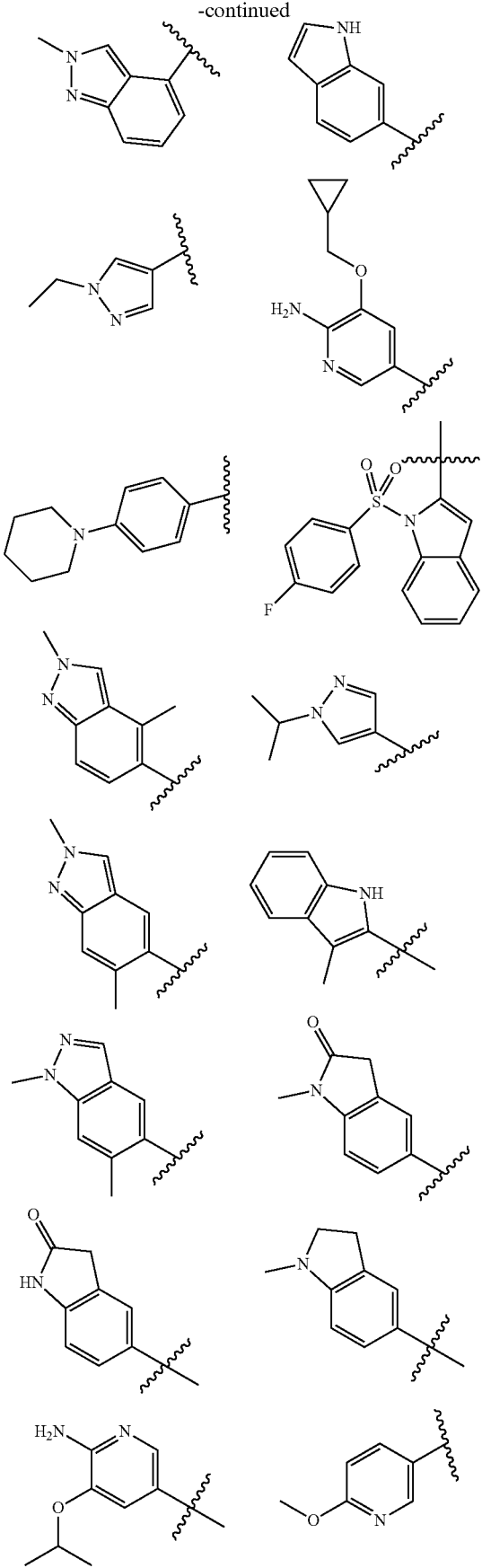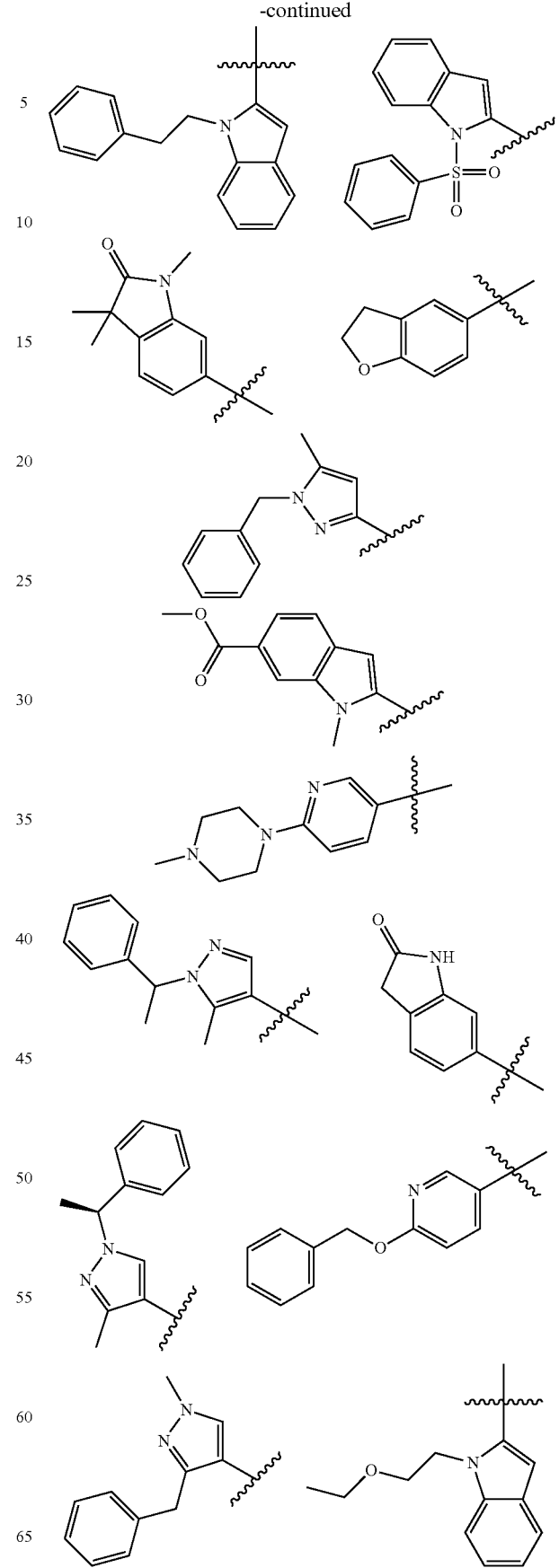

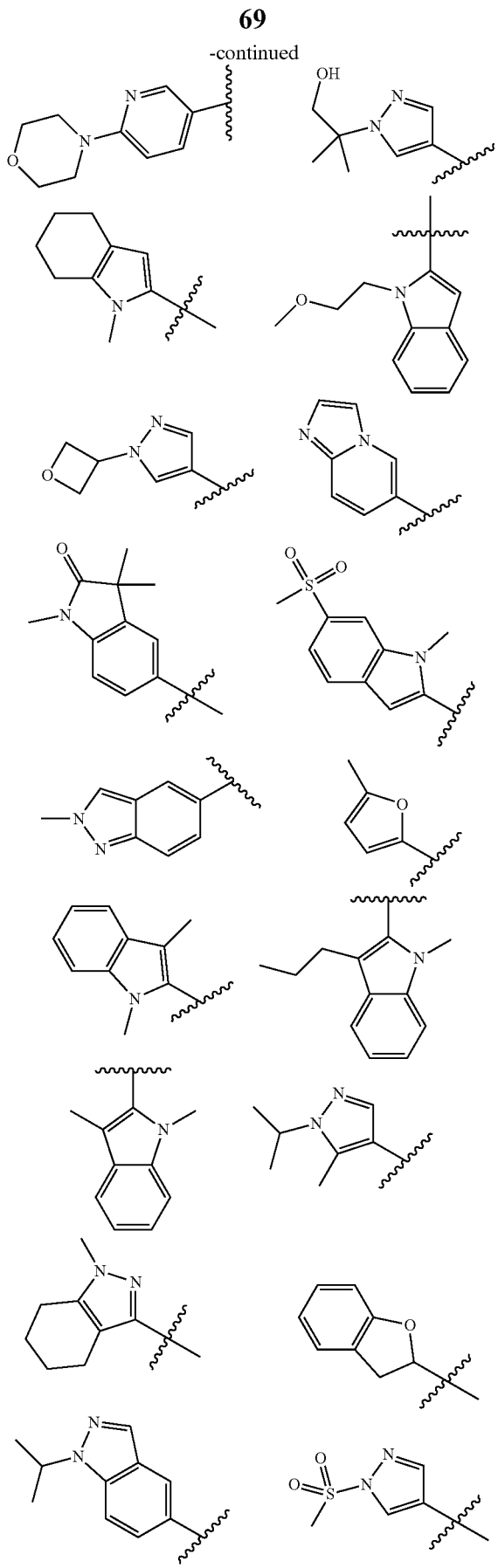

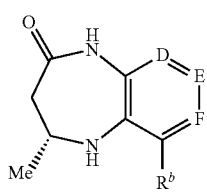

or a salt thereof.

In certain embodiments the compound is a compound of formula (Ie):

$$\text{(Ie)}$$

wherein:

one of D, E, and F is N and the remaining of D, E, and F are CH; and $R^b$ is 6-10 membered aryl or 5-14 membered heteroaryl, wherein any 6-10 membered aryl and 5-14 membered heteroaryl is optionally substituted with one or more groups independently selected from the group consisting of oxo, 3-20 membered carbocyclyl, 3-20 membered heterocyclyl, halo, —$NO_2$, —$N(R^g)_2$, —CN, —C(O)—$N(R^g)_2$, —S(O)—$N(R^g)_2$, —$S(O)_2$—$N(R^g)_2$, —O—$R^g$, —S—$R^g$, —O—C(O)—$R^g$, —C(O)—$R^g$, —C(O)—O—$R^g$, —S(O)—$R^g$, —$S(O)_2$—$R^g$, —C(O)—$N(R^g)_2$, —$N(R^g)$—C(O)—$R^g$, —$Si(R^h)_3$, —$N(R^g)$—C(O)—O—$R^g$, —$N(R^g)$—S(O)—$R^g$, $N(R^g)$—$S(O)_2$—$R^g$, and $C_{1-6}$alkyl, which 3-20 membered carbocyclyl, 3-20 membered heterocyclyl, and $C_{1-6}$alkyl are optionally substituted with one or more groups independently selected from the group consisting of oxo, halo, $C_{1-6}$alkyl, cyano, —$N(R^i)_2$, —O—$R^i$, —S(O)—$R^i$, —$S(O)_2$—$R^i$, —S(O)—$N(R^i)_2$, —$S(O)_2$—$N(R^i)_2$, —$N(R^i)$—S(O)—$R^i$, —$N(R^i)$—C(O)—$R^i$, —$N(R^i)$—C(O)—O—$R^i$, —$N(R^i)$—$S(O)_2$—$R^i$, 3-20 membered heterocyclyl, and 3-20 membered carbocyclyl that is optionally substituted with one or more groups independently selected from the group consisting of halo, and $C_{1-6}$alkyl;

or a salt thereof.

In certain embodiments the compound is a compound of formula (Ie), wherein $R^b$ is:

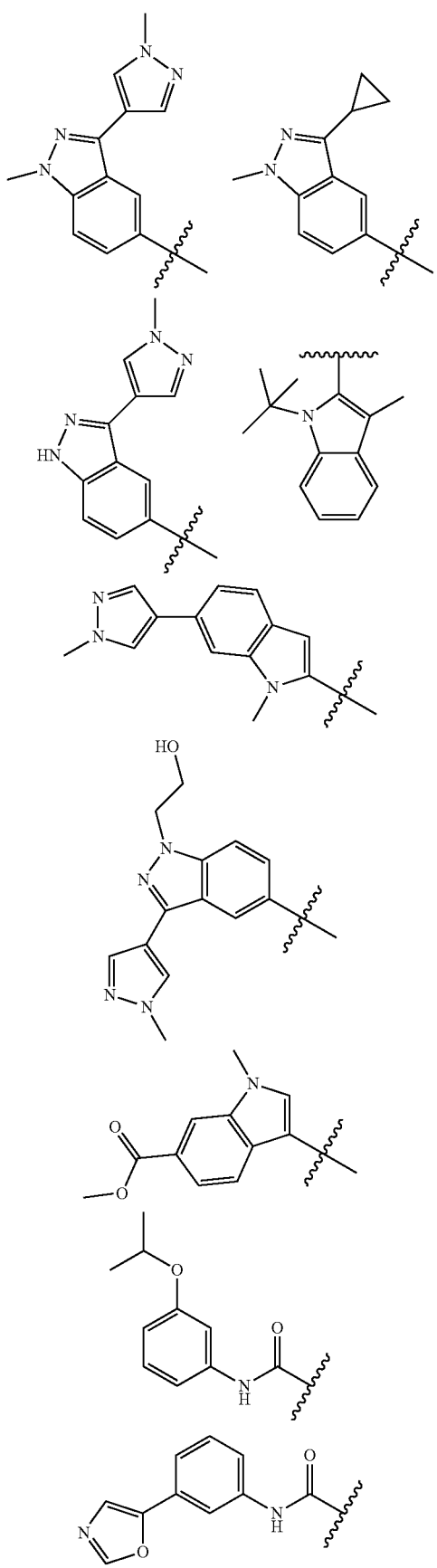
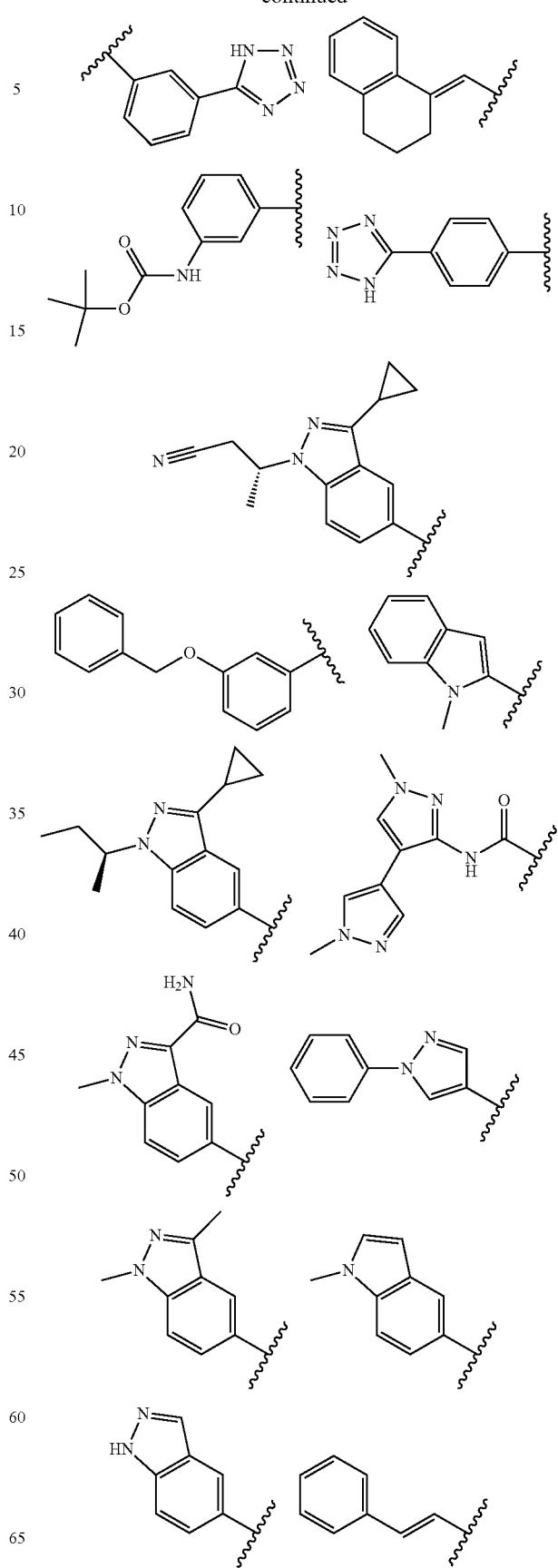
-continued

-continued
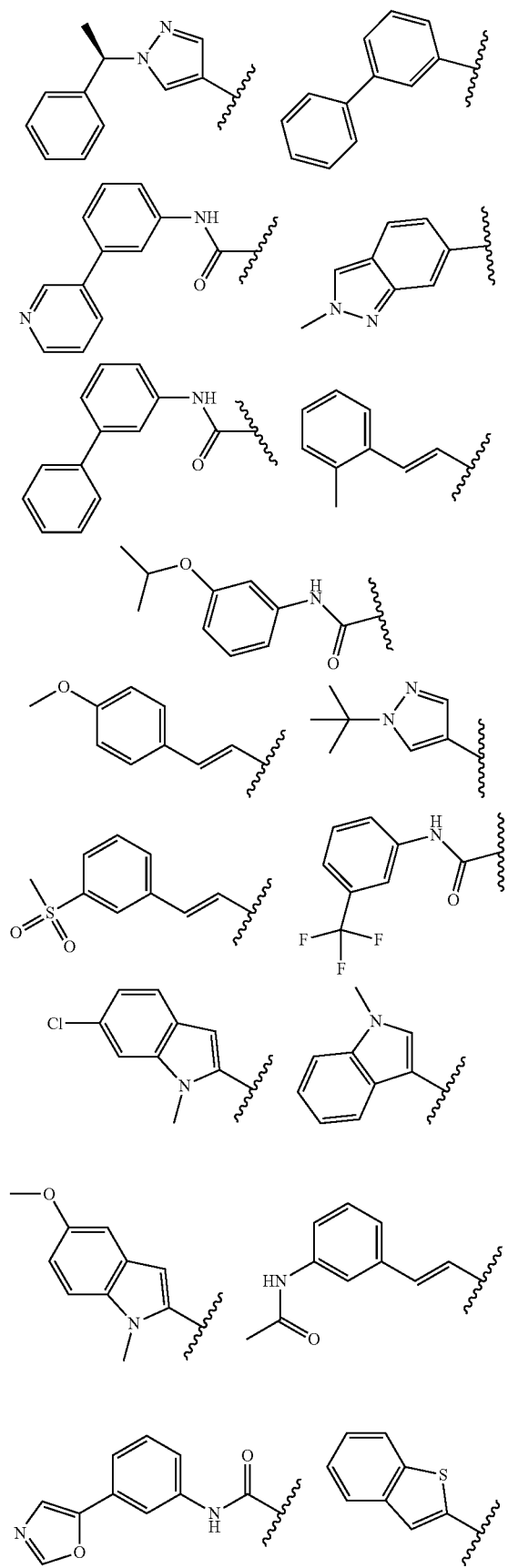
-continued
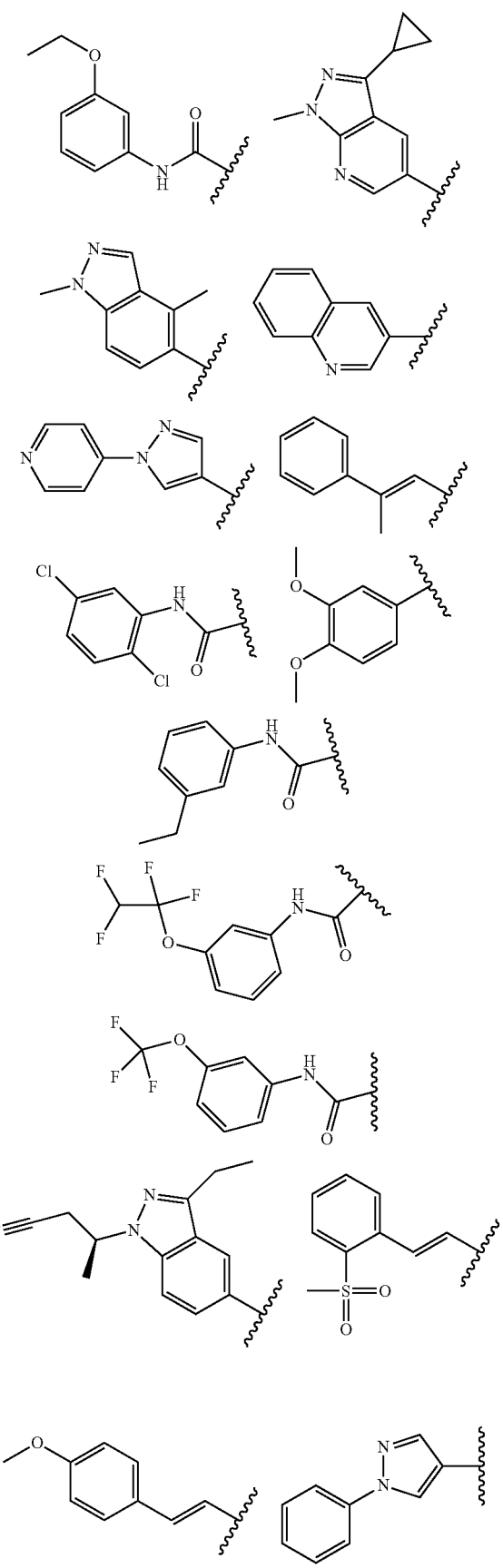

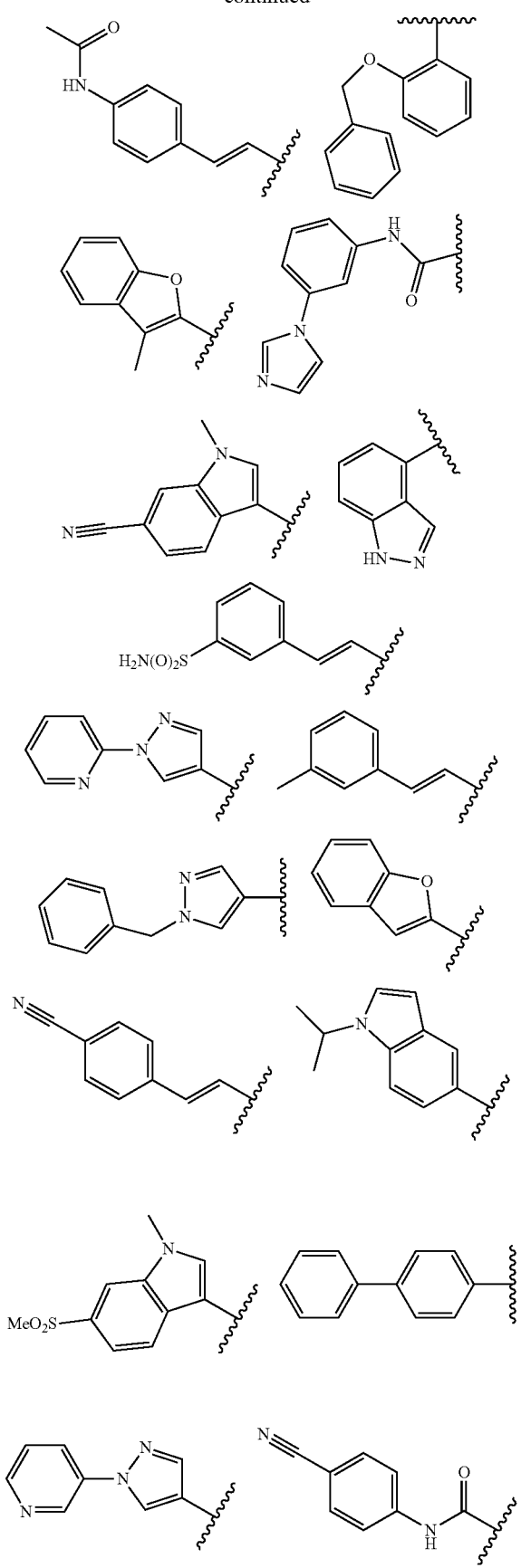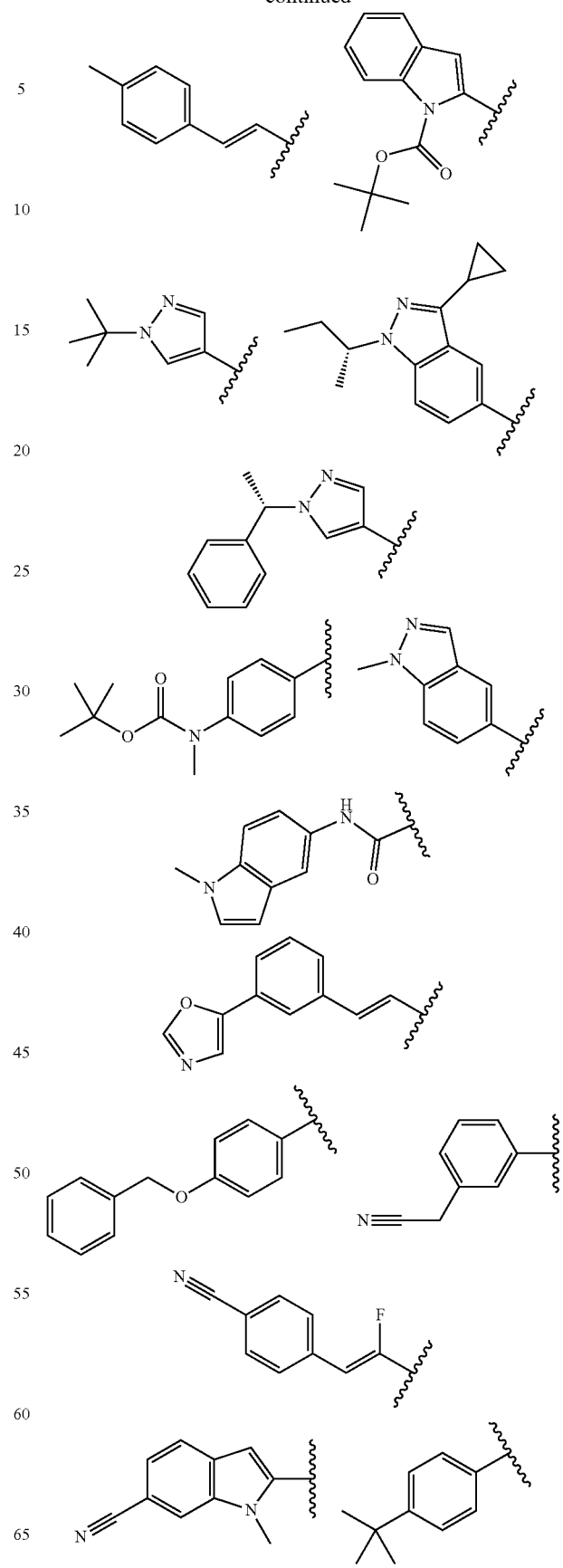

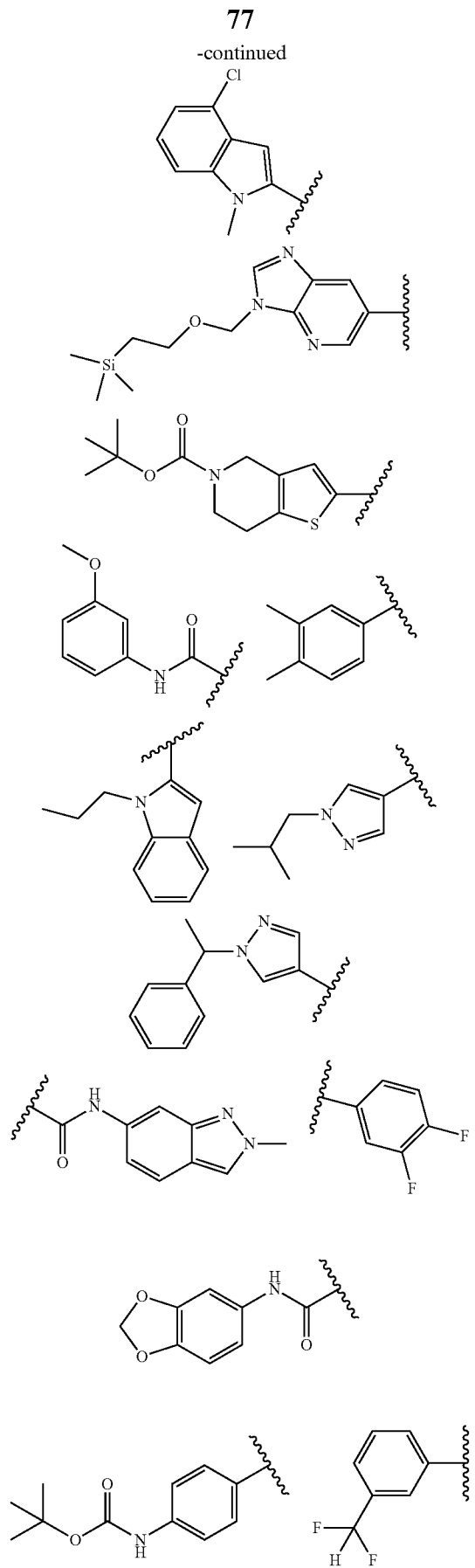
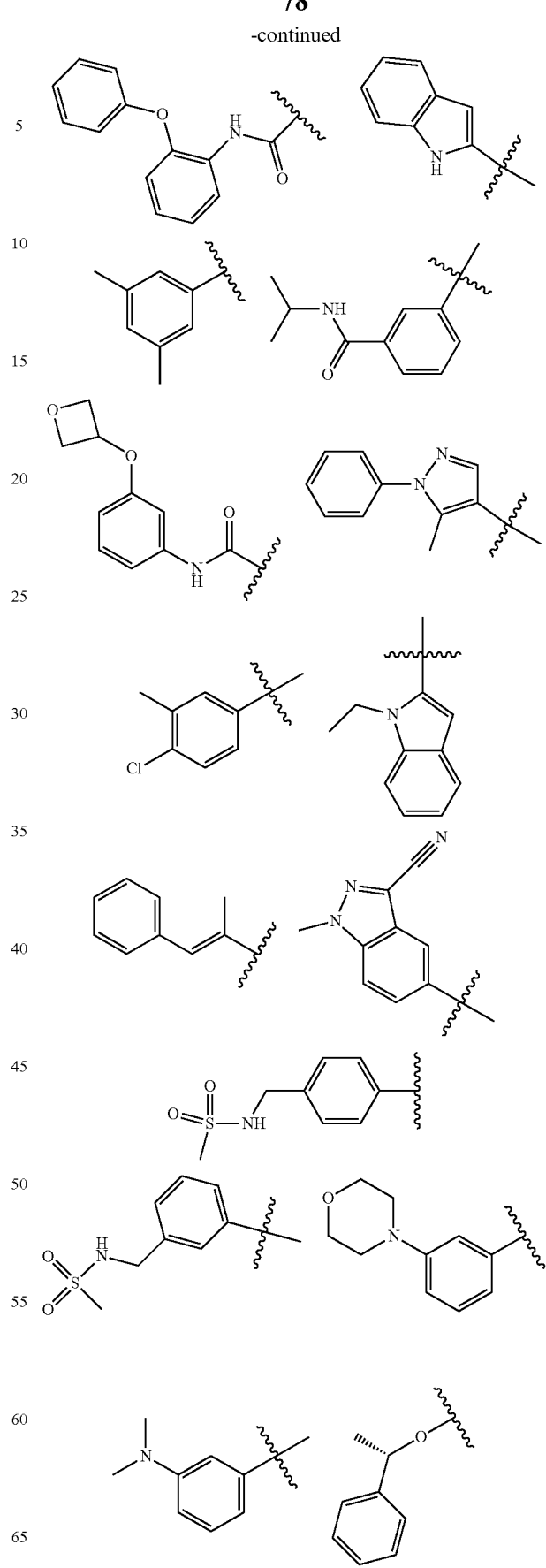

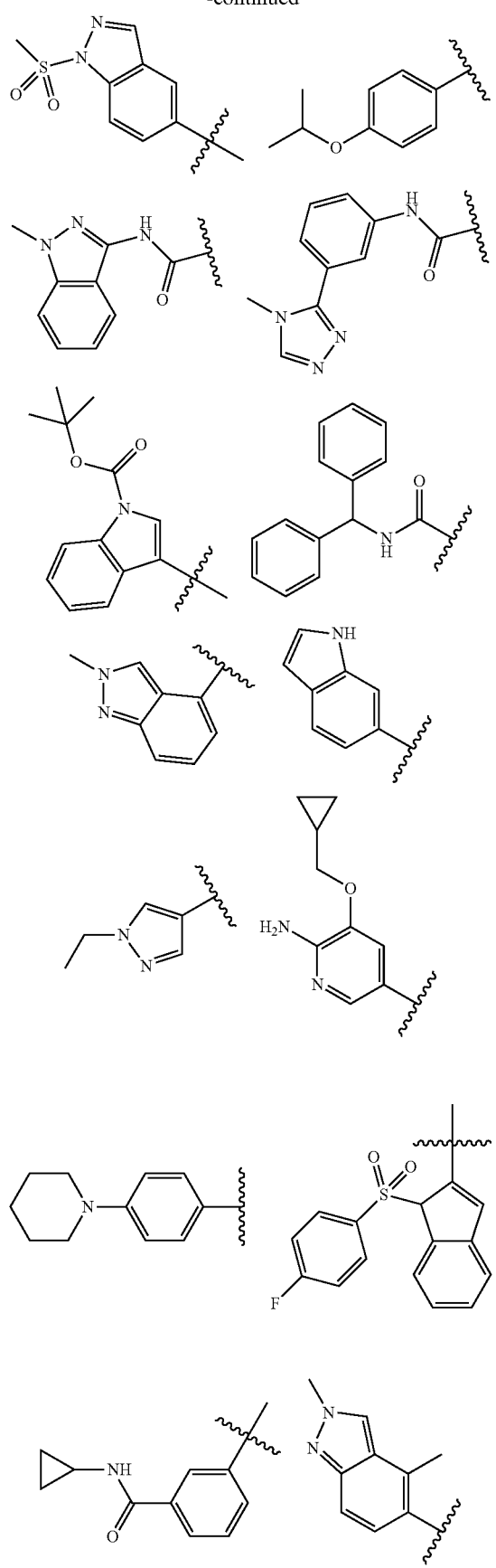
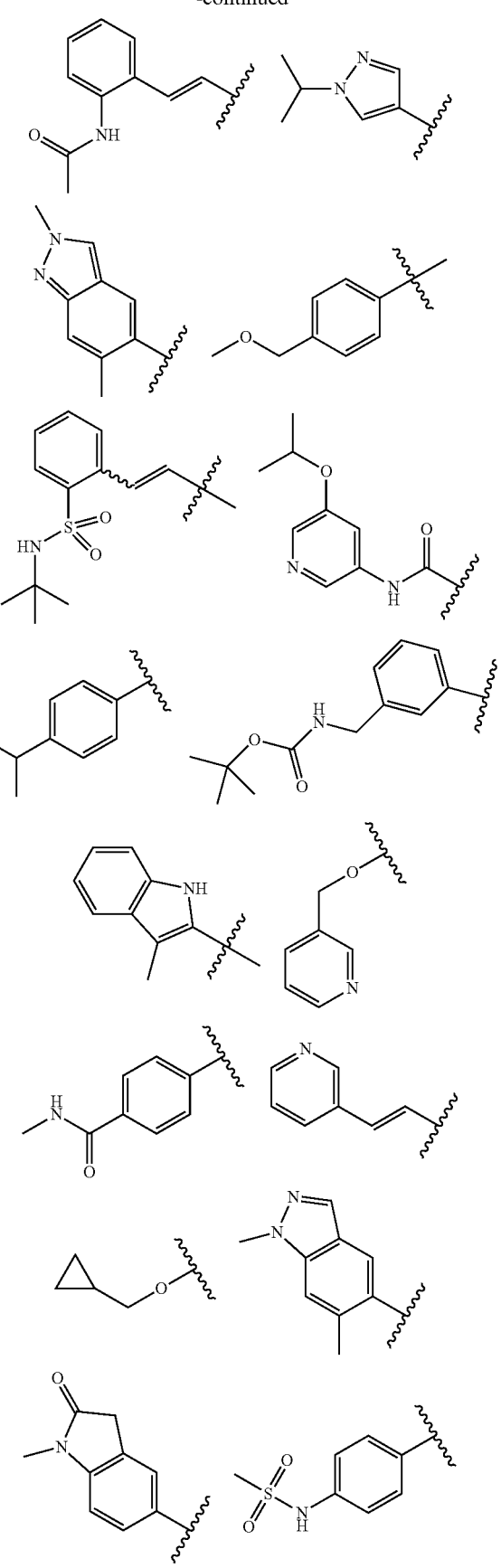

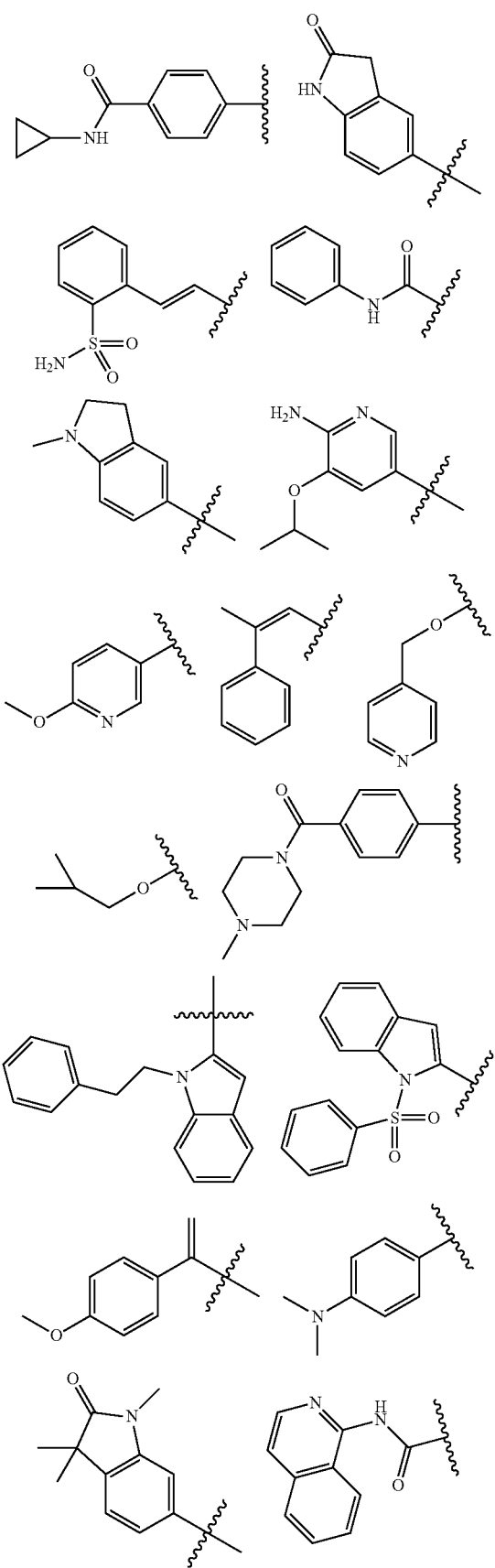
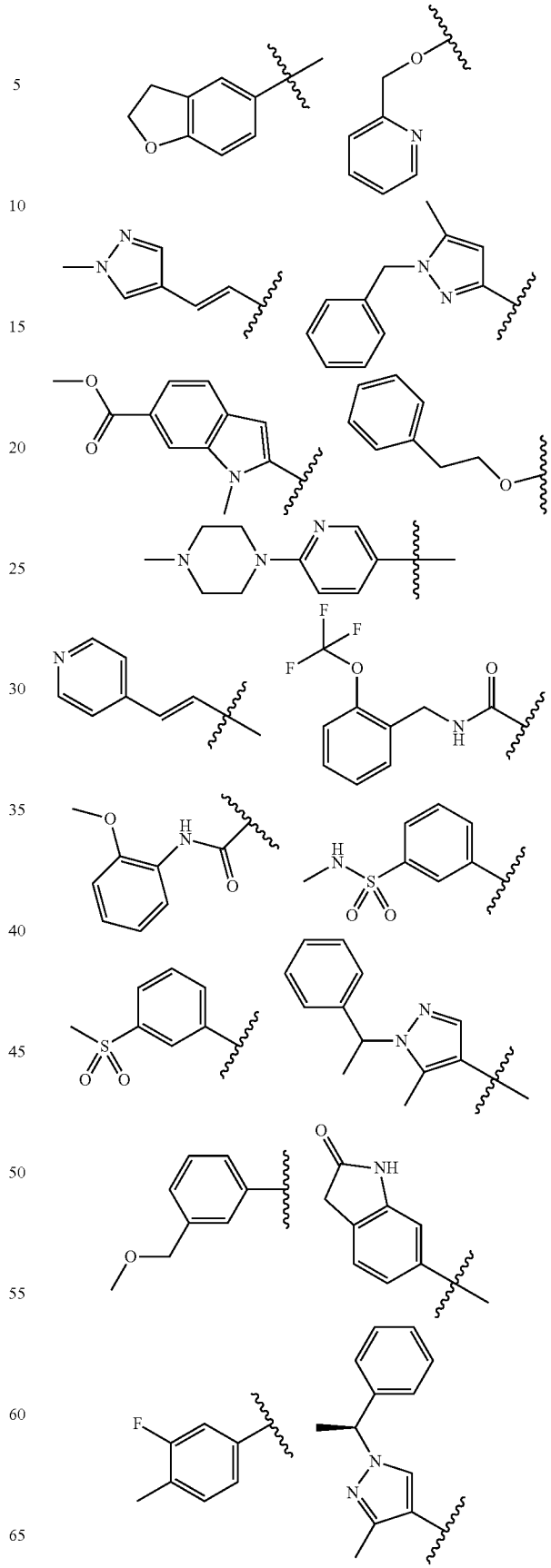

83
-continued
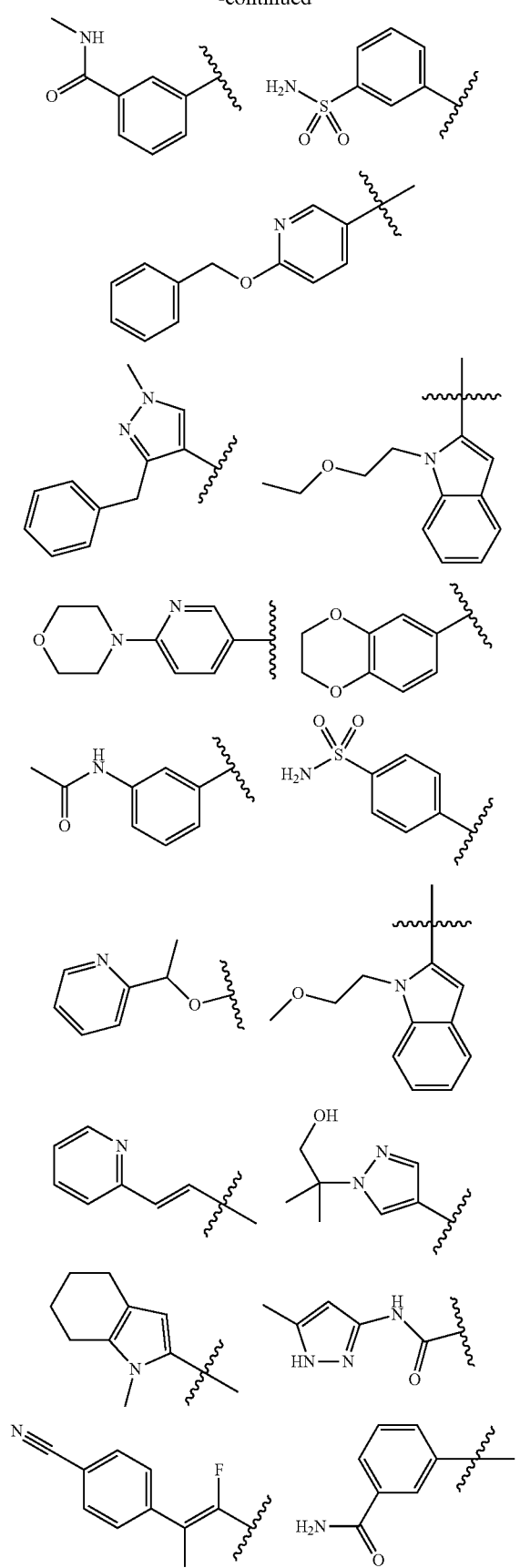
84
-continued
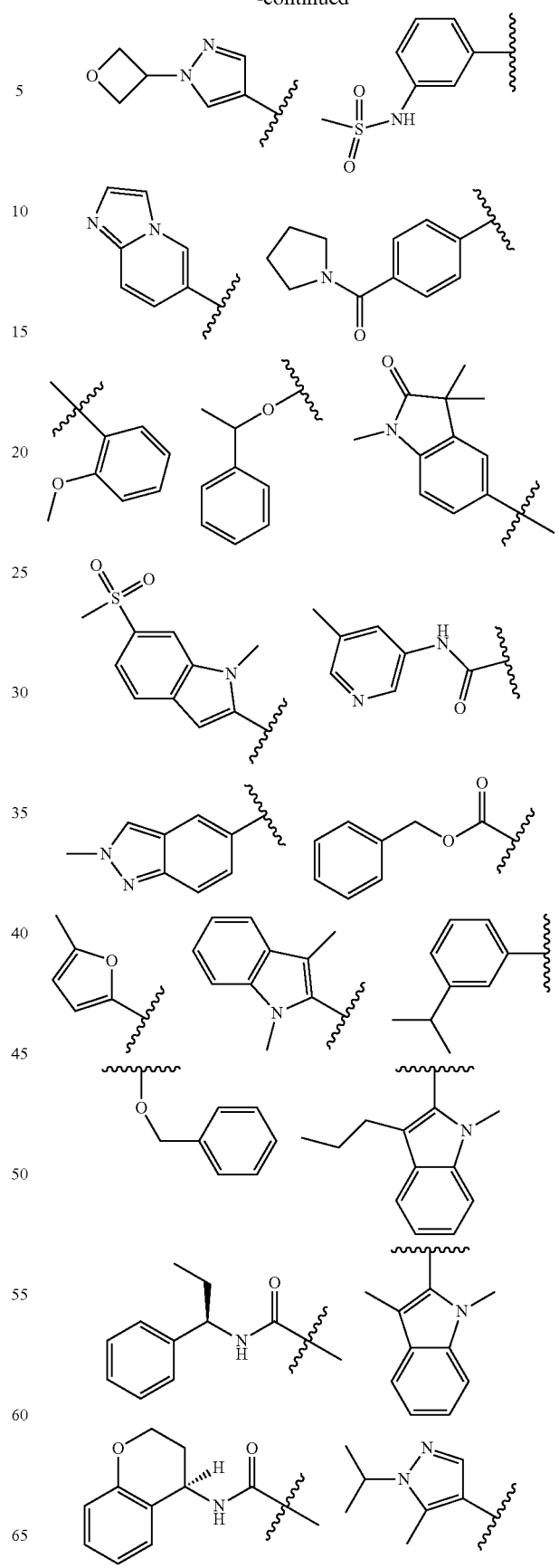

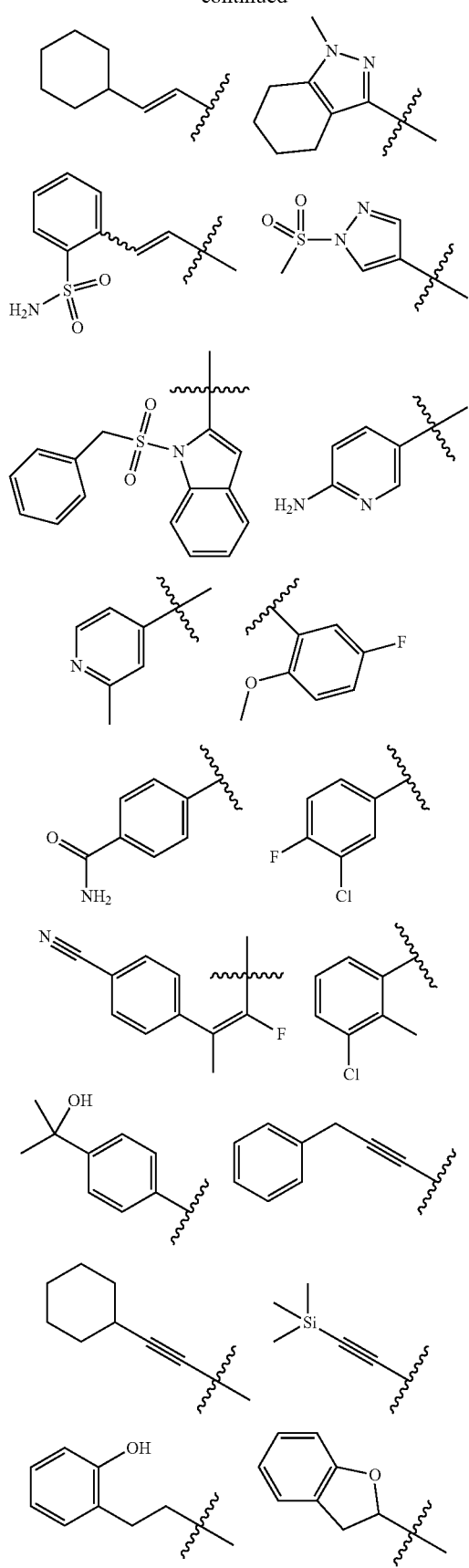
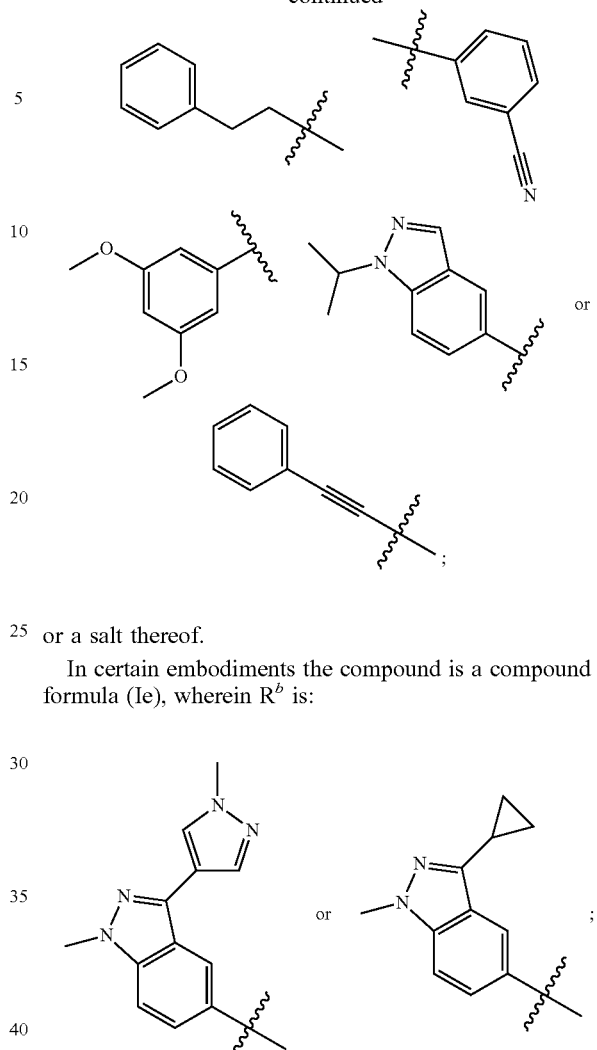

or a salt thereof.

In certain embodiments the compound is a compound of formula (Ie), wherein $R^b$ is:

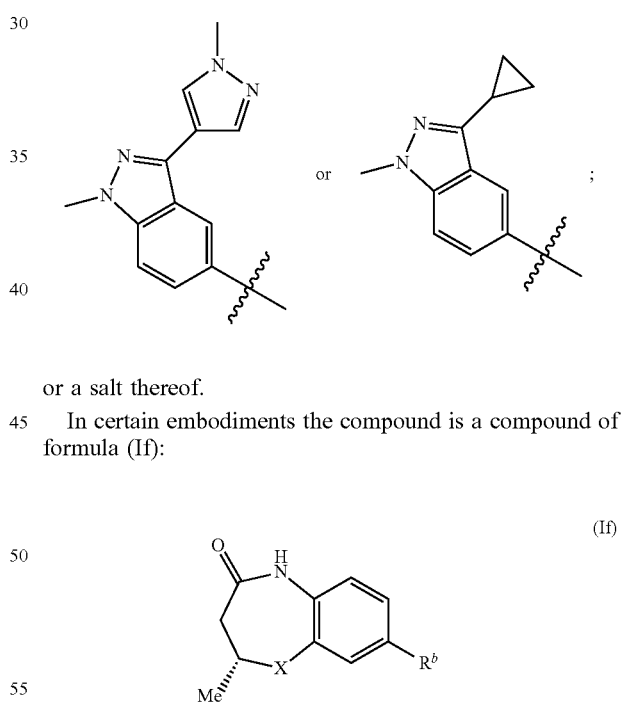

or a salt thereof.

In certain embodiments the compound is a compound of formula (If):

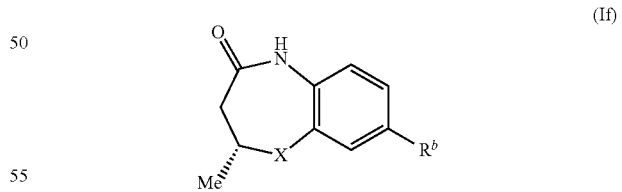

wherein:
X is NH, O, S, or —C(R$^a$)$_2$—:
$R^b$ is —O—R$^d$; and
$R^d$ is C$_{1-6}$alkyl, wherein each C$_{1-6}$alkyl is optionally substituted with one or more groups independently selected from the group consisting of 3-20 membered carbocyclyl and 3-20 membered heterocyclyl.

In certain embodiments the compound is a compound of formula (If), wherein $R^b$ is:

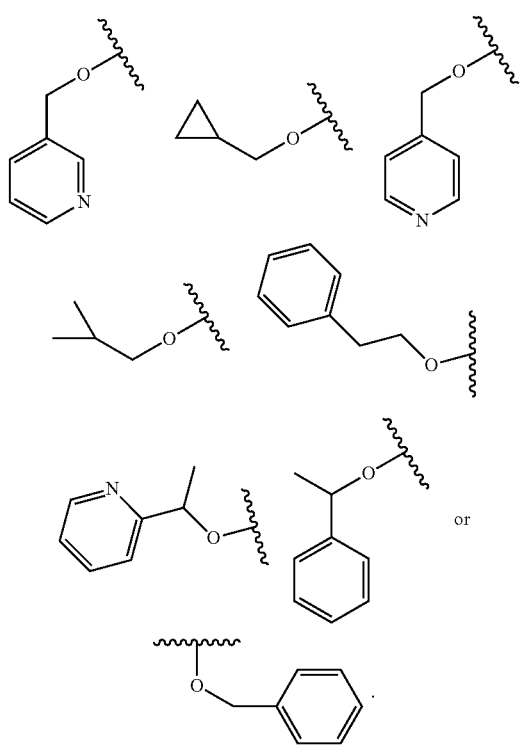
In certain embodiments $R^b$ is:
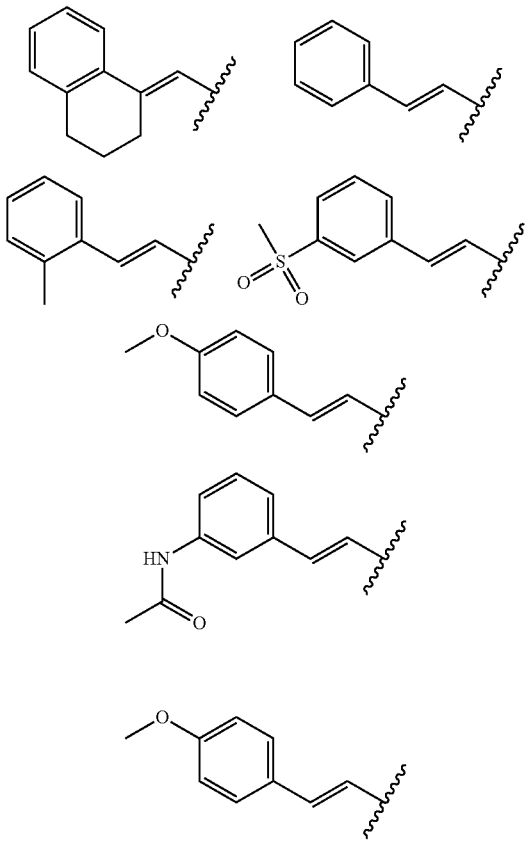
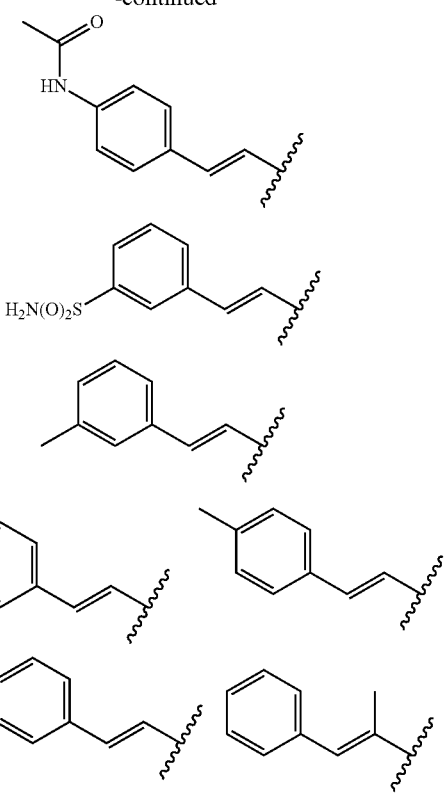
-continued
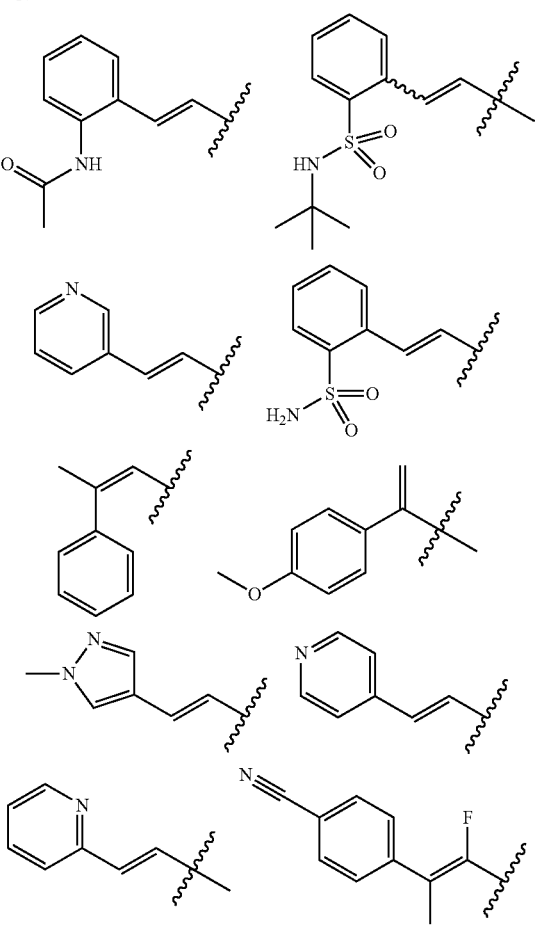

89
-continued
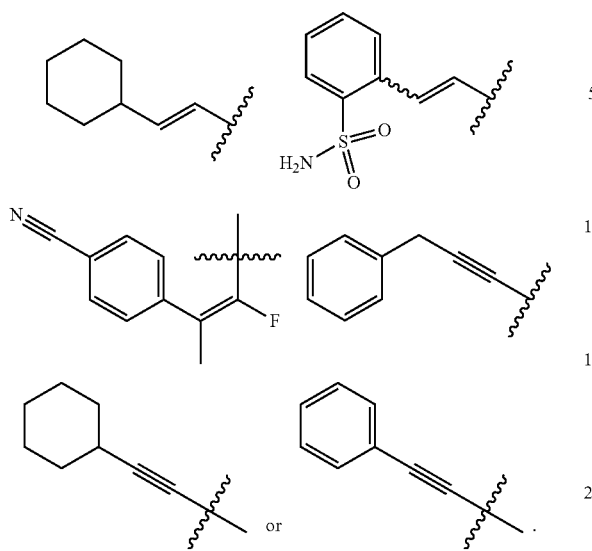
In certain embodiments the compound is a compound selected from the group consisting of:
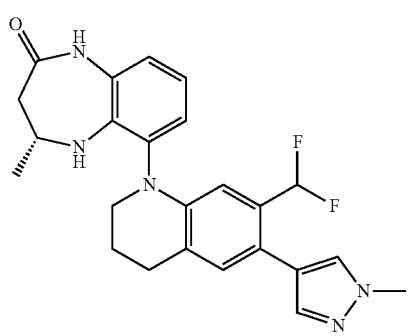
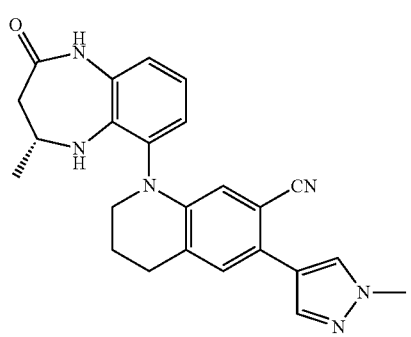
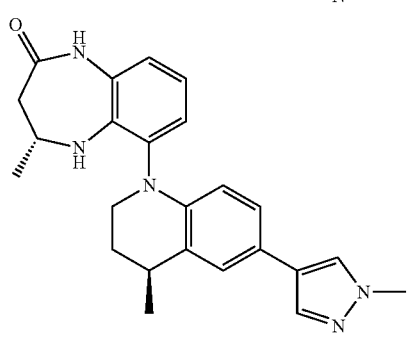
90
-continued
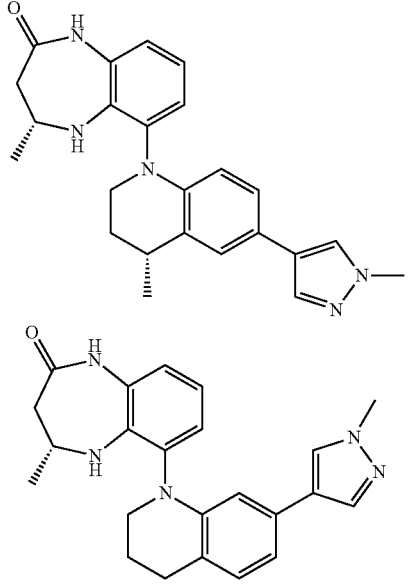
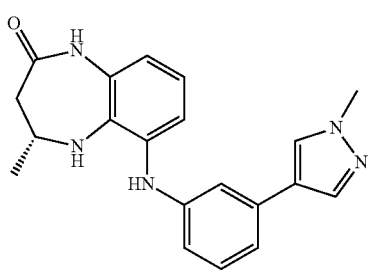
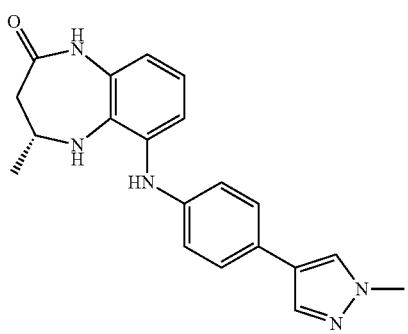
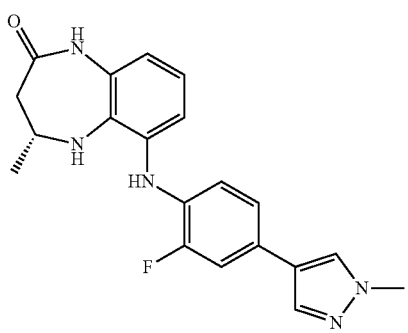

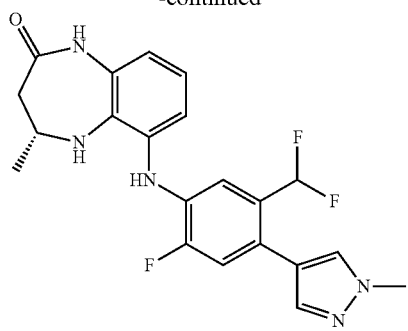
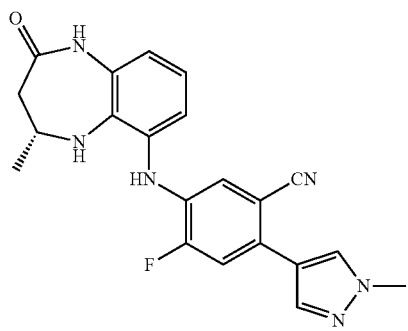
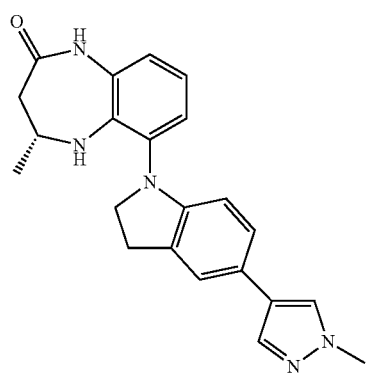
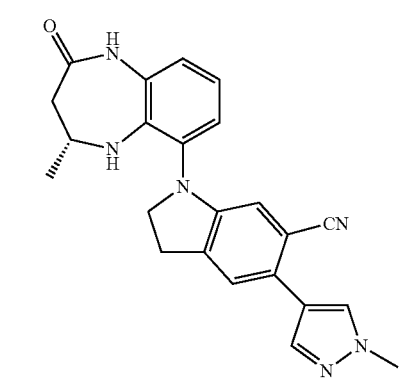
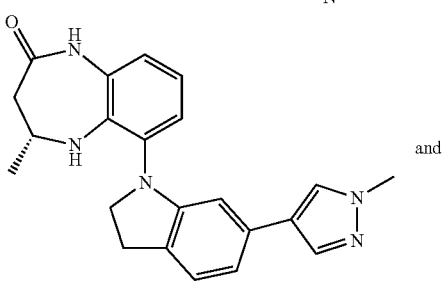
and
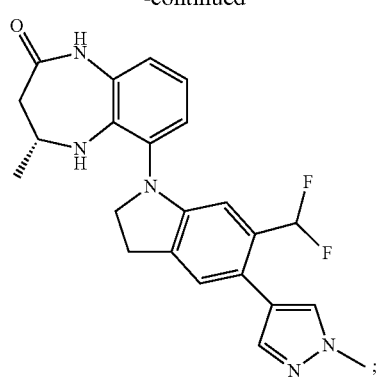
and salts thereof.
In certain embodiments the compound is a compound selected from the group consisting of:
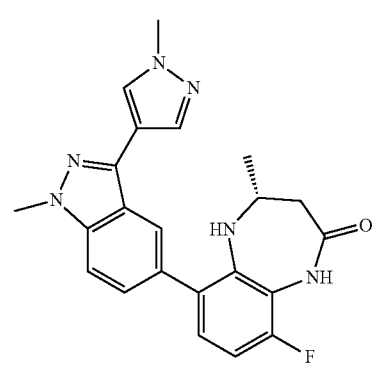
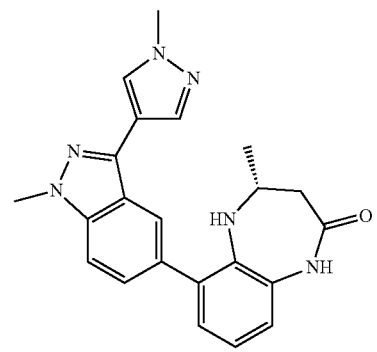
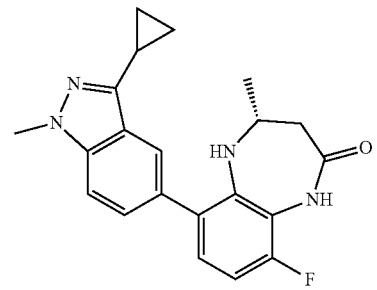

93
-continued
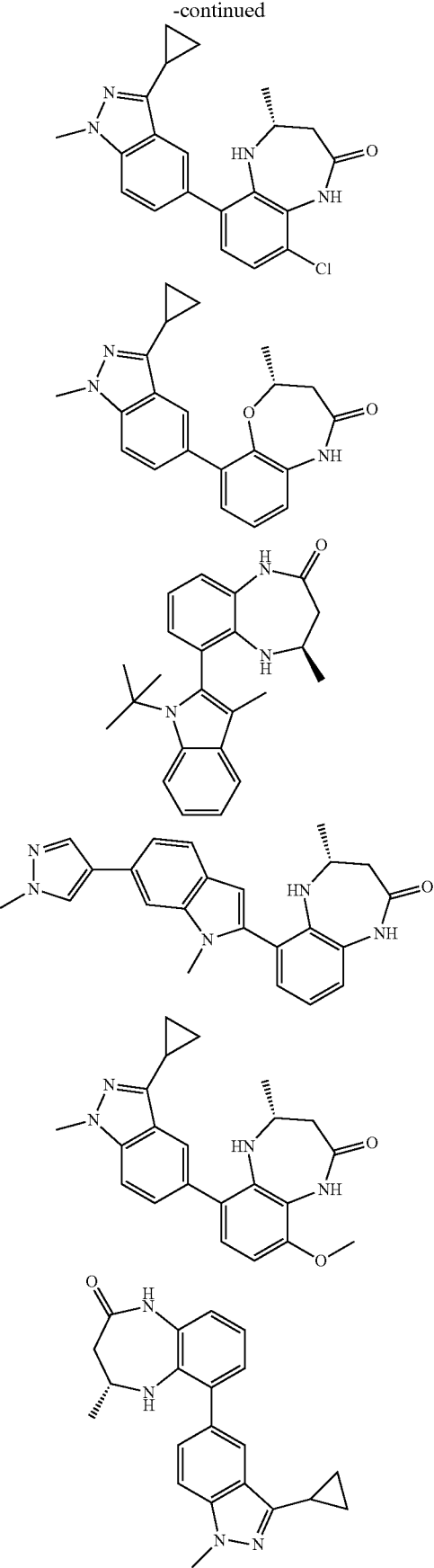
94
-continued
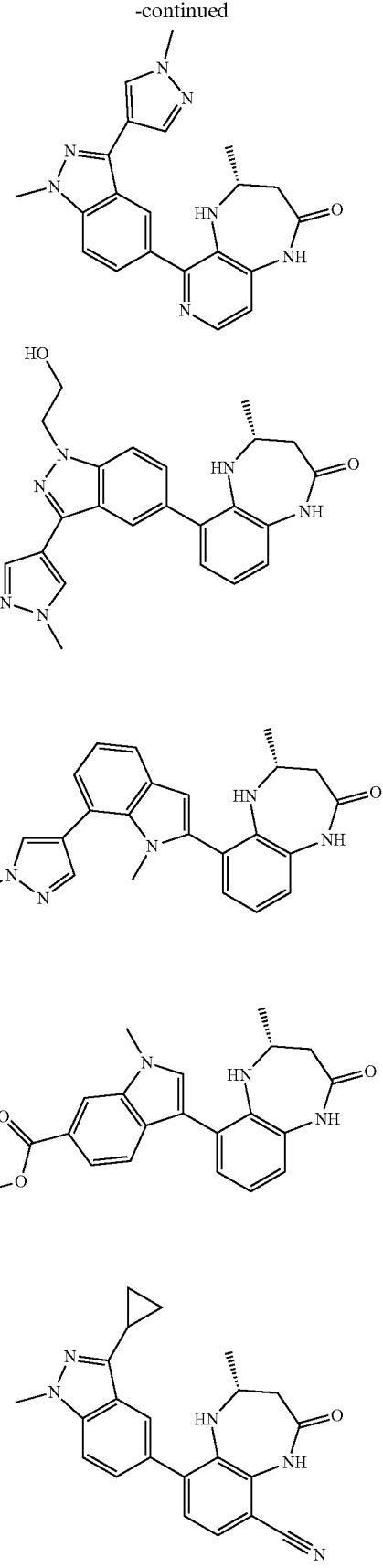

95
-continued
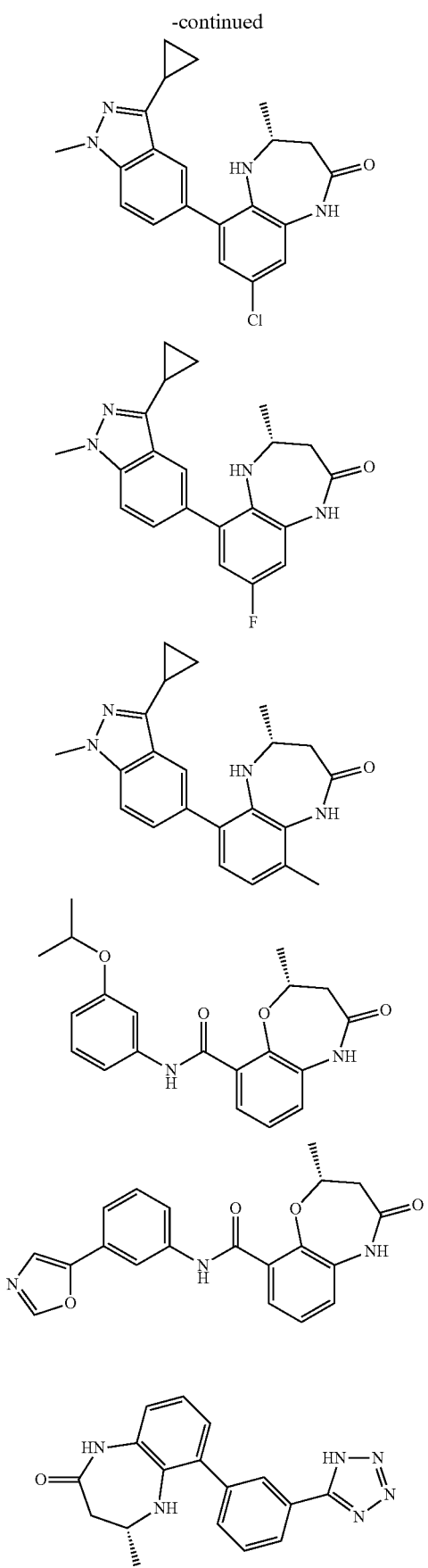
96
-continued
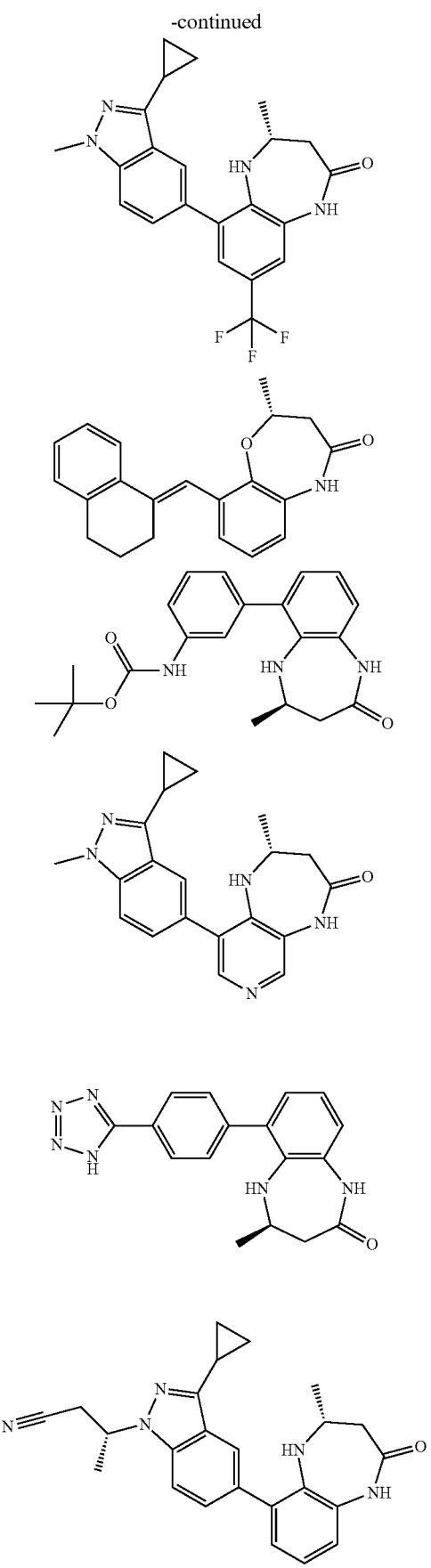

97
-continued
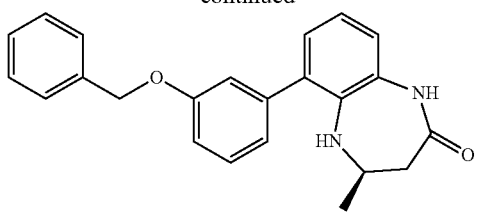
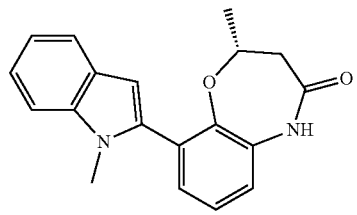
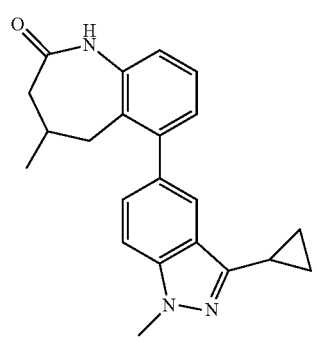
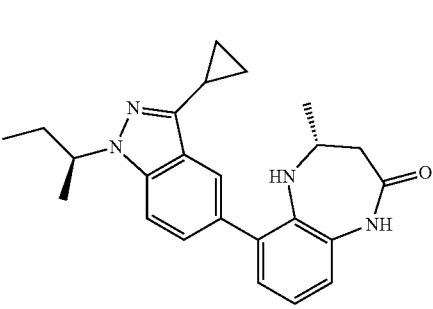
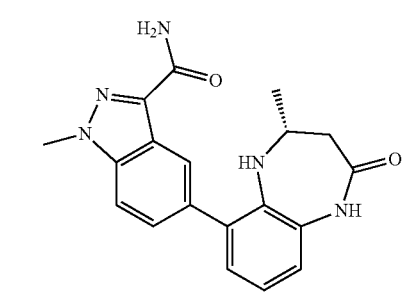
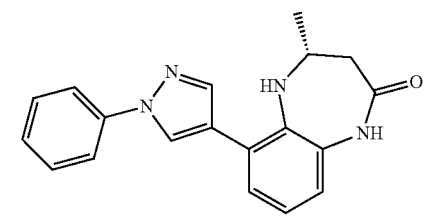
98
-continued
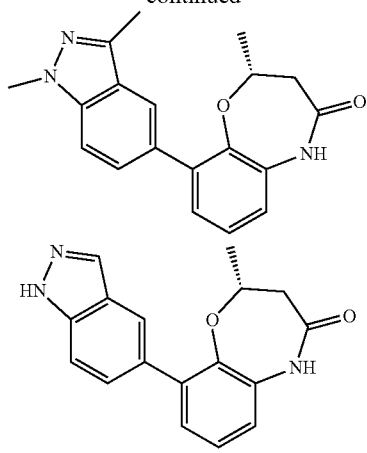
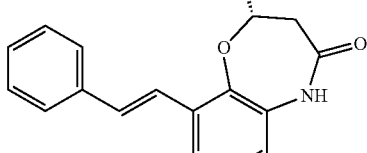
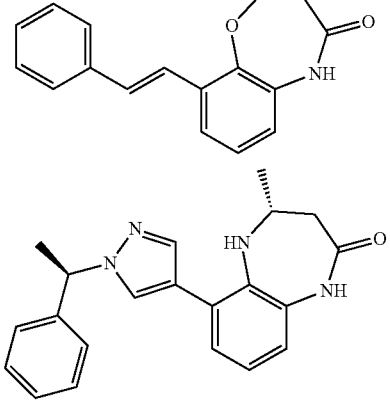
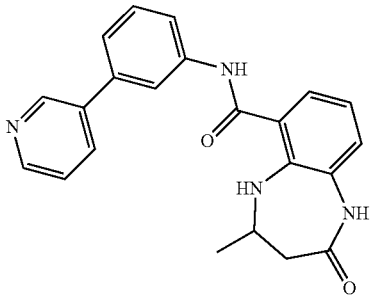
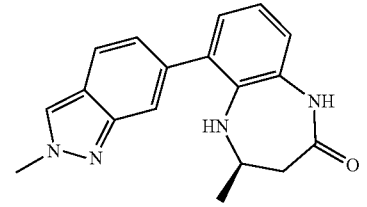
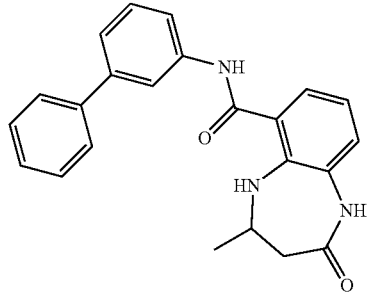

99
-continued
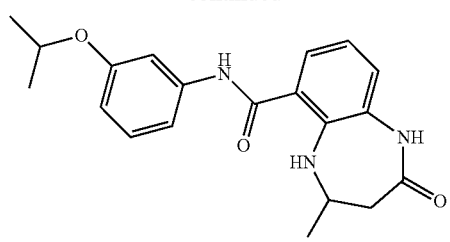
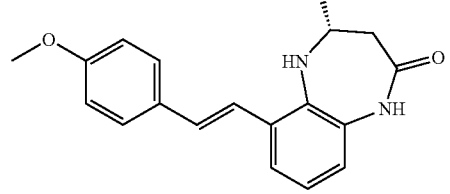
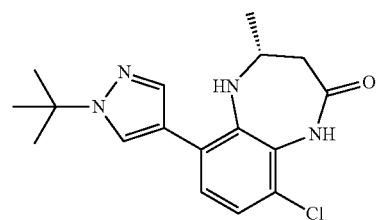
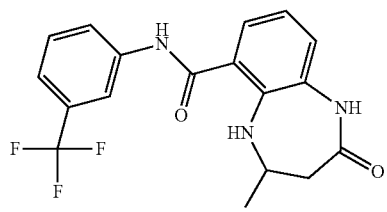
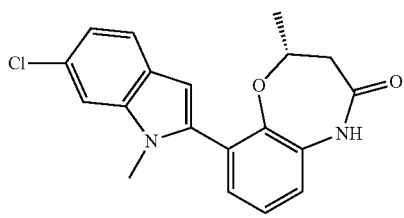
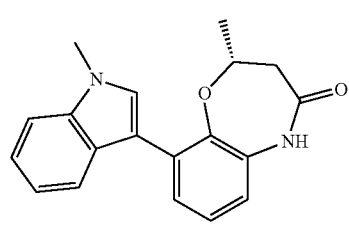
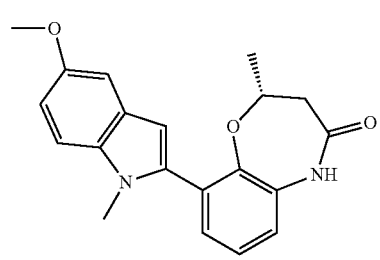
100
-continued
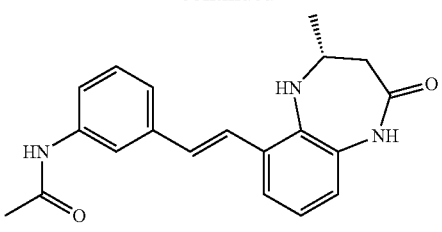
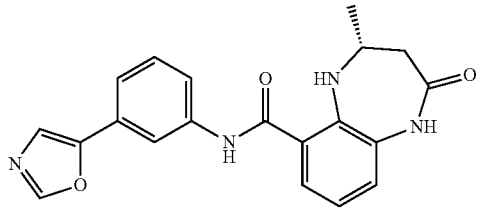
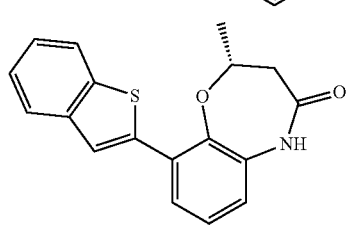
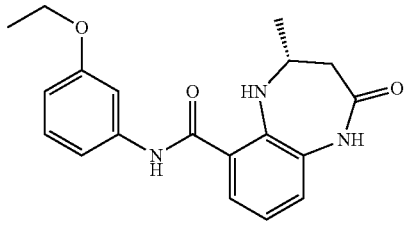
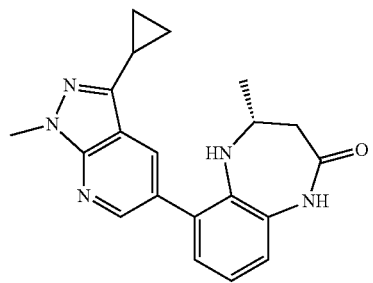
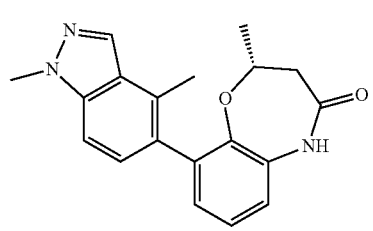
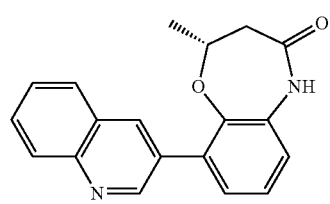

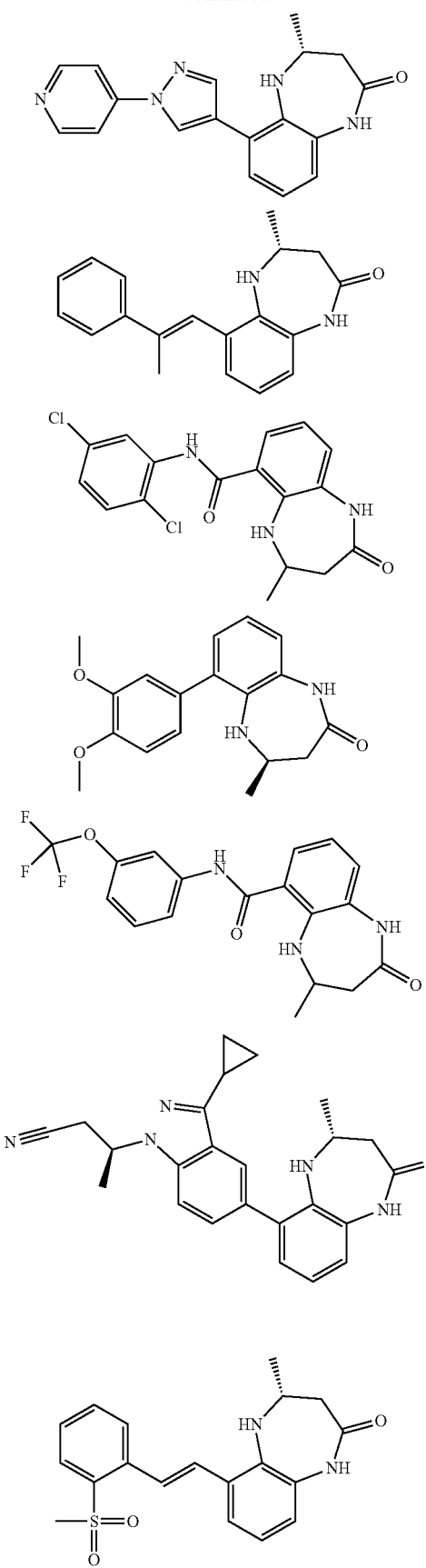
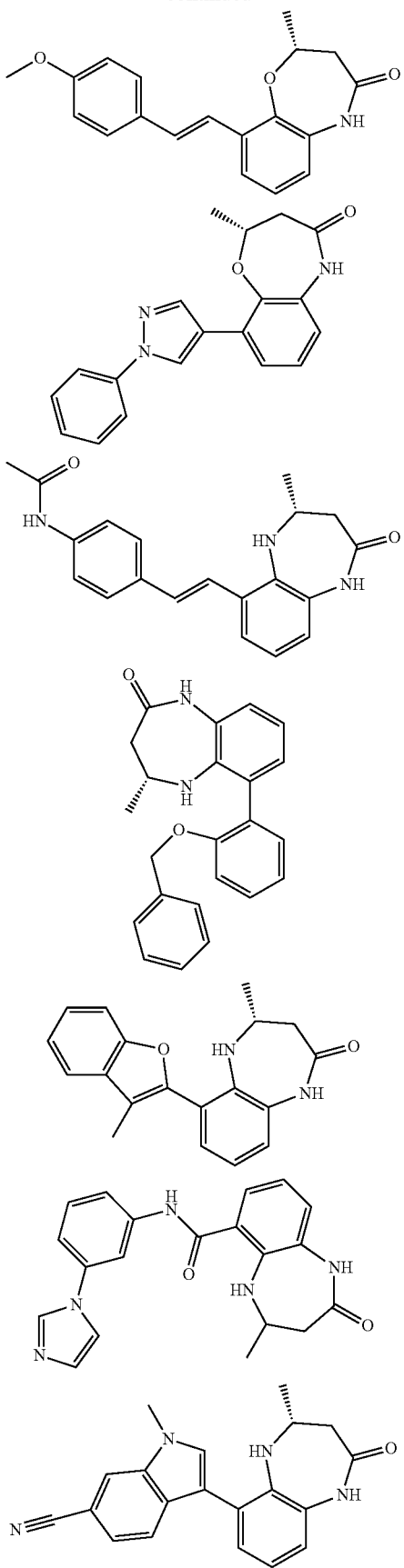

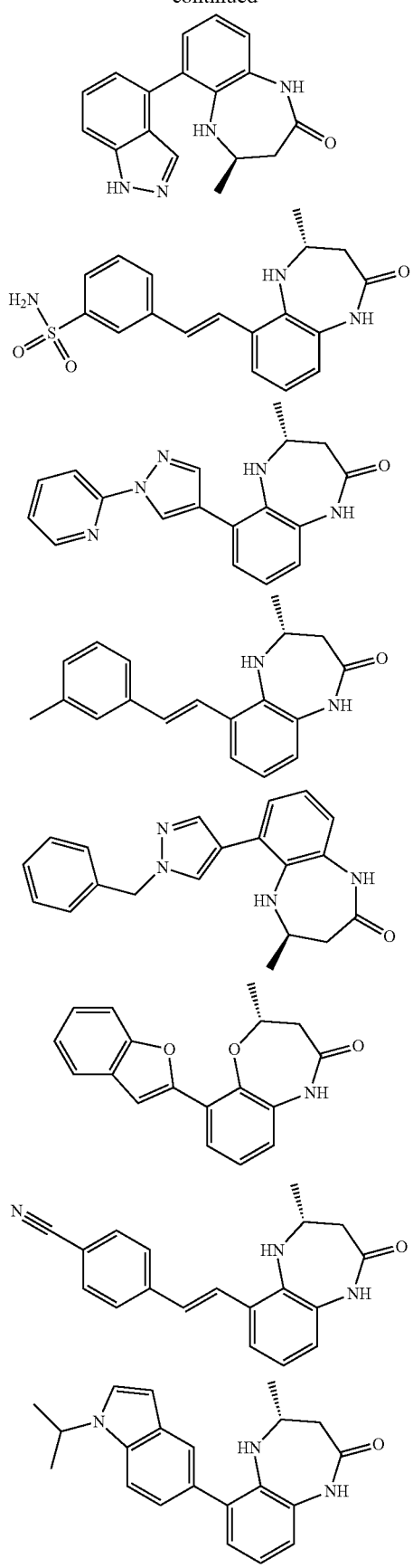
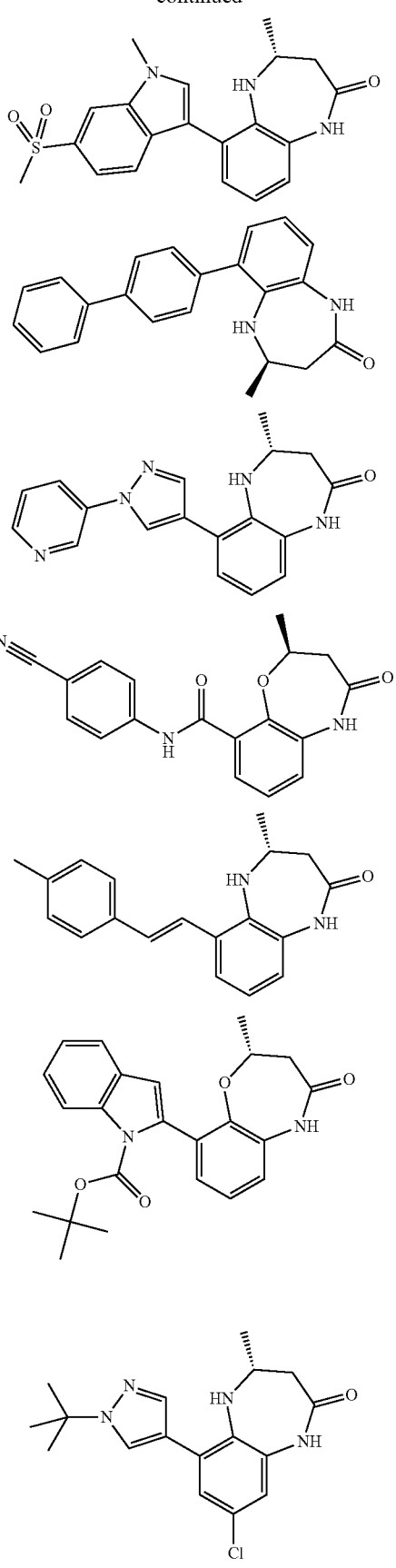

105
-continued
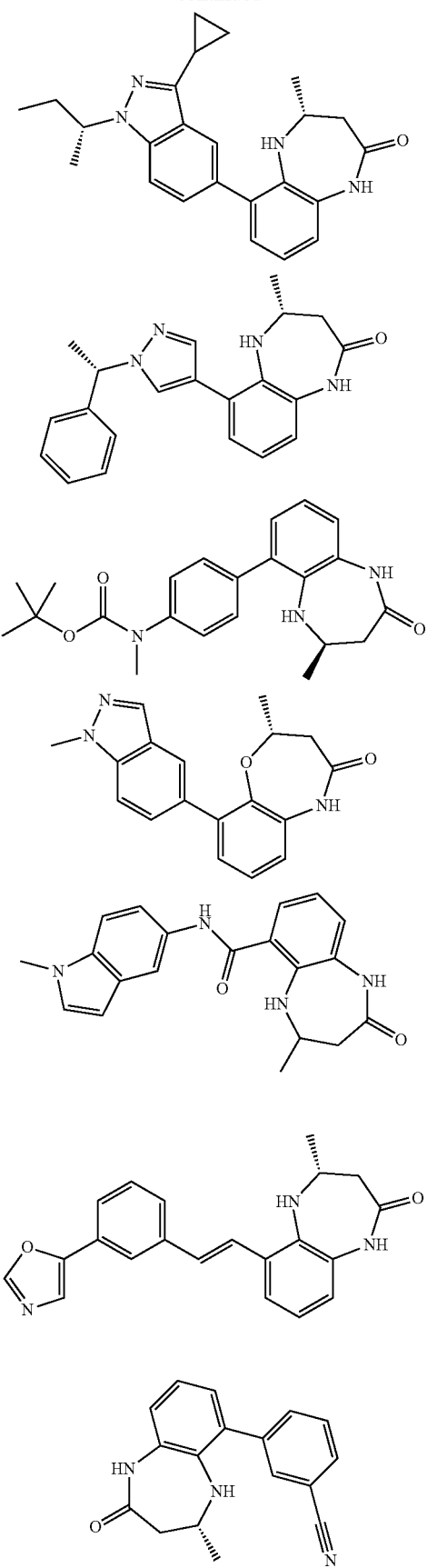
106
-continued
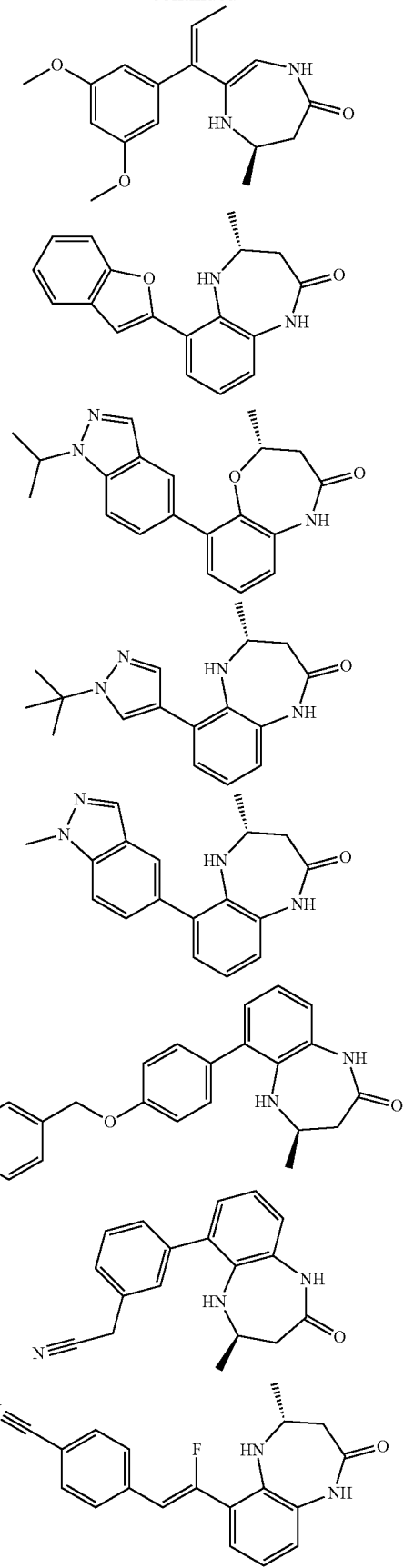

107
-continued
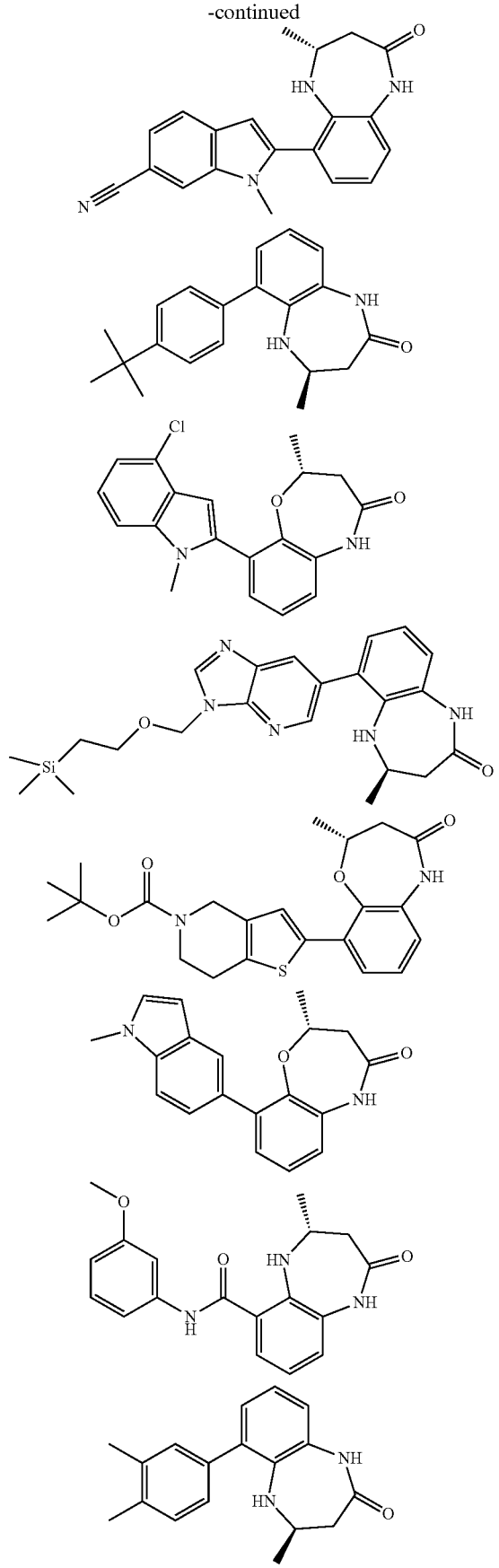
108
-continued
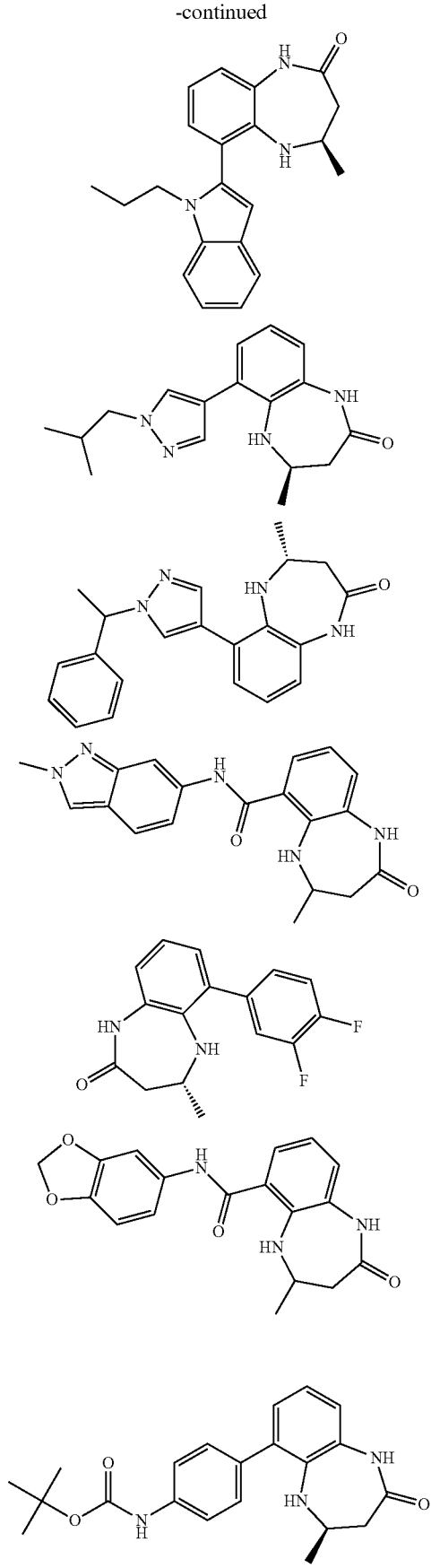

109
-continued
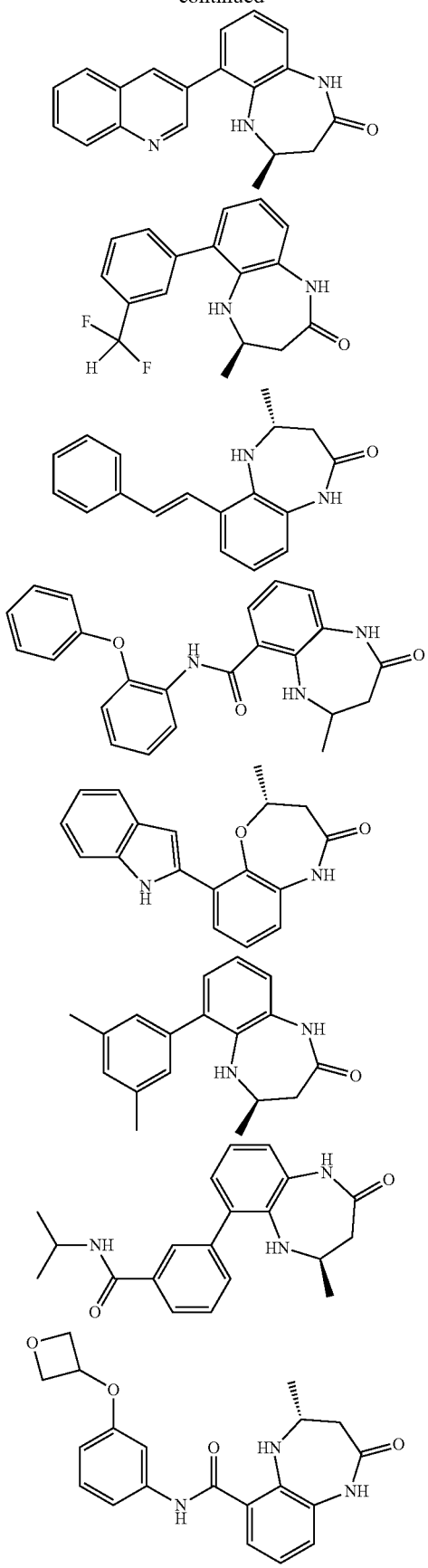
110
-continued
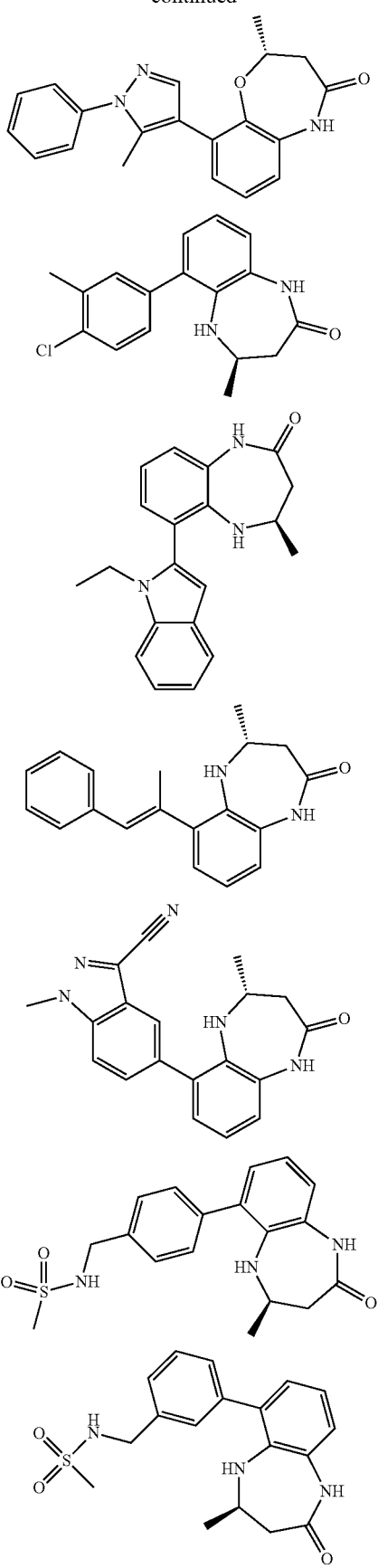

-continued
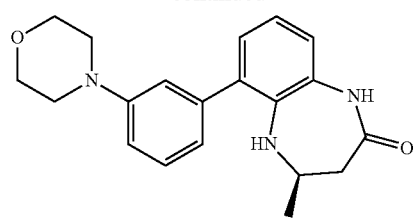
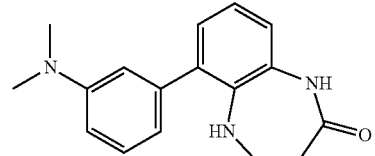
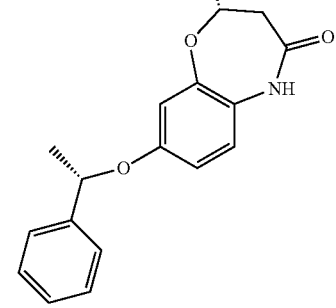
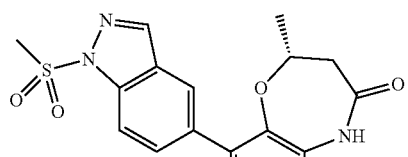
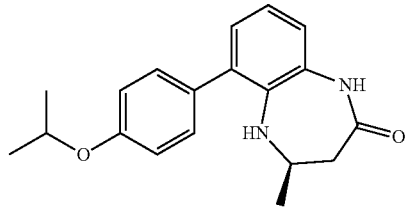
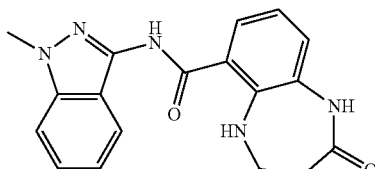
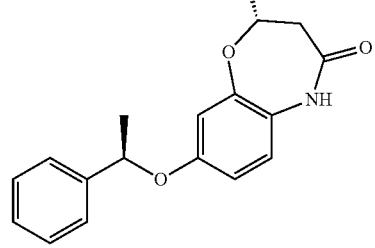
-continued
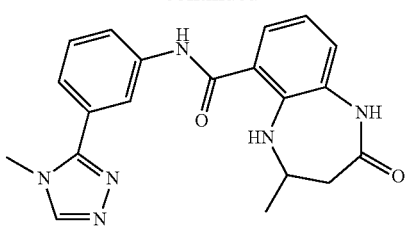
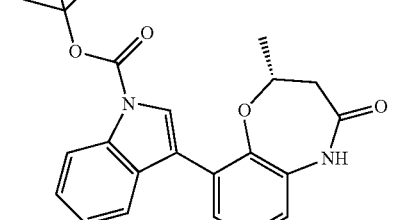
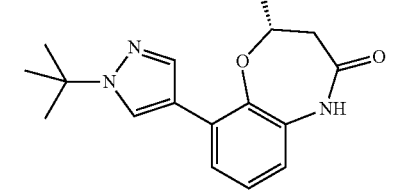
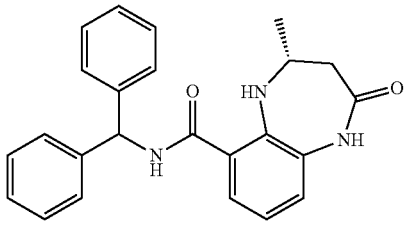
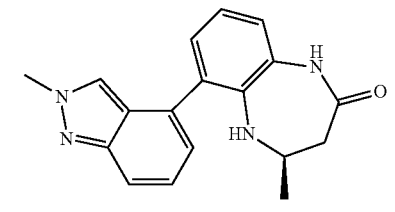
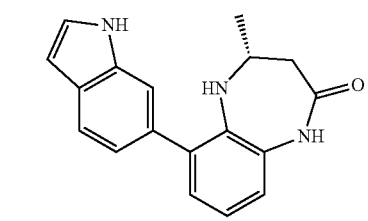
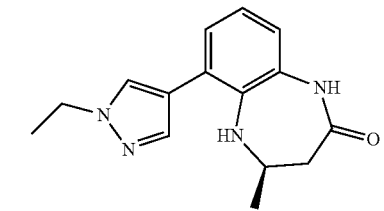

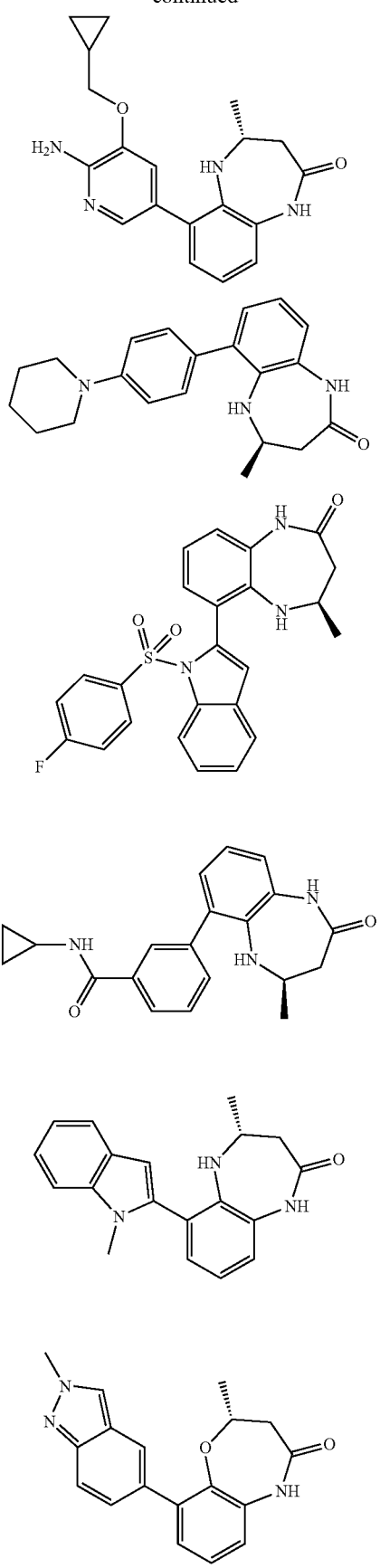
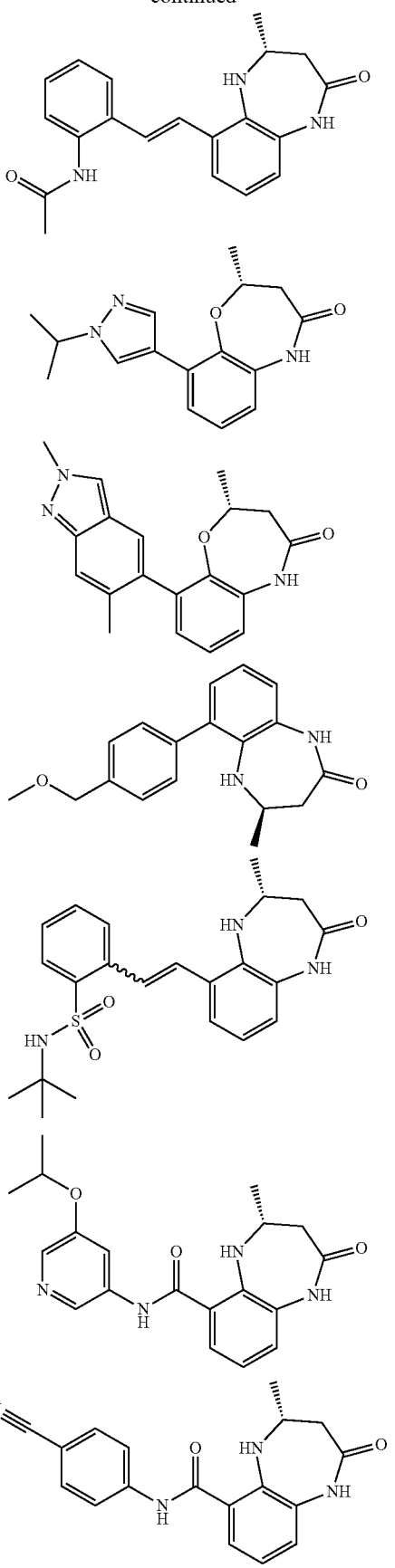

115
-continued
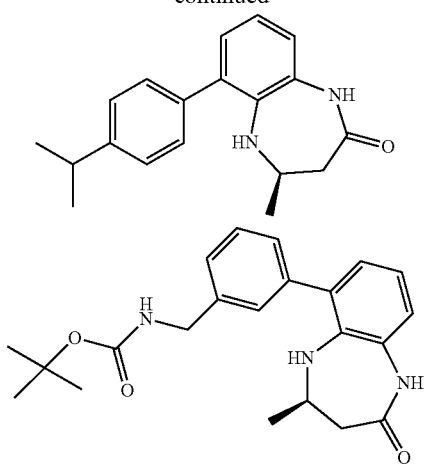
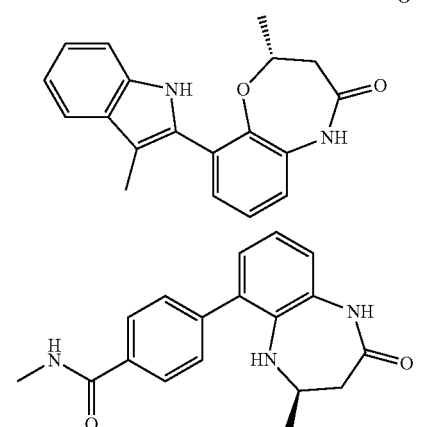
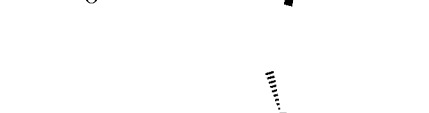
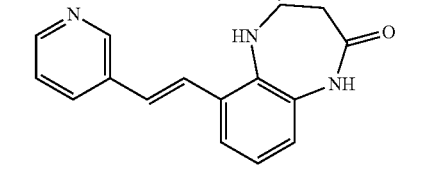
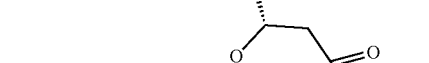
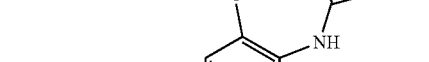
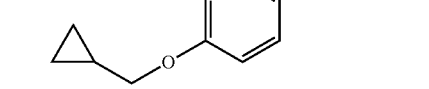
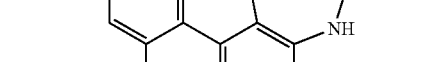
116
-continued
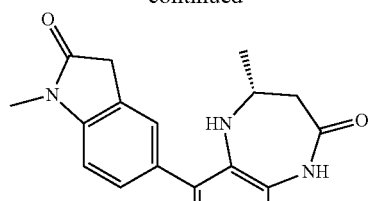
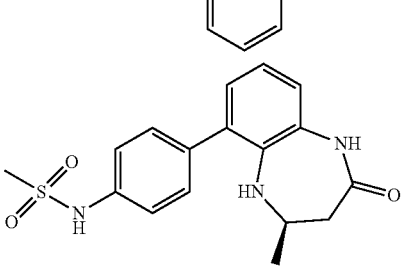
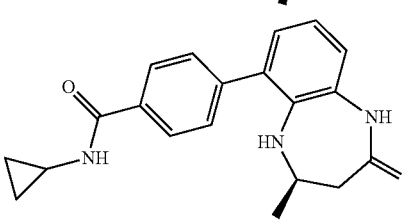
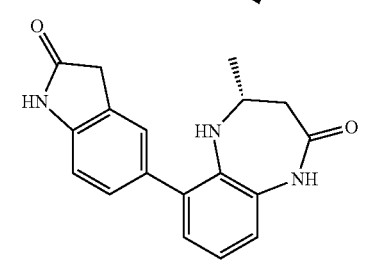
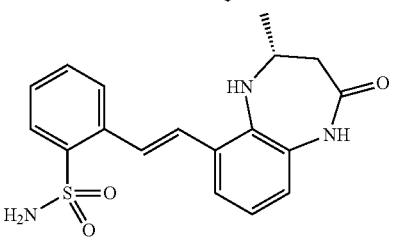
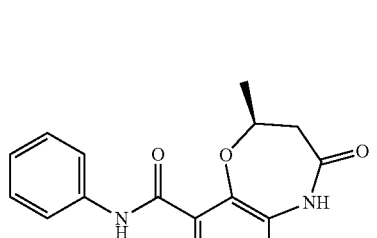
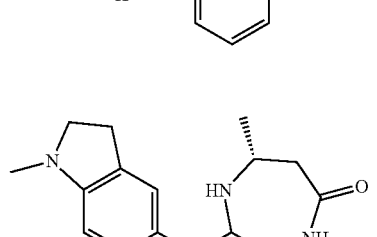

117
-continued
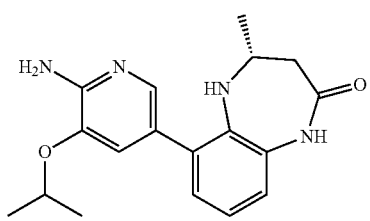
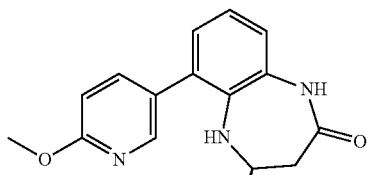
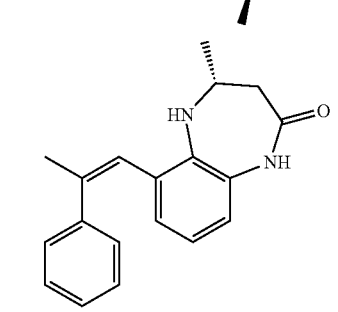
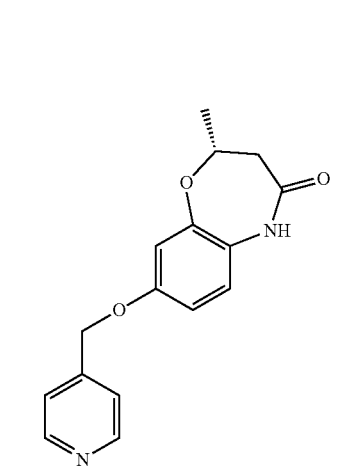
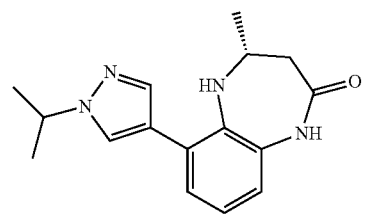
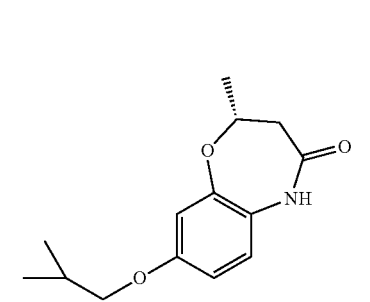
118
-continued
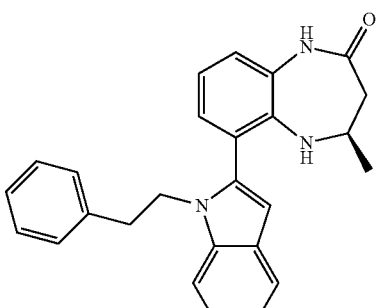
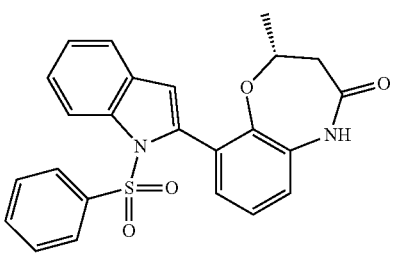
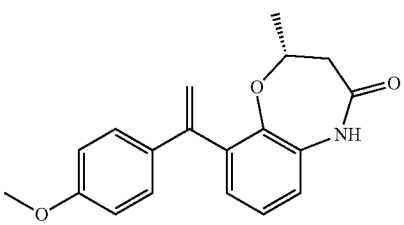
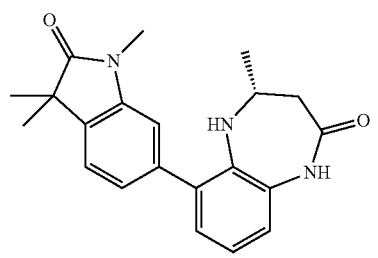
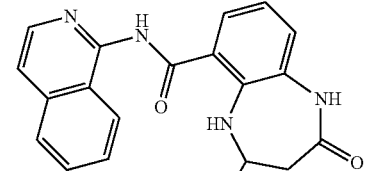
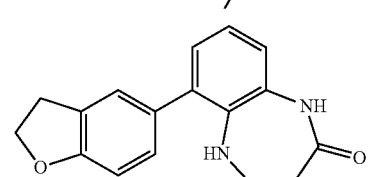
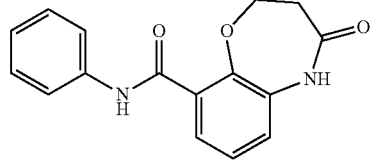

119
-continued
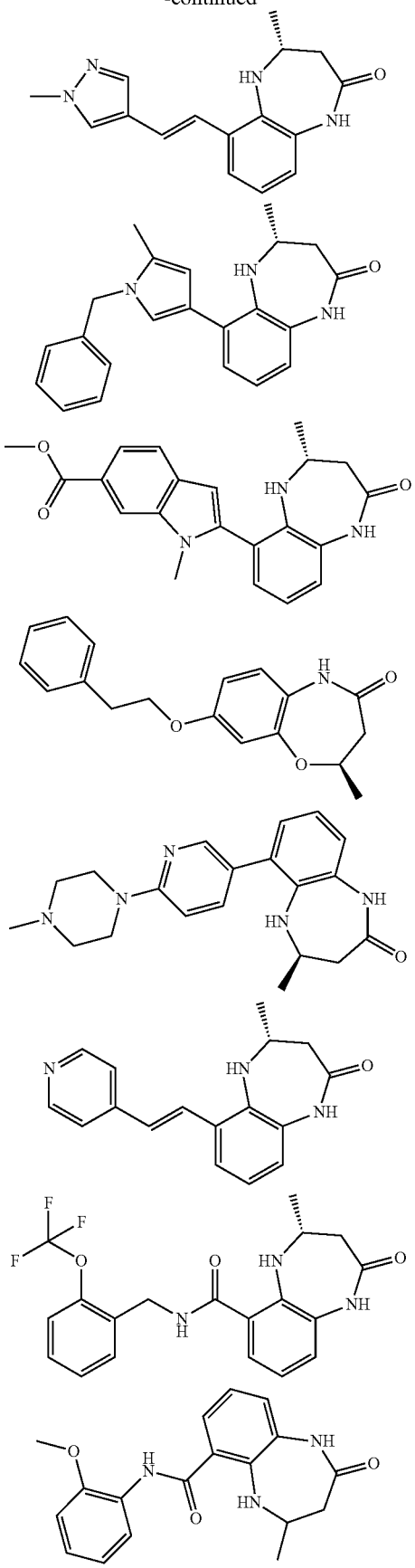
120
-continued
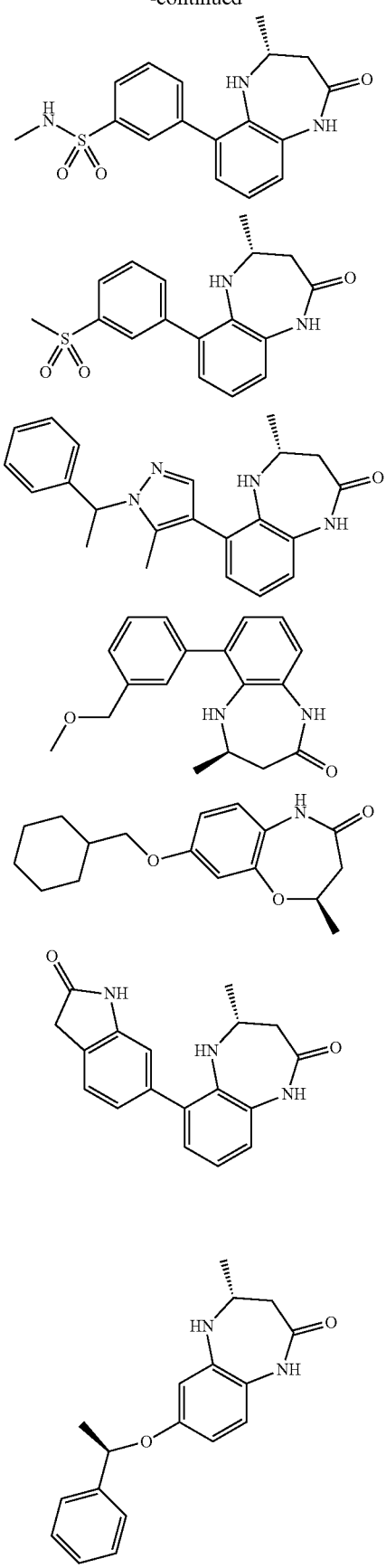

-continued
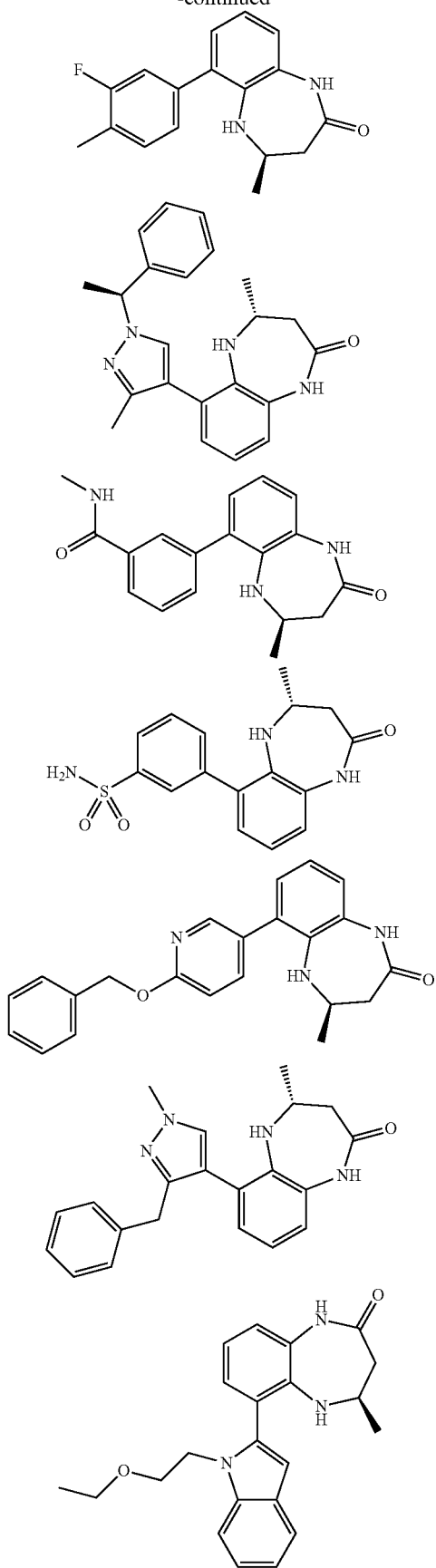
-continued
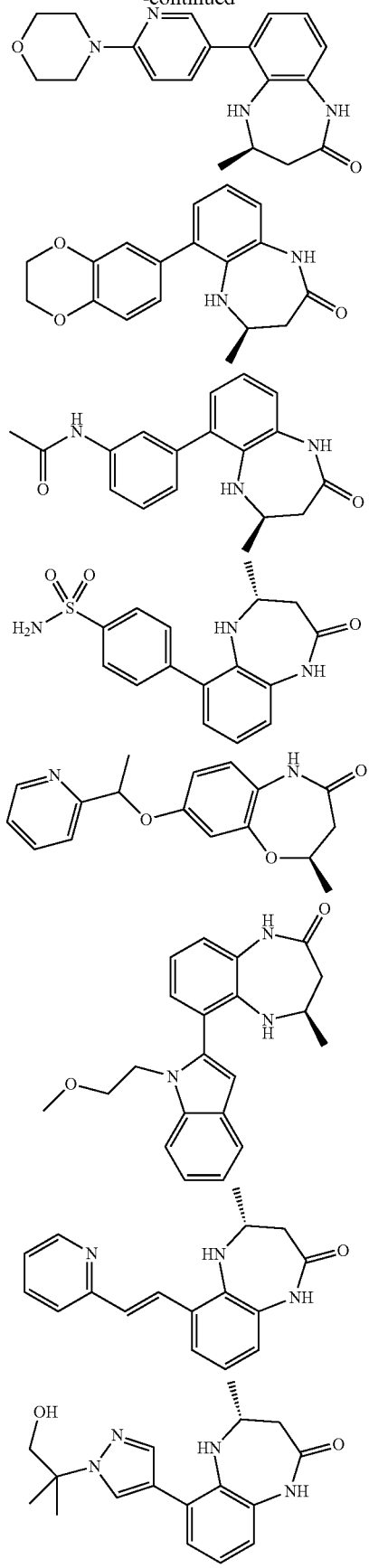

123
-continued
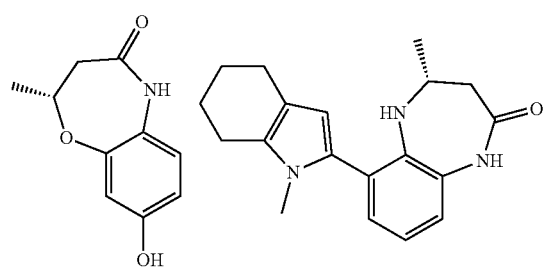
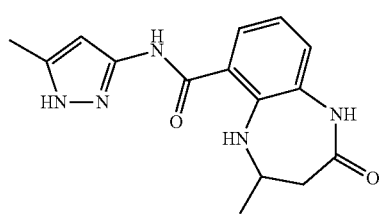
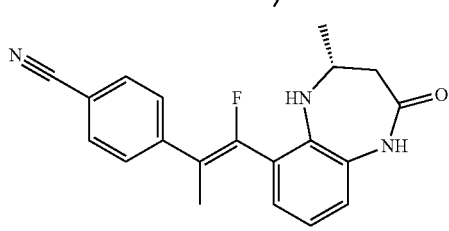
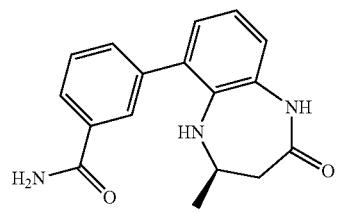
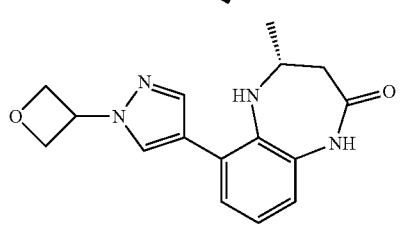
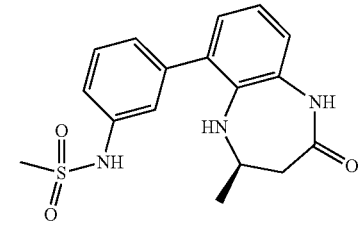
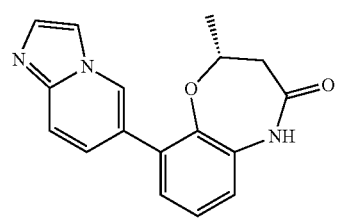
124
-continued
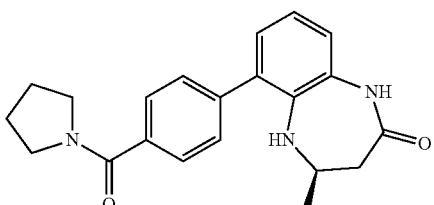
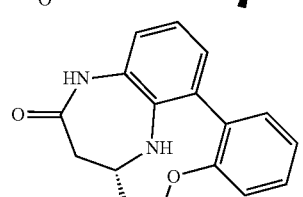
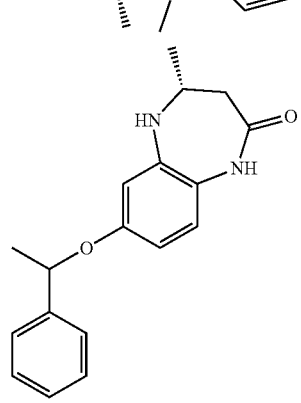
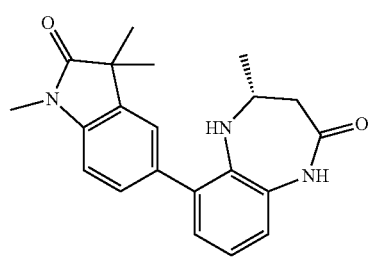
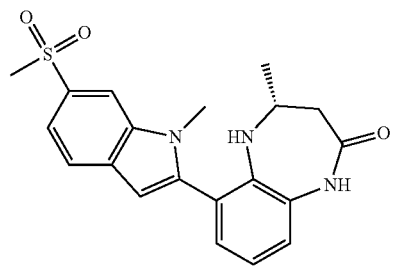
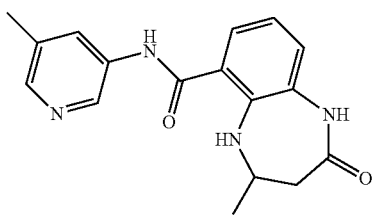

125
-continued
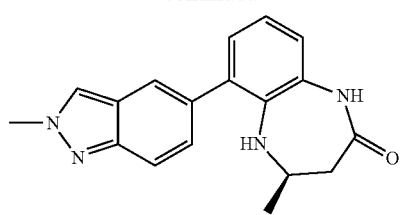
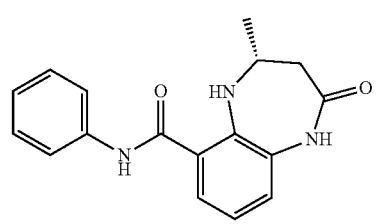
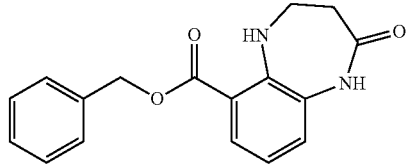
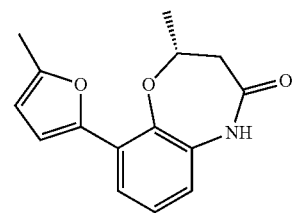
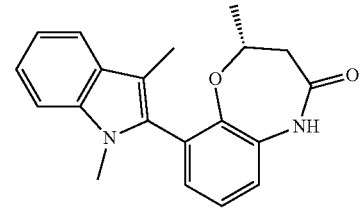
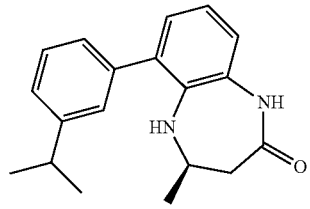
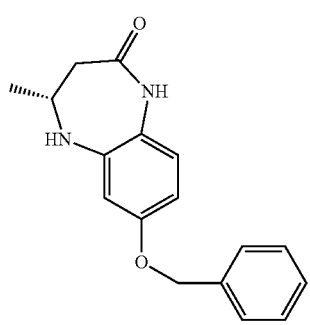
126
-continued
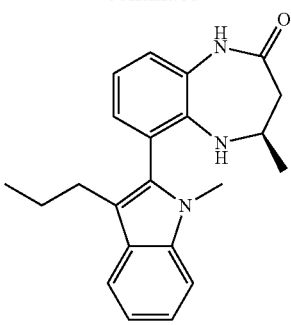
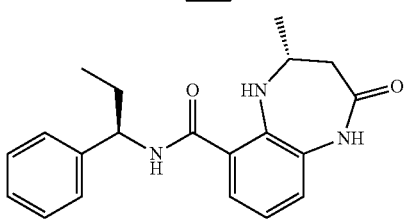
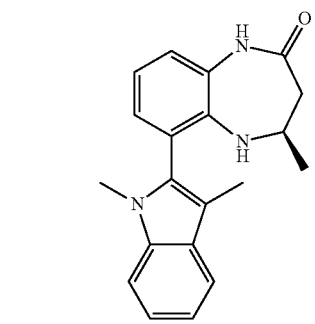
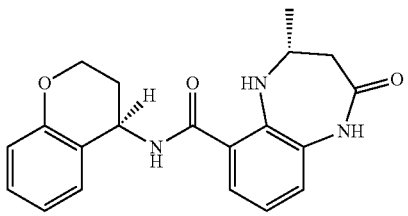
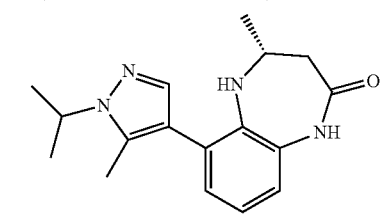
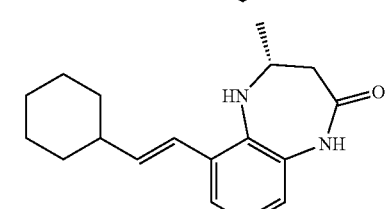
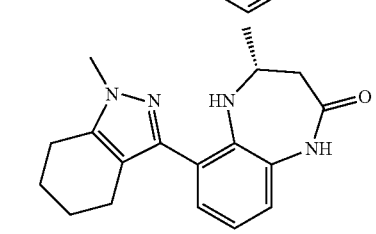

127
-continued
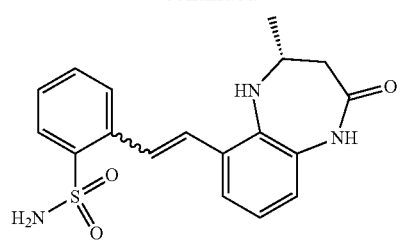
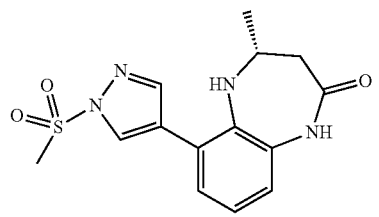
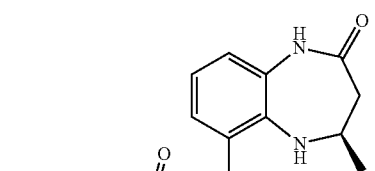
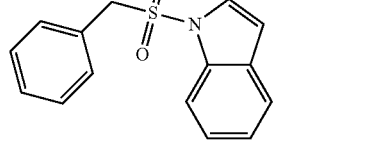
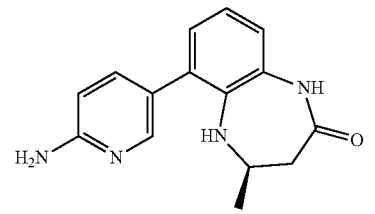
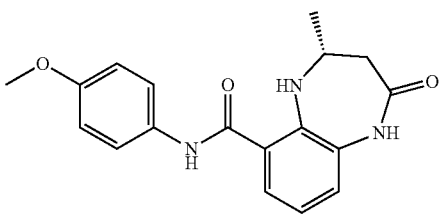
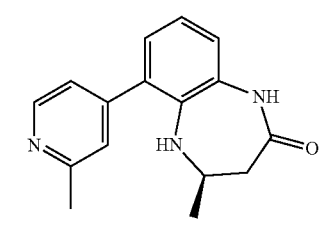
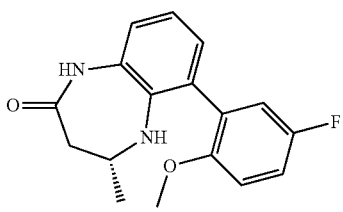
128
-continued
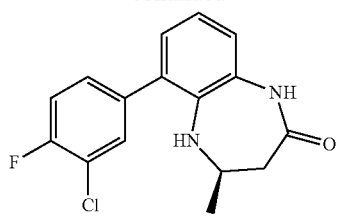
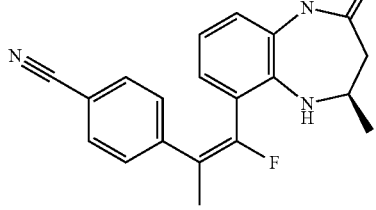
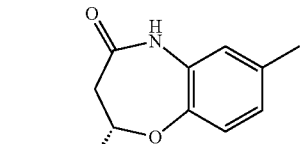
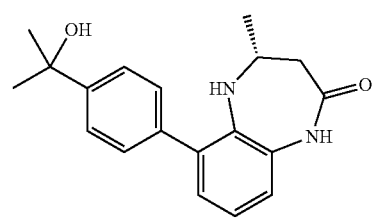
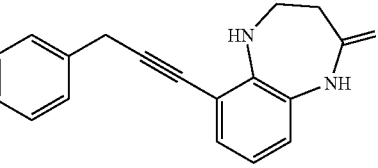
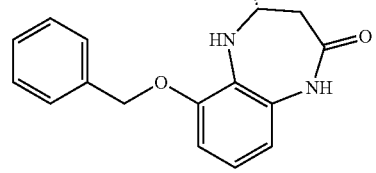
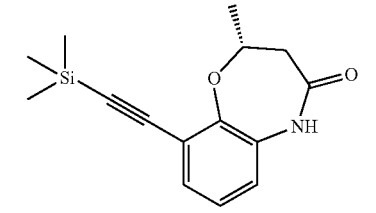
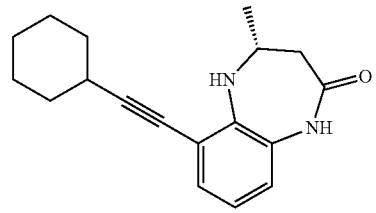

129
-continued
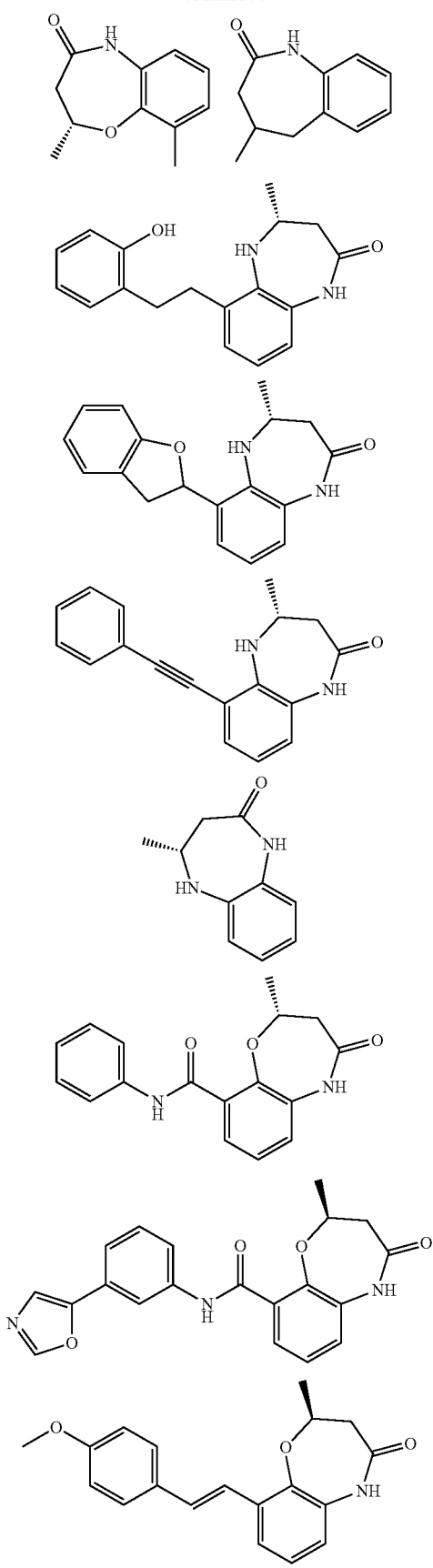
130
-continued
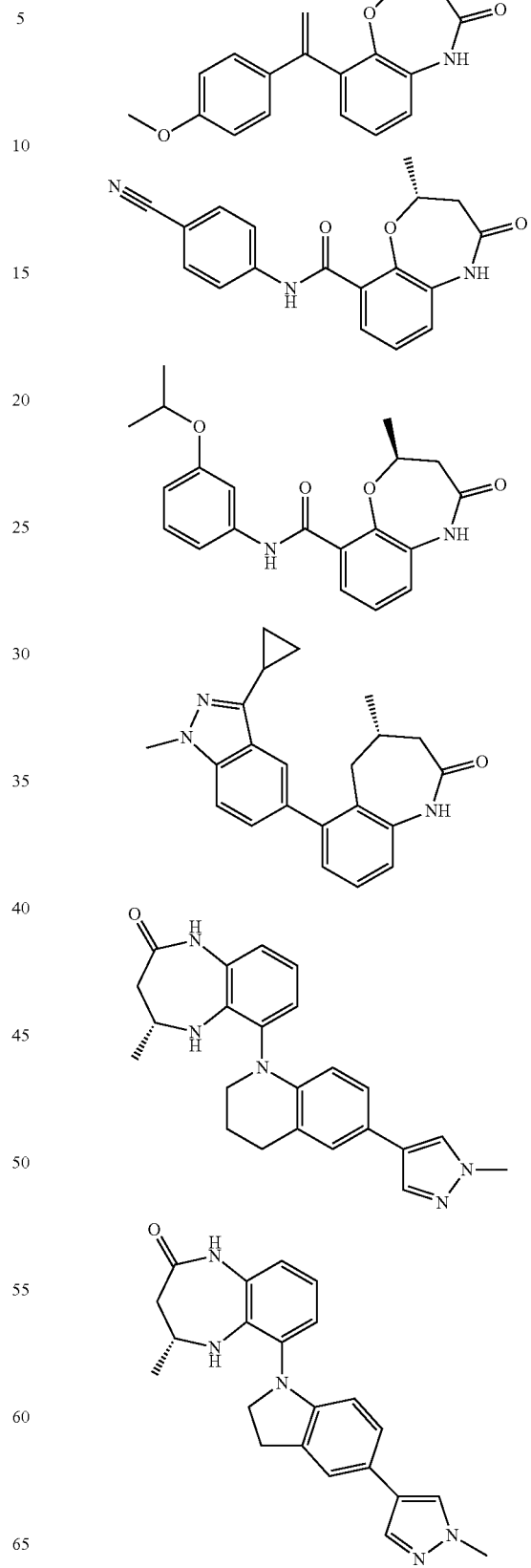

131
-continued
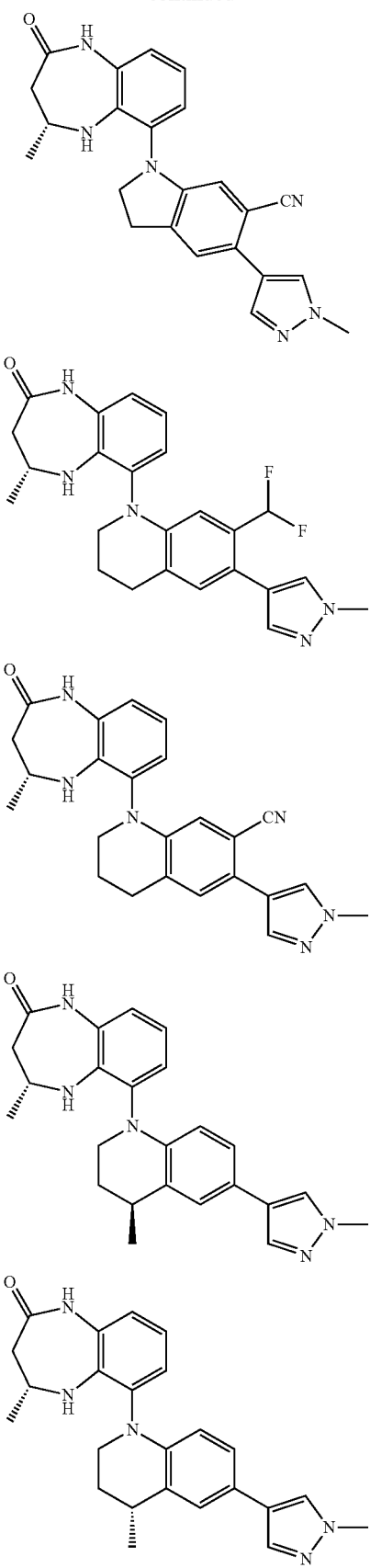
132
-continued
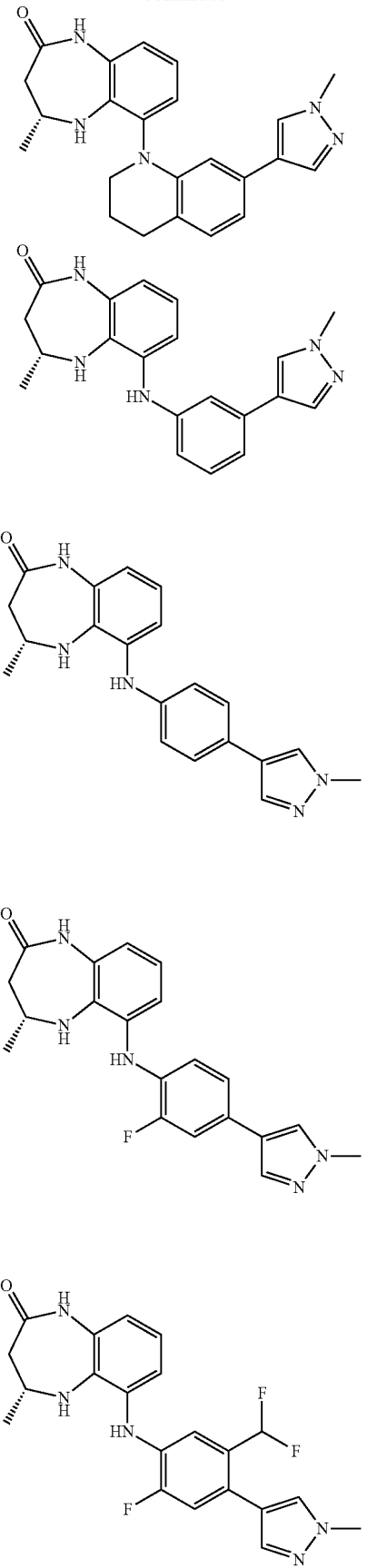

133
-continued
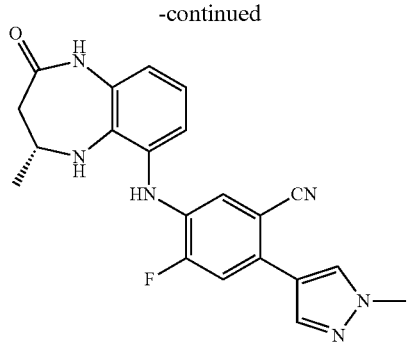
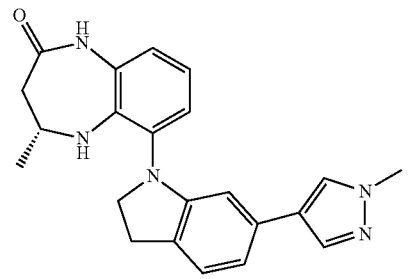
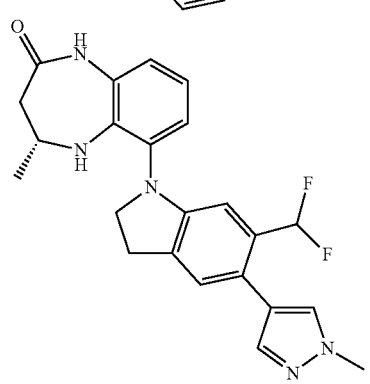
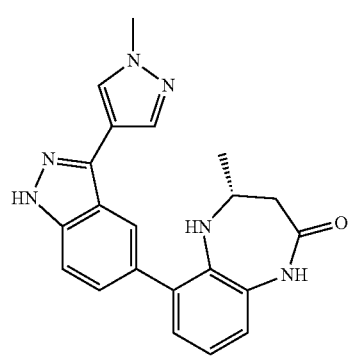
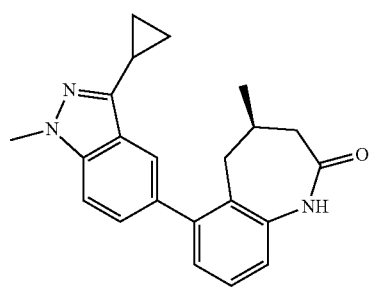
134
-continued
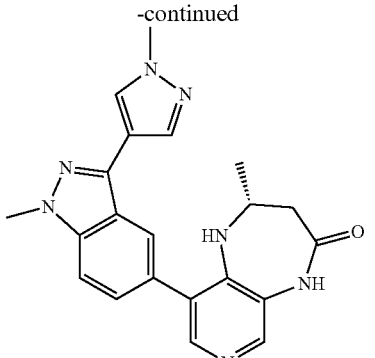
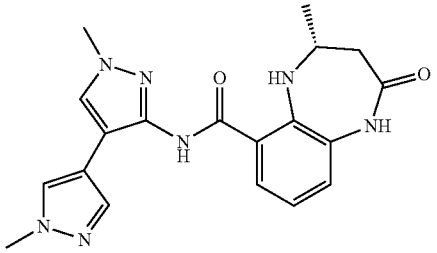
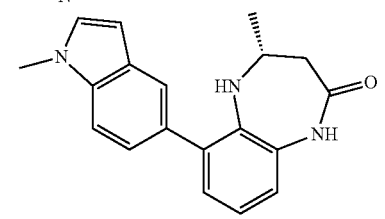
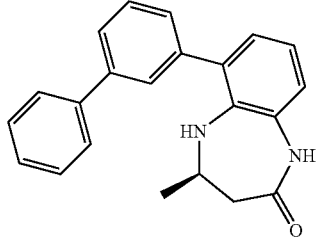
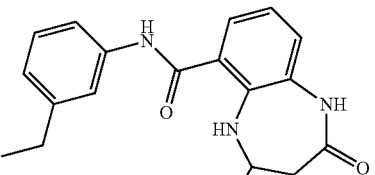
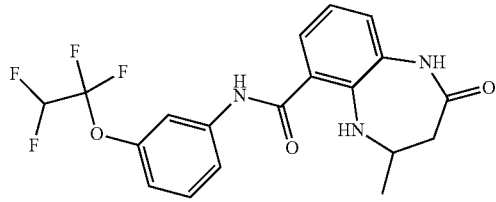
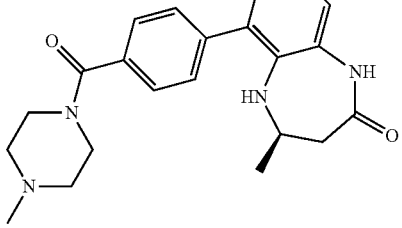

-continued
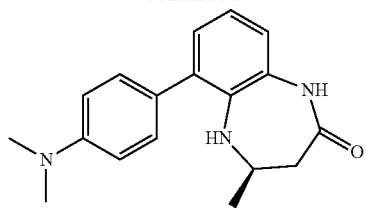
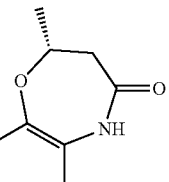
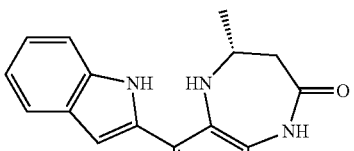
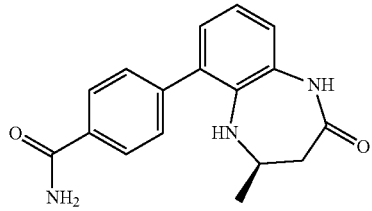
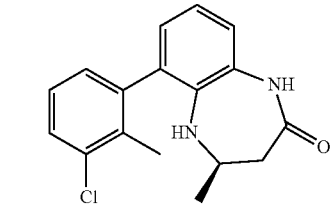
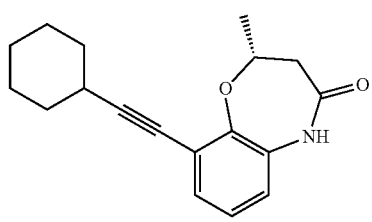
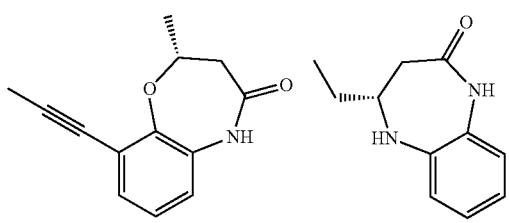
-continued
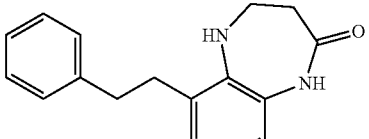
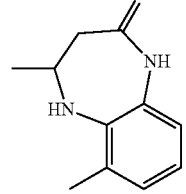
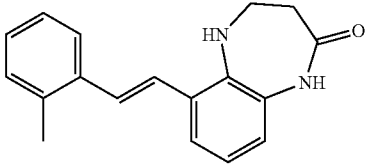
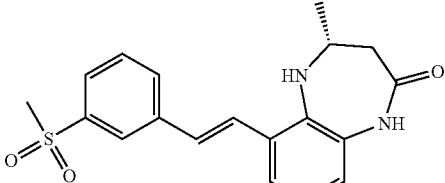
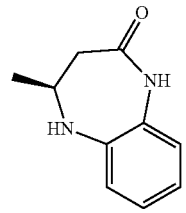
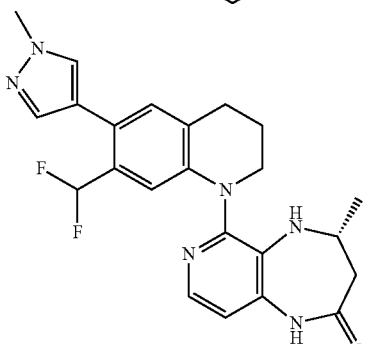
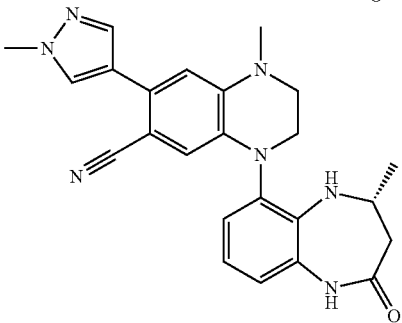

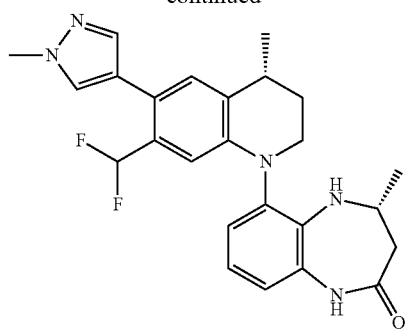
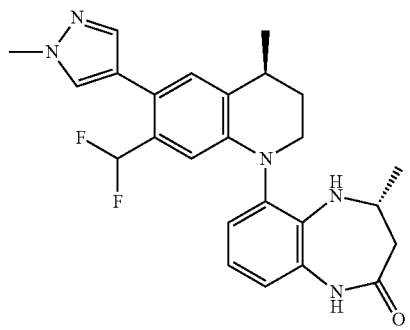
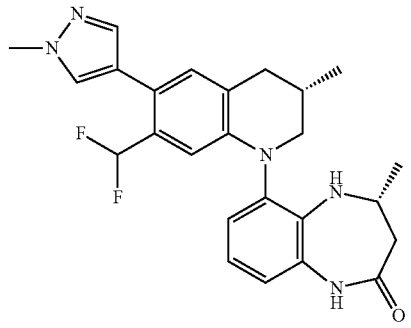
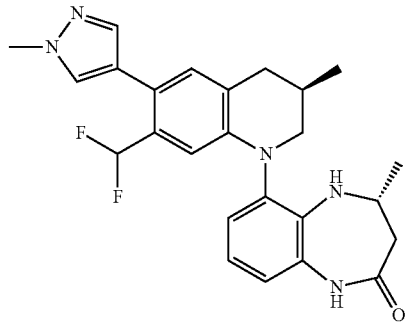
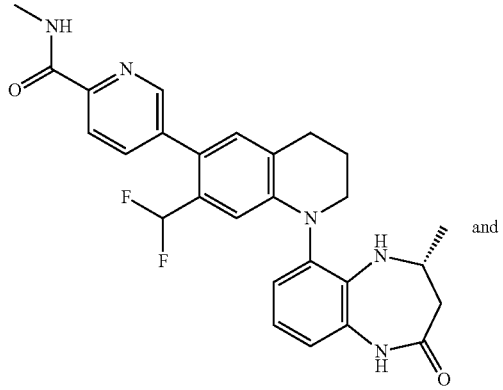

and

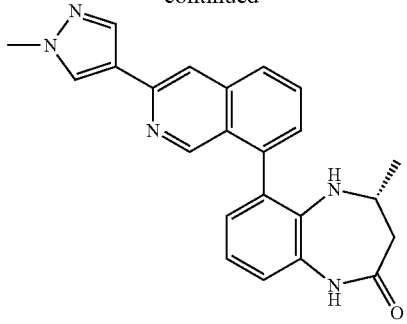

and salts thereof.

In certain embodiments the compound is a compound as described in the Examples herein, or a freebase or salt thereof.

Uses, Formulation and Administration

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain of CBP and/or EP300. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle, injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof for the inhibition of a bromodomain (in vitro or in vivo) (e.g., in vitro or in vivo inhibition of the bromodomain of CBP/EP300).

Another embodiment includes a method for treating a bromodomain-mediated disorder (e.g., CBP/EP300 bromodomain-mediated disorder) in an animal comprising administering a compound of formula (I), or a pharmaceutically acceptable salt thereof to the animal. CBP/EP300-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or a pharmaceutically acceptable salt thereof.

Another embodiment includes a method of extending the duration of response to a cancer therapy in an animal, comprising administering to an animal undergoing the cancer therapy a compound of formula (I) or a pharmaceutically acceptable salt thereof, wherein the duration of response to the cancer therapy when the compound of formula (I) or the pharmaceutically acceptable salt thereof is administered is extended over the duration of response to the cancer therapy in the absence of the administration of the compound of formula (I) or the pharmaceutically acceptable salt thereof.

Another embodiment includes a method of treating cancer in an individual comprising administering to the individual (a) a compound of formula (I) or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, provided are methods of enhancing immune function in an individual having cancer comprising administering an effective amount of any CBP/EP300 bromodomain inhibitors disclosed herein. In some embodiments of any of the methods, the CD8T cells in the individual have enhanced priming, activation, proliferation, and/or cytolytic activity relative to prior to the administration of the CBP/EP300 bromodomain inhibitor. In some embodiments, the number of CD8 T cells is elevated relative to prior to administration of the CBP/EP300 bromodomain inhibitors. In some embodiments, the CD8 T cells have reduced levels of expression of one or more of the following biomarkers: IFNA17, IGF1, FSCN1, SUMO2, C1orf129, EIF2S2, TDGF1, AIDA, CCR4, CD160, MC4R, KRTAP2-2, MTIJP, OR4N2, KRTAP4-5, MTIL//MTIL, IL13, LCEID, KIR2DL2, LOC158696, LIF, IL28A, TAS2R13, CTLA4, and/or FOXP3 relative to prior to administration of the CBP/EP300 bromodomain inhibitor. In some embodiments, the CD8 T cells have reduced levels of expression of CD160 and/or KIR2DL2 relative to prior to administration of the CBP/EP300 bromodomain inhibitor.

In some embodiments of the methods of enhancing immune function, the enhanced immune function is characterized by Treg cells in the individual (e.g., at the tumor site(s)) have reduced levels of expression of one or more of the following markers: IL28A, GPR87, ANKRD37, CABLES1, R-APGEF2, TRIM69, MT1L//MT1L, FAM1138, FOXP3, CSF2, OCM2, GLIPR1, FGFBP2, CTLA4, CST7, GOLGA6L1, IFIT3, FAM13A, APOD, AK2, CLDN1, HSD11B1, DNAJC12, PHEX, IL2, FOXD4L3, GNA15, ZBTB32, RDH10, OR52E5, CYP2A6, GZMH, CCL20, ADM, LOC100131541, RNF122, FAM36A, AMY2B, GPR183, MYOF, IL29, AIDA, SPRYI, ENOPH1, IL1RN, SLAMF1, PGM2L1, SSBP3, MMP23B, HIST1H3J, MYO1B, BEND5, S1PR1, CDK6, GPR56, ZC3HIZA, DOK5, DUSPI, CYB5R2, KCNAB2, LAG3, KLF10, GK, SHC4, IL12RB2, CD109, HAVCR2 (TIM-3), LTA, FAM40B, HMGCSI, HSPA1A, ZNF705A, CMAH, KIF3A, CHN1, KBTBD8, TNF, MOP-1, RASGRP4, INSIG1, SLAMF7, OR10H4, LPL, HIST1H2BJ, LIF, IGF1, IL18RAP, OR52N4, OR1D2, CCR4, CXCR5, IL1R1, MICAL2, NRN1, PICALM, B3GNT5, IFI44L, CXCR3, ICOS, IFTT2, NCR3, HSPA1B, CD80, GNG2, C7orf68, GPR171, RPS10P7, IL23A, LOC283174, PLK2, EMP1, FNBP1L, CD226, RBMS3, IL23R, PTGER4, GZMB, F5, and/or HIST1H2BK relative to prior to administration of CBP/EP300 bromodomain inhibitor. In some embodiments, the Treg cell biomarker is one or more of LAG3, CTLA4, and/or FOXP3. In some embodiments of the methods of enhancing immune function, the enhanced immune function is characterized by enhanced naive T cell responsiveness to CD3/CD28 stimulation in the presence of Treg cells. In some embodiments, the CD8 T cell priming is characterized by increased T cell proliferation and/or enhanced cytolytic activity in CD8 T cells. In some embodiments, the CD8 T cell activation is characterized by an elevated frequency of T-IFN$^+$ CD8 T cells. In some embodiments, the CD8 T cell is an antigen-specific T-cell. In some embodiments, the immune evasion is inhibited.

In some embodiments, the methods provided herein are useful in treating conditions where enhanced immunogenicity is desired such as increasing tumor immunogenicity for the treatment of cancer. For example, provided herein are CBP/EP300 bromodomain inhibitors for use to enhance T-cell function to upregulate cell-mediated immune responses and for the treatment of T cell dysfunctional disorders, tumor immunity. In some embodiments, the CBP/EP300 bromodomain inhibitors promote anti-tumor immunity by inhibiting the suppressive function of regulatory T (Treg) cells and/or relieving T cell exhaustion on chronically stimulated CD8$^+$ T cells. CBP/EP300 bromodomain inhibitors are further useful in reducing FOXP3 expression during extra-thymic Treg cell differentiation. Continual FOXP3 expression is essential to maintain suppressive activity in Treg cells. In some embodiments, reduced FOXP3 expression through CBP/EP300 bromodomain inhibition impairs Treg cells suppressive activity and promotes tumor antiimmunity. Treg cells are highly enriched in tumors derived from multiple cancer indications, including melanoma, NSCLC, renal, ovarian, colon, pancreatic, hepatocellular, and breast cancer. In a subset of these indications, increased intratumoral Treg cell densities are associated with poor patient prognosis. These indications include NSCLC, ovarian, pancreatic, hepatocellular, and breast cancer. CBP/EP300 bromodomain inhibitors are predicted to impair intrtumoral Treg cell function in these cancer indications to enhance effector T cell activity. In other embodiments, the CBP/EP300 bromodomain inhibitors may be used to treat infectious diseases, where some pathogens may have evolved to manipulate regulatory T (Treg) cells to immunosuppress the host to ensure survival, such as in retrovial infections (e.g., HIV), mycobacterial infections (e.g., tuberculosis), and parasitic infections (e.g., *Leishmania* and malaria).

CBP and/or EP300-Mediated Disorders

A "CBP and/or EP300-mediated disorder" is characterized by the participation of the bromodomains of CBP and/or EP300 in the inception, manifestation of one or more symptoms or disease markers, severity, or progression of a disorder. In one embodiment the bromodomain-mediated disorder is a CBP bromodomain-mediated disorder. In one embodiment the bromodomain-mediated disorder is an EP300 bromodomain-mediated disorder.

CBP and/or EP300 bromodomain-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cyst adenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies off-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer.

In certain embodiments, the cancer is melanoma.

CBP and/or EP300-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

CBP and/or EP300-mediated disorders also include AIDS; chronic kidney diseases, including, but are not limited to diabetic nephropathy, hypertensive nephropathy, HIV-associated nephropathy, glomerulonephritis, lupus nephritis, TgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

CBP and/or EP300 inhibitors may also be used to provide male contraception.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer. The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/ day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMAIRA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechiorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl.*

*Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase I inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXANN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab nertansine, cedelizumab, certolizurmab pegol, cidfusituzumab, cidtuzumab, daclizurnab, eculizurmab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumnab, numavizumab, ocrelizumab, omalizumab, palivizumab, pascolizumab, pecfusituzumab, pectuzumrab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H1225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO098/50433, Abgenix/

Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® (Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®)) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5 [[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCR$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; coilchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS®: or OSTAC®), etidronate (DIDROCAL®), NE-58095, zoledronic acidlzoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicarn, meloxicarn, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, aminifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using CBP/EP300 bromodomain inhibitors to treat and/or delay progression of cancer in combination with a PD-1 axis binding antagonist. Further provided herein are methods of enhancing immune function in an individual having cancer comprising administering to the individual an effective amount of a CBP/FP300 bromodomain inhibitor and an effective amount of a PD-1 axis binding antagonist. APD-1 axis binding antagonist includes a PD-1 binding antagonist, a PD-L binding antagonist and a PD-L2 binding antagonist.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof; immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1 106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L binding antagonists include anti-PD-L antibodies, antigen binding fragments thereof; immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1 105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition), In some embodiments, a PD-L2 binding antagonist is an immunoadhesin.

Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1 106, Merck 3475 (also known as: pembrolizumab, lambrolizumab, or MK-3475), nivolumab (BMS-936558), CT-011, and NMPDL3280A. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A and MDX-1 105. MDX-1 105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1 106, also known as MDX-1 106-04, ONO-4538 or BMS-936558, is an anti-PD-1 antibody described in WO2006/121168. Merck 3745, also known as MK-3475 or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1 106. Alternative names for "MDX-1106" include MDX-1 106-04, ONO-4538, BMS-936558 or Nivolumab. In some embodiments, the anti-PD-1 antibody is Nivolumab (CAS Registry Number: 946414-94-4). In some embodiments, the cancer is melanoma, NSCLC, and renal cell carcinoma.

For treating an inflammatory disease or an autoimmune disease, a compound of formula (I) or a pharmaceutically acceptable salt thereof may be co-administered with methotrexate, tofacitinib, 6-mercaptopurine, azathioprinesulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropiumandoxitropium, cyclosporin, FK506, rapamycin, mycophenolatemofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) an dp55TNFRigG (Lenercept), siL-1RI, siL-1RII, siL-6R), an antiinflammatory cytokine (e.g. IL-4, IL-10, IL-11, IL-13 and TGF), celecoxib, folicacid, hydroxychloroquinesulfate, rofecoxib, etanercept, infliximab, adalimumab, certolizumab, tocilizumab, abatacept, naproxen, valdecoxib, sulfasalazine, methylprednisolone, meloxicam, methyl prednisolone acetate, gold sodium thiomalate aspirin, triamcinolone acetonide, propoxyphenenapsylate/apaap folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, saisalate, sulindac, cyanocobalamin/fa/pyridoxine, acetaminophen, alendronatesodium, prednisolone, cortisone, betamethasone, morphinesulfate, lidocainehydrochloride, indomethacin, glucosamrinesulf/chondroitin, amitriptylineHCl, sulfadiazine, oxycodone HCV acetaminophen, olopatadine HCl misoprostol, naproxen sodium, omeprazole, cyclophosphamide, rituximab, IL-1 TRAP, MRA, CTLA4-IG, IL-18BP, anti-IL-12, Anti-IL1S, BIRB-796, SCI0-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe Rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, L-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalinmumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-1; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(AlfaWassermann/J&J), interferon 1A-IF (Serono/Inhale Therapeutics), Peginterferon 2b (Enzon/Schering-Plough), Copolymer 1 (Cop-1; COOPAXONE®; Teva Pharmaceutical Industries, Inc.); hyperbaric oxygen; intravenous immunoglobulin; cladribine; an antibody toorantagoristofotherhumancytokinesorgrowthfactorsandtheirreceptors (e.g. TNF, LT, IL-1, IL-2, IL-6, IL-7, IL-8, L-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamnycin, mycophenolatemofetil, leflunomide, an S1P1 agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAPkinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75TNF receptors, siL-1RI, siL-1RII, or siL-6R), or an antiinflammatory cytokine (e.g. IL-4, IL-10, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatirameracetate, natalizumab, sinnabidol, immunokine NNS03, ABR-215062, AnergiX.MS, chemokine receptor antagonists, BBR-2778, calagualine, CP-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenaccelecoxib, rofecoxib, sulfasalazine, methotrexate, azathioprine, minocyclin, prednisone, an anti-TNF antibody, D2E7 (HU-MIRA®), CA2 (infiiximab), CDP571, a TNFR-Ig construct, (p75NFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterolxinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasonefuroate, salmeterolxinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterolxinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafiriukast, amoxicillin/clavulanate, flunisolide/menthol, chlorpheniramine/hydrocodone, metaproterenol sulfate, methylprednisolone, mometasonefuroate, p-ephedrine/cod/chlorphenir, pirbuterolacetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasonedipropaugmented, fluocinolone acetonide, acitretin, tar shampoo, betamethasonevalerate, mometasonefuroate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coaltar, diflorasone diacetate, etanercept folate, lactic acid, methoxsalen, he/bismuthsubgal/znox/resor, methylprednisolone acetate, prednisone, sunscreen, halcinonide, salicylic acid, anthralin, clocortolone pivalate, coal extract, coaltar/salicylic acid, coaltar/salicylic acid/sulfur, desoximetasone, diazepam, emollient, fluocinonide/emollient, mineral oil/castor oil/nalact, mineral oil/peanut oil, petroleum/isopropylmyristate, psoralen, salicylic acid, soap/tribromsalan, thimerosal/boric acid, celecoxib, infiiximab, cyclosporine, alefacept, efhlizumab, tacrolimus, pimecrolimus, PUVA, UVB, sufasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasonedipropaugmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolatemofetil, or methotrexate); an inhibitor of PDE4, or a purine synthesis inhibitor (e.g. Celicept®). For example, a compound of formula (I) or a pharmaceutically acceptable salt thereof maybe co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LJP394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, an IV protease inhibitor, an immunomodulator, or another retroviral drug. Examples of reverse transcriptase inhibitors include, but are not limited to, abacavir, adefovir, didanosine, dipivoxildelavirdine, efavirenz, emtricitabine, lamivudine, n evirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir ritonavir, saquinavir, and tipranavir. Examples of other retroviral drugs include, but are not limited to, elvitegravir, enfuvirtide, maravirocandraltegravir.

For treating type II diabetes, hepaticsteatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexanide, chlorpropamide, glyburide, glimepiride, glipizide, glicazide, glycopyramide, gliquidone, rapaglinide, nataglinide, tolazamideortolbutamide; agents that are glucagon-like peptide agonists such as exanatide, liraglutideortaspoglutide; agents that inhibit dipeptidyl-peptidase IV such as vildagliptin, sitagliptin, saxagliptin, linagliptin, allogliptinor septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitolor voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calciumgluconate, sodium bicarbonate, albuterol, paricalcitol, doxercalciferol, cinacalcet, or bardoxalone methyl.

The amount of both the compound of formula (I) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CPAF inhibitor.

In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedure for Intermediates A & B

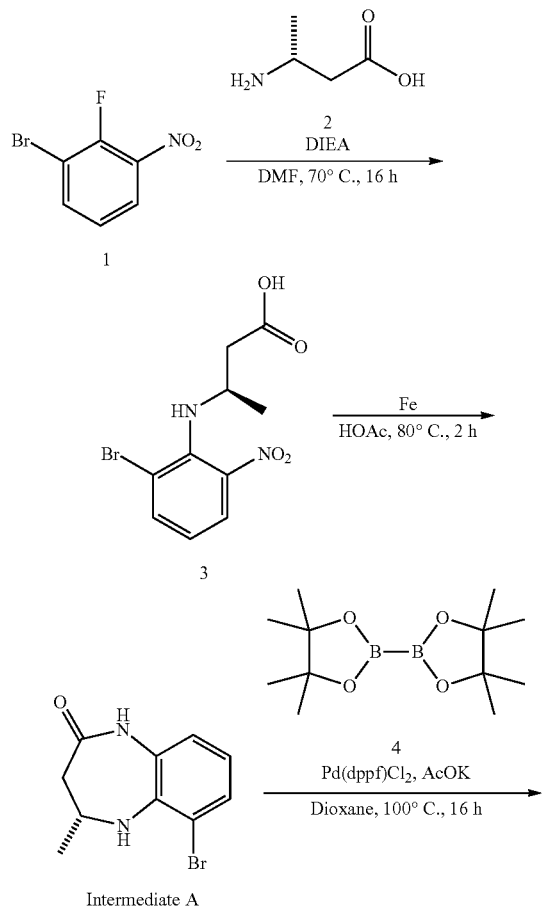

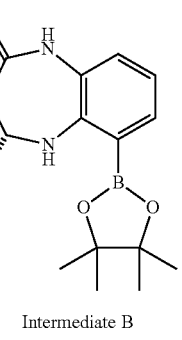

Step 1:

(R)-3-((2-bromo-6-nitrophenyl)amino)butanoic acid

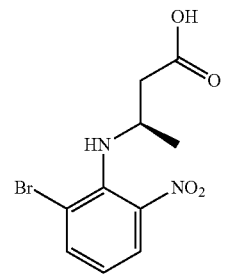 [SMILES: C[C@H](CC(=O)O)Nc1c(Br)cccc1[N+](=O)[O-]]

To a solution of 1-bromo-2-fluoro-3-nitrobenzene (3.0 g, 13.64 mmol) in DMF (50 mL) was added N-ethyl-N-isopropylpropan-2-amine (5.3 g, 40.91 mmol) and (R)-3-aminobutanoic acid (1.7 g, 16.36 mmol) portion-wise. The resulting mixture was heated to 80° C. for 10 h. After cooling the reaction to room temperature, water (30 mL) was added and the mixture was acidified with HCl (1N) to pH 6 and then extracted with EtOAc (100 mL×3). The combined organic layers were dried over anhydrous Na₂SO₄, filtered and concentrated in vacuo to give the title compound (3.7 g, 90%) as a yellow solid that required no further purification.

Step 2:

(R)-6-bromo-4-methyl-4,5-dihydro-1H-benzo[b][1,4]diazepin-2(3H)-one

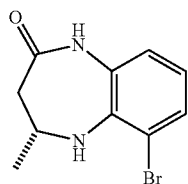

To a solution of (R)-3-((2-bromo-6-nitrophenyl)amino)butanoic acid (7.5 g, 24.74 mmol) in acetic acid (50 mL) was added Fe powder (7.0 g, 0.125 mol). The mixture was heated to 100° C. for 1 h. After cooling the reaction to room temperature, the reaction mixture was filtered and the filtrate was concentrated in vacuo. Water (30 mL) was added and the mixture was extracted with EtOAc (60 mL×3). The combined organic layers were dried over anhydrous Na₂SO₄, filtered and concentrated in vacuo. The crude residue was purified by silica gel chromatography (petroleum ether/EtOAc=3/1) to give the title compound (Intermediate A, 3.2 g, 51%) as a white solid. $^1$H NMR (400 MHz, DMSO-d₆) δ 9.63 (s, 1H), 7.26 (d, J=8.0 Hz, 1H), 6.87 (d, J=7.6 Hz, 1H), 6.71-6.67 (m, 1H), 4.58 (s, 1H), 3.98-3.97 (m, 1H), 2.40-2.41 (m, 1H), 2.21-2.18 (m, 1H), 1.20 (d, J=6.0 Hz, 3H).

Step 3:

(R)-4-methyl-6-(4,4,5,5-tetramethyl-1,3,2-dioxaborolan-2-yl)-4,5-dihydro-1H-benzo[b][1,4]diazepin-2(3H)-one

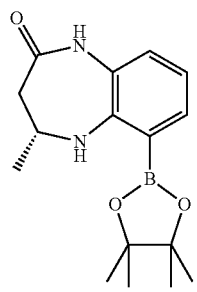

To a solution of (R)-6-bromo-4-methyl-4,5-dihydro-1H-benzo[b][1,4]diazepin-2(3H)-one (1.6 g, 6.27 mmol) in dioxane (25 mL) was added 4,4,4',4',5,5,5',5'-octamethyl-2,2'-bi(1,3,2-dioxaborolane) (2.3 g, 9.41 mmol), KOAc (1.8 g, 18.82 mmol) and [1,1'-bis(diphenylphosphino)ferrocene]dichloropalladium(II) (0.5 g, 0.68 mmol). The mixture was heated to 100° C. for 16 h under nitrogen atmosphere. After cooling the reaction to room temperature, the mixture was filtered and concentrated in vacuo to give the title compound (Intermediate B, 1.8 g, crude) as a brown solid that required no further purification.

Example 1

(4R)-4-methyl-6-[(E)-2-(3-pyridyl)vinyl]-1,3,4,5-tetrahydro-1,5-benzodiazepin-2-one

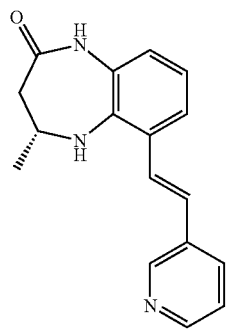 [SMILES: C[C@@H]1CC(=O)Nc2cccc(/C=C/c3cccnc3)c2N1]

Step 1:

(R)-4-methyl-6-vinyl-4,5-dihydro-1-benzo[b][1,4]diazepin-2(3H)-one

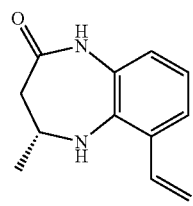

To a solution of (R)-6-bromo-4-methyl-4,5-dihydro-1H-benzo[b][1,4]diazepin-2(3H)-one (Intermediate A, 500 mg, 1.96 mmol) in dioxane (3 mL) and 120 (0.8 mL) were added 4,4,5,5-tetramethyl-2-vinyl-1,3,2-dioxaborolane (445 mg, 2.94 mmol), [1,1'-bis(diphenylphosphino)ferrocene] dichloropalladium(II) (139 mg, 0.19 mmol) and Cs$_2$CO$_3$ (1.3 g, 3.99 mmol). The reaction mixture was irradiated in a microwave at 100° C. for 0.5 h. After cooling the reaction to room temperature, ice water (15 mL) was added and the mixture was extracted with DCM (20 mL×3). The combined organic layers were dried over anhydrous Na$_2$SO$_4$, filtered and concentrated in vacuo. The crude residue was purified by silica gel chromatography (petroleum ether/EtOAc=1/1) to give the title compound (100 mg, 25%) as a brown solid.

Step 2:

(4R)-4-methyl-6-[(E)-2-(3-pyridyl)vinyl]-1,3,4,5-tetrahydro-1,5-benzodiazepin-2-one

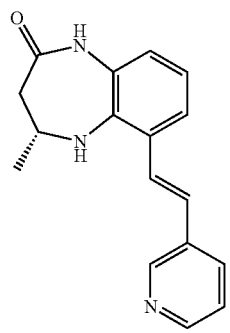

A mixture of (R)-4-methyl-6-vinyl-4,5-dihydro-1H-benzo[b][1,4]diazepin-2(3H)-one (100 mg, 0.49 mmol), 3-bromopyridine (94 mg, 0.59 mmol) and palladium(II) acetate (22 mg, 0.10 mmol) in triethylamine (3 mL) was irradiated in a microwave 120° C. for 0.5 h. After cooling the reaction to room temperature, ice water (5 mL) was added and extracted with EtOAc (10 mL×3). The combined organic layers were dried over anhydrous Na$_2$SO$_4$, filtered and concentrated in vacuo. The crude residue was purified by reverse phase chromatography (acetonitrile 17-17%/0.2% formic acid in water) to give the title compound (6 mg, 4%) as a white solid. $^1$H NMR (400 MHz, CD$_3$OD) δ 8.72 (s, 1H), 8.40 (d, J=4.8 Hz, 1H), 8.12 (d, J=8.0 Hz, 1H), 7.59 (d, J=16.0 Hz, 1H), 7.49-7.45 (m, 2H), 7.10 (d, J=16.4 Hz, 1H), 6.97-6.94 (m, 2H), 4.18-4.14 (m, 1H), 2.58-2.53 (m, 1H), 2.29-2.24 (m, 1H), 1.35 (d, J=6.4 Hz, 3H). LCMS M/Z (M+H) 280.

The following compounds were prepared in a similar fashion to Example 1:

Examples 2 & 3

| Example | Compound Name | NMR | m/z |
|---|---|---|---|
| Example 2 | (4R)-4-methyl-6-[(E)-2-(2-pyridyl)vinyl]-1,3,4,5-tetrahydro-1,5-benzodiazepin-2-one | $^1$H NMR (400 MHz, DMSO-$d_6$) δ 9.51 (s, 1H), 8.58 (d, J = 4.0 Hz, 1H), 7.87 (d, J = 15.6 Hz, 1H), 7.79-7.67 (m, 2H), 7.43 (t, J = 5.2 Hz, 1H) 7.25-7.11 (m, 2H), 6.88 (d, J = 4.4 Hz, 2H), 5.04 (s, 1H), 4.07-3.97 (m, 1H), 2.51-2.43 (m, 1H), 2.17-2.12 (m, 1H), 1.26 (d, J = 6.0 Hz, 3H) | 280 |
| Example 3 | (4R)-4-methyl-6-[(E)-2-(4-pyridyl)vinyl]-1,3,4,5-tetrahydro-1,5-benzodiazepin-2-one | $^1$H NMR (400 MHz, DMSO-$d_6$) δ9.48 (s, 1H), 8.52 (d, J = 6.0 Hz, 2H), 7.74 (d, J = 16.0 Hz, 1H), 7.58 (d, J = 6.0 Hz, 2H), 7.44-7.41 (m, 1H), 7.07 (d, J = 16.0 Hz, 1H), 6.87-6.83 (m, 2H), 5.15 (s, 1H), 4.03-4.01 (m, 1H), 2.43-2.38 (m, 1H), 2.13-2.08 (m, 1H), 1.24 (d, J = 6.4 Hz, 3H) | 280 |

Example 4

(4R)-4-methyl-6-[(E)-2-(1-methylpyrazol-4-yl)vinyl]-1,3,4,5-tetrahydro-1,5-benzodiazepin-2-one

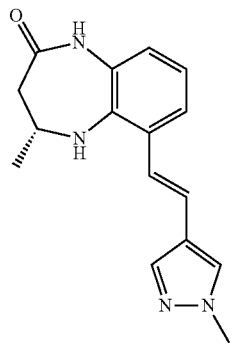

Step 1:

(R,E)-4-methyl-6-(2-(4,4,5,5-tetramethyl-1,3,2-dioxaborolan-2-yl)vinyl)-4,5-dihydro-1H-benzo[b][1,4]diazepin-2(3H)-one

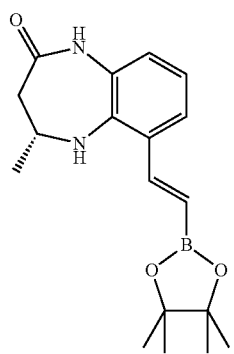

A mixture of (R)-6-bromo-4-methyl-4,5-dihydro-1H-benzo[b][1,4]diazepin-2(3H)-one (Intermediate A, 500.0 mg, 1.96 mmol), (E-6-methyl-2-(2-(4,4,5,5-tetramethyl-1,3,2-dioxaborolan-2-yl)vinyl)-1,3,6,2-dioxazaborocane-4,8-dione (968 mg, 3.13 mmol), $Cs_2CO_3$ (1.6 g, 4.91 mmol), tris(dibenzylideneacetone)dipalladium(O)(183.1 mg, 0.20 mmol) and 2-di-t-butylphosphino-2',4',6'-tri-i-propyl-1,1'-biphenyl (168.2 mg, 0.41 mmol) in MeCN (10 mL) was heated to 70° C. for 15 h under nitrogen atmosphere. After cooling the reaction to room temperature, water (20 mL) was added and the mixture was extracted with EtOAc (20 mL×2). The combined organic layers were dried over anhydrous $Na_2SO_4$, filtered and concentrated in vacuo to give the title compound (800 mg) as brown oil that required no further purification.

Step 2:

(4R)-4-methyl-6-[(E)-2-(1-methylpyrazol-4-yl)vinyl]-1,3,4,5-tetrahydro-1,5-benzodiazepin-2-one

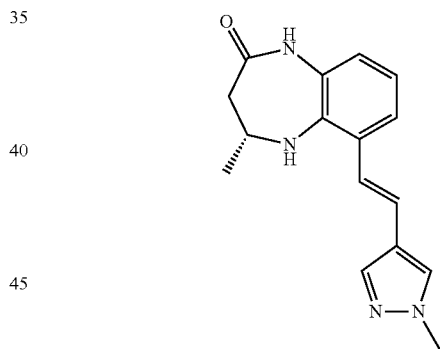

A mixture of (R,E)-4-methyl-6-(2-(4,4,5,5-tetramethyl-1,3,2-dioxaborolan-2-yl)vinyl)-4,5-dihydro-1H-benzo[b][1,4]diazepin-2(3H)-one (100.0 mg, 0.30 mmol), 4-bromo-1-methyl-1H-pyrazole (72 mg, 0.45 mmol), tris(dibenzylidene-acetone)dipalladium(27.9 mg, 0.03 mmol) and 2-di-t-butyl-phosphino-2',4',6'-tri-i-propyl-1,1'-biphenyl (25.2 mg, 0.06 mmol) in MeCN (3 mL) were irradiated in a microwave at 95° C. for 45 min. After cooling the reaction to room temperature, ice water (10 mL) was added and the mixture was extracted with EtOAc (10 mL×2), The combined organic layers were concentrated in vacuo. The crude residue was purified by reverse phase chromatography (acetonitrile 8-38%/0.1% $NH_4OH$ in water) to give the title compound (10 mg, 12%) as a white solid. $^1$H NMR (400 MHz, $CD_3OD$) δ7.79-7.76 (m, 2H), 7.41-7.35 (m, 1H), 7.19 (d, J=16.0 Hz, 1H), 7.00-6.85 (m, 3H), 4.21-4.12 (m, 1H), 3.91 (s, 3H), 2.59-2.54 (m, 1H), 2.30-2.25 (m, 1H), 1.37 (d, J=6.0 Hz, 3H). LCMS M/Z (M+H) 283.

The following compounds were prepared in a similar fashion to Example 4:

Examples 5-12

| Example | Compound Name | NMR | m/z |
|---|---|---|---|
| Example 5 | (4R)-4-methyl-6-[(E)-2-(2-methylsulfonylphenyl)vinyl]-1,3,4,5-tetrahydro-1,5-benzodiazepin-2-one | $^1$H NMR (400 MHz, DMSO-$d_6$) δ 9.53 (s, 1H), 8.13 (d, J = 8.0 Hz, 1H), 7.97 (d, J = 7.5 Hz, 1H), 7.82-7.74 (m, 2H), 7.59-7.50 (m, 2H), 7.40-7.32 (m, 1H), 6.95-6.89 (m, H), 5.17 (s, 1H), 4.08-4.05 (m, 1H), 3.23 (s, 3H), 2.48-2.43 (m, 1H), 2.17-2.12 (m, 1.H), 1.26 (d, J = 6.0 Hz, 3H) | 357 |
| Example 6 | (4R)-4-methyl-6-[(E)-2-(3-methylsulfonylphenyl)vinyl]-1,3,4,5-tetrahydro-1,5-benzodiazepin-2-one | $^1$H NMR (400 MHz, DMSO-$d_6$) δ9.49 (s, 1H), 8.16 (s, 1H), 8.04 (d, J = 8.0 Hz, 1H), 7.81-7.78 (m, 1H), 7.69-7.64 (m, 2H), 7.45-7.41 (m, 1H), 7.25-7.21 (m, 1H), 6.90-6.88 (m, 2H), 5.15 (s, 1H), 4.07-4.05 (m, 1H), 3.26 (s, 3H), 2.48-2.43 (m, 1H), 2.17-2.11 (m, 1H), 1.26 (d, J = 6.0 Hz, 3H) | 357 |
| Example 7 | (4R)-4-methyl-6-[(E)-2-(o-tolyl)vinyl]-1,3,4,5-tetrahydro-1,5-benzodiazepin-2-one | $^1$H NMR (400 MHz, DMSO-$d_6$) δ9.44 (s, 1H), 7.75 (d, J = 7.6 Hz, 1H), 7.38-7.32 (m, 2H), 7.22-7.14 (m, 4H), 6.87-6.81 (m, 2H), 4.96 (s, 1H), 4.05-3.99 (m, 1H), 2.43-2.35 (m, 4 H), 2.13-2.08 (m, 1H), 1.22 (d, J = 6.0 Hz, 3H) | 293 |
| Example 8 | 4-[(E)-2-[(4R)-4-methyl-2-oxo-1,3,4,5-tetrahydro-1,5-benzodiazepin-6-yl]vinyl]benzonitrile | $^1$H NMR (400 MHz, DMSO-$d_6$) δ9.47 (s, 1H), 7.82 (s, 4 H), 7.67 (d, J = 16.0 Hz, 1H), 7.43 (t, J = 6.0 Hz, 1H), 7.17 (d, J = 16.0 Hz, 1H), 6.86 (d, J = 6.0 Hz, 2H), 5.14 (s, 1H), 4.03-4.01 (m, 1H), 2.43-2.38 (m, 1H), 2.13-2.07 (m, 1H), 1.23 (d, J = 6.0 Hz, 3H) | 304 |
| Example 9 | N-[2-[(E)-2-[(4R)-4-methyl-2-oxo-1,3,4,5-tetrahydro-1,5-benzodiazepin-6-yl]vinyl]phenyl]acetamide | $^1$H NMR (400 MHz, CD$_3$OD) δ7.86-7.85 (m, 1H), 7.42-7.31 (m, 5H), 7.16 (d, J = 16.0 Hz, 1H), 7.00-6.92 (m, 2H), 4.21-4.15 (m, 1H), 2.61-2.56 (m, 1H), 2.33-2.29 (m, 1H), 2.20 (s, 3H), 1.38 (d, J = 6.0 Hz, 3H) | 336 |
| Example 10 | 3-[(E)-2-[(4R)-4-methyl-2-oxo-1,3,4,5-tetrahydro-1,5-benzodiazepin-6-yl]vinyl]benzene-sulfonamide | $^1$H NMR (400 MHz, DMSO-$d_6$) δ9.49 (s, 1H), 8.03 (s, 1H), 7.93 (d, J = 7.6 Hz, 1H), 7.70 (d, J = 7.6 Hz, 1H), 7.62-7.58 (m, 2H) 7.45-7.35 (m, 3H), 7.18 (d, J = 16.0 Hz, 1H), 6.88-6.87 (m, 2H), 5.12 (s, 1H), 4.07-3.07 (m, 1H), 2.46-2.41 (m, 1H), 2.16-2.11 (m, 1H), 1.26 (d, J = 6.4 Hz, 3H) | 358 |
| Example 11 | 2-[(E)-2-[(4R)-4-methyl-2-oxo-1,3,4,5-tetrahydro-1,5-benzodiazepin-6-yl]vinyl]benzene-sulfonamide | $^1$H NMR (400 MHz, DMSO-$d_6$) δ 8.03-7.89 (m, 3H),7.65-7.61 (m, 1H), 7.45-7.39 (m, 3H), 7.01-7.97 (m, 2H), 4.24-4.17 (m, 1H), 2.63-2.58 (m, 1H), 2.32-2.27 (m, 1H), 1.38 (d, J = 6.0 Hz, 3H) | 358 |
| Example 12 | (4R)-4-methyl-6-[(E)-2-(3-oxazol-5-ylphenyl)vinyl]-1,3,4,5-tetrahydro-1,5-benzodiazepin-2-one | $^1$H NMR (400 MHz, CD$_3$OD) δ 8.26 (s, 1H), 7.96 (s, 1H), 7.63-7.45 (m, 4 H), 7.13-7.10 (m, 1H), 6.97-6.93 (m, 2H), 4.19-4.14 (m, 1H), 2.58-2.53 (m, 1H), 2.29-2.24 (m, 1H), 1.36 (d, J = 6.0 Hz, 3H) | 346 |

Example 13

(4R)-6-[(E)-2-cyclohexylvinyl]-4-methyl-1,3,4,5-tetrahydro-1,5-benzodiazepin-2-one

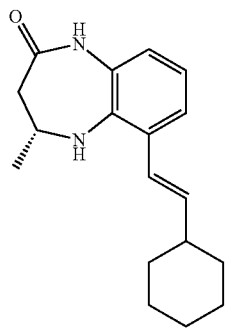 [SMILES: C[C@@H]1CC(=O)Nc2cccc(/C=C/C3CCCCC3)c2N1]

A mixture of (R)-6-bromo-4-methyl-4,5-dihydro-1H-benzo[b][1,4]diazepin-2(3H)-one (Intermediate A, 100 mg, 392 umol), (E)-(2-cyclohexylvinyl)boronic acid (66 mg, 0.43 mmol), Cs$_2$CO$_3$ (255 mg, 0.78 mmol), [1,1'-bis(diphenylphosphino)ferrocene]dichloropalladium(II) (30 ng, 0.04 mmol) in dioxane (2 mL) and H$_2$O (0.5 mL) was heated to 110° C. for 0.5 h under nitrogen atmosphere. After cooling the reaction to room temperature, the solvent was concentrated in vacuo. The crude residue was purified by reverse phase chromatography (acetonitrile 64-74%/0.1% NH$_4$OH in water) to give the title compound (40 mg, 36%) as a light yellow solid. $^1$H NMR (400 MHz, CD$_3$OD) δ 7.21-7.19 (m, 1H), 6.91-6.86 (m, 2H), 6.64-6.59 (m, 1H), 6.10-6.04 (m, 1H), 4.15-4.07 (m, 1H), 2.52-2.49 (m, 1H), 2.28-2.23 (m, 2H), 1.90-1.75 (m, 4H), 1.74-1.68 (m, 1H), 1.40-1.18 (m, 8H). LCMS M/Z (M-+H) 285.

The following compounds were prepared in a similar fashion to Example 13:

Examples 14-19

| Example | Compound Name | NMR | m/z |
|---|---|---|---|
| Example 14 | (4R)-4-methyl-6-(3-methylbenzofuran-2-yl)-1,3,4,5-tetrahydro-1,5-benzodiazepin-2-one | $^1$H NMR (400 MHz, DMSO-$d_6$) δ 7.63 (d, J = 2.8 Hz, 1H), 7.59 (d, J = 2.8 Hz, 1H), 7.46-7.27 (m, 2H), 7.19 (d, J = 2.0 Hz, 1H), 7.07-7.02 (m, 2H), 4.08-4.03 (m, 1H), 2.62-2.58 (m, 1H), 2.35-2.27 (m, 4H), 1.14 (d, J = 6.0 Hz, 3H) | 307 |
| Example 15 | (4R)-4-methyl-6-(1-methylindol-5-yl)-1,3,4,5-tetrahydro-1,5-benzodiazepin-2-one | $^1$H NMR (400 MHz, DSO-$d_6$) δ7.49-7.46 (m, 2H), 7.22-7.21 (m, 1H), 7.15-7.13 (m, 1H), 7.06-7.04 (m, 1H), 7.04-6.95 (m, 1H), 6.47-6.46 (m, 2H), 3.95-3.89 (m, 1H), 3.84 (s, 3H), 2.72-2.67 (m, 1H), 2.30-2.25 (m, 1H), 1.09 (d, J = 6.0 Hz, 3H) | 306 |
| Example 16 | (4R)-6-(1H-indol-2-yl)-4-methyl-1,3,4,5-tetrahydro-1,5-benzodiazepin-2-one | $^1$H NMR (400 MHz, CD$_3$OD) δ 7.58-7.55 (m, 1H), 7.40-7.38 (m, 1H), 7.27-7.25 (m, 1H), 7.15-7.08 (m, 1H), 7.05-7.01 (m, 4H), 6.57 (s, 1H), 4.13-4.06 (m, 1H), 2.76-2.71 (m, 2H), 2.35-2.29 (m, 1H), 1.24 (d, J = 6.0 Hz, 3H) | 292 |
| Example 17 | (4R)-4-methyl-6-[(E)-2-(p-tolyl)vinyl]-1,3,4,5-tetrahydro-1,5-benzodiazepin-2-one | $^1$H NMR (400 MHz, DMSO-$d_6$) δ9.46 (s, 1H), 7.55 (d, J = 8.0 Hz, 2H), 7.48-7.43 (m, 2H), 7.19 (d, J = 7.6 Hz, 1H), 7.05 (d, J = 16.0 Hz, 1H), 6.88-6.83 (m, 1H), 4.99 (s, 1H), 4.04-4.02 (m, 1H), 2.43-2.39 (m, 1H), 2.32 (s, 3H), 2.14-2.09 (m, 1H), 1.25 (d, J = 6.8 Hz, 3H) | 293 |
| Example 18 | (4R)-6-[(E)-2-(4-methoxyphenyl)vinyl]-4-methyl-1,3,4,5-tetrahydro-1,5-benzodiazepin-2-one | $^1$H NMR (400 MHz, DMSO-$d_6$) δ7.58-7.53 (m, 2H), 7.46-7.40 (m, 1H), 7.32-7.29 (m, 1H), 7.05-6.89 (m, 5H), 4.19-4.16 (m, 1H), 3.83 (s, 1H), 2.61-2.55 (m, 1H), 2.33-2.25 (m, 1H), 1.33 (d, J = 6.0 Hz, 3H) | 309 |
| Example 19 | (4R)-4-methyl-6-[(E)-2-(m-tolyl)vinyl]-1,3,4,5-tetrahydro-1,5-benzodiazepin-2-one | $^1$H NMR (400 MHz, CD$_3$OD) δ7.43-7.36 (m, 4H), 7.25-7.19 (m, 1H), 7.03-6.89 (m, 4H), 4.18-4.12 (m, 1H), 2.56-2.51 (m, 1H), 2.35 (s, 3H), 2.28-2.21 (m, 1H), 1.34 (d, J = 6.0 Hz, 3H) | 293 |

Example 20

N-[4-[(E)-2-[(4R)-4-methyl-2-oxo-1,3,4,5-tetrahydro-1,5-benzodiazepin-6-yl]vinyl]phenyl]acetamide

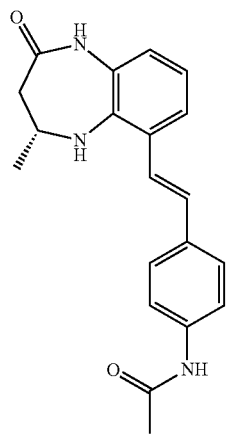 [SMILES: CC(=O)Nc1ccc(/C=C/c2cccc3c2N[C@H](C)CC(=O)N3)cc1]

Step 1:

(R,E)-4-methyl-6-(4-nitrostyryl)-4,5-dihydro-1H-benzo[b][1,4]diazepin-2(3H)-one

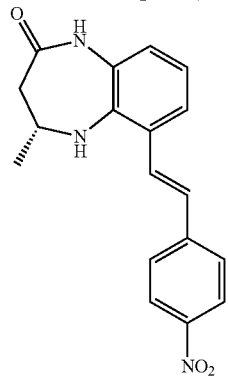

To a solution of (R)-6-bromo-4-methyl-4,5-dihydro-1H-benzo[b][1,4]diazepin-2(3H)-one (Intermediate A, 300 mg, 1.18 mmol) in TEA (5 mL) was added 1-nitro-4-vinylbenzene (263 mg, 1.76 mmol), palladium(II) acetate (53 mg, 0.24 mmol) and tri-o-tolylphosphine (72 mg, 0.24 mmol). The resulting mixture was heated to 120° C. for 1 h under nitrogen atmosphere. After cooling the reaction to room temperature the solvent was concentrated in vacuo. Water (50 mL) was added and the mixture was extracted with EtOAc (50 mL×3). The combined organic layers were washed with brine (50 mL), dried over anhydrous Na$_2$SO$_4$, filtered and concentrated in vacuo. The crude residue was purified by silica gel chromatography (petroleum ether/EtOAc=1/1) to give the title compound (150 mg, 39%) as a yellow solid.

Step 2:

(R,E)-6-(4-aminostyryl)-4-methyl-4,5-dihydro-1H-benzo[b][1,4]diazepin-2(3H)-one

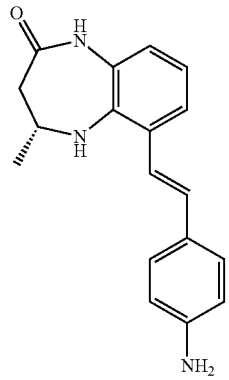 [SMILES: C[C@@H]1CC(=O)Nc2cccc(/C=C/c3ccc(N)cc3)c2N1]

To a solution of (R,E)-4-methyl-6-(4-nitrostyryl)-4,5-dihydro-1H-benzo[b][1,4]diazepin-2(3H)-one (150 mg, 0.46 mmol) in EtOH/H$_2$O (15/i, 8 mL) was added NH$_4$Cl (124 nag, 2.3 mmol) and Fe powder (130 mg, 2.3 mmol). The mixture was heated to 80° C. for 1 h. After cooling the reaction to room temperature, the solution was filtered and the filtrate was diluted with H$_2$O (20 mL). The mixture was extracted with EtOAc (20 mL×3). The combined organic layers were washed with sat. aq. sodium chloride and concentrated in vacuo to give the title compound (50 mg, 37%) as a yellow solid that required no further purification.

Step 3:

N-[4-[(E)-2-[(4R)-4-methyl-2-oxo-1,3,4,5-tetrahydro-1,5-benzodiazepin-6-yl]vinyl]phenyl]acetamide

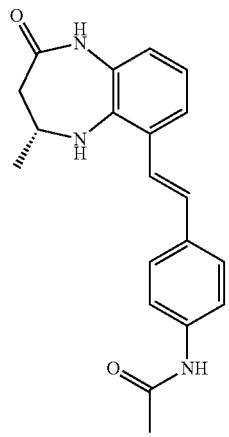 [SMILES: CC(=O)Nc1ccc(/C=C/c2cccc3c2N[C@H](C)CC(=O)N3)cc1]

To a solution of (R,E)-6-(4-aminostyryl)-4-methyl-4,5-dihydro-1H-benzo[b][1,4]diazepin-2(3H)-one (50 mg, 0.17 mmol) in AcOH (5 mL) was added Ac$_2$O (26 mg, 0.26 mmol). The mixture was stirred at 15° C. for 1 h. The mixture was filtered and concentrated in vacuo. The crude residue was purified by reverse phase chromatography (acetonitrile 8-38%/0.1% NH$_4$OH in water) to give the title compound (5 mg, 9%) as a yellow solid. $^1$H NMR (400 MHz, CD$_3$OD) δ 7.58-7.55 (m, 4H), 7.44-7.36 (m, 2H), 7.07-6.93 (m, 3H), 4.22-4.14 (m, 1H), 2.59-2.54 (m, 1H), 2.32-2.24 (m, 1H), 2.15 (s, 3H), 1.38 (d, J=6.4 Hz, 3H). LCMS M/Z (M+H) 336.

The following compound was prepared in a similar fashion to Example 20:

Example 21

| Example | Compound Name | NMR | m/z |
|---|---|---|---|
| Example 21 | N-[3-[(E)-2-[(4R)-4-methyl-2-oxo-1,3,4,5-tetrahydro-1,5-benzodiazepin-6-yl]vinyl]phenyl]acetamide | $^1$H NMR (400 MHz, DMSO-d$_6$) δ 7.86 (s, 1H), 7.48-7.32 (m, 5H), 7.08-6.95 (m, 3H), 4.20-4.18 (m, 1H), 2.59-2.55 (m, 1H), 2.33-2.17 (m, 1H), 2.17 (s, 3H), 1.39 (d, J = 6.0 Hz, 3H). | 336 |

Example 22

(4R)-6-(1-isopropylindol-5-yl)-4-methyl-1,3,4,5-tetrahydro-1,5-benzodiazepin-2-one

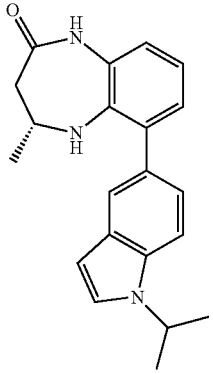 [SMILES: CC(C)n1ccc2cc(-c3cccc4c3N[C@H](C)CC(=O)N4)ccc21]

Step 1:

5-bromo-1-isopropyl-1H-indole

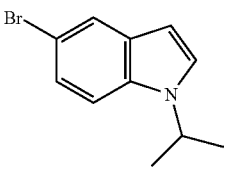

To a solution of 5-bromo-1H-indole (1.0 g, 5.10 mol) in DMF (10 mL) at 0° C. was added NaH (365 mg, 9.13 mmol). The mixture was stirred at 0° C. for 30 min before 2-iodopropane (1.3 g, 7.65 mmol) was added. The mixture was allowed to stir overnight at room temperature. The solution was poured into ice water (20 mL) and the yellow solid was collected by filtration. The precipitate was washed with water and dried in vacuo to give the title compound (1.0 g, 82%) as a yellow solid that required no further purification.

Step 2:

1-isopropyl-5-(4,4,5,5-tetramethyl-1,3,2-dioxaborolan-2-yl)-1H-indole

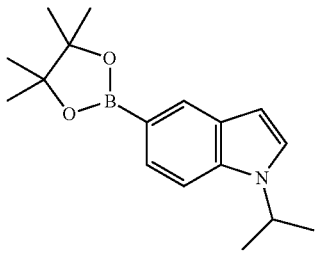 [SMILES: CC(C)n1ccc2cc(B3OC(C)(C)C(C)(C)O3)ccc21]

A mixture of 5-bromo-1-isopropyl-1H-indole (500 mg, 2.10 mmol), 4,4,4',4',5,5,5',5'-octamethyl-2,2'-bi(1,3,2-dioxaborolane) (793 mg, 3.12 mmol), AcOK (613 mg, 6.25 mmol) and [1,1'-bis(diphenylphosphino)ferrocene] dichloropalladium(II) (179 mg, 0.21 mmol) in dioxane (15 mL) was heated to 100° C. for 16 h under nitrogen atmosphere. After cooling the reaction to room temperature the solution was concentrated in vacuo. The crude residue was purified by silica gel chromatography (petroleum ether/EtOAc=5/1) to give the title compound (500 mg, 84%) as a yellow solid.

Step 3

(4R)-6-(1-isopropylindol-5-yl)-4-methyl-1,3,4,5-tetrahydro-1,5-benzodiazepin-2-one

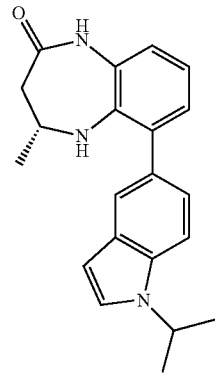 [SMILES: CC(C)n1ccc2cc(-c3cccc4c3N[C@H](C)CC(=O)N4)ccc21]

A mixture of (R)-6-bromo-4-methyl-4,5-dihydro-1H-benzo[b][1,4]diazepin-2(3H)-one (Intermediate A, 150 mg, 0.59 mmol), 1-isopropyl-5-(4,4,55-tetramethyl-1,3,2-dioxaborolan-2-yl)-1H-indole (252 mg, 0.88 mmol), $Cs_2CO_3$ (575 mg, 1.76 mmol) and 1,1'-bis(diphenylphosphion) ferrocene dichloride palladium(II) (51 mg, 0.06 mmol) in dioxane (5 mL) and $H_2O$ (1 mL) was irradiated in a microwave at 100° C. for 1 h. After cooling the reaction to room temperature the solvent was concentrated in vacuo. The crude residue was purified by reverse phase chromatography (acetonitrile 50-60%/0.1% $NH_4$—OH in water) to give the title compound (8 mg, 4%) as a yellow solid. $^1$H NMR (400 MHz, $CD_3OD$) δ 7.55-7.49 (m, 2H), 7.41 (d, J=3.2 Hz, 1H), 7.12-7.04 (m, 2H), 6.96-6.95 (m, 2H), 6.50 (d, J=3.2 Hz, 1H), 4.81-4.77 (m, 1H), 3.97-3.92 (m, 1H), 2.74-2.69 (m, 1H), 2.30-2.25 (m, 1H), 1.54 (d, J=6.8 Hz, 3H), 1.12 (d, J=6.4 Hz, 3H). LCMS M/Z (M+H) 334.

The following compounds were prepared in a similar fashion to Example 22:

Examples 23-27

| Example | Compound Name | NMR | m/z |
| --- | --- | --- | --- |
| Example 23 | (4R)-4-methyl-6-(1-methyl-2-oxo-indolin-5-yl)-1,3,4,5-tetrahydro-1,5-benzodiazepin-2-one | $^1$H NMR (400 MHz, $CD_3OD$) δ 7.30-7.27 (m, 2H), 7.09-7.06 (m, 1H), 6.99-6.94 (m, 3H), 3.98-3.91 (m, 1H), 3.61 (s, 2H), 3.25 (s, 3H), 2.72-2.67 (m, 1H), 2.30-2.25 (m, 1H), 1.15 (d, J = 6.4 Hz, 3H) | 322 |
| Example 24 | (4R)-4-methyl-6-(1,3,3-trimethyl-2-oxo-indolin-5-yl)-1,3,4,5-tetrahydro-1,5-benzodiazepin-2-one | $^1$H NMR (400 MHz, $CD_3OD$) δ 7.30-7.26 (m, 2H), 7.12-7.10 (m, 1H), 6.99-6.95 (m, 3H), 3.99-3.94 (m, 1H), 3.26 (s, 3H), 2.73-2.68 (m, 1H), 2.32-2.27 (m, 1H), 1.38-1.35 (m, 6H), 1.16 (d, J = 6.0 Hz, 3H) | 350 |
| Example 25 | (4R)-4-methyl-6-(1-methylindolin-5-yl)-1,3,4,5-tetrahydro-1,5-benzodiazepin-2-one | $^1$H NMR (400 MHz, $CD_3OD$) δ 7.02-6.90 (m, 5H), 6.60 (d, J = 8.0 Hz, 1H), 3.95-3.90 (m, 1H), 3.34-3.29 (m, 2H), 2.98-2.94 (m, 2H), 2.78 (s, 3H), 2.67-2.65 (m, 1H), 2.27-2.22 (m, 1H), 1.15 (d, J = 6.4 Hz, 3H) | 308 |
| Example 26 | (4R)-4-methyl-6-(1,3,3-trimethyl-2-oxo-indolin-6-yl)-1,3,4,5-tetrahydro-1,5-benzodiazepin-2-one | $^1$H NMR (400 MHz, DMSO-$d_6$) δ 9.59 (s, 1H), 7.43 (d, J = 7.6 Hz, 2H), 7.03-6.88 (m, 5H), 3.92 (s, 2H), 3.15 (s, 3H), 2.65-2.60 (m, 1H), 2.21-2.16 (m, 1H), 1.31 (s, 6H), 1.12 (d, J = 6.4 Hz, 3H) | 350 |
| Example 27 | (4R)-4-methyl-6-(1-methylindazol-5-yl)-1,3,4,5-tetrahydro-1,5-benzodiazepin-2-one | $^1$H NMR (400 MHz, DMSO-$d_6$) δ 9.57 (s, 1H), 8.08 (s, 1H), 7.74-7.70 (m, 2H), 7.39-7.36 (m, 1H), 6.94-6.89 (m, 3H), 4.08 (s, 3H), 3.90-3.83 (m, 1H), 3.81-3.80 (m, 1H), 2.65-2.60 (m, 1H), 2.21-2.18 (m, 1H), 1.07 (d, J = 6.4 Hz, 3H) | 307 |

Example 28

(4R)-6-(1-ethylindol-2-yl)-4-methyl-1,3,4,5-tetra-hydro-1,5-benzodiazepin-2-one

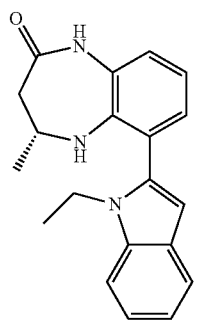 [SMILES: CCn1c(-c2cccc3c2N[C@H](C)CC(=O)N3)cc2ccccc21]

Step 1:

1-ethyl-1H-indole

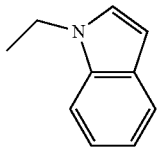

To a suspension of NaH (0.48 g, 12 mmol) in THF (50 mL) at 0° C. was added 1H-indole (1.17 g, 10 mmol) dropwise. The mixture was stirred at 0° C. for 30 min. Iodoethane (1.87 g, 12 mmol) was added and the resulting mixture was allowed to stir at 20° C. for an additional 2 h. Water (50 mL) was added and extracted with EtOAc (100 mL×3). The combined organic layers were dried over anhydrous Na$_2$SO$_4$, filtered and concentrated in vacuo. The crude residue was purified by silica gel chromatography (petroleum ether/EtOAc=5/1) to give the title compound (1.2 g, 83%) as colorless oil.

Step 2:

(1-ethyl-1H-indol-2-yl)boronic acid

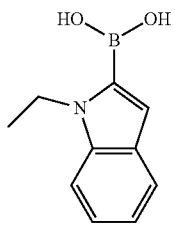

To a solution of 1-ethyl-1H-indole (580 mg, 4 mmol) in dry THF (20 mL) at 0° C. was added t-BuLi/THF (1.3 M, 5.2 mL, 4 mmol) dropwise. The mixture was stirred at 0° C. for 1 h and then triisopropyl borate (4.7 g, 25 mmol) was added. The mixture stirred at 20° C. for an additional 2 h. The mixture was quenched with sat. aq. ammoniunm chloride (30 mL) and extracted with EtOAc (50 mL×3). The combined organic layers were dried over anhydrous Na$_2$SO$_4$, filtered and concentrated in vacuo. The crude residue was purified by silica gel chromatography (petroleum ether/EtOAc=1/1) to give the title compound (0.5 g, 66%) as a white solid.

Step 3:

(4R)-6-(1-ethylindol-2-yl)-4-methyl-1,3,4,5-tetra-hydro-1,5-benzodiazepin-2-one

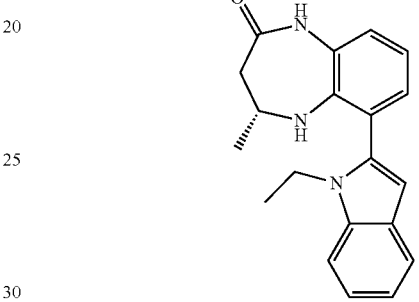

A mixture of (1-ethyl-1H-indol-2-yl)boronic acid (189 mg, 1.0 mmol), (R)-6-bromo-4-methyl-4,5-dihydro-1H-benzo[b][1,4]diazepin-2(3H)-one (Intermediate A, 254 mg, 1.0 mmol), Na$_2$CO$_3$ (212 mg, 2.0 mmol) and tetrakis(triphenylphosphine)palladium(O) (115 mg, 0.1 mmol) in dioxane/water (5 mL/mL) was heated to reflux temperature for 2 h. After cooling the reaction to room temperature, the solvent was concentrated in vacuo. Water (30 mL) was added and extracted with EtOAc (50 mL). The combined organic layers were dried over anhydrous Na$_2$SO$_4$, filtered and concentrated in vacuo. The crude residue was purified by reverse phase chromatography (acetonitrile 49-79%/0.1% NH$_4$OH in water) to give the title compound (44 mg, 14%) as a white solid. $^1$H NMR (400 MHz, CD$_3$OD) δ 7.59 (d, J=8.0 Hz, 1H), 7.45 (d, J=8.4 Hz, 1H), 7.21 (t, J=8.0 Hz, 1H), 7.11-7.07 (m, 3H), 7.00 (t, J=7.2 Hz, 1H), 6.47 (s, 1H), 4.10-3.95 (m, 2H), 3.94-3.86 (m, 1H), 2.69-2.65 (m, 1H), 2.38-2.33 (m, 1H), 1.18 (t, J=7.0 Hz, 1H), 1.11 (d, J=6.0 Hz, 3H). LCMS M/Z (M+H) 320.

The following compounds were prepared in a similar fashion to Example 28:

Examples 29-32

| Example | Compound Name | NMR | m/z |
|---|---|---|---|
| Example 29 | (4R)-4-methyl-6-(1-propylindol-2-yl)-1,3,4,5-tetrahydro-1,5- | $^1$H NMR (400 MHz, CD$_3$OD)δ7.60 (d, J = 8.0 Hz, 1H), 7.46 (d, J = 8.4 Hz, 1H), 7.22 (t, J = 8.0 Hz, 1H), 7.12-7.08 (m, 3H), 7.01 (t, J = 7.2 Hz, | 334 |

| Example | Compound Name | NMR | m/z |
|---|---|---|---|
| | benzodiazepin-2-one | 1H), 6.49 (s, 1H), 4.10-3.95 (m, 2H), 3.95-3.87 (m, 1H), 2.70-2.65 (m, 1H), 2.39-2.34 (m, 1H), 1.66-1.60 (m, 2H), 1.13 (d, J = 6.4 Hz, 1H), 0.74 (t, J = 7.2 Hz, 3H) | |
| Example 30 | (4R)-4-methyl-6-[1-(2-phenylethyl)indol-2-yl]-1,3,4,5-tetrahydro-1,5-benzodiazepin-2-one | $^1$H NMR (400 MHz, CD$_3$OD) δ7.60 (d, J = 7.6 Hz, 1H), 7.49 (d, J = 8.4 Hz, 1H), 7.22 (t, J = 8.0 Hz, 1H), 7.14-7.04 (m, 5H), 6.88 (t, J = 7.2 Hz, 1H), 6.78 (br.s, 1H), 6.72 (d, J = 7.6 Hz, 1H), 6.44 (s, 1H), 4.10-3.95 (m, 2H), 3.91-3.85 (m, 1H), 2.90 (br s, 2H), 2.63-2.61 (m, 1H), 2.34-2.29 (m, 1H), 1.09 (d, J = 6.4 Hz, 3H) | 396 |
| Example 31 | (4R)-6-[1-(2-ethoxyethyl)indol-2-yl]-4-methyl-1,3,4,5-tetrahydro-1,5-benzodiazepin-2-one | $^1$H NMR (400 MHz, CD$_3$OD) δ 7.59 (d, J = 7.6 Hz, 1H), 7.48 (d, J = 7.6 Hz, 1H), 7.20 (t, J = 6.4 Hz, 1H), 7.13-7.06 (m, 3H), 6.97 (t, J = 7.6 Hz, 1H), 6.48 (s, 1H), 4.21 (br s, 2H), 3.95-3.91 (m, 1H), 3.56 (t, J = 5.6 Hz, 2H), 3.31-3.24 (m, 2H), 2.69 (br s, 1H), 2.35-2.31 (m, 1H), 1.14 (d, J = 6.4 Hz, 3H), 1.01 (t, J = 6.6 Hz, 3H) | 364 |
| Example 32 | (4R)-6-[1-(2-methoxyethyl)indol-2-yl]-4-methyl-1,3,4,5-tetrahydro-1,5-benzodiazepin-2-one | $^1$H NMR (400 MHz, CD$_3$OD) δ 7.58 (d, J = 8.0 Hz, 1H), 7.48 (d, J = 8.0 Hz, 1H), 7.20 (t, J = 6.4 Hz, 1H), 7.11-7.06 (m, 3H), 6.98 (t, J = 7.6 Hz, 1H), 6.48 (s, 1H), 4.22 (br. s, 2H), 3.94-3.90 (m, 1H), 3.51 (br s, 2H), 3.11 (s, 3H), 2.70 (br s, 1H), 2.34-2.30 (m, 1H), 1.14 (d, J = 6.4 Hz, 3H) | 350 |

Example 33

(4R)-4-methyl-6-[1-methyl-3-(1-methylpyrazol-4-yl)indazol-4-yl]-1,3,4,5-tetrahydro-1,5-benzodiazepin-2-one

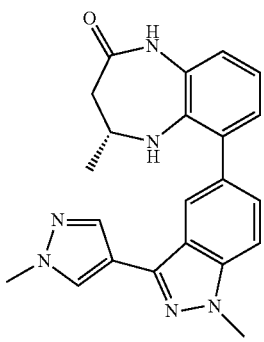 [SMILES: C[C@@H]1CC(=O)Nc2cccc(-c3ccc4c(c3)c(-c3cnn(C)c3)nn4C)c2N1]

Step 1:

5-bromo-1-methyl-3-(1-methyl-1H-pyrazol-4-yl)-H-indazole

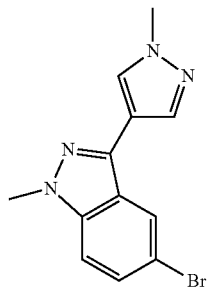 [SMILES: Cn1cc(-c2nn(C)c3ccc(Br)cc23)cn1]

A mixture of 5-bromo-3-iodo-1-methyl-1H-indazole (400 mg, 1.18 mmol), 1-methyl-4-(4,4,5,5-tetramethyl-1,3,2-dioxaborolan-2-yl)-1H-pyrazole (295.4 mg, 1.42 mmol), [1,1'-bis(diphenylphosphino)ferrocene]dichloropalladium(II) (86.2 mg, 0.118 mmol) and potassium carbonate (488.6 mg, 3.54 mmol) in dioxane/H$_2$O (5 mL/0.5 mL) was heated to 100° C. for 16 h under nitrogen atmosphere. After cooling the reaction to room temperature, water (5 mL) was added and the mixture was extracted with EtOAc (10 mL×3). The combined organic lagers were washed with brine, dried over anhydrous Na$_2$SO$_4$, filtered and concentrated in vacuo. The crude residue was purified by silica gel chromatography (petroleum ether/EtOAc=3/1 to 1/1) to give the title compound (270 g, 78.1%) as a white solid. LCMS M/Z (M+H) 291.

Step 2:

1-methyl-3-(1-methyl-1H-pyrazol-4-yl)-5-(4,4,5,5-tetramethyl-1,3,2-dioxaborolan-2-yl)-1H-indazole

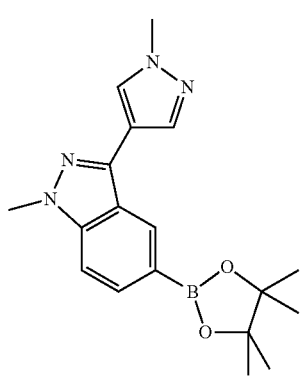

A mixture of 5-bromo-1-methyl-3-(1-methyl-1H-pyrazol-4-yl)-1H-indazole (270 mg, 0.798 mmol), 4,4,4',4',5,5,5',5'-octamethyl-2,2'-bi(1,3,2-dioxaborolane) (243.2 mg, 0.957 mmol), [1,1'-bis(diphenylphosphino)ferrocene]dichloropalladium(II)(58.3 mg, 0.0798 mmol) and potassium acetate (234.6 mg, 2.39 mmol) in dioxane (3 mL) was heated to 100° C. for 2 h under nitrogen atmosphere. After cooling the reaction to room temperature, water (5 mL) was added and the mixture was extracted with EtOAc (10 mL×3). The combined organic lagers were washed with brine, dried over anhydrous Na$_2$SO$_4$, filtered and concentrated in vacuo to give the title compound (320 mg, crude) as brown oil that required no further purification.

Step 3:

(4R)-4-methyl-6-[1-methyl-3-(1-methylpyrazol-4-yl) indazol-5-yl]-1,3,4,5-tetrahydro-1,5-benzodiazepin-2-one

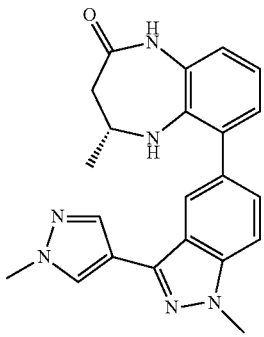 [SMILES: C[C@@H]1CC(=O)Nc2cccc(-c3ccc4c(c3)c(-c3cnn(C)c3)nn4C)c2N1]

A mixture of 1-methyl-3-(1-methyl-H-pyrazol-4-yl)-5-(4,4,5,5-tetramethyl-1,3,2-dioxaborolan-2-yl)-1H-indazole (320 mg, 0.946 mmol), (R)-6-bromo-4-methyl-4,5-dihydro-J1H-benzo[b][1,4]diazepin-2(3H)-one (Intermediate A, 193.1 mg, 0.757 mmol), bis(triphenylphosphine)palladium (II) dichloride (56 mg, 0.08 mmol) and potassium carbonate (313.4 mg, 2.271 mmol) in dioxane/H$_2$O (3 mL/0.3 mL) was heated to 100° C. for 12 h under nitrogen atmosphere. After cooling the reaction to room temperature, water (5 mL) was added and the mixture was extracted with EtOAc (10 mL×3). The combined organic lagers were washed with brine, dried over anhydrous Na$_2$SO$_4$, filtered and concentrated in vacuo. The crude residue was purified by reverse phase chromatography (acetonitrile 26-56%/0.2% formic acid in water) to give the title compound (28 mg, 10%) as a white solid. $^1$H NMR (400 MHz, CDCl$_3$) δ8.03 (s, 1H), 7.93-7.89 (m, 1H), 7.83-7.81 (m, 1H), 7.53-7.49 (m, 1H), 7.43-7.39 (m, 1H), 7.13-7.07 (m, 1H), 7.01-6.92 (m, 2H), 4.15 (s, 3H), 4.01 (s, 3H), 3.99-3.96 (m, 1H), 2.82-2.75 (m, 1H), 2.51-2.45 (m, 1H), 1.19 (d, J=6.27 Hz, 3H). LCMS M/Z (M+H) 387.

Example 34

(4R)-4-methyl-6-[3-(1-methylpyrazol-4-yl)-1H-indazol-5-yl]-1,3,4,5-tetrahydro-1,5-benzodiazepin-2-one

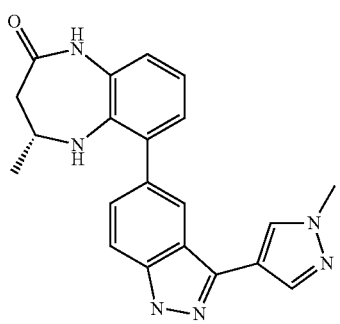

Step 1:

5-bromo-3-iodo-1H-indazole

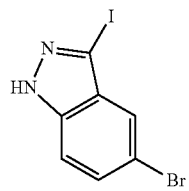

A mixture of 5-bromo-1H-indazole (2.5 g, 10.51 mmol), KOH (2.5 g, 10.51 mmol) and iodine (2.5 g, 10.51 mmol) in DMF (15 mL) at 20° C. was stirred for 16 h. The mixture was filtered and the filtrate was concentrated in vacuo. The crude residue was purified by silica gel chromatography (petroleum ether/EtOAc=3/1) to give the title compound (2.6 g, 81%) as a yellow solid.

Step 2:

5-bromo-3-(1-methyl-1H-pyrazol-4-yl)-1H-indazole

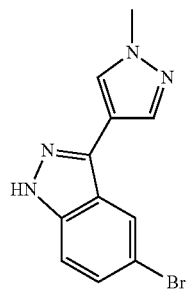

A mixture of 5-bromo-3-iodo-1H-indazole (8.0 g, 33.81 mmol), 1-methyl-4-(4,4,5,5-tetramethyl-1,3,2-dioxaborolan-2-yl)-1H-pyrazole (7.8 g, 50.72 mmol), K$_2$CO$_3$ (9.34 g, 67.60 mmol) and [1,1'-bis(diphenylphosphino)ferrocene]dichloropalladium(II)(2.47 g, 3.38 mmol) in dioxane (60 mL) and H$_2$O (20 mL) was heated to 110° C. for 16 h under nitrogen atmosphere. After cooling the reaction to room temperature, the mixture was filtered and the filtrate was concentrated in vacuo. The crude residue was purified by silica gel chromatography (DCM/MeOH=10/1) to give the title compound (6.3 g, 64%) as a brown solid.

Step 3:

3-(1-methyl-H-pyrazol-4-yl)-5-(4,4,5,5-tetramethyl-1,3,2-dioxaborolan-2-yl)-1H-indazole

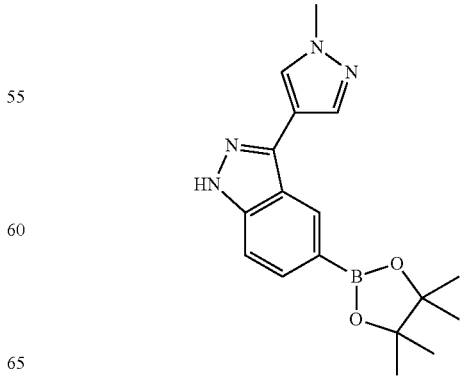

A mixture of 5-bromo-3-(1-methyl-1H-pyrazol-4-yl)-1 1-indazole (2.6 g, 7.41 mmol), 4,4,4',4',5,5,5',5'-octamethyl-2,2'-bi(1,3,2-dioxaborolane) (2.8 g, 11.10 mmol), NaOAc (1.2 g, 14.81 mmol) and [1,1'-bis(diphenylphosphino)ferrocene]dichloropalladium(II) (541 mg, 0.74 mol) in dioxane (25 mL) was heated to 110° C. for 16 h under nitrogen atmosphere. After cooling the reaction to room temperature, the mixture was filtered and the filtrate was concentrated in vacuo. The crude residue was purified by silica gel chromatography (petroleum ether/EtOAc=3/1) to give the title compound (900 mg, 30%) as a yellow solid.

Step 4:

(4R)-4-methyl-6-[3-(1-methylpyrazol-4-yl)-1H-indazol-5-yl]-1,3,4,5-tetrahydro-1,5-benzodiazepin-2-one

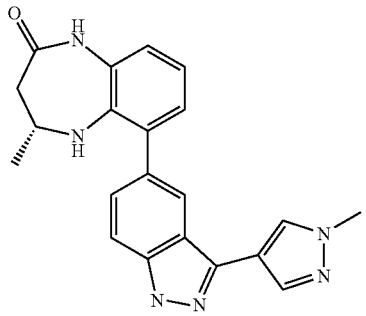

A mixture of 3-(1-methyl-1H-pyrazol-4-yl)-5-(4,4,5,5-tetramethyl-1,3,2-dioxaborolan-2-yl)-1H-indazole (400 mg, 1.00 mmol), (R)-6-bromo-4-methyl-4,5-dihydro-1H-benzo[b][1,4]diazepin-2(3H)-one (Intermediate A, 383 mg, 1.5 mmol), K₂CO₃ (276 mg, 2.00 mmol) and [1,1'-bis(diphenylphosphino)ferrocene]dichloropalladium(II) (73 mg, 0.10 mol) in dioxane (4 mL) and H₂O (2 mL) was irradiated in a microwave at 120° C. for 30 min. After cooling the reaction to room temperature, the mixture was filtered and the filtrate was concentrated in vacuo. The crude residue was purified by reverse phase chromatography (acetonitrile 7-15%/0.1% NH₄OH in water) to give the title compound (340 mg, 75%) as a yellow solid. ¹H NMR (400 MHz, DMSO-d₆) δ 13.03 (s, 1H), 9.59 (s, 1H), 8.41 (s, 1H), 7.96-7.91 (m, 2H), 7.60 (d, J=8.0 Hz, 1H), 7.34 (d, J=6.8 Hz, 1H), 6.97-6.89 (m, 3H), 3.89-3.83 (m, 5H), 2.61 (s, 1H), 2.20 (s, 1H), 1.05 (s, 3H). LCMS M/Z (M+H) 373.

Example 35

(4R)-6-[1-(2-hydroxyethyl)-3-(1-methylpyrazol-4-yl)indazol-5-yl]-4-methyl-1,3,4,5-tetrahydro-1,5-benzodiazepin-2-one

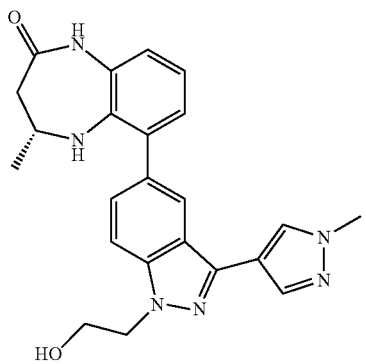

Step 1:

2-(3-(1-methyl-1H-pyrazol-4-yl)-5-(4,4,5,5-tetramethyl-1,3,2-dioxaborolan-2-yl)-1H-indazol-1-yl)ethanol

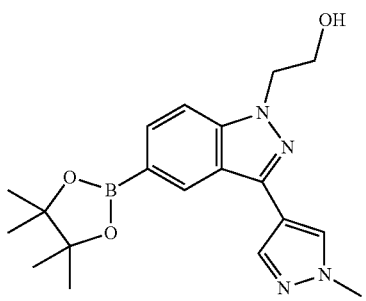

A mixture of 3-(1-methyl-1H-pyrazol-4-yl)-5-(4,4,5,5-tetramethyl-1,3,2-dioxaborolan-2-yl)-1H-indazole (330 mg, 1.02 mmol), 1,3-dioxolan-2-one (270 mg, 3.05 mmol) and Cs₂CO₃ (670 mg, 2.04 mmol) in DMF (3.0 mL) was heated to reflux temperature for 2 h under nitrogen atmosphere. After cooling the reaction to room temperature, water (20 mL) was added and the mixture was extracted with EtOAc (20 mL×3). The combined organic layers were dried over anhydrous Na₂SO₄, filtered and concentrated in vacuo. The crude residue was purified by prep-TLC (DCM/MeOH=20/1) to give the title compound (48 mg, 13%) as a white solid.

Step 2:

(4R)-6-[1-(2-hydroxyethyl)-3-(1-methylpyrazol-4-yl)indazol-5-yl]-4-methyl-1,3,4,5-tetrahydro-1,5-benzodiazepin-2-one

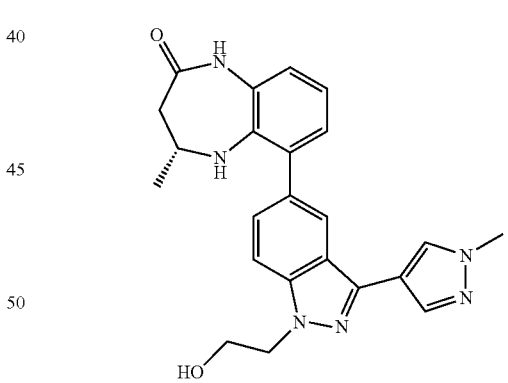

To a solution of 2-(3-(1-methyl-1H-pyrazol-4-yl)-5-(4,4,5,5-tetramethyl-1,3,2-dioxaborolan-2-yl)-1H-indazol-1-yl)ethanol (48 mg, 0.13 mmol), (R)-6-bromo-4-methyl-4,5-dihydro-1H-benzo[b][1,4]diazepin-2(3H)-one (Intermediate A, 35 mg, 0.13 mmol) and K₂CO₃ (37 mg, 0.27 mmol) in dioxane/H₂O=3:1 (3.0 mL) was added [1,1'-bis(diphenylphosphino)ferrocene]dichloropalladium(II) (10 mg, 14 umol). The mixture was stirred at reflux temperature for 30 min. After cooling the reaction to room temperature, water (10 mL) was added and extracted with EtOAc (10 mL×3). The combined organic layers were washed with sat. aq. sodium bicarbonate (10 mL×3), dried over anhydrous Na₂SO₄, filtered and concentrated in vacuo. The crude residue was purified by prep-TLC (DCM/MeOH=20/1) to give the title compound (4 mg, 5%) as a brown solid. $^1$H NMR (400 MHz, CDCl$_3$) δ 8.00 (s, 1H), 7.89 (s, 1H), 7.82 (s, 1H), 7.52 (d, J=8.0 Hz, 1H), 7.43-7.39 (m, 2H), 7.07 (d, J=8.0 z, 1H), 6.96-6.93 (m, 2H), 4.54 (t, J=4.8 Hz, 2H), 4.21-4.18 (m, 2H), 3.99 (s, 3H), 3.96 (m, 1H), 3.62 (s, 1H), 3.03 (t, J=4.8 Hz, 1H), 2.79 (m, 1H), 2.75 (m, 1H), 1.19 (d, J=6.0 Hz, 2H). LCMS M/Z (M±H) 417.

Examples 36 & 37

(R)-6-(1-((R)-sec-butyl)-3-cyclopropyl-1H-indazol-5-yl)-4-methyl-4,5-dihydro-1H-benzo[b][1,4]diazepin-2(3H)-one & (R)-6-(1-((S)-sec-butyl)-3-cyclopropyl-1H-indazol-5-yl)-4-methyl-4,5-dihydro-1H-benzo[b][1,4]diazepin-2(3H)-one

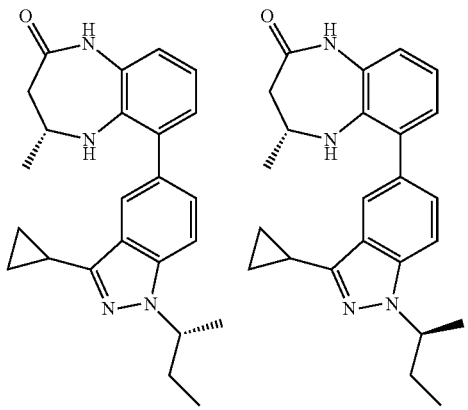 [SMILES: CC[C@@H](C)n1nc(C2CC2)c2cc(-c3cccc4c3N[C@H](C)CC(=O)N4)ccc21 ; CC[C@H](C)n1nc(C2CC2)c2cc(-c3cccc4c3N[C@H](C)CC(=O)N4)ccc21]

Step 1:

(5-bromo-2-fluorophenyl)(cyclopropyl)methanol

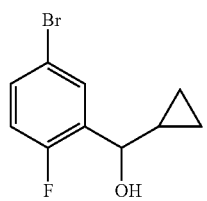 [SMILES: OC(c1cc(Br)ccc1F)C1CC1]

To 5-bromo-2-fluorobenzaldehyde (10 g, 49.3 mmol) in THF (60 mL) at 0° C. was added cyclopropyl magnesium bromide in THF (118 mL, 0.5 M). The mixture was stirred at room temperature for 3 h. The mixture was concentrated in vacuo and the residue was purified by silica gel chromatography (petroleum ether/EtOAc=5/1) to give the title product (5 g, 41%) as colorless oil. $^1$H NMR (400 MHz, CDCl$_3$) δ 7.70-7.68 (m, 1H), 7.40-7.34 (m, 1H), 6.95-6.90 (m, 1H), 4.34 (d, J=8.0 Hz, 1H), 1.23-1.21 (m, 1H), 0.65-0.62 (m, 1H), 0.55-0.45 (m, 3H).

Step 2:

(5-bromo-2-fluorophenyl)(cyclopropyl)methanone

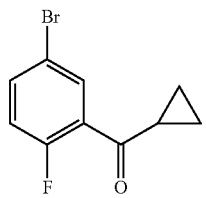 [SMILES: O=C(c1cc(Br)ccc1F)C1CC1]

A mixture of 5-bromo-2-fluorobenzaldehyde (5 g, 20.4 mmol) and MnO$_2$ (8.87 g, 102 mmol) in DCM (50 mL) was heated to 40° C. for 5 h. The mixture was filtered and concentrated in vacuo to give the title compound (4.8 g, 97%) as a brown solid that required no further purification. $^1$H NMR (400 MHz, CDCl$_3$) δ7.87-7.85 (m, 1H), 7.61-7.57 (m, 1H), 7.08-7.03 (m, 1H), 4.13-4.11 (m, 1H), 2.63-2.60 (m, 1H), 1.28-1.26 (m, 2H), 1.11-1.08 (m, 2H).

Step 3:

5-bromo-3-cyclopropyl-1H-indazole

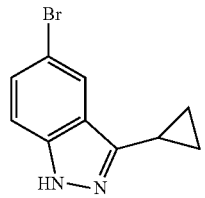 [SMILES: Brc1ccc2[nH]nc(C3CC3)c2c1]

A mixture of (5-bromo-2-fluorophenyl)(cyclopropyl)methanone (5.0 g, 20.60 mmol), hydrazine (4.0 g, 123.66 mmol), CuO (82 ing, 1.00 mmol) and K$_2$CO$_3$ (5.7 g, 41.01 mmol) in DMF (25 mL) was heated to 110° C. for 16 h. After cooling the reaction to room temperature, the mixture was filtered and the filtrate was concentrated in vacuo. The crude residue was purified by silica gel chromatography (petroleum ether/EtOAc=5/1) to give the title compound (2.7 g, 55%) as a brown oil.

Step 4:

5-bromo-1-(sec-butyl)-3-cyclopropyl-1H-indazole

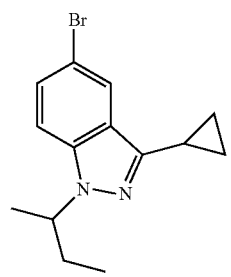 [SMILES: CCC(C)n1nc(C2CC2)c2cc(Br)ccc21]

To a solution of 5-bromo-3-cyclopropyl-1H-indazole (2.5 g, 10.51 mmol) in DMF (15 mL) at 0° C. was added NaH (304 mg, 12.61 mmo). The resulting mixture was stirred at 0° C. for 30 min under nitrogen atmosphere before 2-bromobutane (3.1 g, 15.77 mol) was added. The reaction mixture was stirred at room temperature for an additional 2 h. The mixture was poured into ice-water (50 mL) and extracted with EtOAc (50 mL×2). The combined organic layers were dried over anhydrous Na₂SO₄, filtered and concentrated in vacuo to give the crude product that was purified by silica gel chromatography (petroleum ether/EtOAc=20/1) to give the title compound (2.7 g, 87%) as a yellow solid.

Step 5:

1-(sec-butyl)-3-cyclopropyl-5-(4,4,5,5-tetramethyl-1,3,2-dioxaborolan-2-yl)-1H-indazole

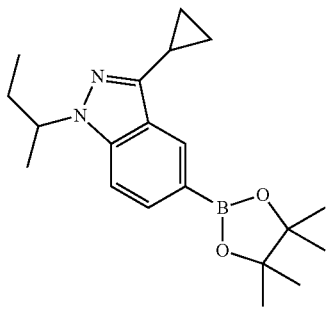 [SMILES: CCC(C)n1nc(C2CC2)c2cc(B3OC(C)(C)C(C)(C)O3)ccc21]

A mixture of 5-bromo-1-(sec-butyl)-3-cyclopropyl-1H-indazole (2.5 g, 8.51 mmol), 4,4,4',4',5,5,5',5'-octamethyl-2,2'-bi(1,3,2-dioxaborolane) (3.6 g, 12.80 mmol), KOAc (1.7 g, 17.01 mmol) and [1,1'-bis(diphenylphosphino)ferrocene] dichloropalladium(II) (625 mg, 0.85 mol) in dioxane (25 mL) was heated to 110° C. for 16 h under nitrogen atmosphere. After cooling the reaction to room temperature, the mixture was filtered and the filtrate was concentrated in vacuo. The crude residue was purified by silica gel chromatography (petroleum ether/EtOAc=10/1) to give the title product (940 mg, 32%) as a yellow solid.

Step 6:

(R)-6-(1-((R)-sec-butyl)-3-cyclopropyl-1H-indazol-5-yl)-4-methyl-4,5-dihydro-1H-benzo[b][1,4]diazepin-2(3H)-one & (R)-6-(1-((S)-sec-butyl)-3-cyclopropyl-H-indazol-5-yl)-4-methyl-4,5-dihydro-1H-benzo[b][1,4]diazepin-2(3H)-one A mixture of 1-(sec-butyl)-3-cyclopropyl-5-(4,4,5,5-tetramethyl-1,3,2-dioxaborolan-2-yl)-1H-indazole (400 mg, 1.2 mmol), (R)-6-bromo-4-methyl-4,5-dihydro-1H-benzo[b][1,4]diazepin-2(3H)-one (Intermediate A, 450 mg, 1.80 mmol), K₂CO₃ (325 mg, 2.41 mmol) and [1,1'-bis(diphenylphosphino)ferrocene]dichloropalladium(II) (86 mg, 0.12 mol) in dioxane (4 mL) and H₂O (2 mL) was irradiated in a microwave at 120° C. for 30 min. After cooling the reaction to room temperature, the mixture was filtered and the filtrate was concentrated in vacuo. The crude residue was purified by silica gel chromatography (petroleum ether/EtOAc=3/1) to give the racemic compound (400 mg, 88%) as a yellow solid that was separated using chiral SFC (AD (250 mm*30 mm, 10 um), 50% IPA+NH₃H₂O 80 mL/min) to give (R)-6-(1-((R)-sec-butyl)-3-cyclopropyl-1-indazol-5-yl)-4-methyl-4,5-dihydro-1H-benzo[b][1,4]diazepin-2(3H)-one (124 mg, first peak) as a white solid and (R)-6-(1-((S)-sec-butyl)-3-cyclopropyl-1H-indazol-5-yl)-4-methyl-4,5-dihydro-1 I-benzo[b][1,4]diazepin-2(3H)-one (145 mg, second peak) as a white solid. Absolute configuration was arbitrarily assigned to each enantiomer. Example 36: ¹H NMR (400 MHz, CD₃OD) δ7.71 (s, 1H), 7.62 (d, J=8.4 Hz, 1H), 7.37-7.34 (m, 1H), 7.08 (d, J=6.0 Hz, 1H), 7.02-6.98 (m, 2H), 4.65-4.61 (m, 1H), 4.03-3.99 (m, 1H), 2.78-2.74 (m, 1H), 2.36-2.27 (m, 2H), 2.15-2.04 (m, 1H), 1.95-1.85 (m, 1H), 1.54 (d, J=6.4 Hz, 3H), 1.19 (d, J=6.0 Hz, 3H), 1.06-1.03 (m, 4H), 0.78 (t, J=7.6 Hz, 3H). LCMS M/Z (M+H) 389. Example 37: ¹H NMR (400 MHz, CD₃OD) δ7.71 (s, 1H), 7.63 (d, J=8.4 Hz, 1H), 7.36 (d, J=8.0 Hz, 1H), 7.10-7.08 (m, 1H), 7.01-6.98 (m, 2H), 4.65-4.62 (m, 1H), 4.04-3.99 (m, 1H), 2.79-2.74 (m, 1H), 2.36-2.24 (m, 2H), 2.15-2.04 (m, 1H), 1.95-1.85 (m, 1H), 1.56 (d, J=6.4 Hz, 3H), 1.19 (d, J=6.4 Hz, 3H), 1.06-1.03 (m, 4H), 0.78 (t, J=7.6 Hz, 3H). LCMS M/Z (M+H) 389.

Example 38 & 39

(R)-3-(3-cyclopropyl-5-((R)-4-methyl-2-oxo-2,3,4,5-tetrahydro-1H-benzo[b][1,4]diazepin-6-yl)-1-indazol-1-yl)butanenitrile & (S)-3-(3-cyclopropyl-5-((R)-4-methyl-2-oxo-2,3,4,5-tetrahydro-1H-benzo[b][1,4]diazepin-6-yl)-1H-indazol-1-yl)butanenitrile

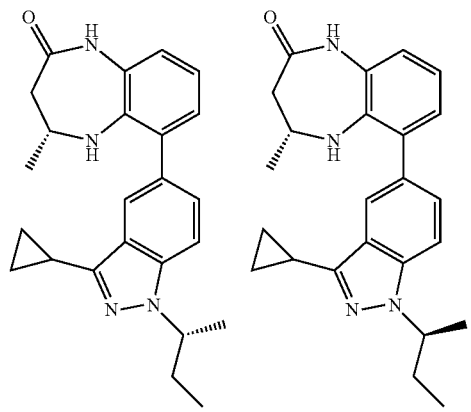 [SMILES: CC[C@@H](C)n1nc(C2CC2)c2cc(-c3cccc4c3N[C@H](C)CC(=O)N4)ccc21 ; CC[C@H](C)n1nc(C2CC2)c2cc(-c3cccc4c3N[C@H](C)CC(=O)N4)ccc21]

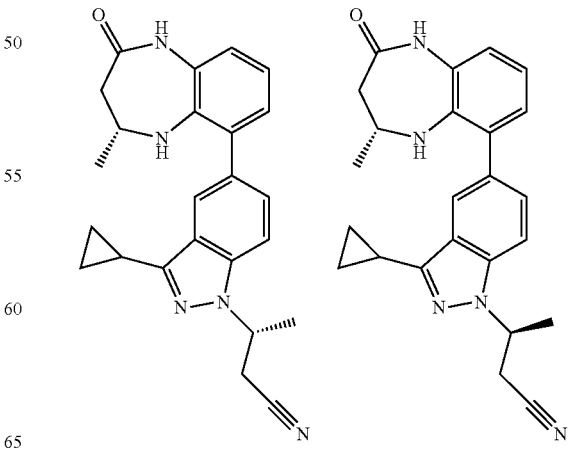

Step 1

3-(5-bromo-3-cyclopropyl-1H-indazol-1-yl)butanenitrile

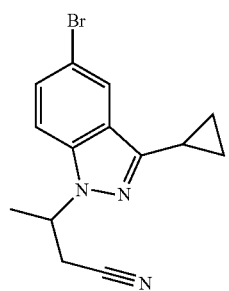 [SMILES: CC(CC#N)n1nc(C2CC2)c2cc(Br)ccc21]

To a solution of 5-bromo-3-cyclopropyl-1H-indazole (2.5 g, 10.51 mmol) in DMF (15 mL) at 0° C. was added NaH (304 mg, 12.61 mmo). The resulting mixture was stirred at 0° C. for 30 min under nitrogen atmosphere before 3-bromobutanenitrile (2.3 g, 15.81 mmol) was added. The reaction mixture stirred at room temperature for an additional 2 h. The mixture was poured into ice-water (50 mL) and extracted with EtOAc (50 mL×2). The combined organic layers were dried over anhydrous $Na_2SO_4$, filtered and concentrated in vacuo to give the crude product that was purified by silica gel chromatography (petroleum ether/EtOAc=20/1) to give the title compound (2.6 g, 81%) as a yellow solid.

Step 2:

3-(3-cylopropropyl-5-(4,4,5,5-tetramethyl-1,3,2-dioxaborolan-2-yl)-1H-indazol-1-yl)butanenitrile

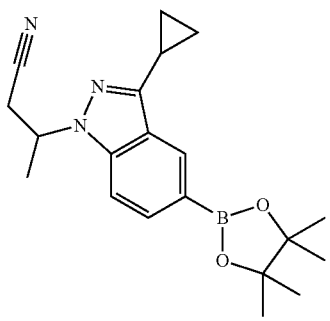 [SMILES: CC(CC#N)n1nc(C2CC2)c2cc(B3OC(C)(C)C(C)(C)O3)ccc21]

A mixture of 3-(5-bromo-3-cyclopropyl-1H-indazol-1-yl) butanenitrile (2.6 g, 7.41 mmol), 4,4,4',4',5,5,5',5'-octamethyl-2,2'-bi(1,3,2-dioxaborolane) (2.8 g, 11.10 mmol), NaOAc (1.2 g, 14.81 mmol) and [1,1'-bis(diphenylphosphino)ferrocene]dichloropalladium(IT) (541 mg, 0.74 mol) in dioxane (25 mL) was heated to 110° C. for 16 h under nitrogen atmosphere. After cooling the reaction to room temperature, the mixture was filtered and the filtrate was concentrated in vacuo. The crude residue was purified by silica gel chromatography (petroleum ether/EtOAc=10/1) to give the title product (900 mg, 30%) as a yellow solid.

Step 3:

(R)-3-(3-cyclopropyl-5-((R)-4-methyl-2-oxo-2,3,4,5-tetrahydro-1H-benzo[b][1,4]diazepin-6-yl)-1H-indazol-1-yl)butanenitrile & (S)-3-(3-cyclopropyl-5-((R)-4-methyl-2-oxo-2,3,4,5-tetrahydro-1-benzo[b][1,4]diazepin-6-yl)-1H-indazol-1-yl)butanenitrile

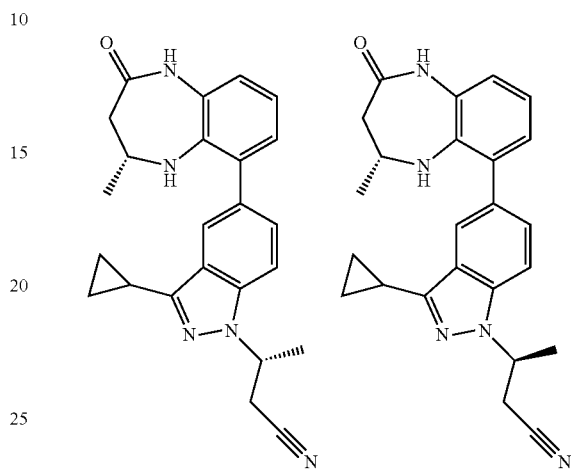

A mixture of 3-(3-cyclopropyl-5-(4,4,5,5-tetramethyl-1,3,2-dioxaborolan-2-yl)-1H-indazol-1-yl)butanenitrile (400 mg, 1.0 mmol), (R)-6-bromo-4-methyl-4,5-dihydro-1H-benzo[h][1,4]diazepin-2(3H)-one (Intermediate A, 383 mg, 1.5 mmol), $K_2CO_3$ (276 mg, 2.0 mmol) and [1,1'-bis(diphenylphosphino)ferrocene]dichloropalladium(II) (73 mg, 0.10 mol) in dioxane (4 mL) and $H_2O$ (2 mL) was irradiated in a microwave at 120° C. for 30 min. After cooling the reaction to room temperature, the mixture was filtered and the filtrate was concentrated in vacuo. The crude residue was purified by silica gel chromatography (petroleum ether/EtOAc=3/1) to give the racemic compound (340 mg, 75%) as a yellow solid that was separated using chiral SFC(OJ (250 mm*30 mm, 20 um), 35% MeOH+$NH_3H_2O$ 80 mL/min) to give (R)-3-(3-cyclopropyl-5-((R)-4-methyl-2-oxo-2,3,4,5-tetrahydro-1H-benzo[b][1,4]diazepin-6-yl)-1H-indazol-1-yl)butanenitrile (79.8 mg, first peak) as a white solid and (S)-3-(3-cyclopropyl-5-((R)-4-methyl-2-oxo-2,3,4,5-tetrahydro-1H-benzo[b][1,4]diazepin-6-yl)-1H-indazol-1-yl)butanenitrile (93.8 mg, second peak) as a white solid. Absolute configuration was arbitrarily assigned to each enantiomer. Example 38: $^1$H NMR (400 MHz, $CD_3OD$) δ 7.74 (s, 1H), 7.68 (d, J=8.4 Hz, 1H), 7.40 (d, J=7.2 Hz, 1H), 7.10-7.07 (m, 1H), 7.03-6.98 (m, 2H), 5.20-5.12 (m, 1H), 4.02-3.98 (m, 1H), 3.16-3.14 (m, 1H), 3.07-3.06 (m, 1H), 2.76-2.73 (m, 1H), 2.36-2.26 (m, 2H), 1.63 (d, J=6.8 Hz, 3H), 1.18 (d, J=6.0 Hz, 3H), 1.07-1.04 (m, 4H). LCMS M/Z (M+H) 400. Example 39: $^1$H NMR (400 MHz, $CD_3OD$) δ 7.75 (s, 1H), 7.68 (d, J=8.4 Hz, 1H), 7.40 (d, J=8.0 Hz, 1H), 7.10-7.08 (m, 1H), 7.02-7.00 (m, 2H), 5.19-5.14 (m, 1H), 4.03-3.98 (m, 1H), 3.16-3.14 (m, 1H), 3.08-3.07 (m, 1H), 2.77-2.74 (m, 1H), 2.36-2.30 (m, 2H), 1.63 (d, J=6.8 Hz, 3H), 1.18 (d, J=6.0 Hz, 3H), 1.08-1.05 (m, 4H). LCMS M/Z (M+H) 400.

Example 40

(4R)-6-[1-(2-hydroxy-1,1-dimethyl-ethyl)pyrazol-4-yl]-4-methyl-1,3,4,5-tetrahydro-1,5-benzodiazepin-2-one

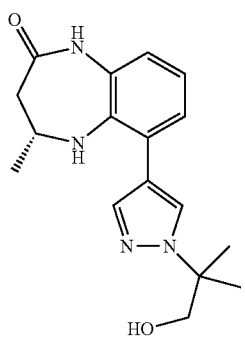 [SMILES: C[C@@H]1CC(=O)Nc2cccc(-c3cnn(C(C)(C)CO)c3)c2N1]

Step 1:

ethyl 2-methyl-2-(4-(4,4,5,5-tetra methyl-1,3,2-dioxaborolan-2-yl)-1H-pyrazol-1-yl)propanoate

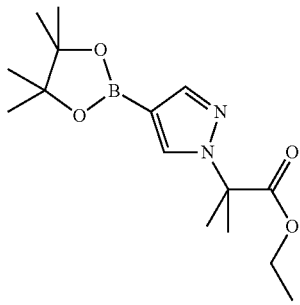 [SMILES: CCOC(=O)C(C)(C)n1cc(B2OC(C)(C)C(C)(C)O2)cn1]

To a solution of 4-(4,4,5,5-tetramethyl-1,3,2-dioxaborolan-2-yl)-1H-pyrazole (500 mg, 2.58 mmol) in DMF (5 mL) was added Cs₂CO₃ (1.68 g, 5.15 mmol) and ethyl 2-bromo-2-methylpropanoate (603 mg, 3.09 mmol). The reaction mixture was stirred at room temperature for 18 h. The mixture was concentrated in vacuo and the crude residue was purified by silica gel chromatography (petroleum ether/EtOAc=10/1) to give the title compound (300 mg, 38%) as a white solid.

Step 2:

2-methyl-2-(4-(4,4,5,5-tetramethyl-1,3,2-dioxaborolan-2-yl)-4H-pyrazol-1-yl)propan-1-ol

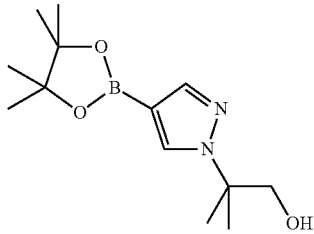 [SMILES: CC(C)(CO)n1cc(B2OC(C)(C)C(C)(C)O2)cn1]

To a solution of 2-methyl-2-(4-(4,4,5,5-tetramethyl-1,3,2-dioxaborolan-2-yl)-1H-pyrazol-1-yl)propanoate (300 mg, 0.98 mmol) in MeOH (5 mL) at room temperature was added NaBH₄ (230 mg, 5.84 mmol). The reaction mixture was stirred at room temperature for 48 h. The mixture was concentrated in vacuo. Water (10 mL) was added and extracted with EtOAc (30 mL×3). The combined organic layers were dried over Na₂SO₄, filtered and concentrated in vacuo to give the title compound (300 mg, crude) as a white solid that required no further purification.

Step 3:

(4R)-6-[(2-hydroxy-1,1-dimethyl-ethyl)pyrazol-4-yl]-4-methyl-1,3,4,5-tetrahydro-1,5-benzodiazepin-2-one

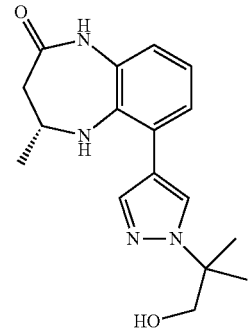 [SMILES: C[C@@H]1CC(=O)Nc2cccc(-c3cnn(C(C)(C)CO)c3)c2N1]

A mixture of 2-methyl-2-(4-(4,4,5,5-tetramethyl-1,3,2-dioxaborolan-2-yl)-1H-pyrazol-1-yl)propan-1-ol (300 mg, 0.88 mmol), potassium carbonate (163 mg, 1.18 mmol), [1,1'-bis(diphenylphosphino)ferrocene]dichloropalladium (II) (44 mg, 0.06 mmol) and (R)-6-bromo-4-methyl-4,5-dihydro-1H-benzo[b][1,4]diazepin-2(3H)-one (Intermediate A, 150 mg, 0.59 mmol) in dioxane (8 mL) and H₂O (2 mL) was heated to 100° C. for 18 h under nitrogen atmosphere. After cooling the reaction to room temperature, the mixture was concentrated in vacuo and the crude residue was purified by silica gel chromatography (DCM/MeOH=20/1). The residue was further purified by reverse phase chromatography (acetonitrile 24-54%/0.1% NH₄OH in water) to give the title compound (18 mg, 18%) as a white solid. ¹H NMR (400 MHz, DMSO-d₆) δ 9.50 (s, 1H), 7.92 (s, 1H), 7.59 (s, 1H), 6.99-6.95 (m, 1H), 6.85-6.79 (m, 2H), 4.92 (s, 1H), 4.05-4.03 (m, 1H), 3.96-3.94 (m, 1H), 3.59 (d, J=4.0 Hz, 2H), 2.20-2.15 (m, 1H), 1.50 (s, 6H), 1.18 (d, J=6.8 Hz, 3H). LCMS M/Z (M+H) 315.

Example 41

(4R)-6-(3-cyclopropyl-1-methyl-pyrazolo[3,4-b]pyridin-5-yl)-4-methyl-1,3,4,5-tetrahydro-1,5-benzodiazepin-2-one

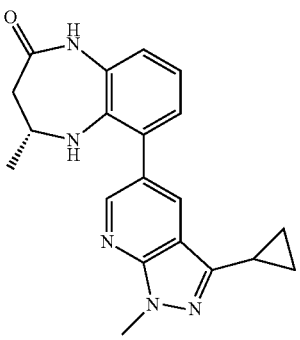 [SMILES: C[C@@H]1CC(=O)Nc2cccc(-c3cnc4c(c3)c(C3CC3)nn4C)c2N1]

Step 1:

(5-bromo-2-fluoropyridin-3-yl)(cyclopropyl)methanol

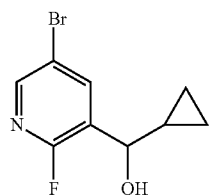 [SMILES: OC(c1cc(Br)cnc1F)C1CC1]

To a solution of 5-bromo-2-fluoronicotinaldehyde (2.0 g, 9.8 mmol) in TI-F (10 mL) at 0° C. was added cyclopropyl magnesium bromide in THF (0.5 M, 24.0 mL) dropwise. The mixture was allowed to stir at 0° C. for 2 h. The reaction mixture was washed with sat. aq. NH$_4$Cl and extracted with EtOAc (50 mL×3). The combined organic layers were dried over anhydrous Na$_2$SO$_4$, filtered and concentrated in vacuo. The crude residue was purified by silica gel chromatography (petroleum Ether/EtOAc=10/1) to give title compound (0.57 g, 24%) as a colorless oil. $^1$H NMR (400 MHz, CDCl$_3$) δ 8.16-8.10 (m, 2H), 4.30 (d, J=7.6 Hz, 1H), 2.14 (s, 1H), 1.17-1.14 (m, 1H), 0.65-0.49 (m, 4H).

Step 2:

5-bromo-2-fluoropyridin-3-yl)(cyclopropyl)methanone

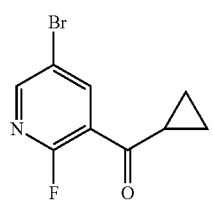 [SMILES: O=C(c1cc(Br)cnc1F)C1CC1]

A mixture of (5-bromo-2-fluoropyridin-3-yl)(cyclopropyl)methanol (0.57 g, 2.32 mmol) and MnO$_2$ (2.01 g, 23.2 mmol) in DCM (10.0 mL) was heated to 40° C. for 16 h. After cooling the reaction to room temperature, the mixture was filtered and concentrated in vacuo to give the title compound (485 mg, 86%) as a white solid.

Step 3:

5-bromo-3-cyclopropyl-1-methyl-1H-pyrazolo[3,4-b]pyridine

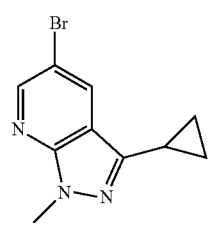

A mixture of (5-bromo-2-fluoropyridin-3-yl)(cyclopropyl)methanone (0.58 g, 2.38 mmol), methylhydrazine (40% aq., 1.37 g, 11.88 mmol), CuO (9.4 mg, 11.9 umol) and K$_2$CO$_3$ (656.9 mg, 4.75 mmol) in DMF (5.0 mL) was heated to 100° C. for 16 h. After cooling the reaction to room temperature, the mixture was filtered and the filtrate was concentrated in vacuo. The crude residue was purified by silica gel chromatography (petroleum ether/EtOAc=10/1) to give the title compound (0.37 g, 62%) as a white solid. LCMS M/Z (M+H) 254.

Step 4:

3-cyclopropyl-1-methyl-5-(4,4,5,5-tetramethyl-1,3,2-dioxaborolan-2-yl)-1H-pyrazolo[3,4-b]pyridine

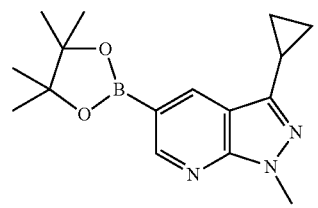 [SMILES: Cn1nc(C2CC2)c2cc(B3OC(C)(C)C(C)(C)O3)cnc21]

A mixture of 5-bromo-3-cyclopropyl-1-methyl-1H-pyrazolo[3,4-b]pyridine (320 mg, 1.27 mmol), 4,4,4',4',5,5,5',5'-octamethyl-2,2'-bi(1,3,2-dioxaborolane) (386.8 mg, 1.52 mmol), KOAc (249 mg, 2.54 mmol) and [1,1'-bis(diphenylphosphino)ferrocene]dichloropalladium(II) (93 mg, 120 umol) in dioxane (5 mL) was irradiated in a microwave at 120° C. for 30 min. After cooling the reaction to room temperature, water (20 mL) was added and the mixture extracted with EtOAc (20 mL×3). The combined organic layers were washed with sat. aq. sodium bicarbonate (10 mL×3), dried over Na$_2$SO$_4$, filtered and concentrated in vacuo. The crude residue was purified by prep-TLC (petroleum ether/EtOAc=10/1) to give the title compound (100 mg, 26%) as a white solid.

Step 5:

(4R)-6-(3-cyclopropyl-methyl-pyrazolo[3,4-b]pyridin-5-yl)-4-methyl-1,3,4,5-tetra hydro-1,5-benzodiazepin-2-one

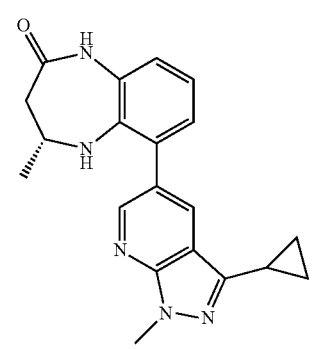 [SMILES: C[C@@H]1CC(=O)Nc2cccc(-c3cnc4c(c3)c(C3CC3)nn4C)c2N1]

A mixture of 3-cyclopropyl-1-methyl-5-(4,4,5,5-tetramethyl-1,3,2-dioxaborolan-2-yl)-1H-pyrazolo[3,4-b]pyridine (100 mg, 0.33 mmol), (R)-6-bromo-4-methyl-4,5-dihydro-1H-benzo[b][1,4]diazepin-2(3H)-one (Intermediate A, 85.3 mg, 0.33 mmol), K$_2$CO$_3$ (69.3 mg, 0.50 mmol) and [1,1'- bis(diphenylphosphino)ferrocene]dichloropalladium(II) (24 mg, 33 umol) in dioxane (1.5 mL) and H₂O (0.5 mL) was irradiated in a microwave at 120° C. for 30 min. After cooling the reaction to room temperature, water (20 mL) was added and extracted with EtOAc (20 mL×3). The combined organic layers were washed with sat, aq. sodium bicarbonate (10 mL×3), dried over anhydrous Na₂SO₄, filtered and concentrated in vacuo. The crude residue was purified by prep-TLC (petroleum ether/EtOAc==1/1) to give the title compound (21 mg, 18%) as a white solid. ¹H NMR (400 MHz, CDCl₃) δ 8.50 (s, 1H), 8.01 (s, 1H), 7.52 (s, 1H), 7.05-6.94 (m, 3H), 4.13 (s, 3H), 3.99 (m, 1H), 3.44 (s, 1H), 2.81-2.77 (m, 1H), 2.51-2.46 (m, 1H), 2.22-2.19 (m, 1H), 1.24 (d, J=6.0 Hz, 2H), 1.08-1.06 (m, 41H). LCMS M/Z (M+H) 348.

Example 42

(4R)-4-methyl-6-[1-(2-pyridyl)pyrazol-4-yl]-1,3,4,5-tetrahydro-1,5-benzodiazepin-2-one

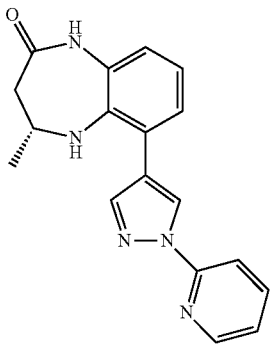 [SMILES: C[C@@H]1CC(=O)Nc2cccc(-c3cnn(-c4ccccn4)c3)c2N1]

Step 1:

2-(4-(4,4,5,5-tetramethyl-1,3,2-dioxaborolan-2-yl)-1H-pyrazol-1-yl)pyridine

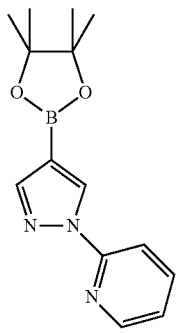 [SMILES: CC1(C)OB(c2cnn(-c3ccccn3)c2)OC1(C)C]

A mixture of 4-(4,4,5,5-tetramethyl-1,3,2-dioxaborolan-2-yl)-1H-pyrazole (500 mg, 2.57 mmol), 2-fluoropyridine (274 mg, 2.83 mmol) and cesium carbonate (1.67 g, 5.14 mmol) in DMF (10 mL) was heated to 100° C. for 16 h. After cooling the reaction to room temperature, the mixture was treated with EtOAc (20 mL) and water (20 mL), The organic layer was separated, washed by brine (20 mL), dried over anhydrous Na₂SO₄, filtered and concentrated in vacuo to give the title compound (500 mg, crude) as colorless oil that required no further purification.

Step 2:

(4R)-4-methyl-6-[1-(2-pyridyl)pyrazol-4-yl]-1,3,4,5-tetrahydro-1,5-benzodiazepin-2-one

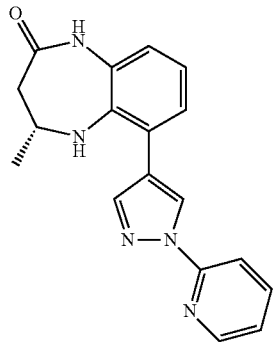 [SMILES: C[C@@H]1CC(=O)Nc2cccc(-c3cnn(-c4ccccn4)c3)c2N1]

A mixture of 2-(4-(4,4,5,5-tetramethyl-1,3,2-dioxaborolan-2-yl)-1H-pyrazol-1-yl)pyridine (250 mg, 0.92 mmol), (R)-6-bromo-4-methy-4,5-dihydro-1-benzo[b][1,4]diazepin-2(3H)-one (Intermediate A, 235 mg, 0.92 mmol), [1,1'-bis(diphenylphosphino)ferrocene]dichloropalladium(II), complex with dichloromethane (66 mg, 0.09 mmol) and potassium carbonate (149 mg, 1.84 mmol) in 1,4-dioxane (10 ml) and H₂O (2 mL) was heated to 100° C. for 4 h under nitrogen atmosphere. After cooling the reaction to room temperature, the mixture was filtered and the filtrate was concentrated in vacuo. The crude residue was purified by reverse phase chromatography (acetonitrile 30-60%/0.2% formic acid in water) to give the title compound (17 mg, 6%) as a white solid. ¹H NMR (400 MHz, CDCl₃) δ 8.70 (s, 1H), 8.46 (d, J=4.0 Hz, 1H), 8.05 (d, J=8.4 Hz, 1H), 7.89 (t, J=7.6 Hz, 1H), 7.85 (s, 1H), 7.38 (s, 1H), 7.28-7.22 (m, 1H), 7.14 (d, J=7.2 Hz, 1H), 7.00-6.85 (m, 2H), 4.15-3.99 (m, 1H), 3.84 (br s, 1H), 2.82-2.76 (m, 1H), 2.52-2.47 (m, 1H), 1.35 (d, J=6.4 Hz, 3H). LCMS M/Z (M+H) 320.

Example 43

(4R)-6-[1-(4-fluorophenyl)sulfonylindol-2-yl]-4-methyl-1,3,4,5-tetrahydro-1,5-benzodiazepin-2-one

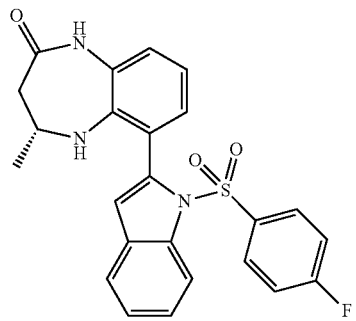 [SMILES: C[C@@H]1CC(=O)Nc2cccc(-c3cc4ccccc4n3S(=O)(=O)c3ccc(F)cc3)c2N1]

Step 1:

1-((4-fluorophenyl)sulfonyl)-1H-indole

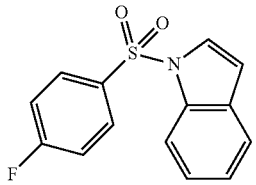 [SMILES: O=S(=O)(c1ccc(F)cc1)n1ccc2ccccc21]

To a suspension of NaH (0.49 g, 12.29 mmol) in THF (50 mL) at 0° C. was added 1H-indole (1.2 g, 10.24 mmol) dropwise. The mixture was stirred at 0° C. for 30 min before 4-fluorobenzene-1-sulfonyl chloride (2.33 g, 11.97 mmol) was added and the resulting mixture was allowed to stir at 20° C. for an additional 2 h. Water (50 mL) was added and the mixture was extracted with EtOAc (100 mL×3). The combined organic layers were dried over anhydrous Na₂SO₄, filtered and concentrated in vacuo. The crude residue was purified by silica gel chromatography (petroleum ether/EtOAc=5/1) to give the title compound (2.5 g, 89%) as colorless oil.

Step 2:

(1-((4-fluorophenyl)sulfonyl)-1H-indol-2-yl)boronic acid

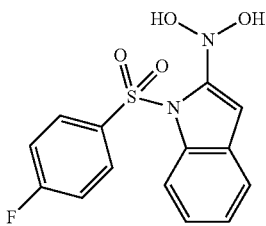 [SMILES: O=S(=O)(c1ccc(F)cc1)n1c(N(O)O)cc2ccccc21]

To a solution of 1-((4-fluorophenyl)sulfonyl)-1H-indole (1.1 g, 4.00 mmol) in dry THF (20 mL) at 0° C. was added t-BuLi/THF (1.3 M, 5.2 mL, 4.00 mmol) dropwise. The mixture was stirred at 0° C. for 1 h and then triisopropyl borate (4.7 g, 24.99 mmol) was added. The mixture was stirred at 20° C. for an additional 2 h. Then the mixture was quenched with sat. aq. ammonium chloride (30 mL) and extracted with EtOAc (50 mL×3). The combined organic layers were dried over anhydrous Na₂SO₄, filtered and concentrated in vacuo. The crude residue was purified by silica gel chromatography (petroleum ether/EtOAc=1/1) to give the title compound (0.4 g, 32%) as a white solid.

Step 3:

(4R)-6-[1-(4-fluorophenyl)sulfonylindol-2-yl]-4-methyl-1,3,4,5-tetrahydro-1,5-benzodiazepin-2-one

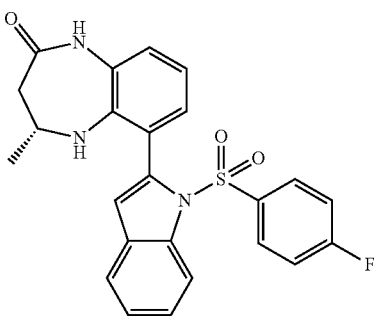 [SMILES: C[C@@H]1CC(=O)Nc2cccc(-c3cc4ccccc4n3S(=O)(=O)c3ccc(F)cc3)c2N1]

A mixture of (1-((4-fluorophenyl)sulfonyl)-1H-indol-2-yl)boronic acid (319 mg, 1.00 mmol), (R)-6-bromo-4-methyl-4,5-dihydro-1H-benzo[b][1,4]diazepin-2(3H)-one (Intermediate A, 255 mg, 1.00 mmol), Na₂CO₃ (212 mg, 2.00 mmol) and tetrakis(triphenylphosphine)palladium(O) (116 mg, 0.10 mmol) in dioxane/water (5 mL/1 mL) was heated to reflux temperature for 2 h. After cooling the reaction to room temperature, the solvent was concentrated in vacuo. Water (30 mL) was added and extracted with EtOAc (50 mL). The combined organic layers were dried over anhydrous Na₂SO₄, filtered and concentrated in vacuo. The crude residue was purified by reverse phase chromatography (acetonitrile 45-75%/0.1% NH₄OH in water) to give the title compound (45 mg, 10%) as a white solid. ¹H NMR (400 MHz, CDCl₃) δ 7.99-7.95 (m, 2H), 7.84 (s, 1H), 7.54 (s, 2H), 7.33-7.23 (m, 4H), 6.96-6.93 (m, 2H), 6.85-6.84 (m, 1H), 6.70 (s, 1H), 3.80 (s, 1H), 2.94 (s, 1H), 2.68-2.64 (m, 1H), 2.37-2.33 (m, 1H), 0.99-0.98 (m, 3H). LCMS M/Z (M+H) 450.

Example 44

4-[(4R)-4-methyl-2-oxo-1,3,4,5-tetrahydro-1,5-benzodiazepin-6-yl]benzenesulfonamide

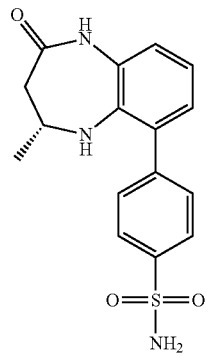 [SMILES: C[C@@H]1CC(=O)Nc2cccc(-c3ccc(S(N)(=O)=O)cc3)c2N1]

A mixture of (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 100 mg, 0.33 mmol), 4-bromobenzenesulfonamide (132 mg, 0.56 mmol), Cs₂CO₃ (323 mg, 0.99 mmol) and 1,1'-bis(diphenylphosphion) ferrocene dichloride palladium(II) (30 mg, 33 umol) in dioxane (3.5 mL) and H₂O (0.8 mL) was irradiated in a microwave at 110° C. for 1 h. After cooling the reaction to room temperature, the reaction mixture was concentrated in vacuo. The crude residue was purified by reverse phase chromatography (acetonitrile 30%/0.2% formic acid in water) to give the title compound (20 mg, 18%) as a white solid. ¹H NMR (400 MHz, CD₃OD) δ 8.00 (d, J=8.4 Hz, 2H), 7.55 (d, J=8.4 Hz, 2H), 7.03-6.97 (m, 3H), 4.02-3.96 (m, 1H), 2.76-2.70 (m, 1H), 2.31-2.27 (m, 1H), 1.17 (d, J=6.4 Hz, 3H). LCMS M/Z (M+H) 332.

The following compounds were prepared in a similar fashion to Example 44:

Examples 45-48

| Example | Compound Name | NMR | m/z |
|---|---|---|---|
| Example 45 | (4R)-6-(1-isopropyl-5-methyl-pyrazol-4-yl)-4-methyl-1,3,4,5-tetrahydro-1,5-benzodiazepin-2-one | $^1$H NMR (400 MHz, CD$_3$OD)δ 7.47 (s, 1H), 6.99-6.93 (m, 3H), 4.66-4.60 (m, 1H), 4.02-3.95 (m, 1H), 2.68-2.63 (m, 1H), 2.35-2.29 (m, 1H), 2.22 (s, 3H), 1.54-1.50 (m, 6H), 1.18 (d, J = 6.0 Hz, 3H) | 299 |
| Example 46 | (4R)-6-[4-(1-hydroxy-1-methyl-ethyl)phenyl]-4-methyl-1,3,4,5-tetrahydro-1,5-benzodiazepin-2-one | $^1$H NMR (400 MHz, CD$_3$OD) δ 7.65-7.61 (m, 2H), 7.36-7.33 (m, 2H), 7.01-6.98 (m, 3H), 4.02-3.94 (m, 1H), 2.76-2.71 (m, 1H), 2.32-2.27 (m, 1H), 1.60 (s, 6H), 1.18 (d, J = 6.4 Hz, 3H) | 311 |
| Example 47 | (4R)-4-methyl-6-[(E)-2-phenylprop-1-enyl]-1,3,4,5-tetrahydro-1,5-benzodiazepin-2-one | $^1$H NMR (400 MHz, CD$_3$OD) δ7.62-7.60 (m, 2H), 7.42-7.32 (m, 2H), 7.05-6.96 (m, 1H,) 6.96-6.95 (m, 1H), 6.95-6.94 (m, 2H), 6.82 (s, 1H), 4.14-4.09 (m, 1H), 2.59-2.54 (m, 1H), 2.34-2.32 (m, 1H), 2.12 (s, 3H), 1.30 (d, J = 6.4 Hz, 6H) | 293 |
| Example 48 | (4R)-4-methyl-6-[(Z)-2-phenylprop-1-enyl]-1,3,4,5-tetrahydro-1,5-benzodiazepin-2-one | $^1$H NMR (400 MHz, CD$_3$OD) δ7.17-7.14 (m, 4H), 6.77-6.74 (m, 1H), 6.62-6.61 (m, 2H), 6.53 (s, 1H), 3.88-3.83 (m, 1H), 2.48-2.43 (m, 1H), 2.30 (s, 3H), 2.20-2.15 (m, 1H), 1.30 (d, J = 6.4 Hz, 3H) | 293 |

Example 49

4-[(Z)-2-fluoro-1-methyl-2-[(4R)-4-methyl-2-oxo-1,3,4,5-tetrahydro-1,5-benzodiazepin-6-yl]vinyl]benzonitrile

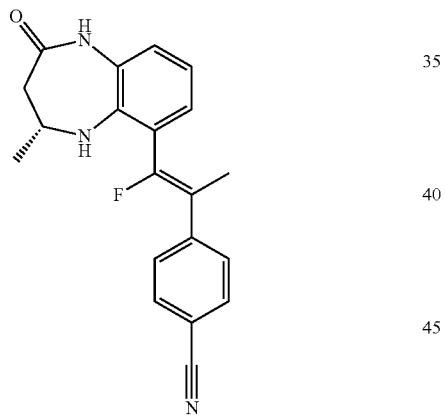

Step 1:

(E)-4-(1-bromo-1-fluoroprop-1-en-2-yl)benzonitrile

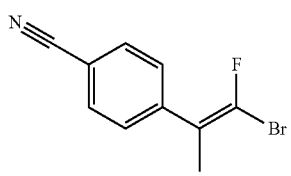

A mixture of 4-acetylbenzonitrile (500 mg, 3.44 mmol), triphenylphosphine (903 mg, 3.44 mmol) and tribromofluoromethane (933 mg, 3.44 mmol) in THF (20 mL) was stirred at 20° C. for 10 h. A solution of diethylzinc (1 M in hexane, 3.4 mL, 3.4 mmol) at 20° C. was added dropwise for 1 h. After being quenched by the addition of methanol (2 mL), the mixture was concentrated in vacuo. The crude residue was purified by silica gel chromatography (petroleum ether/EtOAc=10/1) to give the title product (500 mg, 60%) as a white solid.

Step 2:

4-[(Z)-2-fluoro-1-methyl-2-[(4R)-4-ethyl-2-oxo-1,3,4,5-tetrahydro-1,5-benzodiazepin-6-yl]vinyl]benzonitrile

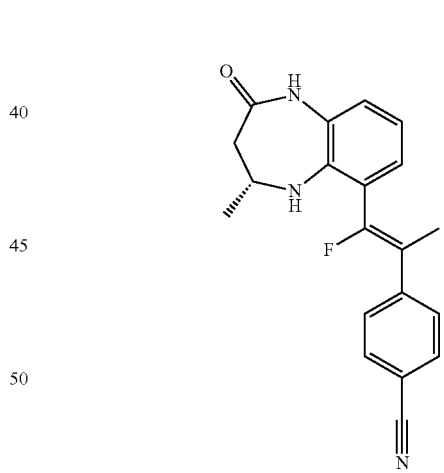

A mixture of (E)-4-(1-bromo-1-fluoroprop-1-en-2-yl) benzonitrile (200 mg, 0.83 mmol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 275 mg, 0.91 mmol), [1,1'-bis(diphenylphosphino)ferrocene]dichloropalladium(II) (60 mg, 0.08 mmol) and Cs$_2$CO$_3$ (547 mg, 1.68 mmol) in 15 mL (dioxane/H$_2$O=5/1) was heated to 100° C. for 1 h. After cooling the reaction to room temperature, the mixture was concentrated in vacuo and the crude residue was dissolved in EtOAc (20 mL), washed with water (15 mL×2). The combined organic layers were concentrated in vacuo and the crude product was purified by reverse phase chromatography (acetonitrile 40-60%/0.1% NH$_4$OH in water) to give the two olefinic isomers, which were further separated using chiral SFC (SFC80; Chiralpak OJ 250×30 mm I.D., 5 um; Supercritical CO$_2$/IPA+NH$_3$.H$_2$O=45/55; 80 mL/min) to give the title compound (10 mg, 3%). $^1$H NMR (400 MHz, DMSO-d$_6$) δ 9.63 (s, 1H), 7.88 (d, J=8.4 Hz, 2H), 7.79 (d, J=8.0 Hz, 2H), 7.09-7.01 (m, 2H), 6.90-6.86 (m, 1H), 4.70 (s, 1H), 3.98 (m, 1H), 2.50-2.46 (m, 1H), 2.23-2.21 (m, 1H), 1.89 (s, 3H), 1.20 (d, J=6.0 Hz, 3H). LCMS M/Z (M+H) 336.

The following compounds were prepared in a similar fashion to Example 49:

Examples 50-52

To a solution of 5-bromo-3-methyl-1H-pyrazole (200 mg, 1.24 mmol) in acetonitrile (15 mL) was added K$_2$CO$_3$ (340 mg, 2.48 mmol). The mixture was stirred at room temperature for 30 min before benzyl bromide (235 mg, 1.37 mmol) was added and heated to 80° C. for 3 h. After cooling the reaction to room temperature, the reaction mixture was filtered and the filtrate was concentrated in vacuo. Water (20 mL) was added and extracted with EtOAc (35 mL×3). The combined organic layers were dried over anhydrous Na$_2$SO$_4$, filtered and concentrated in vacuo to give the title compound (240 mg, crude) that required no further purification.

| Example | Compound Name | NMR | m/z |
|---|---|---|---|
| Example 50 | 4-[(Z)-2-fluoro-2-[(4R)-4-methyl-2-oxo-1,3,4,5-tetrahydro-1,5-benzodiazepin-6-yl]vinyl]benzonitrile | $^1$H NMR (400 MHz, CD$_3$OD) δ 7.84-7.74 (m, 4H), 7.29-7.22 (m, 1H), 7.10-7.01 (m, 2H), 6.28 (d, J = 38.0 Hz, 1H), 4.16-4.11 (m, 1H), 2.69-2.64 (m, 1H), 2.36-2.34 (m, 1H), 1.37 (d, J = 6.0 Hz, 3H) | 322 |
| Example 51 | 4-[(E)-2-fluoro-1-methyl-2-[(4R)-4-methyl-2-oxo-1,3,4,5-tetrahydro-1,5-benzodiazepin-6-yl]vinyl]benzonitrile | $^1$H NMR (400 MHz, DMSO-d$_6$) δ 9.52 (s, 1H), 7.67 (d, J = 8.0 Hz, 2H), 7.32 (d, J = 8.0 Hz, 2H), 6.87-6.85 (m, 1H), 6.72-6.61 (m, 2H), 4.81-4.78 (m, 1H), 3.72 (m, 1H), 2.29-2.26 (m, 1H), 2.15 (s, 3H), 2.07-2.04 (m, 1H), 1.17 (d, J = 6.0 Hz, 3H) | 336 |
| Example 52 | (4R)-4-methyl-6-[(E)-1-methyl-2-phenyl-vinyl]-1,3,4,5-tetrahydro-1,5-benzodiazepin-2-one | $^1$H NMR (400 MHz, DMSO-d$_6$) δ 9.52 (s, 1H), 7.46-7.40 (m, 4H), 7.38-7.27 (m, 1H), 6.90-6.80 (m, 3H), 6.43 (s, 1H), 4.25 (d, J = 2.8 Hz, 1H), 3.95 (s, 1H), 2.57-2.53 (m, 1H), 2.18-2.13 (m, 4H), 1.23 (d, J = 6.8 Hz, 3H) | 293 |

Example 53

(4R)-6-(1-benzyl-5-methyl-pyrazol-3-yl)-4-methyl-1,3,4,5-tetrahydro-1,5-benzodiazepin-2-one

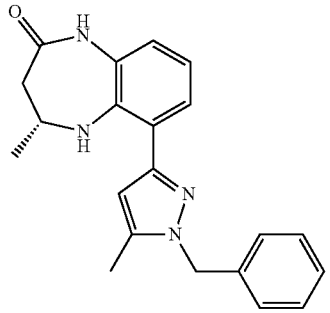 [SMILES: Cc1cc(-c2cccc3c2N[C@H](C)CC(=O)N3)nn1Cc1ccccc1]

Step 1:

1-benzyl-5-bromo-3-methyl-1H-pyrazole

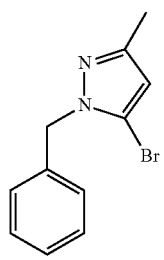

Step 2:

(4R)-6-(1-benzyl-5-methyl-pyrazol-3-yl)-4-methyl-1,3,4,5-tetrahydro-1,5-benzodiazepin-2-one

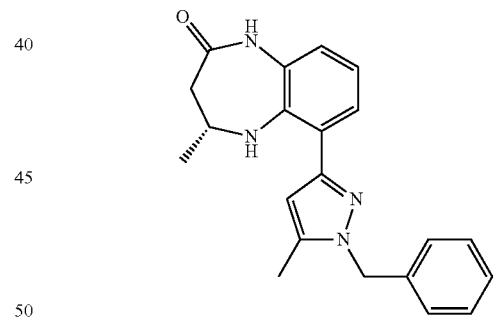

A mixture of 1-benzyl-5-bromo-3-methyl-1H-pyrazole (150 mg, 0.60 mmol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 200 mg, 0.66 mmol), cesium carbonate (390 mg, 1.20 mmol) and [1,1'-bis(diphenylphosphino)ferrocene] dichloropalladium(II) (22 mg, 0.03 mmol) in dioxane (4 mL) and H$_2$O (1 mL) was irradiated in a microwave at 110° C. for 30 min. After cooling the reaction to room temperature, the reaction mixture was filtered and the filtrate was concentrated in vacuo. The crude residue was purified by reverse phase chromatography (acetonitrile 40-60%/0.1% HCl in water) to give the title compound (18 mg, 8%). $^1$H NMR (400 MHz, CD$_3$OD) δ 7.41-7.40 (m, 4H), 7.34-7.32 (m, 2H), 6.95-6.94 (m, 2H), 6.46 (s, 1H), 5.36 (s, 2H), 3.92-3.91 (m, 1H), 2.31 (s, 3H), 2.18-2.16 (m, 1H), 2.54-2.53 (m, 1H), 2.36 (s, 3H), 2.28-2.25 (m, 1H), 1.09 (d, J=6.0 Hz, 3H). LCMS M/Z (M+H) 347.

The following compound was prepared in a similar fashion to Example 53:

| Example | Compound Name | NMR | m/z |
|---|---|---|---|
| Example 54 | (4R)-6-(3-benzyl-1-methyl-pyrazol-4-yl)-4-methyl-1,3,4,5-tetrahydro-1,5-benzodiazepin-2-one | $^1$H NMR (400 MHz, DMSO-$d_6$) δ 9.50 (s, 1H), 7.67 (s, 1H), 7.18-7.10 (m, 3H), 7.02 (d, J = 7.2 Hz, 2H), 6.86-6.85 (m, 1H), 6.75-6.73 (m, 2H), 6.07 (s, 1H), 3.92 (s, 1H), 3.83 (s, 3H), 3.76-3.63 (m, 2 H), 2.43-2.41 (m, 1H), 2.10-2.08 (m, 1H), 1.01 (d, J = 6.4 Hz, 3H) | 347 |

Example 55

(4R)-4-methyl-6-(1-methyl-3-propyl-indol-2-yl)-1,3,4,5-tetrahydro-1,5-benzodiazepin-2-one

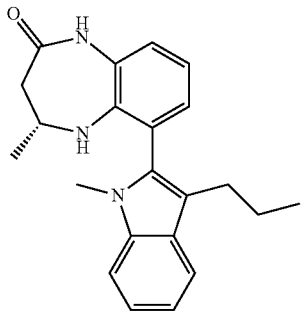 [SMILES: CCCc1c(-c2cccc3c2N[C@H](C)CC(=O)N3)n(C)c2ccccc12]

Step 1:

(E)-1-methyl-3-(prop-1-en-1-yl)-1H-indole

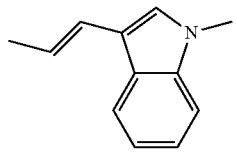

To a solution of ethyltriphenylphosphonium bromide (3.7 g, 10.0 mmol) in dry THF (30 mL) at 0° C. was added t-BuLi/THF (1.3 M, 7.7 mL, 10.0 mmol) dropwise. The mixture was stirred at 0° C. for 1 h before 1-methyl-1H-indole-3-carbaldehyde (1.32 g, 8.33 mmol) was added. The mixture was stirred at 20° C. for an additional 2 h. The mixture was quenched with sat. aq. ammonium chloride (30 mL) and extracted with EtOAc (30 mL×3). The combined organic layers were dried over anhydrous Na$_2$SO$_4$, filtered and concentrated in vacuo. The crude residue was purified by silica gel chromatography (petroleum ether/EtOAc=10/1) to give the title compound (0.9 g, 63%) as a white solid.

Step 2:

1-methyl-3-propyl-1H-indole

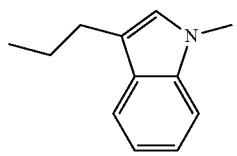

To a solution of (E)-1-methyl-3-(prop-1-en-1-yl)-1H-indole (342 mg, 2.0 mmol) in MeOH (10 mL) and EtOAc (10 mL) was added Pd/C (5% wt, 0.1 g). The mixture was stirred at 20° C. for 1 h under hydrogen atmosphere (15 psi). Then the mixture was filtered and concentrated in vacuo to give the title compound (250 mg, 72%) as colorless oil.

Step 3:

2-bromo-1-methyl-3-propyl-1H-indole

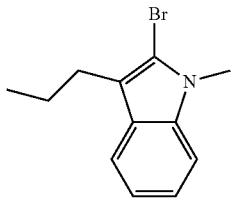

A mixture of 1-methyl-3-propyl-1H-indole (250 mg, 1.45 mmol), copper(II) bromide (650 mg, 2.9 mmol) and tetrabutylammonium bromide (48 mg, 0.15 mmol) in DCE (5 mL) and water (0.5 mL) was stirred at 20° C. for 2 h. The mixture was filtered and concentrated in vacuo. The crude residue was purified by silica gel chromatography (petroleum ether/EtOAc=10/1) to give the title compound (200 mg, 55%) as a colorless oil.

Step 4:

(4R)-4-methyl-6-(1-methyl-3-propyl-indol-2-yl)-1,3,4,5-tetrahydro-1,5-benzodiazepin-2-one

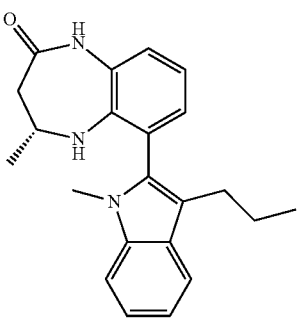 [SMILES: CCCc1c(-c2cccc3c2N[C@H](C)CC(=O)N3)n(C)c2ccccc12]

A mixture of 2-bromo-1-methyl-3-propyl-1H-indole (200 mg, 0.8 mmol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 242 mg, 0.8 mmol), Na$_2$CO$_3$ (170 mg, 1.6 mmol), and tetrakis(triphenylphosphine)palladium(0) (92 mg, 0.08 mmol) were dissolved in dioxane/ water (5 mL/1 mL). The mixture was heated to reflux temperature for 2 h. After cooling the reaction to room temperature, the solvent was concentrated in vacuo. Water (10 mL) was added and the mixture was extracted with EtOAc (10 mL×2). The combined organic layers were dried over anhydrous Na$_2$SO$_4$, filtered and concentrated in vacuo. The crude residue was purified by reverse phase chromatography (acetonitrile 47-77%/0.1% NH$_4$OH in water) to give the title compound (15 mg, 5%) as a white solid. $^1$H NMR (400 MHz, CD$_3$OD) δ 7.61 (d, J=8.0 Hz, 1H), 7.40 (d, J=8.8 Hz, 1H), 7.23 (t, J=8.0 Hz, 1H), 7.12-7.09 (m, 2H), 7.04-7.00 (m, 2H), 3.93-3.85 (m, 1H), 3.49 (s, 3H), 2.75-2.65 (m, 2H), 2.50-2.35 (m, 2H), 1.63-1.58 (m, 2H), 1.12-1.03 (m, 3H), 0.90-0.83 (m, 3H). LCMS M/Z (M+H) 348.

Example 56

(4R)-6-(1-tert-butyl-3-methyl-indol-2-yl)-4-methyl-1,3,4,5-tetrahydro-1,5-benzodiazepin-2-one

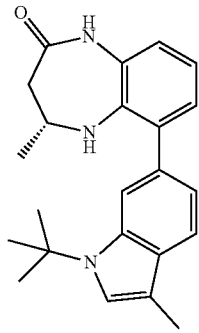 [SMILES: Cc1cn(C(C)(C)C)c2cc(-c3cccc4c3N[C@H](C)CC(=O)N4)ccc12]

Step 1:

2-(2-fluorophenyl)-2-methyloxirane

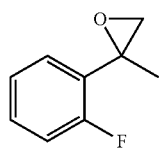

To trimethylsulfonium iodide (6.1 g, 30 mmol) in THF (100 mL) at 0° C. was added t-BuOK (3.4 g, 30 mmol). The mixture was warmed to room temperature and stirred for 5 min before 1-(2-fluorophenyl)ethanone (3.5 g, 25 mmol) was added. The mixture was stirred at room temperature for an additional 3 h. The precipitate was filtered, and the filtrate was concentrated in vacuo. The crude residue was purified by silica gel chromatography (petroleum ether/EtOAc=20/1) to give the title compound (3.0 g, 79%) as colorless oil.
Step 2:

1-(tert-butyl)-3-methyl-1H-indole

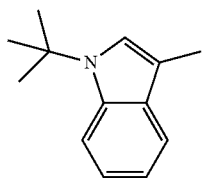

A mixture of 2-(2-fluorophenyl)-2-methyloxirane (1.5 g, 10 mmol) and 2-methylpropan-2-amine (1.46 g, 20 mmol) in DMF (5.0 mL) was irradiated in a microwave at 240° C. for 2 h. After cooling the reaction to room temperature, water (20 mL) was added and extracted with EtOAc (30 mL×3). The combined organic layers were dried over anhydrous Na$_2$SO$_4$, filtered and concentrated in vacuo. The crude residue was purified by silica gel chromatography (petroleum ether/EtOAc=20/1) to give the title compound (1.0 g, 53%) as colorless oil.
Step 3:

6-bromo-1-(tert-buty)-3-methyl-1H-indole

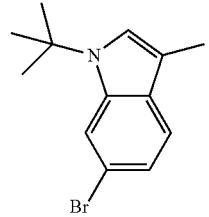

To a solution of 1-(tert-butyl)-3-methyl-1H-indole (561 mg, 3.0 mmol) in (trifluoromethyl)benzene (30 mL) was added N-bromosuccinimide (534 mg, 3.0 mmol). The mixture was heated to reflux temperature for 2 h. After cooling the reaction to room temperature, the mixture was concentrated in vacuo. The crude residue was purified by silica gel chromatography (petroleum ether/EtOAc=10/1) to give the title compound (500 mg, 63%) as colorless oil.
Step 4:

(4R)-6-(1-tert-butyl-3-methyl-indol-2-yl)-4-methyl-1,3,4,5-tetrahydro-1,5-benzodiazepin-2-one

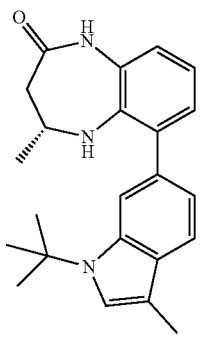

A mixture of 6-bromo-1-(tert-butyl)-3-methyl-1H-indole (130 mg, 0.5 mmol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 150 mg, 0.5 mmol), bis(triphenylphosphine)palladium(II) dichloride (70 mg, 0.1 mmol) and Na$_2$CO$_3$ (106 mg, 1.0 mmol) in MeCN (5.0 mL) and H$_2$O (1.0 mL) was irradiated in a microwave at 130° C. for 30 min. After cooling the reaction to room temperature, the solvent was concentrated in vacuo. The crude residue was purified by prep-TLC (petroleum ether/EtOAc=1/1) to give the title compound (27 mg, 15%) as a white solid. $^1$H NMR (400 MHz, CDCl$_3$) δ 7.69-7.64 (m, 1H), 7.55 (s, 1H), 7.37 (s, 1H), 7.14-7.08 (m, 3H), 6.96-6.91 (m, 2H), 3.97 (s, 1H), 3.86 (s, 1H), 2.83-2.79 (m, 1H), 2.46-2.42 (m, 1H), 2.36-2.32 (m, 3H), 1.76-1.72 (m, 9H), 1.22-1.18 (m, 3H). LCMS M/Z (M+H) 362.

Example 57

(4R)-6-(3-cyclopropyl-1-methyl-indazol-5-yl)-4-methyl-1,3,4,5-tetrahydro-1,5-benzodiazepin-2-one

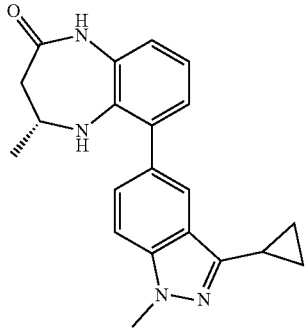 [SMILES: C[C@@H]1CC(=O)Nc2cccc(-c3ccc4c(c3)c(C3CC3)nn4C)c2N1]

Step 1:

5-bromo-3-cyclopropyl-1-methy-1H-indazole

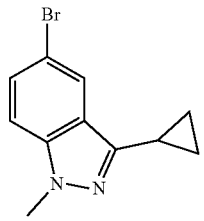

A mixture of (5-bromo-2-fluorophenyl)(cyclopropyl)methanone (5.0 g, 20.60 mmol), methylhydrazine (40% aq., 5.7 g, 123.01 mmol), CuO (82 mg, 1.00 mmol) and $K_2CO_3$ (5.7 g, 41.01 mmol) in DMF (25 mL) was heated to 110° C. for 16 h. After cooling the reaction to room temperature, the mixture was filtered and the filtrate was concentrated in vacuo. The crude residue was purified by silica gel chromatography (petroleum ether/EtOAc=10/1) to give the title product (2.7 g, 52%) as a brown oil. $^1$H NMR (400 MHz, CDCl$_3$) δ 7.85 (s, 1H), 7.40 (d, J=8.8 Hz, 1H), 7.16 (d, J=8.8 Hz, 1H), 3.93 (s, 3H), 2.14-2.09 (m, 1H), 1.01-1.00 (m, 4H).

Step 2:

(4R)-6-(3-cyclopropyl-1-methyl-indazol-5-yl)-4-methyl-1,3,4,5-tetrahydro-1,5-benzodiazepin-2-one

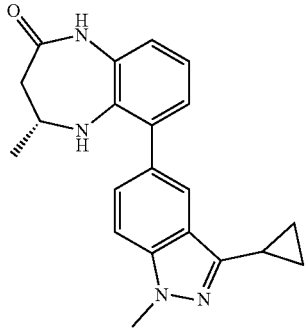 [SMILES: C[C@@H]1CC(=O)Nc2cccc(-c3ccc4c(c3)c(C3CC3)nn4C)c2N1]

A mixture of 5-bromo-3-cyclopropyl-1-methyl-1H-indazole (199 mg, 0.79 mol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 200 mg, 0.66 mmol), potassium carbonate (273 mg, 1.78 mmol) and bis(triphenylphosphine)palladium(II) dichloride (49 mg, 0.07 mmol) in 1,4-dioxane (4 mL) and water (1 mL) was heated to 100° C. for 12 h under nitrogen atmosphere. After cooling the reaction mixture to 25° C., water (20 mL) was added and the mixture extracted with EtOAc (20 mL×2). The combined organic layers were dried over anhydrous $Na_2SO_4$ and concentrated in vacuo. The crude residue was purified by reverse phase chromatography (acetonitrile 26-56%/0.2% formic acid in water) to give the title compound (46 mg, 20%) as a white solid. $^1$H NMR (400 MHz, CD$_3$OD) δ7.74 (s, 1H), 7.59 (d, J=8.4 Hz, 1H), 7.42-7.39 (m, 1H), 7.10-7.00 (m, 3H), 4.02-3.97 (m, 4H), 2.77-2.72 (m, 1H), 2.37-2.26 (m, 2H), 1.17 (d, J=6.8 Hz, 31-1), 1.07-1.03 (m, 4H). LCMS M/Z (M+H) 347.

Example 58

1-methyl-5-[(4R)-4-methyl-2-oxo-1,3,4,5-tetrahydro-1,5-benzodiazepin-6-yl]indazole-3-carboxamide

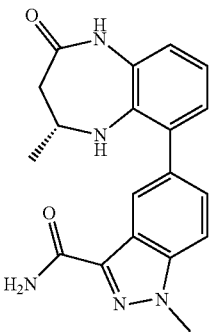 [SMILES: C[C@@H]1CC(=O)Nc2cccc(-c3ccc4c(c3)c(C(N)=O)nn4C)c2N1]

Step 1:

methyl 5-bromo-1-methyl-1H-indazole-3-carboxylate

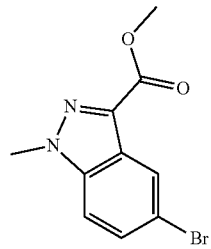

To methyl 5-bromo-1H-indazole-3-carboxylate (762 mg, 3.0 mmol) in acetonitrile (20 ml) at 20° C. was added potassium carbonate (2.0 g, 15 mmol) and methyl iodide (1.1 ml, 15.5 mmol). The mixture was stirred at 20° C. for 10 h under nitrogen atmosphere. The mixture was concentrated in vacuo. The crude residue was purified by silica gel chromatography (petroleum ether/EtOAc=10/1 to 5/1) to give the title compound (600 mg, 75%) as a light yellow solid.

Step 2:

5-bromo-1-methyl-1H-indazole-3-carboxamide

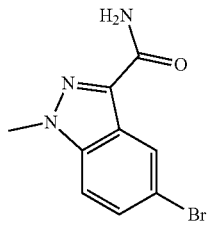

To a mixture of 5-bromo-1-methyl-1H-indazole-3-carboxylate (320 mg, 1.2 mmol) in methanol (5 ml) was added aqueous ammonium hydroxide (5 mL). The mixture was heated to 90° C. for 10 h under nitrogen atmosphere. After cooling the reaction to room temperature, the mixture was concentrated in vacuo to give the title compound (320 mg, crude) as a white solid that required no further purification. LCMS M/Z (M+H) 254.

Step 3:

1-methyl-5-[(4R)-4-methyl-2-oxo-1,3,4,5-tetrahydro-1,5-benizodiazepin-6-yl]indazole-3-carboxamide

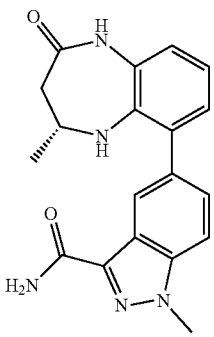 [SMILES: C[C@@H]1CC(=O)Nc2cccc(-c3ccc4c(c3)c(C(N)=O)nn4C)c2N1]

To a mixture of 5-bromo-1-methyl-1-indazole-3-carboxamide (70 mg, 0.28 mmol), cesium carbonate (182 mg, 0.56 mmol) and (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 84 mg, 0.28 mmol) in dioxane (20 ml)/H$_2$O (4 ml) was added [1,1'-bis(diphenylphosphino)ferrocene]dichloropalladium(II) (22 mg, 0.03 mmol). The resulting mixture was heated to 100° C. for 10 h under nitrogen atmosphere. After cooling the reaction to room temperature, the mixture was concentrated in vacuo. The crude residue was purified by reverse phase chromatography (acetonitrile 10-40%/0.2% formic acid in water) to give the title compound (24 mg, 24%) as a white solid. $^1$H NMR (400 MHz, CD$_3$OD) δ 8.23 (s, 1H), 7.77-7.75 (m, 1H), 7.50-7.48 (m, 1H), 7.11-7.09 (m, 1H), 7.02-7.01 (m, 2H), 4.21 (s, 3H), 4.04-4.00 (m, 1H), 2.78-2.74 (m, 1H), 2.59-2.31 (m, 1H), 1.17-1.16 (s, 3H). LCMS M/Z (M+H) 350.

Example 59

1-methyl-5-[(4R)-4-methyl-2-oxo-1,3,4,5-tetrahydro-1,5-benzodiazepin-6-yl]indazole-3-carbonitrile

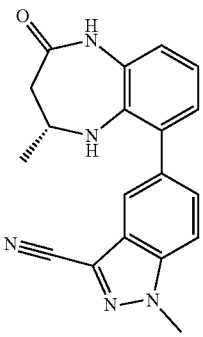 [SMILES: C[C@@H]1CC(=O)Nc2cccc(-c3ccc4c(c3)c(C#N)nn4C)c2N1]

Step 1:

5-bromo-1-methyl-1H-indazole-3-carbonitrile

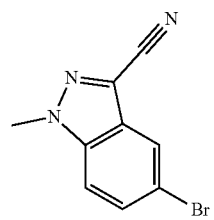

To a solution of 5-bromo-1-methyl-1H-indazole-3-carboxamide (320 mg, crude) in TI-IF (9 ml) was added trifluoromethanesulfonic anhydride (0.9 ml) and pyridine (0.9 ml). The mixture was stirred at 20° C. for 10 h. Water (10 mL) was added and the mixture was extracted with EtOAc (15 mL×3). The combined organic layers were dried over anhydrous Na$_2$SO$_4$, filtered and concentrated in vacuo to give the title compound (320 mg, crude) as a yellow solid that required no further purification.

Step 2:

1-methyl-5-[(4R)-4-methyl-2-oxo-1,3,4,5-tetrahydro-1,5-benzodiazepin-6-yl]indazole-3-carbonitrile

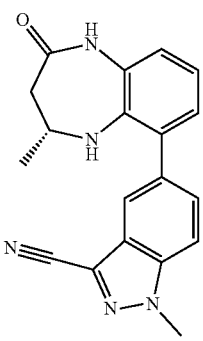 [SMILES: C[C@@H]1CC(=O)Nc2cccc(-c3ccc4c(c3)c(C#N)nn4C)c2N1]

To a mixture of 5-bromo-1-methyl-1H-indazole-3-carbonitrile (200 mg, crude), cesium carbonate (767 rag, 2.36 mmol) and (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 300 mg, 1.2 mmol) in dioxane (20 ml)/H$_2$O (4 ml) was added [1,1'-bis(diphenylphosphino)ferrocene] dichloropalladium(II) (87 mg, 0.12 mmol). The resulting mixture was heated to 100° C. for 10 h under nitrogen atmosphere. After cooling the reaction to room temperature, the mixture was concentrated in vacuo. The crude residue was purified by reverse phase chromatography (acetonitrile 39-59%/0.2% formic acid in water) to give the title compound (46 mg, 12%) as a white solid. $^1$H NMR (400 MHz, CD$_3$OD) δ 7.88 (d, J=8.4 Hz, 1H), 7.79 (s, 1H), 7.60-7.58 (m, 1H), 7.09-7.08 (m, 1H), 7.06-7.02 (m, 2H), 4.25 (s, 3H), 4.03-4.01 (m, 1H), 2.79-2.75 (m, 1H), 2.37-2.33 (m, 1H), 1.19 (s, 3H). LCMS M/Z (M+H) 332.

Example 60

(4R)-4-methyl-6-[1-methyl-6-(1-methylpyrazol-4-yl)indol-2-yl]-1,3,4,5-tetrahydro-1,5-benzodiazepin-2-one

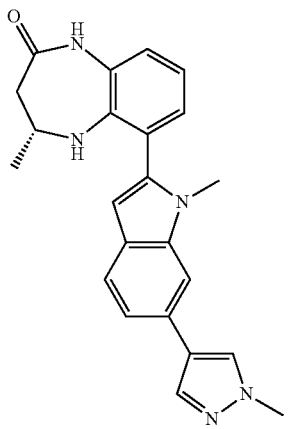

Step 1:

tert-butyl 6-bromo-1H-indole-1-carboxylate

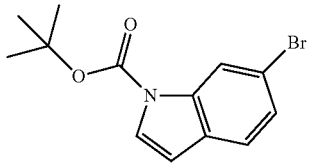 [SMILES: CC(C)(C)OC(=O)n1ccc2ccc(Br)cc21]

To a solution of 6-bromo-1H-indole (10 g, 51 mmol) in dichloromethane (100 mL) was added 4-dimethylaminopyridine (623 mg, 5.1 mmol), triethylamine (15.48 g, 153 mmol) and di-tert-butyl dicarbonate (12.3 g, 56 mmol). The reaction mixture was stirred at room temperature for 16 h. The resulting mixture was concentrated in vacuo. Water (100 mL) was added and the mixture was extracted with EtOAc (100 mL×2). The combined organic layers were dried over anhydrous Na$_2$SO$_4$, filtered and concentrated in vacuo to give the crude product that was purified by silica gel chromatography (petroleum ether/EtOAc=100/1) to give the title compound (15 g, 95%) as a yellow solid.

Step 2:

tert-butyl 6-bromo-2-iodo-1H-indole-1-carboxylate

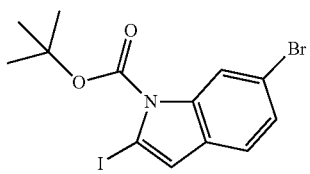 [SMILES: CC(C)(C)OC(=O)n1c(I)cc2ccc(Br)cc21]

To a solution of tert-butyl 6-bromo-1H-indole-1-carboxylate (5 g, 16.88 mmol) in THF (30 mL) was added lithium diisopropylamide in THF (2M, 21 mmol, 10.5 mL) dropwise at −78° C. The resulting mixture was stirred at −78° C. for 1 h under nitrogen atmosphere before 12 (4.7 g, 19 mmol) in THF (100 mL) was added. The resulting mixture was stirred at room temperature for 2 h. Water (100 mL) was added and the mixture was extracted with EtOAc (200 mL×2). The combined organic layers were dried over anhydrous Na$_2$SO$_4$, filtered and concentrated in vacuo to give the crude product that was purified by silica gel chromatography (petroleum ether/EtOAc=100/1) to give the title compound (5.2 g, 73%) as a yellow solid.

Step 3:

6-bromo-2-iodo-1H-indole

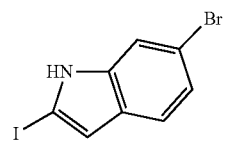 [SMILES: Brc1ccc2cc(I)[nH]c2c1]

To a solution of tert-butyl 6-bromo-2-iodo-1H-indole-1-carboxylate (5.2 g, 12.32 mmol) in MeOH (50 mL) was added sodium hydroxide (5M, 24.6 mL). The reaction mixture was heated to 90° C. for 2 h under nitrogen atmosphere. After cooling the reaction to room temperature, the resulting mixture was concentrated in vacuo. Water (50 mL) was added and the mixture was extracted with EtOAc (100 mL×2). The combined organic layers were dried over anhydrous Na$_2$SO$_4$, filtered and concentrated in vacuo to give the crude product that was purified by silica gel chromatography (petroleum ether/EtOAc=50/1) to give the title compound (3 g, 76%) as a yellow solid.

Step 4:

6-bromo-2-iodo-1-methyl-1H-indole

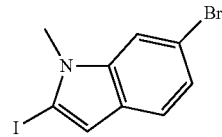

To a solution of 6-bromo-2-iodo-1H-indole (3 g, 9.32 mmol) in THF (20 mL) at 0° C. was added NaH (1.1 g, 27.96 mmol). The resulting mixture was stirred at 0° C. for 30 min under nitrogen atmosphere. Iodomethane (4 g, 27.96 mmol) was added and the reaction mixture was stirred at room temperature for an additional 2 h. The mixture was poured into ice-water and extracted with EtOAc (50 mL×2). The combined organic layers were dried over anhydrous Na₂SO₄, filtered and concentrated in vacuo to give the crude product that was purified by silica gel chromatography (petroleum ether/EtOAc=50/1) to give the title compound (1.36 g, 43%) as a yellow solid.

Step 5:

(R)-6-(6-bromo-1-methyl-1H-indol-2-yl)-4-methyl-4,5-dihydro-1H-benzo[b][1,4]diazepin-2(3H)-one

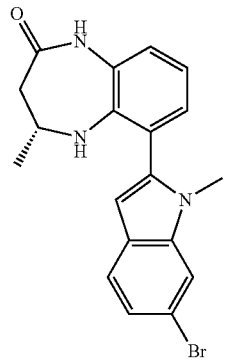

To a solution of 6-bromo-2-iodo-1-methyl-1H-indole (860 mg, 2.56 mmol) in dioxane/H₂O (10 mL, 5/1) was added (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 773 mg, 2.56 mmol), Na₂CO₃ (542.6 mg, 5.12 mmol) and [1,1'-bis(diphenylphosphino)ferrocene]dichloro-palladium(II) (150 mg, 0.2 mmol). The reaction mixture was heated to 80° C. for 3 h under nitrogen atmosphere. After cooling the reaction to room temperature, water (20 mL) was added and the mixture was extracted with EtOAc (50 mL×2). The combined organic layers were dried over anhydrous Na₂SO₄, filtered and concentrated in vacuo to give the crude product that was purified by silica gel chromatography (petroleum ether/EtOAc=1/1) to give the title compound (460 mg, 46%) as a yellow solid.

Step 6:

(4R)-4-methyl-6-[1-methyl-6-(1-methylpyrazol-4-yl)indol-2-yl]-1,3,4,5-tetrahydro-1,5-benzodiazepin-2-one

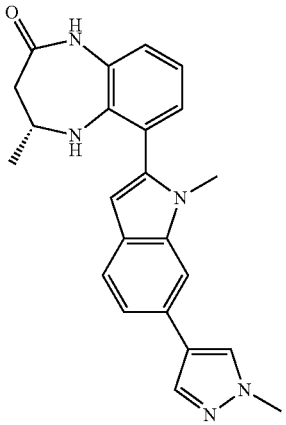

To a solution of (R)-6-(6-bromo-1-methyl-1H-indol-2-yl)-4-methyl-4,5-dihydro-1H-benzo[b][1,4]diazepin-2(3H)-one (460 mg, 1.2 mmol) in dioxane/H₂O (5 mL, 5/1) was added 1-methyl-4-(4,4,5,5-tetramethyl-1,3,2-dioxaborolan-2-yl)-1H-pyrazole (274 mg, 1.32 mmol), Na₂CO₃ (253 mg, 2.39 mmol) and [1,1'-bis(diphenylphosphino)ferrocene]dichloro-palladium(II) (100 mg, 0.12 mmol). The reaction vessel was sealed and irradiated in a microwave at 130° C. for 1 h. After cooling the reaction to room temperature, the reaction mixture was concentrated in vacuo. The crude residue was purified by reverse phase chromatography (acetonitrile 28-58%/0.1% NH₄HCO₃ in water) to give the title compound (36 mg, 8%) as a white solid. ¹H NMR (400 MHz, DMSO-d₆) δ 9.63 (s, 1H), 8.14 (s, 1H), 7.91 (s, 1H), 7.68 (s, 1H), 7.53 (d, J=8.0 Hz, 1H), 7.30 (d, J=8.0 Hz, 1H), 7.02-6.96 (m, 2H), 6.89-6.85 (m, 1H), 6.43 (s, 1H), 4.27 (s, 1H), 3.91-3.82 (m, 4H), 3.54 (s, 3H), 2.62-2.58 (m, 1H), 2.26-2.21 (m, 1H), 1.05 (s, 3H). LCMS M/Z (M+H) 386.

Example 61

(4R)-4-methyl-6-[1-methyl-7-(1-methylpyrazol-4-yl)indol-2-yl]-1,3,4,5-tetrahydro-1,5-benzodiazepin-2-one

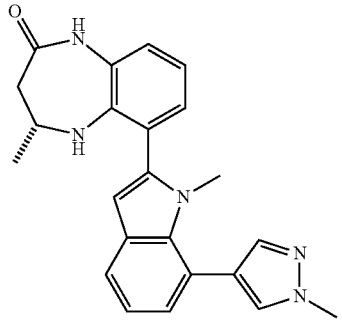

Step 1:

tert-butyl 7-bromo-1H-indole-1-carboxylate

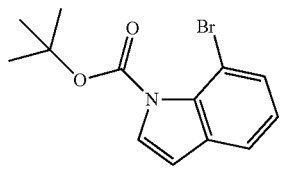 [SMILES: CC(C)(C)OC(=O)n1ccc2cccc(Br)c21]

To a solution of 7-bromo-1H-indole (10 g, 51 mmol) in dichloromethane (100 mL) was added 4-dimethylaminopyridine (623 mg, 5.1 mmol), triethylamine (15.48 g, 153 mmol) and di-tert-butyl dicarbonate (12.3 g, 56 mmol). The reaction mixture was stirred at room temperature for 16 h. The resulting mixture was concentrated in vacuo. Water (100 mL) was added and the mixture was extracted with EtOAc (100 mL×2). The combined organic layers were dried over anhydrous Na₂SO₄, filtered and concentrated in vacuo to give the crude product that was purified by silica gel chromatography (petroleum ether/EtOAc=100/1) to give the title compound (13.6 g, 90%) as a yellow solid.

Step 2:

tert-butyl 7-bromo-2-iodo-1H-indole-1-carboxylate

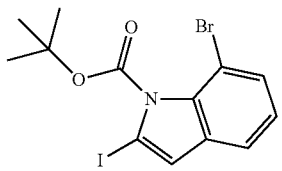 [SMILES: CC(C)(C)OC(=O)n1c(I)cc2cccc(Br)c21]

To a solution of tert-butyl 7-bromo-1H-indole-1-carboxylate (5 g, 16.88 mmol) in THF (30 mL) at −78° C. was added lithium diisopropylamide in THF (2M, 21 mmol, 10.5 mL) dropwise. The resulting mixture was stirred at −78° C. for 1 h under nitrogen atmosphere before $I_2$ (4.7 g, 19 mmol) in THF (100 mL) was added. The resulting mixture was stirred at room temperature for 2 h. Water (100 mL) was added and the mixture was extracted with EtOAc (200 mL×2). The combined organic layers were dried over anhydrous $Na_2SO_4$, filtered and concentrated in vacuo to give the crude product that was purified by silica gel chromatography (petroleum ether/EtOAc=100/1) to give the title compound (5.0 g, 70%) as a yellow solid.

Step 3:

7-bromo-2-iodo-1H-indole

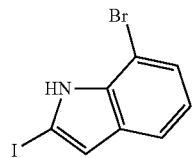 [SMILES: Brc1cccc2cc(I)[nH]c12]

To a solution of tert-butyl 7-bromo-2-iodo-1H-indole-1-carboxylate (2 g, 4.74 mmol) in MeOH (20 mL) was added aqueous sodium hydroxide (5M, 9.5 mL). The reaction mixture was heated to 90° C. for 2 h under nitrogen atmosphere. After cooling the reaction to room temperature, the resulting mixture was concentrated in vacuo. Water (20 mL) was added and the mixture was extracted with EtOAc (50 mL×2). The combined organic layers were dried over anhydrous $Na_2SO_4$, filtered and concentrated in vacuo to give the crude product that was purified by silica gel chromatography (petroleum ether/EtOAc=50/1) to give the title compound (1.4 g, 91%) as a yellow solid.

Step 4:

7-bromo-2-iodo-1-methyl-1H-indole

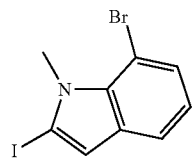

To a solution of 7-bromo-2-iodo-1H-indole (1.4 g, 4.35 mmol) in THF (20 mL) at 0° C. was added NaH (0.52 g, 13.05 mmol). The resulting mixture was stirred at 0° C. for 30 min under nitrogen atmosphere. Iodomethane (2.47 g, 17.39 mmol) was added and the reaction mixture was stirred at room temperature for an additional 2 h. The mixture was poured into ice-water and extracted with EtOAc (50 mL×2). The combined organic layers were dried over anhydrous $Na_2SO_4$, filtered and concentrated in vacuo to give the crude product that was purified by silica gel chromatography (petroleum ether/EtOAc=50/1) to give the title compound (0.6 g, 41%) as a yellow solid.

Step 5:

(R)-6-(7-bromo-1-methyl-1H-indol-2-yl)-4-methyl-4,5-dihydro-1H-benzo[b][1,4]diazepin-2(3H)-one

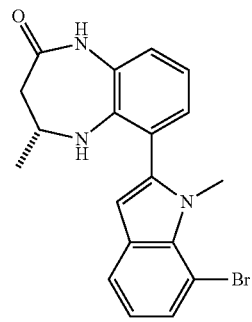 [SMILES: C[C@@H]1CC(=O)Nc2cccc(-c3cc4cccc(Br)c4n3C)c2N1]

To a solution of 7-bromo-2-iodo-1-methyl-1H-indole (600 mg, 1.79 mmol) in dioxane/$H_2O$ (10 mL, 5/1) was added (R)-4-methyl-6-(4,4,5,5-tetramethyl-1,3,2-dioxaborolan-2-yl)-4,5-dihydro-1H-benzo[b][1,4]diazepin-2 (3H)-one (Intermediate B, 647.6 mg, 2.14 mmol), $Na_2CO_3$ (378.6 mg, 3.57 mmol) and [1,1'-bis(diphenylphosphino)ferrocene]dichloropalladium(II) (150 mg, 0.2 mmol). The reaction mixture was heated to 80° C. for 3 h under nitrogen atmosphere. After cooling the reaction to room temperature, water (20 mL) was added and the mixture was extracted with EtOAc (50 mL×2). The combined organic layers were dried over anhydrous $Na_2SO_4$, filtered and concentrated in vacuo to give the crude product that was purified by silica gel chromatography (petroleum ether/EtOAc=1/1) to give the title compound (200 mg, 30%) as a yellow solid.

Step 6:

(4R)-4-methyl-6-[1-methyl-7-(l-methylpyrazol-4-yl)indol-2-yl]-1,3,4,5-tetrahydro-1,5-benzodiazepin-2-one

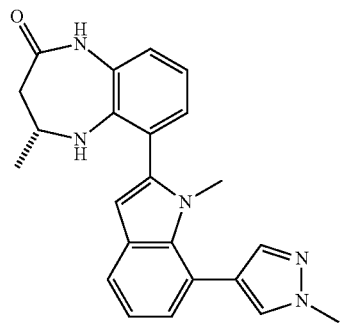

To a solution of (R)-6-(7-bromo-1-methyl-1H-indol-2-yl)-4-methyl-4,5-dihydro-1H-benzo[b][1,4]diazepin-2(3H)-one (200 mg, 0.52 mmol) in dioxane/H$_2$O (5 mL, 5/1) was added 1-methyl-4-(4,4,5,5-tetramethyl-1,3,2-dioxaborolan-2-yl)-1H-pyrazole (166 mg, 1.56 mmol), Na$_2$CO$_3$ (217 mg, 1.04 mmol) and [1,1'-bis(diphenylphosphino)ferrocene]dichloro-palladium(I) (40 mg, 0.05 mmol). The reaction vessel was sealed and irradiated in a microwave at 110° C. for 40 min. After cooling the reaction to room temperature, the reaction mixture was concentrated in vacuo. The crude residue was purified by reverse phase chromatography (acetonitrile 30-60/%/0.1% NH$_4$HCO$_3$ in water) to give the title compound (33 mg, 16%) as a white solid. $^1$H NMR (400 MHz, DMSO-d$_6$) δ9.61 (s, 1H), 7.88 (s, 1H), 7.60 (s, 1H), 7.54 (d, J=8.0 Hz, 1H), 7.07-6.84 (m, 4H), 6.53 (s, 1H), 4.35 (s, 1H), 3.90 (s, 3H), 3.19 (s, 3H), 2.62-2.60 (m, 1H), 2.49-2.20 (m, 2H), 1.09 (s, 3H). LCMS M/Z (M+H) 386.

Example 62

(4R)-4-methyl-6-(1-methyl-4,5,6,7-tetrahydroindazol-3-yl)-1,3,4,5-tetrahydro-1,5-benzodiazepin-2-one

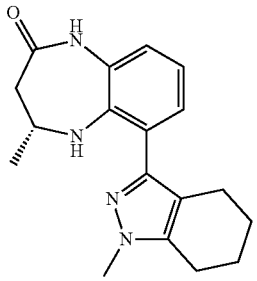 [SMILES: C[C@@H]1CC(=O)Nc2cccc(-c3nn(C)c4c3CCCC4)c2N1]

Step 1:

3-iodo-4,5,6,7-tetrahydro-1H-indazole

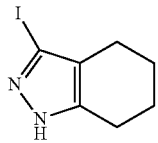

To a solution of 4,5,6,7-tetrahydro-1H-indazole (900 mg, 7.37 mmol) and KOH (827 mg, 14.73 mmol) in DMF (10 ml) was added iodine (3.74 g, 14.73 mmol). The mixture was stirred at room temperature for 8 h. Water (50 mL) was added and the mixture was extracted with EtOAc (50 mL×3). The combined organic layers were dried over anhydrous Na$_2$SO$_4$, filtered and concentrated in vacuo to give the title compound (1.8 g, 98%) as a yellow solid.

Step 2:

3-iodo-1-methyl-4,5,6,7-tetrahydro-1H-indazole

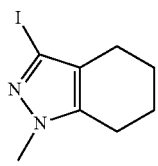

To a solution of 3-iodo-4,5,6,7-tetrahydro-1H-indazole (1.8 g, 7.26 mmol) in THF (20 mL) at 0° C. was added NaH (871 mg, 21.77 mmol). After being stirred at 0° C. for 30 min, MeI (2.6 g, 18.14 mmol) was added and the reaction mixture stirred at room temperature for 1 h. The reaction was quenched by water (20 ml) and the mixture was extracted with EtOAc (20 mL×2). The combined organic layers were dried over anhydrous Na$_2$SO$_4$, filtered and concentrated in vacuo. The crude product was purified by silica gel chromatography (petroleum ether/EtOAc=1:1) to give the title compound (1.2 g, 63%) as a yellow solid. $^1$H NMR (400 MHz, DMSO-d$_6$) δ 3.66 (s, 3H), 2.55-2.52 (m, 2H), 2.21-2.18 (m, 2H), 1.74-1.71 (m, 2H), 1.67-1.64 (m, 2H).

Step 3:

(4R)-4-methyl-6-(1-methyl-4,5,6,7-tetrahydroindazol-3-yl)-1,3,4,5-tetrahydro-1,5-benzodiazepin-2-one

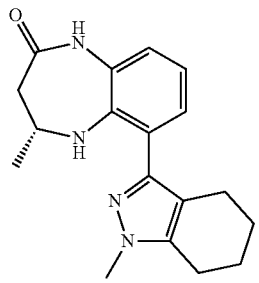 [SMILES: C[C@@H]1CC(=O)Nc2cccc(-c3nn(C)c4c3CCCC4)c2N1]

A mixture of (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 100 mg, 0.33 mmol), 3-iodo-1-methyl-4,5,6,7-tetrahydroindazole (104 mg, 0.40), Na$_2$CO$_3$ (70 mg, 0.66 mmol) and [1,1'-bis(diphenylphosphino)ferrocene]dichloropalladium(II) (24 mg, 0.03 mmol) in 1,4-dioxane (4 mL) and water (1 mL) was heated to 120° C. for 16 h under nitrogen atmosphere. After cooling the reaction to room temperature, the mixture was concentrated in vacuo and the crude residue was purified by reverse phase chromatography (acetonitrile 26-56%/0.2% formic acid in water) to give the title compound (29 mg, 23%) as a white solid. $^1$H NMR (400 MHz, DMSO-d$_6$) δ 9.47 (s, 1H), 7.11-7.04 (m, 1H), 7.01 (s, 1H), 6.86-6.79 (m, 2H), 3.86-3.84 (m, 1H), 3.73 (s, 3H), 2.65-2.62 (m, 2H), 2.51-2.50 (m, 2H), 2.39-2.38 (m, 1H), 2.20-2.18 (m, 1H), 1.80-1.78 (m, 2H), 1.70-1.64 (m, 2H), 1.09 (d, J=6.4 Hz, 3H), LCMS M/Z (M+H) 311.

Example 63

(4R)-4-methyl-6-(1-phenylpyrazol-4-yl)-1,3,4,5-tetrahydro-1,5-benzodiazepin-2-one

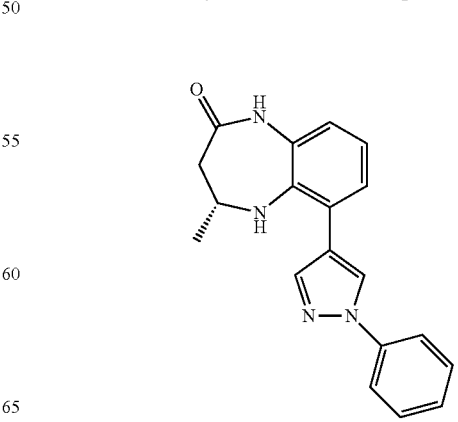

Step 1:

4-iodo-1-phenyl-1H-pyrazole

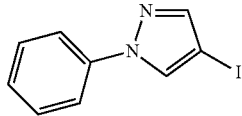 [SMILES: Ic1cnn(-c2ccccc2)c1]

A mixture of 4-iodo-1H-pyrazole (1.00 g, 5.15 mmol), phenylboronic acid (950 mg, 7.73 mmol), copper acetate (1.87 g, 10.3 mmol) and pyridine (1.48 g, 20.6 mmol) in DMF (20 mL) was heated to 80° C. for 16 h under nitrogen atmosphere. After cooling the reaction to room temperature, water (20 mL) was added and the mixture was extracted with EtOAc (20 mL×3). The combined organic layers were washed by brine (30 mL×2), dried over anhydrous $Na_2SO_4$, filtered and concentrated in vacuo to give the title compound (400 mg, crude) as a white solid that required no further purification. LCMS M/Z (M+H) 271.

Step 2:

(4R)-4-methyl-6-(1-phenylpyrazol-4-yl)-1,3,4,5-tetrahydro-1,5-benzodiazepin-2-one

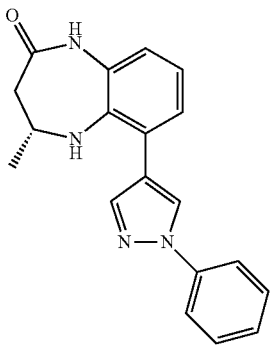

A mixture of 4-iodo-1-phenyl-1H-pyrazole (400 mg, 1.48 mmol), (R)-4-methyl-6-(4,4,5,5-tetramethyl-1,3,2-dioxaborolan-2-yl)-4,5-dihydro-1H-benzo[b][1,4]diazepin-2(3H)-one (Intermediate B, 535 mg, 1.78 mmol), potassium carbonate (408 mg, 2.96 mmol) and [1,1′-bis(diphenylphosphino)ferrocene]dichloropalladium(II), complex with dichloromethane (109 mg, 0.15 mmol) in dioxane (10 mL) and $H_2O$ (2 mL) was heated to 100° C. for 16 h under nitrogen atmosphere. After cooling the reaction to room temperature, the mixture was concentrated in vacuo. The crude residue was purified by reverse phase chromatography (acetonitrile 28-58%/0.2% formic acid in water) to give the title compound (113 mg, 24%) as a gray solid. $^1$H NMR (400 MHz, $CDCl_3$) δ 8.04 (s, 1H), 7.83 (s, 1H), 7.76 (d, J=7.6 Hz, 1H), 7.52 (t, J=7.6 Hz, 2H), 7.48 (br s, 1H), 7.37 (t, J=7.6 Hz, 2H), 7.10 (d, J=1.6 Hz, 1H), 6.97-6.88 (m, 2H), 4.11-3.97 (m, 1H), 3.85 (br s, 1H), 2.81-2.76 (m, 1H), 2.53-2.46 (m, 1H), 1.35 (d, J=6.4 Hz, 3H). LCMS M/Z (M+H) 319.

The following compounds were prepared in a similar fashion to Example 63:

Examples 64-65

| Example | Compound Name | NMR | m/z |
|---|---|---|---|
| Example 64 | (4R)-4-methyl-6-[1-(3-pyridyl)pyrazol-4-yl]-1,3,4,5-tetrahydro-1,5-benzodiazepin-2-one | $^1$H NMR (400 MHz, $CDCl_3$) δ 9.06 (d, J = 2.8 Hz, 1H), 8.63 (d, J = 4.8 Hz, 1H), 8.16-8.10 (m, 1H), 8.08 (s, 1H), 7.89 (s, 1H), 7.49-7.46 (m, 1H), 7.32 (s, 1H), 7.10 (d, J = 7.6 Hz, 1H), 6.99-6.84 (m, 2H), 4.15-3.96 (m, 1H), 3.78 (br s, 1H), 2.81-2.77 (m, 1H), 2.53-2.47 (m, 1H), 1.36 (d, J = 6.4 Hz, 3H) | 320 |
| Example 65 | (4R)-4-methyl-6-[1-(4-pyridyl)pyrazol-4-yl]-1,3,4,5-tetrahydro-1,5-benzodiazepin-2-one | $^1$H NMR (400 MHz, $CDCl_3$) δ 8.74 (d, J = 5.6 Hz, 2H), 8.15 (s, 1H), 7.90 (s, 1H), 7.75 (br s, 1H), 7.70 (d, J = 6.0 Hz, 2H), 7.13-7.03 (m, 1H), 7.00-6.87 (m, 2H), 4.13-3.94 (m, 1H), 3.73 (br s, 1H), 2.79 (dd, J = 13.6, 4.4 Hz, 1H), 2.54-2.47 (m, 1H), 1.35 (d, J = 6.4 Hz, 3H) | 320 |

General Procedure for Intermediate C

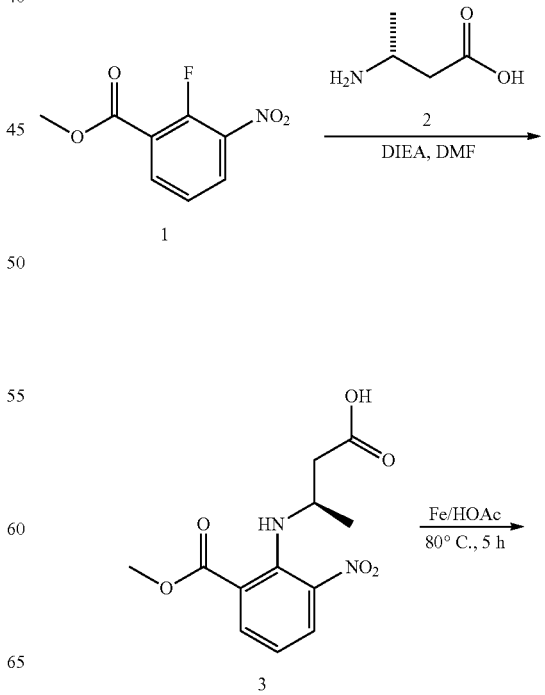

-continued

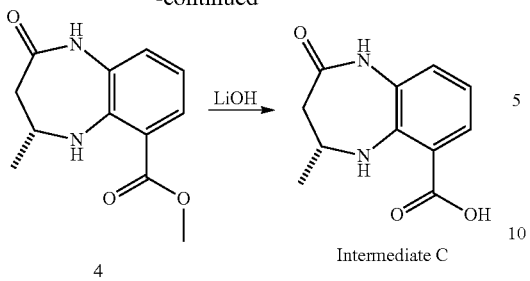

4 → Intermediate C

Step 1:

(R)-3-((2-(methoxycarbonyl)-6-nitrophenyl)amino)butanoic acid

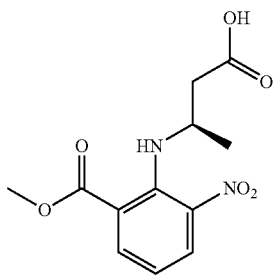 [SMILES: COC(=O)c1cccc([N+](=O)[O-])c1N[C@H](C)CC(=O)O]

To a solution of methyl 2-fluoro-3-nitrobenzoate (4.0 g, 20.09 mmol) in DMF (80 mL) was added N-ethyl-N-isopropylpropan-2-amine (7.8 g, 60.35 mmol) and (R)-3-aminobutanoic acid (2.3 g, 22.30 mmol). The resulting mixture was heated to 80° C. for 15 h. After cooling the reaction to room temperature, water (50 mL) was added and the mixture was extracted with EtOAc (100 mL×3). The combined organic layers were dried over anhydrous Na₂SO₄, filtered and concentrated in vacuo to give the title compound (4.1 g, 73%) as a yellow solid that required no further purification.

Step 2:

(R)-methyl 4-methyl-2-oxo-2,3,4,5-tetrahydro-1H-benzo[b][1,4]diazepine-6-carboxylate

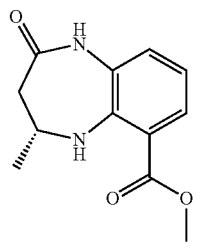

A mixture of (R)-3-((2-(methoxycarbonyl)-6-nitrophenyl)amino)butanoic acid (4.1 g, 14.53 mmol) and Fe powder (4.2 g, 75.21 mol) in acetic acid (50 mL) was heated to 100° C. for 1 h. After cooling the reaction to room temperature, the reaction mixture was filtered and the filtrate was concentrated in vacuo. Water (20 mL) was added and the mixture was extracted with EtOAc (80 mL×3). The combined organic layers were dried over anhydrous Na₂SO₄, filtered and concentrated in vacuo. The crude residue was purified by silica gel chromatography (petroleum ether/EtOAc=3/1) to give the title compound (1.5 g, 44%) as a white solid.

Step 3:

(R)-4-methyl-2-oxo-2,3,4,5-tetrahydro-1H-benzo[b][1,4]diazepine-6-carboxylic acid

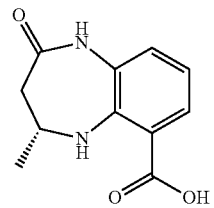

To a solution of (R)-methyl 4-methyl-2-oxo-2,3,4,5-tetrahydro-1H-benzo[b][1,4]diazepine-6-carboxylate (1.3 g, 5.55 mmol) in DMF/H₂O (40 mL/10 mL) was added LiOH (720 mg, 30.06 mmol). The resulting mixture was heated to 80° C. for 15 h. After cooling the reaction to room temperature, the solvent was concentrated in vacuo. Water (20 mL) was added and the mixture was extracted with EtOAc (30 mL×3). The aqueous phase was acidified with HCl (1N) to pH 3. The resulting precipitate was collected by filtration to give the title compound (Intermediate C, 1.0 g, 82%) as a white solid.

Example 66

(4R)-4-methyl-2-oxo-N-[[2-(trifluoromethoxy)phenyl]methyl]-1,3,4,5-tetrahydro-1,5-benzodiazepine-6-carboxamide

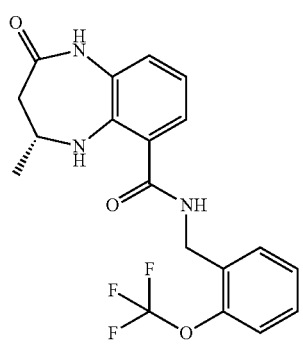 [SMILES: C[C@@H]1CC(=O)Nc2cccc(C(=O)NCc3ccccc3OC(F)(F)F)c2N1]

To a solution of (R)-4-methyl-2-oxo-2,3,4,5-tetrahydro-1-benzo[b][1,4]diazepine-6-carboxylic acid (Intermediate C, 100 mg, 0.45 mmol) in DMF (5 mL) was added (2-(trifluoromethoxy)phenyl)methanamine (104 mg, 0.54 mmol), N-ethyl-N-isopropylpropan-2-amine (176 mg, 1.36 mmol) and HATU (131 mg, 0.54 mmol). The reaction mixture was stirred at 15° C. for 15 h. Ice water (5 mL) was added and the mixture was extracted with EtOAc (10 mL×3). The combined organic layers were concentrated in vacuo. The crude residue was purified by reverse phase chromatography (acetonitrile 40-60%/0.2% formic acid in water) to give the title compound (30 mg, 17%) as a white solid. ¹H NMR (400 MHz, DMSO-d₆) δ 9.54 (s, 1H), 9.02-8.99 (m, 1H), 7.42-7.33 (m, 5H), 7.01-6.99 (m, 1H), 6.80-6.78 (m, 1H), 4.50-4.47 (m, 2H), 3.89-3.85 (m, 1H), 2.41-2.37 (m, 1H), 2.24-2.19 (m, 1H), 1.26 (d, J=6.0 Hz, 3H). LCMS M/Z (M+H) 394.

The following compounds were prepared in a similar fashion to Example 66:

Examples 67-75

| Example | Compound Name | NMR | m/z |
| --- | --- | --- | --- |
| Example 67 | N-(3-isopropoxyphenyl)-2-methyl-4-oxo-3,5-dihydro-2H-1,5-benzoxazepine-9-carboxamide | ¹H NMR (400 MHz, DMSO-d₆) δ7.52 (d, J = 5.2 Hz, 1H), 7.51 (s, 1H), 7.37-7.13 (m, 4H), 6.69 (d, J = 8.0 Hz, 1H), 4.98-4.93 (m, 1H), 4.62-4.56 (m, 1H), 2.84-2.79 (m, 1H), 2.52-2.48 (m, 1H), 1.44 (d, J = 6.4 Hz, 3H), 1.31 (d, J = 6.0 Hz, 6H) | 355 |
| Example 68 | N-(3-isopropoxyphenyl)-2-methyl-4-oxo-3,5-dihydro-2H-1,5-bertzoxazepine-9-carboxamide | ¹H NMR (400 MHz, DMSO-d₆) δ7.51 (d, J = 2.0 Hz, 1H), 7.47 (s, 1H), 7.38-7.17 (m, 4H), 6.70 (d, J = 1.6 Hz, 1H), 4.97-4.91 (m, 1H), 4.62-4.56 (m, 1H), 2.83-2.79 (m, 1H), 2.52-2.46 (m, 1H), 1.44 (d, J = 6.4 Hz, 3H), 1.31 (d, J = 6.0 Hz, 6H) | 355 |
| Example 69 | (4R)-N-benzhydryl-4-methyl-2-oxo-1,3,4,5-tetrahydro-1,5-benzodiazepine-6-carboxamide | ¹H NMR (400 MHz, DMSO-d₆) δ 9.57 (s, 1H), 9.38 (d, J = 8.8 Hz, 1H), 7.40-7.27 (m, 11H), 7.02 (d, J = 7.6 Hz, 1H), 6.83 (d, J = 8.0 Hz, 1H), 6.36 (d, J = 8.8 Hz, 1H), 3.89-3.85 (m, 1H), 2.38-2.35 (m, 1H), 2.21-2.16 (m, 1H), 1.03 (d, J = 6.4 Hz, 3H) | 386 |
| Example 70 | (4R)-N-(4-methoxyphenyl)-4-methyl-2-oxo-1,3,4,5-tetrahydro-1,5-benzodiazepine-6-carboxamide | ¹H NMR (400 MHz, DMSO-d₆) δ 10.2 (s, 1H), 9.6 (s, 1H), 7.58 (d, J = 8.8 Hz, 2H), 7.35 (d, J = 6.4 Hz, 1H), 7.03 (d, J = 6.4 Hz, 1H), 6.90-6.83 (m, 3H), 3.92-3.89 (m, 1H), 3.71 (s, 3H), 2.44-2.39 (m, 1H), 2.24-2.18 (m, 1H), 1.14 (d, J = 6.4 Hz, 3H) | 326 |
| Example 71 | (4R)-N-[(4R)-chroman-4-yl]-4-methyl-2-oxo-1,3,4,5-tetrahydro-1,5-benzodiazepine-6-carboxamide | ¹H NMR (400 MHz, DMSO-d₆) δ 9.56 (s, 1H), 8.91 (d, J = 8.4 Hz, 1H), 7.30-7.28 (m, 1H), 7.20-7.14 (m, 2H), 7.01 (d, J = 6.8 Hz, 1H), 6.85-6.75 (m, 3H), 5.27-5.25 (m, 1H), 4.30-4.22 (m, 2H), 3.97-3.96 (m, 1H), 2.50-2.06 (m, 5H), 1.21 (d, J = 6.4 Hz, 3H) | 352 |
| Example 72 | (4R)-4-methyl-2-oxo-N-[(1R)-1-phenylpropyl]-1,3,4,5-tetrahydro-1,5-benzodiazepine-6-carboxamide | ¹H NMR (400 MHz, CD₃OD) δ 7.37-7.32 (m, 5H), 7.30-7.28 (m, 1H), 7.22-7.06 (m, 1H), 7.05-6.96 (m, 1H), 4.90-4.92 (m, 1H), 3.97-3.92 (m, 1H), 2.46-2.41 (m, 1H), 2.27-2.22 (m, 1H), 1.91-1.87 (m, 2H), 1.01-0.98 (m, 6H) | 338 |
| Example 73 | (4R)-N-(3-methoxyphenyl)-4-methyl-2-oxo-1,3,4,5-tetrahydro-1,5-benzodiazepine-6-carboxamide | ¹H NMR (400 MHz, CD₃OD) δ 7.49-7.47 (m, 1H), 7.38 (s, 1H), 7.27-7.24 (m, 1H), 7.22-7.18 (m, 1H), 7.12-7.11 (m, 1H), 7.00-6.98 (m, 1H), 6.75-6.74 (m, 1H), 4.08-4.05 (m, 1H), 3.83 (s, 3H), 2.61-2.56 (m, 1H), 2.38-2.33 (m, 1H), 1.30 (d, J = 6.4 Hz, 3H) | 326 |
| Example 74 | (4R)-N-(3-ethoxyphenyl)-4-methyl-2-oxo-1,3,4,5-tetrahydro-1,5-benzodiazepine-6-carboxamide | ¹H NMR (400 MHz, CD₃OD) δ 7.47-7.46 (m, 1H), 7.36 (s, 1H), 7.25-7.23 (m, 2H), 7.14-7.11 (m, 1H), 7.00-6.98 (m, 1H), 6.74-6.71 (m, 1H), 4.09-4.03 (m, 3H), 2.61-2.56 (m, 1H), 2.38-2.33 (m, 1H), 1.43-1.39 (m, 3H), 1.30 (d, J = 6.4 Hz, 3H) | 340 |
| Example 75 | (4R)-4-methyl-N-(3-oxazol-5-ylphenyl)-2-oxo-1,3,4,5-tetrahydro-1,5-benzodiazepine-6-carboxamide | ¹H NMR (400 MHz, CD₃OD) δ 8.29 (s, 1H), 8.14 (s, 1H), 7.70-7.65 (m, 1H), 7.56-7.47 (m, 4H), 7.16-7.13 (m, 1H), 7.02-6.99 (m, 1H), 4.11-4.06 (m, 1H), 2.62-2.58 (m, 1H), 2.40-2.35 (m, 1H), 1.31 (d, J = 6.4 Hz, 3H) | 363 |

Example 76

(4R)-4-methyl-N-[3-(oxetan-3-yloxy)phenyl]-2-oxo-1,3,4,5-tetrahydro-1,5-benzodiazepine-6-carboxamide

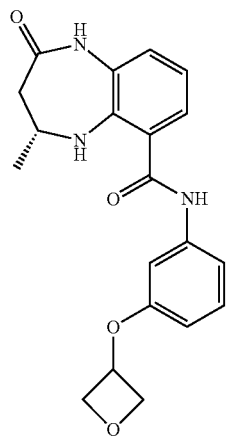 [SMILES: C[C@@H]1CC(=O)Nc2cccc(C(=O)Nc3cccc(OC4COC4)c3)c2N1]

Step 1:

3-(3-nitrophenoxy)oxetane

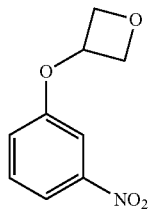

To a solution of oxetan-3-ol (500 mg, 6.75 mmol) in DMF (10 mL) at 0° C. was added NaH (405 mg, 10.13 mmol). The mixture was stirred at 0° C. for 30 min before 1-fluoro-3-nitrobenzene (1.14 g, 8.08 mmol) was added. The mixture was allowed to stir overnight at room temperature before it was poured into ice water (20 mL) and extracted with EtOAc (30 mL×3). The combined organic layers were washed with brine (20 mL), dried over anhydrous Na$_2$SO$_4$, filtered and concentrated in vacuo to give the title compound (500 mg, 32%) as yellow oil.

Step 2:

3-(oxetan-3-yloxy)aniline

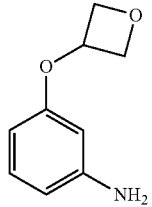 [SMILES: Nc1cccc(OC2COC2)c1]

To a solution of 3-(3-nitrophenoxy)oxetane (200 mg, 1.02 mmol) in MeOH (20 mL) was added Raney Ni (20 mg, 10%) under nitrogen atmosphere. The suspension was degassed under vacuo and purged with H$_2$ several times. The mixture was stirred under H$_2$ (balloon) at room temperature for 2 h. The solid was removed by filtration and the filtrate was concentrated in vacuo to give the title compound (150 mg, 89%) as a pale yellow solid.

Step 3:

(4R)-4-methyl-N-[3-(oxetan-3-yloxy)phenyl]-2-oxo-1,3,4,5-tetrahydro-1,5-benzodiazepine-6-carboxamide

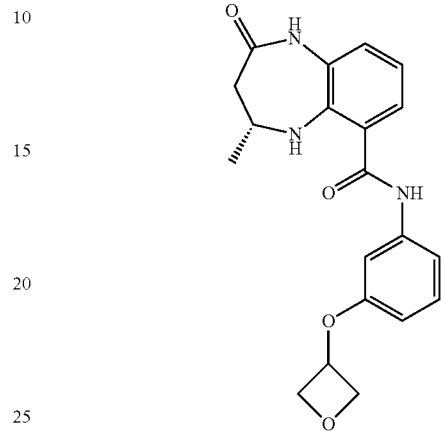

To a solution of (R)-4-methyl-2-oxo-2,3,4,5-tetrahydro-1H-benzo[b][1,4]diazepine-6-carboxylic acid (Intermediate C, 150 mg, 0.68 mmol) in DMF (5 mL) was added 3-(oxetan-3-yloxy)aniline (135 mg, 0.82 mmol), N-ethyl-N-isopropylpropan-2-amine (264 mg, 2.04 mmol) and HATU (297 mg, 0.78 mmol). The mixture was allowed to stir at room temperature for 16 h. The mixture was concentrated in vacuo. The crude residue was purified by reverse phase chromatography (acetonitrile 19-49%/0.1% NH$_4$OH in water) to give the title compound (105 mg, 42%). $^1$H NMR (400 MHz, CD$_3$OD) δ 7.45-7.43 (m, 1H), 7.24-7.22 (m, 3H), 7.11-7.08 (m, 1H), 6.96-6.92 (m, 1H), 6.55-6.53 (m, 1H), 5.28-5.24 (m, 1H), 5.02-4.98 (m, 2H), 4.70-4.67 (m, 2H), 4.04-4.03 (m, 1H), 2.57-2.52 (m, 1H), 2.35-2.30 (m, 1H), 1.26 (d, J=6.4 Hz, 3H). LCMS M/Z (M+H) 368.

Example 77

(4R)—N-(5-isopropoxy-3-pyridyl)-4-methyl-2-oxo-1,3,4,5-tetrahydro-1,5-benzodiazepine-6-carboxamide

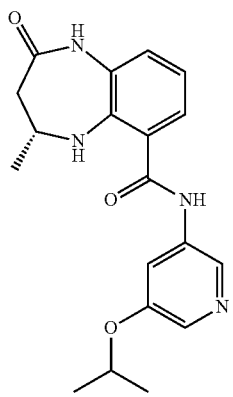 [SMILES: CC(C)Oc1cncc(NC(=O)c2cccc3c2N[C@H](C)CC(=O)N3)c1]

Step 1:

3-bromo-5-isopropoxypyridine

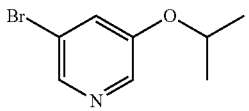

To a solution of 5-bromopyridin-3-ol (500 mg, 2.87 mmol) in DMF (10 mL) at 0° C. was added NaH (133 mg, 3.33 mmol). The mixture was stirred at 0° C. for 30 min before 2-iodopropane (739 mg, 4.35 mmol) was added. The mixture was allowed to stir overnight at room temperature. The solution was poured into ice water (10 mL) and extracted with EtOAc (20 mL×3). The combined organic layers were washed with brine (20 mL), dried over anhydrous $Na_2SO_4$, filtered and concentrated in vacuo to give the title compound (280 mg, 45%) as a yellow oil.

Step 2:

tert-butyl (5-isopropoxypyridin-3-yl)carbamate

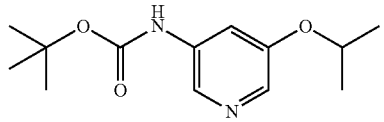 [SMILES: CC(C)Oc1cncc(NC(=O)OC(C)(C)C)c1]

A mixture of 3-bromo-5-isopropoxypyridine (280 mg, 1.30 mmol), tert-butyl carbamate (228 mg, 1.95 mmol), $Cs_2CO_3$ (844 mg, 2.59 mmol), tris(dibenzylidene-acetone) dipalladium(O) (125 mg, 130 umol) and 2-(dicyclohexylphosphino)-2',4',6'-triisopropylbiphenyl (75 mg, 130 umol) dissolved in dioxane (4 mL) and $H_2O$ (1 mL) was irradiated in a microwave at 100° C. for 30 min. After cooling the reaction to room temperature, the mixture was filtered and concentrated in vacuo. The crude residue was purified by silica gel chromatography (petroleum ether/EtOAc=5/1) to give the title compound (150 mg, 46%) as white solid.

Step 3:

5-isopropoxypyridin-3-amine hydrochloride

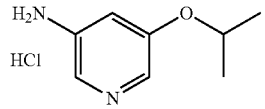

To a solution of tert-butyl (5-isopropoxypyridin-3-yl) carbamate (150 mg, 0.59 mmol) in MeOH (5 mL) was added HCl/MeOH solution (4M, 10 mL) dropwise. The mixture was stirred at room temperature for 3 h. The mixture was concentrated in vacuo to give the title compound (80 mg, 71%) as white solid.

Step 4:

(4R)—N-(5-isopropoxy-3-pyridyl)-4-methyl-2-oxo-1,3,4,5-tetrahydro-1,5-benzodiazepine-6-carboxamide

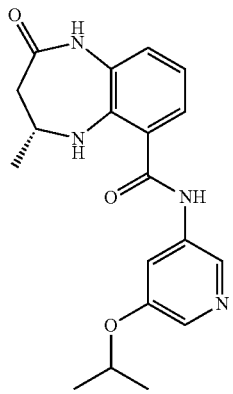 [SMILES: CC(C)Oc1cncc(NC(=O)c2cccc3c2N[C@H](C)CC(=O)N3)c1]

To a solution of 5-isopropoxypyridin-3-amine hydrochloride (80 mg, 0.42 mmol) in pyridine (5 mL) was added (R)-4-methyl-2-oxo-2,3,4,5-tetrahydro-1H-benzo[b][1,4]diazepine-6-carboxylic acid (Intermediate C, 87 mg, 0.40 mmol) and 1-(3-dimethylaminopropyl)-3-ethylcarbodiimide hydrochloride (85 mg, 0.66 mmol). The resulting mixture was allowed to stir at room temperature for 8 h. The mixture was concentrated in vacuo and the crude residue was purified by reverse phase chromatography (acetonitrile 23-43%/ 0.2% formic acid in water) to give the title compound (48 mg, 34%) as a white solid. $^1$H NMR (400 MHz, $CD_3OD$) δ 8.40 (s, 1H), 7.96-7.89 (m, 2H), 7.50-7.48 (m, 1H), 7.13-7.10 (m, 1H), 6.96-6.92 (m, 1H), 4.70-4.65 (m, 1H), 4.07-4.02 (m, 1H), 2.59-2.54 (m, 1H), 2.37-2.31 (m, 1H), 1.37-1.35 (m, 6H), 1.27 (d, J=6.4 Hz, 3H). LCMS M/Z (M+H) 355.

Example 78

(4R)—N-(4-cyanophenyl)-4-methyl-2-oxo-1,3,4,5-tetrahydro-1,5-benzodiazepine-6-carboxamide

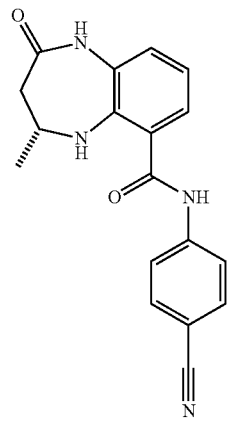

Step 1:

(R)-N-(4-bromophenyl)-4-methyl-2-oxo-2,3,4,5-tetrahydro-1H-benzo[b][1,4]diazepine-6-carboxamide

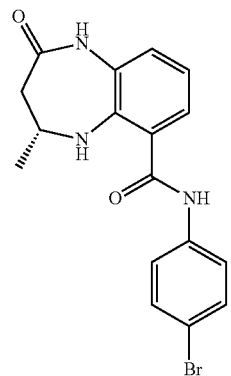 [SMILES: C[C@@H]1CC(=O)Nc2cccc(C(=O)Nc3ccc(Br)cc3)c2N1]

To a solution of (R)-4-methyl-2-oxo-2,3,4,5-tetrahydro-1H-benzo[b][1,4]diazepine-6-carboxylic acid (Intermediate C, 300 mg, 1.36 mmol) in DMF (10 mL) was added 4-bromoaniline (279 mg, 1.62 mmol), HATU (616 mg, 1.62 mmol) and N-ethyl-N-isopropylpropan-2-amine (352 mg, 2.72 mmol). The reaction mixture was stirred at 0° C. for 15 h before it was added to ice-cold water (10 mL). The resulting solid was collected by filtration, washed with water (15 mL) and dried in vacuo to give the title compound (300 mg, 59%) as a white solid.

Step 2:

(4R)-N-(4-cyanophenyl)-4-methyl-2-oxo-1,3,4,5-tetrahydro-1,5-benzodiazepine-6-carboxamide

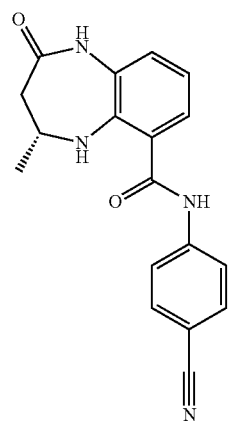 [SMILES: C[C@@H]1CC(=O)Nc2cccc(C(=O)Nc3ccc(C#N)cc3)c2N1]

To a solution of (R)-N-(4-bromophenyl)-4-methyl-2-oxo-2,3,4,5-tetrahydro-1H-benzo[b][1,4]diazepine-6-carboxamide (100 mg, 0.27 mmol) in NMP (3 mL) was added CuCN (48 mg, 0.53 mmol) and CuI (25 mg, 0.13 mmol). The reaction mixture was irradiated in a microwave at 200° C. for 0.5 h. After cooling the reaction to room temperature, the mixture was concentrated in vacuo and the crude residue was dissolved in EtOAc (10 mL) and washed with water (10 mL). The organic layer was concentrated in vacuo. The crude residue was purified by reverse phase chromatography (acetonitrile 13-43%/0.1% NH$_4$OH in water) to give the title compound (15 mg, 18%) as a white solid. $^1$H NMR (400 MHz, DMSO-d$_6$) δ 10.70 (s, 1H), 9.61 (s, 1H), 7.89 (d, J=8.8 Hz, 2H), 7.79 (d, J=8.4 Hz, 2H), 7.38 (d, J=6.8 Hz, 1H) 7.06 (d, J=7.2 Hz, 1H), 6.85 (t, J=8.0 Hz, 1H), 6.58 (s, 1H), 3.94 (s, 1H), 2.47-2.42 (m, 1H), 2.25-2.20 (m, 1H), 1.14 (m, J=6.4 Hz, 2H), LCMS M/Z (M+H) 321.

Example 79 benzyl (4R)-4-methyl-2-oxo-1,3,4,5-tetrahydro-1,5-benzodiazepine-6-carboxylate

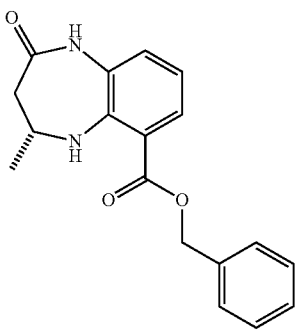 [SMILES: C[C@@H]1CC(=O)Nc2cccc(C(=O)OCc3ccccc3)c2N1]

To a solution of (R)-4-methyl-2-oxo-2,3,4,5-tetrahydro-1H-benzo[b][1,4]diazepine-6-carboxylic acid (Intermediate C, 100 mg, 0.45 mmol) in DMF (5 mL) was added phenylmethanol (60 mg, 0.55 mmol) and triphenylphosphine (179 mg, 0.68 mmol). The solution was degassed with vacuo and purged with N$_2$ for several times before (E)-diisopropyl diazene-1,2-dicarboxylate (180 mg, 0.89 mmol) was added dropwise to the mixture at 0° C. The resulting mixture was allowed to stir at room temperature for 30 min. The solution was concentrated in vacuo and the crude residue was diluted with water (50 mL) and extracted with EtOAc (50 mL×3). The combined organic layers were washed with brine (50 mL), dried over anhydrous Na$_2$SO$_4$, filtered and concentrated in vacuo. The crude residue was purified by reverse phase chromatography (acetonitrile 25-50%/0.1% NH$_4$OH in water) to give the title compound (60 mg, 43%). $^1$H NMR (400 MHz, CD$_3$OD) δ 7.84-7.82 (m, 1H), 7.48-7.37 (m, 5H), 7.15-7.13 (m, 1H), 6.82-6.77 (m, 1H), 5.36 (s, 2H), 4.09-4.03 (m, 1H), 2.62-2.58 (m, 1H), 2.49-2.43 (m, 1H), 1.34 (d, J=6.0 Hz, 3H). LCMS M/Z (M+H) 311.

General Procedure for Intermediate D

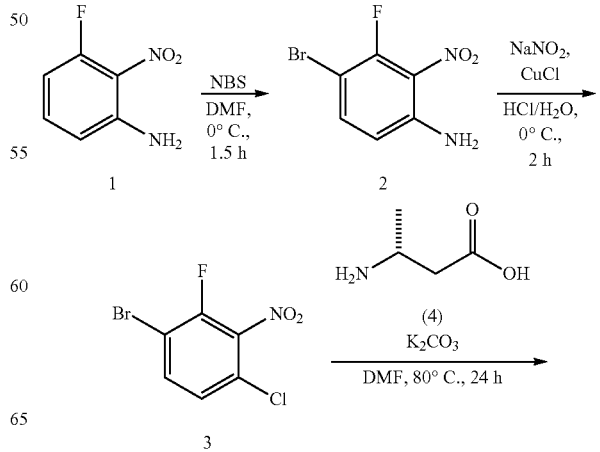

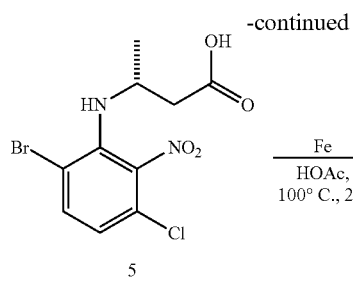
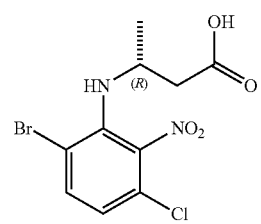

Step 3:

(R)-3-((6-bromo-3-chloro-2-nitrophenyl)amino)butanoic acid

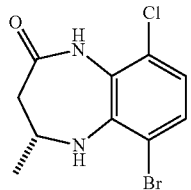

A mixture of 1-bromo-4-chloro-2-fluoro-3-nitrobenzene (500 mg, 1.98 mmol), (R)-3-aminobutanoic acid (243 mg, 2.36 mmol) and potassium carbonate (815 mg, 5.9 mmol) in acetonitrile (6 mL) was heated to 80° C. for 16 h under nitrogen atmosphere. Water (20 mL) was added and the mixture was acidified with HCl (1N) to pH 6 and then extracted with EtOAc (30 mL×3). The combined organic layers were washed with brine (30 mL×3), dried over anhydrous $Na_2SO_4$, filtered and concentrated in vacuo to give the title compound (520 mg, crude) as a gray solid that required no further purification.

Step 4:

(R)-6-bromo-9-chloro-4-methyl-4,5-dihydro-1H-benzo[b][1,4]diazepin-2(3H)-one

Step 1:

4-bromo-3-fluoro-2-nitroaniline

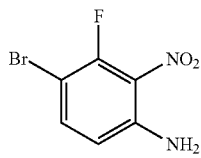 [SMILES: Nc1ccc(Br)c(F)c1[N+](=O)[O-]]

To a solution of 3-fluoro-2-nitroaniline (9.5 g, 60.9 mmol) in dimethyl formamide (100 mL) at 0° C. was added 1-bromopyrrolidine-2,5-dione (9.75 g, 54.8 mmol) dropwise and the reaction mixture stirred for 1.5 h. The reaction mixture was quenched with ice water (100 mL) and extracted with EtOAc (100 mL×3). The organic layers were dried over anhydrous $Na_2SO_4$, filtered and concentrated in vacuo. The crude residue was purified by silica gel chromatography (petroleum ether/EtOAc=10/1) to give the title compound (13.5 g, 94%) as a yellow solid. $^1$H NMR (400 MHz, DMSO-$d_6$) δ7.54-7.50 (m, 1H), 7.16 (s, 2H), 6.76 (d, J=7.6 Hz, 1H).

Step 2:

1-bromo-4-chloro-2-fluoro-3-nitrobenzene

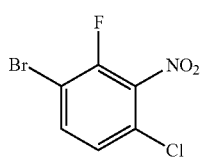 [SMILES: O=[N+]([O-])c1c(Cl)ccc(Br)c1F]

To a solution of 4-bromo-3-fluoro-2-nitroaniline (6.0 g, 25.5 mmol) in concentrated HCl (50 mL) at 0° C. was added $NaNO_2$ (1.94 g, 28.1 mmol) dropwise and the reaction mixture stirred for 1 h before CuCl (3.8 g, 38.3 mmol) in concentrated HCl (2 mL) was added dropwise. The reaction mixture was stirred at 0° C. for 0.5 h. The mixture was adjusted to pH 7 with sat. aq. $NaHCO_3$ and filtered. The filtrate was extracted with EtOAc (50 mL×3), washed with brine, dried over anhydrous $Na_2SO_4$, filtered and concentrated in vacuo. The crude residue was purified by silica gel chromatography (petroleum ether/EtOAc=50/1 to 20/1) to give the title compound (4.8 g, 74%) as a brown solid. $^1$H NMR (400 MHz, DMSO-$d_6$) δ 8.10-8.06 (m, 1H), 77.67-7.65 (m, 1H).

A mixture of (R)-3-((6-bromo-3-chloro-2-nitrophenyl)amino)butanoic acid (520 mg, crude) and Fe powder (430 mg, 7.7 mmol) in acetic acid (5 mL) was heated to 100° C. for 2 h under nitrogen atmosphere. After cooling the reaction to room temperature, the mixture was concentrated in vacuo, before water (20 mL) was added. The mixture was adjusted to pH 8 by potassium carbonate and filtered. The filtrate was extracted with EtOAc (20 mL×3), washed with brine, dried over anhydrous $Na_2SO_4$, filtered and concentrated in vacuo to give the title compound (Intermediate D, 550 mg, crude) as a brown solid that required no further purification.

Example 80

(2R)-6-chloro-9-(3-cyclopropyl-1-methyl-indazol-5-yl)-2-methyl-1,2,3,5-tetrahydro-1,5-benzodiazepin-4-one

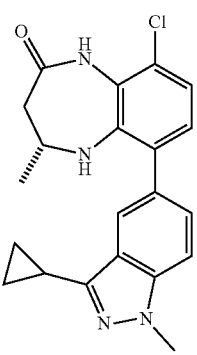 [SMILES: C[C@@H]1CC(=O)Nc2c(Cl)ccc(-c3ccc4c(c3)c(C3CC3)nn4C)c2N1]

Step 1:

3-cyclopropyl-1-methyl-5-(4,4,5,5-tetramethyl-1,3,2-dioxaborolan-2-yl)-1H-indazole

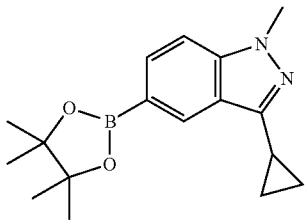 [SMILES: Cn1nc(C2CC2)c2cc(B3OC(C)(C)C(C)(C)O3)ccc21]

A mixture of 5-bromo-3-cyclopropyl-1-methyl-1H-indazole (5.0 g, 19.90 mmol), 4,4,4',4',5,5,5',5'-octamethyl-2,2'-bi(1,3,2-dioxaborolane) (6.1 g, 23.90 mmol), KOAc (4.9 g, 59.7 mmol) and [1,1'-bis(diphenylphosphino)ferrocene]dichloropalladium(II) (1.5 g, 2.00 mol) in dioxane (25 mL) was heated to 110° C. for 16 h under nitrogen atmosphere. After cooling the reaction to room temperature, the mixture was filtered and the filtrate was concentrated in vacuo. The crude residue was purified by silica gel chromatography (petroleum ether/EtOAc=10/1) to give the title product (3.0 g, 51%) as a yellow solid.

Step 2:

(2R)-6-chloro-9-(3-cyclopropyl-1-methyl-indazol-5-yl)-2-methyl-1,2,3,5-tetrahydro-1,5-benzodiazepin-4-one

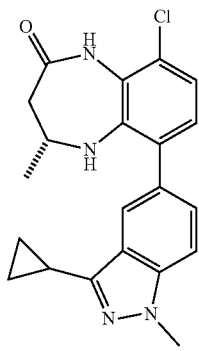 [SMILES: C[C@@H]1CC(=O)Nc2c(Cl)ccc(-c3ccc4c(c3)c(C3CC3)nn4C)c2N1]

A mixture of (R)-6-bromo-9-chloro-4-methyl-4,5-dihydro-1H-benzo[b][1,4]diazepin-2(3H)-one (Intermediate D, 241 mg, 0.83 mmol), 3-cyclopropyl-1-methyl-5-(4,4,5,5-tetramethyl-1,3,2-dioxaborolan-2-yl)-1H-indazole (298 mg, 1.0 mmol), bis(triphenylphosphine)palladium(II) dichloride (58.5 mg, 0.08 mmol) and potassium carbonate (229 mg, 1.66 mmol) in dioxane/H$_2$O (10 mL/2 mL) was heated to 90° C. for 3 h under nitrogen atmosphere. After cooling the reaction to room temperature, water (10 mL) was added and the mixture was extracted with EtOAc (10 mL×3). The organic lagers were washed with brine, dried over anhydrous Na$_2$SO$_4$, filtered and concentrated in vacuo to afford the crude product that was purified by reverse phase chromatography (acetonitrile 36-66%/0.2% formic acid in water) to give the title compound (45.0 mg, 14.2%) as a white solid. $^1$H NMR (400 MHz, CDCl$_3$) δ 7.68 (s, 1H), 7.52-7.31 (m, 3H), 7.15-6.96 (m, 2H), 4.04 (s, 4H), 3.65 (s, 1H), 2.94-2.65 (m, 1H), 2.58-2.35 (m, 1H), 2.30-2.08 (m, 1H), 1.32-1.15 (m, 3H), 1.13-1.00 (m, 4H). LCMS M/Z (M+H) 381.

The following compound was prepared in a similar fashion to Example 80:

| Example | Compound Name | NMR | m/z |
|---|---|---|---|
| Example 81 | (2R)-9-(1-tert-butylpyrazol-4-yl)-6-chloro-2-methyl-1,2,3,5-tetrahydro-1,5-benzodiazepin-4-one | $^1$H NMR (400 MHz, DMSO-d$_6$) δ 9.15 (s, 1H), 8.02 (s, 1H) 7.62 (s, 1H), 7.10-7.03 (m, 2H), 4.16-4.15 (m, 1H), 4.03-4.00 (m, 1H), 2.14-2.09 (m, 1H), 2.00-1.95 (m, 1H), 1.56 (s, 9H), 1.17 (d, J = 6.4 Hz, 3H) | 333 |

Example 82

(4R)-6-(3-cyclopropyl-1-methyl-indazol-5-yl)-4,9-dimethyl-1,3,4,5-tetrahydro-1,5-benzodiazepin-2-one

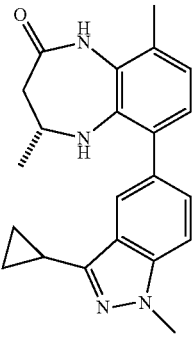 [SMILES: Cc1ccc(-c2ccc3c(c2)c(C2CC2)nn3C)c2c1NC(=O)C[C@@H](C)N2]

A mixture of (R)-9-chloro-6-(3-cyclopropyl-1-methyl-1H-indazol-5-yl)-4-methyl-4,5-dihydro-1H-benzo[b][1,4]diazepin-2(3H)-one (Intermediate D, 250 mg, 0.66 mmol), potassium methyltrifluoroborate (242 mg, 1.98 mmol), palladium acetate (12 mg, 0.07 mmol), di(adamantan-1-yl)(butyl)phosphine (46.6 mg, 0.13 mmol) and cesium carbonate (1.29 g, 3.96 mmol) in toluene (20 mL) and water (5 ml) was heated to 100° C. for 16 h under nitrogen atmosphere. After cooling the reaction to room temperature, the mixture was concentrated in vacuo and the residue was purified by reverse phase chromatography (acetonitrile 40-70%/0.2% formic acid in water) to give the title compound (29 mg, 12%) as a yellow solid. $^1$H NMR (400 MHz, CDCl$_3$) δ 7.68 (s, 1H), 7.42 (d, J=8.4 Hz, 1H), 7.33 (d, J=8.4 Hz, 1H), 7.13-7.00 (m, 2H), 6.93 (d, J=7.6 Hz, 1H), 4.14-3.94 (m, 4H), 3.55 (br s, 1H), 2.81-2.75 (m, 1H), 2.43-2.29 (m, 4H), 2.26-2.13 (m, 1H), 1.21 (d, J=6.4 Hz, 3H), 1.12-0.98 (m, 4H). LCMS M/Z (M+H) 361.

Example 83

(4R)-6-(3-cyclopropyl-1-methyl-indazol-5-yl)-4-methyl-2-oxo-1,3,4,5-tetrahydro-1,5-benzodiazepine-9-carbonitrile

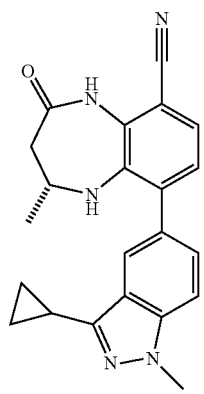 [SMILES: C[C@@H]1CC(=O)Nc2c(C#N)ccc(-c3ccc4c(c3)c(C3CC3)nn4C)c2N1]

A mixture of (R)-9-chloro-6-(3-cyclopropyl-1-methyl-1H-indazol-5-yl)-4-methyl-4,5-dihydro-1H-benzo[b][1,4]diazepin-2(3H)-one (Intermediate D, 250 mg, 0.66 mmol), potassium ferrocyanide (139 mg, 0.33 mmol), tris(dibenzylideneacetone)dipalladium(64 mg, 0.07 mmol), di-tert-butyl(2',4',6'-triisopropyl-[1,1'-biphenyl]-2-yl)phosphine (55.8 mg, 0.13 mmol) and potassium acetate (129 mg, 1.32 mmol) in dioxane (10 mL) and water (10 ml) was heated to 100° C. for 16 h under nitrogen atmosphere. After cooling the reaction to room temperature, the mixture was filtered and the filtrate was concentrated in vacuo. The residue was purified by reverse phase chromatography (acetonitrile 45-55%/0.2% formic acid in water) to give the title compound (38 mg, 16%) as a yellow solid. $^1$H NMR (400 MHz, CDCl$_3$) δ7.70 (s, 1H), 7.53 (s, 1H), 7.46 (d, J=8.8 Hz, 1H), 7.35-7.23 (m, 2H), 7.15 (d, J=8.0 Hz, 1H), 4.10-3.97 (m, 4H), 3.73 (s, 1H), 3.82 (d, J=13.2 Hz, 1H), 2.55-2.50 (m, 1H), 2.28-2.12 (m, 1H), 1.24 (d, J=6.3 Hz, 3H), 1.13-1.00 (m, 4H). LCMS M/Z (M+H) 372.

General Procedure for Intermediate E

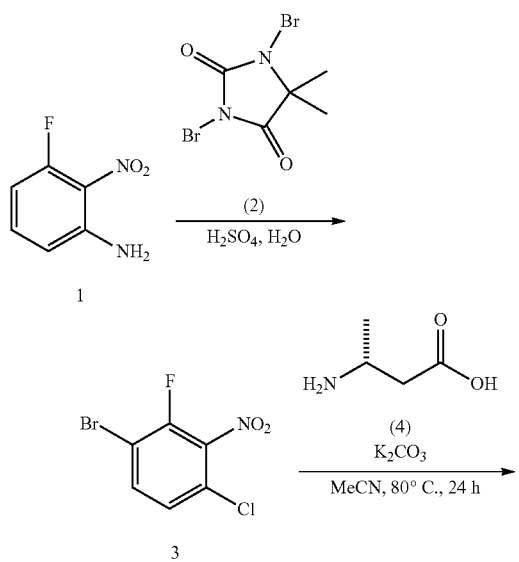

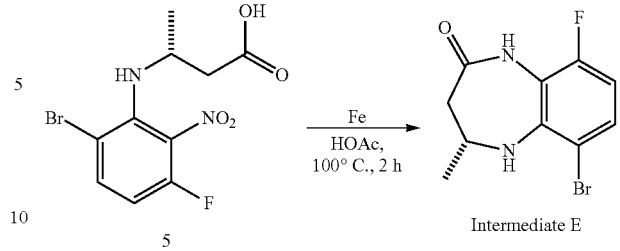

Step 1:

1-bromo-2,4-difluoro-3-nitrobenzene

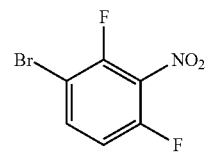 [SMILES: O=[N+]([O-])c1c(F)ccc(Br)c1F]

A mixture of 1,3-difluoro-2-nitrobenzene (2 g, 12.57 mmol) and 1,3-dibromo-5,5-dimethylimidazolidine-2,4-dione (1.98 g, 6.91 mmol) in concentrated sulfuric acid (20 mL) was stirred at 26° C. for 16 h. The reaction mixture was quenched with ice water (20 mL) and extracted with EtOAc (20 mL×3). The organic lagers were dried over anhydrous Na$_2$SO$_4$, filtered and concentrated in vacuo to give the title compound (1.5 g, 50%) as a yellow solid that required no further purification.

Step 2:

(R)-3-((6-bromo-3-fluoro-2-nitrophenyl)amino)butanoic acid

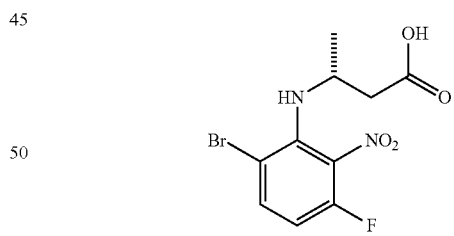

A mixture of 1-bromo-2,4-difluoro-3-nitrobenzene (2.0 g, 8.4 mmol), (R)-3-aminobutanoic acid (865 mg, 8.4 mmol) and potassium carbonate (2.32 g, 16.8 mmol) in acetonitrile (30 mL) was heated to 80° C. for 5 h under nitrogen atmosphere. After cooling the reaction to room temperature, water (20 mL) was added and the mixture was acidified with HCl (2 N) to pH 2 and then extracted with EtOAc (30 mL×3). The combined organic layers were washed with brine (30 mL×3), dried over anhydrous Na$_2$SO$_4$, filtered and concentrated in vacuo to give the title compound (600 mg, crude) as yellow oil that required no further purification.

Step 3:

(R)-6-bromo-9-fluoro-4-methyl-4,5-dihydro-1H-benzo[b][1,4]diazepin-2(3H)-one

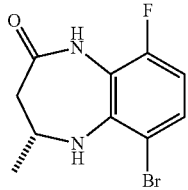

A mixture of (R)-3-((6-bromo-3-fluoro-2-nitrophenyl)amino)butanoic acid (250 mg, 0.78 mmol) and Fe powder (436 mg, 7.8 mmol) in acetic acid (10 mL) was heated to 100° C. for 2 h under nitrogen atmosphere. After cooling the reaction to room temperature, the mixture was concentrated in vacuo. Water (20 mL) was added. The mixture was adjusted to pH=8 by potassium carbonate and filtered. The filtrate was extracted with EtOAC (10 mL×3), washed with brine, dried over anhydrous $Na_2SO_4$, filtered and concentrated in vacuo to give the title compound (Intermediate E, 130 mg) as yellow oil that required no further purification.

Example 84

(2R)-9-(3-cyclopropyl-1-methyl-indazol-5-yl)-6-fluoro-2-methyl-1,2,35-tetrahydro-1,5-benzodiazepin-4-one

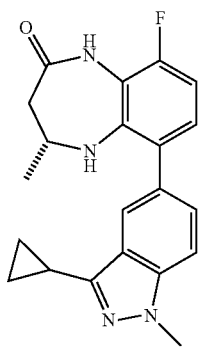 [SMILES: C[C@@H]1CC(=O)Nc2c(F)ccc(-c3ccc4c(c3)c(C3CC3)nn4C)c2N1]

Step 1:

(2R)-9-(3-cyclopropyl-1-methyl-indazol-5-yl)-6-fluoro-2-methyl-1,2,3,5-tetrahydro-1,5-benzodiazepin-4-one

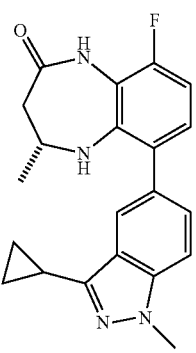

A mixture of (R)-6-bromo-9-fluoro-4-methyl-4,5-dihydro-1H-benzo[b][1,4]diazepin-2(3H)-one (Intermediate E, 130 mg, 0.48 mmol), 3-cyclopropyl-1-methyl-5-(4,4,5,5-tetramethyl-1,3,2-dioxaborolan-2-yl)-1H-indazole (170.0 mg, 0.57 mmol), bis(triphenylphosphine)palladium(II) dichloride (36.5 mg, 0.05 mmol) and potassium carbonate (133.0 mg, 0.96 mmol) in dioxane/$H_2O$ (2 mL/0.2 mL) was heated to 100° C. for 12 h under nitrogen atmosphere. After cooling the reaction to room temperature, water (5 mL) was added and the mixture was extracted with EtOAc (5 mL×3). The combined organic lagers were washed with brine, dried over anhydrous $Na_2SO_4$, filtered and concentrated in vacuo. The crude residue was purified by reverse phase chromatography (acetonitrile 40-70%/0.2% formic acid in water) to give the title compound (28 mg, 11%) as a white solid. $^1$H NMR (400 MHz, $CDCl_3$) δ 7.68 (s, 1H), 7.42 (d, J=8.8 Hz, 1H), 7.39 (br s, 1H), 7.31 (d, J=8.4 Hz, 1H), 6.98-6.97 (m, 1H), 6.75-6.72 (m, 1H), 4.04 (s, 3H), 4.00-3.89 (m, 1H), 3.79 (br s, 1H), 2.84-2.81 (m, 1H), 2.61-2.56 (m, 1H), 2.27-2.15 (m, 1H), 1.22 (d, J=6.3 Hz, 3H), 1.12-0.99 (m, 4H). LCMS M/Z (M+H) 365.

The following compound was prepared in a similar fashion to Example 84:

Examples 85

| Example | Compound Name | NMR | m/z |
|---|---|---|---|
| Example 85 | (2R)-6-fluoro-2-methyl-9-[1-methyl-3-(1-methylpyrazol-4-yl)indazol-5-yl]-1,2,3,5-tetrahydro-1,5-benzodiazepin-4-one | $^1$H NMR (400 MHz, $CDCl_3$) δ8.01 (s, 1H), 7.89 (s, 1H), 7.77 (s, 1H), 7.49 (d, J = 8.4 Hz, 1H), 7.35 (d, J = 8.0 Hz, 1H), 7.30 (s, 1H), 6.98-6.95 (m, 1H), 6.75-6.71 (m, 1H), 4.14 (s, 3H), 4.00 (s, 3H), 3.93-3.92 (m, 1H), 3.77 (s, 1H), 2.82-2.78 (m, 1H), 2.60-2.55 (m, 1H), 1.19 (d, J = 8.0 Hz, 3H) | 405 |

Example 86

(2R)-9-(3-cyclopropyl-1-methyl-indazol-5-yl)-6-methoxy-2-methyl-1,2,3,5-tetrahydro-1,5-benzodiazepin-4-one

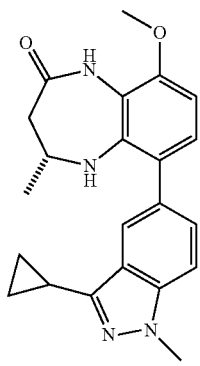 [SMILES: COc1ccc(-c2ccc3c(c2)c(C2CC2)nn3C)c2c1NC(=O)C[C@@H](C)N2]

Step 1:

(R)-3-((6-bromo-3-methoxy-2-nitrophenyl)amino)butanoic acid

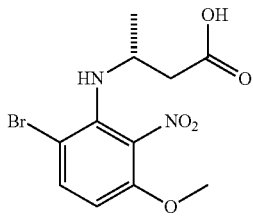 [SMILES: COc1ccc(Br)c(N[C@H](C)CC(=O)O)c1[N+](=O)[O-]]

A mixture of (R)-3-((6-bromo-3-fluoro-2-nitrophenyl)amino)butanoic acid (300 mg, 0.93 mmol) and sodium methoxide (251 mg, 4.65 mmol) in MeOH (10 mL) was heated to 60° C. for 16 h. After cooling the reaction to room temperature, the mixture was acidified with HCl (5 N) to pH 2 and then extracted with EtOAc (20 mL×3). The combined organic layers were washed with brine (20 mL×3), dried over anhydrous $Na_2SO_4$, filtered and concentrated in vacuo to give the title compound (350 mg, crude) as yellow oil that required no further purification.

Step 2:

(R)-6-bromo-9-methoxy-4-methyl-4,5-dihydro-1H-benzo[b][1,4]diazepin-2(3H)-one

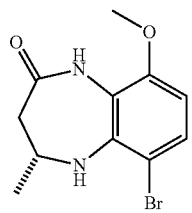 [SMILES: COc1ccc(Br)c2c1NC(=O)C[C@@H](C)N2]

A mixture of (R)-3-((6-bromo-3-methoxy-2-nitrophenyl)amino)butanoic acid (350 mg, 1.05 mmol) and Fe powder (294 mg, 5.25 mmol) in HOAc (10 mL) was heated to 100° C. for 2 h under nitrogen atmosphere. After cooling the reaction to room temperature, the mixture was adjusted to pH 8 by potassium carbonate and filtered. The filtrate was extracted with EtOAc (10 mL×3), washed with brine, dried over anhydrous $Na_2SO_4$, filtered and concentrated in vacuo to give the title compound (220 mg, crude) as yellow oil that required no further purification.

Step 3:

(2R)-9-(3-cyclopropyl-1-methyl-indazol-5-yl)-6-methoxy-2-methyl-1,2,3,5-tetrahydro-1,5-benzodiazepin-4-one

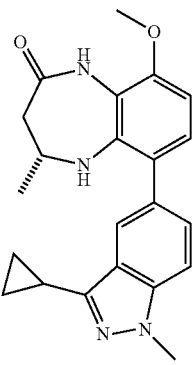 [SMILES: COc1ccc(-c2ccc3c(c2)c(C2CC2)nn3C)c2c1NC(=O)C[C@@H](C)N2]

A mixture of (R)-6-bromo-9-methoxy-4-methyl-4,5-dihydro-1H-benzo[b][1,4]diazepin-2(3H)-one (220 mg, 0.77 mmol), 3-cyclopropyl-1-methyl-5-(4,4,5,5-tetramethyl-1,3,2-dioxaborolan-2-yl)-1H-indazole (230.0 mg, 0.77 mmol), bis(triphenylphosphine)palladium(II) dichloride (56 mg, 0.08 mmol) and potassium carbonate (212.0 mg, 1.54 mmol) in dioxane/$H_2O$ (5:1, 18 mL) was heated to 100° C. for 12 h under nitrogen atmosphere. After cooling the reaction to room temperature, water (5 mL) was added and the mixture was extracted with EtOAc (15 mL×3). The organic lagers were washed with brine, dried over anhydrous $Na_2SO_4$, filtered and concentrated in vacuo. The crude residue was purified by reverse phase chromatography (acetonitrile 35-65%/0.2% formic acid in water) to give the title compound (26 mg, 9%) as a white solid. $^1$H NMR (400 MHz, $CDCl_3$) δ 7.68 (s, 1H), 7.64 (s, 1H), 7.41 (d, J=8.0 Hz, 1H), 7.33 (d, J=8.4 Hz, 1H), 6.98 (d, J=8.4 Hz, 1H), 6.55 (d, J=8.4 Hz, 1H), 4.04 (s, 3H), 3.97-3.87 (m, 4H), 3.73 (br s, 1H), 2.81 (d, J=14.0 Hz, 1H), 2.60-2.54 (m, 1H), 2.28-2.13 (m, 1H), 1.21 (d, J=6.0 Hz, 3H), 1.13-0.98 (m, 4H). LCMS M/Z (M+H) 377.

General Procedure for Intermediate F

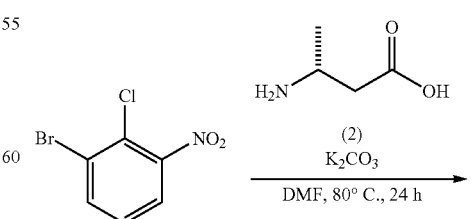

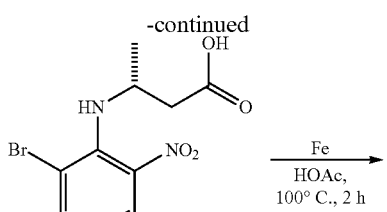

A mixture of (R)-3-((2-bromo-4-chloro-6-nitrophenyl)amino)butanoic acid (630 mg, 1.86 mmol) and Fe powder (520.8 mg, 9.3 mmol) in acetic acid (10 mL) was heated to 100° C. for 2 h under nitrogen atmosphere. After cooling the reaction to room temperature, the mixture was concentrated in vacuo before water (20 mL) was added. The mixture was adjusted to pH 8 with potassium carbonate and filtered. The filtrate was extracted with EtOAc (20 mL×3), washed with brine, dried over anhydrous Na$_2$SO$_4$, filtered and concentrated in vacuo to give crude product that was purified by prep-TLC (petroleum ether/EtOAc=3/1) to give the title compound (Intermediate F, 103 mg, 20%) as a white solid.

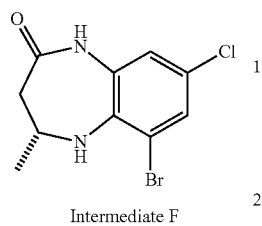

Intermediate F

Step 1:

(R)-3-((2-bromo-4-chloro-6-nitrophenyl)amino)butanoic acid

Example 87

(4R)-8-chloro-6-(3-cyclopropyl-1-methyl-indazol-5-yl)-4-methyl-1,3,4,5-tetrahydro-1,5-benzodiazepin-2-one

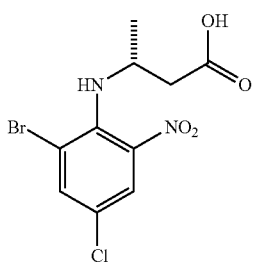 [SMILES: C[C@H](CC(=O)O)Nc1c(Br)cc(Cl)cc1[N+](=O)[O-]]

A mixture of 1-bromo-2,5-dichloro-3-nitrobenzene (1.3 g, 4.8 mmol), (R)-3-aminobutanoic acid (495 mg, 4.8 mmol) and potassium carbonate (1.32 g, 9.6 mmol) in dimethyl formamide (20 mL) was heated to 80° C. for 24 h under nitrogen atmosphere. After cooling the reaction to room temperature, water (20 mL) was added and the mixture was acidified with HCl (1N) to pH 6 and then extracted with EtOAc (30 mL×3). The combined organic layers were washed with brine (30 mL×3), dried over anhydrous Na$_2$SO$_4$, filtered and concentrated in vacuo to give the title compound (630 mg, 39%) as a yellow solid that required no further purification.

Step 2:

(R)-6-bromo-8-chloro-4-methyl-4,5-dihydro-H-benzo[b][1,4]diazepin-2(3H)-one

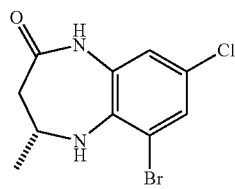

A mixture of (R)-6-bromo-8-chloro-4-methyl-4,5-dihydro-1H-benzo[b][1,4]diazepin-2(3H)-one (Intermediate F, 103 mg, 0.356 mmol), 3-cyclopropyl-1-methyl-5-(4,4,5,5-tetramethyl-1,3,2-dioxaborolan-2-yl)-1H-indazole (127.4 mg, 0.427 mmol), bis(triphenylphosphine)palladium(II) dichloride (28 mg, 0.04 mmol) and potassium carbonate (147.4 mg, 1.07 mmol) in dioxane/H$_2$O (2 mL/0.2 mL) was heated to 100° C. for 12 h under nitrogen atmosphere. After cooling the reaction to room temperature, water (5 mL) was added and the mixture was extracted with EtOAc (5 mL×3). The organic lagers were washed with brine, dried over anhydrous Na$_2$SO$_4$, filtered and concentrated in vacuo to give the crude product that was purified by reverse phase chromatography (acetonitrile 38-59%/0.2% formic acid in water) to give the title compound (13 mg, 10%) as a white solid. $^1$H NMR (400 MHz, CD$_3$OD) δ 7.77 (s, 1H), 7.63-7.59 (m, 1H), 7.44-7.38 (m, 1H), 7.09-7.01 (m, 2H), 4.69-4.60 (m, 1H), 4.02 (s, 4H), 2.80-2.73 (m, 1H), 2.40-2.26 (m, 2H), 1.17 (d, J=6.3 Hz, 3H), 1.11-0.99 (m, 4H). LCMS M/Z (M+H) 381.

The following compound was prepared in a similar fashion to Example 87:

| Example | Compound Name | NMR | m/z |
|---|---|---|---|
| Example 88 | (4R)-6-(1-tert-butylpyrazol-4-yl)-8-chloro-4-methyl-1,3,4,5-tetrahydro-1,5-benzodiazepin-2-one | $^1$H NMR (400 MHz, DMSO-$d_6$) δ 9.61 (s, 1H), 8.08 (s, 1H), 7.66 (s, 1H), 7.06 (d, J = 2.4 Hz, 1H), 6.86 (d, J = 2.4 Hz, 1H), 4.18 (s, 1H), 3.94-3.99 (m, 1H), 2.57-2.52 (m, 1H), 2.23-2.18 (m, 1H), 1.56 (s, 9H), 1.18 (d, J = 6.4 Hz, 3H) | 333 |

General Procedure for Intermediate G

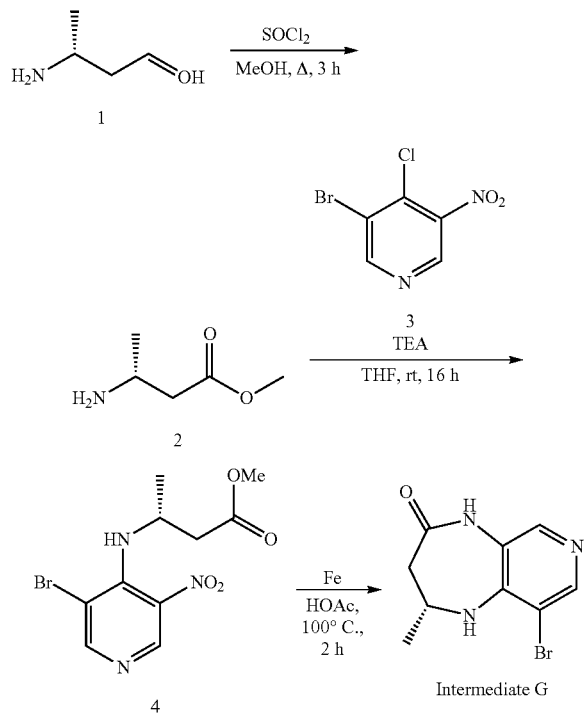

Step 1:

(R)-methyl 3-aminobutanoate

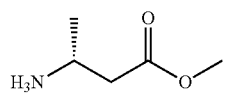

To (R)-3-aminobutanoic acid (2.0 g, 19.0 mmol) in MeOH (40 mL) was added $SOCl_2$ (4.6 g, 38.0 mmol). The reaction mixture was heated to 80° C. for 3 h under nitrogen atmosphere. After cooling the reaction to room temperature, the mixture was concentrated in vacuo. The crude residue was dissolved in DCM/MeOH (10:1, 50 mL), washed with sat. aq. $NaHCO_3$ (50 mL) and the aqueous layer was extracted with DCM/MeOH (10:1, 50 mL×2). The combined organic layers were dried over anhydrous $Na_2SO_4$, filtered and concentrated in vacuo to give the title compound (500 mg, 45%) as a pale brown oil. $^1$H NMR (400 MHz, $CDCl_3$) δ3.70 (s, 3H) 3.44-3.36 (m, 1H) 2.46-2.29 (m, 2H) 1.14 (d, J=6.4 Hz, 2H).

Step 2:

(R)-methyl 3-((3-bromo-5-nitropyridin-4-yl)amino)butanoate

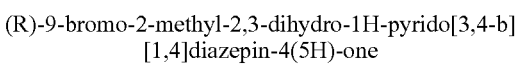

To a solution of 3-bromo-4-chloro-5-nitropyridine (500 mg, 2.0 mmol) and triethylamine (500 mg, 4.5 mmole) in THF (40 mL) was added (R)-methyl 3-aminobutanoate (200 mg, 1.7 mmol). The reaction mixture was stirred at 26° C. for 16 h. The mixture was concentrated in vacuo. The crude residue was purified by silica gel chromatography (petroleum ether/EtOAc=5/1) to give the title compound (400 mg, 63%) as a pale brown solid. LCMS M/Z (M+H) 318.

Step 3:

(R)-9-bromo-2-methyl-2,3-dihydro-1H-pyrido[3,4-b][1,4]diazepin-4(5H)-one

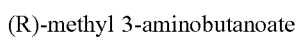

A mixture of (R)-methyl 3-((3-bromo-5-nitropyridin-4-yl)amino)butanoate (400 mg, 1.3 mmol) and Fe powder (400 mg, 7.1 mmol) in acetic acid (20 mL) was heated to 100° C. for 3 h under nitrogen atmosphere. After cooling the reaction to room temperature, the mixture was concentrated in vacuo before water (20 mL) was added. The mixture was adjusted to pH 8 with potassium carbonate and filtered. The filtrate was extracted with EtOAc (20 mL×3), washed with brine, dried over anhydrous $Na_2SO_4$, filtered and concentrated in vacuo. The crude residue was purified by silica gel chromatography (petroleum ether/EtOAc=1/1) to give the title compound (Intermediate G, 260 mg, 81%) as a pale brown solid.

Example 89

(2R)-9-(3-cyclopropyl-1-methyl-Indazol-5-yl)-2-methyl-1,2,3,5-tetrahydropyrido[3,4-b][1,4]diazepin-4-one

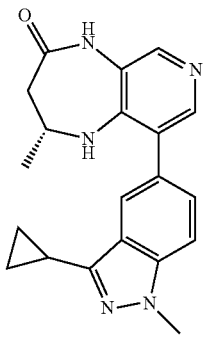 [SMILES: C[C@@H]1CC(=O)Nc2cncc(-c3ccc4c(c3)c(C3CC3)nn4C)c2N1]

To a mixture of (R)-9-bromo-2-methyl-2,3-dihydro-1H-pyrido[3,4-b][1,4]diazepin-4(5H)-one (Intermediate G, 100 mg, 0.4 mmol), sodium carbonate (100 mg, 1.0 mmol) and 3-cyclopropyl-1-methyl-5-(4,4,5,5-tetramethyl-1,3,2-dioxaborolan-2-yl)-1H-indazole (130 mg, 0.4 mmol) in dioxane (20 mL)/H$_2$O (4 mL) was added [1,1'-bis(diphenylphosphino)ferrocene]dichloropalladium(II), complex with dichloromethane (30 mg, 0.04 mmol). The resulting mixture was heated to 110° C. for 16 h under nitrogen atmosphere. After cooling the reaction to room temperature, the mixture was concentrated in vacuo. The crude residue was purified by prep-TLC (DCM/MeOH=10:1) to give the title compound (94 mg, 68%) as a white solid. $^1$H NMR (400 MHz, DMSO-d$_6$) δ 9.70 (s, 1H), 7.94 (s, 1H), 7.74-7.72 (m, 2H), 7.61 (d, J=8.4 Hz, 1H), 7.31 (d, J=8.8 Hz, 1H), 5.16 (d, J=3.2 Hz, 1H), 3.92 (s, 3H), 3.84-3.82 (m, 1H), 2.66-2.51 (m, 1H), 2.53-2.49 (m, 1H), 2.32-2.24 (m, 1H), 1.13-1.12 (m, 2H), 1.03 (s, 3H), 0.96-0.91 (m, 2H). LCMS M/Z (M+H) 348.

The following compound was prepared in a similar fashion to Example 89:

| Example | Compound Name | NMR | m/z |
|---|---|---|---|
| Example 90 | (2R)-2-methyl-9-[1-methyl-3-(1-methylpyrazol-4-yl)indazol-5-yl]-1,2,3,5-tetrahydropyrido[3,4-b][1,4]diazepin-4-one | $^1$H NMR (400 MHz, CDCl$_3$) δ 8.04-8.00 (m, 3H), 7.91 (s, 1H), 7.83 (s, 1H), 7.52 (d, J = 8.4 Hz, 1H), 7.38 (d, J = 8.4 Hz, 1H), 4.45 (s, 1H), 4.14 (s, 3H), 4.01 (s, 3H), 3.98-3.93 (m, 1H), 2.76-2.71 (m, 2H), 1.24 (d, J = 6.4 Hz, 1H) | 388 |

Example 91

(4R)-6-(3-cyclopropyl-1-methyl-indazol-5-yl)-4-methyl-8-(trifluoromethyl)-1,3,4,5-tetrahydro-1,5-benzodiazepin-2-one Step 1:

1-bromo-2-chloro-3-nitro-5-(trifluoromethyl)benzene

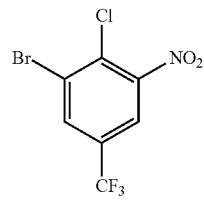 [SMILES: O=[N+]([O-])c1cc(C(F)(F)F)cc(Br)c1Cl]

A mixture of 1-chloro-2-nitro-4-(trifluoromethyl)benzene (1.0 g, 4.4 mmol) and 1,3-dibromo-5,5-dimethylimidazolidine-2,4-dione (0.7 g, 2.45 mmol) in concentrated sulfuric acid (4.1 mL) was stirred at 15° C. for 18 h. The reaction mixture was quenched with ice water (20 mL) and extracted with EtOAc (20 mL×3). The organic lagers were dried over anhydrous Na$_2$SO$_4$, filtered and concentrated in vacuo to give the title compound (1.3 g, 99%) as a white solid that required no further purification. $^1$H NMR (400 MHz, CDCl$_3$) δ 8.11 (s, 1H) 8.00 (s, 1H).

Step 2:

(R)-3-((2-bromo-6-nitro-4-(trifluoromethyl)phenyl)amino)butanoic acid

A mixture of 1-bromo-2-chloro-3-nitro-5-(trifluoromethyl)benzene (1.3 g, 4.3 mmol), (R)-3-aminobutanoic acid (484 mg, 2.8 mmol) and potassium carbonate (1.08 g, 7.8 mmol) in dimethyl formamide (30 mL) was heated to 80° C. for 18 h under nitrogen atmosphere. After cooling the reaction to room temperature, water (20 mL) was added and the mixture was acidified with HCl (2 N) to pH 2 and the mixture was extracted with EtOAc (30 mL×3). The combined organic layers were washed with brine (30 mL×3), dried over anhydrous Na$_2$SO$_4$, filtered and concentrated in vacuo to give the title compound (1.35 g, crude) as a brown oil that required no further purification. LCMS M/Z (M+H) 323.

Step 3:

(R)-6-bromo-4-methyl-8-(trifluoromethyl)-4,5-di-hydro-1H-benzo[b][1,4]diazepin-2(3H)-one

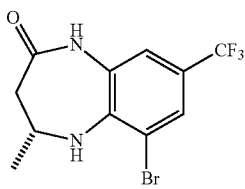 [SMILES: C[C@@H]1CC(=O)Nc2cc(C(F)(F)F)cc(Br)c2N1]

A mixture of (R)-3-((2-bromo-6-nitro-4-(trifluoromethyl)phenyl)amino)butanoic acid (1.3 g, 3.5 mmol) and Fe powder (2.0 g, 17.5 mmol) in acetic acid (10 mL) was heated to 60° C. for 1 h under nitrogen atmosphere. After cooling the reaction to room temperature, the mixture was concentrated in vacuo before water (20 mL) was added. The mixture was adjusted to pH 8 with potassium carbonate and filtered. The filtrate was extracted with EtOAc (10 mL×3), washed with brine, dried over anhydrous Na$_2$SO$_4$, filtered and concentrated in vacuo to give the title compound (1.1 g, crude) as a brown solid that required no further purification. LCMS M/Z (M+H) 323.

Step 4:

(4R)-6-(3-cyclopropyl-1-methyl-indazol-5-yl)-4-methyl-8-(trifluoromethyl)-1,3,4,5-tetrahydro-1,5-benzodiazepin-2-one

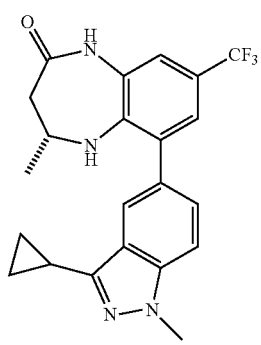 [SMILES: C[C@@H]1CC(=O)Nc2cc(C(F)(F)F)cc(-c3ccc4c(c3)c(C3CC3)nn4C)c2N1]

A mixture of (R)-6-bromo-4-methyl-8-(trifluoromethyl)-4,5-dihydro-1H-benzo[b][1,4]diazepin-2(3H)-one (170 mg, 0.5 mmol), 3-cyclopropyl-1-methyl-5-(4,4,5,5-tetramethyl-1,3,2-dioxaborolan-2-yl)-1H-indazole (189 mg, 0.6 mmol), bis(triphenylphosphine)palladium(II) dichloride (35 mg, 0.05 mmol) and potassium carbonate (219 mg, 1.6 mmol) in dioxane/H$_2$O (5:1, 6 mL) was heated to 100° C. for 12 h under nitrogen atmosphere. After cooling the reaction to room temperature, water (5 mL) was added and the mixture was extracted with EtOAc (5 mL×3). The combined organic lagers were washed with brine, dried over anhydrous Na$_2$SO$_4$, filtered and concentrated in vacuo. The crude residue was purified by reverse phase chromatography (acetonitrile 45-75%/0.2% formic acid in water) to give the title compound (28 mg, 11%) as a white solid. $^1$H NMR (400 MHz, CD$_3$OD) δ 7.78 (s, 1H), 7.61 (d, J=8.8 Hz, 1H), 7.40 (d, J=7.2 Hz 1H), 7.25 (d, J=4.8 Hz, 2H), 4.01 (s, 4H), 2.77-2.73 (m, 1H), 2.51-2.47 (m, 1H), 2.46-2.28 (m, 1H), 1.20 (d, J=6.4 Hz, 3H), 1.06-1.01 (m, 4H). LCMS M/Z (M+H) 415.

Example 92

(4R)-6-(3-cyclopropyl-1-methyl-indazol-5-yl)-8-fluoro-4-methyl-1,3,4,5-tetrahydro-1,5-benzodiazepin-2-one

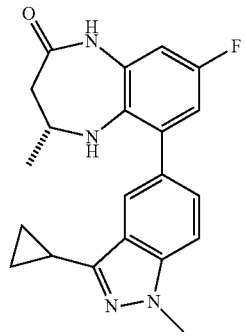 [SMILES: C[C@@H]1CC(=O)Nc2cc(F)cc(-c3ccc4c(c3)c(C3CC3)nn4C)c2N1]

Step 1:

1-bromo-2,5-difluoro-3-nitrobenzene

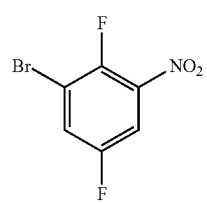 [SMILES: O=[N+]([O-])c1cc(F)cc(Br)c1F]

A mixture of 1,4-difluoro-2-nitrobenzene (2 g, 12.6 mmol) and 1,3-dibromo-5,5-dimethylimidazolidine-2,4-dione (2.0 g, 7.0 mmol) in concentrated sulfuric acid (15 mL) was stirred at 20° C. for 18 h. The reaction mixture was quenched with ice water (100 mL), extracted with EtOAc (20 mL×3). The combined organic lagers were dried over anhydrous Na$_2$SO$_4$, filtered and concentrated in vacuo. The residue was purified by silica gel chromatography (petroleum ether) to give the title compound (0.7 g, 23%) as a colorless oil.

Step 2:

(R)-3-((2-bromo-4-fluoro-6-nitrophenyl)amino)butanoic acid

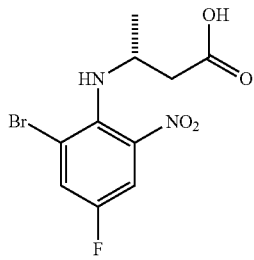 [SMILES: C[C@H](CC(=O)O)Nc1c(Br)cc(F)cc1[N+](=O)[O-]]

A mixture of 1-bromo-2,5-difluoro-3-nitrobenzene (0.7 g, 2.9 mmol), (R)-3-aminobutanoic acid (288 mg, 2.8 mmol) and potassium carbonate (813 g, 5.9 mmol) in acetonitrile (10 mL) was heated to 80° C. for 18 h under nitrogen atmosphere. After cooling the reaction to room temperature, water (20 mL) was added and the mixture was acidified with HCl (2 N) to pH 2 and then extracted with EtOAc (20 mL×3). The combined organic layers were washed with brine (20 mL×3), dried over anhydrous Na$_2$SO$_4$, filtered and concentrated in vacuo to give the title compound (0.5 g, crude) as a brown oil that required no further purification. LCMS M/Z (M+H) 321.

Step 3:

(R)-6-bromo-4-methyl-8-fluoro-4,5-dihydro-1H-benzo[b][1,4]diazepin-2(3H)-one

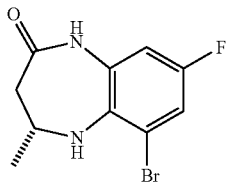

A mixture of (R)-3-((2-bromo-4-fluoro-6-nitrophenyl)amino)butanoic acid (150 mg, 0.47 mmol) and Fe powder (130 mg, 2.3 mmol) in acetic acid (5 mL) was heated to 60° C. for 1 h under nitrogen atmosphere. After cooling the reaction to room temperature, the solvent was concentrated in vacuo. Water (10 mL) was added. The mixture was adjusted to pH 8 with potassium carbonate and filtered. The filtrate was extracted with EtOAc (10 mL×3), washed with brine, dried over anhydrous Na$_2$SO$_4$, filtered and concentrated in vacuo to give the title compound (75 mg, crude) as a brown solid that required no further purification. LCMS M/Z (M+H) 273.

Step 4:

(4R)-6-(3-cyclopropyl-1-methyl-indazol-5-yl)-8-fluoro-4-methyl-1,3,4,5-tetrahydro-1,5-benzodiazepin-2-one

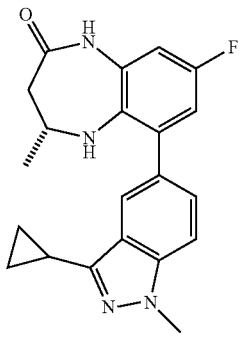 [SMILES: C[C@@H]1CC(=O)Nc2cc(F)cc(-c3ccc4c(c3)c(C3CC3)nn4C)c2N1]

A mixture of (R)-6-bromo-4-methyl-8-fluoro-4,5-dihydro-1H-benzo[b][1,4]diazepin-2(3H)-one (75 mg, 0.275 mmol), 3-cyclopropyl-1-methyl-5-(4,4,5,5-tetramethyl-1,3,2-dioxaborolan-2-yl)-1H-indazole (98 mg, 0.33 mmol), bis(triphenylphosphine)palladium(II) dichloride (20 mg, 0.028 mmol) and potassium carbonate (114 mg, 0.824 mmol) in dioxane/H$_2$O (5:1, 6 mL) was heated to 100° C. for 12 h under nitrogen atmosphere. After cooling the reaction to room temperature, water (5 mL) was added and the mixture was extracted with EtOAc (5 mL×3). The combined organic layers were washed with brine, dried over anhydrous Na$_2$SO$_4$, filtered and concentrated in vacuo. The crude residue was purified by reverse phase chromatography (acetonitrile 35-65%/0.2% formic acid in water) to give the title compound (28.0 mg, 28%) as a white solid. $^1$H NMR (400 MHz, CD$_3$OD) δ 7.76 (s, 1H), 7.58 (d, J=7.2 Hz, 1H), 7.41-7.38 (m, 1H), 6.87 (d, J=8.8 Hz, 1H), 6.79 (d, J=9.2 Hz, 1H), 4.00-3.95 (m, 4H), 2.77-2.74 (d, J=7.2 Hz, 1H), 2.32-2.27 (m, 2H), 1.14 (d, J=6.4 Hz, 3H), 1.06-1.01 (m, 4H). LCMS M/Z (M+H) 365.

Example 93

(4R)-6-(1-benzylsulfonylindol-2-yl)-4-methyl-1,3,4,5-tetrahydro-1,5-benzodiazepin-2-one

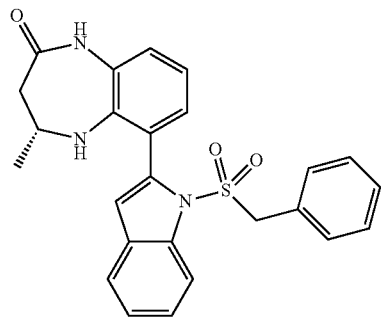 [SMILES: C[C@@H]1CC(=O)Nc2cccc(-c3cc4ccccc4n3S(=O)(=O)Cc3ccccc3)c2N1]

Step 1:

N-(2-ethynylphenyl)-1-phenylmethanesulfonamide

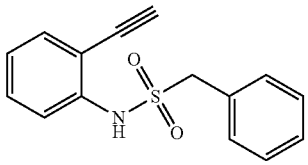 [SMILES: C#Cc1ccccc1NS(=O)(=O)Cc1ccccc1]

To a mixture of 2-ethynylaniline (234 mg, 2.0 mmol) in dry DCM (10 mL) at 20° C. was added pyridine (1.0 mL) and phenylmethanesulfonyl chloride (456 mg, 2.4 mmol). The mixture was stirred at 20° C. for 3 h. The mixture was concentrated in vacuo and extracted with EtOAc (30 mL×3). The combined organic layers were dried over anhydrous $Na_2SO_4$, filtered and concentrated in vacuo. The crude residue was purified by silica gel chromatography (petroleum ether/EtOAc=5/1) to give the title compound (300 mg, 55%) as a yellow oil.

Step 2:

(4R)-6-(1-benzylsulfonylindol-2-yl-4-methyl-1,3,4,5-tetrahydro-1,5-benzodiazepin-2-one

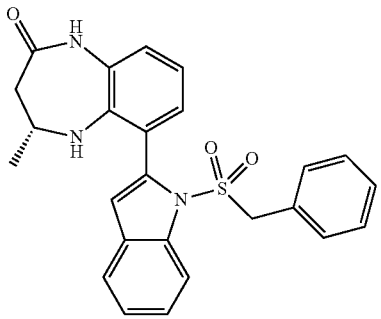 [SMILES: C[C@@H]1CC(=O)Nc2cccc(-c3cc4ccccc4n3S(=O)(=O)Cc3ccccc3)c2N1]

A mixture of N-(2-ethynylphenyl)-1-phenylmethanesulfonamide (300 mg, 1.1 mmol), (R)-6-bromo-4-methyl-4,5-dihydro-1H-benzo[b][1,4]diazepin-2(3H)-one (279 mg, 1.1 mmol), copper(I) iodide (42 mg, 0.22 mmol) and [1,1'-bis(diphenylphosphino)ferrocene]-dichloropalladium(II) (77 mg, 0.11 mmol) in MeCN/TEA (10 mL/2 mL) was heated to reflux temperature for 2 h. After cooling the reaction to room temperature, the solvent was concentrated in vacuo. Water (10 mL) was added and the mixture was extracted with EtOAc (10 mL). The combined organic layers were dried over anhydrous $Na_2SO_4$, filtered and concentrated in vacuo. The crude residue was purified by reverse phase chromatography (acetonitrile 56-86%/0.1% $NH_4OH$ in water) to give the title compound (27 mg, 5%) as a white solid. $^1H$ NMR (400 MHz, $CDCl_3$) 7.99-7.97 (m, 1H), 7.61 (d, J=8.0 Hz, 1H), 7.38-7.26 (m, 4H), 7.18-7.16 (m, 2H), 6.90-6.86 (m, 1H), 6.75-6.73 (m, 3H), 6.54-6.52 (m, 1H), 6.23-6.21 (m, 1H), 4.46-4.43 (m, 1H), 4.30-4.24 (m, 1H), 4.14-3.90 (m, 1H), 3.50-3.40 (m, 1H), 2.99-2.68 (m, 1H), 2.49-2.26 (m, 1H), 1.25 (t, J=6.4 Hz, 3H). LCMS M/Z (M+H) 446.

Example 94

(4R)-4-methyl-6-[1-methyl-3-(1-methylpyrazol-4-yl)indazol-5-yl]-1,3,4,5-tetrahydropyrido[3,4-b][1,4]diazepin-2-one

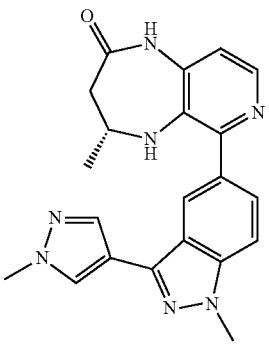 [SMILES: C[C@@H]1CC(=O)Nc2ccnc(-c3ccc4c(c3)c(-c3cnn(C)c3)nn4C)c2N1]

Step 1:

5-(3-fluoro-4-nitropyridin-2-yl)-1-methyl-3-(1-methyl-1H-pyrazol-4-yl)-1H-indazole

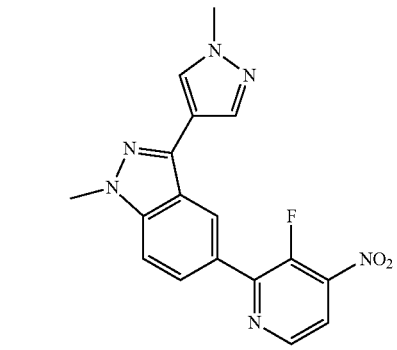 [SMILES: Cn1cc(-c2nn(C)c3ccc(-c4nccc([N+](=O)[O-])c4F)cc23)cn1]

To a solution of 2-chloro-3-fluoro-4-nitropyridine (200 mg, 1.13 mmol), 1-methyl-3-(1-methyl-1H-pyrazol-4-yl)-5-(4,4,5,5-tetramethyl-1,3,2-dioxaborolan-2-yl)-1H-indazole (290 mg, 0.87 mmol) and $K_2CO_3$ (157 mg, 1.13 mmol) in dioxane (5 mL) was added [1,1'-bis(diphenylphosphino)ferrocene]dichloropalladium(I) (43 mg, 0.06 mmol). The mixture was stirred at reflux temperature for 30 min. After cooling the reaction to room temperature, the crude mixture was diluted with water (10 mL) and extracted with EtOAc (10 mL×3). The combined organic layers were washed with sat. aq. sodium bicarbonate (10 mL×3), dried over anhydrous $Na_2SO_4$, filtered and concentrated in vacuo to give the crude product that was purified by silica gel chromatography (petroleum ether/EtOAc=3/1) to give the title compound (160 mg, 52%) as a yellow solid.

Step 2:

(R)-methyl-3-((2-(1-methyl-3-(1-methyl-1H-pyrazol-1-yl)-1H-indazol-5-yl)-4-nitropyridin-3-yl)amino)butanoate

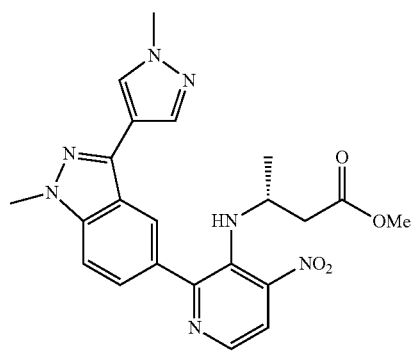 [SMILES: COC(=O)C[C@@H](C)Nc1c([N+](=O)[O-])ccnc1-c1ccc2c(c1)c(-c1cnn(C)c1)nn2C]

To a solution of 5-(3-fluoro-4-nitropyridin-2-yl)-1-methyl-3-(1-methyl-1H-pyrazol-4-yl)-1H-indazole (160 mg, 0.454 mmol) in THF (5 mL) was added (R)-methyl 3-aminobutanoate (80 mg, 0.68 mmol) and TEA (138 mg, 1.36 mmol). The mixture was heated to reflux temperature for 16 h under nitrogen atmosphere. After cooling the reaction to room temperature, the reaction was concentrated in vacuo. The crude residue was purified by prep-TLC (DCM/MeOH=20/1) to give the title compound (80 mg, 39%) as a brown solid.

Step 3:

(4R)-4-methyl-6-[1-methyl-3-(1-methylpyrazol-4-yl)indazol-5-yl]-1,3,4,5-tetrahydropyrido[3,4-b][1,4]diazepin-2-one

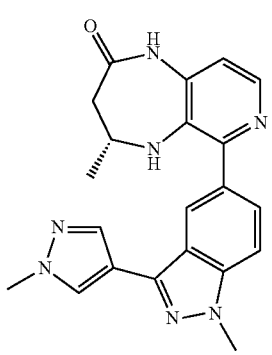 [SMILES: C[C@@H]1CC(=O)Nc2ccnc(-c3ccc4c(c3)c(-c3cnn(C)c3)nn4C)c2N1]

To a solution of (R)-methyl 3-((2-(1-methyl-3-(1-methyl-1H-pyrazol-4-yl)-1H-indazol-5-yl)-4-nitropyridin-3-yl)amino)butanoate (80 mg, 0.18 mmol) in AcOH (3.0 mL) was added Fe powder (49 mg, 0.89 umol). The mixture was heated to 100° C. for 16 h under nitrogen. After cooling the reaction to room temperature, the crude mixture was neutralized with sat. aq. NaHCO₃ and extracted with EtOAc (20 mL×3). The combined organic layers were dried over anhydrous Na₂SO₄, filtered and concentrated in vacuo. The crude residue was purified by prep-TLC (DCM/MeOH=20/1) to give the title compound (16 mg, 23%) as a white solid. $^1$H NMR (400 MHz, CDCl₃) δ 8.13 (d, J=4.8 Hz, 1H), 8.04 (m, 3H), 7.92 (s, 1H), 7.58 (d, J=8.4 Hz, 1H), 7.52 (d, J=8.4 Hz, 1H), 6.78 (d, J=5.2 Hz, 1H), 4.13 (s, 3H), 3.99 (s, 3H), 3.93 (m, 2H), 2.87 (m, 1H), 2.66 (m, 1H), 3.43 (d, J=6.0 Hz, 3H). LCMS M/Z (M+H) 388.

General Procedure for Intermediate H

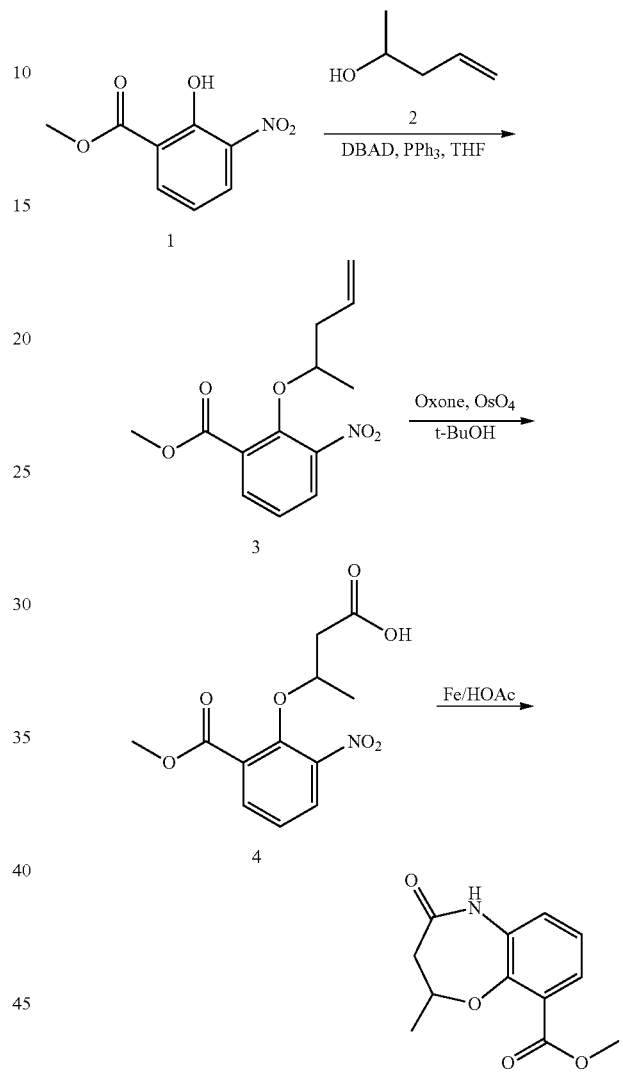

Intermediate H

Step 1:

methyl 3-nitro-2-(pent-4-en-2-yloxy)benzoate

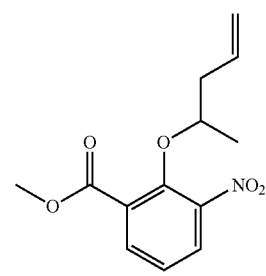 [SMILES: C=CCC(C)Oc1c(C(=O)OC)cccc1[N+](=O)[O-]]

To a solution of methyl 2-hydroxy-3-nitrobenzoate (10.0 g, 50.72 mmol), pent-4-en-2-ol (4.7 g, 54.57 mmol) and triphenylphosphine (24.0 g, 91.50 mol) in THF (200 mL) was added (E)-di-tert-butyl diazene-1,2-dicarboxylate (21.1 g, 91.64 mmol) in small portions over a period of 1 h. The reaction mixture was stirred at room temperature for 3 h. The reaction mixture was concentrated in vacuo and the crude residue was diluted with water (100 mL) and extracted with EtOAc (200 mL×3). The combined organic layers were dried over anhydrous Na$_2$SO$_4$, filtered and concentrated in vacuo. The crude residue was purified by silica gel chromatography (petroleum ether/EtOAc=10/1) to give the title compound (5.2 g, 39%) as a yellow solid.

Step 2:

3-(2-(methoxycarbonyl)-6-nitrophenoxy)butanoic acid

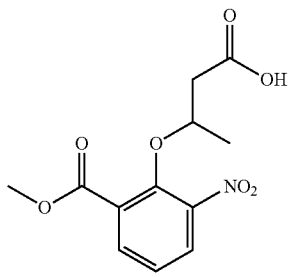 [SMILES: COC(=O)c1cccc([N+](=O)[O-])c1OC(C)CC(=O)O]

To a solution of methyl 3-nitro-2-(pent-4-en-2-yloxy)benzoate (2.4 g, 9.05 mmol) and oxone (11.7 g, 18.2 mmol) in DMF (50 mL) was added a solution of OsO$_4$ (23 mg, 0.01 mol) in t-BuOH (0.5 mL) dropwise. The reaction mixture was stirred at room temperature for 15 h. Water (150 mL) was added and the mixture was extracted with EtOAc (120 mL×3). The combined organic layers were dried over anhydrous Na$_2$SO$_4$, filtered and concentrated in vacuo to give the title compound (2.5 g, 98%) as a yellow solid that required no further purification.

Step 3:

methyl 2-methyl-4-oxo-2,3,4,5-tetrahydrobenzo[b][1,4]oxazepine-9-carboxylate

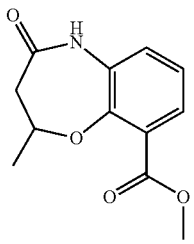

To a solution of 3-(2-(methoxycarbonyl)-6-nitrophenoxy)butanoic acid (5.2 g, 18.36 mmol) in acetic acid (100 mL) was added Fe powder (5.1 g, 91.32 mmol). The resulting mixture was heated to 80° C. for 1 h. After cooling the reaction to room temperature, the reaction mixture was filtered and the filtrate was concentrated in vacuo. Water (100 mL) was added and the mixture was extracted with EtOAc (150 mL×3). The combined organic layers were dried over anhydrous Na$_2$SO$_4$, filtered and concentrated in vacuo. The crude residue was purified by silica gel chromatography (petroleum ether/EtOAc=3/1) to give the title compound (Intermediate H, 2.0 g, 46%). $^1$H NMR (400 MHz, DMSO-d$_6$) δ 9.81 (s, 1H), 7.35-7.33 (m, 1H), 6.99 (d, J=4.4 Hz, 1H), 4.85-4.80 (m, 1H), 2.63-2.58 (m, 1H), 2.42-2.37 (m, 1H), 1.36 (d, J=6.0 Hz, 3H).

Example 95

2-methyl-4-oxo-N-phenyl-3,5-dihydro-2H-1,5-benzoxazepine-9-carboxamide

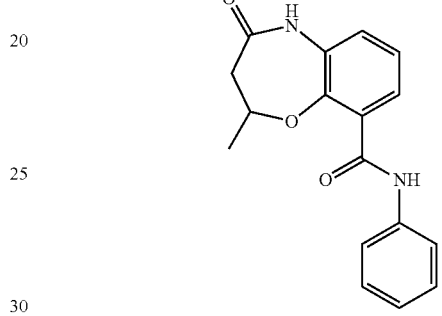

To a solution of aniline (79.2 mg, 0.85 mmol) in DCM (5 mL) at 0° C. was added a solution of AlMe$_3$ (2.0 M in toluene, 0.4 mL, 0.85 mmol). The reaction mixture was allowed to warm to room temperature and stirred for 30 minutes until the gas evolution ceased. A solution of methyl 2-methyl-4-oxo-2,3,4,5-tetrahydrobenzo[b][1,4]oxazepine-9-carboxylate (Intermediate H, 100 mg, 0.43 mmol) in DCM (2 mL) was added and the mixture was heated to reflux temperature for 15 h. After cooling the reaction to room temperature, the reaction mixture carefully quenched with 5% aq HCl (2 mL). The combined organic layers were separated and the aqueous layer was extracted with DCM (10 mL×3). The combined organic layers were washed with sat. aq. NaHCO$_3$ (10 mL) and brine (10 mL), dried over anhydrous Na$_2$SO$_4$, filtered and concentrated in vacuo. The crude residue was purified by reverse phase chromatography (acetonitrile 30-50%/0.2% formic acid in water) to give the title compound (35 mg, 28%) as a white solid. $^1$H NMR (400 MHz, DMSO-d$_6$) δ 10.23 (s, 1H), 9.83 (s, 1H), 7.70 (d, J=7.6 Hz, 1H), 7.36-7.28 (m, 3H), 7.18-7.07 (m, 3H), 4.87-4.83 (m, 1H), 2.77-2.72 (m, 1H), 2.50-2.43 (m, 1H), 1.30 (d, J=7.6 Hz, 3H). LCMS M/Z (M+H) 297.

The following compounds were prepared in a similar fashion to Example 95:

Examples 96-99

| Example | Compound Name | NMR | m/z |
| --- | --- | --- | --- |
| Example 96 | 2-methyl-4-oxo-N-phenyl-3,5-dihydro-2H- | $^1$H NMR (400 MHz, CD$_3$OD) δ 7.67 (d, J = 7.6 Hz, 2H), 7.66-7.55 (m, 1H), 7.38-7.34 (m, | 297 |

| Example | Compound Name | NMR | m/z |
|---|---|---|---|
| | 1,5-benzoxazepine-9-carboxamide | 2H), 7.24-7.15 (m, 3H), 4.98-4.96 (m, 1H), 2.85-2.80 (m, 1H), 2.53-2.48 (m, 1H), 1.45 (d, J = 6.4 Hz, 3H) | |
| Example 97 | 2-methyl-4-oxo-N-phenyl-3,5-dihydro-2H-1,5-benzoxazepine-9-carboxamide | $^1$H NMR (400 MHz, CD$_3$OD) δ 7.67 (d, J = 7.6 Hz, 2H), 7.66-7.55 (m, 1H), 7.38-7.34 (m, 2H), 7.24-7.15 (m, 3H), 4.98-4.96 (m, 1H), 2.85-2.80 (m, 1H), 2.53-2.48 (m, 1H), 1.45 (d, J = 6.4 Hz, 3H) | 297 |
| Example 98 | 2-methyl-N-(3-oxazol-5-ylphenyl)-4-oxo-3,5-dihydro-2H-1,5-benzoxazepine-9-carboxamide | $^1$H NMR (400 MHz, DMSO-d$_6$) δ10.40 (s, 1H), 9.85 (s, 1H), 8.47 (s, 1H), 8.17 (s, 1H), 7.66-7.64 (m, 2H), 7.48-7.17 (m, 5H), 4.88-4.84 (m, 1H), 2.78-2.73 (m, 1H), 2.46-2.41 (m, 1H), 1.30 (d, J = 6.4 Hz, 3H) | 364 |
| Example 99 | 2-methyl-N-(3-oxazol-5-ylphenyl)-4-oxo-3,5-dihydro-2H-1,5-benzoxazepine-9-carboxamide | $^1$H NMR (400 MHz, DMSO-d$_6$) δ10.41 (s, 1H), 9.85 (s, 1H), 8.47 (s, 1H), 8.17 (s, 1H), 7.66-7.64 (m, 2H), 7.48-7.17 (m, 5H), 4.88-4.84 (m, 1H), 2.78-2.73 (m, 1H), 2.46-2.41 (m, 1H), 1.30 (d, J = 6.4 Hz, 3H) | 364 |

General Procedure for Intermediate I

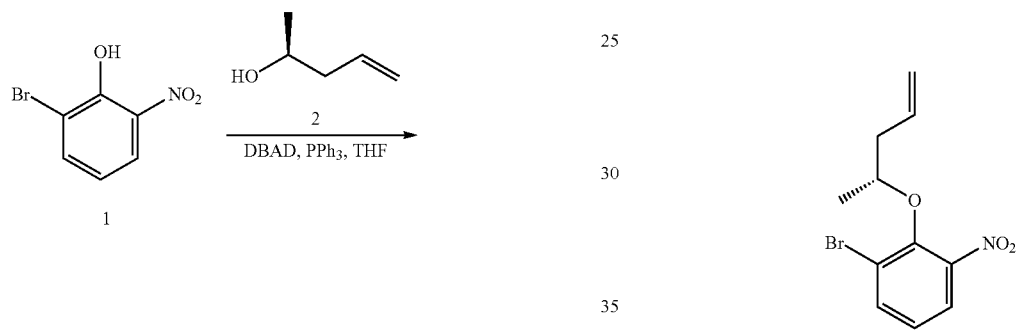

Step 1:

(R)-1-bromo-3-nitro-2-(pent-4-en-2-yloxy)benzene

To a solution of 2-bromo-6-nitrophenol (10.0 g, 45.87 mmol), (S)-pent-4-en-2-ol (4.7 g, 54.57 mmol) and triphenylphosphine (24.0 g, 91.50 mol) in THF (200 mL) was added (E)-di-tert-butyl diazene-1,2-dicarboxylate (21.1 g, 91.64 mmol) in small portions over a period of 1 h. The reaction mixture was stirred at room temperature for an additional 3 h. The mixture was concentrated in vacuo. Water (300 mL) was added and the mixture was extracted with EtOAc (200 mL×3). The combined organic layers were dried over anhydrous Na$_2$SO$_4$, filtered and concentrated in vacuo. The crude residue was purified by silica gel chromatography (petroleum ether/EtOAc=10/1) to give the title compound (5.2 g, 40%) as a yellow solid.

Step 2:

(R)-3-(2-bromo-6-nitrophenoxy)butanoic acid

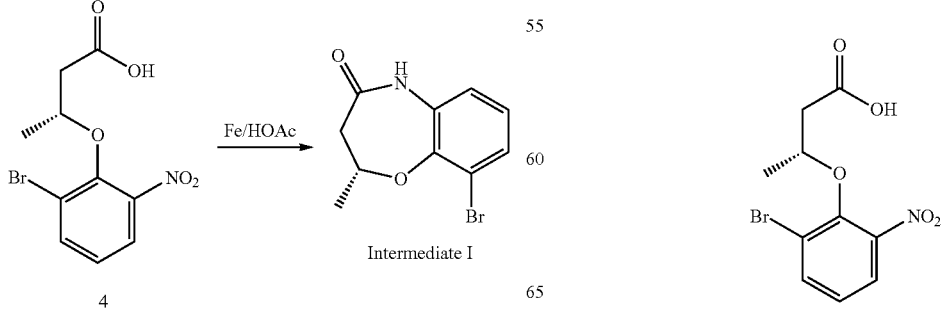

To a solution of (R)-1-bromo-3-nitro-2-(pent-4-en-2-yloxy)benzene (2.6 g, 9.09 mmol) and oxone (11.7 g, 18.2 mmol) in DMF (50 mL) was added a solution of OsO$_4$ (23 mg, 0.01 mol) in t-BuOH (0.5 mL) dropwise. The reaction mixture was stirred at room temperature for 15 h. Water (150 mL) was added and the mixture was extracted with EtOAc (120 mL×3). The combined organic layers were dried over anhydrous Na$_2$SO$_4$, filtered and concentrated in vacuo to give the title compound (2.8 g, 100%) as a yellow solid that required no further purification.

Step 3:

(R)-9-bromo-2-methyl-2,3-dihydrobenzo[b][1,4]oxazepin-4(5H)-one

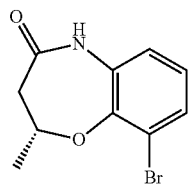

A mixture of (R)-3-(2-bromo-6-nitrophenoxy)butanoic acid (5.6 g, 18.42 mmol) and Fe powder (5.1 g, 91.32 mmol) in acetic acid (100 mL) was heated to 80° C. for 1 h. After cooling the reaction to room temperature, the reaction mixture was filtered and the filtrate was concentrated in vacuo. Water (100 mL) was added and the mixture was extracted with EtOAc (150 mL×3). The combined organic layers were dried over Na$_2$SO$_4$, filtered and concentrated in vacuo. The crude residue was purified by silica gel chromatography (petroleum ether/EtOAc=3/1) to give the title compound (Intermediate I, 2.0 g, 42%). $^1$H NMR (400 MHz, DMSO-d$_6$) δ9.81 (s, 1H), 7.35-7.33 (m, 1H), 6.99 (d, J=4.4 Hz, 1H), 4.85-4.80 (m, 1H), 2.63-2.58 (m, 1H), 2.42-2.37 (m, 1H), 1.36 (d, J=6.0 Hz, 3H).

Example 100

(R,E)-9-(4-methoxystyryl)-2-methyl-2,3-dihydrobenzo[b][1,4]oxazepin-4(5H)-one

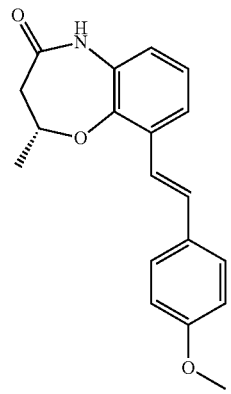

A mixture of (R)-9-bromo-2-methyl-2,3-dihydrobenzo[b][1,4]oxazepin-4(5H)-one (Intermediate 1, 100 mg, 0.39 mmol), (E)-(4-methoxystyryl)boronic acid (84 mg, 0.32 mmol), 2-(dicyclohexylphosphino)-2,4',6'-triisopropylbiphenyl(18.68 mg, 0.039 mmol), tris(dibenzylideneacetone)dipalladium(O) (35.72 mg, 0.039 mmol) and NaOH (2 M, 1.6 mL, 3.2 mmol) in MeCN (5 mL) was irradiated in a microwave at 90° C. for 0.5 h. After cooling the reaction to room temperature, ice water (5 mL) was added and the mixture was extracted with EtOAc (10 mL×3). The combined organic layers were dried over anhydrous Na$_2$SO$_4$, filtered and concentrated in vacuo. The crude residue was purified by reverse phase chromatography (acetonitrile 50-80%/0.2% formic acid in water). The product was further purified using chiral SFC (SFC80; Chiralpak AS 250×30 mm I.D., 5 um; Supercritical CO$_2$/EtOH+NH$_3$.H$_2$O=30/70; 80 mL/min) to give the title compound (5 mg, 4%) as a yellow solid. $^1$H NMR (400 MHz, CD$_3$OD) δ 7.56-7.49 (m, 3H), 7.35 (d, J=16.4 Hz, 1H), 7.19-7.13 (m, 2H), 6.94 (d, J=8.8 Hz, 3H), 4.96-4.93 (m, 1H), 3.83 (s, 3H), 2.76-2.73 (m, 1H), 2.49-2.44 (m, 1H), 1.51 (d, J=6.0 Hz, 3H). LCMS M/Z (M+H) 310.

The following compounds were prepared in a similar fashion to Example 100. The intermediate bromide for Examples 101 and 103 was prepared in a similar fashion to Intermediate I using the corresponding (R)-pent-4-en-2-ol instead.

Examples 101-103

| Example | Compound Name | NMR | m/z |
| --- | --- | --- | --- |
| Example 101 | (S,E)-9-(4-methoxystyryl)-2-methyl-2,3-dihydrobenzo[b][1,4]oxazepin-4(5H)-one | $^1$H NMR (400 MHz, CD$_3$OD) δ 7.56-7.49 (m, 3H), 7.35 (d, J = 16.4 Hz, 1H), 7.19-7.13 (m, 2H), 6.97-6.93 (m, 3H), 4.96-4.93 (m, 1H), 3.83 (s, 3H), 2.76-2.73 (m, 1H), 2.49-2.44 (m, 1H), 1.5 (d, J = 6.0 Hz, 3H) | 310 |
| Example 102 | (R)-9-(1-(4-methoxyphenyl)vinyl)-2-methyl-2,3-dihydrobenzo[b][1,4]oxazepin-4(5H)-one | $^1$H NMR (400 MHz, CD$_3$OD) δ7.21 (d, J = 8.8 Hz, 2H), 7.13 (d, J = 4.4 Hz, 2H), 7.07-7.04 (m, 1H), 6.88-6.66 (m, 2H), 5.57 (s, 1H), 5.16 (s, 1H), 4.02-3.96 (s, 1H), 3.80 (s, 3H), 3.94 (s, 1H), 2.77-2.72 (m, 1H), 2.28-2.23 (m, 1H), 1.09 (d, J = 6.4 Hz, 3H) | 310 |

| Example | Compound Name | NMR | m/z |
|---|---|---|---|
| Example 103 | (S)-9-(1-(4-methoxyphenyl)vinyl)-2-methyl-2,3-dihydrobenzo[b][1,4]oxazepin-4(5H)-one | $^1$H NMR (400 MHz, CD$_3$OD) δ7.21 (d, J = 7.2 Hz, 2H), 7.14-7.12 (m, 2H), 7.07-7.04 (m, 1H), 6.88-6.66 (m, 2H), 5.57 (s, 1H), 5.16 (s, 1H), 4.02-3.96 (s, 1H), 3.80 (s, 3H), 3.94 (s, 1H), 2.77-2.72 (m, 1H), 2.28-2.23 (m, 1H), 1.09 (d, J = 6.4 Hz, 3H) | 310 |

Example 104

(2R)-2-methyl-9-(5-methyl-2-furyl)-3,5-dihydro-2H-1,5-benzoxazepin-4-one

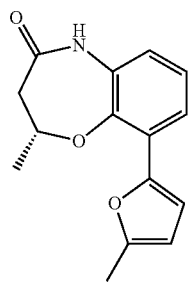 [SMILES: Cc1ccc(-c2cccc3c2O[C@H](C)CC(=O)N3)o1]

A mixture of (R)-9-bromo-2-methyl-2,3-dihydrobenzo[b][1,4]oxazepin-4(5H)-one (Intermediate I, 100 mg, 0.39 mmol), (5-methylfuran-2-yl)boronic acid (92.00 mg, 0.73 mmol), (2-dicyclohexylphosphino-2',4',6'-triisopropyl-1,1'-biphenyl)[2-(2'-amino-1,1'-biphenyl)]palladium(II)methanesulfonate (32.42 mg, 0.04 mmol) and NaOH (2 M, 1.6 mL, 3.2 mmol) in MeCN (3 mL) was irradiated in a microwave at 90° C. for 0.5 h. After cooling the reaction to room temperature, ice water (5 mL) was added and the mixture was extracted with EtOAc (10 mL×3). The combined organic layers were dried over anhydrous Na$_2$SO$_4$, filtered and concentrated in vacuo. The crude residue was purified by reverse phase chromatography (acetonitrile 35-65%/0.1% NH$_4$OH in water). The product was further purified using chiral SFC (SFC80; Chiralpak AS 250×30 mm I.D., 5 um; Supercritical CO$_2$/EtOH+NH$_3$.H$_2$O=40/60; 50 mL/min) to give the title compound (11.7 mg, 12%) as a white solid. $^1$H NMR (400 MHz, DMSO-d$_6$) δ 9.69 (s, 1H), 7.46 (d, J=6.4 Hz, 1H), 7.12 (t, J=8.0 Hz, 1H), 6.92 (d, J=6.4 Hz, 1H), 6.82 (d, J=3.2 Hz, 1H), 6.22 (d, J=2.4 Hz, 1H), 4.82-4.78 (m, 1H), 2.79-2.74 (m, 1H), 2.34-2.29 (m, 4H), 1.43 (d, J=6.0 Hz, 3H). LCMS M/Z (M+H) 258.

General Procedure for Intermediate J

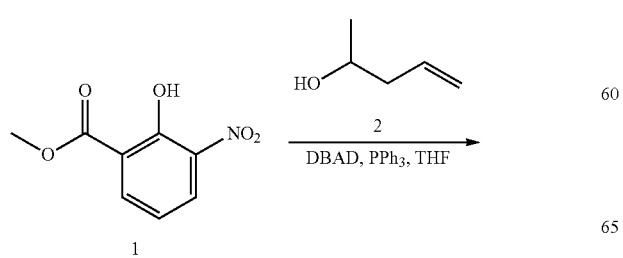

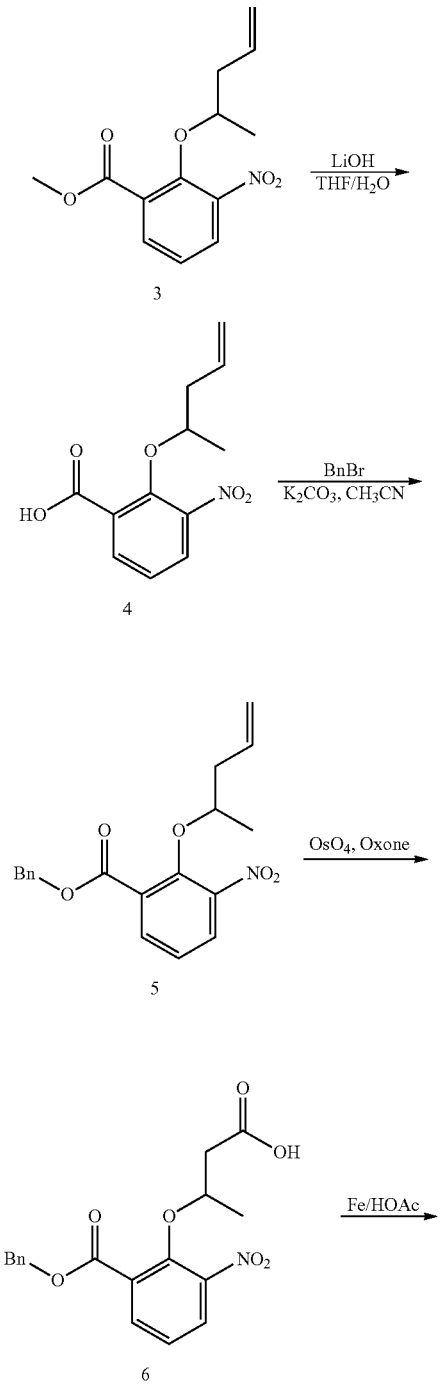

-continued

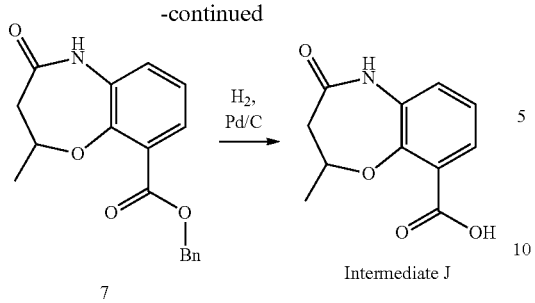

Intermediate J

Step 1:

methyl 3-nitro-2-(pent-4-en-2-yloxy)benzoate

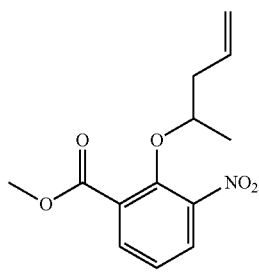 [SMILES: C=CCC(C)Oc1c(C(=O)OC)cccc1[N+](=O)[O-]]

To a solution of methyl 2-hydroxy-3-nitrobenzoate (9.0 g, 45.65 mmol), pent-4-en-2-ol (4.7 g, 54.57 mmol) and triphenylphosphine (24.0 g, 91.50 mol) in THF (200 mL) was added (E)-di-tert-butyl diazene-1,2-dicarboxylate (21.1 g, 91.64 mmol) in small portions over a period of 1 h. The reaction mixture was stirred at room temperature for 3 h. The mixture was concentrated in vacuo. Water (200 mL) was added and the mixture was extracted with EtOAc (200 mL×3). The combined organic layers were dried over anhydrous $Na_2SO_4$, filtered and concentrated in vacuo. The crude residue was purified by silica gel chromatography (petroleum ether/EtOAc=10/1) to give the title compound (6.0 g, 50%) as a yellow solid.

Step 2:

3-nitro-2-(pent-4-en-2-yloxy)benzoic acid

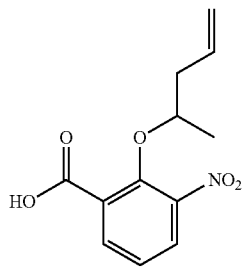 [SMILES: C=CCC(C)Oc1c(C(=O)O)cccc1[N+](=O)[O-]]

To a solution of methyl 3-nitro-2-(pent-4-en-2-yloxy) benzoate (9.0 g, 33.93 mmol) in THF/$H_2O$ (4:1, 200 mL) was added LiOH (4.0 g, 0.17 mol). The resulting mixture was heated to 80° C. for 15 h. After cooling the reaction to room temperature, the reaction was quenched with the addition of sat. aq. $NH_4Cl$ solution (10 mL). The mixture was concentrated in vacuo. Water (100 mL) was added and the mixture was extracted with EtOAc (200 mL×3). The combined organic layers were concentrated in vacuo to give the title compound (8.1 g, 95%) as a white solid that required no further purification.

Step 3:

benzyl 3-nitro-2-(pent-4-en-2-yloxy)benzoate

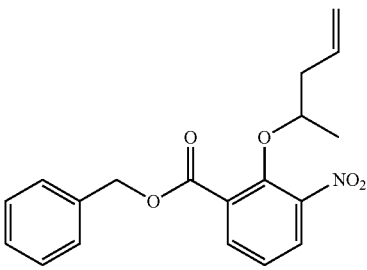 [SMILES: C=CCC(C)Oc1c(C(=O)OCc2ccccc2)cccc1[N+](=O)[O-]]

To a solution of 3-nitro-2-(pent-4-en-2-yloxy)benzoic acid (8.1 g, 32.24 mol) in MeCN (100 mL) was added $K_2CO_3$ (8.9 g, 64.40 mmol) and (bromomethyl)benzene (5.5 g, 32.24 mmol). The resulting mixture was heated to 50° C. for 10 h. After cooling the reaction to room temperature, the suspension was filtered and the filtrate was concentrated in vacuo. Water (30 mL) was added and the mixture was extracted with EtOAc (100 mL×3). The combined organic layers were dried over anhydrous $Na_2SO_4$, filtered and concentrated in vacuo to give the title compound (10.1 g, 92%) as a yellow solid that required no further purification.

Step 4:

3-(2-(((benzyloxy)carbonyl)-6-nitrophenoxy)butanoic acid

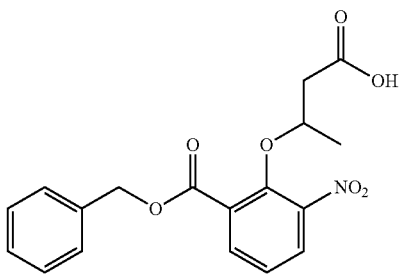 [SMILES: CC(CC(=O)O)Oc1c(C(=O)OCc2ccccc2)cccc1[N+](=O)[O-]]

To a solution of benzyl 3-nitro-2-(pent-4-en-2-yloxy) benzoate (9.3 g, 27.24 mmol) and oxone (35.1 g, 54.6 mmol) in DMF (150 mL) was added a solution of $OsO_4$ (69 mg, 0.27 mol) in t-BuOH (1.5 mL) dropwise. The reaction mixture was stirred at room temperature for 15 h. Water (300 mL) was added and the mixture was extracted with EtOAc (200 mL×3). The combined organic layers were dried over anhydrous $Na_2SO_4$, filtered and concentrated in vacuo to give the title compound (9.8 g, 100%) as a yellow solid that required no further purification.

Step 5:

2-methyl-4-oxo-2,3,4,5-tetrahydrobenzo[b][1,4]ox-azepine-9-carboxylic acid

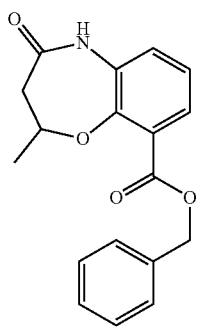 [SMILES: CC1CC(=O)Nc2cccc(C(=O)OCc3ccccc3)c2O1]

To a solution of 3-(2-((benzyloxy)carbonyl)-6-nitrophenoxy)butanoic acid (9.8 g, 27.27 mmol) and Fe powder (7.6 g, 136.09 mmol) in acetic acid (150 mL) was heated to 100° C. for 2 h. After cooling the reaction to room temperature, the reaction mixture was filtered and the filtrate was concentrated in vacuo. Water (100 mL) was added and the mixture was extracted with EtOAc (200 mL×3). The combined organic layers were dried over anhydrous $Na_2SO_4$, filtered and concentrated in vacuo. The crude residue was purified by silica gel chromatography (petroleum ether/EtOAc=3/1) to give the title compound (4.1 g, 48%) as a white solid.

Step 6:

2-methyl-4-oxo-2,3,4,5-tetrahydrobenzo[b][1,4]ox-azepine-9-carboxylic acid

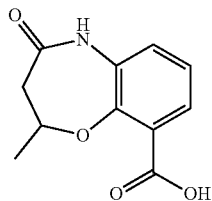

To a solution of 2-methyl-4-oxo-2,3,4,5-tetrahydrobenzo[b][1,4]oxazepine-9-carboxylic acid (3.11 g, 10 mmol) in MeOH (60 mL) was added Pd/C (wt. 5%, 0.6 g) under nitrogen atmosphere. The suspension was degassed under vacuum and then purged with Hz. The reaction mixture was stirred at 25° C. for 3 h under a $H_2$ atmosphere. The reaction mixture was filtered and the filtrate was concentrated in vacuo to give the title compound (Intermediate J, 2.21 g, 100%) as a white solid.

Example 105

N-(4-cyanophenyl)-2-methyl-4-oxo-3,5-dihydro-2H-1,5-benzoxazepine-9-carboxamide

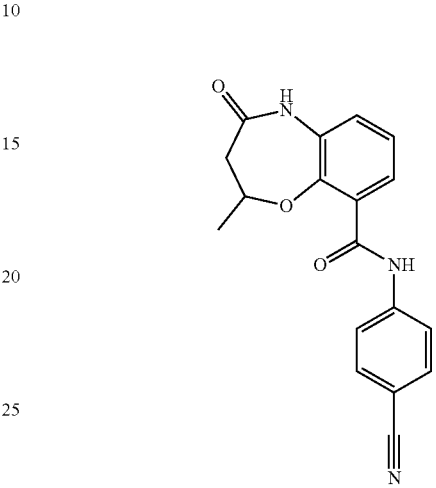

To a solution of (R)-4-methyl-2-oxo-2,3,4,5-tetrahydro-1H-benzo[b][1,4]diazepine-6-carboxylic acid (Intermediate J, 50 mg, 0.23 mmol) in DMF (3 mL) was added 4-isocyanatobenzonitrile (42 mg, 0.29 mmol) and N-ethyl-N-isopropylpropan-2-amine (64 mg, 0.50 mmol). The reaction mixture was stirred at 25° C. for 0.5 h. Ice water (5 mL) was added and the mixture was extracted with EtOAc (10 mL×3). The combined organic layers were dried over anhydrous $Na_2SO_4$, filtered and concentrated in vacuo. The crude residue was purified by reverse phase chromatography (acetonitrile 20-50%/0.1% $NH_4OH$ in water). The residue was further purified using chiral SFC (SFC80; Chiralpak OJ 250×30 mm I.D., 5 um; Supercritical $CO_2$/MeOH+$NH_3$.$H_2O$=40/60; 80 mL/min) to give the title compound (6 mg, 8%) as a white solid. $^1$H NMR (400 MHz, DMSO-$d_6$) δ10.69 (s, 1H), 9.86 (s, 1H), 7.91-7.81 (m, 4H), 7.30-7.17 (m, 3H), 4.85-4.80 (m, 1H), 2.76-2.71 (m, 1H), 2.47-2.42 (m, 1H), 1.27 (d, J=6.4 Hz, 3H). LCMS M/Z (M+H) 322.

The following compound was prepared in a similar fashion to Example 105:

| Example | Compound Name | NMR | m/z |
|---|---|---|---|
| Examples 106 | N-(4-cyanophenyl)-2-methyl-4-oxo-3,5-dihydro-2H-1,5-benzoxazepine-9-carboxamide | $^1$H NMR (400 MHz, DMSO-$d_6$) δ10.69 (s, 1H), 9.86 (s, 1H), 7.90 (d, J = 8.4 Hz, 2H), 7.82 (d, J = 8.4 Hz, 2H), 7.30-7.16 (m, 3H), 4.85-4.80 (m, 1H), 2.76-2.71 (m, 1H), 2.47-2.43 (m, 1H), 1.27 (d, J = 6.0 Hz, 3H) | 322 |

Example 107

6-(3-cyclopropyl-1-methyl-indazol-5-yl)-4-methyl-1,3,4,5-tetrahydro-1-benzazepin-2-one

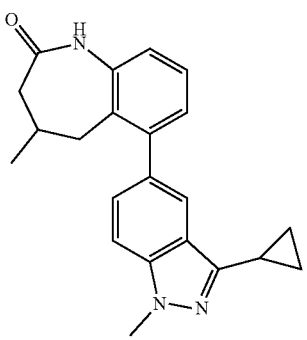 [SMILES: CC1CC(=O)Nc2cccc(-c3ccc4c(c3)c(C3CC3)nn4C)c2C1]

Step 1:

ethyl 4-(2-bromophenyl)-3-methylbut-2-enoate

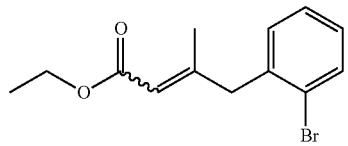 [SMILES: CCOC(=O)C=C(C)Cc1ccccc1Br]

To 1-(2-bromophenyl)propan-2-one (10.0 g, 47.2 mmol) in THF (100 mL) at room temperature was added t-BuOK (7.93 g, 70.8 mmol) and ethyl 2-(diethoxyphosphoryl)acetate (15.9 g, 70.8 mmol). The resulting mixture was heated to 80° C. for 2 h under nitrogen atmosphere. After cooling the reaction to room temperature, the mixture was concentrated in vacuo. The crude residue was purified by silica gel chromatography (petroleum ether/EtOAc=20/1) to give the title compound (9.0 g, 68%) as clear oil.

Step 2:

ethyl 4-(2-bromophenyl)-3-methylbutanoate

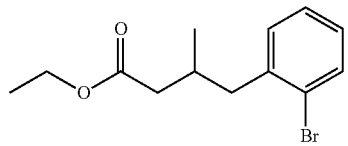 [SMILES: CCOC(=O)CC(C)Cc1ccccc1Br]

To a mixture of ethyl 4-(2-bromophenyl)-3-methylbut-2-enoate (1 g, 3.5 mmol) and platinum dioxide (200 mg, 0.88 mmol) in EtOAc (30 ml) was stirred at 23° C. for 10 h under hydrogen atmosphere (15 psi). The mixture was filtered and the filtrate was concentrated in vacuo to give the title compound (1.0 g, crude) as a yellow oil that required no further purification.

Step 3:

4-(2-bromophenyl)-3-methylbutanoic acid

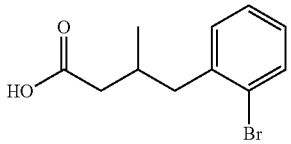

To a solution of ethyl 4-(2-bromophenyl)-3-methylbutanoate (1 g, crude) in THF (30 ml) and H$_2$O (30 ml) was added lithium hydroxide monohydrate (1 g, 25 mmol). The mixture was heated to 60° C. for 10 h. After cooling the reaction to room temperature, the mixture was washed with EtOAc (20 mL). The aqueous layer was acidified with HCl (2 N) to pH 2-3 and the mixture was extracted with EtOAc (20 mL×3). The combined organic layers were dried over anhydrous Na$_2$SO$_4$, filtered and concentrated in vacuo to give the title compound (1 g, crude) as a yellow oil that required no further purification.

Step 4:

5-bromo-3-methyl-3,4-dihydronaphthalen-1(2H)-one

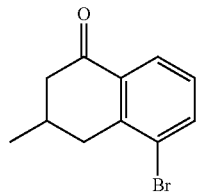

To 4-(2-bromophenyl)-3-methylbutanoic acid (1 g, crude) in polyphosphoric acid (20 g) was heated to 90° C. for 2 h. Then the mixture was cooled to 60° C. and water (50 mL) was added. The mixture was extracted with EtOAc (20 mL×3). The combined organic layers were dried over anhydrous Na$_2$SO$_4$, filtered and concentrated in vacuo to give the title compound (700 mg, crude) as yellow oil that required no further purification. LCMS M/Z (M+H) 239.

Step 5:

5-bromo-3-methyl-3,4-dihydronaphthalen-1(2H)-one oxime

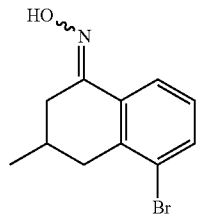

To a mixture of 5-bromo-3-methyl-3,4-dihydronaphthalen-1(2H)-one (700 mg, crude) and hydroxylamine hydrochloride (221 mg, 3.2 mmol) in ethanol (3.6 ml) was added pyridine (2.2 ml). The mixture was heated to 70° C. for 10 h. After cooling the reaction to room temperature, the mixture was concentrated in vacuo to give the title compound (800 mg, crude) as a yellow oil that required no further purification.

Step 6:

6-bromo-4-methyl-4,5-dihydro-1H-benzo[b]azepin-2(3H)-one

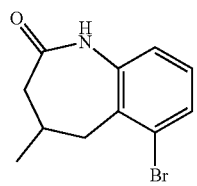

A mixture of 5-bromo-3-methyl-3,4-dihydronaphthalen-1(2H)-one oxime (800 mg, crude) and polyphosphoric acid (11 g) was heated to 130° C. for 1 h. After cooling the reaction to room temperature, water (50 mL) was added and the mixture was extracted with EtOAc (50 mL×3). The combined organic layers were dried over anhydrous Na$_2$SO$_4$, filtered and concentrated in vacuo. The crude residue was purified by silica gel chromatography (petroleum ether/EtOAc=10/1 to 3/1) to give the title compound (500 mg, 62%) as a light yellow solid. LCMS M/Z (M+H) 254.

Step 7:

6-(3-cyclopropyl-1-methyl-indazol-5-yl)-4-methyl-1,3,4,5-tetrahydro-1-benzazepin-2-one

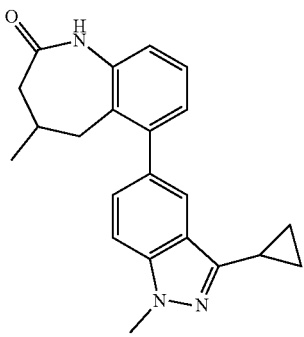 [SMILES: CC1CC(=O)Nc2cccc(-c3ccc4c(c3)c(C3CC3)nn4C)c2C1]

A mixture of 6-bromo-4-methyl-4,5-dihydro-1H-benzo[b]azepin-2(3H)-one (500 mg, 2.0 mmol), potassium carbonate (552 mg, 4.0 mmol), bis(triphenylphosphine)palladium(II) dichloride (140 mg, 2 mmol) and 3-cyclopropyl-1-methyl-5-(4,4,5,5-tetramethyl-1,3,2-dioxaborolan-2-yl)-1H-indazole (626 mg, 2 mmol) in dioxane (30 mL)/H$_2$O (4 mL) was heated to 100° C. for 10 h under nitrogen atmosphere. After cooling the reaction to room temperature, the mixture was concentrated in vacuo. The crude residue was purified by reverse phase chromatography (acetonitrile 50-80%/0.2% formic acid in water) to give the title compound (300 mg, 43%) as a white solid. $^1$H NMR (400 MHz, CD$_3$OD) δ 7.68 (s, 1H), 7.54 (d, J=8.8 Hz, 1H), 7.39 (d, J=1.6 Hz, 1H), 7.34-7.30 (m, 1H), 7.20-7.17 (m, 1H), 7.07 (d, J=8.0 Hz, 1H), 4.01 (s, 3H), 2.75-2.72 (m, 1H), 2.62-2.59 (m, 2H), 2.39-2.25 (m, 2H), 2.09-2.07 (m, 1H), 1.07-1.01 (m, 7H). LCMS M/Z (M+H) 346.

Examples 108 & 109

(4R)-6-(3-cyclopropyl-1-methyl-indazol-5-yl)-4-methyl-1,3,4,5-tetrahydro-1-benzazepin-2-one & (4S)-6-(3-cyclopropyl-1-methyl-indazol-5-yl)-4-methyl-1,3,4,5-tetrahydro-1-benzazepin-2-one

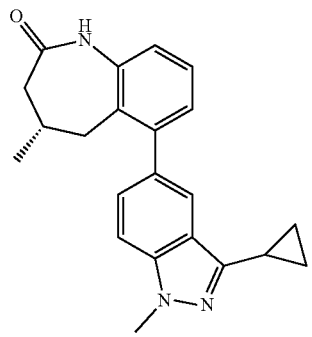

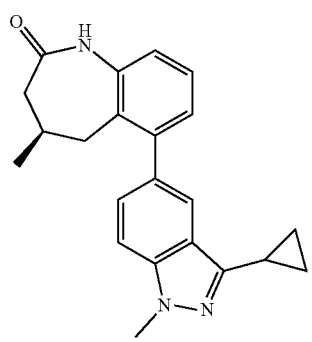

Racemic 6-(3-cyclopropyl-1-methyl-indazol-5-yl)-4-methyl-1,3,4,5-tetrahydro-1-benzazepin-2-one was separated using chiral SFC (SFC80; Chiralpak AD 250×30 mm I.D., 5 um; Supercritical CO$_2$/EtOH+NH$_3$.H$_2$O=75/25; 60 mL/min) to give (4R)-6-(3-cyclopropyl-1-methyl-indazol-5-yl)-4-methyl-1,3,4,5-tetrahydro-1-benzazepin-2-one (71 mg, first peak) and (4S)-6-(3-cyclopropyl-1-methyl-indazol-5-yl)-4-methyl-1,3,4,5-tetrahydro-1-benzazepin-2-one (59 mg, second peak) as a white solid. Absolute configuration was arbitrarily assigned to each enantiomer. Example 108: $^1$H NMR (400 MHz, CD$_3$OD) δ 7.67 (s, 1H), 7.54 (d, J=8.4 Hz, 1H), 7.39 (d, J=1.2 Hz, 1H), 7.36-7.30 (m, 1H), 7.19-7.17 (m, 1H), 7.08 (d, J=8.0 Hz, 1H), 4.02 (s, 3H), 2.75-2.72 (m, 1H), 2.62-2.59 (m, 2H), 2.39-2.27 (m, 2H), 2.08-2.05 (m, 1H), 1.07-1.01 (m, 7H). LCMS M/Z (M+H) 346. Example 109: $^1$H NMR (400 MHz, CD$_3$OD) δ 7.67 (s, 1H), 7.53 (d, J=8.8 Hz, 1H), 7.39 (d, J=1.6 Hz, 1H), 7.32-7.29 (m, 1H), 7.19-7.17 (m, 1H), 7.08 (d, J=8.0 Hz, 1H), 4.01 (s, 3H), 2.76-2.71 (m, 1H), 2.62-2.59 (m, 2H), 2.38-2.26 (m, 2H), 2.08-2.06 (m, 1H), 1.07-1.01 (m, 7H). LCMS M/Z (M+H) 346.

Example 110

(2R)-8-hydroxy-2-methyl-3,5-dihydro-2H-1,5-benzoxazepin-4-one

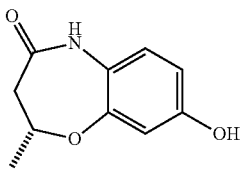

Step 1:

(R)-3-(5-(benzyloxy)-2-nitrophenoxy)butanoic acid

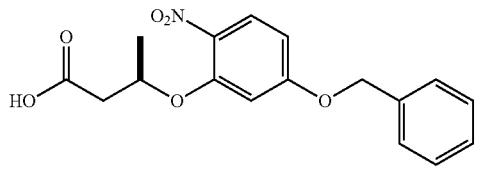 [SMILES: C[C@H](CC(=O)O)Oc1cc(OCc2ccccc2)ccc1[N+](=O)[O-]]

To sodium (R)-3-hydroxybutanoate (1 g, 4.04 mmol, 1 equiv) in DMF at 0° C. was added sodium hydride (170 mg, 4.25 mmol, 1.05 equiv). The mixture was stirred at 0° C. for 30 min before 4-(benzyloxy)-2-fluoro-1-nitrobenzene (536 mg, 4.25 mmol, 1.05 equiv) was added and the mixture stirred for an additional 18 h. The mixture was diluted with EtOAc and washed with 1N HCl. The organic layer was dried over anhydrous $Na_2SO_4$, filtered and concentrated in vacuo. The crude residue was purified by column chromatography (eluting with hexanes/EtOAc) to give the title compound (140 mg, 10%). LCMS M/Z (M+H) 332.

Step 2:

(R)-8-(benzyloxy)-2-methyl-2,3-dihydrobenzo[b][1,4]oxazepin-4(5H)-one

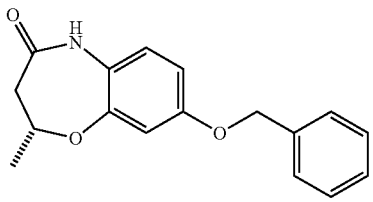 [SMILES: C[C@@H]1CC(=O)Nc2ccc(OCc3ccccc3)cc2O1]

A mixture of (R)-3-(5-(benzyloxy)-2-nitrophenoxy)butanoic acid (140 mg, 0.423 mmol) and Fe powder (189 mg, 3.38 mmol) in acetic acid (0.5 mL) was heated to 110° C. for 16 h. After cooling the reaction to room temperature, the reaction mixture was filtered and the filtrate was concentrated in vacuo. The crude residue was purified by silica gel chromatography (petroleum ether/EtOAc=3/1) to give the title compound (75 mg, 63%) as a white solid. LCMS M/Z (M+H) 284.

Step 3:

(2R)-8-hydroxy-2-methyl-3,5-dihydro-2H-1,5-benzoxazepin-4-one

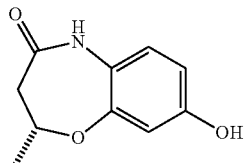

To a solution of (R)-8-(benzyloxy)-2-methyl-2,3-dihydrobenzo[b][1,4]oxazepin-4(5H)-one (75 mg, 0.265 mmol) in MeOH (2 mL) was added Pd/C (5% wt, 28 mg). The mixture was stirred at 20° C. for 2 h under hydrogen atmosphere. The mixture was filtered and concentrated in vacuo to give the title compound (24 mg, 47%) as a white solid. $^1$H NMR (400 MHz, DMSO-$d_6$) δ 9.36 (s, 1H), 9.33 (s, 1H), 6.79 (d, J=8.7 Hz, 1H), 6.47 (dd, J=8.6, 2.6 Hz, 1H), 6.41 (d, J=2.7 Hz, 1H), 4.69 (m, 1H), 2.53 (m, 1H), 2.29 (d, J=7.5 Hz, 1H), 1.28 (d, J=6.2 Hz, 3H). LCMS M/Z (M+H) 194.

Example 111

(2R)-2-methyl-8[(1S)-1-phenylethoxy]-3,5-dihydro-2H-1,5-benzoxazepin-4-one

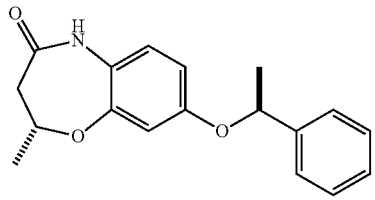 [SMILES: C[C@@H]1CC(=O)Nc2ccc(O[C@@H](C)c3ccccc3)cc2O1]

To a solution of triphenylphosphine polymer bound 3.2 mmol/g (162 mg), (R)-8-hydroxy-2-methyl-2,3-dihydrobenzo[b][1,4]oxazepin-4(5H)-one (0.05 g, 0.259 mmol), (R)-1-phenylethanol (0.095 g, 0.776 mmol) in THF (2 mL) at room temperature was added a solution of (E)-di-tert-butyl diazene-1,2-dicarboxylate (0.119 g, 0.518 mmol) in THF (1 mL) dropwise. The reaction mixture was stirred at room temperature for 18 h. The mixture was filtered through celite and concentrated in vacuo. The residue was purified by silica gel chromatography (eluting with hexanes/EtOAc) to give the title compound (44 mg, 57%) as an amorphous solid. $^1$H NMR (400 MHz, DMSO-$d_6$) δ 9.24-9.55 (m, 1H), 7.35 (d, J=17.6 Hz, 4H), 7.17-7.28 (m, 1H), 6.78-6.87 (m, 1H), 6.58-6.67 (m, 1H), 6.43-6.57 (m, 1H), 5.32-5.49 (m, 1H), 4.56-4.72 (m, 1H), 2.51-2.54 (m, 1H), 2.26-2.35 (m, 1H), 1.50 (d, J=6.2 Hz, 3H), 1.26 (d, J=6.2 Hz, 3H). LCMS M/Z (M+H) 298.

The following compounds were prepared in a similar fashion to Example 111:

Examples 112-117

| Example | Compound Name | NMR | m/z |
|---|---|---|---|
| Example 112 | (2R)-8-(cyclopropylmethoxy)-2-methyl-3,5-dihydro-2H-1,5-benzoxazepin-4-one | $^1$H NMR (400 MHz, DMSO-d$_6$) δ 9.43 (s, 1H), 6.89 (d, J = 8.7 Hz, 1H), 6.64 (dd, J = 8.7, 2.7 Hz, 1H), 6.56 (d, J = 2.7 Hz, 1H), 4.71 (m, 1H), 3.74 (d, J = 6.9 Hz, 2H), 2.50-2.58 (m, 1H), 2.32 (dd, J = 14.1, 7.4 Hz, 1H), 1.29 (d, J = 6.2 Hz, 3H), 1.17 (br s, 1H), 0.48-0.59 (m, 2H), 0.23-0.32 (m, 2H) | 248 |
| Example 113 | (2R)-8-isobutoxy-2-methyl-3,5-dihydro-2H-1,5-benzoxazepin-4-one | $^1$H NMR (400 MHz, DMSO-d$_6$) δ 9.44 (s, 1H), 6.89 (d, J = 8.7 Hz, 1H), 6.65 (dd, J = 8.7, 2.9 Hz, 1H), 6.57 (d, J = 2.9 Hz, 1H), 4.71 (m, 1H), 3.67 (d, J = 6.5 Hz, 2H), 2.54 (dd, J = 14.1, 4.7 Hz, 1H), 2.33 (dd, J = 14.1, 7.4 Hz, 1H), 1.90-2.02 (m, 1H), 1.29 (d, J = 6.2 Hz, 3H), 0.95 (d, J = 6.7 Hz, 6H) | 250 |
| Example 114 | (2R)-2-methyl-8-(3-pyridylmethoxy)-3,5-dihydro-2H-1,5-benzoxazepin-4-one | $^1$H NMR (400 MHz, DMSO-d$_6$) δ 9.48 (s, 1H), 8.65 (br s, 1H), 8.54 (d, J = 3.3 Hz, 1H), 7.85 (d, J = 7.8 Hz, 1H), 7.42 (dd, J = 7.7, 4.8 Hz, 1H), 6.93 (d, J = 8.5 Hz, 1H), 6.76 (dd, J = 8.6, 2.8 Hz, 1H), 6.71 (d, J = 2.9 Hz, 1H), 5.10 (s, 2H), 4.73 (m, 1H), 2.55 (dd, J = 14.1, 4.5 Hz, 1H), 2.35 (dd, J = 14.1, 7.5 Hz, 1H), 1.30 (d, J = 6.2 Hz, 3H) | 285 |
| Example 115 | (2R)-2-methyl-8-(4-pyridylmethoxy)-3,5-dihydro-2H-1,5-benzoxazepin-4-one | $^1$H NMR (400 MHz, DMSO-d$_6$) δ 9.48 (s, 1H), 8.57 (d, J = 4.7 Hz, 2H), 7.41 (d, J = 5.4 Hz, 2H), 6.93 (d, J = 8.7 Hz, 1H), 6.72-6.78 (m, 1H), 6.69 (d, J = 2.7 Hz, 1H), 5.13 (s, 2H), 4.63-4.80 (m, 1H), 2.53 (m, 1H), 2.36 (m, 1H), 1.29 (d, J = 6.2 Hz, 3H) | 285 |
| Example 116 | (2R)-2-methyl-8-(2-pyridylmethoxy)-3,5-dihydro-2H-1,5-benzoxazepin-4-one | $^1$H NMR (400 MHz, DMSO-d$_6$) δ 9.47 (s, 1H), 8.56 (d, J = 4.7 Hz, 1H), 7.82 (dt, J = 7.7, 1.6 Hz, 1H), 7.49 (d, J = 7.8 Hz, 1H), 7.33 (dd, J = 7.6, 4.9 Hz, 1H), 6.92 (d, J = 8.7 Hz, 1H), 6.75 (dd, J = 8.7, 2.7 Hz, 1H), 6.69 (d, J = 2.7 Hz, 1H), 5.12 (s, 2H), 4.72 (m, 1H), 2.55 (dd, J = 14.1, 4.5 Hz, 1H), 2.34 (dd, J = 14.1, 7.4 Hz, 1H), 1.29 (d, J = 6.2 Hz, 3H) | 285 |
| Example 117 | (2R-2-methyl-8-[(1R)-1-phenylethoxy]-3,5-dihydro-2H-1,5-benzoxazepin-4-one | 1H NMR (400 MHz, DMSO-d$_6$) δ 9.40 (s, 1H), 7.36-7.42 (m, 2H), 7.30-7.36 (m, 2H), 7.21-7.28 (m, 1H), 6.83 (d, J = 8.7 Hz, 1H), 6.63 (dd, J = 8.7, 2.7 Hz, 1H), 6.54 (d, J = 2.7 Hz, 1H), 5.43 (q, J = 6.2 Hz, 1H), 4.67 (dd, J = 11.6, 6.7 Hz, 1H), 2.52 (d, J = 4.9 Hz, 1H), 2.27 (dd, J = 14.1, 7.6 Hz, 1H), 1.52 (d, J = 6.5 Hz, 3H), 1.21 (d, J = 6.2 Hz, 3H) | 298 |

Example 118

(2R)-8-(cyclohexylmethoxy)-2-methyl-3,5-dihydro-2H-1,5-benzoxazepin-4-one

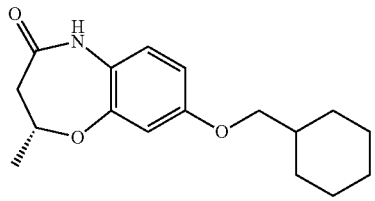 [SMILES: C[C@@H]1CC(=O)Nc2ccc(OCC3CCCCC3)cc2O1]

To a solution of (2R)-8-hydroxy-2-methyl-3,5-dihydro-2H-1,5-benzoxazepin-4-one (30 mg, 0.155 mmol) in THF (2.0 mL) was added cyclohexylmethanol (70 mg, 0.62 mmol), di-tert-butyl azodicarboxylate (145 mg, 0.62 mmol) and triphenylphosphine (160 mg, 0.62 mmol). The mixture was heated to 50° C. for overnight. After cooling the reaction to room temperature, the reaction mixture was filtered and concentrated in vacuo. The crude residue was purified by prep-HPLC (acetonitrile 5-85%/0.1% NH$_4$OH in water) to give the title compound (15.2 mg, 34%) as an off-white solid. $^1$H NMR (400 MHz, DMSO-d$_6$) δ 9.42 (s, 1H), 6.90 (d, J=8.7 Hz, 1H), 6.69-6.61 (m, 1H), 6.57 (d. J=2.8 Hz, 1H), 4.79-4.66 (m, 1H), 3.72 (d, J=6.3 Hz, 2H), 2.60-2.50 (m, 1H), 2.40-2.29 (m, 1H), 1.82-1.59 (m, 6H), 1.31 (d, J=6.2 Hz, 3H), 1.27-1.09 (m, 3H), 1.09-0.95 (m, 2H). LCMS M/Z (M+H) 290.

The following compounds were prepared in a similar fashion to Example 118:

Examples 119 & 120

| Example | Compound Name | NMR | m/z |
|---|---|---|---|
| Example 119 | (2R)-methyl-8-[1-(2-pyridyl)ethoxy]-3,5-dihydro-2H-1,5-benzoxazepin-4-one | $^1$H NMR (400 MHz, DMSO-$d_6$) δ 9.40 (d, J = 5.7 Hz, 1H), 8.58-8.51 (m, 1H), 7.83-7.73 (m, 1H), 7.46-7.37 (m, 1H), 7.33-7.24 (m, 1H), 6.89-6.81 (m, 1H), 6.68-6.59 (m, 1H), 6.60-6.50 (m, 1H), 5.44-5.34 (m, 1H), 4.75-4.61 (m, 1H), 3.17 (d, J = 4.8 Hz, 1H), 2.39-2.23 (m, 1H), 1.62-1.51 (m, 3H), 1.33-1.17 (m, 3H) | 299 |
| Example 120 | (2R)-2-methyl-8-(2-phenylethoxy)-3,5-dihydro-2H-1,5-benzoxazepin-4-one | $^1$H NMR (400 MHz, DMSO-$d_6$) δ 9.43 (s, 1H), 7.35-7.25 (m, 4H), 7.25-7.17 (m, 1H), 6.90 (d, J = 8.7 Hz, 1H), 6.70-6.62 (m, 1H), 6.59 (d, J = 2.8 Hz, 1H), 4.78-4.66 (m, 1H), 4.15 (t, J = 6.8 Hz, 2H), 3.00 (t, J = 6.8 Hz, 2H), 2.59-2.51 (m, 1H), 2.40-2.29 (m, 1H), 1.30 (d, J = 6.2 Hz, 3H) | 298 |

Example 121

(4R)-methyl-7-(1-phenylethoxy)-1,3,4,5-tetrahydro-1,5-benzodiazepin-2-one

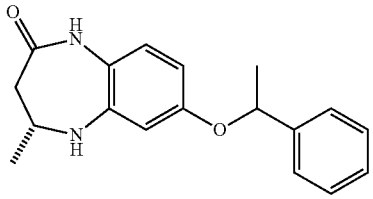 [SMILES: CC(Oc1ccc2c(c1)N[C@H](C)CC(=O)N2)c1ccccc1]

Step 1:

2-fluoro-1-nitro-4-(1-phenylethoxy)benzene

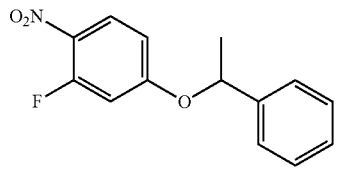 [SMILES: CC(Oc1ccc([N+](=O)[O-])c(F)c1)c1ccccc1]

To a solution of 3-fluoro-4-nitrophenolin toluene was added (1-bromoethyl)benzene and silver carbonate. The mixture was heated to 50° C. for 30 min. After cooling the reaction to room temperature, the reaction mixture was filtered and concentrated in vacuo. The crude residue was purified by silica gel chromatography to give the title compound. LCMS M/Z (M+H) 262.

Step 2:

(3R)-3-(2-nitro-5-(1-phenylethoxy)phenylamino) butanoic acid

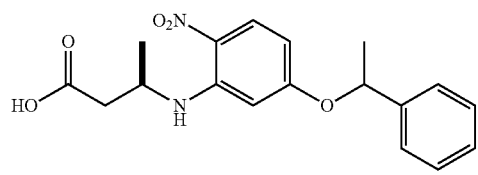 [SMILES: CC(Oc1ccc([N+](=O)[O-])c(N[C@H](C)CC(=O)O)c1)c1ccccc1]

To a solution of 2-fluoro-1-nitro-4-(1-phenylethoxy)benzene (0.486 g, 1.860 mmol) in DMSO (10 mL) was added (R)-3-aminobutanoic acid HCl (0.389 g, 2.79 mmol) and potassium carbonate (0.514 g, 3.72 mmol). The mixture was heated to 100° C. for 18 h. After cooling the reaction to room temperature, 1N HCl was added and the mixture was extracted with EtOAc twice. The combined organic layers were dried over anhydrous MgSO$_4$, filtered and concentrated in vacuo. The crude residue was purified by silica gel chromatography (methanol/DCM) to give the title compound as an amorphous solid. LCMS M/Z (M+H) 345.

Step 3:

(4R)-methyl-7-(1-phenylethoxy)-1,3,4,5-tetrahydro-1,5-benzodiazepin-2-one

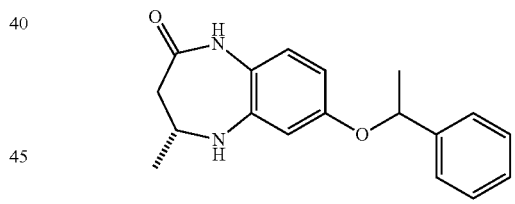

To a solution of (3R)-3-(2-nitro-5-(1-phenylethoxy)phenylamino)butanoic acid (0.133 g, 0.386 mmol) in ethanol (4 mL) and acetic acid (0.4 mL) was added iron powder (0.173 g, 3.09 mmol). The mixture was heated to 110° C. for 3 h. After cooling the reaction to room temperature, the reaction mixture was filtered and the filtrate was concentrated in vacuo. The crude residue was purified by prep-HPLC (acetonitrile/0.1% trifluoroacetic acid in water) to give the title compound (92 mg, 80%) as an off-white amorphous solid mixture of diastereomers. $^1$H NMR (400 MHz, DMSO-$d_6$) δ 9.28 (br s, 2H), 7.30-7.43 (m, 8H), 7.22-7.28 (m, 2H), 6.66-6.74 (m, 2H), 6.46-6.53 (m, 2H), 6.31-6.41 (m, 2H), 5.33 (q, J=6.3 Hz, 4H), 3.76-3.89 (m, 2H), 2.39 (dd, J=13.5, 4.2 Hz, 2H), 2.10-2.19 (m, 2H), 1.51 (d, J=6.4 Hz, 3H), 1.50 (d, J=6.4 Hz, 3H), 1.17 (d, J=6.4 Hz, 3H), 1.14 (d, J=6.4 Hz, 3H). LCMS M/Z (M+H) 297.

The following compound was prepared in a similar fashion to Example 121:

Example 122

| Example | Compound Name | NMR | m/z |
|---|---|---|---|
| Example 122 | (4R)-7-benzyloxy-4-methyl-1,3,4,5-tetrahydro-1,5-benzodiazepin-2-one | $^1$H NMR (400 MHz, DMSO-$d_6$) δ 9.24 (s, 1H), 7.18-7.49 (m, 5H), 6.74 (d, J = 8.7 Hz, 1H), 6.50 (d, J = 2.7 Hz, 1H), 6.36 (dd, J = 8.7, 2.7 Hz, 1H), 5.30 (d, J = 2.5 Hz, 1H), 4.97 (s, 2H), 3.78 (dt, J = 6.4, 3.6 Hz, 1H), 2.39 (dd, J = 13.3, 4.0 Hz, 1H), 2.17 (dd, J = 13.2, 7.4 Hz, 1H), 1.15 (d, J = 8.0 Hz, 3H) | 283 |

Example 123

(4R)-4-methyl-7-[(1R)-1-phenylethoxy]-1,3,4,5-tetrahydro-1,5-benzodiazepin-2-one

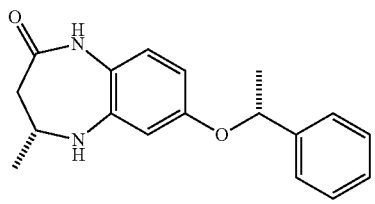 [SMILES: CC(Oc1ccc2c(c1)N[C@H](C)CC(=O)N2)c1ccccc1]

Step 1:

(R)-3-(5-hydroxy-2-nitrophenyl)amino)butanoic acid

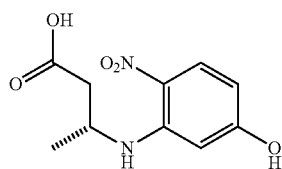 [SMILES: C[C@H](CC(=O)O)Nc1cc(O)ccc1[N+](=O)[O-]]

To a solution of 3-fluoro-4-nitrophenol (1.535 g, 9.77 mmol) in DMSO (25 mL) was added (R)-3-aminobutanoic acid, HCl (1.5 g, 10.75 mmol) and potassium carbonate (2.70 g, 19.54 mmol).

The mixture was heated to 100° C. for 18 h. After cooling the reaction to room temperature, the reaction mixture was filtered and the filtrate was concentrated in vacuo. The residue was purified by silica gel chromatography (DCM/methanol) to give the title compound (900 mg, 38%) as an orange oil. LCMS M/Z (M+H) 241.

Step 2:

(R)-7-hydroxy-4-methyl-1,3,4,5-tetrahydro-2H-benzo[b][1,4]diazepin-2-one

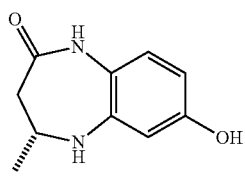

To a solution of (R)-3-(5-hydroxy-2-nitrophenylamino) butanoic acid (0.433, 1.803 mmol) in ethanol (10 mL) and acetic acid (2 mL) was added iron powder (0.805 g, 14.42 mmol). The mixture was heated to 110° C. for 18 h. After cooling the reaction to room temperature, the reaction mixture was filtered and the filtrate was concentrated in vacuo. The residue was purified by silica gel chromatography (DCM/methanol) as an amorphous solid that required no further purification. LCMS M/Z (M+H) 193.

Step 3:

(4R)-4-methyl-7-[(1R)-1-phenylethoxy]-1,3,4,5-tetrahydro-1,5-benzodiazepin-2-one

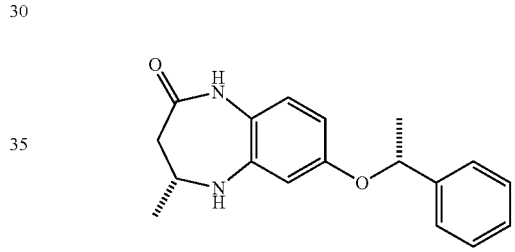

To a solution of triphenylphosphine polymer bound 3.2 mmol/g (0.134 g, 0.510 mmol), (R)-7-hydroxy-4-methyl-4,5-dihydro-1H-benzo[b][1,4]diazepin-2(3H)-one (0.049 g, 0.255 mmol), (S)-1-phenylethanol (0.092 ml, 0.765 mmol) in THF (2 mL) at room temperature was added a solution of (E)-di-tert-butyl diazene-1,2-dicarboxylate (0.117 g, 0.510 mmol) in THF (1 mL) dropwise. The reaction mixture was stirred at room temperature for 18 h. The mixture was filtered through celite and concentrated in vacuo. The crude residue was purified by prep-HPLC (acetonitrile/0.1% trifluoroacetic acid in water) to give the title compound (7.3 mg, 7%) as an off-white amorphous solid. $^1$H NMR (400 MHz, DMSO-$d_d$) δ9.28 (s, 1H), 7.30-7.40 (m, 4H), 7.21-7.28 (m, 1H), 6.70 (d, J=8.8 Hz, 1H), 6.52 (br s, 1H), 6.36 (d, J=6.6 Hz, 1H), 5.33 (q, J=6.3 Hz, 1H), 3.82 (dd, J=10.7, 6.7 Hz, 1H), 2.39 (dd, J=13.5, 4.1 Hz, 1H), 2.13 (dd, J=13.4, 7.3 Hz, 1H), 1.51 (d, J=6.2 Hz, 3H), 1.14 (d, J=6.4 Hz, 3H). LCMS M/Z (M+H) 297.

Example 124

(4R)-4-methyl-6-[(E)-styryl]-1,3,4,5-tetrahydro-1,5-benzodiazepin-2-one

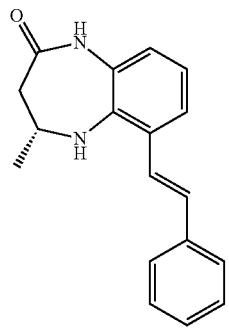 [SMILES: C[C@@H]1CC(=O)Nc2cccc(/C=C/c3ccccc3)c2N1]

To a solution of (R)-6-bromo-4-methyl-4,5-dihydro-1H-benzo[b][1,4]diazepin-2(3H)-one (Intermediate A, 510 mg, 2.0 mmol) in dimethylacetamide (10 mL) was added styrene (0.25 g, 2.4 mmol), dichloro[1,1'-bis(di-t-butylphosphino)ferrocene]palladium(I) (0.0652 g, 0.1 mmol), tetrabutylammonium chloride (0.0556 g, 0.2 mmol) and triethylamine (0.41 mL, 3 mmol). The reaction mixture was heated to 80° C. for 18 h. After cooling the reaction to room temperature, EtOAc was added and the mixture was washed with brine (×3). The organic layer was dried over anhydrous $Na_2SO_4$, filtered and concentrated in vacuo. The crude residue was purified by silica gel chromatography (hexanes/EtOAc) to give the title compound (472 mg, 85%) as an off-white amorphous solid. $^1$H NMR (400 MHz, DMSO-$d_6$) δ 9.49 (s, 1H), 8.08 (d, J=7.8 Hz, 1H), 7.91 (d, J=7.8 Hz, 1H), 7.78 (d, J=15.8 Hz, 1H), 7.63 (t, J=7.5 Hz, 1H), 7.54 (s, 2H), 7.39-7.51 (m, 3H), 6.84-6.94 (m, 2H), 5.09 (s, 1H), 3.98-4.11 (m, 1H), 2.44 (dd, J=12.8, 4.8 Hz, 1H), 2.14 (dd, J=12.9, 7.1 Hz, 1H), 1.26 (d, J=6.0 Hz, 3H). LCMS M/Z (M+H) 279.

The following compounds were prepared in a similar fashion to Example 124:

Examples 125 & 126

| Example | Compound Name | NMR | m/z |
|---|---|---|---|
| Example 125 | N-tert-butyl-2-[2-(4-methyl-2-oxo-1,3,4,5-tetrahydro-1,5-benzodiazepin-6-yl)vinyl]benzenesulfonamide | $^1$H NMR (400 MHz, DMSO-$d_6$) δ 9.50 (s, 1H), 8.08 (d, J = 7.4 Hz, 1H), 7.93 (dd, J = 7.9, 1.2 Hz, 1H), 7.23-7.82 (m, 6H), 6.53-7.15 (m, 3H), 3.76-4.11 (m, 1H), 2.31-2.47 (m, 1H), 2.06-2.19 (m, 1H), 1.19-1.28 (m, 3H), 1.10-1.17 (m, 9H) (TFA salt) (rotamers) | 414 |
| Example 126 | 2-[2-(4-methyl-2-oxo-1,3,4,5-tetrahydro-1,5-benzodiazepin-6-yl)vinyl]benzenesulfonamide | $^1$H NMR (400 MHz, DMSO-$d_6$) δ 9.49 (s, 1H), 8.08 (d, J = 7.8 Hz, 1H), 7.91 (d, J = 7.8 Hz, 1H), 7.78 (d, J = 15.8 Hz, 1H), 7.62 (t, J = 7.5 Hz, 1H), 7.54 (s, 2H), 7.38-7.51 (m, 3H), 6.86-6.94 (m, 2H), 5.09 (s, 1H), 4.05 (d, J = 6.0 Hz, 1H), 2.44 (dd, J = 12.9, 4.9 Hz, 1H), 2.13 (d, J = 12.8, 7.3 Hz, 1H), 1.26 (d, J = 6.0 Hz, 3H) | 358 |

The following compounds were prepared in a similar fashion to Examples 110 & 123 from the corresponding hydroxyl/amino propanoates and appropriately substituted chloro- or fluoro-substituted nitrobenzene:

Examples 127-133

| Example | Compound Name | NMR | m/z |
|---|---|---|---|
| Example 127 | (2R)-2,9-dimethyl-3,5-dihydro-2H-1,5-benzoxazepin-4-one | $^1$H NMR (400 MHz, DMSO-$d_6$) δ 9.58 (br s, 1H), 6.93-6.97 (m, 2H), 6.81-6.85 (m, 1H), 4.77 (sxt, J = 6.3 Hz, 1H), 2.57 (dd, J = 13.9, 5.0 Hz, 1H), 2.35 (dd, J = 14.1, 6.95 Hz, 1H), 2.21 (s, 3H), 1.34 (d, J = 6.47 Hz, 3H) | 192 |
| Example 128 | (2R)-2,7-dimethyl-3,5-dihydro-2H-1,5-benzoxazepin-4-one | $^1$H NMR (400 MHz, DMSO-$d_6$) δ 9.60 (br s, 1H), 6.79-6.92 (m, 3H), 4.64-4.75 (m, 1H), 2.56 (dd, J = 14.0, 4.9 Hz, 1H), 2.34 (dd, J = 14.0, 7.6 Hz, 1H), 2.23 (s, 3H), 1.29 (d, J = 6.2 Hz, 3H) | 192 |
| Example 129 | (4R)-6-benzyloxy-4-methyl-1,3,4,5-tetrahydro-1,5-benzodiazepin-2-one | $^1$H NMR (400 MHz, DMSO-$d_6$) δ 9.46 (s, 1H), 7.43-7.50 (m, 2H), 7.38 (t, J = 7.4 Hz, 2H), 7.32 (d, J = 7.1 Hz, 1H), 6.76 (dd, J = 8.0, 1.1 Hz, 1H), 6.66 (t, J = 8.0 Hz, 1H), 6.50-6.57 (m, 1H), 5.12 (s, 2H), 4.48 (d, J = 2.2 Hz, 1H), 3.85-3.98 (m, 1H), 2.41 (dd, J = 13.3, 4.1 Hz, 1H), 2.20 (dd, J = 13.4, 8.0 Hz, 1H), 1.18 (d, J = 6.2 Hz, 3H) | 283 |

| Example | Compound Name | NMR | m/z |
|---|---|---|---|
| Example 130 | 4,6-dimethyl-1,3,4,5-tetrahydro-1,5-benzodiazepin-2-one | $^1$H NMR (400 MHz, DMSO-$d_6$) δ 9.36 (s, 1H), 6.84 (dd, J = 7.2, 1.1 Hz, 1H), 6.60-6.76 (m, 2H), 4.33 (br s, 1H), 3.85-4.01 (m, 1H), 2.35 (dd, J = 13.1, 4.8 Hz, 1H), 2.19 (s, 3H), 2.11 (dd, J = 13.1, 7.7 Hz, 1H), 1.19 (d, J = 6.2 Hz, 3H) | 191 |
| Example 131 | (2R)-2-methyl-1,2,3,5-tetrahydro-1,5-benzodiazepin-4-one | $^1$H NMR (400 MHz, DMSO-$d_6$) δ 9.41 (s, 1H), 6.76-6.94 (m, 3H), 6.60-6.73 (m, 1H), 5.25 (br s, 1H), 3.81 (m, 1H), 2.42 (dd, J = 13.3, 3.9 Hz, 1H), 2.18 (dd, J = 13.3, 7.3 Hz, 1H), 1.17 (d, J = 6.4 Hz, 3H) | 177 |
| Example 132 | (2R)-2-ethyl-1,2,3,5-tetrahydro-1,5-benzodiazepin-4-one | $^1$H NMR (400 MHz, DMSO-$d_6$) δ 9.44 (s, 1H), 6.82-6.92 (m, 3H), 6.65-6.72 (m, 1H), 5.32 (br s, 1H), 3.53-3.63 (m, 1H), 2.43 (dd, J = 13.3, 3.7 Hz, 1H), 2.22-2.31 (m, 1H), 1.45-1.61 (m, 2H), 0.90 (t, J = 14.7 Hz, 3H) | 191 |
| Example 133 | (2S)-2-methyl-1,2,3,5-tetrahydro-1,5-benzodiazepin-4-one | $^1$H NMR (400 MHz, DMSO-$d_6$) δ 9.41 (s, 1H), 6.77-6.91 (m, 3H), 6.63-6.74 (m, 1H), 5.25 (br s, 1H), 3.68-3.87 (m, 1H), 2.42 (dd, J = 13.3, 3.9 Hz, 1H), 2.18 (dd, J = 13.4, 7.3 Hz, 1H), 1.17 (d, J = 6.2 Hz, 3H) | 177 |

Example 134

(4R)-4-methyl-6-(2-phenylethynyl)-1,3,4,5-tetrahydro-1,5-benzodiazepin-2-one

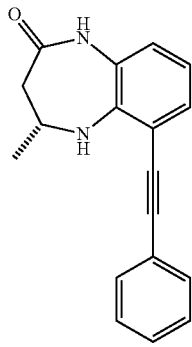 [SMILES: C[C@@H]1CC(=O)Nc2cccc(C#Cc3ccccc3)c2N1]

To a solution of (R)-6-chloro-4-methyl-4,5-dihydro-1Hbenzo[b][1,4]diazepin-2(3H)-one (Intermediate A, 67 mg, 0.318 mmol), dichloropalladium bisacetonitrile (8.25 mg, 0.032 mmol), dicyclohexyl(2',4',6'-triisopropylbiphenyl-2-yl)phosphine (30.3 mg, 0.064 mmol), cesium carbonate (269 mg, 0.827 mmol) under a nitrogen atmosphere was added phenylacetylene (45.4 µl, 0.413 mmol) followed by acetonitrile (1 mL). The mixture was heated to 80° C. for 36 h. After cooling the reaction to room temperature, the reaction mixture was diluted with EtOAc, filtered and concentrated in vacuo. The residue was purified by silica gel chromatography (eluting with hexanes/EtOAc/0.1% triethylamine) to give the title compound (8.5 mg, 10%) as an off-white amorphous solid. $^1$H NMR (400 MHz, DMSO-$d_6$) δ 10.22-10.29 (m, 1H), 7.52-7.56 (m, 3H), 7.46-7.52 (m, 1H), 7.21-7.28 (m, 1H), 7.00 (s, 1H), 6.83-6.89 (m, 1H), 6.50 (s, 1H), 4.62-4.73 (m, 1H), 3.06-3.16 (m, 1H), 2.85-2.95 (m, 2H), 1.28 (d, J=6.5 Hz, 3H). LCMS M/Z (M+H) 277.

The following compounds were prepared in a similar fashion to Example 134:

Examples 135-138

| Example | Compound Name | NMR | m/z |
|---|---|---|---|
| Example 135 | (4R)-6-(2-cyclohexylethynyl)-4-methyl-1,3,4,5-tetrahydro-1,5-benzodiazepin-2-one | $^1$H NMR (400 MHz, DMSO-$d_6$) δ 9.56 (s, 1H), 7.00 (dd, J = 7.6, 1.3 Hz, 1H), 6.83-6.89 (m, 1H), 6.65-6.72 (m, 1H), 4.61 (s, 1H), 3.91-4.03 (m, 1H), 2.64-2.76 (m, 1H), 2.37-2.45 (m, 1H), 2.27-2.35 (m, 1H), 1.83 (br s, 2H), 1.63-1.72 (m, 2H), 1.50 (d, J = 8.9 Hz, 2H), 1.31-1.42 (m, 4H), 1.23 (d, J = 6.5 Hz, 3H). | 283 |
| Example 136 | (4R)-4-methyl-6-(3-phenylprop-1-ynyl)-1,3,4,5-tetrahydro-1,5-benzodiazepin-2-one | $^1$H NMR (400 MHz, DMSO-$d_6$) δ 10.11-10.19 (m, 1H), 7.28 (d, J = 1.6 Hz, 4H), 7.10-7.18 (m, 1H), 6.84-6.94 (m, 1H), 6.71-6.79 (m, 1H), 6.13 (s, 1H), 4.70-4.84 (m, 1H), 4.09-4.24 (m, 1H), 3.53-4.02 (m, 2H), 2.91-3.07 (m, 1H), 2.77-2.89 (m, 1H), 1.12 (d, J = 6.5 Hz, 3H) | 291 |
| Example 137 | (2R)-2-methyl-9-(2-trimethylsilylethynyl)-3,5-dihydro-2H-1,5-benzoxazepin-4-one | $^1$H NMR (500 MHz, DMSO-$d_6$) δ 9.74 (br s, 1H), 7.17 (dd, J = 6.4, 2.8 Hz, 1H), 7.04 (d, J = 3.8 Hz, 1H), 7.03 (s, 1H), 4.81-4.91 (m, 1H), 2.45-2.57 (m, 2H), 1.35 (d, J = 6.2 Hz, 3H), 0.22 (s, 9H) | 274 |

-continued

| Example | Compound Name | NMR | m/z |
|---|---|---|---|
| Example 138 | (2R)-9-(2-cyclohexylethynyl)-2-methyl-3,5-dihydro-2H-1,5-benzoxazepin-4-one | $^1$H NMR (500 MHz, DMSO-$d_6$) δ 9.69 (s, 1H), 7.10 (dd, J = 7.6, 1.8 Hz, 1H), 6.99-7.04 (m, 1H), 6.96 (dd, J = 7.9, 1.8 Hz, 1H), 4.77-4.90 (m, 1H), 2.63-2.71 (m, 1H), 2.56 (dd, J = 14.2, 5.0 Hz, 1H), 2.42 (dd, J = 14.2, 7.9 Hz, 1H), 1.75-1.86 (m, 2H), 1.63-1.75 (m, 2H), 1.48 (s, 3H), 1.30-1.41 (m, 6H) | 284 |

Example 139

(2R)-9-(benzofuran-2-yl)-2-methyl-3,5-dihydro-2H-1,5-benzoxazepin-4-one

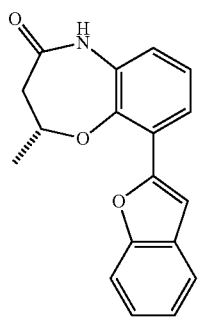 [SMILES: C[C@@H]1CC(=O)Nc2cccc(-c3cc4ccccc4o3)c2O1]

A disposable reaction vial was charged with benzofuran-2-ylboronic acid (95 mg, 0.586 mmol), (R)-9-bromo-2-methyl-2,3-dihydrobenzo[b][1,4]oxazepin-4(5H)-one (Intermediate A, 75 mg, 0.293 mmol), potassium carbonate (81 mg, 0.586 mmol), methanesulfonato(2-di-t-butylphosphino-2',4',6'-tri-i-propyl-1,1'-biphenyl)(2'-amino-1,1'-biphenyl-2-yl)palladium(II) precatalyst (10.82 mg, 0.015 mmol), a stirbar, and 1,4-dioxane/water (19:1) (2 mL) before being degassed (4 vacuum/nitrogen refill cycles) and heated to 100° C. for 6 h. After cooling the reaction to room temperature, the reaction mixture was concentrated in vacuo. The residue was purified by silica gel chromatography (eluting with hexanes/EtOAc) to give the title compound as an off-white amorphous solid. $^1$H NMR (500 MHz, DMSO-$d_6$) δ 9.79 (br s, 1H), 7.72 (td, J=8.0, 1.5 Hz, 2H), 7.62 (d, J=9.0 Hz, 1H), 7.42 (d, J=0.9 Hz, 1H), 7.34 (dt, J=7.7, 1.3 Hz, 1H), 7.27 (dt, J=7.5, 1.0 Hz, 1H), 7.23 (t, J=7.8 Hz, 1H), 7.08 (dd, J=7.9, 1.7 Hz, 1H), 4.89-4.97 (m, J=5.4 Hz, 1H), 2.82 (dd, J=14.3, 5.6 Hz, 1H), 2.39 (dd, J=14.3, 4.7 Hz, 1H), 1.49 (d, J=6.2 Hz, 3H). LCMS M/Z (M+H) 294.

The following compounds were prepared from either Intermediate A or Intermediate I in a similar fashion to Example 139. Synthesis of selected building blocks is shown prior to the table.

Mixture of 3-methyl-1-(1-phenylethyl)-4-(4,4,5,5-tetramethyl-1,3,2-dioxaborolan-2-yl)-1H-pyrazole & 5-methyl-1-(1-phenylethyl)-4-(4,4,5,5-tetramethyl-1,3,2-dioxaborolan-2-yl)-1H-pyrazole

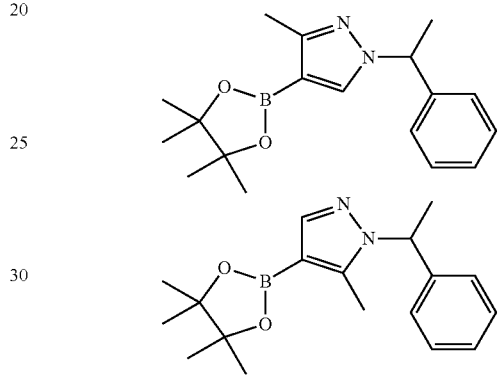

Step 1:

To a solution of 4-bromo-3-methyl-1H-pyrazole (0.805 g, 5 mmol) and cesium carbonate (3.26 g, 10.00 mmol) in acetonitrile (5 mL) was added (1-bromoethyl)benzene (0.682 ml, 5.00 mmol).

The mixture was heated to 50° C. for 18 h. After cooling the reaction to room temperature, the reaction mixture was filtered and the filtrate was concentrated in vacuo. The residue was purified by silica gel chromatography (eluting with hexanes and EtOAc) to give a colorless oil that required no further purification.

The alkylated indoles and indazoles for Examples 157-160 were prepared using similar conditions as described above.

Step 2:

To a solution of methanesulfonato(2-dicyclohexylphosphino-2',6'-dimethoxy-1,1'-biphenyl)(2'-amino-1,1'-biphenyl-2-yl)palladium(II) dichloromethane adduct (15.30 mg, 0.020 mmol) and a mixture of 3-methyl-1-(1-phenylethyl)-4-(4,4,5,5-tetramethyl-1,3,2-dioxaborolan-2-yl)-1H-pyrazole and 5-methyl-1-(1-phenylethyl)-4-(4,4,5,5-tetramethyl-1,3,2-dioxaborolan-2-yl)-1H-pyrazole (104 mg, 0.392 mmol) in dioxane (2 mL) under a nitrogen atmosphere was added 4,4,5,5-tetramethyl-1,3,2-dioxaborolane (114 µl, 0.784 mmol) and triethylamine (164 µl, 1.177 mmol). The mixture was heated to 100° C. for 2.5 h. After cooling the reaction to room temperature, the reaction mixture was diluted with EtOAc, filtered and the filtrate was concentrated in vacuo. The residue was used in the synthesis of Examples 182 and 183.

1-(1-phenylethyl)-4-(4,4,5,5-tetramethyl-1,3,2-di-oxaborolan-2-yl)-1H-pyrazole

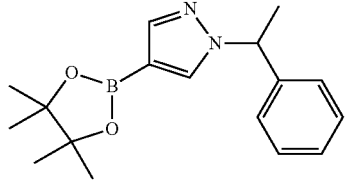 [SMILES: CC(c1ccccc1)n1cc(B2OC(C)(C)C(C)(C)O2)cn1]

To a solution of 4-(4,4,5,5-tetramethyl-1,3,2-dioxaborolan-2-yl)-1H-pyrazole (1 g, 5.15 mmol) and cesium carbonate (2.015 g, 6.18 mmol) in acetonitrile (50 mL) was added 1-bromoethyl)benzene (0.774 ml, 5.67 mmol). The mixture was heated to 50° C. for 18 h. After cooling the reaction to room temperature, the reaction mixture was filtered and the filtrate was concentrated in vacuo. The residue was purified by silica gel chromatography (eluting with hexanes and EtOAc) to give the title compound as a colorless oil, which was used in the synthesis of Example 173.

The following two bromides were prepared as described and then converted into their corresponding pinacol boronates using the same conditions as described for the building block used in Step 1 of Example 80.

2-bromo-1,3-dimethyl-1H-indole

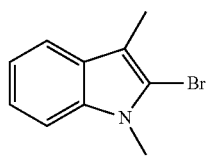

The indole bromide used for Example 151 was prepared according to the following literature procedure: Bedford, R. B.; Fey, N.; Haddow, M. F.; Sankey, R. F. *Chem. Commun.* 2011, 47, 3649-3651.

(E)-1-(bromomethylene)-1,2,3,4-tetrahydronaphtha-lene

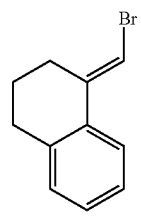

The bromide used for Example 169 was prepared according to the following literature procedure: Bhorge, Y. R.; Chang, S.-H.; Chang, C.-T.; Yan, T.-H. *Tetrahedron* 2012, 68, 4846-4851.

Examples 140-187

| Example | Compound Name | NMR | m/z |
|---------|---------------|-----|-----|
| Example 140 | (2R)-9-(benzothiophen-2-yl)-2-methyl-3,5-dihydro-2H-1,5-benzoxazepin-4-one | $^1$H NMR (500 MHz, DMSO-d$_6$) δ 9.77 (br s, 1H), 7.96-7.99 (m, 1H), 7.94 (s, 1H), 7.86-7.89 (m, 1H), 7.65-7.68 (m, 1H), 7.39 (dt, J = 7.2, 1.3 Hz, 1H), 7.36 (dt, J = 7.2, 1.3 Hz, 1H), 7.20 (t, J = 7.9 Hz, 1H), 7.05 (dd, J = 7.9, 1.5 Hz, 7H), 4.82-4.91 (m, 1H), 2.84 (dd, J = 14.0, 6.5 Hz, 1H), 2.30 (ddd, J = 14.0, 4.0, 0.9 Hz, 1H), 1.45 (d, J = 6.2 Hz, 3H) | 310 |
| Example 141 | (2R)-2-methyl-9-[(E)-styryl]-3,5-dihydro-2H-1,5-benzoxazepin-4-one | $^1$H NMR (500 MHz, DMSO-d$_6$) δ 9.67 (br s, 1H), 7.59 (d, J = 7.4 Hz, 2H), 7.55 (dd, J = 8.0, 1.0 Hz, 1H), 7.41-7.46 (m, J = 10.0 Hz, 1H), 7.39 (t, J = 7.7 Hz, 2H), 7.24-7.31 (m, 2H), 7.11 (t, J = 7.8 Hz, 1H), 6.95 (dd, J = 7.8, 1.1 Hz, 1H), 4.83-4.93 (m, 1H), 2.62 (dd, J = 14.1, 5.1 Hz, 1H), 2.39 (dd, J = 13.9, 7.0 Hz, 1H), 1.40 (d, J = 6.2 Hz, 3H) | 280 |
| Example 142 | (2R)-2-methyl-9-(1-methylindol-2-yl)-3,5-dihydro-2H-1,5-benzoxazepin-4-one | $^1$H NMR (500 MHz, DMSO-d$_6$) δ 9.81 (br s, 1H), 7.55 (d, J = 7.8 Hz, 1H), 7.44-7.48 (m, 1H), 7.13-7.22 (m, 4H), 7.05 (ddd, J = 8.0, 7.0, 1.0 Hz, 1H), 6.47 (d, J = 0.8 Hz, 1H), 4.63 (dquin, J = 6.7, 4.9 Hz, 1H), 3.55 (s, 3H), 2.64 (dd, J = 14.2, 4.8 Hz, 1H), 2.39 (dd, J = 14.1, 7.1 Hz, 1H), 0.97 (d, J = 6.2 Hz, 3H) | 307 |

| Example | Compound Name | NMR | m/z |
|---|---|---|---|
| Example 143 | tert-butyl 2-[(2R)-2-methyl-4-oxo-3,5-dihydro-2H-1,5-benzoxazepin-9-yl]indole-1-carboxylate | $^1$H NMR (500 MHz, DMSO-$d_6$) δ 9.80 (s, 1H), 8.09 (d, J = 8.3 Hz, 1H), 7.61 (d, J = 7.6 Hz, 1H), 7.32 (dt, J = 7.8, 1.2 Hz, 1H), 7.24 (t, J = 7.5 Hz, 1H), 7.13-7.21 (m, 2H), 7.08 (dd, J = 7.5, 2.0 Hz, 1H), 6.68 (s, 1H), 4.43-4.62 (m, 1H), 2.52-2.61 (m, 1H), 2.28-2.40 (m, 1H), 1.25 (s, 9H), 0.89 (s, 3H) | 393 |
| Example 144 | (2R)-9-[1-(benzenesulfonyl)indol-2-yl]-2-methyl-3,5-dihydro-2H-1,5-benzoxazepin-4-one | $^1$H NMR (500 MHz, DMSO-$d_6$) δ 9.82 (s, 1H), 7.98-8.10 (m, 1H), 7.65-7.72 (m, 1H), 7.62 (t, J = 7.3 Hz, 1H), 7.55 (d, J = 7.6 Hz, 2H), 7.47-7.52 (m, 2H), 7.35 (t, J = 7.4 Hz, 1H), 7.26 (t, J = 7.5 Hz, 1H), 7.07-7.21 (m, 3H), 6.71-6.85 (m, 1H), 4.74-4.91 (m, 1H), 2.88 (dd, J = 14.5, 3.8 Hz, 1H), 2.38-2.49 (m, 1H), 1.20 (d, J = 5.8 Hz, 3H) | 433 |
| Example 145 | (2R)-2-methyl-9-(3-methyl-1H-indol-2-yl)-3,5-dihydro-2H-1,5-benzoxazepin-4-one | $^1$H NMR (400 MHz, DMSO-$d_6$) δ 10.85 (s, 1H), 9.77 (s, 1H), 7.49 (d, J = 7.8 Hz, 1H), 7.34 (td, J = 8.0, 0.9 Hz, 1H), 7.20 (s, 1H), 7.19 (d, J = 0.9 Hz, 1H), 7.04-7.11 (m, 2H), 6.99 (ddd, J = 7.9, 7.0, 1.1 Hz, 1H). 4.70 (dquin, J = 6.6, 5.1 Hz, 1H), 2.63 (dd, J = 13.8, 5.1 Hz, 1H), 2.35 (dd, J = 13.8, 6.9 Hz, 1H), 2.21 (s, 3H), 0.99 (d, J = 6.2 Hz, 3H) | 307 |
| Example 146 | (2R)-2-methyl-9-(1-methylindol-5-yl)-3,5-dihydro-2H-1,5-benzoxazepin-4-one | Not Determined | 307 |
| Example 147 | (2R)-9-(1-tert-butylpyrazol-4-yl)-2-methyl-3,5-dihydro-2H-1,5-benzoxazepin-4-one | $^1$H NMR (400 MHz, DMSO-$d_6$) δ 9.64 (br s, 1 H), 8.19 (br s, 1 H), 7.89 (br s, 1 H), 7.42 (d, J = 7.4 Hz, 1 H), 7.06 (br s, 1 H), 6.87 (br s, 1 H), 4.74 (br s, 1 H), 2.71 (br s, 1 H), 2.30 (d, J = 14.7 Hz, 1 H), 1.56 (s, 9 H), 1.37 (d, J = 5.6 Hz, 3 H). | 300 |
| Example 148 | (2R)-2-methyl-9-(3-quinolyl)-3,5-dihydro-2H-1,5-benzoxazepin-4-one | $^1$H NMR (400 MHz, DMSO-$d_6$) δ 9.81 (s, 1H), 9.03 (d, J = 2.1 Hz, 1H), 8.45 (d, J = 2.0 Hz, 1H), 8.05 (dd, J = 7.9, 3.5 Hz, 2H), 7.79 (ddd, J = 8.4, 7.0, 1.3 Hz, 1H), 7.65 (ddd, J = 8.1, 7.0, 0.8 Hz, 1H), 7.31 (dd, J = 7.6, 1.8 Hz, 1H), 7.24 (t, J = 7.7 Hz, 1H), 7.14 (dd, J = 7.8, 1.6 Hz, 1H), 4.72 (dquin, J = 6.3, 5.0 Hz, 1H), 2.72 (dd, J = 14.3, 4.9 Hz, 1H), 2.39 (dd, J = 14.1 , 6.7 Hz, 1H), 1.03 (d, J = 6.2 Hz, 3H) | 305 |
| Example 149 | tert-butyl 2-[(2R)-2-methyl-4-oxo-3,5-dihydro-2H-1,5-benzoxazepin-9-yl]-6,7-dihydro-4H-thieno[3,2-c]pyridine-5-carboxylate | $^1$H NMR (400 MHz, DMSO-$d_6$) δ 9.70 (s, 1H), 7.50 (dd, J = 1.9, 1.5 Hz, 1H), 7.38 (s, 1H), 7.11 (t, J = 7.9 Hz, 1H), 6.93 (dd, J = 7.9, 1.5 Hz, 1H), 4.74-4.82 (m, 1H), 4.44 (br s, 2H), 3.65 (t, J = 5.8 Hz, 2H), 2.75-2.84 (m, 3H), 2.25 (dd, J = 13.7, 3.0 Hz, 1H), 1.39-1.47 (m, 12H) | 415 |
| Example 150 | (2R)-2-methyl-9-(1-phenylpyrazol-4-yl)-3,5-dihydro-2H,5-benzoxazepin-4-one | $^1$H NMR (400 MHz, DMSO-$d_6$) δ 9.70 (s, 1H), 8.84 (s, 1H), 8.19 (s, 1H), 7.83-7.94 (m, 2H), 7.44-7.59 (m, 3H), 7.34 (tt, J = 7.5, 0.8 Hz, 1H), 7.13 (t, J = 7.8 Hz, 1H), 6.94 (dd, J = 8.0, 1.6 Hz, 1H), 4.83 (sxt, J = 6.0 Hz, 1H), 2.74 (dd, J = 14.1, 5.6 Hz, 1H), 2.33 (dd, J = 14.1, 4.9 Hz, 1H), 1.39 (d, J = 6.2 Hz, 3H) | 320 |
| Example 151 | (2R)-9-(1,3-dimethylindol-2-yl)-2-methyl-3,5-dihydro-2H-1,5-benzoxazepin-4-one | $^1$H NMR (400 MHz, DMSO-$d_6$) (~1:1 mixture of rotomers) δ 9.81 (d, J = 4.0 Hz, 2H), 7.52 (d, J = 7.8 Hz, 2H), 7.41 (d, J = 8.0 Hz, 2H), 7.13-7.25 (m, 6H), 7.06 (s, 4H), 4.62-4.71 (m, 1H), 4.41-4.50 (m, 1H), 3.47 (s, 3H), 3.45 (s, 3H), 2.12 (s, 3H), 2.10 (s, 3H), 0.96 (d, J = 6.2 Hz, 3H), 0.78 (d, J = 6.2 Hz, 3H) | 321 |

-continued

| Example | Compound Name | NMR | m/z |
|---|---|---|---|
| Example 152 | tert-butyl 3-[(2R)-2-methyl-4-oxo-3,5-dihydro-2H-1,5-benzoxazepin-9-yl]indole-1-carboxylate | $^1$H NMR (400 MHz, DMSO-d$_6$) δ 9.77 (s, 1H), 8.14 (d, J = 8.3 Hz, 1H), 7.86 (s, 1H), 7.64 (td, J = 8.1, 0.9 Hz, 1H), 7.25-7.41 (m, 3H), 7.19 (t, J = 7.8 Hz, 1H), 7.06 (dd, J = 7.9, 1.7 Hz, 1H), 4.64 (sxt, J = 6.0 Hz, 1H), 2.70 (dd, J = 14.2, 5.2 Hz, 1H), 2.35 (dd, J = 14.1, 5.8 Hz, 1H), 1.65 (s, 9H), 1.11 (d, J = 6.2 Hz, 3H) | 393 |
| Example 153 | (2R)-2-methyl-9-(5-methyl-1-phenyl-pyrazol-4-yl)-3,5-dihydro-2H-1,5-benzoxazepin-4-one | $^1$H NMR (400 MHz, DMSO-d$_6$) δ 9.71 (s, 1H), 7.75 (s, 1H), 7.52-7.60 (m, 4H), 7.42-7.48 (m, 1H), 7.10-7.17 (m, 2H), 7.00 (dd, J = 7.1, 2.5 Hz, 1H), 4.71 (sxt, J = 6.1 Hz, 1H), 2.67 (dd, J = 13.9, 5.2 Hz, 1H), 2.33 (dd, J = 13.9, 6.1 Hz, 1H), 2.29 (s, 3H), 1.17 (d, J = 6.2 Hz, 3H) | 334 |
| Example 154 | (2R)-9-(1-isopropylpyrazol-4-yl)-2-methyl-3,5-dihydro-2H-1,5-benzoxazepin-4-one | $^1$H NMR (400 MHz, DMSO-d$_6$) δ 9.64 (s, 1H), 8.14 (s, 1H), 7.87 (s, 1H), 7.39 (dd, J = 7.8, 1.3 Hz, 1H), 7.06 (t, J = 7.8 Hz, 1H), 6.86 (dd, J = 7.9, 1.5 Hz, 1H), 4.69-4.80 (m, 1H), 4.54 (td, J = 13.3, 6.6 Hz, 1H), 2.71 (dd, J = 14.1, 5.8 Hz, 1H), 2.29 (dd, J = 13.8, 4.5 Hz, 1H), 1.41-1.50 (m, 6H), 1.37 (d, J = 6.2 Hz, 3H) | 286 |
| Example 155 | (2R)-2-methyl-9-(1-methylindol-3-yl)-3,5-dihydro-2H-1,5-benzoxazepin-4-one | $^1$H NMR (400 MHz, DMSO-d$_6$) δ 9.67 (s, 1H), 7.70 (d, J = 8.0 Hz, 1H), 7.63 (s, 1H), 7.48 (d, J = 8.0 Hz, 1H), 7.38 (dd, J = 7.7, 1.7 Hz, 1H), 7.07-7.23 (m, 3H), 6.93 (dd, J = 7.8, 1.6 Hz, 1H), 4.65 (sxt, J = 5.9 Hz, 1H), 3.86 (s, 3H), 2.67 (dd, J = 13.8, 5.6 Hz, 1H), 2.27 (dd, J = 13.4, 5.4 Hz, 1H), 1.14 (d, J = 6.2 Hz, 3H) | 307 |
| Example 156 | (2R)-2-methyl-9-(1-methylindazol-5-yl)-3,5-dihydro-2H-1,5-benzoxazepin-4-one | $^1$H NMR (400 MHz, DMSO-d$_6$) δ 9.73 (s, 1H), 8.08 (s, 1H), 7.81 (s, 1H), 7.66 (d, J = 8.70 Hz, 1H), 7.52 (dd, J = 8.8, 1.2 Hz, 1H), 7.13-7.18 (m, 2H), 7.03 (dd, J = 3.57, 5.80 Hz, 1H), 4.65 (sxt, J = 6.0 Hz, 1H), 4.07 (s, 3H), 2.68 (dd, J = 14.1, 5.1 Hz, 1H), 2.32 (dd, J = 13.8, 6.2 Hz, 1H), 1.00 (d, J = 6.2 Hz, 3H) | 308 |
| Example 157 | (2R)-9-(1,4-dimethylindazol-5-yl)-2-methyl-3,5-dihydro-2H-1,5-benzoxazepin-4-one | $^1$H NMR (400 MHz, DMSO-d$_6$) δ 9.74 (s, 1H), 8.11 (d, J = 0.9 Hz, 1H), 7.44 (d, J = 8.7 Hz, 1H), 7.20 (br s, 1H), 7.13 (t, J = 7.8 Hz, 1H), 7.05 (dd, J = 8.0, 1.9 Hz, 1H), 6.97 (d, J = 7.1 Hz, 1H), 4.42-4.57 (m, 1H), 4.05 (s, 3H), 2.64-2.77 (m, 1H), 2.31 (br s, 4H), 0.71-1.00 (m, 3H) | 322 |
| Example 158 | (2R)-9-(2,4-dimethylindazol-5-yl)-2-methyl-3,5-dihydro-2H-1,5-benzoxazepin-4-one | $^1$H NMR (400 MHz, DMSO-d$_6$) δ 9.73 (s, 1H), 8.38 (s, 1H), 7.39 (d, J = 8.9 Hz, 1H), 7.12 (t, J = 7.6 Hz, 1H), 6.99-7.07 (m, 2H), 6.97 (d, J = 7.4 Hz, 1H), 4.51 (qd, J = 11.9, 5.9 Hz, 1H), 4.17 (s, 3H), 2.60-2.79 (m, 1H), 2.30-2.40 (m, 1H), 2.16-2.29 (m, 3H), 0.76-1.01 (m, 3H) | 322 |
| Example 159 | (2R)-9-(1,6-dimethylindazol-5-yl)-2-methyl-3,5-dihydro-2H-1,5-benzoxazepin-4-one | $^1$H NMR (400 MHz, DMSO-d$_6$) (~1:1 mixture of rotamers) δ 9.74 (s, 2H), 7.96 (d, J = 0.9 Hz, 2H), 7.49 (br s, 4H), 7.13 (t, J = 7.6 Hz, 2H), 7.06 (d, J = 7.6 Hz, 2H), 6.95 (dd, J = 7.4, 1.8 Hz, 2H), 4.48-4.63 (m, 1H), 4.31-4.45 (m, 1H), 4.03 (s, 6H), 2.64-2.80 (m, 1H), 2.37-2.48 (m, 2H), 2.23-2.34 (m, 1H), 2.04-2.23 (m, 6H), 0.96 (br s, 3H), 0.79 (br s, 3H) | 322 |
| Example 160 | (2R)-9-(2,6-dimethylindazol-5-yl)-2-methyl-3,5-dihydro-2H-1,5-benzoxazepin-4-one | $^1$H NMR (400 MHz, DMSO-d$_6$) (~1:1 mixture of rotamers) δ 9.73 (s, 2H), 8.23 (s, 2H), 7.37-7.48 (m, 4H), 7.11 (t, J = 7.5 Hz, 2H), 7.04 (d, J = 1.6 Hz, 2H), 6.95 (dd, J = 7.3, | 322 |

| Example | Compound Name | NMR | m/z |
|---|---|---|---|
| | | 1.7 Hz, 2H), 4.53-4.62 (m, 1H), 4.34-4.43 (m, 1H), 4.14 (s, 6H), 2.69-2.79 (m, 1H), 2.38-2.48 (m, 2H), 2.22-2.31 (m, 1H), 2.08 (br s, 6H), 0.98 (br s, 3H), 0.81 (br s, 3H) | |
| Example 161 | (2R)-9-(5-methoxy-1-methyl-indol-2-yl)-2-methyl-3,5-dihydro-2H-1,5-benzoxazepin-4-one | $^1$H NMR (400 MHz, DMSO-$d_6$) δ 9.80 (s, 1H), 7.36 (d, J = 8.9 Hz, 1H), 7.12-7.22 (m, 3H), 7.06 (d, J = 2.5 Hz, 1H), 6.80 (dd, J = 8.8, 2.3 Hz, 1H), 6.38 (s, 1H), 4.63 (dquin, J = 6.5, 4.9 Hz, 1H), 3.77 (s, 3H), 3.51 (s, 3H), 2.63 (dd, J = 13.9, 4.8 Hz, 1H), 2.38 (dd, J = 14.2, 7.3 Hz, 1H), 0.97 (d, J = 6.2 Hz, 3H) | 337 |
| Example 162 | (2R)-9-(4-chloro-1-methyl-indol-2-yl)-2-methyl-3,5-dihydro-2H-1,5-benzoxazepin-4-one | $^1$H NMR (400 MHz, DMSO-$d_6$) δ 9.84 (s, 1H), 7.49 (td, J = 7.9, 1.0 Hz, 1H), 7.11-7.24 (m, 5H), 6.49 (d, J = 0.9 Hz, 1H), 4.58-4.68 (m, 1H), 3.57 (s, 3H), 2.65 (dd, J = 14.1, 4.7 Hz, 1H), 2.41 (dd, J = 14.3, 7.1 Hz, 1H), 0.98 (d, J = 6.2 Hz, 3H) | 341 |
| Example 163 | (2R)-9-(6-chloro-1-methyl-indol-2-yl)-2-methyl-3,5-dihydro-2H-1,5-benzoxazepin-4-one | $^1$H NMR (400 MHz, DMSO-$d_6$) δ 9.82 (s, 1H), 7.60 (d, J = 1.8 Hz, 1H), 7.56 (d, J = 8.3 Hz, 1H), 7.11-7.23 (m, 3H), 7.06 (dd, J = 8.4, 1.9 Hz, 1H), 6.50 (d, J = 0.7 Hz, 1H), 4.57-4.68 (m, 1H), 3.57 (s, 3H), 2.63 (dd, J = 14.2, 4.8 Hz, 1H), 2.40 (dd, J = 14.2, 7.3 Hz, 1H), 0.96 (d, J = 6.2 Hz, 3H) | 341 |
| Example 164 | (2R)-9-imidazo[1,2-a]pyridin-6-yl-2-methyl-3,5-dihydro-2H-1,5-benzoxazepin-4-one | $^1$H NMR (400 MHz, DMSO-$d_6$) δ 9.78 (s, 1H), 8.68 (d, J = 0.9 Hz, 1H), 7.99 (d, J = 0.5 Hz, 1H), 7.56-7.62 (m, 2H), 7.38 (dd, J = 9.1, 1.6 Hz, 1H), 7.15-7.25 (m, 2H), 7.08 (dd, J = 7.6, 2.0 Hz, 1H), 4.71 (qd, J = 11.8, 6.2 Hz, 1H), 2.70 (dd, J = 14.2, 5.0 Hz, 1H), 2.36 (dd, J = 14.2, 6.4 Hz, 1H), 1.11 (d, J = 6.2 Hz, 3H) | 294 |
| Example 165 | (2R)-9-(1,3-dimethylindazol-5-yl)-2-methyl-3,5-dihydro-2H-1,5-benzoxazepin-4-one | $^1$H NMR (400 MHz, DMSO-$d_6$) δ 9.73 (s, 1H), 7.75 (s, 1H), 7.57 (d, J = 8.7 Hz, 1H), 7.51 (dd, J = 8.7, 1.5 Hz, 1H), 7.12-7.20 (m, 2H), 7.02 (dd, J = 7.4, 2.2 Hz, 1H), 4.64 (qd, J = 11.9, 6.1 Hz, 1H), 3.98 (s, 3H), 2.70 (dd, J = 13.9, 5.2 Hz, 1H), 2.49 (s, 3H), 2.32 (dd, J = 14.1, 6.0 Hz, 1H), 1.03 (d, J = 6.2 Hz, 3H) | 322 |
| Example 166 | (2R)-9-(3-cyclopropyl-1-methyl-indazol-5-yl)-2-methyl-3,5-dihydro-2H-1,5-benzoxazepin-4-one | $^1$H NMR (400 MHz, DMSO-$d_6$) δ 9.73 (s, 1H), 7.82 (dd, J = 1.5, 0.8 Hz, 1H), 7.56 (dd, J = 8.7, 0.8 Hz, 1H), 7.49 (dd, J = 8.7, 1.5 Hz, 1H), 7.19 (dd, J = 7.7, 2.1 Hz, 1H), 7.15 (t, J = 7.5 Hz, 1H), 7.03 (dd, J = 7.6, 2.0 Hz, 1H), 4.64 (sxt, J = 5.9 Hz, 1H), 3.95 (s, 3H), 2.71 (dd, J = 13.8, 5.4 Hz, 1H), 2.25-2.36 (m, 2H), 1.05 (d, J = 6.2 Hz, 3H), 0.92-1.01 (m, 4H) | 348 |
| Example 167 | (2R)-9-(1-isopropylindazol-5-yl)-2-methyl-3,5-dihydro-2H-1,5-benzoxazepin-4-one | $^1$H NMR (400 MHz, DMSO-$d_6$) δ 9.73 (s, 1H), 8.09 (s, 1H), 7.81 (dd, J = 1.3, 0.7 Hz, 1H), 7.71 (d, J = 8.9 Hz, 1H), 7.49 (dd, J = 8.7, 1.6 Hz, 1H), 7.12-7.18 (m, 2H), 7.03 (dd, J = 5.6, 4.0 Hz, 1H), 5.01 (spt, J = 6.5 Hz, 1H), 4.66 (sxt, J = 6.0 Hz, 1H), 2.70 (dd, J = 13.9, 5.2 Hz, 1H), 2.32 (dd, J = 13.9, 6.1Hz, 1H), 1.50 (d, J = 6.7 Hz, 6H), 1.03 (d, J = 6.2 Hz, 3H) | 336 |
| Example 168 | (2R)-9-(1H-indazol-5-yl)-2-methyl-3,5-dihydro-2H-1,5-benzoxazepin-4-one | $^1$H NMR (400 MHz, DMSO-$d_6$) δ 13.09 (s, 1H), 9.73 (s, 1H), 8.10 (s, 1H), 7.82 (s, 1H), 7.57 (d, J = 8.7 Hz, 1H), 7.47 (dd, J = 8.7, 1.6 Hz, 1H), 7.11-7.19 (m, 2H), 7.03 (dd, J = 6.2, 3.3 Hz, 1H), 4.65 (sxt, J = 6.0 Hz, 1H), 2.67 (dd, J = 13.9, 5.2 Hz, | 294 |

| Example | Compound Name | NMR | m/z |
|---|---|---|---|
| Example 169 | (R,E)-9-((3,4-dihydronaphthalen-1(2H)-ylidene)methyl)-2-methyl-2,3-dihydrobenzo[6][1,4]oxazepin-4(5H)-one | 1H), 2.32 (dd, J = 13.9, 6.4 Hz, 1H), 1.00 (d, J = 6.2 Hz, 3H) $^1$H NMR (500 MHz, DMSO-d$_6$) δ 9.66 (s, 1H), 7.67-7.76 (m, 1H), 7.18-7.22 (m, 2H), 7.07-7.16 (m, 4H), 6.95 (dd, J = 7.3, 2.1 Hz, 1H), 4.81 (dd, J = 12.5, 6.2 Hz, 1H), 2.78-2.83 (m, 2H), 2.61-2.71 (m, 2H), 2.58 (dd, J = 13,7, 4.9 Hz, 1H), 2.40 (dd, J = 13.9, 7.6 Hz, 1H), 1.66-1.82 (m, 2H), 1.25-1.32 (m, 3H) | 320 |
| Example 170 | (4R)-6-(benzofuran-2-yl)-4-methyl-1,3,4,5-tetrahydro-1,5-benzodiazepin-2-one | $^1$H NMR (400 MHz, DMSO-d$_6$) δ 9.61 (br s, 1H), 7.68 (ddd, J = 7.5, 1.5, 0.7 Hz, 1H), 7.62 (d, J = 8.0 Hz, 1H), 7.38 (dd, J = 7.5, 1.9 Hz, 1H), 7.25-7.35 (m, 2H), 7.21 (d, J = 0.9 Hz, 1H), 6.99 (dd, J = 8.0. 1.9 Hz, 1H), 6.95 (q, J = 7.6 Hz, 1H), 4.93 (d, J = 3.0 Hz, 1H), 4.04-4.15 (m, 1H), 2.56 (d, J = 13.5, 4.5 Hz, 1H), 2.24 (dd, J = 13.5, 6.5 Hz, 1H), 1.24 (d, J = 6.2 Hz, 3H) | 293 |
| Example 171 | (4R)-4-methyl-6-(1-methylindol-2-yl)-1,3,4,5-tetrahydro-1,5-benzodiazepin-2-one | $^1$H NMR (400 MHz, DMSO-d$_6$) δ 9.63 (s, 1H), 7.58 (d, J = 7.8 Hz, 1H), 7.48 (d, J = 8.0 Hz, 1H), 7.19 (s, 1H), 7.08 (d, J = 7.1 Hz, 1H), 7.02 (dd, J = 7.7, 1.5 Hz, 1H), 6.94-6.99 (m, 1H), 6.88 (d, J = 7.8 Hz, 1H), 6.47 (s, 1H), 4.25 (d, J = 3.1 Hz, 1H), 3.83-3.94 (m, 1H), 2.55-2.64 (m, 1H), 2.20-2.28 (m, 1H), 1.05 (d, J = 6.2 Hz, 3H) | 306 |
| Example 172 | (4R)-6-(1-tert-butylpyrazol-4-yl)-4-methyl-1,3,4,5-tetrahydro-1,5-benzodiazepin-2-one | $^1$H NMR (400 MHz, DMSO-d$_6$) δ 9.50 (s, 1H), 8.00 (s, 1H), 7.60 (s, 1H), 7.00 (dd, J = 6.1, 3.0 Hz, 1H), 6.78-6.88 (m, 2H), 4.03 (d, J = 2.7 Hz, 1H), 3.92-4.00 (m, 1H), 2.53 (d, J = 4.9 Hz, 1H), 2.20 (d, J = 6.0 Hz, 1H), 1.51-1.61 (m, 9H), 1.17 (d, J = 6.2 Hz, 3H) | 299 |
| Example 173 | 4-methyl-6-[1-(1-phenylethyl)pyrazol-4-yl]-1,3,4,5-tetrahydro-1,5-benzodiazepin-2-one | $^1$H NMR (400 MHz, DMSO-d$_6$) δ 9.50 (s, 1H), 8.07 (d, J = 2.7 Hz, 1H), 7.63 (s, 1H), 7.38-7.24 (m, 5H), 6.98 (dd, J = 6.4, 2.8 Hz, 1H), 6.87-6.79 (m, 2H), 5.65 (d, J = 6.0 Hz, 1H), 3.99 (br s, 1H), 3.93 (br s, 1H), 2.55-2.50 (m, 1H), 2.16 (dd, J = 13.2, 6.0 Hz, 1H), 1.85 (d, J = 7.1 Hz, 3H), 1.13 (dd, J = 6.2, 1.8 Hz, 3H) | 347 |
| Example 174 | (4R)-6-(3,4-dimethylphenyl)-4-methyl-1,3,4,5-tetrahydro-1,5-benzodiazepin-2-one | $^1$H NMR (400 MHz, DMSO-d$_6$) δ 9.56 (s, 1H), 7.23 (d, J = 7.6 Hz, 1H), 7.13 (s, 1H), 7.05-7.10 (m, 1H), 6.83-6.93 (m, 3H), 3.86 (d, J = 5.4 Hz, 1H), 3.74 (br s, 1H), 2.59 (dd, J = 13.0, 4.8 Hz, 1H), 2.24-2.30 (m, 6H), 2.18 (dd, J = 13.3, 5.9 Hz, 1H), 1.09 (d, J = 6.2 Hz, 3H) | 281 |
| Example 175 | (4R)-6-(1H-indol-6-yl)-4-methyl-1,3,4,5-tetrahydro-1,5-benzodiazepin-2-one | $^1$H NMR (400 MHz, DMSO-d$_6$) δ 11.17 (br s, 1H), 9.57 (s, 1H), 7.63 (d, J = 8.0 Hz, 1H), 7.32-7.42 (m, 2H), 6.82-7.02 (m, 3H), 6.47 (br s, 1H), 3.86-3.96 (m, 1H), 3.84 (br s, 1H), 2.63 (dd, J = 13, 4.8 Hz, 1H), 2.20 (dd, J = 13.0, 5.5 Hz, 1H), 1.08 (d, J = 6.0 Hz, 3H) | 292 |
| Example 176 | (4R)-6-(3,4-dimethoxyphenyl)-4-methyl-1,3,4,5-tetrahydro-1,5-benzodiazepin-2-one | $^1$H NMR (400 MHz, DMSO-d$_6$) δ 9.55 (s, 1H), 7.05 (d, J = 8.25 Hz, 1H), 6.80-6.97 (m, 5H), 3.86-3.94 (m, 1H), 3.82 (d, J = 2.90 Hz, 1H), 3.80 (s, 3H), 3.77 (s, 3H), 2.61 (dd, J = 13.2, 4.9 Hz, 1H), 2.17 (dd, J = 13.0, 5.5 Hz, 1H), 1.12 (d, J = 6.2 Hz, 3H) | 313 |

| Example | Compound Name | NMR | m/z |
|---|---|---|---|
| Example 177 | (4R)-4-methyl-6-(2-oxoindolin-6-yl)-1,3,4,5-tetrahydro-1,5-benzodiazepin-2-one | $^1$H NMR (400 MHz, DMSO-$d_6$) δ 10.42 (s, 1H), 9.57 (s, 1H), 7.30 (d, J = 7.5 Hz, 1H), 6.81-6.98 (m, 4H), 6.75 (s, 1H), 3.84 (br s, 2H), 3.52 (s, 2H), 2.60 (dd, J = 13.3, 4.6 Hz, 1H), 2.18 (dd, J = 12.6, 5.7 Hz, 1H), 1.11 (d, J = 6.0 Hz, 3H) | 308 |
| Example 178 | (4R)-4-methyl-6-(2-oxoindolin-5-yl)-1,3,4,5-tetrahydro-1,5-benzodiazepin-2-one | $^1$H NMR (400 MHz, DMSO-$d_6$) δ 10.46 (s, 1H), 9.55 (s, 1H), 7.18 (s, 1H), 7.15 (d, J = 7.8 Hz, 1H), 6.83-6.92 (m, 4H), 3.88 (br s, 1H), 3.79 (br s, 1H), 3.52 (s, 2H), 2.60 (dd, J = 13.2, 4.7 Hz, 1H), 2.13-2.21 (m, 1H), 1.10 (d, J = 6.2 Hz, 3H) | 308 |
| Example 179 | (4R)-4-methyl-6-(1-methylsulfonylpyrazol-4-yl)-1,3,4,5-tetrahydro-1,5-benzodiazepin-2-one | $^1$H NMR (400 MHz, DMSO-$d_6$) δ 9.55 (s, 1H), 8.38 (d, J = 0.9 Hz, 1H), 8.11 (d, J = 0.9 Hz, 1H), 7.00-7.11 (m, 1H), 6.81-6.96 (m, 2H), 4.35 (br s, 1H), 3.97 (br s, 1H), 3.58 (d, J = 1.3 Hz, 3H), 2.55 (dd, J = 13.2, 4.5 Hz, 1H), 2.18 (dd, J = 13.0, 5.9 Hz, 1H), 1.12-1.24 (m, 3H) | 321 |
| Example 180 | 3-[(4R)-4-methyl-2-oxo-1,3,4,5-tetrahydro-1,5-benzodiazepin-6-yl]benzenesulfonamide | $^1$H NMR (400 MHz, DMSO-$d_6$) δ 9.62 (s, 1H), 7.77-7.89 (m, 2H), 7.56-7.73 (m, 2H), 7.38 (s, 2H), 6.89-7.02 (m, 3H), 3.91 (d, J = 1.8 Hz, 2H), 2.63 (dd, J = 12.9, 4.5 Hz, 1H), 2.20 (dd, J = 13.0, 5.2 Hz, 1H), 1.12 (d, J = 5.8 Hz, 3H) | 332 |
| Example 181 | N-methyl-3-[(4R)-4-methyl-2-oxo-1,3,4,5-tetrahydro-1,5-benzodiazepin-6-yl]benzenesulfonamide | $^1$H NMR (400 MHz, DMSO-$d_6$) δ 9.61 (s, 1H), 7.61-7.82 (m, 4H), 7.49 (q, J = 5.05 Hz, 1H), 6.89-7.01 (m, 3H), 4.01 (d, J = 2.45 Hz, 1H), 3.86-3.96 (m, 1H), 2.64 (dd, J = 13.0, 4.8 Hz, 1H), 2.45 (d, J = 4.91 Hz, 3H), 2.20 (dd, J = 13.0, 5.5 Hz, 1H), 1.12 (d, J = 6.2 Hz, 3H) | 346 |
| Example 182 | (4R)-4-methyl-6-[3-methyl-1-[(1S)-1-phenylethyl]pyrazol-4-yl]-1,3,4,5-tetrahydro-1,5-bezodiazepin-2-one | $^1$H NMR (400 MHz, DMSO-$d_6$) δ 9.55 (s, 1H), 7.86 (s, 1H), 7.31-7.38 (m, 2H), 7.24-7.30 (m, 3H), 6.78-6.93 (m, 3H), 5.55 (q, J = 7.1 Hz, 1H), 3.80-3.94 (m, 1H), 2.46-2.49 (m, 1H), 2.19 (dd, J = 13.3, 6.8 Hz, 1H), 2.04 (s, 3H), 1.82 (d, J = 7.1 Hz, 3H), 1.05 (d, J = 6.0 Hz, 3H) | 361 |
| Example 183 | 4-methyl-6-[5-methyl-1-(1-phenylethyl)pyrazol-4-yl]-1,3,4,5-tetrahydro-1,5-benzodiazepin-2-one | $^1$H NMR (400 MHz, DMSO-$d_6$) δ 9.53 (br s, 1H), 7.50 (d, J = 2.5 Hz, 1H), 7.22-7.39 (m, 3H), 7.17 (t, J = 6.2 Hz, 2H), 6.84-6.92 (m, 1H), 6.74-6.83 (m, 2H), 5.65 (quin, J = 7.1 Hz, 1H), 3.74-3.93 (m, 1H), 2.42-2.48 (m, 1H), 2.13-2.24 (m, 1H), 2.02 (d, J = 2.5 Hz, 3H), 1.84 (dd, J = 6.9, 2.7 Hz, 3H), 0.93-1.11 (m, 3H) | 361 |
| Example 184 | (4R)-6-(1-benzylpyrazol-4-yl)-4-methyl-1,3,4,5-tetrahydro-1,5-benzodiazepin-2-one | $^1$H NMR (400 MHz, DMSO-$d_6$) δ 9.51 (s, 1H), 8.05 (s, 1H), 7.63 (s, 1H), 7.25-7.40 (m, 3H), 6.97 (dd, J = 6.1, 2.3 Hz, 1H), 6.79-6.88 (m, 2H), 5.37 (s, 2H), 3.94 (br. s, 1H), 2.54 (d, J = 4.7 Hz, 1H), 2.15 (dd, J = 13.0, 5.7 Hz, 1H), 1.15 (d, J = 6.2 Hz, 3H) | 333 |
| Example 185 | (4R)-6-(1-isopropylpyrazol-4-yl)-4-methyl-1,3,4,5-tetrahydro-1,5-benzodiazepin-2-one | $^1$H NMR (400 MHz, DMSO-$d_6$) δ 9.50 (s, 1H), 7.96 (s, 1H), 7.59 (s, 1H), 6.98 (dd, J = 2.90, 6.02 Hz, 1H), 6.79-6.88 (m, 2H), 4.53 (td, J = 13.4, 6.7 Hz, 1H), 3.97 (d, J = 5.8 Hz, 1H), 2.54 (d, J = 4.9 Hz, 1H), 2.17 (dd, J = 13.2, 5.8 Hz, 1H), 1.46 (d, J = 6.7 Hz, 6H), 1.17 (d, J = 6.0 Hz, 3H) | 285 |
| Example 186 | (4R)-4-methyl-6-[1-(oxetan-3-yl)pyrazol-4-yl]-1,3,4,5-tetrahydro-1,5-benzodiazepin-2-one | $^1$H NMR (400 MHz, DMSO-$d_6$) δ 9.51 (s, 1H), 8.04-8.12 (m, 1H), 7.74 (s, 1H), 6.98 (dd, J = 6.7, 2.7 Hz, 1H), 6.80-6.88 (m, 2H), 5.58-5.69 (m, 1H), 4.91-4.99 (m, 4H), | 299 |

-continued

| Example | Compound Name | NMR | m/z |
|---|---|---|---|
| Example 187 | (4R)-4-methyl-6-(3-methylsulfonylphenyl)-1,3,4,5-tetrahydro-1,5-benzodiazepin-2-one | 4.10 (d, J = 2.9 Hz, 1H), 3.97 (td, J = 8.8, 5.7 Hz, 1H), 2.55 (dd, J = 13.0, 5.0 Hz, 1H), 2.16 (dd, J = 13.0, 5.7 Hz, 1H), 1.18 (d, J = 6.2 Hz, 3H) <br> $^1$H NMR (400 MHz, DMSO-d$_6$) δ 9.61 (s, 1H), 7.93 (d, J = 6.7 Hz, 1H), 7.89 (s, 1H), 7.70-7.78 (m, 2H), 6.83-7.01 (m, 3H), 4.07 (br s, 1H), 3.91 (br s, 1H), 3.26 (s, 3H), 2.65 (dd, J = 13.2, 4.7 Hz, 1H), 2.21 (dd, J = 13.2, 5.6 Hz, 1H), 1.14 (d, J = 6.2 Hz, 3H) | 331 |

Example 188 methyl 1-methyl-3-[(4R)-4-methyl-2-oxo-1,3,4,5-tetrahydro-1,5-benzodiazepin-6-yl]indole-6-carboxylate

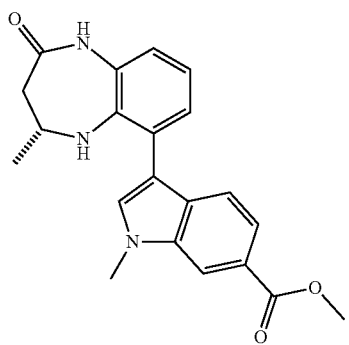 [SMILES: COC(=O)c1ccc2c(-c3cccc4c3N[C@H](C)CC(=O)N4)cn(C)c2c1]

To a solution of (R)-6-bromo-4-methyl-4,5-dihydro-1H-benzo[b][1,4]diazepin-2(3H)-one (Intermediate A, 100 mg, 0.392 mmol) in NMP (2 mL) under a nitrogen atmosphere was added methyl 1-methyl-1H-indole-6-carboxylate (0.148 g, 0.784 mmol), diacetoxy palladium (0.009 g, 0.039 mmol), potassium carbonate (0.108 g, 0.784 mmol), and pivalic acid (0.020 g, 0.196 mmol). The reaction mixture was heated to 110° C. for 5 h. After cooling the reaction to room temperature, the reaction mixture was concentrated in vacuo. The residue was purified by flash chromatography followed by preparative HPLC to give the title compound (38 mg, 20%). $^1$H NMR (400 MHz, DMSO-d$_6$) 9.58 (s, 1H), 8.17 (d, J=0.7 Hz, 1H), 7.69 (dd, J=8.4, 1.5 Hz, 2H), 7.69 (s, 1H), 7.49 (d, J=8.5 Hz, 1H), 6.85-7.01 (m, 3H), 3.94 (s, 3H), 3.89-3.92 (m, 1H), 3.88 (s, 3H), 2.66 (dd, J=13.2, 4.7 Hz, 1H), 2.18-2.25 (m, 1H), 1.05 (d, J=6.2 Hz, 3H). LCMS M/Z (M+H) 364.

The following compounds were prepared in a similar fashion to Example 188. Synthesis of selected building blocks is shown before the table.

1-methyl-6-(methylsulfonyl)-1H-indole

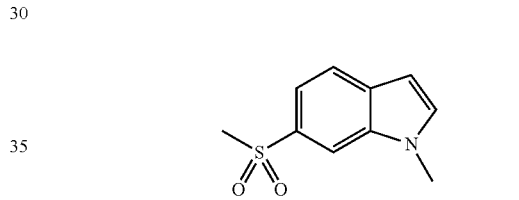

The N-methyl indole starting material used in examples G02792117 and G02792118 was prepared according to the following literature procedure: Hebeisen, P., Kitas, E. A., Minder, R. E., Mohr, P., Wessel, H. P. Animothiazole derivatives. WO2009068467, Jun. 4, 2009.

Examples 189-194

| Example | Compound Name | NMR | m/z |
|---|---|---|---|
| Example 189 | (4R)-4-methyl-6-(1-methyl-4,5,6,7-tetrahydroindol-2-yl)-1,3,4,5-tetrahydro-1,5-benzodiazepin-2-one | $^1$H NMR (400 MHz, DMSO-d$_6$) δ 9.54 (s, 1H), 6,89 (dd, J = 7.6, 2.0 Hz, 1H), 6.76-6.84 (m, 2H), 5.79 (s, 1H), 4.10 (d, J = 3.1 Hz, 1H), 3.81-3.91 (m, 1H), 3.19 (s, 3H), 2.52-2.58 (m, 3H), 2.45 (t, J = 5.9 Hz, 2H), 2.20 (dd, J = 13.5, 6.4 Hz, 1H), 1.74-1.84 (m, 2H), 1.63-1.73 (m, 2H), 1.09 (d, J = 6.5 Hz, 3H) | 310 |
| Example 190 | 1-methyl-2-[(4R)-4-methyl-2-oxo-1,3,4,5-tetrahydro-1,5-benzodiazepin-6-yl]indole-6-carbonitrile | $^1$H NMR (400 MHz, DMSO-d$_6$) δ 9.64 (s, 1H), 8.12 (s, 1H), 7.74 (d, J = 8.3 Hz, 1H), 7.40 (dd, J = 8.0, 1.3 Hz, 1H), 7.04 (dd, J = 7.8, 1.8 Hz, 1H), 6.96 (dd, J = 7.5, 1.8 Hz, 1H), 6.87 (t, J = 7.8 Hz, 1H), 6.63 (d, J = 0.5 Hz, 1H), 4.38 (d, J = 3.3 Hz, 1H), 3.84-3.94 (m, 1H), 3.60 (s, 3H), 2.64 (dd, J = 13.0, 4.1 Hz, 1H), 2.24 (dd, J = 13.2, 6.0 Hz, 1H), 1.06 (d, J = 6.2 Hz, 3H) | 331 |

| Example | Compound Name | NMR | m/z |
|---|---|---|---|
| Example 191 | (4R)-4-methyl-6-(1-methyl-6-methylsulfonyl-indol-3-yl)-1,3,4,5-tetrahydro-1,5-benzodiazepin-2-one | $^1$H NMR (400 MHz, DMSO-$d_6$) δ 9.57 (s, 1H), 8.13 (s, 1H), 7.76 (s, 1H), 7.57-7.60 (m, 2H), 6.91-7.00 (m, 2H), 6.84-6.89 (m, 1H), 3.97 (s, 3H), 3.85-3.91 (m, 1H), 3.22 (s, 3H), 2.63-2.69 (m, 1H), 2.17-2.24 (m, 1H), 1.05 (d, J = 6.2 Hz, 3H) | 384 |
| Example 192 | (4R)-4-methyl-6-(1-methyl-6-methylsulfonyl-indol-2-yl)-1,3,4,5-tetrahydro-1,5-benzodiazepin-2-one | $^1$H NMR (400 MHz, DMSO-$d_6$) δ 9.65 (s, 1H), 8.08 (s, 1H), 7.80 (d, J = 8.47 Hz, 1H), 7.59 (dd, J = 8.4, 1.7 Hz, 1H), 7.04 (dd, J = 7.8, 1.6 Hz, 1H), 6.97 (dd, J = 7.6, 1.6 Hz, 1H), 6.88 (t, J = 7.6 Hz, 1H), 6.64 (s, 1H), 3.91 (s, 1H), 3.64 (s, 3H), 3.22 (s, 3H), 2.64 (dd, J = 13.2, 3.8 Hz, 1H), 2.24 (dd, J = 13.3, 6.4 Hz, 1H), 1.07 (d, J = 6.2 Hz, 3H) | 384 |
| Example 193 | methyl 1-methyl-2-[(4R)-4-methyl-2-oxo-1,3,4,5-tetrahydro-1,5-benzodiazepin-6-yl]indole-6-carboxylate | $^1$H NMR (400 MHz, DMSO-$d_6$) δ 9.65 (s, 1H), 8.13 (s, 1H), 7.65-7.73 (m, 2H), 7.04 (dd, J = 7.8, 1.6 Hz, 1H), 6.97 (dd, J = 7.8, 1.6 Hz, 1H), 6.88 (t, J = 7.8 Hz, 1H), 6.58 (s, 1H), 3.85-3.94 (m, 4H), 3.61 (s, 3H), 2.63 (dd, J = 13.2, 4.0 Hz, 1H), 2.24 (dd, J = 13.3, 6.4 Hz, 1H), 1.06 (d, J = 6.2 Hz, 3H) | 364 |
| Example 194 | 1-methyl-3-[(4R)-4-methyl-2-oxo-1,3,4,5-tetrahydro-1,5-benzodiazepin-6-yl]indole-6-carbonitrile | $^1$H NMR (400 MHz, DMSO-$d_6$) δ 9.56 (s, 1H), 8.17 (dd, J = 1.3, 0.7 Hz, 1H), 7.74 (s, 1H), 7.53 (dd, J = 8.3, 0.7 Hz, 1H), 7.38 (dd, J = 8.3, 1.6 Hz, 1H), 6.96 (dd, J = 7.3, 1.8 Hz, 1H), 6.93 (dd, J = 8.0, 1.8 Hz, 1H), 6.83-6.88 (m, 1H), 3.92 (s, 3H), 3.84-3.91 (m, 1H), 2.65 (dd, J = 13.2, 4.5 Hz, 1H), 2.20 (dd, J = 13.5, 5.9 Hz, 1H), 1.04 (d, J = 6.2 Hz, 3H) | 331 |

Example 195

4-methyl-1,3,4,5-tetrahydro-1-benzazepin-2-one

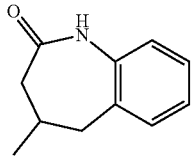

Step 1:

tert-butyl 1-imino-3-methyl-1,2,3,4-tetrahydronaphthalene-2-carboxylate

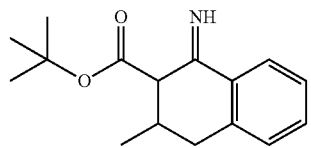 [SMILES: CC1Cc2ccccc2C(=N)C1C(=O)OC(C)(C)C]

To a solution of N,N-diisopropylamine (5.79 mL, 41.0 mmol) in diglyme (1000 mL) at −78° C. was added butyllithium (16.39 mL, 41.0 mmol) slowly. The reaction mixture was allowed to stirred at 0° C. for 10 min, and then re-cooled to −78° C. To the reaction mixture was added 2-methylbenzonitrile (2.4 g, 20.49 mmol) over 10 min and stirred for 5 min before (E)-tert-butyl but-2-enoate (2.91 g, 20.49 mmol) was added. After stirring for an additional 15 min at −78° C., the reaction was allowed to warm to 20° C. and stirred at this temperature for 45 min. The reaction mixture was quenched with sat. aq. NH$_4$Cl and extracted with diethylether (×4). The combined organic layers were dried over anhydrous Na$_2$SO$_4$, filtered and concentrated in vacuo to give the title compound as a yellow oil that required no further purification. LCMS M/Z (M+H) 260.

Step 2:

3-methyl-3,4-dihydronaphthalen-1 (2H)-one

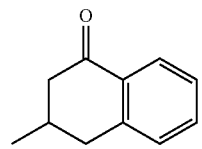

To a solution of tert-butyl 1-imino-3-methyl-1,2,3,4-tetrahydronaphthalene-2-carboxylate (5 g, 19.28 mmol) in MeOH (20 mL) was added 6N aqueous hydrochloric acid (20 mL, 120 mmol) at room temperature. The reaction was heated to 70° C. (gas evolution was observed) for 1.5 h before the reaction was diluted with water, and the product was extracted with diethylether (repeated 4 times). The combined organic layers were dried over sodium sulfate, filtered, and concentrated in vacuo. The residue was purified by flash chromatography (hexanes/diethylether 19:1 to 8:2) to give the title compound (yield not determined). LCMS M/Z (M+H) 161.

Step 3:

3-methyl-3,4-dihydronaphthalen-1 (2H)-one oxime

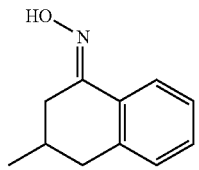

To a solution of 3-methyl-3,4-dihydronaphthalen-1(2H)-one (500 mg, 3.12 mmol) and hydroxylamine hydrochloride (260 mg, 3.75 mmol) in methanol (20 mL) was added sodium hydroxide (150 mg, 3.75 mmol). After the reaction was stirred overnight at room temperature, additional hydroxylamine hydrochloride (108 mg, 1.56 mmol) and sodium hydroxide (62.4 mg, 1.56 mmol) were added. Then the reaction was heated to 70° C. for about 1.5 h before it was concentrated in vacuo. The residue was suspended in a mixture of EtOAc and dichloromethane (9:1), filtered through celite and the filtrate was concentrated in vacuo to give the title compound as a white solid (547 mg, 100%). LCMS M/Z (M+H) 176.

Step 4:

4-methyl-1,3,4,5-tetrahydro-1-benzazepin-2-one

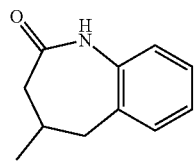

Polyphosphoric acid (10 mL) was added to 3-methyl-3,4-dihydronaphthalen-1(2H)-one oxime (547 mg, 3.12 mmol) and the mixture was heated to 120° C. for 2 h. Then the reaction was cooled to 50° C. before it was quenched with water (200 mL) (exothermic process) (preforming the quench a lower temperature was difficult due to the high viscosity of the reaction mixture). The product was extracted with dichloromethane (repeated 4 times), and the combined organic layers were washed with a saturated solution of sodium bicarbonate, dried over sodium sulfate, filtered and concentrated in vacuo. The residue was purified by silica gel chromatography (hexanes/EtOAc 85:15 to 65:35) to give the title compound as a white solid (425 mg, 78%). $^1$H NMR (400 MHz, DMSO-$d_6$) δ 9.53 (br s, 1H), 7.17-7.26 (m, 2H), 7.07 (tt, J=7.5, 1.2 Hz, 1H), 6.95 (d, J=8.0 Hz, 1H), 2.81 (dd, J=13.4, 6.7 Hz, 1H), 2.44-2.53 (m, 1H), 2.31 (dd, J=13.3, 6.6 Hz, 1H), 2.21 (dd, J=12.3, 6.9 Hz, 1H), 1.79 (dd, J=12.3, 6.9 Hz, 1H), 0.99 (dd, J=6.7, 1.3 Hz, 3H). LCMS M/Z (M+H) 176.

Example 196

(4R)-4-methyl-2-oxo-N-phenyl-1,3,4,5-tetrahydro-1,5-benzodiazepine-6-carboxamide

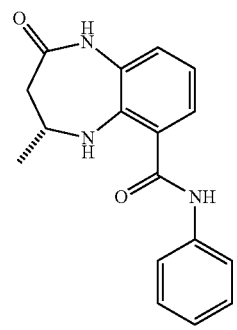 [SMILES: C[C@@H]1CC(=O)Nc2cccc(C(=O)Nc3ccccc3)c2N1]

To a solution of (R)-4-methyl-2-oxo-2,3,4,5-tetrahydro-1H-benzo[b][1,4]diazepine-6-carboxylic acid (Intermediate C, 50 mg, 0.227 mmol) and aniline (106 mg, 1.135 mmol) in dimethylacetamide (2 mL) at 0° C. was added (1-cyano-2-ethoxy-2-oxoethylidenaminooxy)dimethylamino-morpholino-carbenium hexafluorophosphate (COMU, 126 mg, 0.295 mmol). The reaction mixture was stirred at 0° C. for 45 min before additional COMU (50 mg) was added. The mixture was concentrated in vacuo. The residue was purified by silica gel chromatography (eluting with hexanes and EtOAc) to give the title compound (48 mg) as a yellow amorphous solid. $^1$H NMR (400 MHz, DMSO-$d_6$) δ 10.34 (s, 1H), 9.61 (s, 1H), 7.66-7.75 (m, 2H), 7.39 (dd, J=7.8, 1.3 Hz, 1H), 7.34 (t, J=8.0 Hz, 2H), 7.10 (tt, J=7.4, 1.0 Hz, 1H), 7.07 (dd, J=7.9, 1.5 Hz, 1H), 6.87 (t, J=7.8 Hz, 1H), 6.67 (d, J=2.2 Hz, 1H), 3.89-4.01 (m, 1H), 2.45 (dd, J=13.5, 4.0 Hz, 1H), 2.24 (dd, J=13.4, 8.0 Hz, 1H), 1.17 (d, J=6.2 Hz, 3H). LCMS M/Z (M+H) 296.

Examples 197 & 198

(4R)-6-(2,3-dihydrobenzofuran-2-yl)-4-methyl-4,5-dihydro-1H-benzo[b][1,4]diazepin-2(3H)-one & (R)-6-(2-hydroxyphenethyl)-4-methyl-4,5-dihydro-1H-benzo[b][1,4]diazepin-2(3H)-one

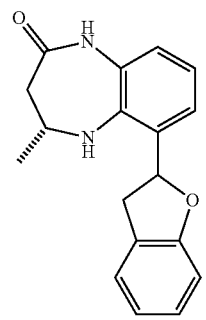 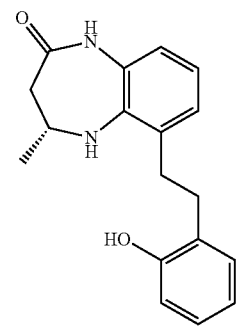

To a solution of (4R)-6-(benzofuran-2-yl)-4-methyl-1,3,4,5-tetrahydro-1,5-benzodiazepin-2-one (Example 170, 40 mg, 0.137 mmol) in 3:1 EtOAc/acetone mixture (4 mL) was added palladium on carbon (36 mg). The reaction was stirred at room temperature for 5 h under an atmosphere of hydrogen (1 atm) then the hydrogen was removed and the reaction filtered through celite. The filtrate was concentrated in vacuo, and the residue was purified silica gel chromatography (hexanes/EtOAc 8:2 to 2:8) and then reverse phase chromatography (acetonitrile/water 10:90 to 100:0 with 0.1% TFA) to give (4R)-6-(2,3-dihydrobenzofuran-2-yl)-4-methyl-4,5-dihydro-1H-benzo[b][1,4]diazepin-2(3H)-one (Example 197, 19 mg, 32%, second peak) and (R)-6-(2-hydroxyphenethyl)-4-methyl-4,5-dihydro-1H-benzo[b][1,4]diazepin-2(3H)-one (Example 198, 10 mg, 18%, first peak). Example 197: $^1$H NMR ~1:1 Mixture of diastereomers. (400 MHz, DMSO-$d_6$) δ 9.49 (s, 1H), 7.24 (t, J=6.80 Hz, 1H), 7.15 (t, J=7.5 Hz, 1H), 7.06 (ddd, J=7.2, 5.4, 1.7 Hz, 1H), 6.78-6.91 (m, 4H), 6.05 (q, J=9.3 Hz, 1H), 3.95 (sxt, J=5.7 Hz, 1H), 3.73 (dt, J=16.2, 9.5 Hz, 1H), 2.96-3.10 (m, 1H), 2.46 (dd, J=13.0, 5.0 Hz, 1H), 2.07-2.20 (m, 1H), 1.20 (t, J=6.0 Hz, 3H). LCMS M/Z (M+H) 295. Example 198: $^1$H NMR (400 MHz, DMSO-$d_6$) δ 9.75 (s, 1H), 8.67 (t, J=6.0 Hz, 1H), 7.31-7.38 (m, 3H), 7.26 (s, 2H), 7.13 (t, J=7.6 Hz, 1H), 7.09 (dd, J=7.8, 1.8 Hz, 1H), 4.75 (q, J=6.0 Hz, 1H), 4.45 (d, J=6.0 Hz, 2H), 2.74 (dd, J=14.3, 5.4 Hz, 1H), 2.30 (dd, J=14.3, 4.9 Hz, 1H), 1.26 (d, J=6.2 Hz, 3H). LCMS M/Z (M+H) 297.

Example 199

(2R)-9-ethynyl-2-methyl-3,5-dihydro-2H-1,5-benzoxazepin-4-one

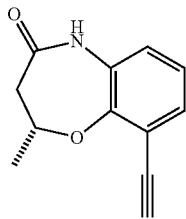

To a solution of (2R)-2-methyl-9-(2-trimethylsilylethynyl)-3,5-dihydro-2H-1,5-benzoxazepin-4-one (Example 137, 30 mg, 0.110 mmol) in THF (4 mL) was added water (0.1 mL) and a 1 M TBAF solution in THF (0.13 mL, 0.13 mmol). The reaction was stirred at room temperature for 2.5 h then quenched with MeOH and concentrated in vacuo. The residue was purified by flash chromatography (hexanes/EtOAc 7:3 to 0:10) to give the title compound (12 mg, 55%). $^1$H NMR (500 MHz, DMSO-$d_6$) δ 9.74 (s, 1H), 7.21 (dd, J=6.9, 2.2 Hz, 1H), 7.01-7.09 (m, 2H), 4.81-4.90 (m, 1H), 4.24 (s, 1H), 2.59 (dd, J=14.3, 4.7 Hz, 1H), 2.44 (dd, J=14.2, 7.9 Hz, 1H), 1.36 (d, J=6.2 Hz, 3H). LCMS M/Z (M+H) 202.

Example 200

(2R)-9-(1H-indol-2-yl)-2-methyl-3,5-dihydro-2H-1,5-benzoxazepin-4-one

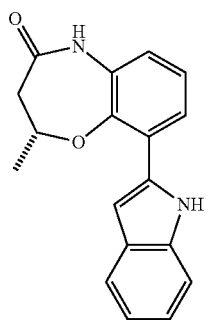 [SMILES: C[C@@H]1CC(=O)Nc2cccc(-c3cc4ccccc4[nH]3)c2O1]

To a solution of tert-butyl 2-[(2R)-2-methyl-4-oxo-3,5-dihydro-2H-1,5-benzoxazepin-9-yl]indole-1-carboxylate (Example 143) in dichloromethane (4 mL) was added trifluoroacetic acid (1.4 mL). The reaction was stirred at room temperature for 1.5 h then concentrated in vacuo. The residue was purified by silica gel chromatography (hexanes/EtOAc 9:1 to 0:10) to give the title compound (24 mg, 92%). $^1$H NMR (500 MHz, DMSO-$d_6$) δ 11.22 (s, 1H), 9.72 (s, 1H), 7.57 (dd, J=7.8, 1.3 Hz, 1H), 7.55 (d, J=7.8 Hz, 1H), 7.44 (d, J=8.0 Hz, 1H), 7.20 (t, J=7.8 Hz, 1H), 7.09 (t, J=7.5 Hz, 1H), 6.97-7.02 (m, 2H), 6.95 (d, J=2.2 Hz, 1H), 4.85 (sxt, J=6.0 Hz, 1H), 2.73 (dd, J=13.9, 5.7 Hz, 1H), 2.33 (dd, J=13.8, 5.5 Hz, 1H), 1.34 (d, J=6.2 Hz, 3H). LCMS M/Z (M+H) 293.

Example 201

(2R)-2-methyl-9-(1-methylsulfonylindazol-5-yl)-3,5-dihydro-2H-1,5-benzoxazepin-4-one

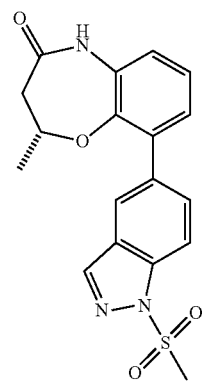 [SMILES: C[C@@H]1CC(=O)Nc2cccc(-c3ccc4c(cnn4S(C)(=O)=O)c3)c2O1]

To a solution of (2R)-9-(I-indazol-5-yl)-2-methyl-3,5-dihydro-2H-1,5-benzoxazepin-4-one (Example 168, 0.070 g, 0.24 mmol) in dichloromethane (3 mL) was added pyridine (0.057 g, 0.720 mmol) and methanesulfonyl chloride (0.022 g, 0.192 mmol) at 0° C. The reaction mixture was stirred at 0° C. for 10 min and then warmed to room temperature for 6 h. To the mixture was added additional pyridine (0.057 g, 0.720 mmol) and methanesulfonyl chloride (0.022 g, 0.192 mmol). The reaction was quenched with sat. aq. NH$_4$Cl, and the mixture was extracted with EtOAc (repeated 3 times). The combined organic layers were dried over anhydrous Na$_2$SO$_4$, filtered and concentrated in vacuo. The residue was purified by flash chromatography (hexanes/EtOAc 19:1 to 0:10) to give the title compound (21 mg, 24%). $^1$H NMR (400 MHz, DMSO-$d_6$) δ 9.76 (s, 1H), 8.96 (d, J=0.9 Hz, 1H), 7.84 (t, J=1.0 Hz, 1H), 7.75 (td, J=9.3, 0.9 Hz, 1H), 7.56 (dd, J=9.1, 1.6 Hz, 1H), 7.18 (d, J=0.5 Hz, 1H), 7.17 (s, 1H), 7.04-7.10 (m, 1H), 4.68 (qd, J=11.8, 6.1 Hz, 1H), 3.76 (s, 3H), 2.69 (dd, J=14.2, 5.2 Hz, 1H), 2.36 (dd, J=13.9, 6.6 Hz, 1H), 1.06 (d, J=6.2 Hz, 3H). LCMS M/Z (M+H) 372.

Example 202

(4R)-4-methyl-6-(2-phenylethyl)-1,3,4,5-tetrahydro-1,5-benzodiazepin-2-one

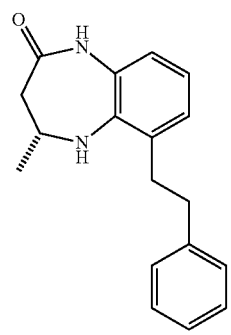 [SMILES: C[C@@H]1CC(=O)Nc2cccc(CCc3ccccc3)c2N1]

A disposable reaction tube was charged with 5 mol % Pd/C (68.3 mg, 0.032 mmol) and a stirbar before being evacuated and backfilled with nitrogen. To this mixture was added (R,E)-4-methyl-6-styryl-4,5-dihydro-1H-benzo[b][1,4]diazepin-2(3H)-one (Example 124, 63 mg, 0.161 mmol) in ethyl acetate (2 mL) followed by ethanol (2 mL), and the atmosphere was evacuated and backfilled three times with hydrogen. The mixture was stirred at room temperature for 4 h before the atmosphere was replaced by air. The catalyst was removed by filtration, and the filtrate was concentrated with celite. The residue was for purified by silica gel chromatography (eluting with hexanes/ethyl acetate). Concentration in vacuo yielded the title compound (25.9 mg, 57%) as a white, amorphous solid. $^1$H NMR (400 MHz, DMSO-$d_6$) δ 9.34-9.43 (m, 1H), 7.23-7.31 (m, 4H), 7.15-7.22 (m, 1H), 6.86-6.92 (m, 1H), 6.75 (s, 2H), 4.40-4.46 (m, 1H), 3.85-3.95 (m, 1H), 2.82 (s, 4H), 2.33-2.41 (m, 1H), 2.02-2.11 (m, 1H), 1.22 (d, J=6.02 Hz, 3H). LCMS M/Z (M+H) 281.

General Procedure for Intermediate K

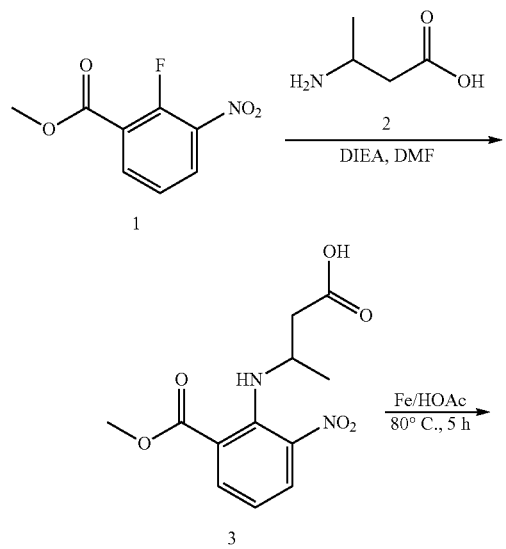

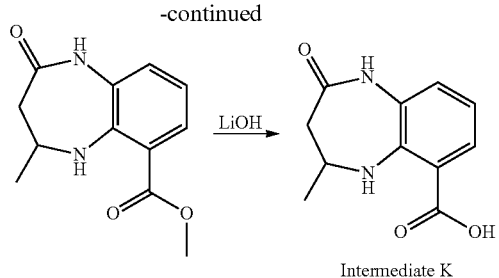

Step 1:

3-((2-(methoxycarbonyl)-6-nitrophenyl)amino)butanoic acid

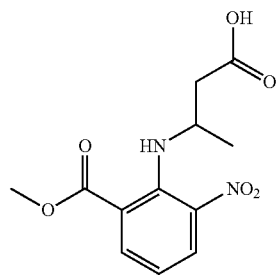 [SMILES: COC(=O)c1cccc([N+](=O)[O-])c1NC(C)CC(=O)O]

To a solution of methyl 2-fluoro-3-nitrobenzoate (534 mg, 2.68 mmol) in DMF (2 mL) was added N-ethyl-N-isopropylpropan-2-amine (1405 μl, 8.04 mmol) and 3-aminobutanoic acid (393 mg, 2.82 mmol). The resulting mixture was heated to 80° C. for 15 h. After cooling the reaction to room temperature, water (50 mL) was added and the mixture was extracted with EtOAc (100 mL×3). The combined organic layers were dried over anhydrous Na$_2$SO$_4$, filtered and concentrated in vacuo to give the title compound.

Step 2:

3-((2-amino-6-(methoxycarbonyl)phenyl)amino)butanoic acid

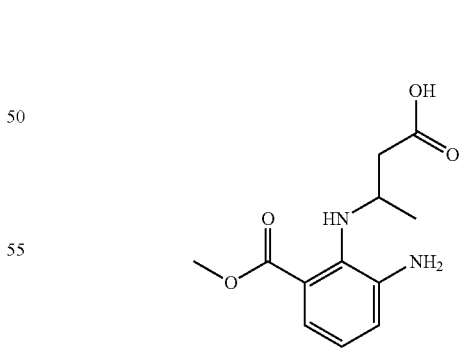

A disposable tube was charged with 5 mol % Pd/C (285 mg, 0.134 mmol) and a stirbar before being evacuated and backfilled with nitrogen. To this mixture was added 3-(2-(methoxycarbonyl)-6-nitrophenylamino)butanoic acid (757 mg, 2.68 mmol) in 1:1 ethyl acetate/ethanol (10 mL), and the vessel was evacuated and backfilled with hydrogen three times. The mixture stirred at room temperature for 1 h before

305 the catalyst was filtered off. The mixture was concentrated in vacuo and the crude residue required no further purification. LCMS M/Z (M+H) 253.

Step 3:

methyl 4-methyl-2-oxo-2,3,4,5-tetrahydro-1H-benzo[b][1,4]diazepine-6-carboxylate

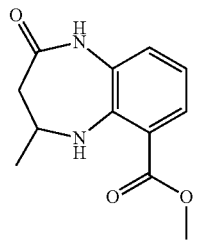

A disposable tube was charged with 3-(2-amino-6-(methoxycarbonyl)phenylamino)butanoic acid (677 mg, 2.68 mmol) and a stirbar. Dimethylformamide (5 mL) was added, followed by HATU (1122 mg, 2.95 mmol), and DIEA (937 µl, 5.37 mmol). The mixture was stirred at room temperature 18 h before being diluted with ethyl acetate, washed three times with brine, and concentrated in vacuo with celite. The residue was purified by silica gel chromatography (eluting with hexanes/ethyl acetate) to yield the title compound (0.527 g, 84%). LCMS M/Z (M+H) 235.

Step 4:

4-methyl-2-oxo-2,3,4,5-tetrahydro-1H-benzo[b][1,4]diazepine-6-carboxylic acid

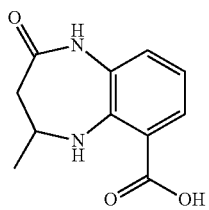 [SMILES: CC1CC(=O)Nc2cccc(C(=O)O)c2N1]

To a solution of methyl 4-methyl-2-oxo-2,3,4,5-tetrahydro-1H-benzo[b][1,4]diazepine-6-carboxylate (0.527 g, 2.250 mmol) in THF (5 mL) was added LiOH in water (11.25 ml, 11.25 mmol). The resulting mixture was heated to 80° C. for 15 h. After cooling the reaction to room temperature, the solvent was concentrated in vacuo. Water (20 mL) was added and the mixture was extracted with EtOAc (30 mL×3). The aqueous phase was acidified with HCl (1N) to pH 3. The resulting precipitate was collected by filtration to give the title compound (Intermediate K, 374 mg, 75%) as a white solid. LCMS M/Z (M+H) 221.

Example 203

N-(2-methoxyphenyl)-4-methyl-2-oxo-1,3,4,5-tetrahydro-1,5-benzodiazepine-6-carboxamide

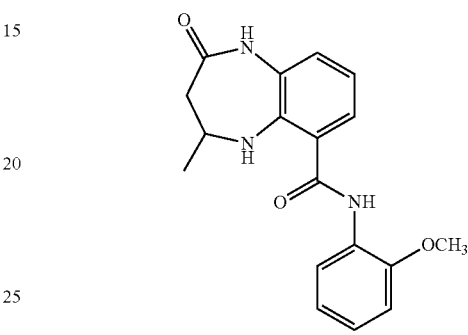

To a solution of 4-methyl-2-oxo-1,3,4,5-tetrahydro-1,5-benzodiazepine-6-carboxylic acid (Intermediate K, 42 mg, 0.19 mmol), 2-methoxyaniline (31 mg, 0.25 mmol) and triethylamine (40 uL, 0.29 mmol) in DMF (1.5 mL) was added HATU (110 mg, 0.29 mmol). The reaction mixture stirred at room temperature overnight. The mixture was concentrated in vacuo and the residue was dissolved in DCM (5 mL) and water (2 mL). The organic layer was separated and concentrated in vacuo. The crude residue was purified by reverse phase chromatography (acetonitrile 5-85%/0.1% formic acid in water) to give the title compound (4.3 mg, 7%). $^1$H NMR (400 MHz, DMSO-d$_6$) δ 9.77 (s, 1H), 9.58 (s, 1H), 7.75 (dd, J=7.9, 1.6 Hz, 1H), 7.49 (dd, J=7.8, 1.5 Hz, 1H), 7.18 (ddd, J=8.2, 7.4, 1.7 Hz, 1H), 7.13-7.03 (m, 2H), 7.02-6.92 (m, 1H), 6.88 (t, J=7.8 Hz, 1H), 6.75 (d, J=3.1 Hz, 1H), 3.99-3.86 (m, 1H), 3.83 (s, 3H), 2.48-2.42 (m, 1H), 2.31-2.21 (m, 1H), 1.19 (d, J=6.3 Hz, 3H). LCMS M/Z (M+H) 326.

The following compounds were prepared in a similar fashion to Example 203:

Examples 204-221

| Example | Compound Name | NMR | m/z |
|---|---|---|---|
| Example 204 | 4-methyl-N-(1-methylindol-5-yl)-2-oxo-1,3,4,5-tetrahydro-1,5-benzodiazepine-6-carboxamide | $^1$H NMR (400 MHz, DMSO-d$_6$) δ 10.18 (s, 1H), 9.57 (s, 1H), 7.94 (t, J = 1.4 Hz, 1H), 7.46-7.36 (m, 3H), 7.30 (d, J = 3.0 Hz, 1H), 7.09-7.02 (m, 1H), 6.87 (t, J = 7.8 Hz, 1H), 6.79 (s, 1H), 6.40 (d, J = 3.0 Hz, 1H), 3.98-3.90 (m, 1H), 3.78 (s, 3H), 2.44 (d, J = 4.0 Hz, 1H), 2.30-2.22 (m, 1H), 1.18 (d, J = 6.2 Hz, 3H) | 349 |
| Example 205 | N-(1-isoquinolyl)-4-methyl-2-oxo-1,3,4,5-tetrahydro-1,5-benzodiazepine-6-carboxamide | Not Determined | 347 |
| Example 206 | 4-methyl-2-oxo-N-[3-(3-pyridyl)phenyl]-1,3,4,5-tetrahydro-1,5- | $^1$H NMR (400 MHz, DMSO-d$_6$) δ 10.46 (s, 1H), 9.60 (s, 1H), 8.90 (dd, J = 2.4, 0.8 Hz, 1H), 8.63 (dd, J = 4.9, 1.6 Hz, 1H), | 373 |

| Example | Compound Name | NMR | m/z |
|---|---|---|---|
| | benzodiazepine-6-carboxamide | 8.18-8.06 (m, 2H), 7.82-7.75 (m, 1H), 7.64-7.57 (m, 1H), 7.54-7.46 (m, 2H), 7.44 (dd, J = 7.8, 1.5 Hz, 1H), 7.12-7.06 (m, 1H), 6.97-6.78 (m, 2H), 4.01-3.91 (m, 1H), 2.48-2.44 (m, 1H), 2.30-2.21 (m, 1H), 1.18 (d, J = 6.3 Hz, 3H) | |
| Example 207 | N-(3-ethylphenyl)-4-methyl-2-oxo-1,3,4,5-tetrahydro-1,5-benzodiazepine-6-carboxamide | $^1$H NMR (400 MHz, DMSO-$d_6$) δ 10.25 (s, 1H), 9.58 (s, 1H), 7.57 (t, J = 1.9 Hz, 2H), 7.54-7.48 (m, 1H), 7.42-7.35 (m, 1H), 7.24 (t, J = 7.8 Hz, 1H), 7.10-7.03 (m, 1H), 6.99-6.92 (m, 1H), 6.86 (t, J = 7.8 Hz, 1H), 6.68 (d, J = 2.6 Hz, 1H), 3.99-3.90 (m, 1H), 2.60 (q, J = 7.6 Hz, 2H), 2.51-2.42 (m, 1H), 2.29-2.19 (m, 1H), 1.23-1.14 (m, 6H) | 324 |
| Example 208 | 4-methyl-2-oxo-N-[3-(1,1,2,2-tetrafluoroethoxy)phenyl]-1,3,4,5-tetrahydro-1,5-benzodiazepine-6carboxamide | $^1$H NMR (400 MHz, DMSO-$d_6$) δ 10.18 (s, 1H), 9.57 (s, 1H), 7.94 (t, J = 1.4 Hz, 1H), 7.46-7.36 (m, 3H), 7.30 (d, J = 3.0 Hz, 1H), 7.09-7.02 (m, 1H), 6.87 (t, J = 7.8 Hz, 1H), 6.79 (s, 1H), 6.40 (d, J = 3.0 Hz, 1H), 3.98-3.90 (m, 1H), 3.78 (s, 3H), 2.44 (d, J = 4.0 Hz, 1H), 2.30-2.22 (m, 1H), 1.18 (d, J = 6.2 Hz, 3H) | 412 |
| Example 209 | N-(3-imidazol-1-ylphenyl)-4-methyl-2-oxo-1,3,4,5-tetrahydro-1,5-benzodiazepine-6-carboxamide | $^1$H NMR (400 MHz, DMSO-$d_6$) δ 10.56 (s, 1H), 9.61 (s, 1H), 8.56 (s, 1H), 8.06 (t, J = 2.1 Hz, 1H), 7.80 (t, J = 1.5 Hz, 1H), 7.70 (ddd, J = 8.2, 2.0, 1.0 Hz, 1H), 7.53 (t, J = 8.1 Hz, 1H), 7.46-7.38 (m, 2H), 7.36-7.32 (m, 1H), 7.12-7.04 (m, 1H), 6.96-6.86 (m, 1H), 6.70 (d, J = 9.3 Hz, 1H), 4.03-3.87 (m, 1H), 2.47-2.43 (m, 1H), 2.30-2.22 (m, 1H), 1.18 (d, J = 6.2 Hz, 3H) | 362 |
| Example 210 | N-(1,3-benzodioxol-5-yl)-4-methyl-2-oxo-1,3,4,5-tetrahydro-1,5-benzodiazepine-6-carboxamide | $^1$H NMR (400 MHz, DMSO-$d_6$) δ 10.22 (s, 1H), 9.57 (s, 1H), 7.39-7.32 (m, 2H), 7.16-7.02 (m, 2H), 6.92-6.81 (m, 2H), 6.66 (d, J = 2.6 Hz, 1H), 6.00 (s, 2H), 3.99-3.89 (m, 1H), 2.48-2.40 (m, 1H), 2.29-2.19 (m, 1H), 1.17 (d, J = 6.2 Hz, 3H) | 340 |
| Example 211 | 4-methyl-N-(1-methylindazol-3-yl)-2-oxo-1,3,4,5-tetrahydro-1,5-benzodiazepine-6-carboxamide | $^1$H NMR (400 MHz, DMSO-$d_6$) δ 10.76 (s, 1H), 9.59 (s, 1H), 7.74-7.66 (m, 1H), 7.64-7.54 (m, 2H), 7.45-7.36 (m, 1H), 7.17-7.05 (m, 3H), 6.85 (t, J = 7.8 Hz, 1H), 4.00-3.93 (m, 4H), 2.50-2.44 (m, 1H), 2.36-2.25 (m, 1H), 1.19 (d, J = 6.2 Hz, 3H) | 350 |
| Example 212 | 4-methyl-N-(2-methylindazol-6-yl)-2-oxo-1,3,4,5-tetrahydro-1,5-benzodiazepine-6-carboxamide | $^1$H NMR (400 MHz, DMSO-$d_6$) δ 10.32 (s, 1H), 9.59 (s, 1H), 8.25 (d, J = 1.0 Hz, 1H), 8.10-8.05 (m, 1H), 7.67-7.60 (m, 1H), 7.45-7.38 (m, 1H), 7.31-7.23 (m, 1H), 7.11-7.04 (m, 1H), 6.88 (t, J = 7.8 Hz, 1H), 6.68 (d, J = 2.6 Hz, 1H), 4.13 (s, 3H), 4.01-3.92 (m, 1H), 2.50-2.40 (m, 1H), 2.30-2.20 (m, 1H), 1.18 (d, J = 6.2 Hz, 3H) | 350 |
| Example 213 | N-(3-isopropoxyphenyl)-4-methyl-2-oxo-1,3,4,5-tetrahydro-1,5-benzodiazepine-6-carboxamide | Not Determined | 354 |
| Example 214 | 4-methyl-2-oxo-N-[3-(trifluoromethyl)phenyl]-1,3,4,5-tetrahydro-1,5-benzodiazepine-6-carboxamide | $^1$H NMR (400 MHz, DMSO-$d_6$) δ 10.61 (s, 1H), 9.60 (s, 1H), 8.19 (t, J = 2.1 Hz, 1H), 7.96 (dd, J = 7.8, 1.9 Hz, 1H), 7.65-7.53 (m, 1H), 7.50-7.39 (m, 2H), 7.09 (dd, J = 7.9, 1.5 Hz, 1H), 6.88 (t, J = 7.8 Hz, 1H), 6.65 (d, J = 2.6 Hz, 1H), 4.03-3.89 (m, 1H), 2.48-2.43 (m, 1H), 2.25 (dd, J = 13.4, 7.8 Hz, 1H), 1.18 (d, J = 6.2 Hz, 3H) | 364 |
| Example 215 | 4-methyl-2-oxo-N-(3-phenylphenyl)-1,3,4,5-tetrahydro-1,5-benzodiazepine-6-carboxamide | $^1$H NMR (400 MHz, DMSO-$d_6$) δ 10.41 (s, 1H), 9.59 (s, 1H), 8.04 (t, J = 1.8 Hz, 1H), 7.76-7.66 (m, 1H), 7.67-7.58 (m, 2H), 7.53-7.33 (m, 7H), 7.08 (dd, J = 7.9, 1.5 Hz, 1H), 6.88 (t, J = 7.8 Hz, 1H), 6.71 (d, J = 2.5 Hz, 1H), 4.05-3.90 (m, 1H), 2.49-2.43 (m, 1H), 2.30-2.20 (m, 1H), 1.18 (d, J = 6.2 Hz, 3H) | 372 |
| Example 216 | N-(2,5-dichlorophenyl)-4-methyl-2-oxo-1,3,4,5-tetrahydro-1,5-benzodiazepine-6-carboxamide | Not Determined | 364 |
| Example 217 | 4-methyl-2-oxo-N-[3-(trifluoromethoxy)phenyl]-1,3,4,5-tetrahydro-1,5- | $^1$H NMR (400 MHz, DMSO-$d_6$) δ 10.57 (s, 1H), 9.60 (s, 1H), 7.85 (td, J = 2.1, 1.0 Hz, 1H), 7.73-7.66 (m, 1H), 7.47 (t, J = 8.2 Hz, | 380 |

| Example | Compound Name | NMR | m/z |
|---|---|---|---|
| | benzodiazepine-6-carboxamide | 1H), 7.40 (dd, J = 7.8, 1.5 Hz, 1H), 7.13-7.02 (m, 2H), 6.87 (t, J = 7.8 Hz, 1H), 6.62 (d, J = 2.6 Hz, 1H), 4.04-3.88 (m, 1H), 2.48-2.42 (m, 1H), 2.30-2.18 (m, 1H), 1.18 (d, J = 6.3 Hz, 3H) | |
| Example 218 | 4-methyl-N-[3-(4-methyl-1,2,4-triazol-3-yl)phenyl]-2-oxo-1,3,4,5-tetrahydro-1,5-benzodiazepine-6-carboxamide | $^1$H NMR (400 MHz, DMSO-$d_6$) δ 10.51 (s, 1H), 9.60 (s, 1H), 8.57 (s, 1H), 8.12 (t, J = 1.9 Hz, 1H), 7.91-7.83 (m, 1H), 7.56-7.40 (m, 3H), 7.08 (dd, J = 7.9, 1.5 Hz, 1H), 6.88 (t, J = 7.8 Hz, 1H), 6.69 (d, J = 2.6 Hz, 1H), 4.03-3.90 (m, 1H), 3.76 (s, 3H), 2.45 (d, J = 4.1 Hz, 1H), 2.30-2.21 (m, 1H), 1.18 (d, J = 6.3 Hz, 3H) | 377 |
| Example 219 | 4-methyl-N-(5-methyl-1H-pyrazol-3-yl)-2-oxo-1,3,4,5-tetrahydro-1,5-benzodiazepine-6-carboxamide | $^1$H NMR (400 MHz, DMSO-$d_6$) δ 12.08 (s, 1H), 10.65 (s, 1H), 9.54 (s, 1H), 7.41 (dd, J = 7.8, 1.5 Hz, 1H), 7.03 (dd, J = 7.8, 1.5 Hz, 1H), 6.97 (d, J = 2.6 Hz, 1H), 6.80 (t, J = 7.8 Hz, 1H), 6.33 (s, 1H), 4.01-3.85 (m, 1H), 2.46-2.40 (m, 1H), 2.31-2.16 (m, 4H), 1.17 (d, J = 6.2 Hz, 3H) | 300 |
| Example 220 | 4-methyl-2-oxo-N-(2-phenoxyphenyl)-1,3,4,5-tetrahydro-1,5-benzodiazepine-6-carboxamide | Not Determined | 388 |
| Example 221 | 4-methyl-N-(5-methyl-3-pyridyl)-2-oxo-1,3,4,5-tetrahydro-1,5-benzodiazepine-6-carboxamide | $^1$H NMR (400 MHz, DMSO-$d_6$) δ 10.64 (s, 1H), 9.61 (s, 1H), 8.80 (d, J = 2.3 Hz, 1H), 8.29 (dd, J = 1.8, 0.9 Hz, 1H), 8.15 (t, J = 2.1 Hz, 1H), 7.43 (dd, J = 7.8, 1.5 Hz, 1H), 7.10 (dd, J = 7.9, 1.5 Hz, 1H), 6.88 (t, J = 7.8 Hz, 1H), 4.04-3.90 (m, 1H), 2.48-2.43 (m, 1H), 2.37 (d, J = 0.9 Hz, 3H), 2.31-2.21 (m, 1H), 1.19 (d, J = 6.3 Hz, 3H). | 311 |

Example 222

(4R)-6-(2-methoxyphenyl)-4-methyl-1,3,4,5-tetrahydro-1,5-benzodiazepin-2-one

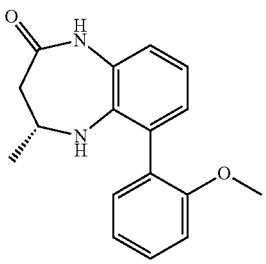 [SMILES: COc1ccccc1-c1cccc2c1N[C@H](C)CC(=O)N2]

To a solution of (4R)-6-bromo-4-methyl-1,3,4,5-tetrahydro-1,5-benzodiazepin-2-one (Intermediate A, 51 mg, 0.20 mmol) in MeOH was added (2-methoxyphenyl)boronic acid (30 mg, 0.20 mmol), SiliCat DPP-Pd (50 mg, 0.013 mmol) and $K_2CO_3$ (83 mg, 0.60 mmol). The reaction mixture was irradiated in a microwave for 15 min at 110° C. The mixture was filtered and concentrated. The crude residue was purified by reverse phase chromatography (acetonitrile 5-85%/0.1% formic acid in water) to give the title compound (9.3 mg, 17%) as a white solid. $^1$H NMR (400 MHz, DMSO-$d_6$) 9.49 (s, 1H), 7.45-7.34 (m, 1H), 7.18-7.07 (m, 2H), 7.07-7.00 (m, 1H), 6.94-6.75 (m, 3H), 3.97-3.79 (m, 1H), 3.72 (s, 3H), 3.47 (d, J=2.9 Hz, 1H), 2.47-2.42 (m, 1H), 2.20-1.99 (m, 1H), 1.07-0.83 (m, 3H). LCMS M/Z (M+H) 283.

The following compounds were prepared in a similar fashion to Example 222:

Examples 223-227

| Example | Compound Name | NMR | m/z |
|---|---|---|---|
| Example 223 | (4R)-6-(3,4-difluorophenyl)-4-methyl-1,3,4,5-tetrahydro-1,5-benzodiazepin-2-one | $^1$H NMR (400 MHz, DMSO-$d_6$) δ 9.54 (s, 1H), 7.57-7.34 (m, 2H), 7.22-7.11 (m, 1H), 6.99-6.81 (m, 3H), 4,01 (d, J = 3.1 Hz, 1H), 3.95-3.81 (m, 1H), 2.61 (dd, J = 13.1, 4.8 Hz, 1H), 2.17 (dd, J = 13.1, 5.6 Hz, 1H), 1.12 (d, J = 6.2 Hz, 3H) | 289 |
| Example 224 | (4R)-4-methyl-6-[3-(1H-tetrazol-5-yl)phenyl]-1,3,4,5-tetrahydro-1,5-benzodiazepin-2-one | Not Determined | 321 |

-continued

| Example | Compound Name | NMR | m/z |
|---|---|---|---|
| Example 225 | (4R)-6-(5-fluoro-2-methoxy-phenyl)-4-methyl-1,3,4,5-tetrahydro-1,5-benzodiazepin-2-one | $^1$H NMR (400 MHz, DMSO-$d_6$) δ 9.57-9.42 (m, 1H), 7.21 (td, J = 8.7, 3.2 Hz, 1H), 7.10 (dd, J = 9.1, 4.6 Hz, 1H), 7.00 (dd, J = 8.9, 3.2 Hz, 1H), 6.92 (dd, J = 7.5, 1.9 Hz, 1H), 6.88-6.76 (m, 2H), 3.97-3.74 (m, 1H), 3.70 (s, 3H), 3.62 (d, J = 3.0 Hz, 1H), 2.48-2.44 (m, 1H), 2.13 (dd, J = 13.0, 6.8 Hz, 1H), 1.07-0.91 (m, 3H) | 301 |
| Example 226 | 3-[(4R)-4-methyl-2-oxo-1,3,4,5-tetrahydro-1,5-benzodiazepin-6-yl]benzonitrile | $^1$H NMR (400 MHz, DMSO-$d_6$) δ 9.56 (s, 1H), 7.87-7.77 (m, 2H), 7.73-7.62 (m, 2H), 7.01-6.84 (m, 3H), 4.05 (d, ,I-3.1 Hz, 1H), 3.94-3.80 (m, 1H), 2.63 (dd, J = 13.1, 4.7 Hz, 1H), 2.25-2.14 (m, 1H), 1.11 (d, J = 6.2 Hz, 3H) | 278 |
| Example 227 | (4R)-6(2-benzyloxyphenyl)-4-methyl-1,3,4,5-tetrahydro-1,5-benzodiazepin-2-one | $^1$H NMR (400 MHz, DMSO-$d_6$) δ 9.47 (s, 1H), 7.43-7.12 (m, 8H), 7.12-7.00 (m, 1H), 6.95-6.79 (m, 3H), 5.14-5.04 (m, 1H), 3.81 (s, 1H), 3.57 (d, J = 3.1 Hz, 1H), 2.25 (s, 1H), 1.92 (s, 1H), 1.05-0.82 (m, 3H) | 359 |

Example 228

(R)—N-(1,1'-dimethyl-1H,1'H-[4,4'-bipyrazol]-3-yl)-4-methyl-2-oxo-2,3,4,5-tetrahydro-1H-benzo[b][1,4]diazepine-6-carboxamide

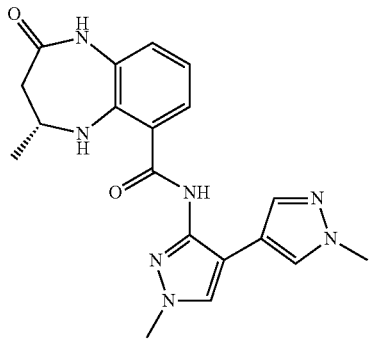 [SMILES: C[C@@H]1CC(=O)Nc2cccc(C(=O)Nc3nn(C)cc3-c3cnn(C)c3)c2N1]

Step 1:

(R)—N-(4-bromo-1-methyl-1H-pyrazol-3-yl)-4-methyl-2-oxo-2,3,4,5-tetrahydro-1H-benzo[b][1,4]diazepine-6-carboxamide

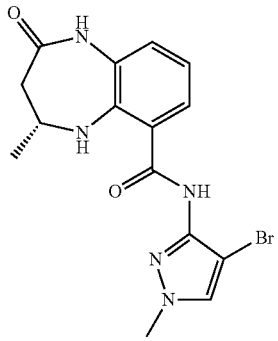 [SMILES: C[C@@H]1CC(=O)Nc2cccc(C(=O)Nc3nn(C)cc3Br)c2N1]

To a solution of (4R)-4-methyl-2-oxo-1,3,4,5-tetrahydro-1,5-benzodiazepine-6-carboxylic acid (Intermediate C, 100 mg, 0.45 mmol) in DMF (2 mL) was added HATU (352 mg, 0.9 mmol) and Triethylamine (92 mg, 0.91 mmol, and the mixture was stirred at room temperature for 10 min. The mixture was then charged with 4-bromo-1-methyl-pyrazol-3-amine (160 mg, 0.9 mmol) and stirred at room temperature for an additional 1 h. The mixture was concentrated in vacuo and diluted with EtOAc and water. The aqueous was discarded and the organic was washed once with water, dried over anhydrous Na$_2$SO$_4$, filtered, and concentrated in vacuo. The residue was purified by silica gel chromatography (1-10% MeOH in DCM) to afford the title compound (130 mg, 76%).

Step 2:

(R)—N-(1,1'-dimethyl-1H,1'H-[4,4'-bipyrazol]-3-yl)-4-methyl-2-oxo-2,3,4,5-tetrahydro-1H-benzo[b][1,4]diazepine-6-carboxamide

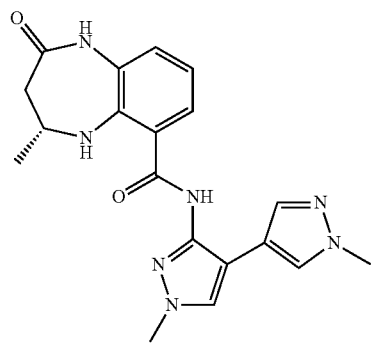 [SMILES: C[C@@H]1CC(=O)Nc2cccc(C(=O)Nc3nn(C)cc3-c3cnn(C)c3)c2N1]

To a solution of (4R)—N-(4-bromo-1-methyl-pyrazol-3-yl)-4-methyl-2-oxo-1,3,4,5-tetrahydro-1,5-benzodiazepine-6-carboxamide (54 mg, 0.14 mmol) in dioxane (0.5 mL) and 2M aqueous K2CO3 (0.5 mL) was added (1-methylpyrazol-4-yl)boronic acid (36 mg, 0.29 mmol) and [1,1'-bis(diphenylphosphino)ferrocene]dichloropalladium(II) (11 mg, 0.015 mmol). The mixture was heated to 120° C. for 10 min. After cooling the reaction to room temperature, the mixture was diluted with EtOAc and water. The aqueous layer was discarded and the organic layer was washed with water, dried over anhydrous Na$_2$SO$_4$, filtered, and concentrated in vacuo. The residue was purified by reverse phase HPLC (acetonitrile 5-85%/0.1% NH$_4$OH in water) to afford the title compound (45 mg, 86%). $^1$H NMR (400 MHz, DMSO-d$_6$) δ 9.82 (s, 1H), 9.57 (s, 1H), 7.86 (d, J=5.9 Hz, 2H), 7.63 (s, 1H), 7.50 (dd, J=7.6, 1.5 Hz, 1H), 7.11-7.01 (m, 2H), 6.87 (t, J=7.8 Hz, 1H), 3.90 (s, 1H), 3.84 (d, J=5.5 Hz, 6H), 3.29 (d, J=7.6 Hz, 1H), 3.17 (d, J=5.2 Hz, 1H), 2.51-2.40 (m, 2H), 2.27 (dd, J=13.4, 8.0 Hz, 1H), 1.15 (d, J=6.3 Hz, 3H), 3.90 (s, 1H), 3.84 (d, J=5.5 Hz, 6H), 3.29 (d, J=7.6 Hz, 1H), 3.17 (d, J=5.2 Hz, 1H), 2.51-2.40 (m, 2H), 2.27 (dd, J=13.4, 8.0 Hz, 1H), 1.15 (d, J=6.3 Hz, 3H). LCMS M/Z (M+H) 380.

Example 229

(R)-6-(4-isopropylphenyl)-4-methyl-4,5-dihydro-1H-benzo[b][1,4]diazepin-2(3H)-one

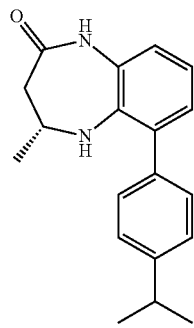 [SMILES: CC(C)c1ccc(-c2cccc3c2N[C@H](C)CC(=O)N3)cc1]

To a solution of (R)-6-bromo-4-methyl-4,5-dihydro-1H-benzo[b][1,4]diazepin-2(3H)-one (Intermediate A, 50 mg, 0.20 mmol) in dioxane (0.5 ml) was added 4-isopropylphenylboronic acid (38.57 g, 0.52 mmol), 0.5 ml of 2M aqueous potassium carbonate and 1,1'-bis(diphenylphosphino)ferrocene]dichloropalladium(II) (16 mg, 0.02 mmol, 65%). The mixture was then heated to 130° C. for 1 h. The mixture was diluted with EtOAc and washed with water. The organic layer was dried over anhydrous Na$_2$SO$_4$, filtered and concentrated. The crude product was purified by reverse phase HPLC (acetonitrile 5-85%/0.1% NH$_4$OH in water) to afford the title compound (39 mg, 0.13 mmol). $^1$H NMR (400 MHz, DMSO-d$_6$) δ 9.53 (s, 1H), 7.39-7.31 (m, 2H), 7.32-7.24 (m, 2H), 6.95-6.82 (m, 3H), 3.88 (qd, J=6.0, 3.1 Hz, 1H), 3.75 (d, J=3.1 Hz, 1H), 2.94 (h, J=6.9 Hz, 1H), 2.60 (dd, J=13.1, 4.8 Hz, 1H), 2.18 (dd, J=13.2, 5.7 Hz, 1H), 1.25 (d, J=6.9 Hz, 6H), 1.09 (d, J=6.2 Hz, 3H). LCMS M/Z (M+H) 295.

The following examples were synthesized in a similar fashion to Example 229:

Examples 230-287

| Example | Compound Name | NMR | m/z |
| --- | --- | --- | --- |
| Example 230 | (4R)-6-(3-fluoro-4-methyl-phenyl)-4-methyl-1,3,4,5-tetrahydro-1,5-benzodiazepin-2-one | $^1$H NMR (400 MHz, DMSO-d$_6$) δ 9.54 (s, 1H), 7.37 (t, J = 8.0 Hz, 1H), 7.16-7.05 (m, 2H), 6.97-6.81 (m, 3H), 3.92-3.83 (m, 2H), 2.60 (dd, J = 13.1, 4.5 Hz, 1H), 2.28 (d, J = 1.9 Hz, 3H), 2.23-2.12 (m, 1H), 1.11 (d, J = 5.8 Hz, 3H). | 285 |
| Example 231 | (4R)-6-[4-(dimethylamino)phenyl]-4-methyl-1,3,4,5-tetrahydro-1,5-benzodiazepin-2-one | $^1$H NMR (400 MHz, DMSO-d$_6$) δ 9.50 (s, 1H), 7.22-7.13 (m, 2H), 6.92-6.77 (m, 5H), 3.88 (qd, J = 5.6, 3.2 Hz, 1H), 3.73 (d, J = 3.2 Hz, 1H), 2.94 (s, 6H), 2.60 (dd, J = 13.2, 4.9 Hz, 1H), 2.17 (dd, J = 13.2, 5.5 Hz, 1H), 1.11 (d, J = 6.2 Hz, 3H). | 296 |
| Example 232 | 3-[(4R)-4-meth-2-oxo-1,3,4,5-tetrahydro-1,5-benzodiazepin-6-yl]benzamide | $^1$H NMR (400 MHz, DMSO-d$_6$) δ 9.56 (s, 1H), 8.00 (s, 1H), 7.93-7.84 (m, 2H), 7.62-7.47 (m, 2H), 7.36 (s, 1H), 6.99-6.85 (m, 3H), 3.94-3.80 (m, 2H), 2.61 (dd, J = 13.1, 4.8 Hz, 1H), 2.20 (dd, J = 13.2, 5.9 Hz, 1H), 1.09 (d, J = 6.2 Hz, 3H). | 296 |
| Example 233 | 4-[(4R)-4-methyl-2-oxo-1,3,4,5-tetrahydro-1,5-benzodiazepin-6-yl]benzamide | Not determined | 296 |
| Example 234 | (4R)-4-methyl-6-(3-quinolyl)-1,3,4,5-tetrahydro-1,5-benzodiazepin-2-one | $^1$H NMR (400 MHz, DMSO-d$_6$) δ 9.56 (s, 1H), 8.00 (s, 1H), 7.93-7.84 (m, 2H), 7.62-7.47 (m, 2H), 7.36 (s, 1H), 6.99-6.85 (m, 3H), 3.94-3.80 (m, 2H), 2.61 (dd, J = 13.1, 4.8 Hz, 1H), 2.20 (dd, J = 13.2, 5.9 Hz, 1H), 1.09 (d, J = 6.2 Hz, 3H), | 304 |
| Example 235 | (4R)-6-(4-chloro-3-methyl-phenyl)-4-methyl-1,3,4,5-tetrahydro-1,5-benzodiazepin-2-one | $^1$H NMR (400 MHz, DMSO-d$_6$) δ 9.54 (s, 1H), 7.49 (d, J = 8.2 Hz, 1H), 7.34 (d, J = 2.1 Hz, 1H), 7.20 (dd, J = 8.1, 2.2 Hz, 1H), 6.97-6.81 (m, 3H), 3.93-3.83 (m, 2H), 2.60 (dd, J = 13.0, 4.5 Hz, 1H), 2.38 (s, 3H), 2.18 (dd, J = 13.1, 5.5 Hz, 1H), 1.11 (d, J = 5.7 Hz, 3H). | 301 |

-continued

| Example | Compound Name | NMR | m/z |
|---|---|---|---|
| Example 236 | (4R)-6-(3,5-dimethylphenyl)-4-methyl-1,3,4,5-tetrahydro-1,5-benzodiazepin-2-one | $^1$H NMR (400 MHz, DMSO-$d_6$) δ 9.53 (s, 1H), 7.03 (s, 1H), 6.98-6.80 (m, 5H), 3.91-3.80 (m, 1H), 3.73 (d, J = 3.0 Hz, 1H), 2.57 (dd, J = 13.2, 4.7 Hz, 1H), 2.32 (s, 6H), 2.20 (dd, J = 13.2, 6.1 Hz, 1H), 1.09 (d, J = 6.2 Hz, 3H). | 281 |
| Example 237 | N-[4-[(4R)-4-methyl-2-oxo-1,3,4,5-tetrahydro-1,5-benzodiazepin-6-yl]phenyl]methanesulfonamide | $^1$H NMR (400 MHz, DMSO-$d_6$) δ 9.83 (s, 1H), 9.53 (s, 1H), 7.36-7.26 (m, 4H), 6.96-6.81 (m, 3H), 3.94-3.78 (m, 2H), 3.04 (s, 3H), 2.59 (dd, J = 13.1, 4.9 Hz, 1H), 2.17 (dd, J = 13.1, 5.7 Hz, 1H), 2.07 (s, 2H), 1.10 (d, J = 6.2 Hz, 3H). | 346 |
| Example 238 | N-[3-[(4R)-4-methyl-2-oxo-1,3,4,5-tetrahydro-1,5-benzodiazepin-6-yl]phenyl]methanesulfonamide | $^1$H NMR (400 MHz, DMSO-$d_6$) δ 9.70 (s, 1H), 9.54 (s, 1H), 7.44 (t, J = 7.8 Hz, 1H), 7.27-7.18 (m, 2H), 7.09 (dt, J = 7.6, 1.3 Hz, 1H), 6.98-6.84 (m, 3H), 3.97-3.85 (m, 2H), 3.03 (s, 3H), 2.61 (dd, J = 13.1, 4.9 Hz, 1H), 2.16 (dd, J = 13.1, 5.2 Hz, 1H), 1.11 (d, J = 6.1 Hz, 3H). | 346 |
| Example 239 | (4R)-4-methyl-6-[4-(pyrrolidine-1-carbonyl)phenyl]-1,3,4,5-tetrahydro-1,5-benzodiazepin-2-one | $^1$H NMR (400 MHz, DMSO-$d_6$) δ 9.56 (s, 1H), 7.64-7.57 (m, 2H), 7.46-7.37 (m, 2H), 6.98-6.85 (m, 3H), 3.89 (dt, J = 13.8, 4.3 Hz, 2H), 3.48 (dt, J = 12.1, 6.4 Hz, 4H), 2.61 (dd, J= 13.2, 4.7 Hz, 1H), 2.19 (dd, J = 13.1, 5.6 Hz, 1H), 1.86 (dt, J = 19.6, 8.2 Hz, 4H), 1.10 (d, J = 6.0 Hz, 3H). | 350 |
| Example 240 | (4R)-6-(6-amino-3-pyridyl)-4-methyl-1,3,4,5-tetrahydro-1,5-benzodiazepin-2-one | $^1$H NMR (400 MHz, DMSO-$d_6$) δ 9.50 (s, 1H), 7.87 (dd, J = 2.5, 0.8 Hz, 1H), 7.37 (dd, J = 8.5, 2.5 Hz, 1H), 6.92-6.78 (m, 3H), 6.56-6.45 (m, 1H), 6.00 (s, 2H), 3.94-3.78 (m, 2H), 2.58 (dd, J = 13.1, 4.9 Hz, 1H), 2.16 (dd, J = 13.2, 5.6 Hz, 1H), 1.13 (d, J = 6.1 Hz, 3H). | 269 |
| Example 241 | (4R)-6-(6-benzyloxy-3-pyridyl)-4-methyl-1,3,4,5-tetrahydro-1,5-benzodiazepin-2-one | $^1$H NMR (400 MHz, DMSO-$d_6$) δ 9.54 (s, 1H), 8.14 (d, J = 2.3 Hz, 1H), 7.72 (dd, J = 8.5, 2.5 Hz, 1H), 7.52-7.29 (m, 5H), 7.00-6.82 (m, 4H), 5.39 (s, 2H), 4.00 (d, J = 3.1 Hz, 1H), 3.89 (qd, J = 5.6, 3.3 Hz, 1H), 2.61 (dd, J = 13.1, 4.8 Hz, 1H), 2.17 (dd, J = 13.1, 5.5 Hz, 1H), 1.13 (d, J = 6.2 Hz, 3H). | 360 |
| Example 242 | (4R)-6-(3-chloro-4-fluoro-phenyl)-4-methyl-1,3,4,5-tetrahydro-1,5-benzodiazepin-2-one | $^1$H NMR (400 MHz, DMSO-$d_6$) δ 9.55 (s, 1H), 7.58-7.44 (m, 2H), 7.35 (ddd, J = 8.5, 4.8, 2.2 Hz, 1H), 6.97-6.81 (m, 3H), 4.03 (d, J = 3.0 Hz, 1H), 3.87 (dt, J = 9.0, 5.6 Hz, 1H), 2.61 (dd, J = 13.1, 4.7 Hz, 1H), 2.19 (dd, J = 13.2, 5.7 Hz, 1H), 1.12 (d, J = 6.2 Hz, 3H). | 305 |
| Example 243 | (4R)-6-(2,3-dihydro-1,4-benzodioxin-6-yl)-4-methyl-1,3,4,5-tetrahydro-1,5-benzodiazepin-2-one | $^1$H NMR (400 MHz, DMSO-$d_6$) δ 9.51 (s, 1H), 6.98-6.76 (m, 6H), 4.28 (s, 2H), 3.86 (s, 2H), 3.81 (s, 1H), 3.19, 2.58 (dd, J = 13.6, 5.1 Hz, 2H), 2.16 (dd, J = 13.6, 5.5 Hz, 1H), 1.10 (d, J = 5.4 Hz, 3H). | 311 |
| Example 244 | (4R)-6-(3,5-dimethoxyphenyl)-4-methyl-1,3,4,5-tetrahydro-1,5-benzodiazepin-2-one | $^1$H NMR (400 MHz, DMSO-$d_6$) δ 9.53 (s, 1H), 6.95-6.81 (m, 3H), 6.50 (dd, J = 14.6, 2.2 Hz, 3H), 3.87 (dt, J = 13.6, 4.5 Hz, 2H), 3.77 (s, 6H), 2.59 (dd, J = 13.2, 4.7 Hz, 1H), 2.18 (dd, J = 13.1, 5.7 Hz, 1H), 1.11 (d, J = 6.0 Hz, 3H). | 313 |
| Example 245 | (4R)-4-methyl-6-(3-phenylphenyl)-1,3,4,5-tetrahydro-1,5-benzodiazepin-2-one | $^1$H NMR (400 MHz, DMSO-$d_6$) δ 9.56 (s, 1H), 7.75-7.53 (m, 5H), 7.52-7.42 (m, 2H), 7.38 (tt, J = 8.2, 1.4 Hz, 2H), 7.03-6.86 (m, 3H), 3.96-3.87 (m, 2H), 3.30 (d, J = 10.1 Hz, 1H), 2.63 (dd, J = 13.0, 4.6 Hz, 1H), 2.21 (dd, J = 13.1, 5.6 Hz, 1H), 1.11 (d, J = 5.9 Hz, 3H). | 329 |
| Example 246 | (4R)-4-methyl-6-(4-phenylphenyl)-1,3,4,5-tetrahydro-1,5-benzodiazepin-2-one | $^1$H NMR (400 MHz, DMSO-$d_6$) δ 9.56 (s, 1H), 7.82-7.70 (m, 4H), 7.54-7.34 (m, 5H), 6.98-6.85 (m, 3H), 3.92 (dt, J = 12.0, 4.0 Hz, 2H), 2.64 (dd, J = 13.2, 4.8 Hz, 1H), 2.25-2.15 (m, 1H), 1.13 (d, J = 5.9 Hz, 3H). | 329 |
| Example 247 | (4R)-4-methyl-6-[6-(4-methylpiperazin-1-yl)-3-pyridyl]-1,3,4,5-tetrahydro-1,5-benzodiazepin-2-one | $^1$H NMR (400 MHz, DMSO-$d_6$) δ 9.51 (s, 1H), 8.14-8.05 (m, 1H), 7.53 (dd, J = 8.8, 2.5 Hz, 1H), 6.94-6.80 (m, 5H), 3.92-3.84 (m, 1H), 3.52 (q, J = 6.2, 5.6 Hz, 5H), 2.61 (dd, J = 13.0, 4.6 Hz, 1H), 2.45-2.33 (m, 6H), 1.13 (d, J = 5.8 Hz, 3H). | 352 |

-continued

| Example | Compound Name | NMR | m/z |
|---|---|---|---|
| Example 248 | (4R)-4-methyl-6-(6-morpholino-3-pyridyl)-1,3,4,5-tetrahydro-1,5-benzodiazepin-2-one | $^1$H NMR (400 MHz, DMSO-d$_6$) δ 9.51 (s, 1H), 8.10 (d, J = 2.3 Hz, 1H), 7.56 (dd, J = 8.7, 2.5 Hz, 1H), 6.95-6.80 (m, 4H), 3.90 (d, J = 3.0 Hz, 2H), 3.72 (dd, J = 5.7, 4.0 Hz, 5H), 3.29 (d, J = 14.8 Hz, 1H), 2.61 (dd, J = 13.0, 4.7 Hz, 1H), 2.16 (dd, J = 13.1, 5.2 Hz, 1H), 1.13 (d, J = 5.9 Hz, 3H). | 339 |
| Example 249 | (4R)-6-[6-amino-5-(cyclopropylmethoxy)-3-pyridyl]-4-methyl-1,3,4,5-tetrahydro-1,5-benzodiazepin-2-one | $^1$H NMR (400 MHz, DMSO-d$_6$) δ 9.50 (s, 1H), 7.48 (d, J = 1.8 Hz, 1H), 6.98 (d, J = 1.9 Hz, 1H), 6.92-6.78 (m, 3H), 5.70 (s, 2H), 4.06 (q, J = 5.3 Hz, 1H), 3.17 (d, J = 5.2 Hz, 3H), 2.60 (dd, J = 13.0, 4.7 Hz, 1H), 1.32-1.19 (m, 1H), 1.07 (s, 3H), 0.62-0.52 (m, 2H), 0.39-0.29 (m, 2H). | 339 |
| Example 250 | (4R)-6-(6-amino-5-isopropoxy-3-pyridyl)-4-methyl-1,3,4,5-tetrahydro-1,5-benzodiazepin-2-one | $^1$H NMR (400 MHz, DMSO-d$_6$) δ 9.50 (s, 1H), 7.47 (d, J = 1.8 Hz, 1H), 7.03 (d, J = 1.9 Hz, 1H), 6.92-6.79 (m, 3H), 5.74 (s, 2H), 4.62 (hept, J = 6.1 Hz, 1H), 3.96-3.86 (m, 2H), 2.16 (dd, J = 13.1, 5.0 Hz, 1H), 1.33-1.11 (m, 9H), 1.07 (s, 1H). | 327 |
| Example 251 | tert-butyl N-methyl-N-[4-[(4R)-4-methyl-2-oxo-1,3,4,5-tetrahydro-1,5-benzodiazepin-6-yl]phenyl]carbamate | $^1$H NMR (400 MHz, DMSO-d$_6$) δ 9.55 (s, 1H), 7.43-7.29 (m, 4H), 6.97-6.83 (m, 3H), 3.89 (s, 1H), 3.73 (d, J = 3.0 Hz, 1H), 3.24 (s, 3H), 2.59 (dd, J = 13.2, 4.8 Hz, 1H), 2.19 (dd, J = 13.2, 5.8 Hz, 1H), 1.42 (s, 9H), 1.09 (d, J = 6.2 Hz, 3H), | 382 |
| Example 252 | 2-[3-[(4R)-4-methyl-2-oxo-1,3,4,5-tetrahydro-1,5-benzodiazepin-6-yl]phenyl]acetonitrile | $^1$H NMR (400 MHz, DMSO-d$_6$) δ 9.56 (s, 1H), 7.51 (t, J = 7.6 Hz, 1H), 7.41-7.29 (m, 3H), 6.98-6.86 (m, 3H), 4.09 (s, 2H), 3.90 (s, 1H), 3.80 (d, J = 3.1 Hz, 1H), 2.19 (dd, J = 13.7, 5.3 Hz, 1H), 1.10 (d, J = 6.2 Hz, 3H). | 292 |
| Example 253 | N-cyclopropy4-4-[(4R)-4-methyl-2-oxo-1,3,4,5-tetrahydro-1,5-benzodiazepin-6-yl]benzamide | $^1$H NMR (400 MHz, DMSO-d$_6$) δ 9.56 (s, 1H), 8.46 (d, J = 4.3 Hz, 1H), 7.91 (d, J = 8.2 Hz, 2H), 7.47-7.40 (m, 2H), 6.98-6,86 (m, 3H), 3.89 (s, 1H), 3.83 (s, 1H), 3.30 (d, J = 9.7 Hz, 17H), 2.87 (s, 1H), 2.62 (dd, J = 13.2, 4.8 Hz, 1H), 2.18 (dd, J = 13.1, 5.7 Hz, 1H), 1.10 (d, J = 6.1 Hz, 3H), 0.71 (td, J = 7.1, 4.6 Hz, 2H), 0.63-0.55 (m, 2H), | 336 |
| Example 254 | N-cyclopropyl-3-[(4R)-4-methyl-2-oxo-1,3,4,5-tetrahydro-1,5-benzodiazepin-6-yl]benzamide | $^1$H NMR (400 MHz, DMSO-d$_6$) δ 9.56 (s, 1H), 8.44 (d, J = 4.1 Hz, 1H), 7.88-7.78 (m, 2H), 7.59-7.46 (m, 2H), 6.99-6.85 (m, 3H), 3.87 (s, 1H), 3.81 (d, J = 3.0 Hz, 1H), 2.86 (td, J = 7.4, 3.8 Hz, 1H), 2.59 (dd, J = 13.1, 4.7 Hz, 1H), 2.20 (dd, J = 13.2, 6.0 Hz, 1H), 1.11-1.04 (m, 3H), 0.68 (ddd, J = 7.1, 4.9, 2.1 Hz, 2H), 0.56 (tt, J = 5.4, 2.7 Hz, 2H). | 336 |
| Example 255 | (4R)-6-[4-(methoxymethyl)phenyl]-4-methyl-1,3,4,5-tetrahydro-1,5-benzodiazepin-2-one | $^1$H NMR (400 MHz, DMSO-d$_6$) δ 9.55 (s, 1H), 7.45-7.30 (m, 4H), 6.96-6.83 (m, 3H), 4.47 (s, 2H), 3.92-3.83 (m, 1H), 3.75 (d, J = 3.2 Hz, 1H), 3.42-3.21 (m, 3H), 2.60 (dd, J = 13.1, 4.8 Hz, 1H), 2.18 (dd, J = 13.2, 5.7 Hz, 1H), 1.08 (d, J = 6.2 Hz, 3H). | 297 |
| Example 256 | tert-butyl N-[[3-[(4R)-4-methyl-2-oxo-1,3,4,5-tetrahydro-1,5-benzodiazepin-6-yl]phenyl]methyl]carbamate | $^1$H NMR (400 MHz, DMSO-d$_6$) δ 9.55 (s, 1H), 7.47-7.35 (m, 2H), 7.29-7.19 (m, 3H), 6.97-6.85 (m, 3H), 4.18 (d, J = 6.2 Hz, 2H), 3.88 (s, 1H), 3.73 (s, 1H), 3.30 (d, J = 7.0 Hz, 11H), 2.59 (dd, J = 13.2, 4.9 Hz, 1H), 2.17 (dd, J = 13.2, 5.6 Hz, 1H), 1.38 (s, 8H), 1.09 (d, J = 6.2 Hz, 3H). | 382 |
| Example 257 | (4R)-6-(3-chloro-2-methyl-phenyl)-4-methyl-1,3,4,5-tetrahydro-1,5-benzodiazepin-2-one | $^1$H NMR (400 MHz, DMSO-d$_6$) δ 9.55 (d, J = 3.6 Hz, 1H), 7.47 (dt, J = 8.0, 1.3 Hz, 1H), 7.29 (t, J = 7.8 Hz, 1H), 7.12 (ddd, J = 7.5, 4.5, 1.3 Hz, 1H), 6.95 (dd, J = 7.9, 1.6 Hz, 1H), 6.89-6.70 (m, 2H), 3.64 (dd, J = 10.9, 3.2 Hz, 1H), 3.30 (d, J = 6.7 Hz, 2H), 2.19 (td, J = 13.1, 6.7 Hz, 1H), 2.08 (d, J = 12.8 Hz, 3H), 1.00 (dd, J = 11.2, 6.3 Hz, 3H). | 301 |
| Example 258 | N-methyl-4-[(4R)-4-methyl-2-oxo-1,3,4,5-tetrahydro-1,5-benzodiazepin-6-yl]benzamide | $^1$H NMR (400 MHz, DMSO-d$_6$) δ 9.56 (s, 1H), 8.46 (d, J = 5.1 Hz, 1H), 7.98-7.88 (m, 2H), 7.49-7.41 (m, 2H), 6.99-6.85 (m, 3H), 3.87 (dd, J = 18.8, 4.9 Hz, 2H), 3.35-3.24 (m, 5H), 2.81 (d, J = 4.5 Hz, 3H), 2.62 (dd, J = 13.1, 4.8 Hz, 1H), 2.19 (dd, J = 13.2, 5.5 Hz, 1H), 1.10 (d, J = 6.1 Hz, 3H). | 310 |

-continued

| Example | Compound Name | NMR | m/z |
|---|---|---|---|
| Example 259 | (4R)-6-(4-benzyloxyphenyl)-4-methyl-1,3,4,5-tetrahydro-1,5-benzodiazepin-2-one | $^1$H NMR (400 MHz, DMSO-d$_6$) δ 9.52 (s, 1H), 7.52-7.24 (m, 7H), 7.16-7.07 (m, 2H), 6.94-6.80 (m, 3H), 5.15 (s, 2H), 3.87 (s, 1H), 3.74 (d, J = 3.1 Hz, 1H), 3.35-3.23 (m, 5H), 2.59 (dd, J = 13.1, 4.8 Hz, 1H), 2.17 (dd, J = 13.1, 5.8 Hz, 1H), 1.09 (d, J = 6.2 Hz, 3H). | 359 |
| Example 260 | tert-butyl N-[3-[(4R)-4-methyl-2-oxo-1,3,4,5-tetrahydro-1,5-benzodiazepin-6-yl]phenyl]carbamate | $^1$H NMR (400 MHz, DMSO-d$_6$) δ 9.54 (s, 1H), 9.43 (s, 1H), 7.53-7.40 (m, 3H); 7.35 (t, J = 7.9 Hz, 1H), 6.99-6.83 (m, 4H), 3.90 (t, J = 5.2 Hz, 1H), 3.77 (d, J = 3.1 Hz, 1H), 2.58 (dd, J = 13.1, 4.9 Hz, 1H), 2.17 (dd, J = 13.1, 5.7 Hz, 1H), 1.47 (s, 9H), 1.09 (d, J = 6.2 Hz, 3H). | 368 |
| Example 261 | N-[3-[(4R)-4-methyl-2-oxo-1,3,4,5-tetrahydro-1,5-benzodiazepin-6-yl]phenyl]acetamide | $^1$H NMR (400 MHz, DMSO-d$_6$) δ 10.00 (s, 1H), 9.55 (s, 1H), 7.66-7.52 (m, 2H), 7.39 (t, J = 7.8 Hz, 1H), 7.01 (dt, J = 7.6, 1.3 Hz, 1H), 6.97-6.84 (m, 3H); 3.91 (s, 1H), 3.80 (d, J = 3.3 Hz, 1H), 3.30 (d, J = 7.9 Hz, 4H), 2.60 (dd, J = 13.1, 4.9 Hz, 1H), 2.17 (dd, J = 13.2, 5.5 Hz, 1H), 2.05 (s, 3H), 1.09 (d, J = 6.2 Hz, 3H). | 310 |
| Example 262 | tert-butyl N-[4-[(4R)-4-methyl-2-oxo-1,3,4,5-tetrahydro-1,5-benzodiazepin-6-yl]phenyl]carbamate | $^1$H NMR (400 MHz, DMSO-d$_6$) δ 9.52 (s, 1H), 9.43 (s, 1H), 7.59-7.52 (m, 2H), 7.28-7.20 (m, 2H), 6.93-6.82 (m, 3H), 3.87 (dt, J = 10.9, 5.5 Hz, 1H), 3.74 (d, J = 3.2 Hz, 1H), 3.28 (d, J = 6.9 Hz, 10H), 2.58 (dd, J = 13.1, 4.9 Hz, 1H), 2.17 (dd, J = 13.1, 5.7 Hz, 1H), 1.49 (s, 9H), 1.09 (d, J = 6.3 Hz, 3H), | 368 |
| Example 263 | (4R)-6-(6-methoxy-3-pyridyl)-4-methyl-1,3,4,5-tetrahydro-1,5-benzodiazepin-2-one | $^1$H NMR (400 MHz, DMSO-d$_6$) δ 9.54 (s, 1H), 8.13 (d, J = 2.4 Hz, 1H), 7.69 (dd, J = 8.5, 2.5 Hz, 1H), 6.98-6.82 (m, 4H), 3.98 (d, J = 3.0 Hz, 1H), 3.90 (s, 3H), 3.42-3.15 (m, 1H), 2.61 (dd, J = 13.1, 4.8 Hz, 1H), 2.17 (dd, J = 13.1, 5.5 Hz, 1H), 1.12 (d, J = 6.2 Hz, 3H). | 284 |
| Example 264 | (4R)-6-(1-isobutylpyrazol-4-yl)-4-methyl-1,3,4,5-tetrahydro-1,5-benzodiazepin-2-one | $^1$H NMR (400 MHz, DMSO-d$_6$) δ 9.48 (s, 1H), 7.91 (d, J = 0.9 Hz, 1H), 7.58 (d, J = 0.8 Hz, 1H), 6.97 (dd, J = 6.5, 2.6 Hz, 1H), 6.89-6.78 (m, 2H), 4.00-3.88 (m, 4H), 2.23-2.04 (m, 2H), 1.15 (d, J = 6.0 Hz, 3H), 0.87 (dd, J = 6.7, 1.8 Hz, 6H). | 299 |
| Example 265 | (4R)-6-[3-(difluoromethyl)phenyl]-4-methyl-1,3,4,5-tetrahydro-1,5-benzodiazepin-2-one | $^1$H NMR (400 MHz, DMSO-d$_6$) δ 9.57 (s, 1H), 7.67-7.51 (m, 4H), 6.99-6.85 (m, 3H), 3.94-3.81 (m, 2H), 2.61 (dd, J = 13.2, 4.7 Hz, 1H), 2.21 (dd, J = 13.1, 5.7 Hz, 1H), 1.10 (d, J = 6.1 Hz, 3H). | 303 |
| Example 266 | (4R)-4-methyl-6-(2-methylindazol-4-yl)-1,3,4,5-tetrahydro-1,5-benzodiazepin-2-one | $^1$H NMR (400 MHz, DMSO-d$_6$) δ 9.58 (s, 1H), 8.11 (s, 1H), 7,61 (d, J = 8.7 Hz, 1H), 7.32 (dd, J = 8.7, 6.7 Hz, 1H), 7.01-6.85 (m, 4H), 4.15 (d, J = 10.4 Hz, 3H), 3.78 (q, J = 5.6, 4.4 Hz, 2H), 2.62 (dd, J = 13.4, 4.4 Hz, 1H), 2.20 (dd, J = 13.3, 6.3 Hz, 1H), 0.94 (d, J = 5.9 Hz, 3H). | 307 |
| Example 267 | (4R)-4-methyl-6-(2-methylindazol-6-yl)-1,3,4,5-tetrahydro-1,5-benzodiazepin-2-one | $^1$H NMR (400 MHz, DMSO-d$_6$) δ 9.55 (s, 1H), 8.37 (s, 1H), 7.78 (d, J = 8.5 Hz, 1H), 7.51 (s, 1H), 7.04-6.84 (m, 4H), 4.19 (s, 3H), 3.85 (dd, J = 26.7, 4.4 Hz, 2H), 2.62 (dd, J = 13.1, 4.8 Hz, 1H), 2.20 (dd, J = 13.2, 5.8 Hz, 1H), 1.07 (d, J = 6.1 Hz, 3H). | 307 |
| Example 268 | (4R)-4-methyl-6-[3-(2-trimethylsilylethoxymethyl)imidazo[4,5-b]pyridin-6-yl]-1,3,4,5-tarahydro-1,5-benzodiazepin-2-one | $^1$H NMR (400 MHz, DMSO-d$_6$) δ 9.63 (s, 1H), 8.71 (s, 1H), 8.42 (d, J = 2.0 Hz, 1H), 8.12 (d, J = 2.1 Hz, 1H), 7.07-6.92 (m, 3H), 5.75 (s, 2H), 3.96 (d, J = 7.3 Hz, 1H), 3.19 (s, 3H), 2.72 (dd, J = 13.1, 4.8 Hz, 1H), 2.26 (dd, J = 12.9, 5.5 Hz, 1H), 1.15 (d, J = 6.2 Hz, 3H), 1.01-0.87 (m, 2H), 0.06 (s, 9H). | 424 |
| Example 269 | (4R)-4-methyl-6-(2-methyl-4-pyridyl)-1,3,4,5-tetrahydro-1,5-benzodiazepin-2-one | $^1$H NMR (400 MHz, DMSO-d$_6$) δ 9.57 (s, 1H), 8.50 (d, J = 5.1 Hz, 1H), 7.25 (d, J = 1.7 Hz, 1H), 7.18 (dd, J = 5.0, 1.7 Hz, 1H), 7.01-6.85 (m, 3H), 4.05 (d, J = 3.1 Hz, 1H), 3.95-3.85 (m, 1H), 2.67-2.53 (m, 1H), 2.50 (s, 3H), 2,19 (dd, J = 13.2, 5.6 Hz, 1H), 1.13 (d, J = 6.2 Hz, 3H). | 268 |
| Example 270 | (4R)-6-(4-tert-butylphenyl)-4-methyl-1,3,4,5-tetrahydro-1,5-benzodiazepin-2-one | $^1$H NMR (400 MHz, DMSO-d$_6$) δ 9.54 (s, 1H), 7.54-7.46 (m, 2H), 7.34-7.26 (m, 2H), 6.95-6.82 (m, 3H), 3.77 (d, J = 3.2 Hz, 1H), 2.60 (dd, J = 13.2, 4.9 Hz, 1H), 2.18 (dd, J = 13.1, 5.7 Hz, 1H), 1.33 (s, 9H), 1.09 (d, J = 6.2 Hz, 3H). | 309 |

-continued

| Example | Compound Name | NMR | m/z |
|---|---|---|---|
| Example 271 | (4R)-4-methyl-6-(2-methylindazol-5-yl)-1,3,4,5-tetrahydro-1,5-benzodiazepin-2-one | $^1$H NMR (400 MHz, DMSO-$d_6$) δ 9.54 (s, 1H), 8.36 (s, 1H), 7.71-7.61 (m, 2H), 7.20 (dd, J = 8.8, 1.7 Hz, 1H), 6.97-6.83 (m, 3H), 4.19 (s, 3H), 3.89 (q, J = 7.2, 5.4 Hz, 1H), 3.80 (d, J = 3.0 Hz, 1H), 2.61 (dd, J = 13.1, 4.8 Hz, 1H), 2.20 (dd, J = 13.2, 5.8 Hz, 1H), 1.07 (d, J = 6.2 Hz, 3H). | 307 |
| Example 272 | (4R)-6-(1H-indazol-4-yl)-4-methyl-1,3,4,5-tetrahydro-1,5-benzodiazepin-2-one | $^1$H NMR (400 MHz, DMSO-$d_6$) δ 13.20 (s, 1H), 9.59 (s, 1H), 7.78 (s, 1H), 7.57 (d, J = 8.4 Hz, 1H), 7.44 (dd, J = 8.5, 6.9 Hz, 1H), 7.07-6.86 (m, 4H), 3.83-3.75 (m, 2H), 3.31 (d, J = 5.0 Hz, 12H), 2.67 (dd, J = 12.9, 4.2 Hz, 1H), 2.21 (dd, J = 13.4, 5.9 Hz, 1H), 0.95 (d, J = 6.0 Hz, 3H). | 293 |
| Example 273 | (4R)-6-(2,3-dihydrobenzofuran-5-yl)-4-methyl-1,3,4,5-tetrahydro-1,5-benzodiazepin-2-one | $^1$H NMR (400 MHz, DMSO-$d_6$) δ 9.51 (s, 1H), 7.19 (d, J = 1.8 Hz, 1H), 7.05 (dd, J = 8.1, 2.0 Hz, 1H), 6.92-6.79 (m, 4H), 4.57 (t, J = 8.7 Hz, 2H), 3.86 (qt, J = 9.1, 4.5 Hz, 1H), 3.75 (d, J = 3.2 Hz, 1H), 3.22 (t, J = 8.8 Hz, 2H), 2.58 (dd, J = 13.2, 4.8 Hz, 1H), 2.17 (dd, J = 13.2, 5.7 Hz, 1H), 1.10 (d, J = 6.1 Hz, 3H). | 295 |
| Example 274 | (4R)-6-(4-isopropoxyphenyl)-4-methyl-1,3,4,5-tetrahydro-1,5-benzodiazepin-2-one | $^1$H NMR (400 MHz, DMSO-$d_6$) δ 9.52 (s, 1H), 7.29-7.21 (m, 2H), 7.04-6.96 (m, 2H), 6.93-6.80 (m, 3H), 4.65 (p, J = 6.0 Hz, 1H), 3.87 (ddt, J = 8.9, 5.9, 3.4 Hz, 1H), 3.75 (d, J = 3.1 Hz, 1H), 2.58 (dd, J = 13.1, 4.9 Hz, 1H), 2.17 (dd, J = 13.1, 5.7 Hz, 1H), 1.30 (dd, J = 6.0, 1.4 Hz, 6H), 1.09 (d, J = 6.2 Hz, 3H), | 311 |
| Example 275 | (4R)-6-(1-ethylpyrazol-4-yl)-4-methyl-1,3,4,5-tetrahydro-1,5-benzodiazepin-2-one | $^1$H NMR (400 MHz, DMSO-$d_6$) δ 9.47 (s, 1H), 7.92 (s, 1H), 7.58 (s, 1H), 6.96 (dd, J = 6.6, 2.6 Hz, 1H), 6.88-6.77 (m, 2H), 4.17 (q, J = 7.3 Hz, 2H), 4.05-3.91 (m, 2H), 2.16 (dd, J = 13.1, 5.7 Hz, 1H), 1.42 (t, J = 7.2 Hz, 3H), 1.18 (d, J = 6.3 Hz, 3H). | 271 |
| Example 276 | (4R)-4-methyl-6-[4-(1-piperidyl)phenyl]-1,3,4,5-tetrahydro-1,5-benzodiazepin-2-one | $^1$H NMR (400 MHz, DMSO-$d_6$) δ 9.50 (s, 1H), 7.23-7.14 (m, 2H), 7.05-6.97 (m, 2H), 6.91-6.79 (m, 3H), 3.93-3.83 (m, 1H), 3.74 (d, J = 3.1 Hz, 1H), 3.23-3.16 (m, 4H), 2.59 (dd, J = 13.1, 4.9 Hz, 1H), 2.17 (dd, J = 13.3, 5.5 Hz, 1H), 1.68-1.51 (m, 6H), 1.10 (d, J = 6.1 Hz, 3H). | 336 |
| Example 277 | (4R)-4-methyl-6-[4-(1H-tetrazol-5-yl)phenyl]-1,3,4,5-tetrahydro-1,5-benzodiazepin-2-one | Not determined | 321 |
| Example 278 | (4R)-4-methyl-6-[4-(4-methylpiperazine-1-carbonyl)phenyl]-1,3,4,5-tetrahydro-1,5-benzodiazepin-2-one | $^1$H NMR (400 MHz, DMSO-$d_6$) δ 9.56 (s, 1H), 7.52-7.38 (m, 4H), 6.98-6.84 (m, 3H), 3.91 (q, J = 7.1, 4.9 Hz, 2H), 3.30 (d, J = 9.7 Hz, 4H), 2.62 (dd, J = 13.2, 4.7 Hz, 1H), 2.33 (s, 5H), 2.21 (s, 3H), 1.11 (d, J = 6.0 Hz, 3H). | 379 |
| Example 279 | N-[[3-[(4R)-4-methyl-2-oxo-1,3,4,5-tetrahydro-1,5-benzodiazepin-6-yl]phenyl]methyl]-methanesulfonamide | $^1$H NMR (400 MHz, DMSO-$d_6$) δ 9.55 (s, 1H), 7.56 (s, 1H), 7.47 (t, J = 7.6 Hz, 1H), 7.41-7.32 (m, 3H), 7.27 (dt, J = 7.3, 1.4 Hz, 1H), 6.98-6.84 (m, 3H), 4.25-4.18 (m, 2H), 3.76 (d, J = 3.1 Hz, 1H), 2.86 (d, J = 16.7 Hz, 3H), 2.60 (dd, J = 13.2, 4.9 Hz, 1H), 2.18 (dd, J = 13.1, 5.8 Hz, 1H), 1.08 (d, J = 6.2 Hz, 3H). | 379 |
| Example 280 | N-[[4-[(4R)-4-methyl-2-oxo-1,3,4,5-tetrahydro-1,5-benzodiazepin-6-yl]phenyl]methyl]-methanesulfonamide | $^1$H NMR (400 MHz, DMSO-$d_6$) δ 9.55 (s, 1H), 7.57 (s, 2H), 7.45 (d, J = 8.1 Hz, 2H), 7.40-7.23 (m, 3H), 6.98-6.84 (m, 1H), 4.22 (s, 2H), 3.88 (qd, J = 6.0, 3.2 Hz, 1H), 3.73 (d, J = 3.1 Hz, 1H), 2.87 (d, J = 24.4 Hz, 3H), 2.60 (dd, J = 13.2, 4.8 Hz, 1H), 2.18 (dd, J = 13.2, 5.7 Hz, 1H), 1.08 (d, J = 6.2 Hz, 3H). | 360 |

-continued

| Example | Compound Name | NMR | m/z |
|---|---|---|---|
| Example 281 | [(4R)-6-(3-isopropylphenyl)-4-methyl-1,3,4,5-tetrahydro-1,5-benzodiazepin-2-one | $^1$H NMR (400 MHz, DMSO-$d_6$) δ 9.54 (s, 1H), 7.40 (t, J = 7.6 Hz, 1H), 7.31-7.21 (m, 2H), 7.16 (dt, J = 7.5, 1.4 Hz, 1H), 6.96-6.83 (m, 3H), 3.88 (qd, J = 6.0, 2.9 Hz, 1H), 3.68 (d, J = 3.0 Hz, 1H), 2.95 (hept, J = 6.9 Hz, 1H), 2.60 (dd, J = 13.2, 4.9 Hz, 1H), 2.20 (dd, J = 13.2, 5.9 Hz, 1H), 1.24 (dd, J = 6.9, 1.9 Hz, 6H), 1.09 (d, J = 6.2 Hz, 3H), | 295 |
| Example 282 | N-isopropyl-3-[(4R)-4-methyl-2-oxo-1,3,4,5-tetrahydro-1,5-benzodiazepin-6-yl]benzamide | $^1$H NMR (400 MHz, DMSO-$d_6$) δ 9.57 (s, 1H), 8.24 (d, J = 7.8 Hz, 1H), 7.87 (dt, J = 9.7, 1.8 Hz, 2H), 7.59-7.46 (m, 2H), 6.99-6.86 (m, 3H), 4.17-4.06 (m, 1H), 3.88 (s, 1H), 3.81 (d, J = 3.0 Hz, 1H), 3.30 (d, J = 6.5 Hz, 14H), 2.59 (dd, J = 13.2, 4.7 Hz, 1H), 2.21 (dd, J = 13.1, 6.1 Hz, 1H), 1.20-1.05 (m, 9H). | 338 |
| Example 283 | N-methyl-3-[(4R)-4-methyl-2-oxo-1,3,4,5-tetrahydro-1,5-benzodiazepin-6-yl]benzamide | $^1$H NMR (400 MHz, DMSO-$d_6$) δ 9.57 (s, 1H), 8.47 (s, 1H), 7.89-7.79 (m, 2H), 7.62-7.47 (m, 2H), 6.99-6.85 (m, 3H), 3.90-3.80 (m, 2H), 2.81 (dd, J = 12.1, 4.5 Hz, 3H), 2.60 (dd, J = 13.2, 4.7 Hz, 1H), 2.20 (dd, J = 13.1, 6.0 Hz, 1H), 1.08 (d, J = 6.1 Hz, 3H), | 310 |
| Example 284 | (4R)-6-[3-(methoxymethyl)phenyl]-4-methyl-1,3,4,5,-tetrahydro-1,5-benzodiazepin-2-one | $^1$H NMR (400 MHz, DMSO-$d_6$) δ 9.55 (s, 1H), 7.46 (t, J = 7.5 Hz, 1H), 7.38-7.24 (m, 3H), 6.97-6.83 (m, 3H), 4.47 (s, 2H), 3.92-3.82 (m, 1H), 3.74 (d, J = 3.1 Hz, 1H), 3.36-3.22 (m, 3H), 2.59 (dd, J = 13.2, 4.8 Hz, 1H), 2.19 (dd, J = 13.2, 5.9 Hz, 1H), 1.08 (d, J = 6.2 Hz, 3H). | 297 |
| Example 285 | (4R)-4-methyl-6-(3-morpholinophenyl)-1,3,4,5-tetrahydro-1,5-benzodiazepin-2-one | $^1$H NMR (400 MHz, DMSO-$d_6$) δ 9.53 (s, 1H), 7.33 (dd, J = 8.4, 7.4 Hz, 1H), 7.02-6.82 (m, 5H), 6.82-6.74 (m, 1H), 3.77-3.70 (m, 6H), 3.19-3.05 (m, 4H), 2.59 (dd, J = 13.1, 4.9 Hz, 1H), 2.18 (dd, J = 13.1, 5.7 Hz, 1H), 1.09 (d, J = 6.1 Hz, 3H), | 338 |
| Example 286 | (4R)-6-(3-benzyloxyphenyl)-4-methyl-1,3,4,5-tetrahydro-1,5-benzodiazepin-2-one | $^1$H NMR (400 MHz, DMSO-$d_6$) δ 9.54 (s, 1H), 7.51-7.25 (m, 6H), 7.15-7.00 (m, 1H), 7.00-6.82 (m, 5H), 5.15 (s, 2H), 3.84-3.74 (m, 2H), 3.30 (d, J = 7.9 Hz, 4H), 2.57 (dd, J = 13.2, 4.8 Hz, 1H), 2.16 (dd, J = 13.2, 5.8 Hz, 1H), 1.06 (d, J = 6.0 Hz, 3H). | 359 |
| Example 287 | (4R)-6-[3-(dimethylamino)phenyl]-4-methyl-1,3,4,5-tetrahydro-1,5-benzodiazepin-2-one | $^1$H NMR (400 MHz, DMSO-$d_6$) δ 9.52 (s, 1H), 7.28 (dd, J = 8.4, 7.3 Hz, 1H), 6.94-6.81 (m, 3H), 6.75 (ddd, J = 8.5, 2.6, 0.9 Hz, 1H), 6.66-6.57 (m, 2H), 3.86 (qd, J = 6.1, 3.2 Hz, 1H), 3.77 (d, J = 3.1 Hz, 1H), 2.92 (s, 6H), 2.59 (dd, J = 13.2, 4.9 Hz, 1H), 2.18 (dd, J = 13.2, 5.8 Hz, 1H), 1.09 (d, J = 6.2 Hz, 3H). | 296 |

Examples 288 & 289

(4R)-methyl-6-[1-(1-phenylethyl)pyrazol-4-yl]-1,3,4,5-tetrahydro-1,5-benzodiazepin-2-one & (4S)-methyl-6-[1-(1-phenylethyl)pyrazol-4-yl]-1,3,4,5-tetrahydro-1,5-benzodiazepin-2-one

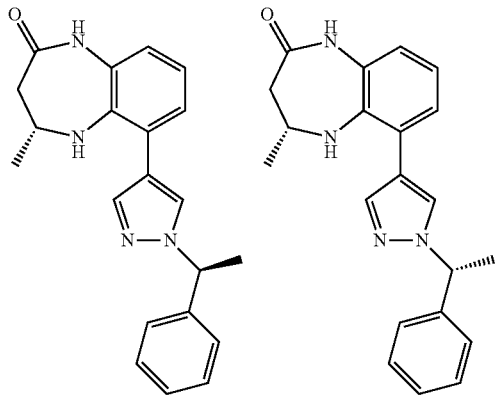 [SMILES: C[C@@H]1CC(=O)Nc2cccc(-c3cnn([C@@H](C)c4ccccc4)c3)c2N1 ; C[C@@H]1CC(=O)Nc2cccc(-c3cnn([C@H](C)c4ccccc4)c3)c2N1]

Racemic 4-methyl-6-[1-(1-phenylethyl)pyrazol-4-yl]-1,3,4,5-tetrahydro-1,5-benzodiazepin-2-one (Example 173, 65 mg) was separated using chiral SFC (Regis WhelkO-1(s,s) (150 mm*21.2 mm), 40% Methanol w/0.1% NH$_4$OH) to (4R)-methyl-6-[(1-phenylethyl)pyrazol-4-yl]-1,3,4,5-tetrahydro-1,5-benzodiazepin-2-one (21 mg, first peak) and (4S)-methyl-6-[1-(1-phenylethyl)pyrazol-4-yl]-1,3,4,5-tetrahydro-1,5-benzodiazepin-2-one (23 mg, second peak). Absolute configuration was arbitrarily assigned to each enantiomer. Example 288: $^1$H NMR (400 MHz, DMSO-$d_6$) 9.50 (s, 1H), 8.07 (d, J=2.7 Hz, 1H), 7.63 (s, 1H), 7.36-7.23 (m, 5H), 6.99 (dd, J=2.8, 6.4 Hz, 1H), 6.87-6.79 (m, 2H), 5.65 (d, J=6.0 Hz, 1H), 3.99 (br s, 1H), 3.93 (br s, 1H), 2.55-2.50 (m, 1H), 2.14 (dd, J=6.0, 13.2 Hz, 1H), 1.85 (d, J=7.1 Hz, 3H), 1.13 (dd, J=1.8, 6.2 Hz, 3H). LCMS M/Z (M+H) 347. Example 289: $^1$H NMR (400 MHz, DMSO-$d_6$) δ 9.50 (s, 1H), 8.07 (d. J=2.7 Hz, 1H), 7.63 (s, 1H), 7.38-7.24 (m, 5H), 6.98 (dd, J=2.8, 6.4 Hz, 1H), 6.87-6.79 (m, 2H), 5.65 (d, J=6.0 Hz, 1H), 3.99 (br s, 1H), 3.93 (br s, 1H), 2.55-2.50 (m, 1H), 2.16 (dd, J=6.0, 13.2 Hz, 1H), 1.85 (d, J=7.1 Hz, 3H), 1.13 (dd, J=1.8, 6.2 Hz, 3H). LCMS M/Z (M+H) 347.

Example 290

(R)-4-methyl-6-(6-(1-methyl-1H-pyrazol-4-yl)-3,4-dihydroquinolin-1(2H)-yl)-4,5-dihydro-1H-benzo[b][1,4]diazepin-2(3H)-one

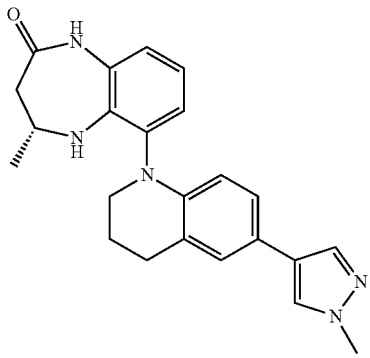 [SMILES: C[C@@H]1CC(=O)Nc2cccc(N3CCCc4cc(-c5cnn(C)c5)ccc43)c2N1]

Step 1:

6-(1-methyl-1H-pyrazol-1-yl)-1,2,3,4-tetrahydroquinoline

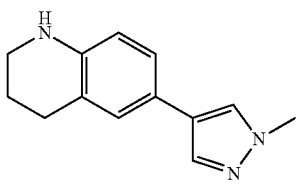 [SMILES: Cn1cc(-c2ccc3c(c2)CCCN3)cn1]

A mixture of 6-bromo-1,2,3,4-tetrahydroquinoline (17.0 g, 80.16 mmol), 1-methyl-4-(4,4,5,5-tetramethyl-1,3,2-dioxaborolan-2-yl)-1H-pyrazole (25.0 g, 120.23 mmol), $K_2CO_3$ (33.2 g, 240.47 mmol) and [1,1'-bis(diphenylphosphino)ferrocene]dichloropalladium(II) (5.8 g, 8.02 mmol) in dioxane/$H_2O$ (5:1, 150 mL) was heated to 120° C. for 16 hours under nitrogen atmosphere. After cooling to room temperature, the mixture was filtered and the filtrate was concentrated in vacuo. The crude residue was purified by silica gel chromatography (petroleum ether/EtOAc=1/1) to give the title product (8.0 g, 47%) as a yellow solid. $^1$H NMR (400 MHz, $CD_3OD$) δ 7.71 (s, 1H), 7.62 (s, 1H), 7.08-7.06 (m, 2H), 6.50 (d, J=8.4 Hz, 1H), 3.87 (s, 3H), 3.23 (t, J=5.2 Hz, 1H), 2.75 (t, J=6.4 Hz, 1H), 1.94-1.88 (m, 2H).

Step 2:

(R)-4-methyl-6-(6-(1-methyl-1H-pyrazol-4-yl)-3,4-dihydroquinolin-1 (2H)-yl)-4,5-dihydro-1H-benzo[b][1,4]diazepin-2(3H)-one

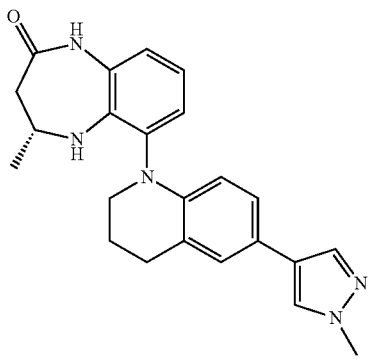 [SMILES: C[C@@H]1CC(=O)Nc2cccc(N3CCCc4cc(-c5cnn(C)c5)ccc43)c2N1]

To a solution of (R)-6-bromo-4-methyl-4,5-dihydro-1H-benzo[b][1,4]diazepin-2(3H)-one (Intermediate A, 300 mg, 1.18 mmol) in dioxane (10 mL) was added 6-(1-methyl-1H-pyrazol-4-yl)-1,2,3,4-tetrahydroquinoline (301 mg, 1.41 mmol), t-BuONa (340 mg, 3.53 mmol) and dichloro[1,3-bis(2,6-di-3-pentylphenyl)imidazol-2-ylidene](3-chloro-pyridyl)palladium(II) (78 mg, 0.1 mmol). The mixture was heated to 120° C. for 16 hours under nitrogen atmosphere. After cooling to room temperature, the mixture was filtered and the filtrate was concentrated in vacuo. The crude residue was diluted with water (10 mL) and the mixture was extracted with EtOAc (10 mL×3). The combined organic layers were washed with sat. aq. sodium bicarbonate (10 mL×3), dried over anhydrous $Na_2SO_4$ and concentrated in vacuo. The crude residue was purified by reverse phase chromatography (acetonitrile 25-55%/0.1% $NH_4HCO_3$ in water) to give the title compound (70 mg, 15%) as a white solid. $^1$H NMR (400 MHz, $CDCl_3$) δ 7.65 (s, 1H), 7.48 (s, 1H), 7.36 (s, 1H), 7.17 (S, 1H), 7.02-6.97 (m, 2H), 6.84-6.77 (m, 2H), 6.20-6.10 (m, 1H), 4.55-4.46 (m, 1H), 3.97-3.91 (m, 1H), 3.92 (s, 3H), 3.51-3.41 (m, 3H), 3.01-2.91 (m, 2H), 2.71-2.68 (m, 1H), 2.54-2.52 (m, 1H), 2.15-2.14 (m, 2H), 1.30-1.20 (m, 3H). LCMS M/Z (M+H) 388.

Examples 291-304

Examples 291-304 are synthesized using a similar Pd-coupling procedure as Example 290.

291

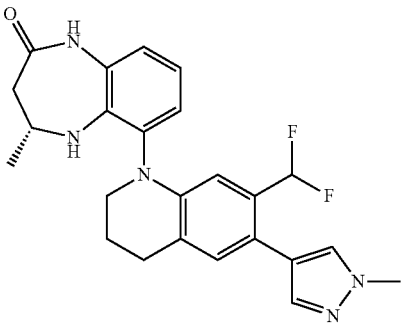

292

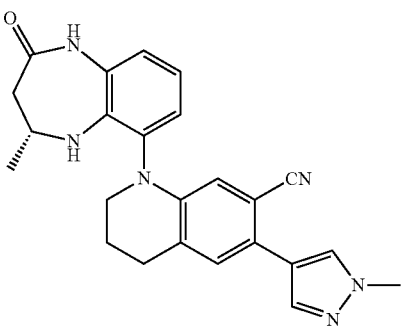

293

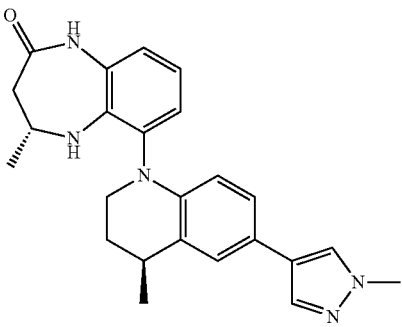

327
-continued
294
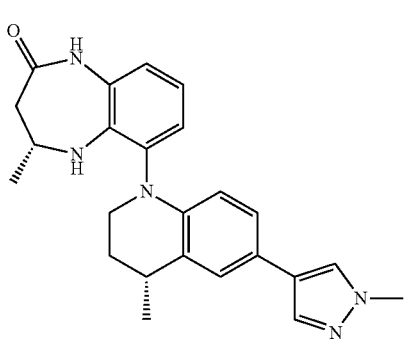
295
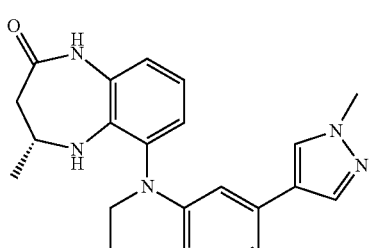
296
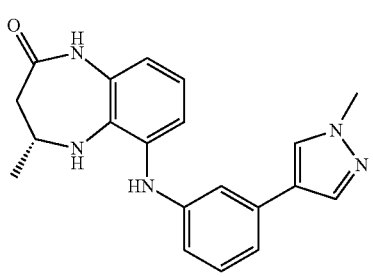
297
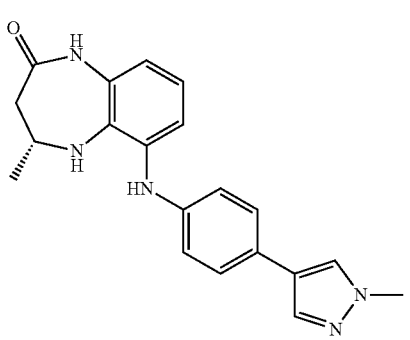
298
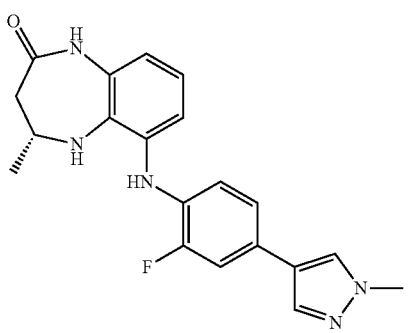
328
-continued
299
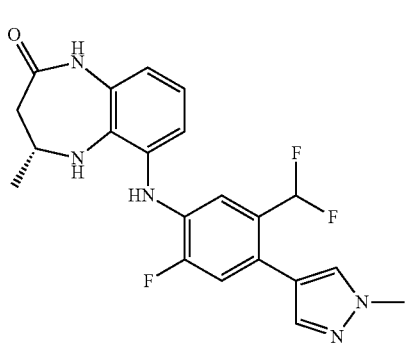
300
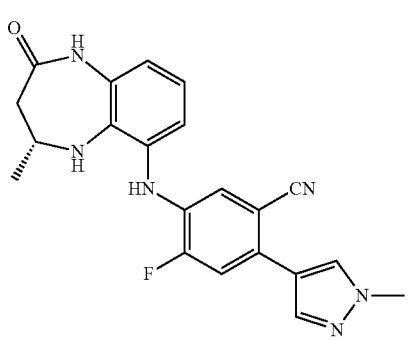
301
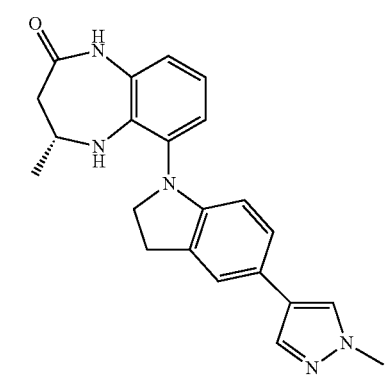
302
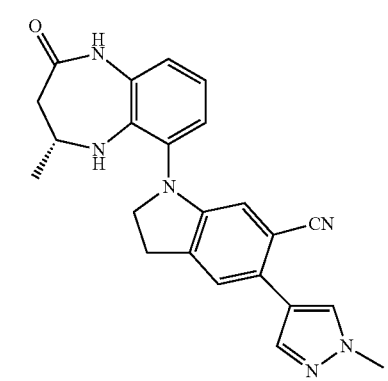

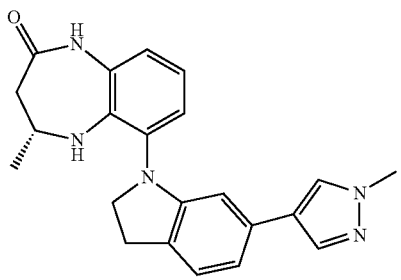

and

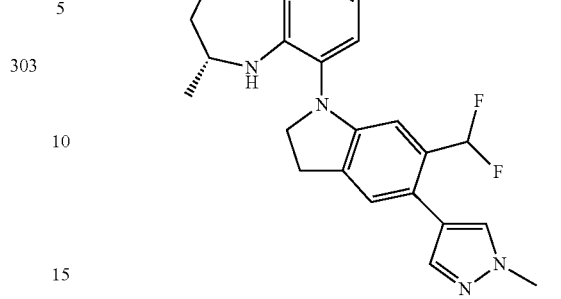

and salts thereof.

The following compounds were prepared in a similar fashion to Example 290:

Examples 291-304

| Example | Compound Name | NMR | m/z |
|---|---|---|---|
| Example 291 | (4R)-6-[7-(difluoromethyl)-6-(1-methylpyrazol-4-yl)-3,4-dihydro-2H-quinolin-1-yl]-4-methyl-1,3,4,5-tetrahydro-1,5-benzodiazepin-2-one | $^1$H NMR (400 MHz, CDCl$_3$) δ 7.71 (s, 1H), 7.53 (s, 1H), 7.40 (s, 1H), 7.07 (s, 1H), 6.98-6.95 (m, 1H), 6.87-6.82 (m, 2H), 6.54 (s, 1H), 6.46 (t. J = 55.6 Hz, 1H), 4.38-4.30 (m, 1H), 4.00-3.94 (m, 4H), 3.59-3.56 (m, 1H), 3.46-3.36 (m,1H), 3.05-2.97 (m, 1H), 2.95-2.85 (m, 1H), 2.79-2.60 (m, 1H), 2.58-2.44 (m, 1H), 2.15-2.08 (m, 2H), 1.27-1.17 (m, 3H) | 438 |
| Example 292 | 1-[(4R)-4-methyl-2-oxo-1,3,4,5-tetrahydro-1,5-benzodiazepin-6-yl]-6-(1-methylpyrazol-4-yl)-3,4-dihydro-2H-quinoline-7-carbonitrile | $^1$H NMR (400 MHz, CDCl$_3$) δ 7.85 (s, 1H), 7.74 (s, 1H), 7.44 (d, J = 5.6 Hz, 1H), 7.21 (s, 1H), 6.93-6.83 (m, 3H), 6.42-6.39 (m, 1H), 4.32-4.26 (m, 1H), 3.98-3.94 (m, 4H), 3.56-3.50 (m, 1H), 3.44-3.41 (m, 1H), 3.04-3.01 (m, 1H), 3.00-2.95 (m, 1H), 2.72-2.69 (m, 1H), 2.58-2.54 (m, 1H), 2.16-2.11 (m, 2H), 1.28-1.22 (m, 3H) | 413 |
| Example 293 | (R, R)-4-methyl-6-[4-methyl-6-(1-methylpyrazol-4-yl)-3,4-dihydro-2H-quinolin-1-yl]-1,3,4,5-tetrahydro-1,5-benzodiazepin-2-one | $^1$H NMR (400 MHz,DMSO-d$_6$) δ 9.62 (s, 1H), 7.96-7.80 (m, 1H), 7.70-7.56 (m, 1H), 7.37-7.17 (m, 1H), 7.08-6.95 (m, 1H), 6.92-6.64 (m, 3H), 6.05-5.86 (m, 1H), 4.71-4.44 (m, 1H), 3.96-3.68 (m, 4H), 3.57-3.35 (m, 2H), 3.22-2.88 (m, 2H), 2.32-1.69 (m, 3H), 1.42-1.28 (m, 3H), 1.18-1.04 (m, 3H) | 402 |
| Example 294 | (R, S)-4-methyl-6-[4-methyl-6-(1-methylpyrazol-4-yl)-3,4-dihydro-2H-quinolin-1-yl]-1,3,4,5-tetrahydro-1,5-benzodiazepin-2-one | $^1$H NMR (400 MHz,DMSO-d$_6$) δ 9.61 (s, 1H), 7.88 (s, 1H), 7.75-7.56 (m, 1H), 7.36-7.15 (m, 1H), 7.00 (d, J = 8.4 Hz, 1H), 6.92-6.69 (m, 3H), 6.12-5.85 (m, 1H), 4.83-4.40 (m, 1H), 4.18-3.69 (m, 5H), 3.49-3.21 (m, 1H), 2.34-1.43 (m, 2H), 1.41-1.18 (m, 5H), 1.17-1.00 (m, 3H), 0.92-0.74 (m, 1H) | 402 |
| Example 295 | (4R)-4-methyl-6-[7-(1-methylpyrazol-4-yl)-3,4-dihydro-2H-quinolin-1-yl]-1,3,4,5-tetrahydro-1,5-benzodiazepin-2-one | $^1$H NMR (400 MHz, DMSO-d$_6$) δ9.64 (s, 1H), 7.69 (s, 1H), 7.44 (s., 1H), 6.96 (d, J = 8.0 Hz, 1H), 6.93-6.70 (m, 4H), 6.14 (s., 1H), 4.76-4.55 (m, 1H), 3.97-3.80 (m, 1H), 3.76 (s, 3H), 3.48-3.44 (m, 2H), 2.95-2.71 (m, 2H), 2.33-1.80 (m, 4H), 1.21-1.01 (m, 3H) | 388 |
| Example 296 | (4R)-4-methyl-6-[3-(1-methylpyrazol-4-yl)anilino]-1,3,4,5-tetrahydro-1,5-benzodiazepin-2-one | $^1$H NMR (400 MHz, DMSO-d$_6$) δ 9.51 (s, 1H), 7.97 (s, 1H), 7.69 (s, 1H), 7.35 (s, 1H), 7.12-6.92 (m, 1H), 6.88-6.87 (m, 3H), 6.76-6.69 (m, 2H), 6.58 (d, J = 8.0 Hz, 1H), 4.45 (s, 1H), 3.93-3.85 (m, 1H), 3.83 (s, 3H), 2.54-2.53 (m, 1H), 2.19-2.15 (m, 1H), 1.12 (d, J = 6.0 Hz, 3H) | 348 |
| Example 297 | (4R)-4-methyl-6-[4-(1-methylpyrazol-4- | $^1$H NMR (400 MHz, DMSO-d$_6$) δ 9.50 (s, 1H), 7.94 (s, 1H), 7.69 (s, 1H), 7.35-7.33 | 348 |

| Example | Compound Name | NMR | m/z |
|---|---|---|---|
| | yl)anilino]-1,3,4,5-tetrahydro-1,5-benzodiazepin-2-one | (m, 3H), 6.88-6.85 (m, 1H), 6.78-6.72 (m, 3H), 6.69-6.67 (m, 1H), 4.44 (s, 1H), 3.91-3.86 (m, 1H), 3.82 (s, 3H), 2.55-2.51 (m, 1H), 2.18-2.13 (m, 1H), 1.13 (d, J = 6.0 Hz, 3H) | |
| Example 298 | (4R)-6-[2-fluoro-4-methylpyrazol-4-yl)anilino]-4-methyl-1,3,4,5-tetrahydro-1,5-benzodiazepin-2-one | $^1$H NMR (400 MHz, DMSO-d$_6$) δ 9.51 (s, 1H), 8.03 (s, 1H), 7.77 (s, 1H), 7.39 (d, J = 12.8 Hz, 3H), 7.19-7.17 (m, 2H), 6.75-6.67 (m, 4H), 4.45 (s, 1H), 3.91-3.85 (m, 1H), 3.82 (s, 3H), 2.49-2.47 (m, 1H), 2.18-2.13 (m, 1H), 1.13 (d, J = 6.0 Hz, 3H) | 366 |
| Example 299 | (4R)-6-[5-(difluoromethyl)-2-fluoro-4-(1-methylpyrazol-4-yl)anilino]-4-methyl-1,3,4,5-tetrahydro-1,5-benzodiazepin-2-one | $^1$H NMR (400 MHz, DMSO-d$_6$) δ 9.57 (s, 1H), 7.83(s, 1H), 7.57(s, 1H), 7.53(s, 1H), 7.27 (d, J = 12.0 Hz, 1H), 6.88-6.76 (m, 4H), 6.86 (t, J = 54.0 Hz, 1H), 4.64 (s, 1H), 3.91-3.89 (m, 1H), 3.87 (s, 3H), 2.54-2.53 (m, 1H), 2.20-2.15 (m, 1H), 1.11 (d, J = 6.0 Hz, 3H) | 416 |
| Example 300 | 4-fluoro-5-[[(4R)-4-methyl-2-oxo-1,3,4,5-tetrahydro-1,5-benzodiazepin-6-yl]amino-2-(1-methylpyrazol-4-yl)benzonitrile | $^1$H NMR (400 MHz, DMSO-d$_6$) δ9.58 (s, 1H), 8.16 (s, 1H), 7.88 (s, 1H), 7.68 (s, 1H), 7.56 (d, J = 12.8 Hz, 1H), 6.87-6.75 (m, 4H), 4.72 (s, 1H), 3.91-3.89 (m, 1H),3.88 (s, 3H), 2.43-2.18 (m, 2H), 1.12 (d. J = 6.0 Hz, 3H) | 391 |
| Example 301 | (4R)-4-methyl-6-[5-(1-methylpyrazol-4-yl)indolin-1-yl]-1,3,4,5-tetrahydro-1,5-benzodiazepin-2-one | $^1$H NMR (400 MHz, DMSO-d$_6$) δ9.61 (s, 1H), 7.93 (s, 1H), 7.69 (s, 1H), 7.36 (s, 1H), 7.14 (d, J = 8.0 Hz, 1H), 6.93 (d, J = 7.6 Hz, 1H), 6.84-6.70 (m, 2H), 6.14 (d, J = 7.6 Hz, 1H), 3.97-3.96 (m, 1H), 3.82 (s, 3H), 3.12 (t, J = 8.0 Hz, 2H), 2.68-2.55 (m, 3H), 2.39-2.23 (m, 1H), 1.20 (d, J = 6.0 Hz, 3H) | 374 |
| Example 302 | 1-[(4R)-4-methyl-2-oxo-1,3,4,5-tetrahydro-1,5-benzodiazepin-6-yl]-5-(1-methylpyrazol-4-yl)indoline-6-carbonitrile | $^1$H NMR (400 MHz, DMSO-d$_6$) δ9.63 (s, 1H), 8.08 (s, 1H), 7.80 (s, 1H), 7.46 (s, 1H), 6.96 (d J = 7.6 Hz, 1H), 6.86 (d, J = 6.8 Hz, 1H), 6.80-6.75 (m, 1H), 6.29 (s, 1H), 5.03 (s, 1H), 4.00-3.92 (m, 1H), 3.89 (s, 3H), 3.22 (t, J = 8.4 Hz, 2H), 2.67-2.55 (m, 2H), 2.45-2.28 (m, 2H), 1.20 (d, J = 6.0 Hz, 3H) | 399 |
| Example 303 | (4R)-4-methyl-6-[6-(1-methylpyrazol-4-yl)indolin-1-yl]-1,3,4,5-tetrahydro-1,5-benzodiazepin-2-one | $^1$H NMR (400 MHz, CDCl$_3$) δ7.62 (s, 1H),7.47 (s, 1H),7.27 (s, 1H), 7.20 (d,J = 7.6 Hz,1H),7.03- 7.01 (m, 1H),6.91 (d,J = 7,2 Hz,1H), 6.82-6.77 (m, 2H), 6.34 (s, 1H),4.85-4.62 (m, 1H), 4.04-4.02(m, 1H), 3.89 (s, 3H), 3.88-3.80 (m, 1H), 3.70-3.51 (m, 1H), 3.17 (t, J = 8.0 Hz, 2H), 2.79-2.76 (m, 1H),2.60-2.54 (m, 1H), 1.62 (t, J = 6.4 Hz,3H) | 374 |
| Example 304 | (4R)-6-[6-(difluoromethyl)-5-(1-methylpyrazol-4-yl)indolin-1-yl]-4-methyl-1,3,4,5-tetrahydro-1,5-benzodiazepin-2-one | $^1$H NMR (400 MHz, CDCl$_3$) δ 9.60 (s, 1H), 7.73 (s, 1H), 7.48 (s, 1H), 7.20 (s, 1H), 6.93 (d,J = 7.6 Hz,1H), 6.86-6.84 (m, 1H),6.78-6.74 (m, 1H), 6.75 (t, J = 53.6 Hz, 1H), 6.29 (s, 1H), 3.98-3.91 (m, 1H), 3.85 (s, 3H), 3.16-3.09 (m, 3H), 2.59-2.53 (m, 2H), 2.29-2.24 (m, 2H),1.18-1.15 (m, 3H). | 424 |

Example 305

(4R)-6-[7-(difluoromethyl)-6-(1-methylpyrazol-4-yl)-3,4-dihydro-2H-quinolin-1-yl]-4-methyl-1,3,4,5-tetrahydropyrido[3,4-b][1,4]diazepin-2-one

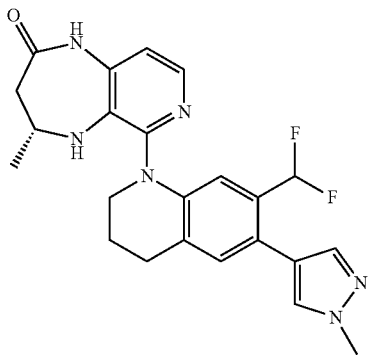 [SMILES: C[C@@H]1CC(=O)Nc2ccnc(N3CCCc4cc(-c5cnn(C)c5)c(C(F)F)cc43)c2N1]

Step 1:

7-difluoromethyl)-1-(3-fluoro-1-nitropyridin-2-yl)-6-(1-methyl-1H-pyrazol-4-yl)-1,2,3,4-tetrahydroquinoline

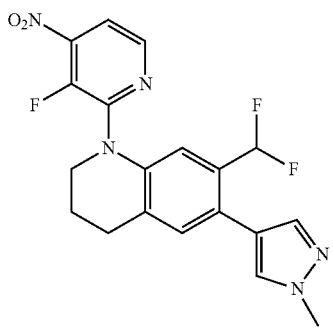 [SMILES: Cn1cc(-c2cc3c(cc2C(F)F)N(c2nccc([N+](=O)[O-])c2F)CCC3)cn1]

To a solution of 2-chloro-3-fluoro-4-nitro-pyridine (100 mg, 0.57 mmol) in dioxane (4 mL) was added 7-(difluoromethyl)-6-(1-methylpyrazol-4-yl)-1,2,3,4-tetrahydroquinoline (115 mg, 0.44 mmol), $Cs_2CO_3$ (284 mg, 0.87 mmol), 4,5-bis(diphenylphosphino)-9,9-dimethylxanthene (25 mg, 0.4 mmol) and palladium(II) acetate (10 mg, 0.04 mmol). The reaction mixture was irradiated in a microwave at 140° C. for 1 h. After cooling the reaction to room temperature, the reaction mixture was concentrated in vacuo. The crude residue was purified by silica gel chromatography (petroleum ether/EtOAc=1/1) to give the title compound (24 mg, 11%) as a red solid. LCMS M/Z (M+H) 404.

Step 2:

(R)-methyl 3-((2-(7-(difluoromethyl)-6-(1-methyl-1H-pyrazol-4-yl)-3,4-dihydroquinolin-1 (2H)-yl)-4-nitropyridin-3-yl)amino)butanoate

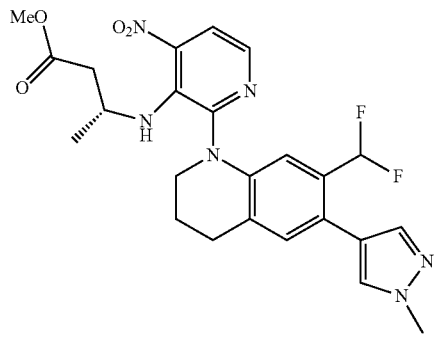 [SMILES: COC(=O)C[C@@H](C)Nc1c([N+](=O)[O-])ccnc1N1CCCc2cc(-c3cnn(C)c3)c(C(F)F)cc21]

A mixture of 7-(difluoromethyl)-1-(3-fluoro-4-nitro-2-pyridyl)-6-(1-methylpyrazol-4-yl)-3,4-dihydro-2H-quinoline (100 mg, 0.25 mmol), triethylamine (0.07 mL, 0.50 mmol) and methyl (3R)-3-aminobutanoate (44 mg, 0.37 mmol) in THF (2 mL) was heated to 60° C. for 12 h under a nitrogen atmosphere. After cooling the reaction to room temperature, the reaction mixture was concentrated in vacuo. The crude residue was purified by silica gel chromatography (petroleum ether/EtOAc=1/1) to give the title compound (80 mg, 65%) as a red solid. LCMS M/Z (M+H) 501.

Step 3:

(4R)-6-[7-(difluoromethyl)-6-(1-methylpyrazol-4-yl)-3,4-dihydro-2H-quinolin-1-yl]-4-methyl-1,3,4,5-tetrahydropyrido[3,4-b][1,4]diazepin-2-one

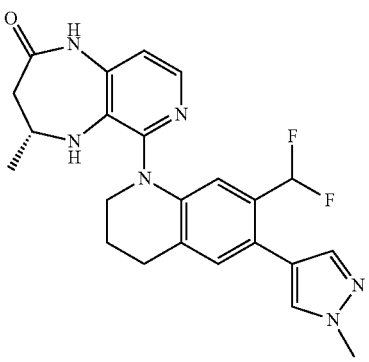 [SMILES: C[C@@H]1CC(=O)Nc2ccnc(N3CCCc4cc(-c5cnn(C)c5)c(C(F)F)cc43)c2N1]

A mixture of (R)-methyl 3-((2-(7-(difluoromethyl)-6-(1-methyl-1H-pyrazol-4-yl)-3,4-dihydroquinolin-1 (21)-yl)-4-nitropyridin-3-yl)amino)butanoate (100 mg, 0.20 mmol) and Fe powder (56 mg, 1 mmol) in acetic acid (2 mL) was heated to 100° C. for 12 h under a nitrogen atmosphere. After cooling the reaction to room temperature, the mixture was filtered and the filtrate was concentrated in vacuo. The crude residue was purified by reverse phase chromatography (acetonitrile 15-35/0.2% formic acid in water) to give the title compound (8 mg, 9%) as a white solid. $^1$H NMR (400 MHz, DMSO-$d_6$) δ10.01 (s, 1H), 7.78-7.67 (m, 2H), 7.49 (s, 1H), 7.13 (s, 1H), 6.86 (d, J=5.2 Hz, 1H), 6.76 (t, J=55.2 Hz, 1H), 6.35 (s, 1H), 5.03 (s, 1H), 3.90-3.82 (m, 4H), 3.50-3.46 (m, 2H), 2.92-2.86 (m, 2H), 2.72-2.64 (m, 2H), 2.10-2.06 (m, 2H), 1.14 (d, J=6.4 Hz, 3H). LCMS M/Z (M+H) 439.

Example 306

1-methyl-4-[(4R)-4-methyl-2-oxo-1,3,4,5-tetrahydro-1,5-benzodiazepin-6-yl]-7-(1-methylpyrazol-4-yl)-2,3-dihydroquinoxaline-6-carbonitrile

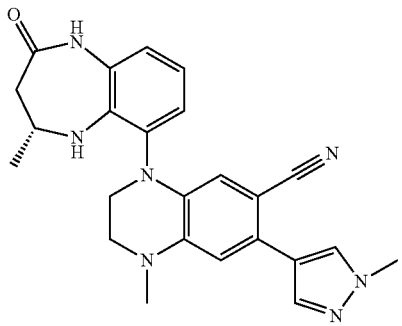 [SMILES: C[C@@H]1CC(=O)Nc2cccc(N3CCN(C)c4cc(-c5cnn(C)c5)c(C#N)cc43)c2N1]

Step 1:

2-bromo-4-fluoro-5-nitrobenzonitrile

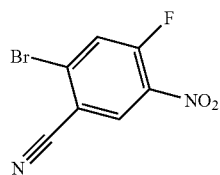 [SMILES: N#Cc1cc([N+](=O)[O-])c(F)cc1Br]

To a solution of 2-bromo-4-fluoro-benzonitrile (30 g, 150 mmol) in sulfuric acid (40 mL) at 0° C. was added potassium nitrate (16.7 g, 165 mmol). The reaction mixture was stirred at 18° C. for 1.5 h. The mixture was poured into ice water and extracted with EtOAc (60 mL×3). The combined organic layers were washed with brine (100 ml), dried over anhydrous Na$_2$SO$_4$, filtered and concentrated in vacuo to give the title compound (36 g, 98%) as a yellow solid that required no further purification. $^1$H NMR (400 MHz, CD$_3$OD) δ8.67 (d, J=7.6 Hz, 1H), 8.07 (d, J=10.4 Hz, 1H).

Step 2:

2-bromo-4-((2-hydroethyl)(methyl)amino)-5-nitrobenzonitrile

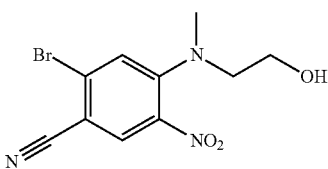 [SMILES: CN(CCO)c1cc(Br)c(C#N)cc1[N+](=O)[O-]]

A mixture of 2-bromo-4-fluoro-5-nitro-benzonitrile (5.0 g, 20.41 mmol), N,N-diisopropylethylamine (5.27 g, 40.81 mmol) and 2-(methylamino)ethanol (1.84 g, 24.49 mmol) in DMF (20 mL) was heated to 80° C. for 16 h. After cooling the reaction to room temperature, the reaction mixture was concentrated in vacuo. The crude residue was purified by silica gel chromatography (petroleum ether/EtOAc=1/1) to give the title compound (4.5 g, 74%) as yellow oil. $^1$H NMR (400 MHz, CDCl$_3$) δ 8.03 (s, 1H), 7.46 (s, 1H), 3.91 (t, J=5.2 Hz, 2H), 3.56 (t, J=5.2 Hz, 2H), 2.95 (s, 3H).

Step 3:

2-bromo-4-((2-chloroethyl)(methyl)amino)-5-nitrobenzonitrile

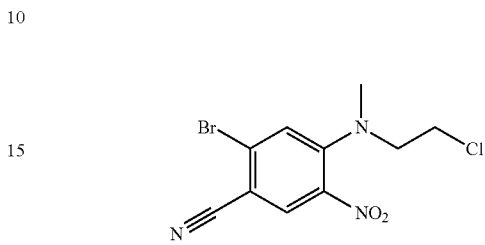

To a solution of 2-bromo-4-((2-hydroxyethyl)(methyl)amino)-5-nitrobenzonitrile (4.5 g, 15 mmol) and pyridine (1.21 mL, 15 mmol) in DCM (50 mL) at 0° C. was added thionylchloride (2.18 mL, 30 mmol) dropwise. The reaction mixture was stirred at 20° C. for 16 h and then concentrated in vacuo. DCM (20 mL) was added and the mixture was washed with sat. aq. NaHCO$_3$ (10 mL). The organic phase was dried over anhydrous Na$_2$SO$_4$, filtered and concentrated in vacuo to give the title compound (4.7 g, 98%) as yellow oil that required no further purification.

Step 4:

5-amino-2-bromo-4-((2-chloroethyl)methyl)amino)benzonitrile

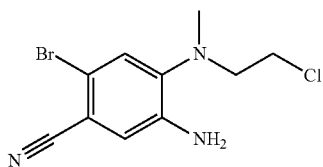 [SMILES: CN(CCCl)c1cc(Br)c(C#N)cc1[N+](=O)[O-]]

To a solution of 2-bromo-4-((2-chloroethyl)(methyl)amino)-5-nitrobenzonitrile (4.7 g, 14.75 mmol) in acetic acid (40 mL) was added Fe powder (4.12 g, 73.77 mmol). The reaction mixture was stirred at 20° C. for 1 h. Water (40 mL) was added and the mixture was made basic with sat. aq. NaHCO$_3$ to pH 8 and then extracted with EtOAc (50 mL×3). The combined organic layers were dried over anhydrous Na$_2$SO$_4$, filtered and concentrated in vacuo to give the title compound (4 g, 94%) as a yellow solid that required no further purification.

Step 5:

7-bromo-1-methyl-1,2,3,4-tetrahydroquinoxaline-6-carbonitrile

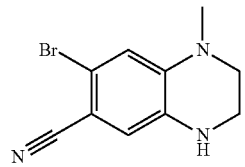

A mixture of 5-amino-2-bromo-4-((2-chloroethyl)(methyl)amino)benzonitrile (4.0 g, 13.86 mmol), potassium iodide (4.6 g, 27.72 mmol) and K₂CO₃ (5.75 g, 41.58 mmol) in DMF (20 mL) was heated to 80° C. for 7 h. After cooling the reaction to room temperature, water (40 mL) was added and the mixture was extracted with EtOAc (100 mL×3). The combined organic layers were dried over anhydrous Na₂SO₄, filtered and concentrated in vacuo to give the title compound (3 g, 86%) as a brown solid. LCMS M/Z (M+H) 251.8.

Step 6:

1-methyl-7-(1-methyl-1H-pyrazol-4-yl)-1,2,3,4-tetrahydroquinoxaline-6-carbonitrile

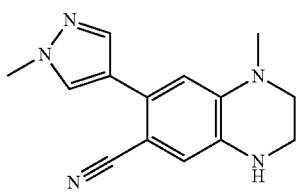 [SMILES: CN1CCNc2cc(C#N)c(-c3cnn(C)c3)cc21]

To a solution of 7-bromo-1-methyl-1,2,3,4-tetrahydroquinoxaline-6-carbonitrile (400 mg, 1.59 mmol), 1-methyl-4-(4,4,5,5-tetramethyl-1,3,2-dioxaborolan-2-yl)-1H-pyrazole (400 mg, 1.9 mmol) and Na₂CO₃ (500 mg, 4.76 mmol) in THF (10 mL) and H₂O (2 mL) was added chloro(2-dicyclohexylphosphino-2',4',6'-tri-i-propyl-1,1'-biphenyl)(2'-amino-1,1'-biphenyl-2-yl) palladium(II)(120 mg, 0.16 mmol) and 2-(dicyclohexylphosphino)-2',4',6'-triisopropylbiphenyl (76 mg, 0.16 mmol). The resulting mixture was heated to 70° C. for 16 h under nitrogen atmosphere. After cooling to room temperature, the mixture was filtered and concentrated in vacuo. The crude residue was purified by silica gel chromatography (petroleum ether/EtOAc=1/2) to give the title compound (310 mg, 77%) as a brown solid. LCMS M/Z (M+H) 254.

Step 7:

1-methyl-4-[(4R)-4-methyl-2-ox-1,3,4,5-tetrahydro-1,5-benzodiazepin-6-yl]-7-(1-methylpyrazol-4-yl)-2,3-dihydroquinoxaline-6-carbonitrile

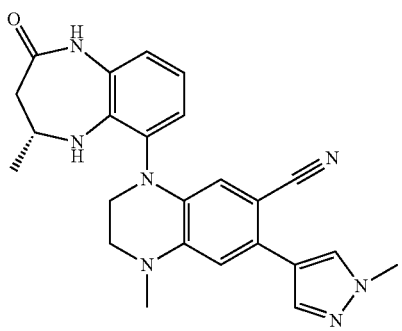 [SMILES: C[C@@H]1CC(=O)Nc2cccc(N3CCN(C)c4cc(-c5cnn(C)c5)c(C#N)cc43)c2N1]

To a solution of 1-methyl-7-(1-methyl-1H-pyrazol-4-yl)-1,2,3,4-tetrahydroquinoxaline-6-carbonitrile (150 mg, 0.59 mmol) and (R)-6-bromo-4-methyl-4,5-dihydro-1H-benzo[b][1,4]diazepin-2(3H)-one (Intermediate A, 166 mg, 0.65 mmol) in 1,4-dioxane (5 mL) was added t-BuONa (171 mg, 1.78 mmol) and dichloro[1,3-bis(2,6-di-3-pentylphenyl)imidazol-2-ylidene](3-chloropyridyl)palladium(II) (47 mg, 0.06 mmol). The reaction mixture was heated to 120° C. for 16 h under a argon atmosphere. After cooling to room temperature, the mixture was filtered and concentrated in vacuo. The crude residue was purified by reverse phase chromatography (acetonitrile 20-50%/0.2% formic acid in water) to give the title compound (21 mg, 8%) as a white solid. ¹H NMR (400 MHz, CDCl₃) δ7.89 (s, 1H), 7.76 (s, 1H), 7.34 (s, 1H), 6.96-6.83 (m, 3H), 6.62 (s, 1H), 6.32 (s, 1H), 4.41-4.33 (m, 1H), 3.99-3.92 (m, 1H), 3.95 (s, 3H), 3.80-3.75 (m, 2H), 3.46-3.41 (m, 2H), 3.09 (s, 3H), 2.76-2.52 (m, 2H), 1.28-1.22 (m, 3H). LCMS M/Z (M+H) 428.

Examples 307 & 308

(R,R)-6-[7-(difluoromethyl)-4-methyl-6-(1-methylpyrazol-4-yl)-3,4-dihydro-2H-quinolin-1-yl]-4-methyl-1,3,4,5-tetrahydro-1,5-benzodiazepin-2-one & (R,S)-6-[7-(difluoromethyl)-4-methyl-6-(1-methylpyrazol-4-yl)-3,4-dihydro-2H-quinolin-1-yl]-4-methyl-1,3,4,5-tetrahydro-1,5-benzodiazepin-2-one

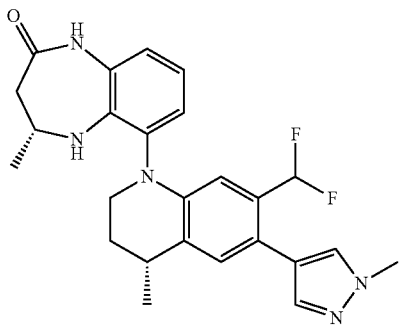

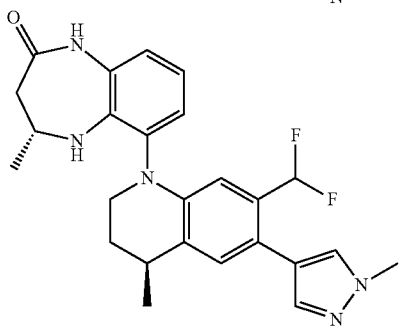

Step 1:

2,2-difluoro-2-(4-methylquinolin-7-yl)-1-phenylethanone

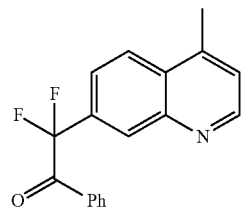 [SMILES: Cc1ccnc2cc(C(F)(F)C(=O)c3ccccc3)ccc12]

To a solution of 7-chloro-4-methyl-quinoline (5.0 g, 28.15 mmol) in toluene (100 mL) was added 2,2-difluoro-1-phenyl-ethanone (8.79 g, 56.3 mmol), chloro[(tricyclohexylphosphine)-2-(2'-aminobiphenyl)]palladium(II) (1.66 g, 2.81 mmol) and K$_3$PO$_4$ (23.9 g, 112.59 mmol). The reaction mixture was heated to 120° C. for 16 h under a nitrogen atmosphere. After cooling to room temperature, water (100 mL) was added and the mixture was extracted with DCM (100 mL×2). The combined organic layers were dried over anhydrous Na$_2$SO$_4$, filtered and concentrated in vacuo to give the title compound (5 g, crude) as a brown oil that required no further purification. LCMS M/Z (M+H) 298.

Step 2:

7-(difluoromethyl)-4-methylquinoline

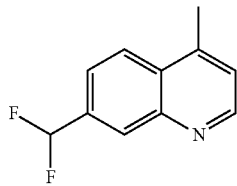

To a solution of 2,2-difluoro-2-(4-methyl-7-quinolyl)-1-phenyl-ethanone (5.0 g, 16.82 mmol) in toluene (100 mL) and water (6 mL) was added KOH (5.66 g, 100.91 mmol). The reaction mixture was heated to 100° C. for 16 h. After cooling to room temperature, water (100 mL) was added and the mixture was extracted with DCM (100 mL×2). The combined organic layers were dried over anhydrous Na$_2$SO$_4$, filtered and concentrated in vacuo. The crude residue was purified by silica gel chromatography (petroleum ether/EtOAc=10/1) to give the title compound (3.7 g, 80%) as a yellow oil. LCMS M/Z (M+H) 194.

Step 3:

7-(difluoromethyl)-4-methyl-1,2,3,4-tetrahydroquinoline

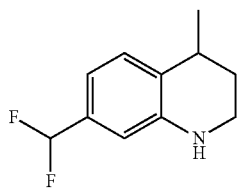

To a solution of 7-(difluoromethyl)-4-methyl-quinoline (3.7 g, 19.15 mmol) and sodiumcyanoborohydride (6.02 g, 95.76 mmol) in MeOH (200 mL) at 0° C. was added boron trifluoride diethyl etherate (20.67 mL, 38.30 mmol) dropwise. The reaction mixture was heated to 100° C. for 36 h under a nitrogen atmosphere. After cooling the reaction to room temperature, sat. aq. NaHCO$_3$ (100 mL) was added and the mixture was extracted with DCM (100 mL×2). The combined organic layers were dried over anhydrous Na$_2$SO$_4$, filtered and concentrated in vacuo. The crude residue was purified by silica gel chromatography (petroleum ether/EtOAc=50/1) to give the mixture of 7-(difluoromethyl)-4-methyl-1,2,3,4-tetrahydroquinoline and 7-(difluoromethyl)-4-methyl-1,2-dihydroquinoline (2.5 g, ratio=7:2) as a brown oil. The resulting mixture was dissolved in MeOH (50 mL) and 10% Pd/C (403 mg, 0.19 mmol) was added. The mixture was stirred at 25° C. for 1 h under a hydrogen atmosphere (15 psi). The reaction was filtered and concentrated in vacuo. The crude residue was purified by silica gel chromatography (petroleum ether/EtOAc=100/1) to give the title compound (1.9 g, 50%) as a light yellow oil. LCMS M/Z (M+H) 198.

Step 4:

6-bromo-7-(difluoromethyl)-4-methyl-1,2,3,4-tetrahydroquinoline

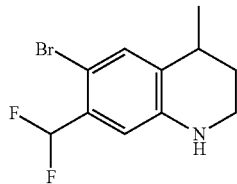

To a solution of 7-(difluoromethyl)-4-methyl-1,2,3,4-tetrahydroquinoline (700 mg, 3.55 mmol) in DCM (10 mL) at 0° C. was added 1-bromopyrrolidine-2,5-dione (632 mg, 3.55 mmol) portionwise. The resulting mixture was stirred at room temperature for 1 h. Water (10 mL) was added and the mixture was extracted with DCM (20 mL×2). The combined organic layers were dried over anhydrous Na$_2$SO$_4$, filtered and concentrated in vacuo to give the title compound (1 g, crude) as a red oil that required no further purification. LCMS M/Z (M+H) 276.

Step 5:

7-(difluoromethyl)-4-methyl-6-(1-methyl-1H-pyrazol-4-yl)-1,2,3,4-tetrahydroquinoline

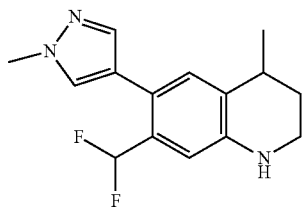 [SMILES: CC1CCNc2cc(C(F)F)c(-c3cnn(C)c3)cc21]

To a solution of 6-bromo-7-(difluoromethyl)-4-methyl-1,2,3,4-tetrahydroquinoline (1.0 g, 3.62 mmol), 1-methyl-4-(4,4,5,5-tetramethyl-1,3,2-dioxaborolan-2-yl)-1H-pyrazole (904 mg, 4.35 mmol) and Na$_2$CO$_3$ (1.15 g, 10.86 mmol) in THF (15 mL) and H$_2$O (3 mL) was added chloro(2-dicyclohexylphosphino-2',4',6'-tri-i-propyl-1,1'-biphenyl)(2'-amino-1,1'-biphenyl-2-yl) palladium(II)(285 mg, 0.36 mmol) and 2-(dicyclohexylphosphino)-2',4',6'-triisopropyl-biphenyl (173 mg, 0.36 mmol). The resulting mixture was heated to 60° C. for 16 h under a nitrogen atmosphere. After cooling to room temperature, the mixture was filtered and concentrated in vacuo. The crude residue was purified by silica gel chromatography (petroleum ether/EtOAc=3/1) to give the title compound (400 mg, 40%) as a red oil. $^1$H NMR (400 MHz, CDCl$_3$) δ 7.53 (s, 1H), 7.40 (s, 1H), 7.05 (s, 1H), 6.81 (s, 1H), 6.54 (t, J=55.2 Hz, 1H), 3.95 (s, 3H), 3.45-3.23

(m, 2H), 3.00-2.79 (m, 1H), 1.99-1.97 (m, 1H), 1.73-1.69 (m, 1H), 1.31 (d, J=6.8 Hz, 3H).

Step 6:

(R,R)-[7-(difluoromethyl)-4-methyl-6-(1-methyl-pyrazol-4-yl)-3,4-dihydro-2H-quinolin-1-yl]-4-methyl-1,3,4,5-tetrahydro-1,5-benzodiazepin-2-one & (R,S)-6-[7-(difluoromethyl)-4-methyl-6-(1-methylpyrazol-4-yl)-3,4-dihydro-2H-quinolin-1-yl]-4-methyl-1,3,4,5-tetrahydro-1,5-benzodiazepin-2-one

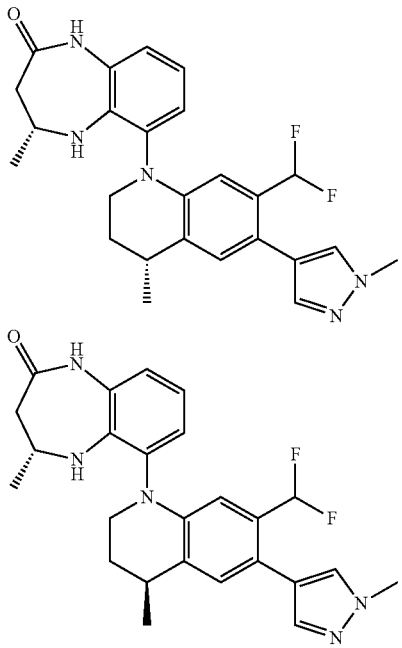

To a solution of 7-(difluoromethyl)-4-methyl-6-(1-methylpyrazol-4-yl)-1,2,3,4-tetrahydroquinoline (300 mg, 1.08 mmol) and (R)-6-bromo-4-methyl-4,5-dihydro-1H-benzo[b][1,4]diazepin-2(3H)-one (Intermediate A, 304 mg, 1.19 mmol) in 1,4-dioxane (5 mL) was added t-BuONa (312 mg, 3.25 mmol) and dichloro[1,3-bis(2,6-di-3-pentylphenyl)imidazol-2-ylidene](3-chloropyridyl)palladium(II) (86 mg, 0.11 mmol). The reaction mixture was heated to 110° C. for 16 h under argon atmosphere. After cooling to room temperature, the mixture was filtered and concentrated in vacuo. The mentioned-above procedures were repeated. The combined crude residue was purified by reverse phase chromatography (acetonitrile 38-68%/0.05% NH$_4$OH in water) to give the racemic compound (30 mg, 3.1%) as a pale yellow solid that was separated using chiral SFC(SFC80; Chiralpak AS 250×30 mm, 5 um; Supercritical CO$_2$/EtOH+DEA=55/45, 50 mL/min) to give (R,R)-6-[7-(difluoromethyl)-4-methyl-6-(1-methylpyrazol-4-yl)-3,4-dihydro-2H-quinolin-1-yl]-4-methyl-1,3,4,5-tetrahydro-1,5-benzodiazepin-2-one (8 mg, first peak) as a yellow solid and (R,S)-6-[7-(difluoromethyl)-4-methyl-6-(1-methylpyrazol-4-yl)-3,4-dihydro-2H-quinolin-1-yl]-4-methyl-1,3,4,5-tetrahydro-1,5-benzodiazepin-2-one (12 mg, second peak) as a yellow solid. Absolute configuration was arbitrarily assigned to each enantiomer. Example 307: $^1$H NMR (400 MHz, DMSO-d$_6$) δ 9.66-9.65 (m, 1H), 7.74-7.73 (m, 1H), 7.48 (s, 1H), 7.17-7.15 (m, 1H), 6.95-6.72 (m, 4H), 6.30-6.29 (m, 1H), 4.72-4.63 (m, 1H), 3.90-3.85 (m, 4H), 3.62-3.44 (m, 1H), 3.28-3.04 (m, 2H), 2.30-2.20 (m, 2H), 2.08-1.80 (m, 1H), 1.37-1.34 (m, 3H), 1.30-1.23 (m, 1H), 1.17-1.09 (m, 3H). LCMS M/Z (M+H) 452. Example 308: $^1$H NMR (400 MHz, DMSO-d$_6$) δ 9.67-9.65 (m, 1H), 7.74 (s, 1H), 7.48 (s, 1H), 7.19-7.15 (m, 1H), 6.92-6.71 (m, 4H), 6.29-6.25 (m, 1H), 4.80-4.55 (m, 1H), 3.90-3.85 (m, 4H), 3.57-3.49 (m, 1H), 2.29-2.22 (m, 2H), 2.08-1.80 (m, 1H), 1.38-1.20 (m, 5H), 1.18-1.07 (m, 3H), 0.90-0.83 (m, 1H). LCMS M/Z (M+H) 452.

Examples 309 & 310

(R,S)-6-[7-(difluoromethyl)-3-methyl-6-(1-methyl-pyrazol-4-yl)-3,4-dihydro-2H-quinolin-1-yl]-4-methyl-1,3,4,5-tetrahydro-1,5-benzodiazepin-2-one & (R,R)-6-[7-(difluoromethyl)-3-methyl-6-(1-methylpyrazol-4-yl)-3,4-dihydro-2H-quinolin-1-yl]-4-methyl-1,3,4,5-tetrahydro-1,5-benzodiazepin-2-one

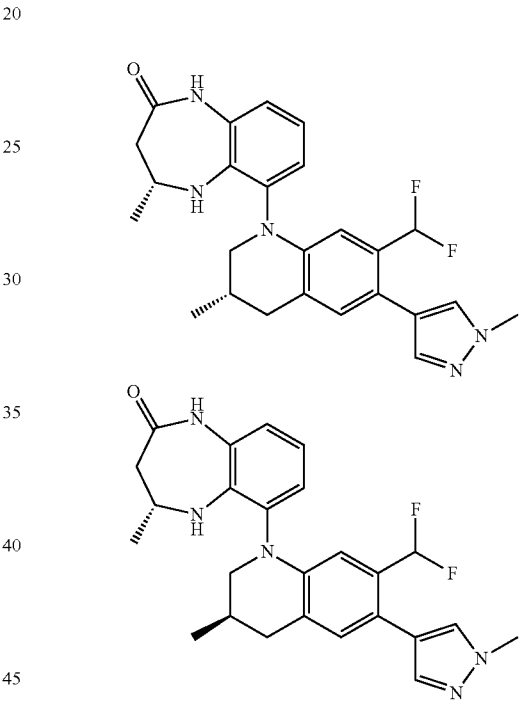

Example 309 & 310 were prepared in a similar fashion to Examples 307 & 308 using the corresponding 7-bromo-3-methylquinoline instead of 7-chloro-4-methyl-quinoline. (4R)-6-[7-(difluoromethyl)-3-methyl-6-(1-methylpyrazol-4-yl)-3,4-dihydro-2H-quinolin-1-yl]-4-methyl-1,3,4,5-tetrahydro-1,5-benzodiazepin-2-one (10 mg) was separated using chiral SFC (SFC80, Chiralpak AD 250×30 mm I.D., 5 um; Supercritical CO$_2$/MEOH+NH$_3$.H$_2$O=60/40; 80 ml/min) to give (R,S)-6-[7-(difluoromethyl)-3-methyl-6-(1-methylpyrazol-4-yl)-3,4-dihydro-2H-quinolin-1-yl]-4-methyl-1,3,4,5-tetrahydro-1,5-benzodiazepin-2-one (1 mg, first peak) as a white solid and (R,R)-6-[7-(difluoromethyl)-3-methyl-6-(1-methylpyrazol-4-yl)-3,4-dihydro-2H-quinolin-1-yl]-4-methyl-1,3,4,5-tetrahydro-1,5-benzodiazepin-2-one (1 mg, second peak) as a white solid. Absolute configuration was arbitrarily assigned to each enantiomer. Example 309: $^1$H NMR (400 MHz, DMSO-d$_6$) δ 9.65 (s, 1H), 7.71 (s, 1H), 7.47 (s, 1H), 7.09-7.08 (m, 1H), 6.92-6.87 (m, 2H), 6.84-6.75 (m, 1H), 6.72 (t, J=56.0 Hz, 1H), 6.31-6.26 (m, 1H), 5.33-5.31 (m, 1H), 3.92-3.80 (m, 4H), 3.30-3.29 (m, 1H), 3.24-2.86 (m, 3H), 2.30-2.25 (m, 1H), 2.06-1.90 (m, 2H), 1.23 (s, 3H), 1.11-1.03 (m, 3H). LCMS M/Z (M+H) 452. Example 310: $^1$H NMR (400 MHz, DMSO-d$_6$) δ 9.65-7.63 (m, 1H), 7.71 (s, 1H), 7.47-7.46 (m, 1H), 7.08 (s, 1H), 6.97-6.77 (m, 3H), 6.74-6.64 (m, 1H), 6.31-6.28 (m, 1H), 5.35-5.29 (m, 1H), 3.88-3.82 (m, 4H), 3.24-3.19 (m, 1H), 3.04-2.86 (m, 3H), 2.53-2.52 (m, 1H), 2.02-1.97 (m, 2H), 1.23 (s, 3H), 1.18-1.03 (m, 3H). LCMS M/Z (M+H) 452.

Example 311

5-[7-(difluoromethyl)-1-[(4R)-4-methyl-2-oxo-1,3,4,5-tetrahydro-1,5-benzodiazepin-6-yl]-3,4-dihydro-2H-quinolin-6-yl]-N-methyl-pyridine-2-carboxamide

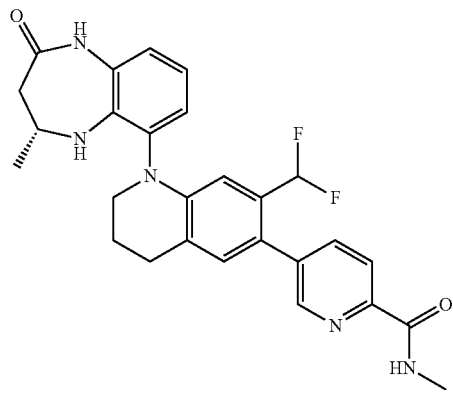 [SMILES: CNC(=O)c1ccc(-c2cc3c(cc2C(F)F)N(c2cccc4c2N[C@H](C)CC(=O)N4)CCC3)cn1]

Step 1:

7-(difluoromethyl)-1-(2-fluoro-3-nitrophenyl)-1,2,3,4-tetrahydroquinoline

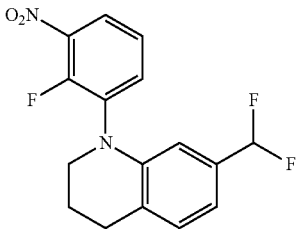 [SMILES: O=[N+]([O-])c1cccc(N2CCCc3ccc(C(F)F)cc32)c1F]

To a solution of 3-bromo-2-fluoronitrobenzene (1.0 g, 4.55 mmol) and 7-(difluoromethyl)-1,2,3,4-tetrahydroquinoline (833 mg, 4.55 mmol) in DMF (20 mL) was added 4,5-bis(diphenylphosphino)-9,9-dimethylxanthene (526 mg, 0.91 mmol), Cs$_2$CO$_3$ (4.44 g, 13.64 mmol) and palladium(II) acetate (102 mg, 0.45 mmol). The resulting mixture was heated to 130° C. for 16 h under a nitrogen atmosphere. After cooling the reaction to room temperature, the reaction mixture was filtered and concentrated in vacuo. The crude residue was purified by silica gel chromatography (petroleum ether/EtOAc=30/1) to give the title compound (450 mg, 31%) as a red solid. $^1$H NMR (400 MHz, CDCl$_3$) δ 7.87 (d, J=7.2 Hz, 1H), 7.59 (d, J=7.2 Hz, 1H), 7.30-7.25 (m, 1H), 7.13 (d, J=7.6 Hz, 1H), 6.87 (d, J=8.0 Hz, 1H), 6.49 (s, 1H), 6.41 (d, J=56.8 Hz, 1H), 3.61 (t, J=5.6 Hz, 2H), 2.91 (t, J=6.0 Hz, 2H), 2.11-2.04 (m, 2H).

Step 2:

6-bromo-7-(difluoromethyl)-1-(2-fluoro-3-nitrophenyl)-1,2,3,4-tetrahydroquinoline

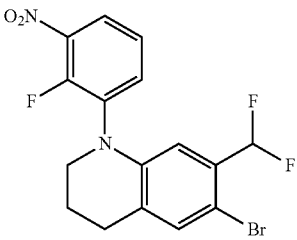 [SMILES: O=[N+]([O-])c1cccc(N2CCCc3cc(Br)c(C(F)F)cc32)c1F]

To a solution of 7-(difluoromethyl)-1-(2-fluoro-3-nitrophenyl)-3,4-dihydro-2H-quinoline (450 mg, 1.4 mmol) in DCM (10 mL) at 0° C. was added 1-bromopyrrolidine-2,5-dione (249 mg, 1.4 mmol) portionwise. The resulting mixture was stirred at room temperature for 1 h. The reaction was quenched with H$_2$O (20 mL) and extracted with DCM (20 mL). The organic phase was separated, dried over anhydrous Na$_2$SO$_4$, filtered and concentrated in vacuo. The crude residue was purified by silica gel chromatography (petroleum ether/EtOAc=30/1) to give the title compound (500 mg, 89%) as a red solid. $^1$H NMR (400 MHz, CDCl$_3$) δ 7.97-7.87 (m, 1H), 7.66-7.55 (m, 1H), 7.36-7.28 (m, 2H), 6.74 (t, J=54.8 Hz, 1H), 6.64 (s, 1H), 3.62 (J=5.6 Hz, 2H), 2.91 (t, J=6.0 Hz, 2H), 2.14-2.02 (m, 2H).

Step 3:

(R)-3-((2-(6-bromo-7-(difluoromethyl)-3,4-dihydroquinolin-1(2H)-yl)-6-nitrophenyl)amino)butanoic acid

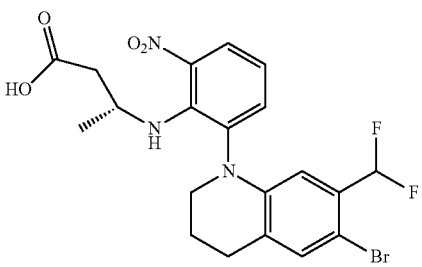 [SMILES: C[C@H](CC(=O)O)Nc1c(N2CCCc3cc(Br)c(C(F)F)cc32)cccc1[N+](=O)[O-]]

To a solution of 6-bromo-7-(difluoromethyl)-1-(2-fluoro-3-nitro-phenyl)-3,4-dihydro-2H-quinoline (450 mg, 1.12 mmol) in DMF (10 mL) was added Cs$_2$CO$_3$ (1.10 mg, 3.37 mmol) and (3R)-3-aminobutanoic acid (174 mg, 1.68 mmol). The resulting mixture was heated to 90° C. for 16 h. After cooling to room temperature, water (10 mL) was added and the mixture was extracted with EtOAc (20 mL). The aqueous phase was acidified with HCl (2 N) to pH 3-4 and then extracted with EtOAc (20 mL). The organic phase was separated, dried over anhydrous Na$_2$SO$_4$, filtered and concentrated in vacuo to give the title compound (200 mg, crude) as red oil that required no further purification. LCMS M/Z (M+H) 484.

Step 4:

(R)-6-(6-bromo-7-(difluoromethyl)-3,4-dihydroquinolin-1(2H)-yl)-4-methyl-4,5-dihydro-1H-benzo[b][1,4]diazepin-2(3H)-one

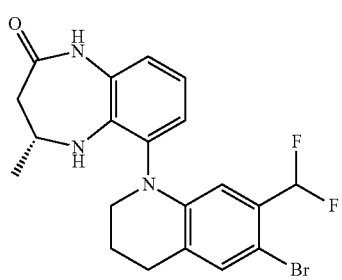 [SMILES: C[C@@H]1CC(=O)Nc2cccc(N3CCCc4cc(Br)c(C(F)F)cc43)c2N1]

To a solution of (R)-3-((2-(6-bromo-7-(difluoromethyl)-3,4-dihydroquinolin-1 (2H)-yl)-6-nitrophenyl)amino)butanoic acid (150 mg, 0.31 mmol) in acetic acid (3 mL) was added Fe powder (90 mg, 1.55 mmol). The resulting mixture was heated to 100° C. for 2 h. After cooling to room temperature, the mixture was filtered and filtrate was made basic with sat. aq. NaHCO$_3$ to pH 8 and then extracted with EtOAc (20 mL×2). The organic phase was separated, dried over anhydrous Na$_2$SO$_4$, filtered and concentrated in vacuo to give the title compound (100 mg, crude) as red oil that required no further purification. LCMS M/Z (M+H) 436.

Step 5:

(R)-5-(7-(difluoromethyl)-1-(4-methyl-2-oxo-2,3,4,5-tetrahydro-1H-benzo[b][1,4]diazepin-6-yl)-1,2,3,4-tetrahydroquinolin-6-yl)-N-methylpicolinamide

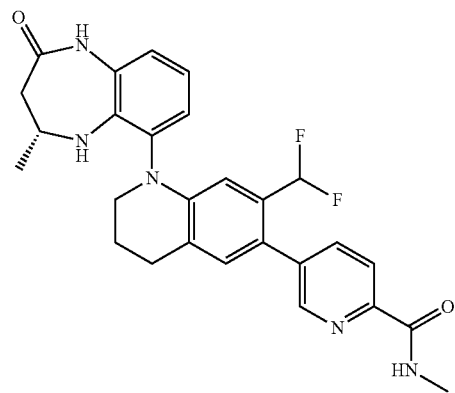 [SMILES: CNC(=O)c1ccc(-c2cc3c(cc2C(F)F)N(c2cccc4c2N[C@H](C)CC(=O)N4)CCC3)cn1]

To a solution of (R)-6-(6-bromo-7-(difluoromethyl)-3,4-dihydroquinolin-1(2H)-yl)-4-methyl-4,5-dihydro-1-benzo[b][1,4]diazepin-2(3H)-one (100 mg, 0.23 mmol) in THF (2 mL) and H$_2$O (0.5 mL) was added 2-(N-methylaminocarbonyl)pyridine-5-boronicacidpincolester (90 mg, 0.34 mmol), chloro(2-dicyclohexylphosphino-2',4',6'-tri-i-propyl-1,1'-biphenyl)(2'-amino-1,1'-biphenyl-2-yl) palladium (II)(18 mg, 0.02 mmol), 2-(dicyclohexylphosphino)-2',4',6'-triisopropylbiphenyl(11 mg, 0.02 mmol) and Na$_2$CO$_3$ (73 mg, 0.69 mmol). The reaction mixture was irradiated in a microwave at 60° C. for 0.5 h. The reaction was concentrated in vacuo and the residue was purified by reverse phase chromatography (acetonitrile 34-64%/0.05% NH$_4$OH in water) to give the title compound (19 mg, 17%) as a white solid. $^1$H NMR (400 MHz, DMSO-d$_6$) δ 9.66 (d, J=4.8 Hz, 1H), 8.80 (d, J=4.4 Hz, 1H), 8.52 (s, 1H), 8.05 (d, J=8.0 Hz, 1H), 7.87 (d, J=8.0 Hz, 1H), 7.12 (s, 1H), 7.00-6.89 (m, 2H), 6.86-6.83 (m, 1H), 6.81 (t, J=51.2 Hz, 1H), 6.35 (d, J=7.2 Hz, 1H), 4.87-4.64 (m, 1H), 3.98-3.80 (m, 1H), 3.61-3.40 (m, 2H), 2.98-2.93 (m, 2H), 2.84 (d, J=4.4 Hz, 3H), 2.61-2.55 (m, 1H), 2.31-2.25 (m, 1H), 2.23-1.95 (m, 2H), 1.31-1.03 (m, 3H). LCMS M/Z (M+H) 492.

Example 312

(4R)-4-methyl-6-[3-(1-methylpyrazol-1-yl)-8-isoquinolyl]-1,3,4,5-tetrahydro-1,5-benzodiazepin-2-one

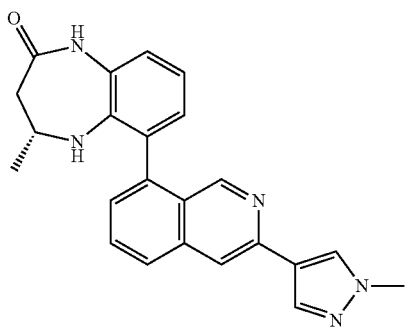

Step 1:

8-chloro-3-(1-methyl-1H-pyrazol-4-yl)isoquinoline

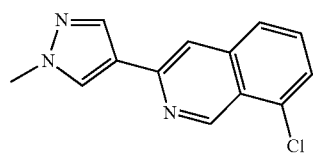 [SMILES: Cn1cc(-c2cc3cccc(Cl)c3cn2)cn1]

To a solution of 3-bromo-8-chloroisoquinoline (500 mg, 2.1 mmol) in dioxane/H$_2$O (12 mL, 5:1) was added 1-methyl-4-(4,4,5,5-tetramethyl-1,3,2-dioxaborolan-2-yl)-1H-pyrazole (472 mg, 2.3 mmol), [1,1'-bis(diphenylphosphino)ferrocene]dichloropalladium(II) (75 mg, 0.1 mmol) and Na$_2$CO$_3$ (437 mg, 4.1 mmol). The reaction mixture was heated to 90° C. for 16 h under a nitrogen atmosphere. After cooling to room temperature, the mixture was filtered and filtrate was diluted with EtOAc (30 mL) and washed with H$_2$O (20 mL×2). The organic phase was dried over anhydrous Na$_2$SO$_4$, filtered and concentrated in vacuo. The crude residue was purified by silica gel chromatography (DCM/MeOH=20/1) to give the title compound (430 mg, 85%) as a yellow solid. $^1$H NMR (400 MHz, DMSO-d$_6$) δ9.49 (s, 1H), 8.37 (s, 1H), 8.14 (s, 1H), 8.10 (s, 1H), 7.89-7.86 (m, 1H), 7.72-7.70 (m, 2H), 3.92 (s, 3H).

Step 2:

3-(1-methyl-1H-pyrazol-4-yl)-8-(4,4,5,5-tetramethyl-1,3,2-dioxaborolan-2-yl)isoquinoline

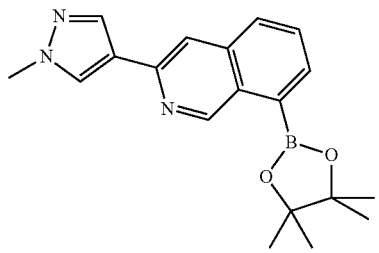

To a solution of 8-chloro-3-(1-methyl-1H-pyrazol-4-yl)isoquinoline (300 mg, 1.2 mmol) in DMF (8 mL) was added 4,4,4',4',5,5,5',5'-octamethyl-2,2'-bi(1,3,2-dioxaborolane) (938 mg, 3.7 mmol), [1,1'-bis(diphenylphosphino)ferrocene]dichloropalladium(II) (45 mg, 0.06 mmol) and potassium acetate (242 mg, 2.5 mmol). The reaction mixture was heated to 120° C. for 16 h under a nitrogen atmosphere. After cooling to room temperature, the mixture was filtered and the filtrate was diluted with EtOAc (40 mL) and washed with $H_2O$ (30 mL×2). The organic phase was dried over anhydrous $Na_2SO_4$, filtered and concentrated in vacuo. The crude residue was purified by silica gel chromatography (DCM/MeOH=50/1) to give the title compound (240 mg, crude) as a yellow solid that required no further purification. LCMS M/Z (M+H) 336.

Step 3:

(4R)-4-methyl-6-[3-(1-methylpyrazol-4-yl)-8-isoquinolyl]-1,3,4,5-tetrahydro-1,5-benzodiazepin-2-one

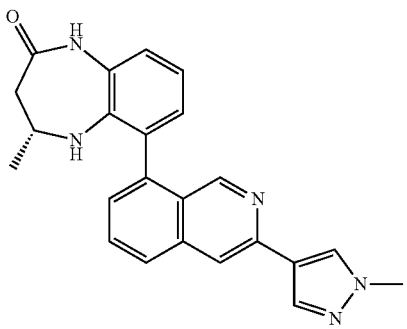

To a solution of 3-(1-methyl-1H-pyrazol-4-yl)-8-(4,4,5,5-tetramethyl-1,3,2-dioxaborolan-2-yl)isoquinoline (100 mg, 0.3 mmol) in THF (10 mL) and $H_2O$ (2 mL) was added (4R)-6-bromo-4-methyl-1,3,4,5-tetrahydro-1,5-benzodiazepin-2-one (91 mg, 0.36 mmol), chloro(2-dicyclohexylphosphino-2',4',6'-tri-i-propyl-1,1'-biphenyl)(2'-amino-1,1'-biphenyl-2-yl) palladium(II) (24 mg, 0.03 mmol), 2-(dicyclohexylphosphino)-2',4',6'-triisopropylbiphenyl(14 mg, 0.03 mmol) and $Na_2CO_3$ (95 mg, 0.9 mmol). The reaction mixture was heated to 60° C. for 16 h under a nitrogen atmosphere. After cooling to room temperature, the reaction was concentrated in vacuo and the residue was diluted with DCM (10 mL) and washed with $H_2O$ (10 mL×2). The organic phase was dried over anhydrous $Na_2SO_4$, filtered and concentrated in vacuo. The crude residue was purified by reverse phase chromatography (acetonitrile 30-60%/0.05% $NH_4OH$ in water) to give the title compound (32 mg, 25%) as a white solid. $^1H$ NMR (400 MHz, DMSO-$d_6$) δ9.42 (s, 1H), 8.81 (d, J=8.0 Hz, 1H), 8.26 (s, 1H), 8.08 (s, 1H), 8.04 (s, 1H), 7.94 (d, J=8.0 Hz, 1H), 7.85-7.76 (m, 1H), 7.42 (d, J=7.2 Hz, 1H), 7.10 (d, J=4.8 Hz, 1H), 6.96-6.89 (m, 2H), 3.92 (s, 3H), 3.76-3.72 (m, 1H), 3.66-3.57 (m, 2H), 2.29-2.24 (m, 1H), 0.96-0.79 (m, 3H). LCMS M/Z (M+H) 384.

Example 313

$IC_{50}$ Measurements for Inhibitors Using CBP TR-FRET Binding Assay

His/Flag epitope tagged CBP was cloned, expressed, and purified to homogeneity. CBP binding and inhibition was assessed by monitoring the engagement of a biotinylated small molecule compound with the target using the TR-FRET assay technology (Perkin-Elmer). Specifically, in a 384 well ProxiPlate CBP (4 nM final) was combined with biotin-ligand (60 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 10 minutes incubation at room temperature, a mixture Eu-W1024 Anti-6×His antibody (Perkin Elmer ADO 110) and SureLight™ Allophycocyanin-Streptavidin (APC-SA, Perkin Elmer CR130-100) were added to a final concentrations of 0.2 nMolar antibody and 50 nMolar APC-SA, respectively. After twenty minutes of equilibration, the plates were read on an Envision instrument and $IC_{50}$s calculated using a four parameter non-linear curve fit.

$IC_{50}$ Measurements for Inhibitors Using BRD4 AlphaLisa Binding Assay

His/Flag epitope tagged BRD4 $BD1_{42\text{-}168}$ was cloned, expressed, and purified to. BRD4 binding and inhibition was assessed by monitoring the engagement of biotinylated H4-tetraacetyl peptide (New England Peptide, NEP2069-1/13) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minutes incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit.

MYC_RPL19 QuantiGene Assay in MV-4-11 Cells

QuantiGene 2.0 Reagent system, Affymetrix: HUMAN MYCN; V-myc myelocytomatosis viral related oncogene, neuroblastoma derived (avian); NM_005378 SA-15008. 10,000 MV-4-11 cells (GNE in-house) were plated in 75 ul complete media: RPMI-1640 (GNE in-house), 10% FBS (Life Technologies, cat. no. 10082), 1% Pen-strep (GNE in-house), in 96 well clear flat bottom plates (Costar, cat. no. 3595). 25 ul compound was added for 4 hours at 37 deg C. in a 1:3 serial dilution 10-point dose response, with a final DMSO concentration=0.2%. The cells were then lysed according to the assay kit's protocol and frozen at −80 deg C. The following day, an appropriate volume of Working Probe Set was prepared by combining the following reagents in the order listed: Nuclease-free water, Lysis Mixture, Blocking Reagent, and 2.0 Probe Set (MYC or RPL19). 20 ul of the working probe set was added into each assay well on the capture plate, and then 80 ul of the lysates were transferred into the assay plates. The capture plate was placed in a 55 deg C. incubator for overnight hybridization (16-20 hours). The following day, wash buffer was prepared according to manufacturer's recommendations. The capture plates were washed with 300 ul per well of 1× wash buffer three times. Then 100 ul Pre-Amplifier was added to the plate for a 60 minute incubation at 55 deg C. After the incubation, the capture plate was washed with 300 ul per well of 1× wash buffer three times, and 100 ul Amplifier was added to the plate for a 60 minute incubation at 55 deg C. The capture plate was again washed with 300 ul per well of 1× wash buffer three times, and 100 ul Label Probe was added to the plate for a 60 minute incubation at 50 deg C. Then the capture plate was washed with 300 ul per well of 1× wash buffer three times, and 100 ul 2.0 Substrate was added to each well of the plate. The plates were incubated at RT for 5 minutes in the dark and read on the Envision using the luminescence protocol, with an integration time set at 0.2 seconds.

Data for representative compounds of formula (I) from the three assays described above is provided in the following table.

| Example | Compound | CBP HTRF $IC_{50}$ | BRD4 Alpha $IC_{50}$ | Myc $IC_{50}$ |
|---|---|---|---|---|
| 1 | | 0.498 | >5.2632 | |
| 2 | | 0.704 | 2.537 | |
| 3 | | 0.608 | 12.464 | |
| 4 | | 0.586 | | |
| 5 | | 0.213 | 6.877 | |

-continued

| Example | Compound | CBP HTRF IC$_{50}$ | BRD4 Alpha IC$_{50}$ | Myc IC$_{50}$ |
|---|---|---|---|---|
| 6 | | 0.180 | | |
| 7 | | 0.166 | | |
| 8 | | 0.251 | 20.5 | 2.214 |
| 9 | | 0.457 | 15.218 | |
| 10 | | 0.229 | 2.257 | |
| 11 | | 0.255 | 7.014 | 0.537 |

-continued

| Example | Compound | CBP HTRF IC$_{50}$ | BRD4 Alpha IC$_{50}$ | Myc IC$_{50}$ |
|---|---|---|---|---|
| 12 | | 0.291 | 4.752 | |
| 13 | | 0.921 | 6.940 | |
| 14 | | 0.224 | 2.761 | |
| 15 | | 0.153 | 5.836 | |
| 16 | | 0.590 | 2.314 | |
| 17 | | 0.261 | 3.621 | |
| 18 | | 0.174 | 1.473 | |

-continued

| Example | Compound | CBP HTRF IC$_{50}$ | BRD4 Alpha IC$_{50}$ | Myc IC$_{50}$ |
|---|---|---|---|---|
| 19 | | 0.236 | 3.458 | |
| 20 | | 0.221 | | |
| 21 | | 0.189 | 4.160 | |
| 22 | | 0.252 | 6.080 | 2.254 |
| 23 | | 0.503 | >19.7 | |
| 24 | | 0.820 | >19.7 | |

-continued

| Example | Compound | CBP HTRF IC$_{50}$ | BRD4 Alpha IC$_{50}$ | Myc IC$_{50}$ |
|---|---|---|---|---|
| 25 | | 0.509 | 5.727 | |
| 26 | | 0.560 | 14.505 | |
| 27 | | 0.306 | 13.011 | |
| 28 | | 0.384 | 5.090 | |
| 29 | | 0.331 | 2.255 | |

-continued

| Example | Compound | CBP HTRF IC$_{50}$ | BRD4 Alpha IC$_{50}$ | Myc IC$_{50}$ |
|---|---|---|---|---|
| 30 | | 0.544 | 2.726 | |
| 31 | | 0.677 | 3.161 | |
| 32 | | 0.696 | 8.505 | |
| 33 | | 0.019 | 2.574 | 0.215 |

-continued

| Example | Compound | CBP HTRF IC$_{50}$ | BRD4 Alpha IC$_{50}$ | Myc IC$_{50}$ |
|---|---|---|---|---|
| 34 | | 0.027 | 3.126 | 0.183 |
| 35 | | 0.057 | | |
| 36 | | 0.266 | 4.967 | |
| 37 | | 0.125 | 3.442 | |
| 38 | | 0.119 | 2.742 | 0.851 |

-continued

| Example | Compound | CBP HTRF IC$_{50}$ | BRD4 Alpha IC$_{50}$ | Myc IC$_{50}$ |
|---|---|---|---|---|
| 39 | | 0.210 | 4.760 | 2.957 |
| 40 | | 0.719 | 19.7++ | 19.763 |
| 41 | | 0.195 | 6.822 | |
| 42 | | 0.235 | 2.671 | |
| 43 | | 0.440 | | |
| 44 | | 0.690 | 15.431 | |

-continued

| Example | Compound | CBP HTRF IC$_{50}$ | BRD4 Alpha IC$_{50}$ | Myc IC$_{50}$ |
|---|---|---|---|---|
| 45 | | 0.913 | >19.7 | |
| 46 | | 1.050 | >19.7 | |
| 47 | | 0.200 | 3.250 | |
| 48 | | 0.526 | 3.708 | |
| 49 | | 0.736 | >19.7 | |
| 50 | | 0.310 | 8.061 | |

-continued

| Example | Compound | CBP HTRF IC$_{50}$ | BRD4 Alpha IC$_{50}$ | Myc IC$_{50}$ |
|---|---|---|---|---|
| 51 | | 1.033 | 16.612 | |
| 52 | | 0.384 | 4.646 | |
| 53 | | 0.588 | 10.819 | |
| 54 | | 0.663 | 5.181 | |
| 55 | | 0.851 | >10.5 | |

-continued

| Example | Compound | CBP HTRF IC$_{50}$ | BRD4 Alpha IC$_{50}$ | Myc IC$_{50}$ |
|---|---|---|---|---|
| 56 | | 0.037 | 0.898 | 0.428 |
| 57 | | 0.049 | 4.028 | 0.495 |
| 58 | | 0.132 | 5.727 | |
| 59 | | 0.385 | 13.056 | |
| 60 | | 0.040 | 0.637 | 0.326 |

-continued

| Example | Compound | CBP HTRF IC$_{50}$ | BRD4 Alpha IC$_{50}$ | Myc IC$_{50}$ |
|---|---|---|---|---|
| 61 | | 0.065 | 1.801 | 0.404 |
| 62 | | 0.936 | >19.7 | |
| 63 | | 0.149 | 2.487 | |
| 64 | | 0.254 | 5.974 | |
| 65 | | 0.199 | 5.611 | |
| 66 | | 0.616 | 10.482 | |

-continued

| Example | Compound | CBP HTRF IC$_{50}$ | BRD4 Alpha IC$_{50}$ | Myc IC$_{50}$ |
|---|---|---|---|---|
| 67 | | >19.7 | >19.7 | |
| 68 | | 0.100 | 4.509 | 1.530 |
| 69 | | 0.424 | >19.7 | |
| 70 | | 0.994 | >10.5 | |
| 71 | | 0.910 | 5.121 | |
| 72 | | 0.894 | 19.7++ | |

| Example | Compound | CBP HTRF IC$_{50}$ | BRD4 Alpha IC$_{50}$ | Myc IC$_{50}$ |
|---|---|---|---|---|
| 73 | | 0.320 | 5.583 | 1.766 |
| 74 | | 0.266 | 4.133 | 1.339 |
| 75 | | 0.192 | 5.607 | 0.889 |
| 76 | | 0.377 | 6.874 | 2.191 |
| 77 | | 0.157 | 9.297 | 2.035 |
| 78 | | 0.483 | 17.939 | |

-continued

| Example | Compound | CBP HTRF IC$_{50}$ | BRD4 Alpha IC$_{50}$ | Myc IC$_{50}$ |
|---|---|---|---|---|
| 79 | | 0.838 | 5.067 | |
| 80 | | 0.030 | 1.686 | 0.217 |
| 81 | | 0.175 | 6.128 | |
| 82 | | 0.099 | 3.651 | |
| 83 | | 0.082 | 4.914 | 0.401 |

-continued

| Example | Compound | CBP HTRF IC$_{50}$ | BRD4 Alpha IC$_{50}$ | Myc IC$_{50}$ |
|---|---|---|---|---|
| 84 | | 0.026 | 1.477 | |
| 85 | | 0.010 | 0.995 | 0.049 |
| 86 | | 0.046 | 2.778 | 0.158 |
| 87 | | 0.083 | 4.688 | 0.534 |
| 88 | | 0.265 | 13.045 | |

-continued

| Example | Compound | CBP HTRF IC$_{50}$ | BRD4 Alpha IC$_{50}$ | Myc IC$_{50}$ |
|---------|----------|--------------------|-----------------------|---------------|
| 89 | | 0.118 | >19.7 | 0.720 |
| 90 | | 0.052 | >19.7 | 0.413 |
| 91 | | 0.106 | 13.966 | |
| 92 | | 0.098 | 3.915 | 0.878 |

-continued

| Example | Compound | CBP HTRF IC$_{50}$ | BRD4 Alpha IC$_{50}$ | Myc IC$_{50}$ |
|---|---|---|---|---|
| 93 | | 0.967 | 10.484 | |
| 94 | | 0.054 | 7.744 | 0.864 |
| 95 | | 0.566 | >19.7 | |
| 96 | | >19.7 | >19.7 | |
| 97 | | 0.506 | 22.137 | |
| 98 | | >19.7 | >19.7 | |

-continued

| Example | Compound | CBP HTRF IC$_{50}$ | BRD4 Alpha IC$_{50}$ | Myc IC$_{50}$ |
|---|---|---|---|---|
| 99 | | 0.100 | 1.479 | |
| 100 | | 0.213 | 2.128 | |
| 101 | | 1.899 | 5.940 | |
| 102 | | 0.548 | 4.675 | |
| 103 | | >19.7 | >19.7 | |
| 104 | | 0.840 | 1.373 | |
| 105 | | >19.7 | >19.7 | |

-continued

| Example | Compound | CBP HTRF IC$_{50}$ | BRD4 Alpha IC$_{50}$ | Myc IC$_{50}$ |
|---|---|---|---|---|
| 106 | | 0.303 | 8.014 | 1.667 |
| 107 | | 0.122 | 1.700 | |
| 108 | | 6.911 | 18.773 | |
| 109 | | 0.040 | 0.894 | 0.327 |
| 110 | | 0.723 | 18.206 | |

-continued

| Example | Compound | CBP HTRF IC$_{50}$ | BRD4 Alpha IC$_{50}$ | Myc IC$_{50}$ |
|---|---|---|---|---|
| 111 | | 0.394 | 2.218 | >4.0 |
| 112 | | 0.500 | 9.334 | |
| 113 | | 0.538 | 13.714 | |
| 114 | | 0.493 | 2.172 | |
| 115 | | 0.528 | 7.575 | |

-continued

| Example | Compound | CBP HTRF IC$_{50}$ | BRD4 Alpha IC$_{50}$ | Myc IC$_{50}$ |
|---|---|---|---|---|
| 116 | | 0.563 | 10.162 | |
| 117 | | 0.398 | 1.822 | |
| 118 | | 0.647 | 3.081 | |
| 119 | | 0.691 | 3.100 | |
| 120 | | 0.599 | 4.280 | |

-continued

| Example | Compound | CBP HTRF IC$_{50}$ | BRD4 Alpha IC$_{50}$ | Myc IC$_{50}$ |
|---|---|---|---|---|
| 121 | | 0.815 | 11.344 | |
| 122 | | 0.844 | >19.7 | |
| 123 | | 0.652 | 12.865 | |
| 124 | | 0.361 | 5.560 | 2.511 |
| 125 | | <0.4803 | 2.176 | |

-continued

| Example | Compound | CBP HTRF IC$_{50}$ | BRD4 Alpha IC$_{50}$ | Myc IC$_{50}$ |
|---|---|---|---|---|
| 126 | | | | |
| 127 | | 2.365 | 7.472 | |
| 128 | | 1.036 | 18.258 | |
| 129 | | 1.326 | 2.729 | |
| 130 | | 13.376 | >19.7 | |
| 131 | | 2.129 | >19.7 | |
| 132 | | 8.617 | 39.8 | |

-continued
| Example | Compound | CBP HTRF IC$_{50}$ | BRD4 Alpha IC$_{50}$ | Myc IC$_{50}$ |
|---|---|---|---|---|
| 133 | 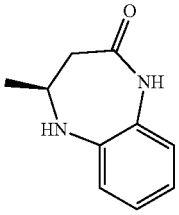 | >19.7 | >19.7 | |
| 134 | 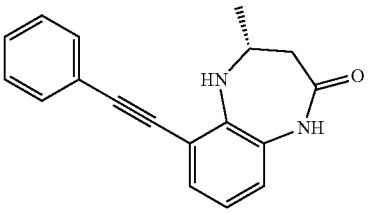 [SMILES: C[C@@H]1CC(=O)Nc2cccc(C#Cc3ccccc3)c2N1] | >19.7 | >10.5 | |
| 135 | 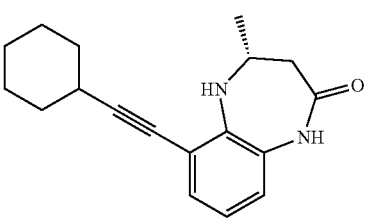 [SMILES: C[C@@H]1CC(=O)Nc2cccc(C#CC3CCCCC3)c2N1] | 2.350 | 16.534 | |
| 136 | 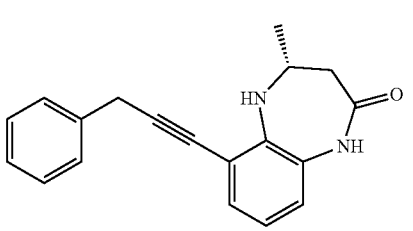 [SMILES: C[C@@H]1CC(=O)Nc2cccc(C#CCc3ccccc3)c2N1] | 1.191 | 3.766 | |
| 137 | 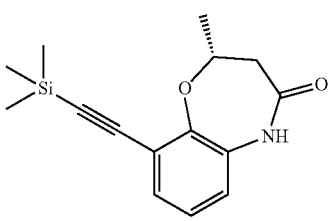 [SMILES: C[C@@H]1CC(=O)Nc2cccc(C#C[Si](C)(C)C)c2O1] | 2.076 | >19.7 | |
| 138 | 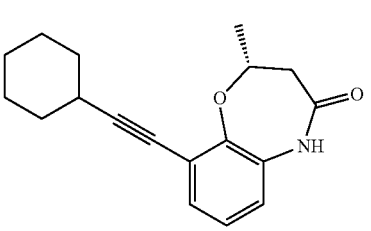 [SMILES: C[C@@H]1CC(=O)Nc2cccc(C#CC3CCCCC3)c2O1] | 1.510 | >19.7 | |
| 139 | 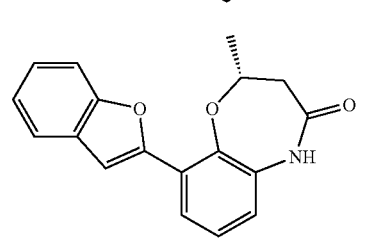 | 0.247 | 0.658 | |

-continued
| Example | Compound | CBP HTRF IC$_{50}$ | BRD4 Alpha IC$_{50}$ | Myc IC$_{50}$ |
|---|---|---|---|---|
| 140 | 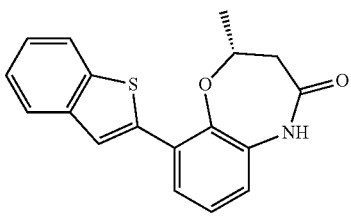 [SMILES: C[C@@H]1CC(=O)Nc2cccc(-c3cc4ccccc4s3)c2O1] | 0.192 | 0.953 | |
| 141 | 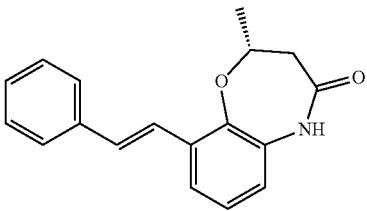 [SMILES: C[C@@H]1CC(=O)Nc2cccc(/C=C/c3ccccc3)c2O1] | 0.154 | 1.098 | |
| 142 | 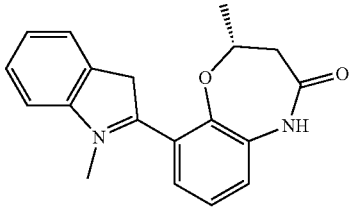 | 0.200 | 4.756 | 1.718 |
| 143 | 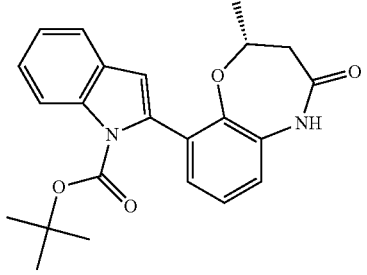 [SMILES: C[C@@H]1CC(=O)Nc2cccc(-c3cc4ccccc4n3C(=O)OC(C)(C)C)c2O1] | 0.265 | 4.339 | |
| 144 | 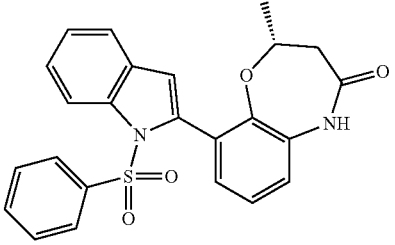 [SMILES: C[C@@H]1CC(=O)Nc2cccc(-c3cc4ccccc4n3S(=O)(=O)c3ccccc3)c2O1] | 0.547 | >19.7 | |
| 145 | 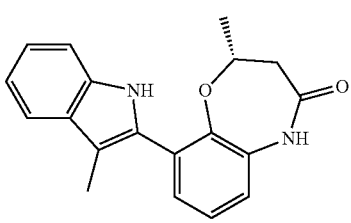 [SMILES: Cc1c(-c2cccc3c2O[C@H](C)CC(=O)N3)[nH]c2ccccc12] | 0.493 | 6.578 | 6.770 |

-continued
| Example | Compound | CBP HTRF IC$_{50}$ | BRD4 Alpha IC$_{50}$ | Myc IC$_{50}$ |
|---|---|---|---|---|
| 146 | 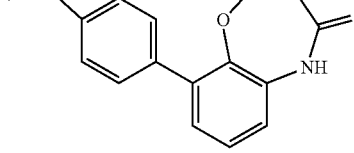 | 0.320 | 1.686 | |
| 147 | 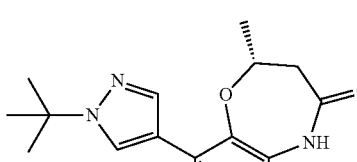 | 0.417 | 13.898 | |
| 148 | 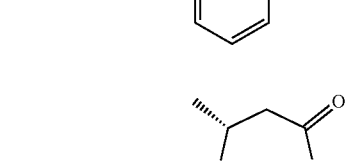 | 0.197 | 2.471 | |
| 149 | 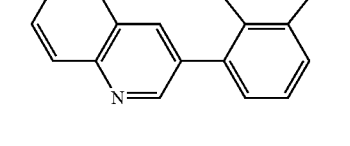 | 0.318 | 0.396 | |
| 150 | 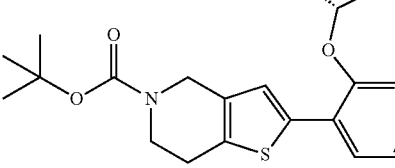 | 0.215 | 1.242 | |
| 151 | 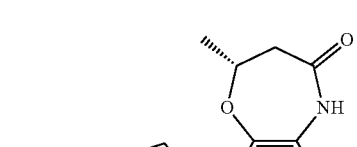 | 0.843 | >19.7 | |

-continued

| Example | Compound | CBP HTRF IC$_{50}$ | BRD4 Alpha IC$_{50}$ | Myc IC$_{50}$ |
|---|---|---|---|---|
| 152 | | 0.412 | 13.293 | |
| 153 | | 0.381 | 10.261 | 1.949 |
| 154 | | 0.467 | 15.207 | 3.234 |
| 155 | | 0.186 | 8.072 | 1.536 |
| 156 | | 0.143 | 11.534 | 1.228 |
| 157 | | 0.265 | 12.348 | 0.968 |

-continued

| Example | Compound | CBP HTRF IC$_{50}$ | BRD4 Alpha IC$_{50}$ | Myc IC$_{50}$ |
|---|---|---|---|---|
| 158 | | 0.451 | 15.223 | 2.866 |
| 159 | | 0.502 | 5.778 | |
| 160 | | 0.472 | 9.222 | |
| 161 | | 0.161 | 6.079 | 1.271 |
| 162 | | 0.313 | 8.098 | |
| 163 | | 0.182 | 14.944 | 1.734 |

-continued

| Example | Compound | CBP HTRF IC$_{50}$ | BRD4 Alpha IC$_{50}$ | Myc IC$_{50}$ |
|---|---|---|---|---|
| 164 | | 0.776 | >19.7 | |
| 165 | | 0.163 | 7.444 | 0.734 |
| 166 | | 0.086 | 5.128 | 0.369 |
| 167 | | 0.304 | 11.225 | 2.610 |
| 168 | | 0.154 | 5.764 | 1.799 |
| 169 | | 0.106 | | |

-continued

| Example | Compound | CBP HTRF IC$_{50}$ | BRD4 Alpha IC$_{50}$ | Myc IC$_{50}$ |
|---|---|---|---|---|
| 170 | | 0.303 | 3.113 | |
| 171 | | 0.447 | 8.342 | 5.468 |
| 172 | | 0.456 | 20.167 | 6.872 |
| 173 | | 0.336 | 12.109 | |
| 174 | | 0.322 | 14.044 | 1.558 |
| 175 | | 0.428 | | |
| 176 | | 0.270 | | |

-continued

| Example | Compound | CBP HTRF IC$_{50}$ | BRD4 Alpha IC$_{50}$ | Myc IC$_{50}$ |
|---|---|---|---|---|
| 177 | | 0.648 | 15.234 | |
| 178 | | 0.504 | 14.084 | |
| 179 | | 0.967 | >19.7 | |
| 180 | | 0.660 | >19.7 | |
| 181 | | 0.635 | >19.7 | |
| 182 | | 0.654 | >19.7 | |

-continued

| Example | Compound | CBP HTRF IC$_{50}$ | BRD4 Alpha IC$_{50}$ | Myc IC$_{50}$ |
|---|---|---|---|---|
| 183 | | 0.638 | >19.7 | |
| 184 | | 0.310 | 2.973 | |
| 185 | | 0.531 | 19.7 | 9.030 |
| 186 | | 0.758 | 18.546 | |
| 187 | | 0.635 | 10.658 | |
| 188 | | 0.204 | 6.402 | 0.275 |
| 189 | | 0.734 | 17.808 | |

-continued

| Example | Compound | CBP HTRF IC$_{50}$ | BRD4 Alpha IC$_{50}$ | Myc IC$_{50}$ |
|---|---|---|---|---|
| 190 | | 0.289 | 17.156 | 1.733 |
| 191 | | 0.388 | >19.7 | 1.098 |
| 192 | | 0.825 | >19.7 | |
| 193 | | 0.591 | >19.7 | |
| 194 | | 0.226 | 6.891 | |
| 195 | | 3.675 | >19.7 | |

-continued

| Example | Compound | CBP HTRF IC$_{50}$ | BRD4 Alpha IC$_{50}$ | Myc IC$_{50}$ |
|---|---|---|---|---|
| 196 | | 0.838 | 15.832 | |
| 197 | | 8.038 | >19.7 | |
| 198 | | 7.583 | >19.7 | |
| 199 | | 2.599 | 8.884 | |
| 200 | | 0.370 | 1.753 | |
| 201 | | 0.395 | 5.513 | 3.839 |

-continued

| Example | Compound | CBP HTRF IC$_{50}$ | BRD4 Alpha IC$_{50}$ | Myc IC$_{50}$ |
|---|---|---|---|---|
| 202 | | 9.015 | >19.7 | |
| 203 | | 0.635 | 22.498 | 3.268 |
| 204 | | 0.286 | 4.581 | |
| 205 | | 0.561 | 16.291 | |
| 206 | | 0.158 | 5.592 | |
| 207 | | 0.190 | 6.441 | 1.730 |

-continued

| Example | Compound | CBP HTRF IC$_{50}$ | BRD4 Alpha IC$_{50}$ | Myc IC$_{50}$ |
|---|---|---|---|---|
| 208 | | 0.209 | 4.550 | |
| 209 | | 0.226 | 11.601 | 3.784 |
| 210 | | 0.351 | 9.962 | |
| 211 | | 0.397 | 13.197 | |
| 212 | | 0.218 | 9.099 | 1.665 |
| 213 | | 0.093 | 5.990 | 2.099 |
| 214 | | 0.181 | 6.502 | |

-continued

| Example | Compound | CBP HTRF IC$_{50}$ | BRD4 Alpha IC$_{50}$ | Myc IC$_{50}$ |
|---|---|---|---|---|
| 215 | | 0.159 | 2.324 | |
| 216 | | 0.201 | 9.671 | |
| 217 | | 0.209 | 5.644 | |
| 218 | | 0.403 | 18.233 | |
| 219 | | 0.735 | 18.759 | |
| 220 | | 0.369 | 13.320 | |

-continued
| Example | Compound | CBP HTRF IC$_{50}$ | BRD4 Alpha IC$_{50}$ | Myc IC$_{50}$ |
|---|---|---|---|---|
| 221 | 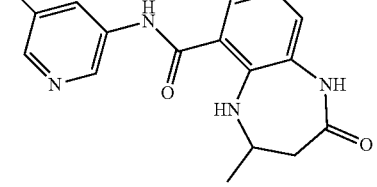 | 0.826 | 18.339 | |
| 222 | 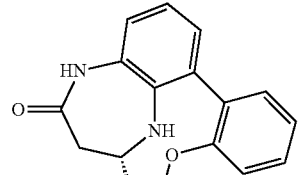 | 0.791 | >19.7 | |
| 223 | 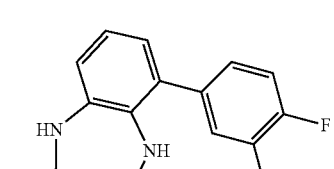 | 0.347 | >19.7 | |
| 224 | 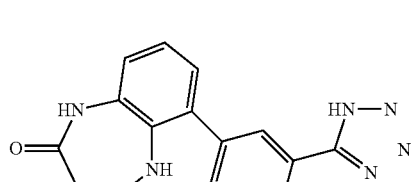 | 0.102 | >19.7 | >19.9 |
| 225 | 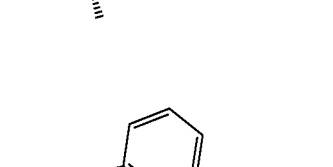 | 0.998 | >19.7 | |
| 226 | 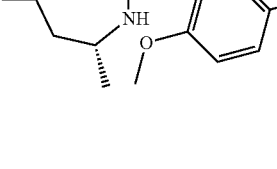 | 0.291 | >19.7 | |

| Example | Compound | CBP HTRF IC$_{50}$ | BRD4 Alpha IC$_{50}$ | Myc IC$_{50}$ |
|---|---|---|---|---|
| 227 | | 0.224 | 5.624 | |
| 228 | | 0.126 | 6.706 | 0.735 |
| 229 | | 0.487 | 13.443 | |
| 230 | | 0.654 | 7.405 | |
| 231 | | 0.559 | 12.867 | |
| 232 | | 0.744 | 9.720 | |

-continued

| Example | Compound | CBP HTRF IC$_{50}$ | BRD4 Alpha IC$_{50}$ | Myc IC$_{50}$ |
|---|---|---|---|---|
| 233 | | 1.012 | | |
| 234 | | 0.353 | 5.794 | |
| 235 | | 0.381 | 3.589 | |
| 236 | | 0.374 | 3.021 | |
| 237 | | 0.503 | 14.921 | |
| 238 | | 0.772 | 6.143 | |
| 239 | | 0.790 | 17.448 | |

-continued

| Example | Compound | CBP HTRF IC$_{50}$ | BRD4 Alpha IC$_{50}$ | Myc IC$_{50}$ |
|---|---|---|---|---|
| 240 | | 0.978 | 11.591 | |
| 241 | | 0.661 | 2.512 | |
| 242 | | 1.016 | 8.551 | |
| 243 | | 0.681 | 6.215 | |
| 244 | | 0.297 | 1.586 | |
| 245 | | 0.155 | 1.252 | |
| 246 | | 0.253 | 2.913 | |

-continued

| Example | Compound | CBP HTRF IC$_{50}$ | BRD4 Alpha IC$_{50}$ | Myc IC$_{50}$ |
|---|---|---|---|---|
| 247 | | 0.607 | 3.350 | |
| 248 | | 0.677 | 2.571 | |
| 249 | | 0.435 | 1.511 | |
| 250 | | 0.509 | 1.007 | |
| 251 | | 0.275 | 13.481 | |
| 252 | | 0.308 | 2.111 | |

-continued

| Example | Compound | CBP HTRF IC$_{50}$ | BRD4 Alpha IC$_{50}$ | Myc IC$_{50}$ |
|---|---|---|---|---|
| 253 | | 0.503 | 15.395 | |
| 254 | | 0.445 | 11.234 | |
| 255 | | 0.477 | 8.546 | |
| 256 | | 0.493 | 4.284 | |
| 257 | | 1.039 | 7.770 | |
| 258 | | 0.495 | 10.771 | |
| 259 | | 0.306 | 2.254 | |

-continued

| Example | Compound | CBP HTRF IC$_{50}$ | BRD4 Alpha IC$_{50}$ | Myc IC$_{50}$ |
|---|---|---|---|---|
| 260 | | 0.113 | 2.626 | |
| 261 | | 0.689 | 4.774 | |
| 262 | | 0.351 | 3.926 | |
| 263 | | 0.521 | 10.903 | |
| 264 | | 0.335 | 14.346 | |
| 265 | | 0.358 | 3.650 | |
| 266 | | 0.425 | 6.216 | |

-continued

| Example | Compound | CBP HTRF IC$_{50}$ | BRD4 Alpha IC$_{50}$ | Myc IC$_{50}$ |
|---|---|---|---|---|
| 267 | | 0.158 | 3.023 | |
| 268 | | 0.317 | 3.379 | |
| 269 | | 0.995 | 8.461 | |
| 270 | | 0.311 | 11.572 | |
| 271 | | 0.831 | >19.7 | |
| 272 | | 0.227 | 6.622 | |
| 273 | | 0.561 | 6.398 | |

-continued

| Example | Compound | CBP HTRF IC$_{50}$ | BRD4 Alpha IC$_{50}$ | Myc IC$_{50}$ |
|---|---|---|---|---|
| 274 | | 0.396 | 4.140 | |
| 275 | | 0.431 | 7.530 | |
| 276 | | 0.440 | 4.155 | |
| 277 | | 0.119 | | |
| 278 | | 0.542 | >19.7 | |
| 279 | | 0.391 | 2.217 | |
| 280 | | 0.387 | 13.946 | |

-continued

| Example | Compound | CBP HTRF IC$_{50}$ | BRD4 Alpha IC$_{50}$ | Myc IC$_{50}$ |
|---|---|---|---|---|
| 281 | | 0.100 | 3.191 | 1.942 |
| 282 | | 0.156 | 10.615 | 3.909 |
| 283 | | 0.202 | 10.383 | |
| 284 | | 0.176 | 10.514 | |
| 285 | | 0.113 | 2.598 | |
| 286 | | 0.045 | 1.722 | |

-continued

| Example | Compound | CBP HTRF IC$_{50}$ | BRD4 Alpha IC$_{50}$ | Myc IC$_{50}$ |
|---|---|---|---|---|
| 287 | | 0.210 | 2.956 | 1.413 |
| 288 | | 0.268 | 7.646 | |
| 289 | | 0.155 | 6.920 | |
| 290 | | 0.014 | 3.24 | 0.376 |
| 291 | | 0.003 | 5.71 | 0.055 |

-continued

| Example | Compound | CBP HTRF IC$_{50}$ | BRD4 Alpha IC$_{50}$ | Myc IC$_{50}$ |
|---|---|---|---|---|
| 292 | | 0.004 | 4.80 | 0.029 |
| 293 | | 0.035 | 9.02 | 1.812 |
| 294 | | 0.009 | 2.98 | 0.950 |
| 295 | | 0.142 | 14.29 | |
| 296 | | 0.009 | 4.71 | 0.152 |

-continued

| Example | Compound | CBP HTRF IC$_{50}$ | BRD4 Alpha IC$_{50}$ | Myc IC$_{50}$ |
|---|---|---|---|---|
| 297 | | 0.020 | 5.22 | 0.280 |
| 298 | | 0.040 | 14.71 | 0.969 |
| 299 | | 0.006 | 6.04 | 0.095 |
| 300 | | 0.012 | 8.19 | 0.147 |

-continued

| Example | Compound | CBP HTRF IC$_{50}$ | BRD4 Alpha IC$_{50}$ | Myc IC$_{50}$ |
|---|---|---|---|---|
| 301 | | 0.046 | 5.44 | |
| 302 | | 0.010 | 5.30 | 0.168 |
| 303 | | 0.052 | 13.77 | |
| 304 | | 0.003 | 3.11 | 0.047 |

-continued
| Example | Compound | CBP HTRF IC$_{50}$ | BRD4 Alpha IC$_{50}$ | Myc IC$_{50}$ |
|---|---|---|---|---|
| 305 | 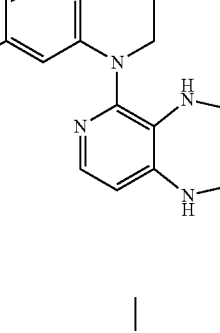 | 0.004 | 5.16 | 0.044 |
| 306 | 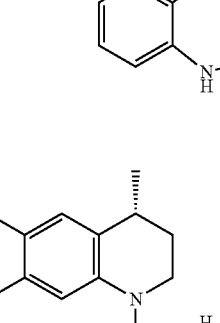 | 0.003 | 4.36 | 0.009 |
| 307 | 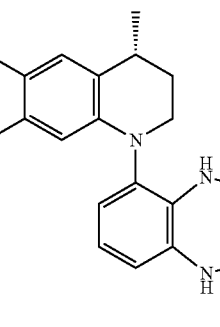 | 0.019 | 11.62 | 2.813 |
| 308 | 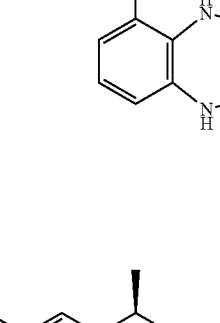 | 0.003 | 3.24 | 0.311 |

-continued

| Example | Compound | CBP HTRF IC$_{50}$ | BRD4 Alpha IC$_{50}$ | Myc IC$_{50}$ |
|---|---|---|---|---|
| 309 | | 0.007 | 3.83 | |
| 310 | | 0.015 | 10.03 | |
| 311 | | 0.003 | 4.18 | |
| 312 | | 0.009 | 4.05 | 0.222 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (Ia) or (If):

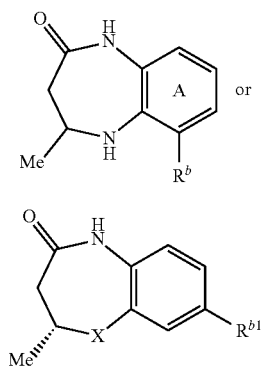

or a salt thereof, wherein:

X is NH;

ring A is substituted with one or more groups $R^b$ that are independently selected from the group consisting of $R^c$, —I, —NO$_2$, —N(R$^d$)$_2$, —CN, —C(O)—N(R$^d$)$_2$, —S(O)—N(R$^d$)$_2$, —S(O)$_2$—N(R$^d$)$_2$, —O—R$^d$, —S—R$^d$, —O—C(O)—R$^d$, —O—C(O)—O—R$^d$, —C(O)—R$^d$, —S(O)—R$^d$, —S(O)$_2$—R$^d$, —O—C(O)—N(R$^d$)$_2$, —N(R$^d$)—C(O)—OR$^d$, —N(R$^d$)—C(O)—N(R$^d$)$_2$, —N(R$^d$)—C(O)—R$^d$, —N(R$^d$)—S(O)—R$^d$, —N(R$^d$)—S(O)$_2$—R$^d$, —N(R$^d$)—S(O)—N(R$^d$)$_2$, —CH=C(Re)$_2$, and —N(R$^d$)—S(O)$_2$—N(R$^d$)$_2$;

each $R^c$ is independently selected from the group consisting of C$_{2-6}$alkenyl, C$_{2-6}$ alkynyl, 3-20 membered carbocyclyl, 3-20 membered heterocyclyl, wherein any C$_{1-6}$ alkyl, C$_{2-6}$ alkenyl, C$_{2-6}$alkynyl, 3-20 membered carbocyclyl, and 3-20 membered heterocyclyl is optionally substituted with one or more groups $R^f$;

each $R^f$ is independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—R$^g$, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R$^g$, —N(R$^g$)—S(O)—R$^g$, N(R$^g$)—S(O)$_2$—R$^g$, and C$_{1-6}$ alkyl, which 3-20 membered carbocyclyl, 3-20 membered heterocyclyl, and C$_{1-6}$ alkyl are optionally substituted with one or more groups $R^i$;

each $R^g$ is independently selected from the group consisting of hydrogen, C$_{1-6}$ alkyl, C$_{2-6}$alkenyl, C$_{2-6}$ alkynyl, 3-20 membered carbocyclyl, and 3-20 membered heterocyclyl, wherein each C$_{1-6}$ alkyl, C$_{2-6}$ alkenyl, C$_{2-6}$alkynyl, C$_{1-6}$ alkoxy, 3-20 membered carbocyclyl, and 3-20 membered heterocyclyl is optionally substituted with one or more groups $R^j$, or two $R^g$ are taken together with the nitrogen to which they are attached to form a 3-20 membered heterocyclyl that is optionally substituted with one or more groups independently selected from the group consisting of oxo, halo and C$_{1-3}$ alkyl that is optionally substituted with one or more groups independently selected from the group consisting of oxo and halo;

each $R^h$ is independently selected from the group consisting of H, C$_{1-6}$ alkyl, C$_{2-6}$ alkenyl, C$_{2-6}$ alkynyl, and C$_{3-6}$ carbocyclyl;

each $R^j$ is independently selected from the group consisting of oxo, halo, amino, hydroxyl, —Si(R$^k$)$_3$, 3-20 membered carbocyclyl, 3-20 membered heterocyclyl, and C$_1$-C$_6$ alkyl, wherein any 3-20 membered carbocyclyl, 3-20 membered heterocyclyl, and C$_1$-C$_6$ alkyl is optionally substituted with one or more groups independently selected from the group consisting of oxo, C$_1$-C$_4$alkyl, and halo;

each $R^k$ is independently selected from the group consisting of H, C$_{1-6}$ alkyl, C$_{2-6}$ alkenyl, C$_{2-6}$ alkynyl, and C$_{3-6}$ carbocyclyl;

each $R^i$ is independently selected from the group consisting of oxo, halo, C$_{1-6}$alkyl, cyano, —N(R$^l$)$_2$, —S(O)—R$^l$, —S(O)$_2$—R$^l$, —S(O)—N(R$^l$)$_2$, —S(O)$_2$—N(R$^l$)$_2$, —N(R$^l$)—S(O)—R$^l$, —N(R$^l$)—C(O)—O—R$^l$, —N(R$^l$)—S(O)$_2$—R$^l$, 3-20 membered heterocyclyl, and 3-20 membered carbocyclyl that is optionally substituted with one or more groups independently selected from the group consisting of halo, and C$_{1-6}$alkyl;

each $R^l$ is independently selected from the group consisting of hydrogen, C$_{1-6}$ alkyl, C$_{2-6}$alkenyl, C$_{2-6}$ alkynyl, 3-20 membered carbocyclyl, and 3-20 membered heterocyclyl, wherein each C$_{1-6}$ alkyl, C$_{2-6}$ alkenyl, C$_{2-6}$alkynyl, C$_{1-6}$ alkoxy, 3-20 membered carbocyclyl, and 3-20 membered heterocyclyl is optionally substituted with one or more groups $R^m$; or two $R^l$ are taken together with the nitrogen to which they are attached to form a 3-20 membered heterocyclyl that is optionally substituted with one or more groups independently selected from the group consisting of oxo, halo and C$_{1-3}$ alkyl that is optionally substituted with one or more groups independently selected from the group consisting of oxo and halo; and each $R^m$ is independently selected from the group consisting of oxo, halo, amino, hydroxyl, —Si(R$^n$)$_3$, 3-20 membered carbocyclyl, 3-20 membered heterocyclyl, and C$_1$-C$_6$ alkyl, wherein any 3-20 membered carbocyclyl, 3-20 membered heterocyclyl, and C$_1$-C$_6$ alkyl is optionally substituted with one or more groups independently selected from the group consisting of oxo, C$_1$-C$_4$alkyl, and halo;

each $R^n$ is independently selected from the group consisting of H, C$_{1-6}$ alkyl, C$_{2-6}$ alkenyl, C$_{2-6}$ alkynyl, and C$_{3-6}$ carbocyclyl;

each $R^d$ is independently selected from the group consisting of hydrogen, C$_{1-6}$ alkyl, C$_{2-6}$alkenyl, C$_{2-6}$ alkynyl, 3-20 membered carbocyclyl, and 3-20 membered heterocyclyl, wherein each C$_{1-6}$ alkyl, C$_{2-6}$ alkenyl, C$_{2-6}$alkynyl, 3-20 membered carbocyclyl, and 3-20 membered heterocyclyl is optionally substituted with one or more groups $R^o$, or two $R^d$ are taken together with the nitrogen to which they are attached to form a 3-20 membered heterocyclyl that is optionally substituted with one or more groups independently selected from the group consisting of oxo, halo and C$_{1-3}$ alkyl that is optionally substituted with one or more groups independently selected from the group consisting of oxo and halo;

each $R^o$ is independently selected from the group consisting of oxo, halo, amino, hydroxyl, cyano, —O—R$^p$, 3-20 membered carbocyclyl, 3-20 membered heterocyclyl, and C₁-C₆ alkyl, wherein any $C_1$-$C_6$ alkyl, 3-20 membered carbocyclyl and 3-20 membered heterocyclyl is optionally substituted with one or more groups independently selected from the group consisting of oxo, $C_1$-$C_4$ alkyl, —O—$R^q$, and halo;

each $R^p$ is independently selected from the group consisting of hydrogen, $C_{1-6}$ alkyl, $C_{2-6}$alkenyl, $C_{2-6}$ alkynyl, 3-20 membered carbocyclyl, and 3-20 membered heterocyclyl, wherein each $C_{1-6}$ alkyl, $C_{2-6}$ alkenyl, $C_{2-6}$alkynyl, $C_{1-6}$ alkoxy, 3-20 membered carbocyclyl, and 3-20 membered heterocyclyl is optionally substituted with one or more groups $R^r$, each $R^r$ is independently selected from the group consisting of oxo, halo, amino, hydroxyl, —Si($R^s$)₃, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^s$ is independently selected from the group consisting of H, $C_{1-6}$alkyl, $C_{2-6}$alkenyl, $C_{2-6}$ alkynyl, and $C_{3-6}$ carbocyclyl;

each $R^q$ is independently selected from the group consisting of hydrogen, $C_{1-6}$ alkyl, $C_{2-6}$alkenyl, $C_{2-6}$ alkynyl, 3-20 membered carbocyclyl, and 3-20 membered heterocyclyl, wherein each $C_{1-6}$ alkyl, $C_{2-6}$ alkenyl, $C_{2-6}$alkynyl, $C_{1-6}$ alkoxy, 3-20 membered carbocyclyl, and 3-20 membered heterocyclyl is optionally substituted with one or more groups $R^t$, each $R^t$ is independently selected from the group consisting of oxo, halo, amino, hydroxyl, —Si($R^u$)₃, 3-20 membered carbocyclyl, 3-20 membered heterocyclyl, and $C_1$-$C_6$ alkyl, wherein any 3-20 membered carbocyclyl, 3-20 membered heterocyclyl, and $C_1$-$C_6$ alkyl is optionally substituted with one or more groups independently selected from the group consisting of oxo, $C_1$-$C_4$alkyl, and halo;

each $R^u$ is independently selected from the group consisting of H, $C_{1-6}$ alkyl, $C_{2-6}$ alkenyl, $C_{2-6}$ alkynyl, and $C_{3-6}$ carbocyclyl;

two $R^e$ groups taken together with the carbon to which they are attached form a 3-20 membered carbocyclyl; and $R^b$ is:

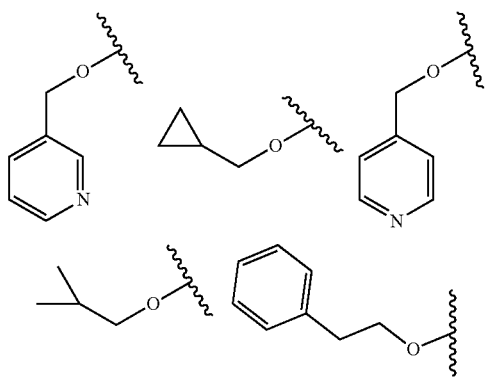

-continued

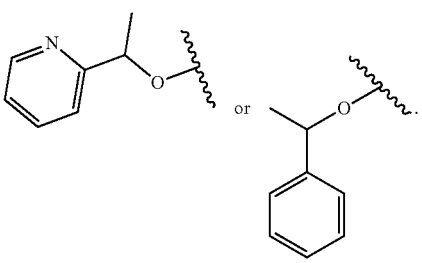

2. The compound of claim 1 wherein ring A is optionally substituted with one or more groups $R^b$ that are independently selected from the group consisting of $R^c$, —I, —C(O)—N($R^d$)₂, —O—$R^d$, and —CH=C($R^e$)₂ or a salt thereof.

3. The compound of claim 1 which is a compound of formula (Ia):

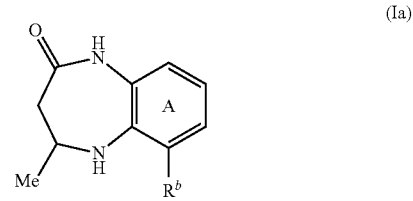

wherein ring A is optionally substituted with one or more additional groups $R^b$ that are independently selected from the group consisting of $R^c$, —I, —NO₂, —N($R^d$)₂, —CN, —C(O)—N($R^d$)₂, —S(O)—N($R^d$)₂, —S(O)₂—N($R^d$)₂, —O—$R^d$, —S—$R^d$, —O—C(O)—$R^d$, —O—C(O)—O—$R^d$, —C(O)—$R^d$, —C(O)—O—$R^d$, —S(O)—$R^d$, —S(O)₂—$R^d$, —O—C(O)—N($R^d$)₂, —N($R^d$)—C(O)—O$R^d$, —N($R^d$)—C(O)—N($R^d$)₂, —N($R^d$)—C(O)—$R^d$, —N($R^d$)—S(O)—$R^d$, —N($R^d$)—S(O)₂—$R^d$, —N($R^d$)—S(O)—N($R^d$)₂, —CH=C($R^e$)₂, and —N($R^d$)—S(O)₂—N($R^d$)₂; or a salt thereof.

4. The compound of claim 3, wherein ring A is optionally substituted with one or more additional groups $R^b$ that are independently selected from the group consisting of $R^c$, —I, —C(O)—N($R^d$)₂, —O—$R^d$, and —CH=C($R^e$)₂ or a salt thereof.

5. The compound of claim 3 wherein $R^b$ is ethenyl, ethynyl,

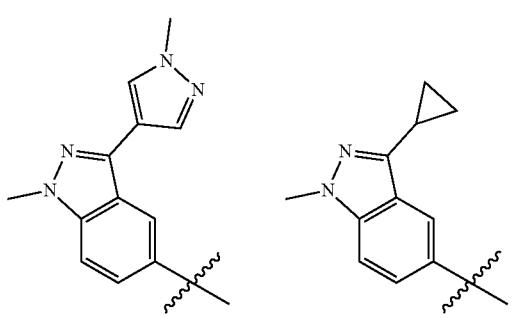

461
-continued
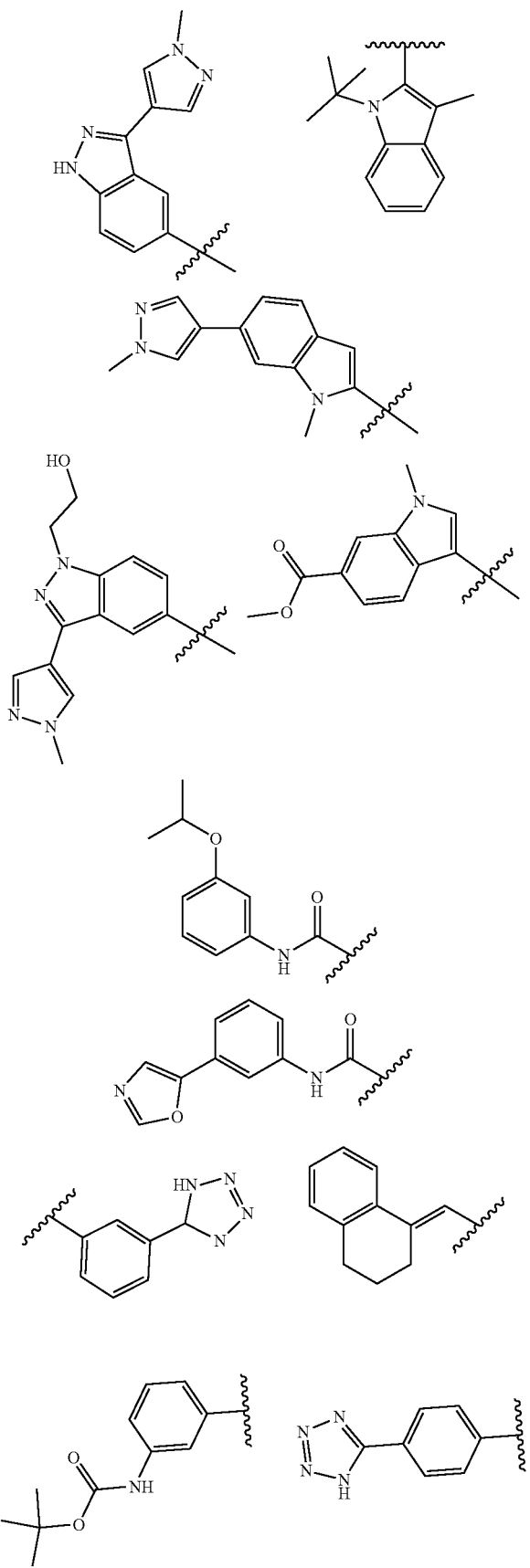
462
-continued
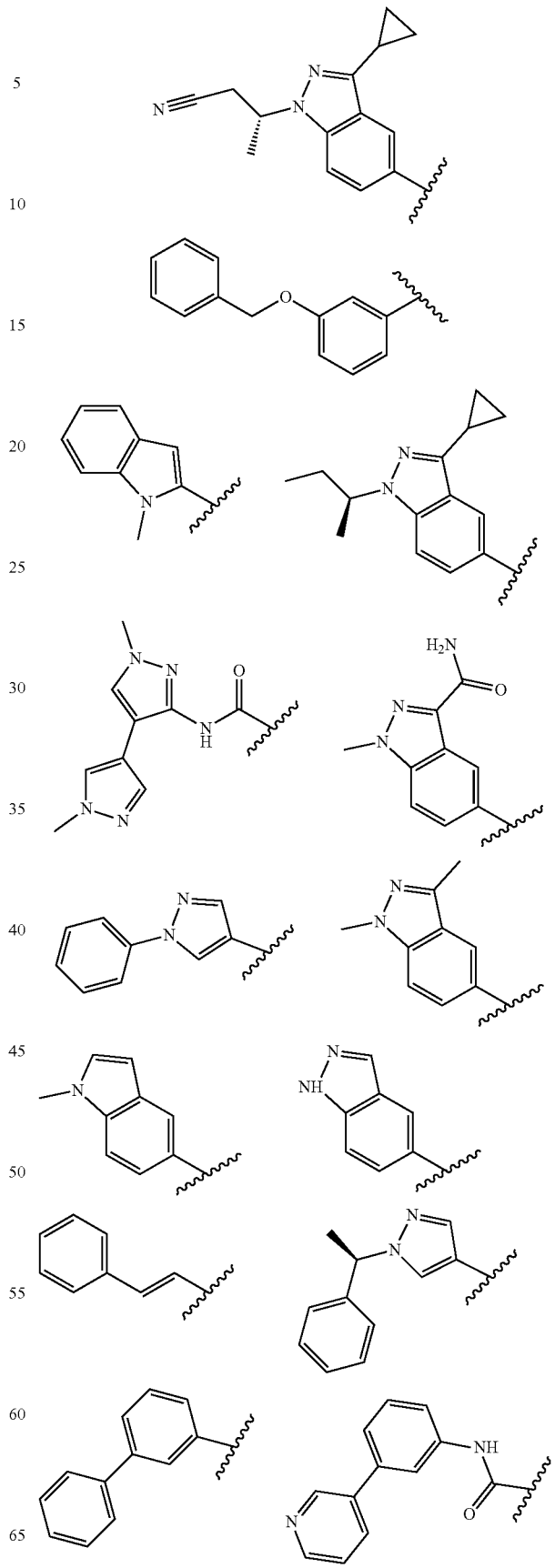

463
-continued
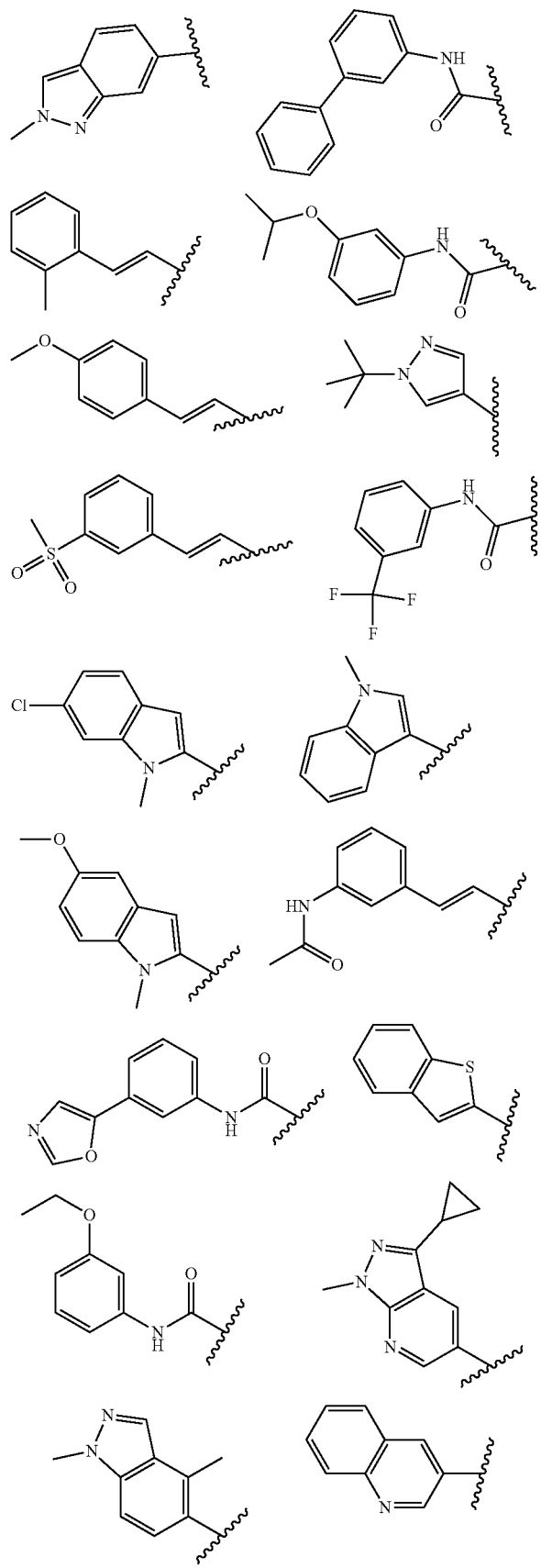
464
-continued
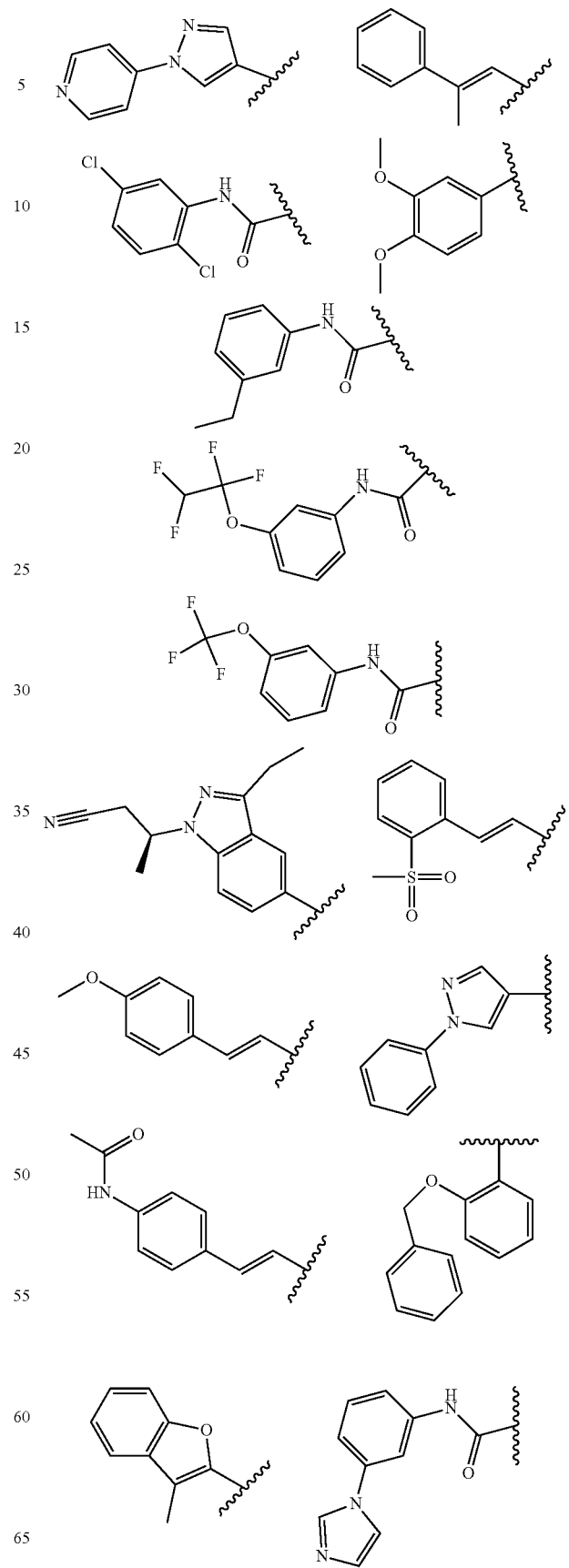

465
-continued
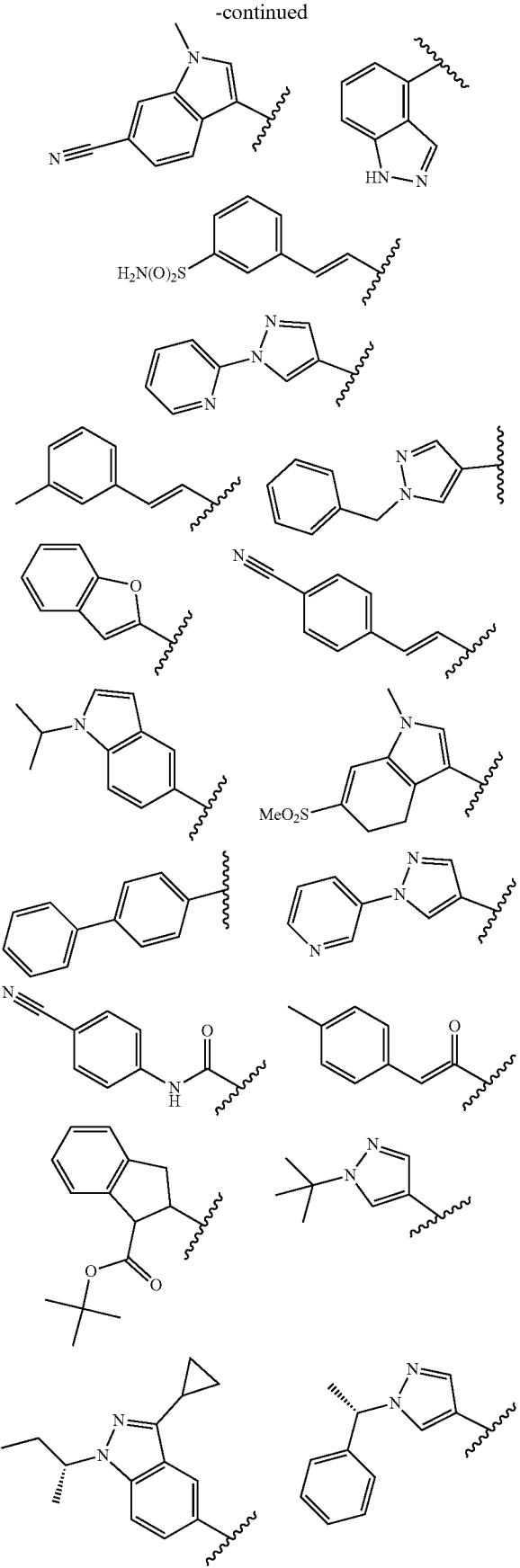
466
-continued
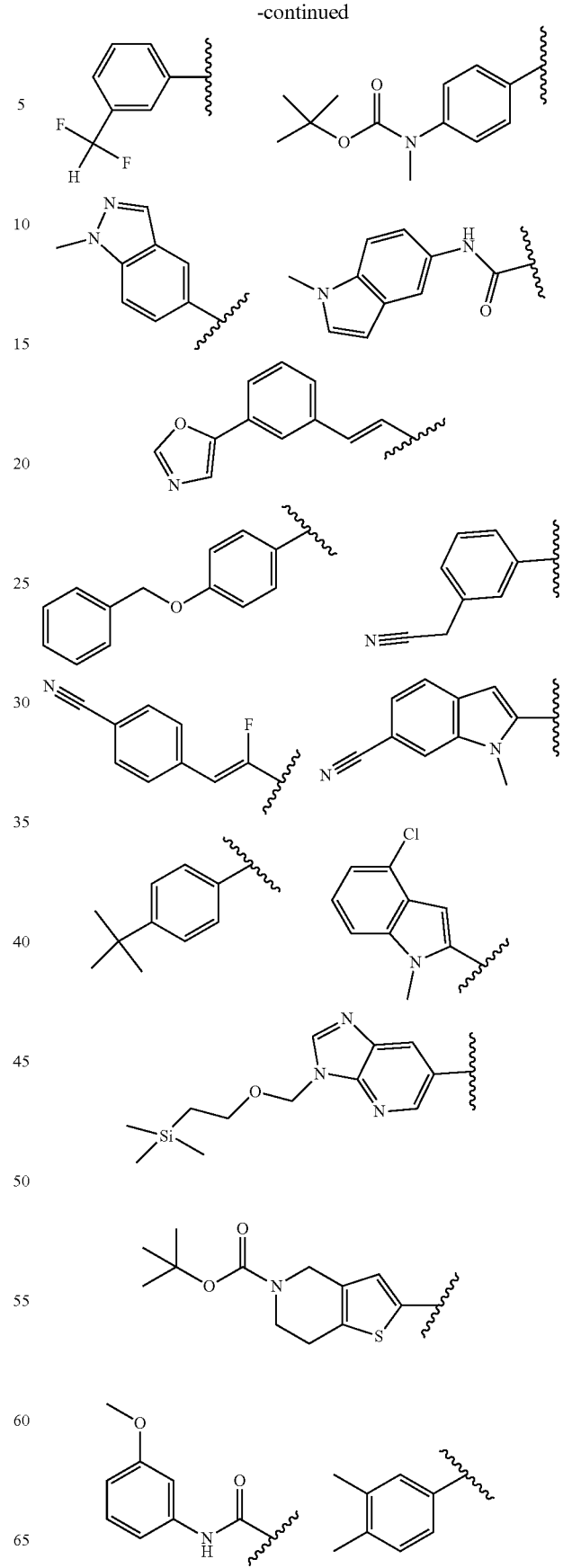

467
-continued
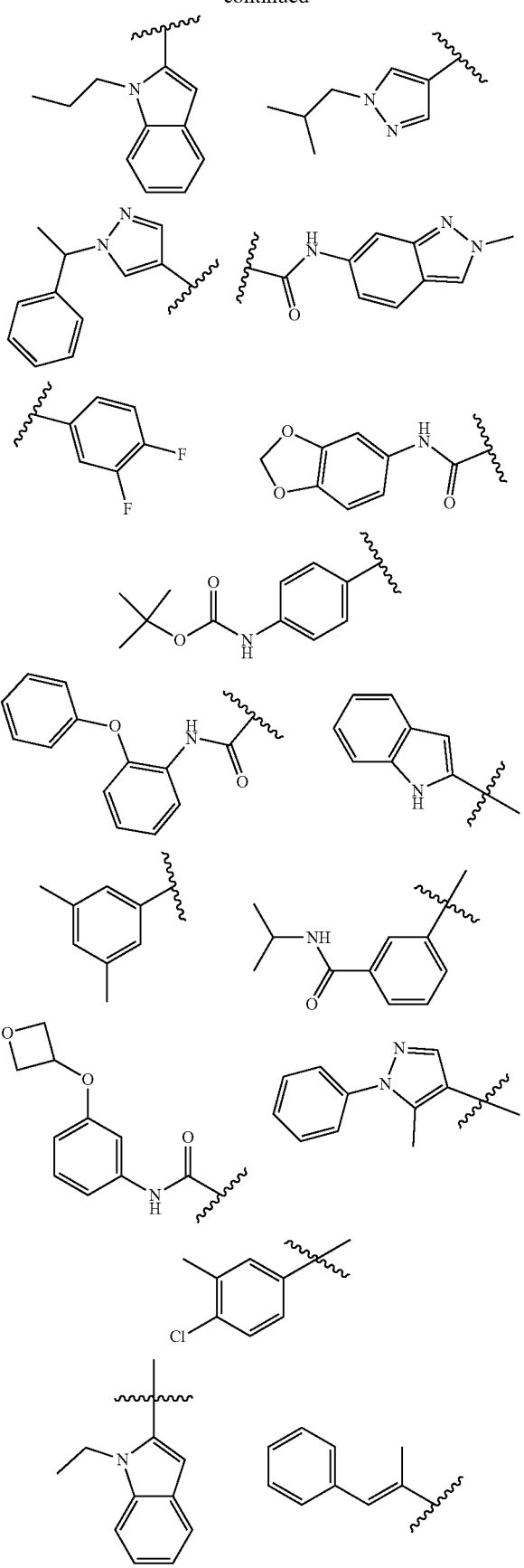
468
-continued
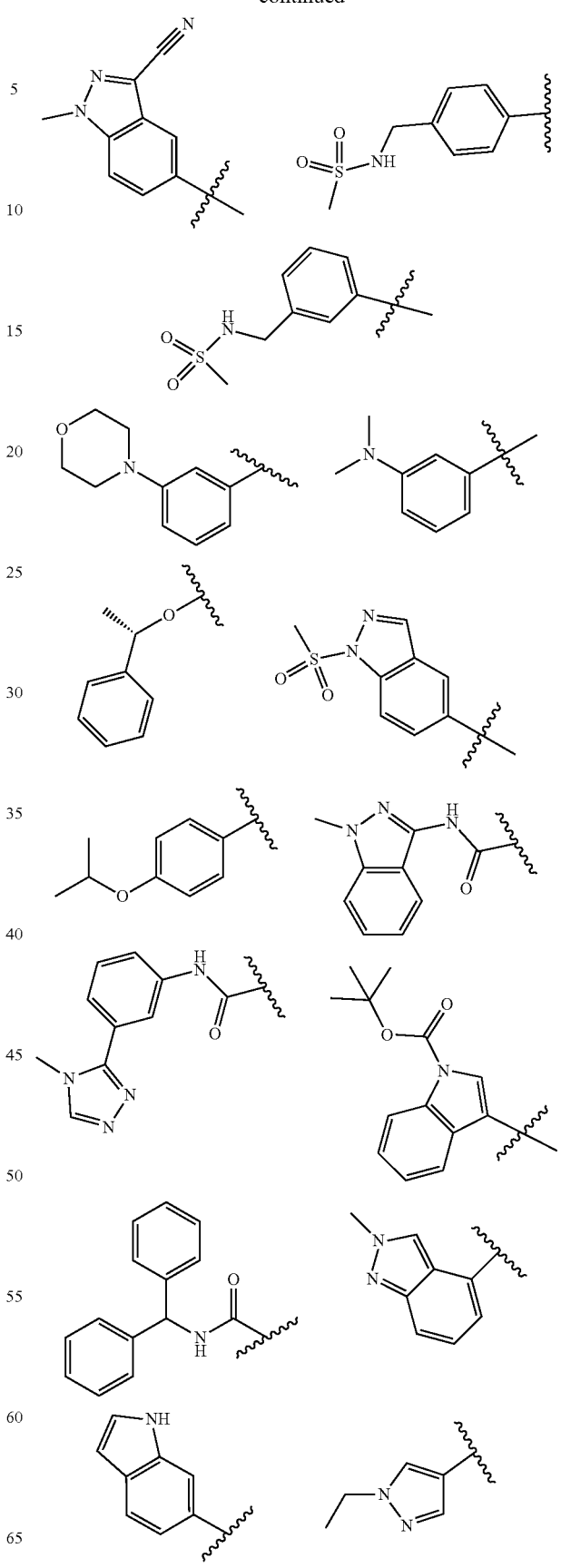

469
-continued
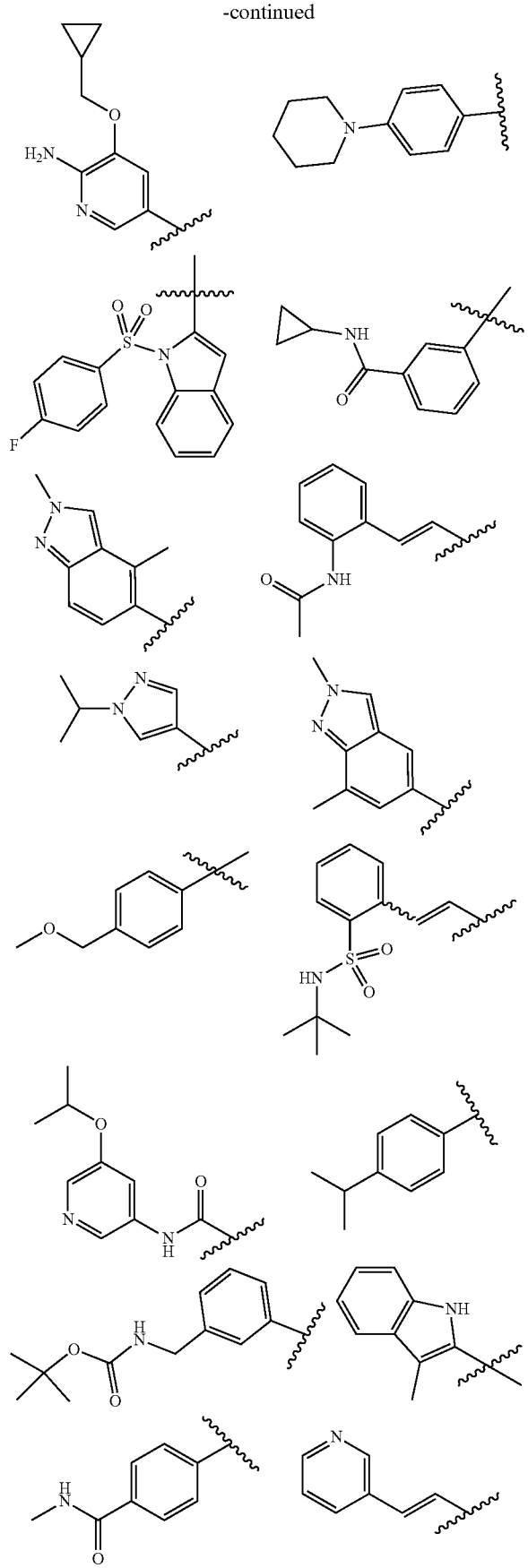
470
-continued
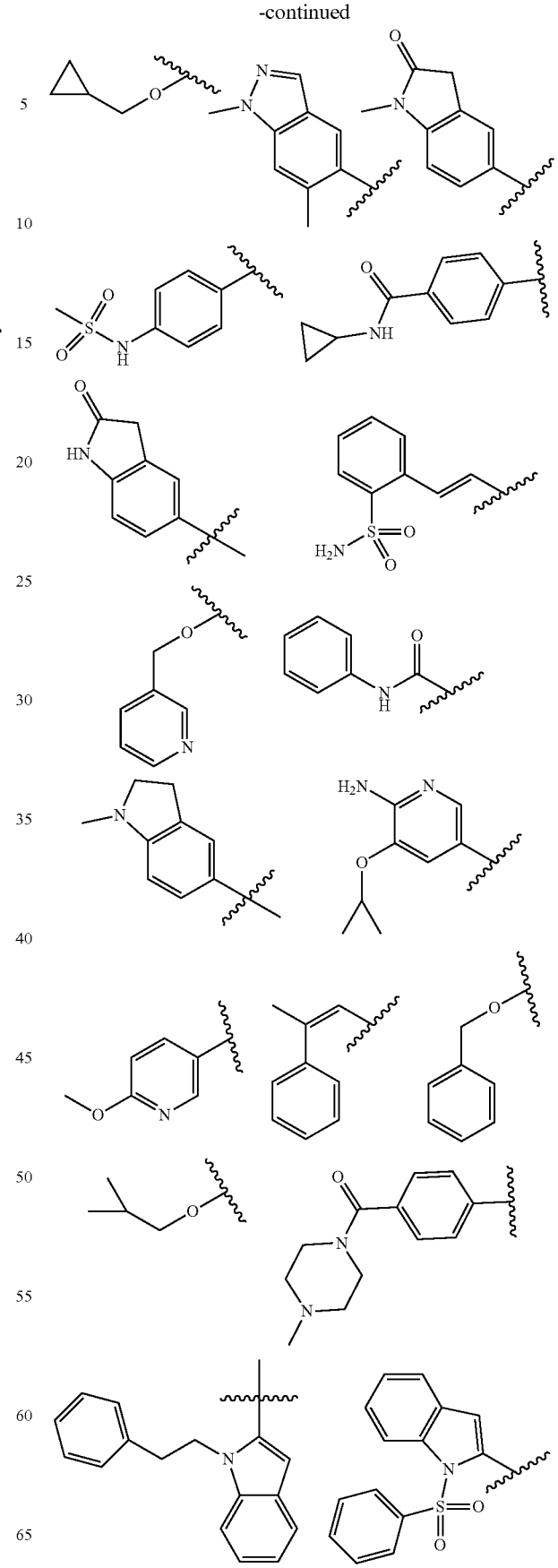

471
-continued
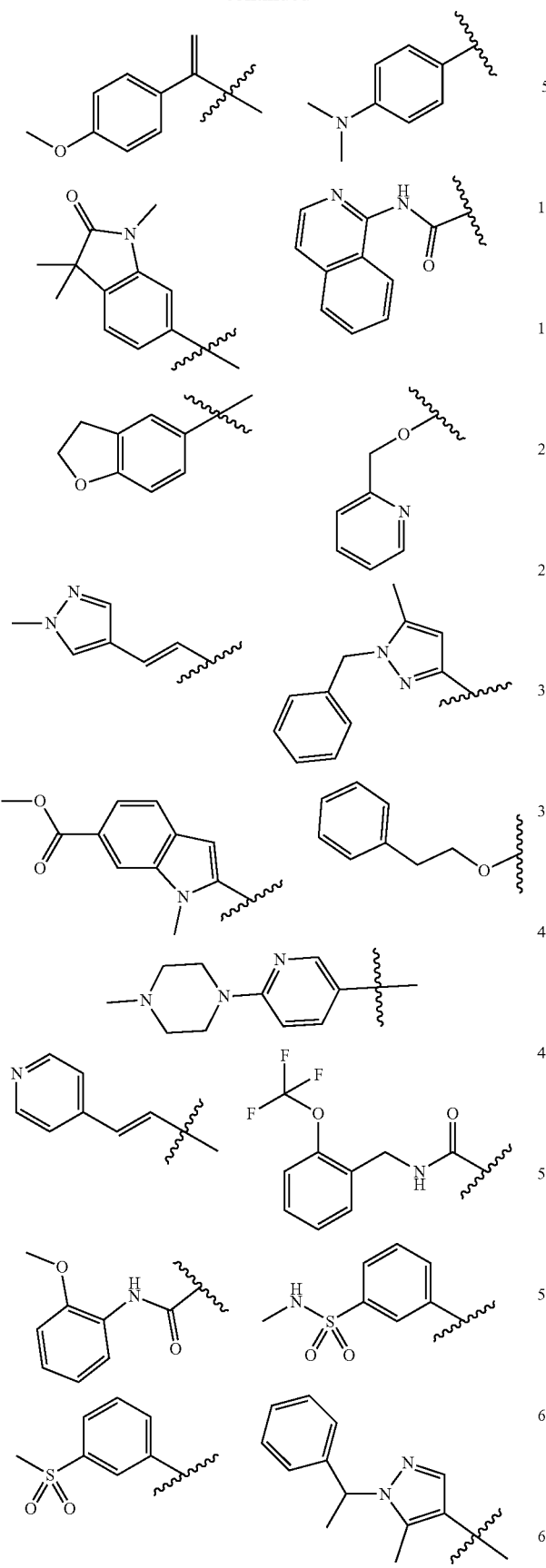
472
-continued
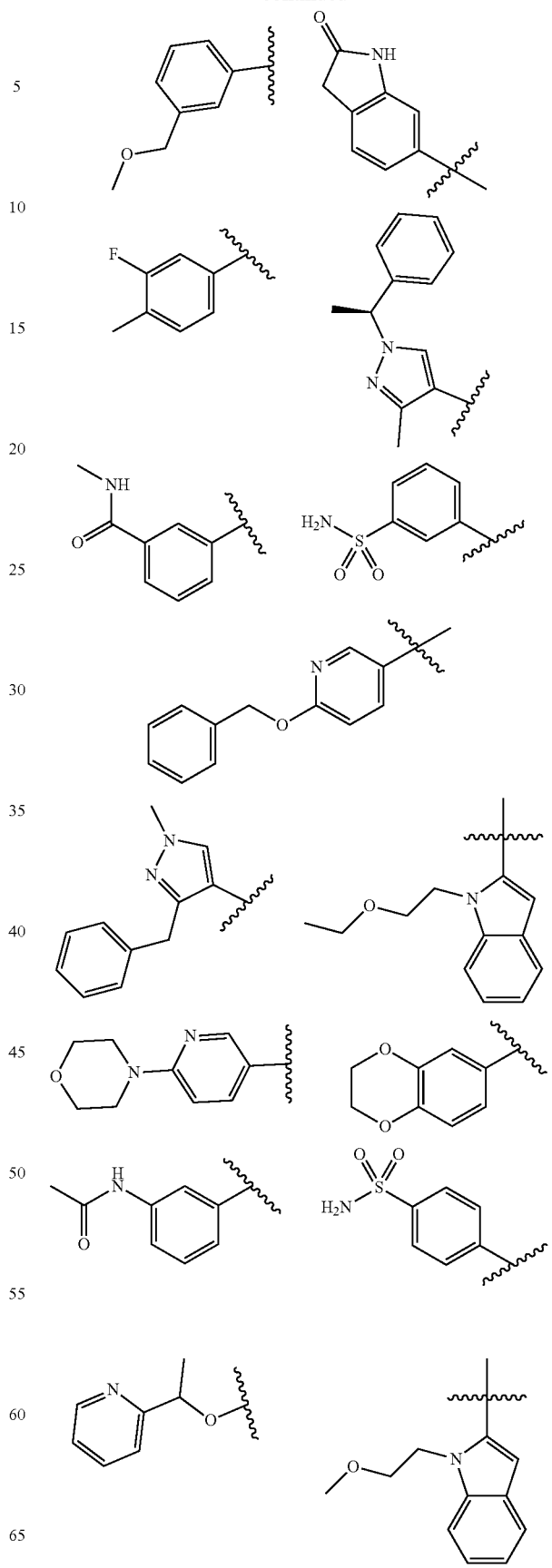

473
-continued
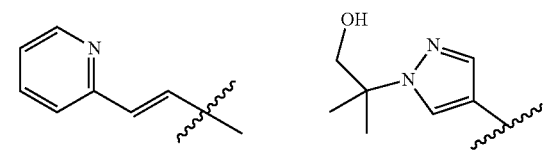
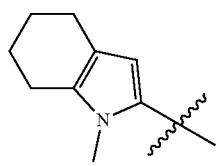
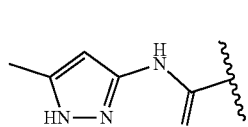
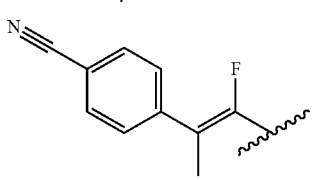
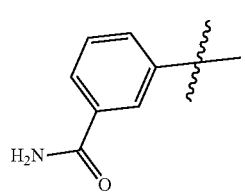
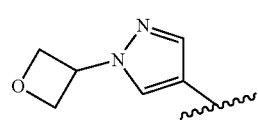
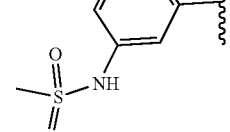
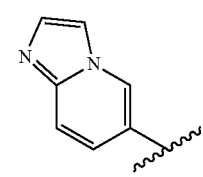
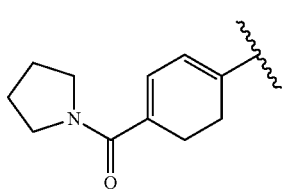
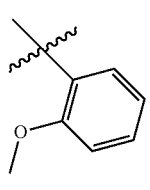
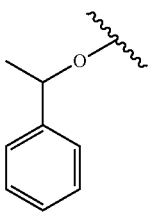
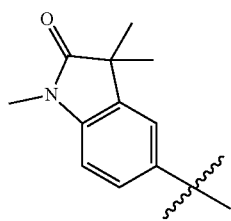
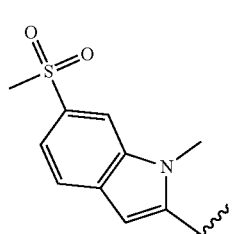
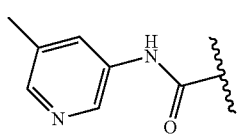
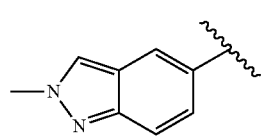
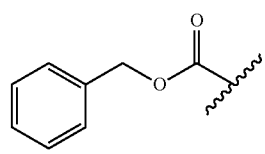
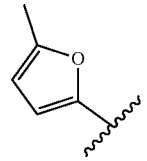
474
-continued
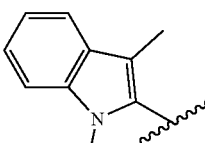
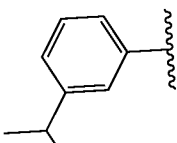
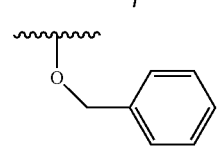
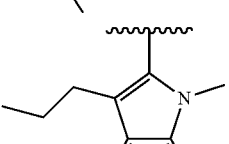
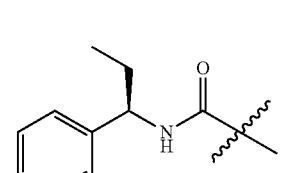
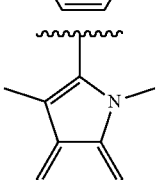
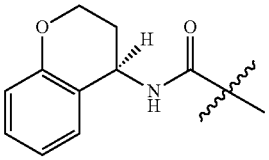
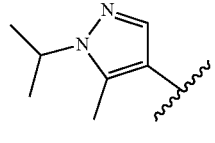
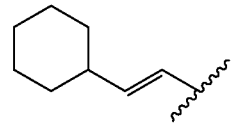
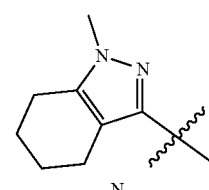
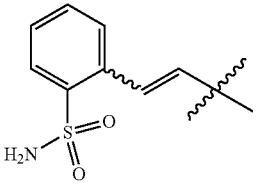
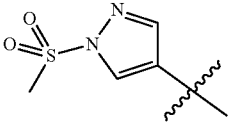
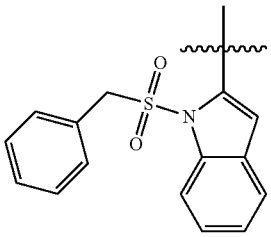
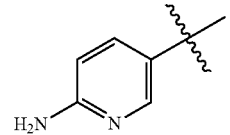
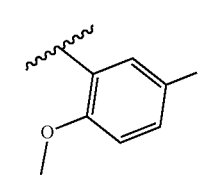
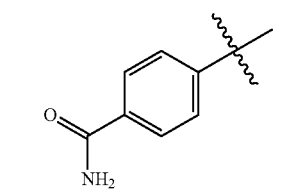
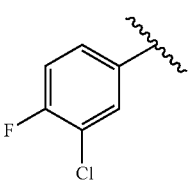
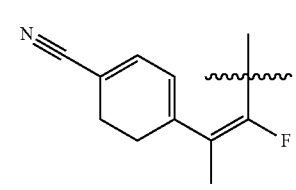

475
-continued
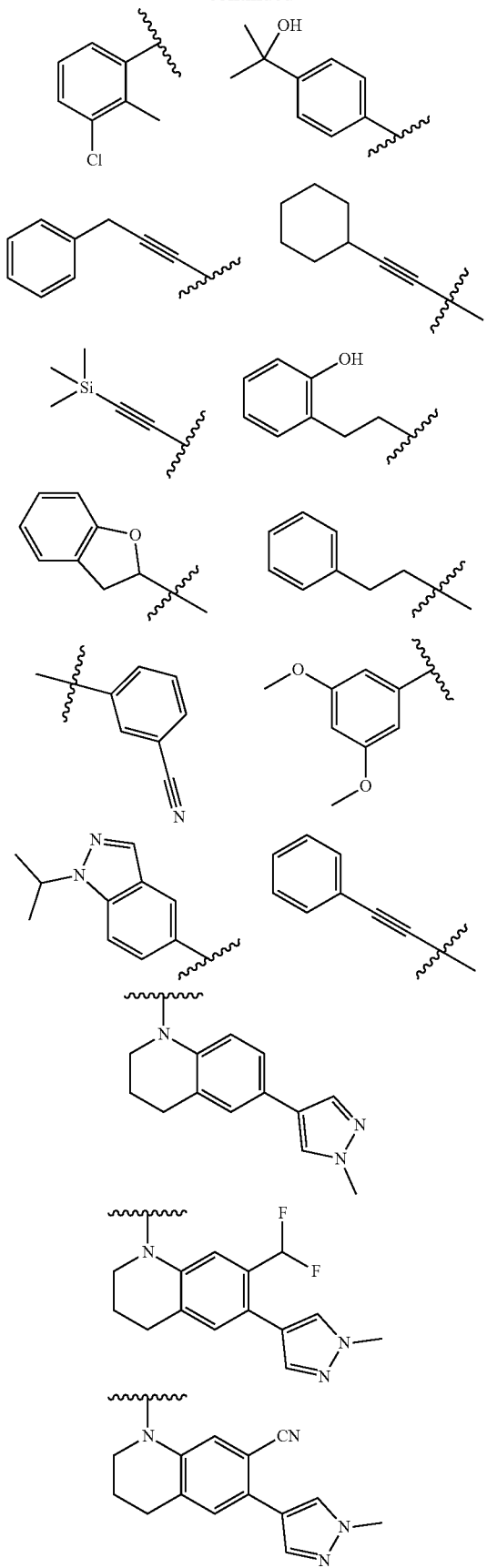
476
-continued
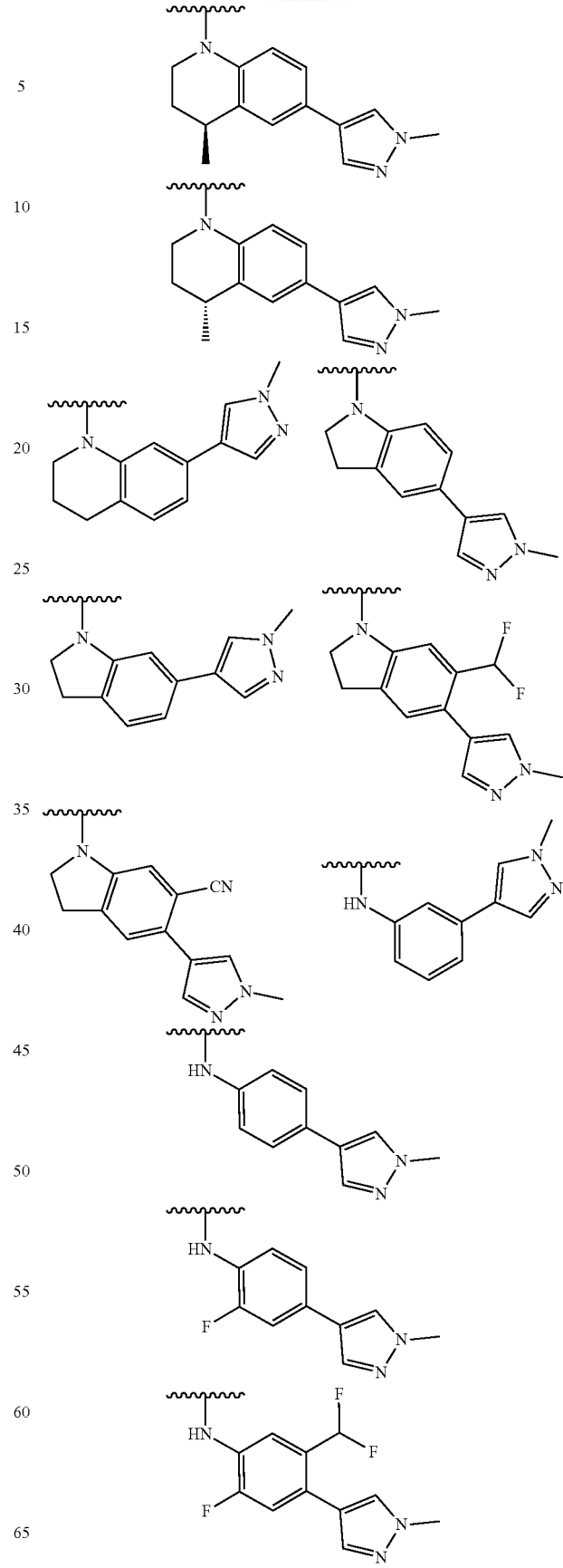

-continued

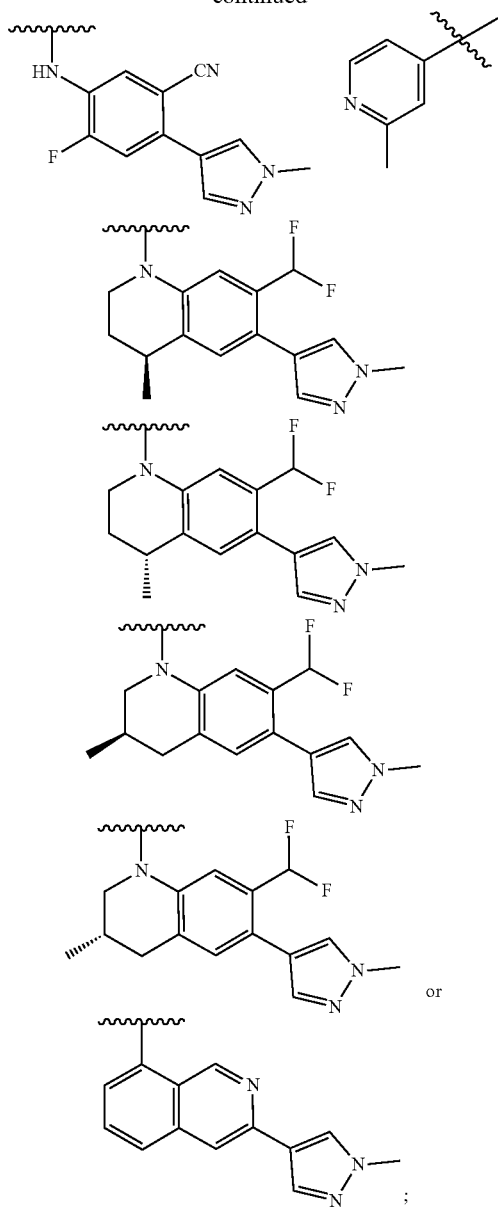

or a salt thereof.

6. The compound of claim 1 which is a compound of formula (Ib):

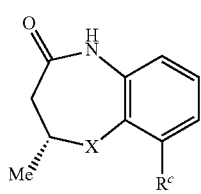

(Ib)

wherein:
X is NH;
$R^c$ is $C_{2-6}$alkenyl, $C_{2-6}$alkynyl, 6-10 membered aryl, and 5-14 membered heteroaryl, wherein any $C_{2-6}$ alkenyl, $C_{2-6}$alkynyl, 6-10 membered aryl, and 5-14 membered heteroaryl is optionally substituted with one or more groups $R^f$ independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—W, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R$^g$, —N(R$^g$)—S(O)—R$^g$, N(R$^g$)—S(O)$_2$—R$^g$, and $C_{1-6}$alkyl, which 3-20 membered carbocyclyl, 3-20 membered heterocyclyl, and $C_{1-6}$alkyl are optionally substituted with one or more groups $R^i$ independently selected from the group consisting of oxo, halo, $C_{1-6}$alkyl, cyano, —N(R$^i$)$_2$, —S(O)$_2$—R$^i$, —S(O)—N(R$^i$)$_2$, —S(O)$_2$—N(R$^i$)$_2$, —N(R$^i$)—S(O)—R$^i$, —N(R$^i$)—C(O)—O—R$^i$, —N(R$^i$)—S(O)$_2$—R$^i$, 3-20 membered heterocyclyl, and 3-20 membered carbocyclyl that is optionally substituted with one or more groups independently selected from the group consisting of halo, and $C_{1-6}$alkyl; and $R^h$ is independently selected from the group consisting of H, $C_{2-6}$ alkenyl, $C_{2-6}$alkynyl, and $C_{3-6}$ carbocyclyl;
or a salt thereof.

7. The compound of claim 6 wherein $R^c$ is:

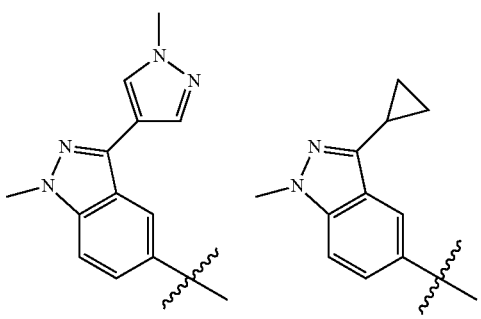

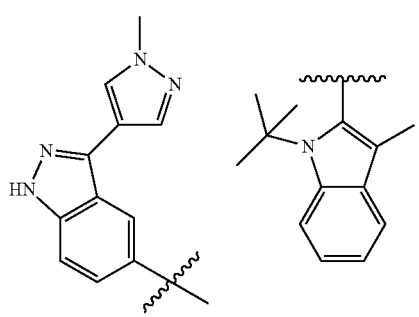

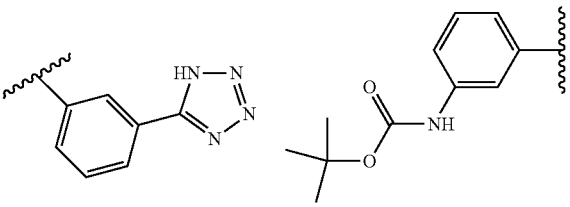

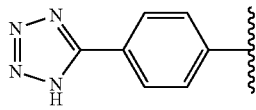

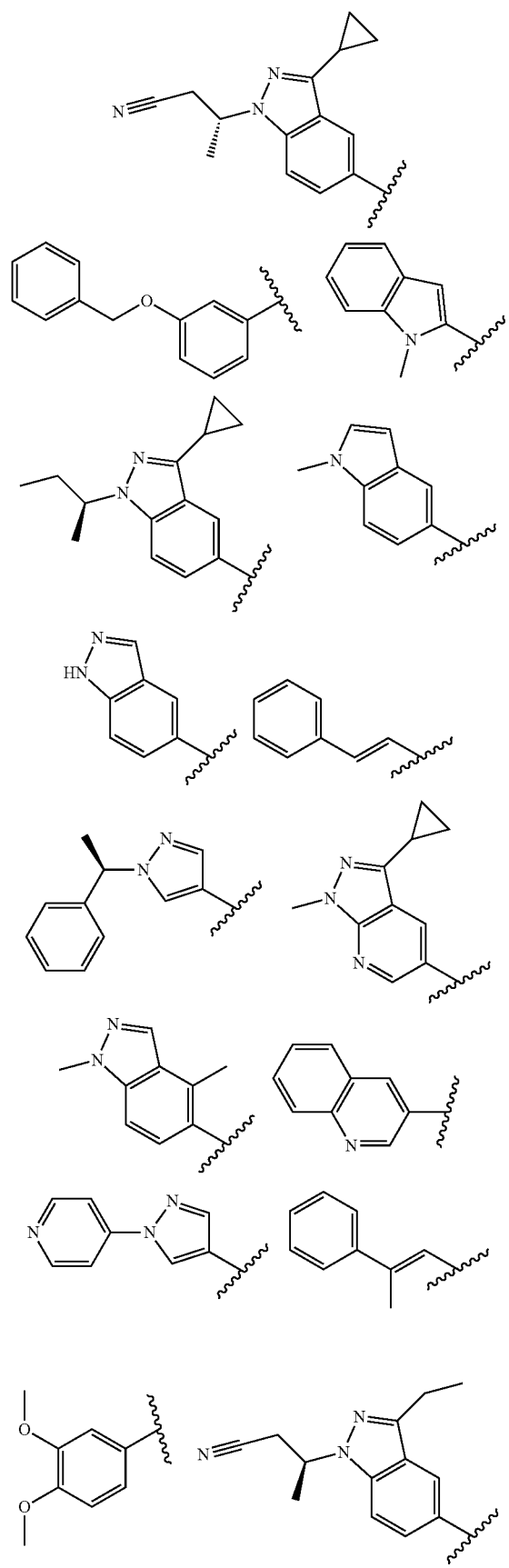
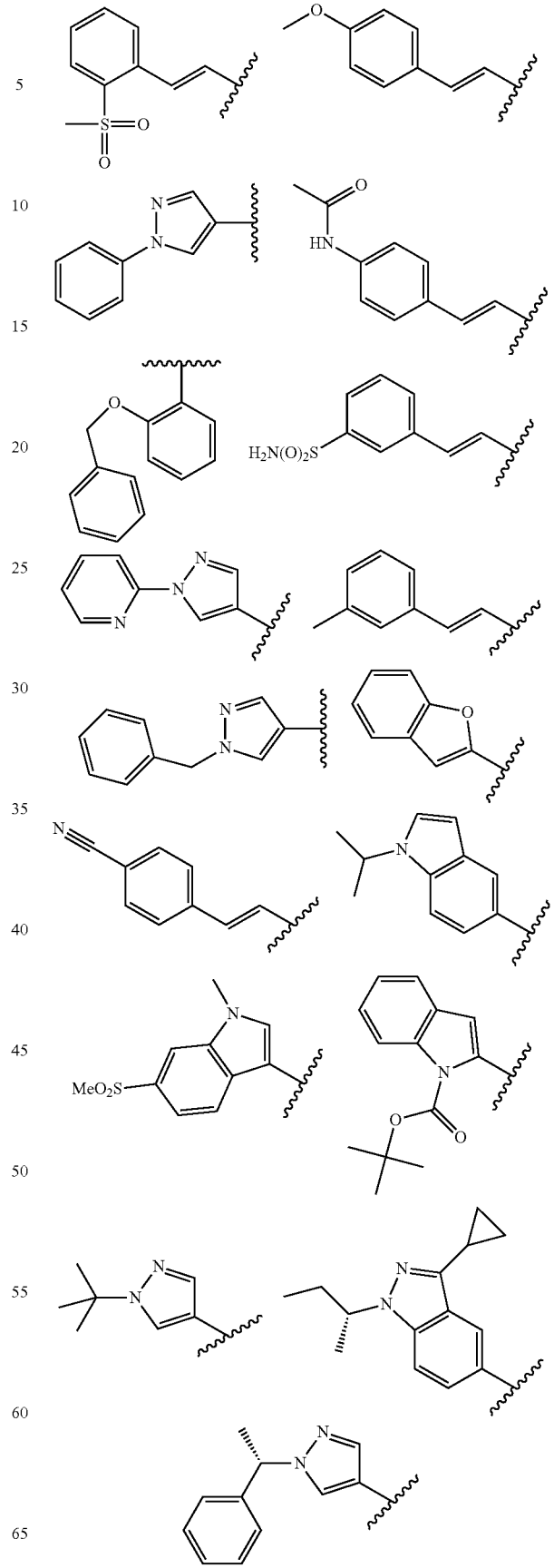

481
-continued
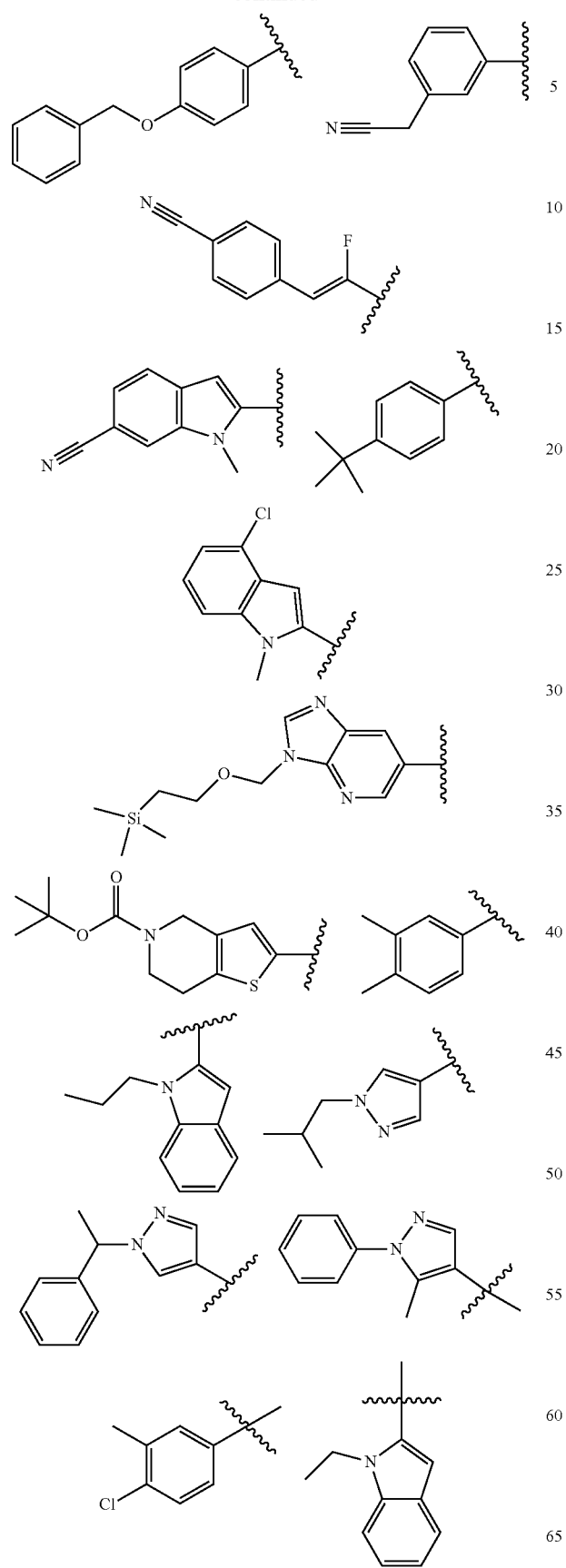
482
-continued
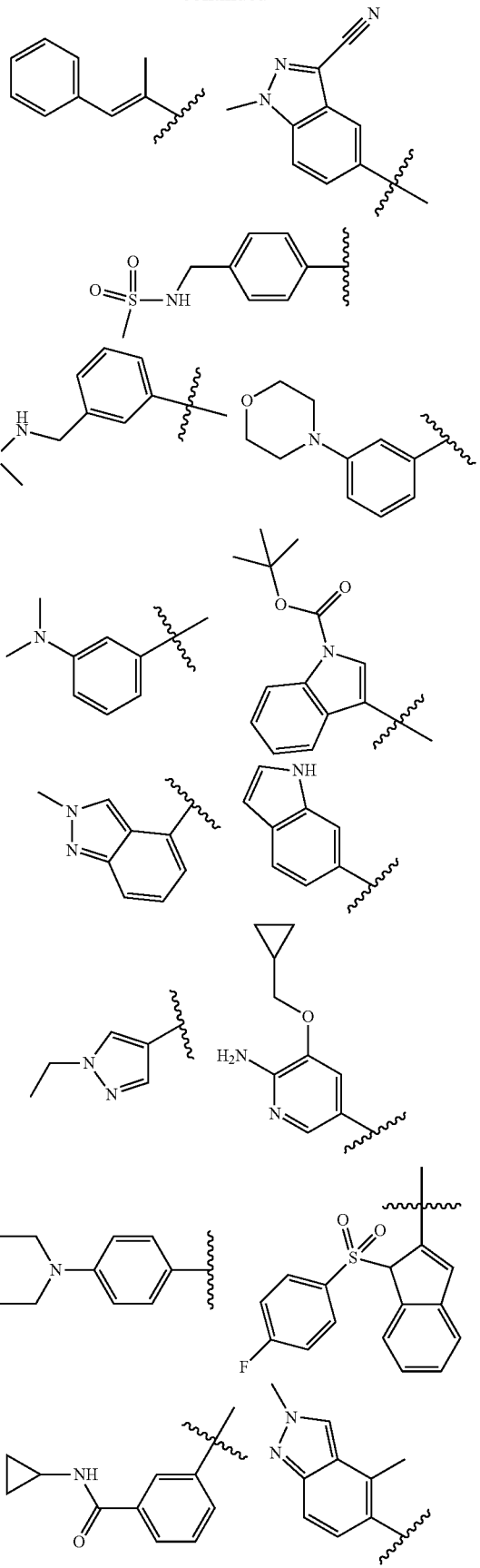

483
-continued
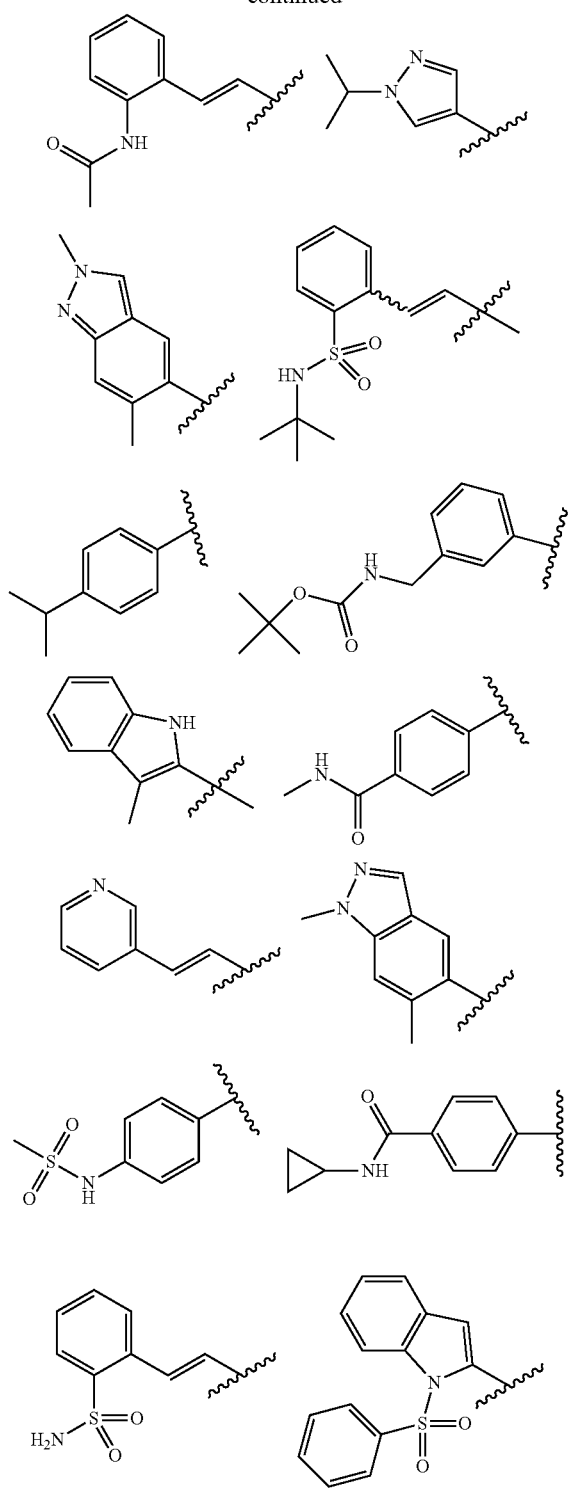
484
-continued
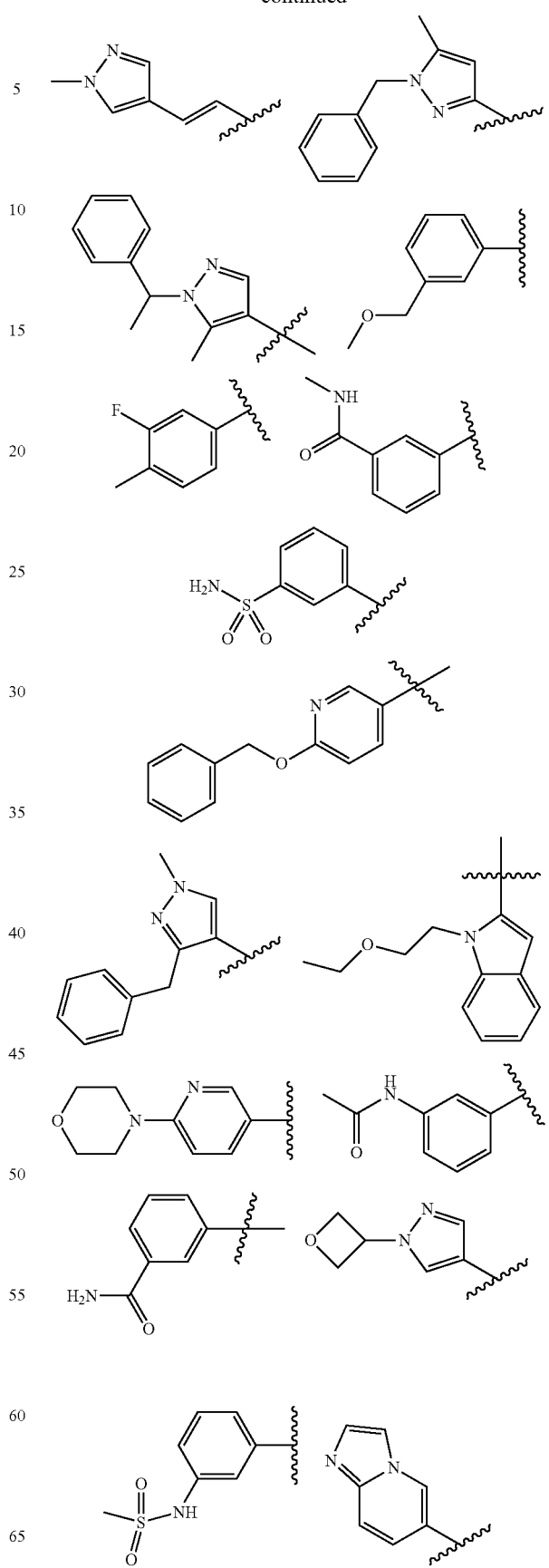

485
-continued
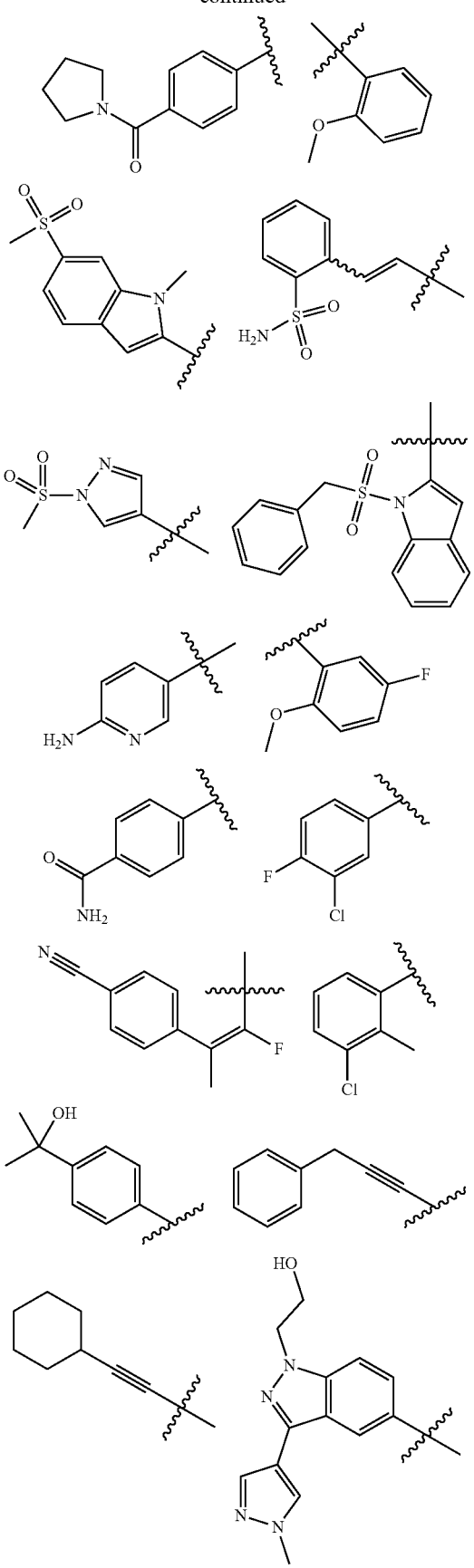
486
-continued
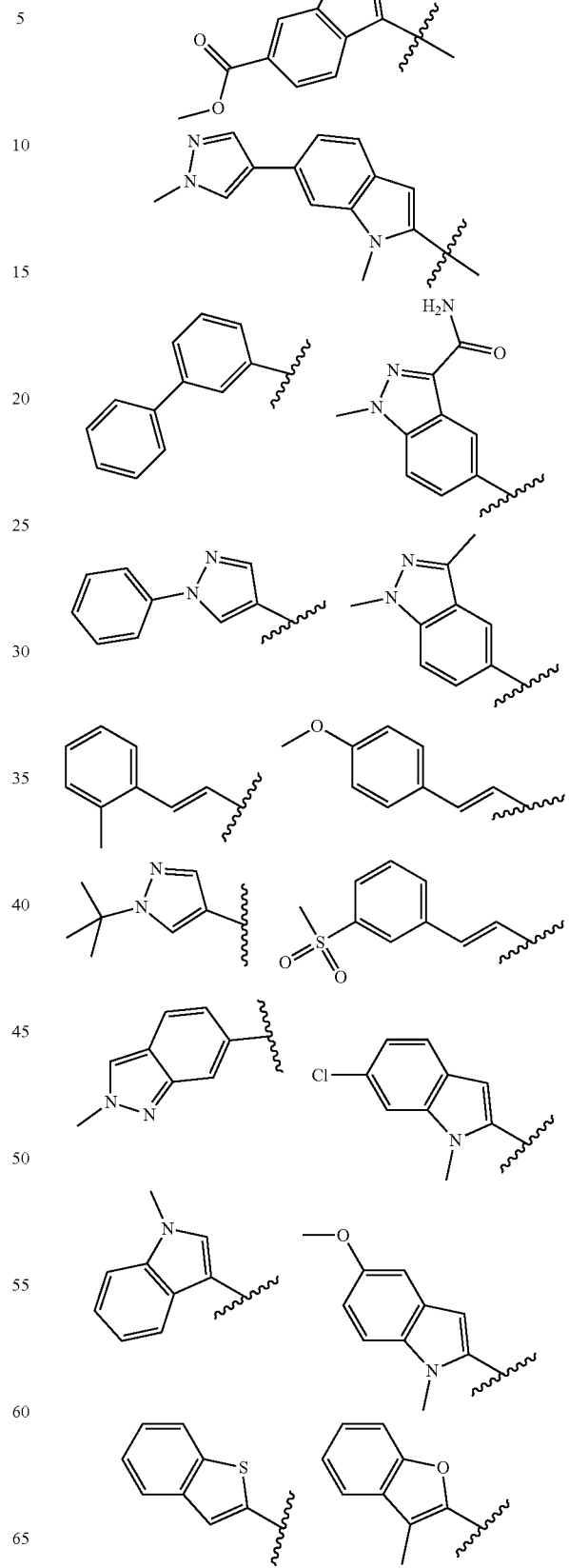

487
-continued
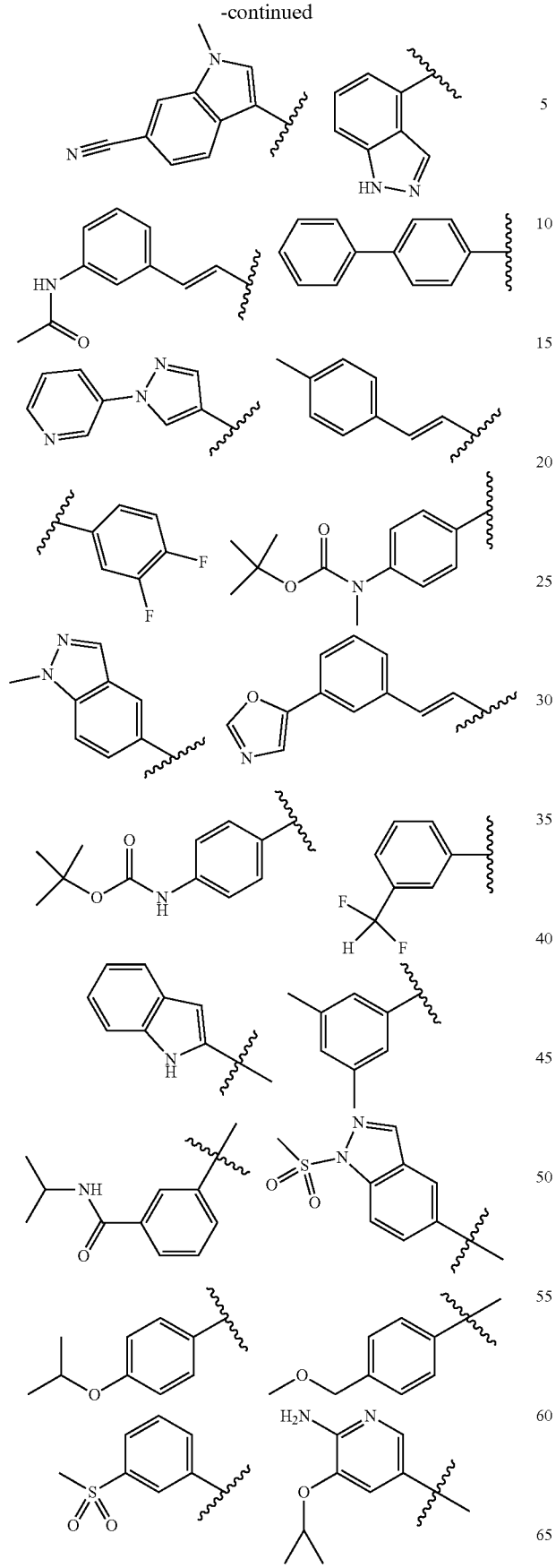
488
-continued
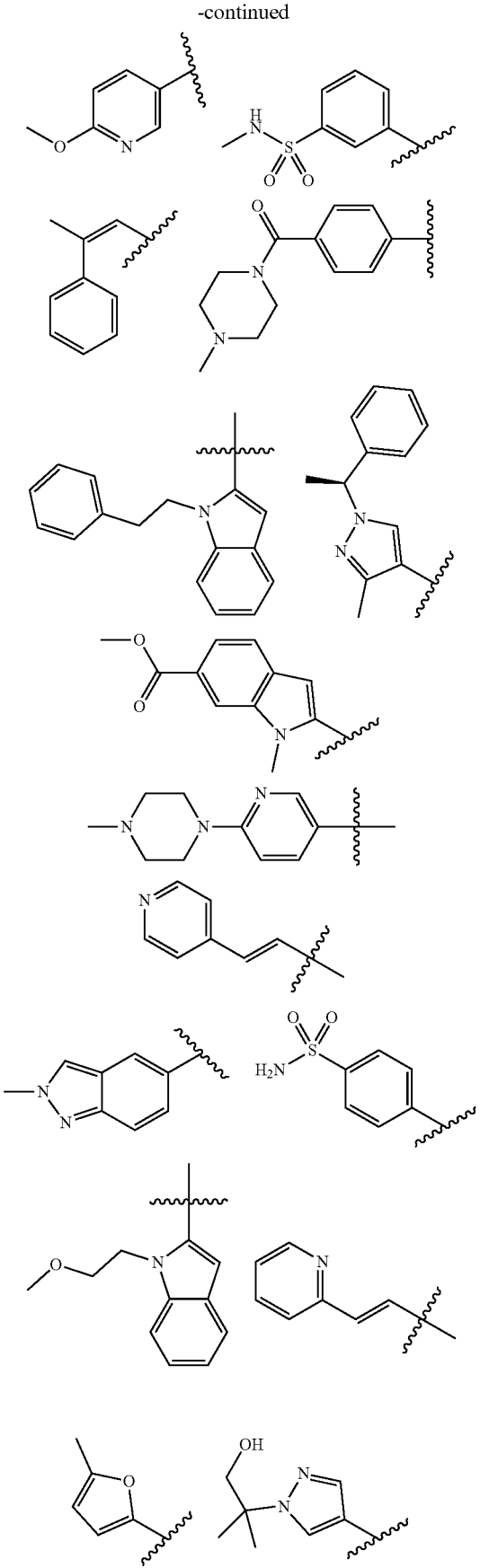

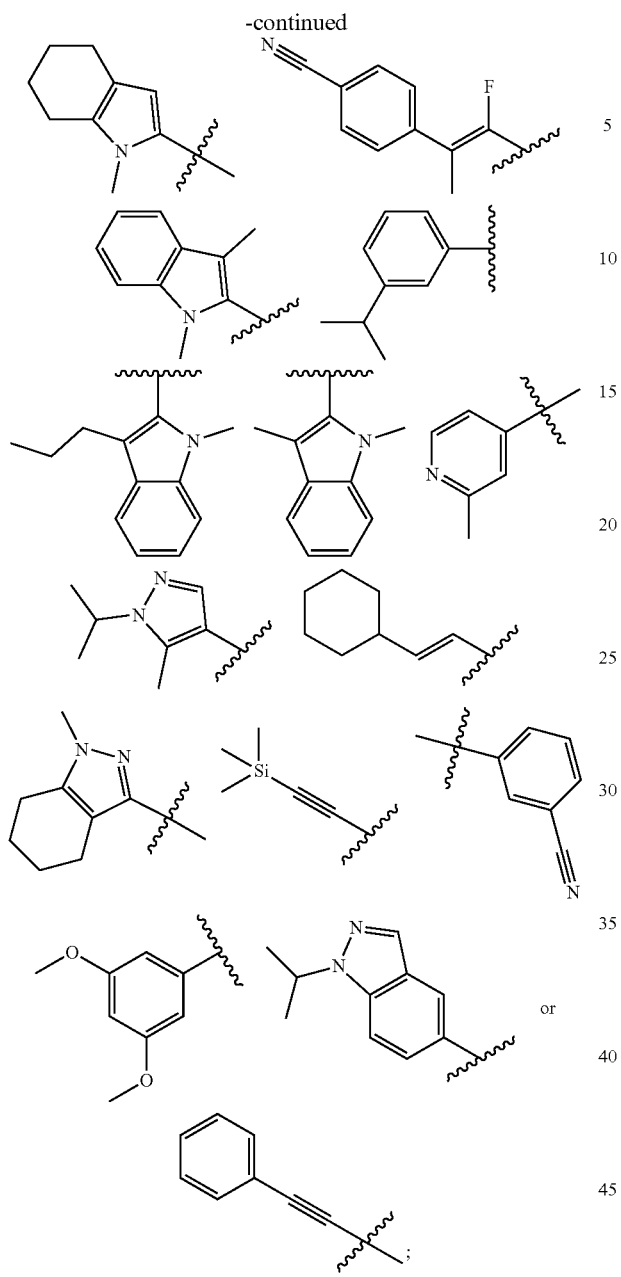

or a salt thereof.

8. The compound of claim 1 which is a compound of formula (Ic):

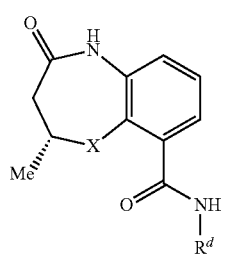

(Ic)

wherein:
X is NH;
$R^d$ is $C_{1-6}$ alkyl, 6-10 membered aryl, or 5-10 membered heteroaryl, wherein each $C_{1-6}$alkyl, 6-10 membered aryl, or 5-10 membered heteroaryl is optionally substituted with one or more groups $R^o$ independently selected from the group consisting of oxo, halo, amino, hydroxyl, cyano, —O—$R^p$, 3-20 membered carbocyclyl, 3-20 membered heterocyclyl, and $C_1$-$C_6$ alkyl, wherein any $C_1$-$C_6$ alkyl, 3-20 membered carbocyclyl and 3-20 membered heterocyclyl is optionally substituted with one or more groups independently selected from the group consisting of oxo, $C_1$-$C_4$ alkyl, —O—$R^q$, and halo;
$R^p$ is independently selected from the group consisting of hydrogen, $C_{1-6}$ alkyl, $C_{2-6}$ alkenyl, $C_{2-6}$ alkynyl, 3-20 membered carbocyclyl, and 3-20 membered heterocyclyl, wherein each $C_{1-6}$ alkyl, $C_{2-6}$ alkenyl, $C_{2-6}$alkynyl, $C_{1-6}$ alkoxy, 3-20 membered carbocyclyl, and 3-20 membered heterocyclyl is optionally substituted with one or more halo;
$R^q$ is $C_{1-6}$ alkyl is optionally substituted with one or more halo;
or a salt thereof.

9. The compound of claim 8 wherein $R^d$ is:

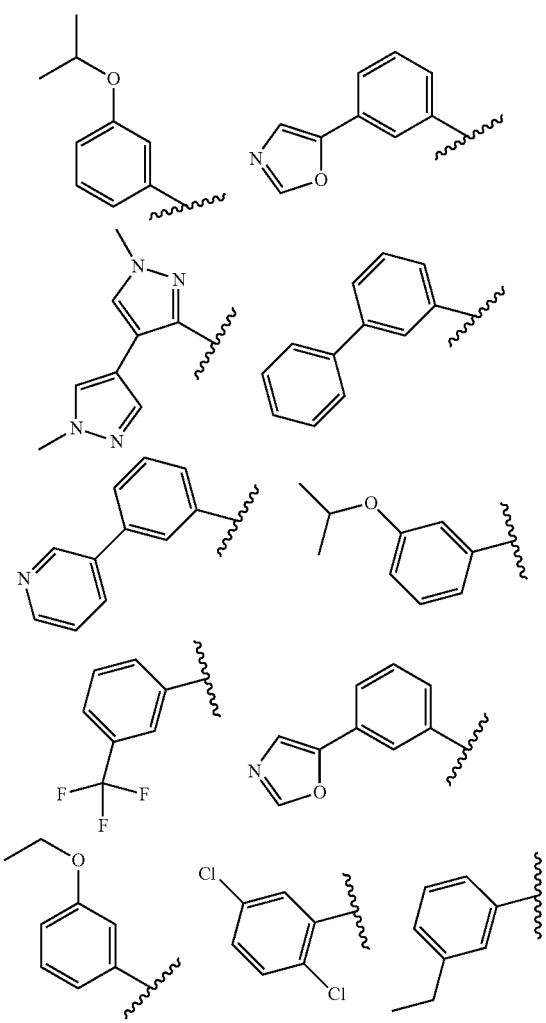

-continued

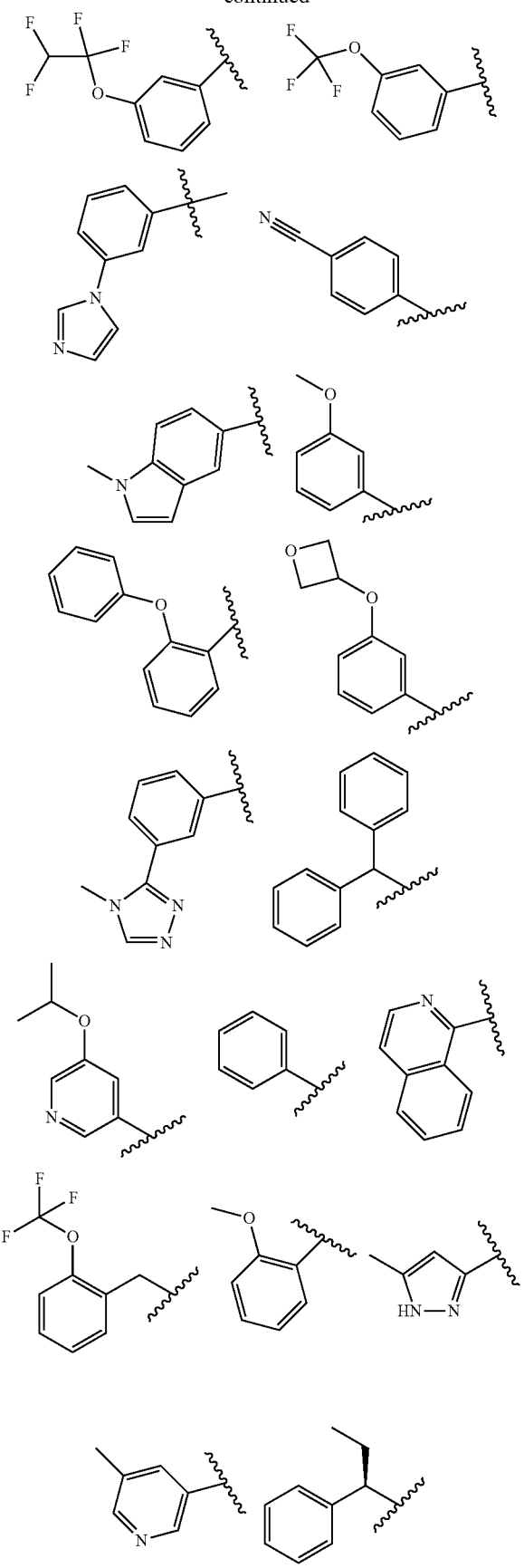

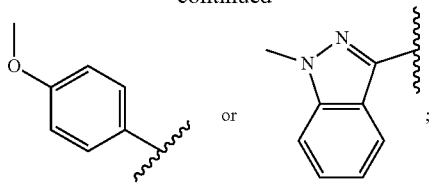

or a salt thereof.

10. The compound of claim 1 which is a compound of formula (Id):

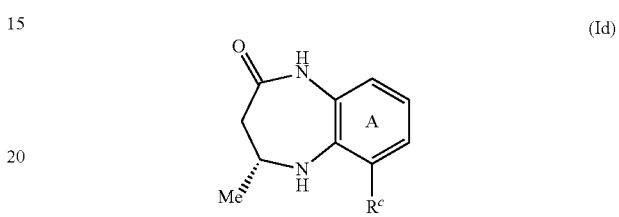

wherein:
R$^c$ is -(6-10 membered aryl)-Y or 5-14 membered heteroaryl, wherein any 6-10 membered aryl and 5-14 membered heteroaryl is optionally substituted with one or more groups independently selected from the group consisting of oxo, 3-20 membered carbocyclyl, 3-20 membered heterocyclyl, halo, —NO$_2$, —N(R$^g$)$_2$, —CN, —C(O)—N(R$^g$)$_2$, —S(O)—N(R$^g$)$_2$, —S(O)$_2$—N(R$^g$)$_2$, —O—R$^g$, —S—R$^g$, —O—C(O)—W, —C(O)—R$^g$, —C(O)—O—R$^g$, —S(O)—R$^g$, —S(O)$_2$—R$^g$, —C(O)—N(R$^g$)$_2$, —N(R$^g$)—C(O)—R$^g$, —Si(R$^h$)$_3$, —N(R$^g$)—C(O)—O—R$^g$, —N(R$^g$)—S(O)—R$^g$, N(R$^g$)—S(O)$_2$—R$^g$, and C$_{1-6}$ alkyl, which 3-20 membered carbocyclyl, 3-20 membered heterocyclyl, and C$_{1-6}$ alkyl are optionally substituted with one or more groups R$^i$;
Y is (6-10 membered aryl) or (5-14 membered heteroaryl) optionally substituted with one or more groups R$^i$;
each R$^i$ is independently selected from the group consisting of oxo, halo, C$_{1-6}$alkyl, cyano, —N(R$^j$)$_2$, —S(O)$_2$—R$^j$, —S(O)—N(R$^j$)$_2$, —S(O)$_2$—N(R$^j$)$_2$, —N(R$^j$)—S(O)—R$^j$, —N(R$^j$)—C(O)—O—R$^j$, —N(R$^j$)—S(O)$_2$—R$^j$, 3-20 membered heterocyclyl, and 3-20 membered carbocyclyl that is optionally substituted with one or more groups independently selected from the group consisting of halo, and C$_{1-6}$alkyl;
each R$^j$ is independently selected from the group consisting of hydrogen, C$_{1-6}$ alkyl, C$_{2-6}$alkenyl, C$_{2-6}$ alkynyl, 3-20 membered carbocyclyl, and 3-20 membered heterocyclyl, wherein each C$_{1-6}$ alkyl, C$_{2-6}$ alkenyl, C$_{2-6}$alkynyl, C$_{1-6}$ alkoxy, 3-20 membered carbocyclyl, and 3-20 membered heterocyclyl is optionally substituted with one or more groups R$^m$;
each R$^m$ is independently selected from the group consisting of oxo, halo, amino, hydroxyl, —Si(R$^n$)$_3$, 3-20 membered carbocyclyl, 3-20 membered heterocyclyl, and C$_1$-C$_6$ alkyl, wherein any 3-20 membered carbocyclyl, 3-20 membered heterocyclyl, and C$_1$-C$_6$ alkyl is optionally substituted with one or more groups independently selected from the group consisting of oxo, C$_1$-C$_4$alkyl, and halo; and
each R$^n$ is independently selected from the group consisting of H, C$_{1-6}$ alkyl, C$_{2-6}$ alkenyl, C$_{2-6}$ alkynyl, and C$_{3-6}$ carbocyclyl;
or a salt thereof.

11. The compound claim 10 wherein $R^c$ is:
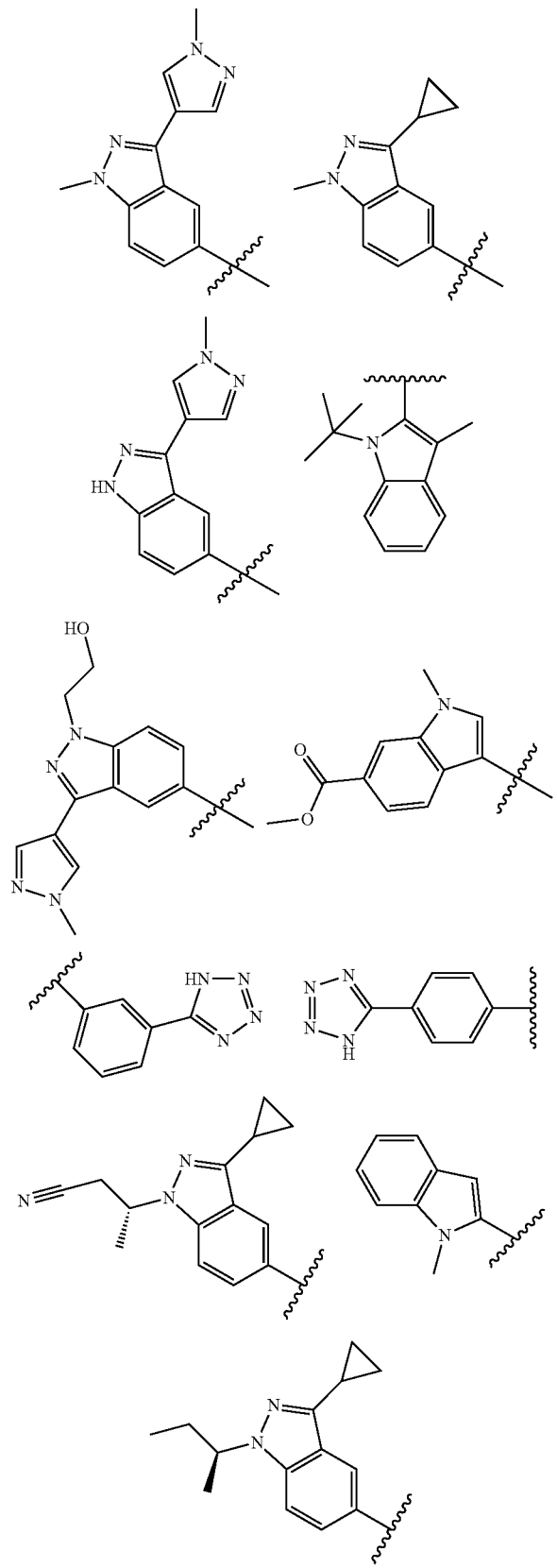
-continued
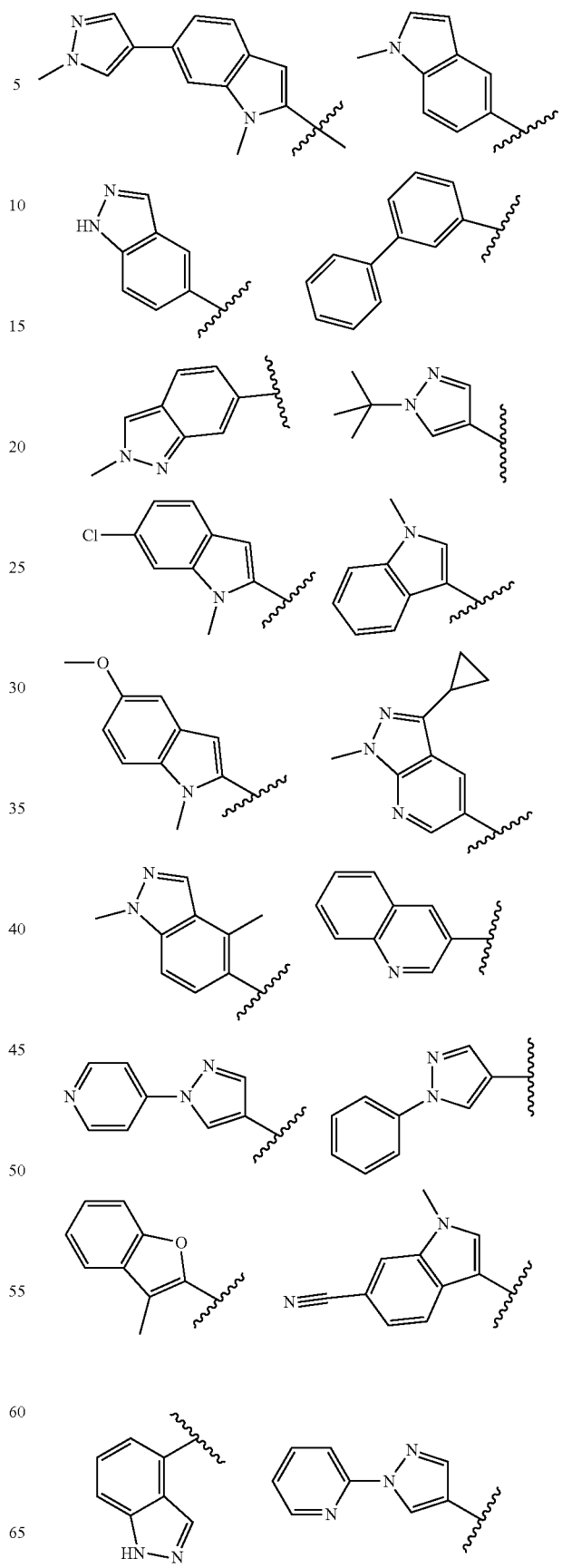

495
-continued
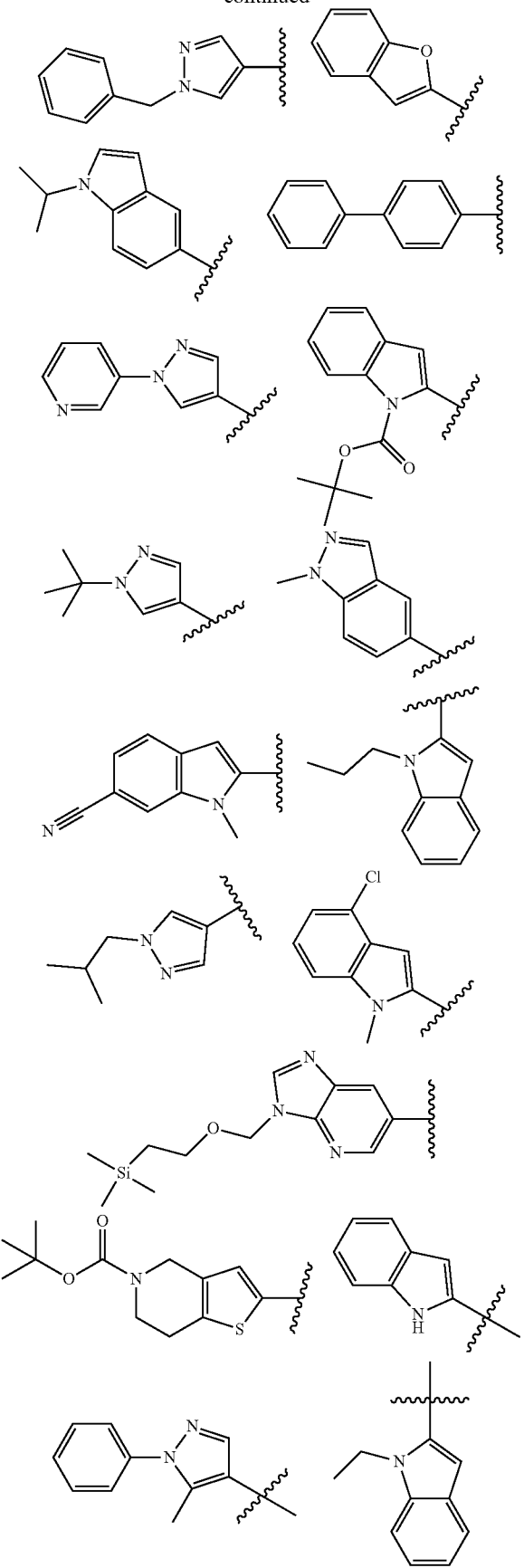
496
-continued
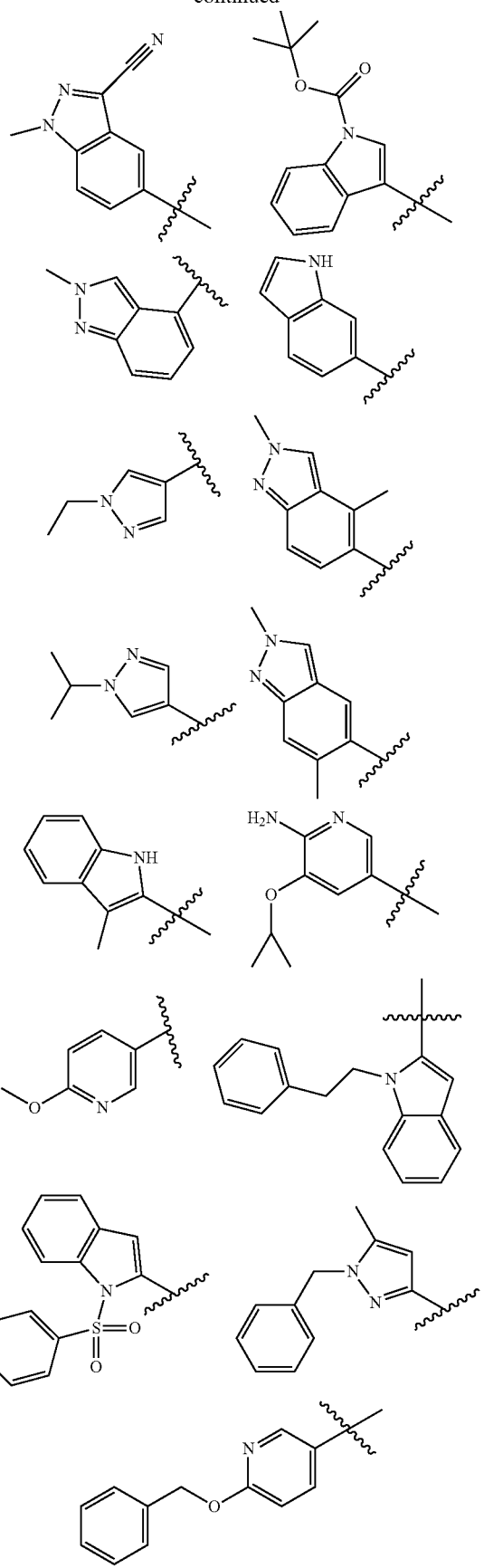

497
-continued
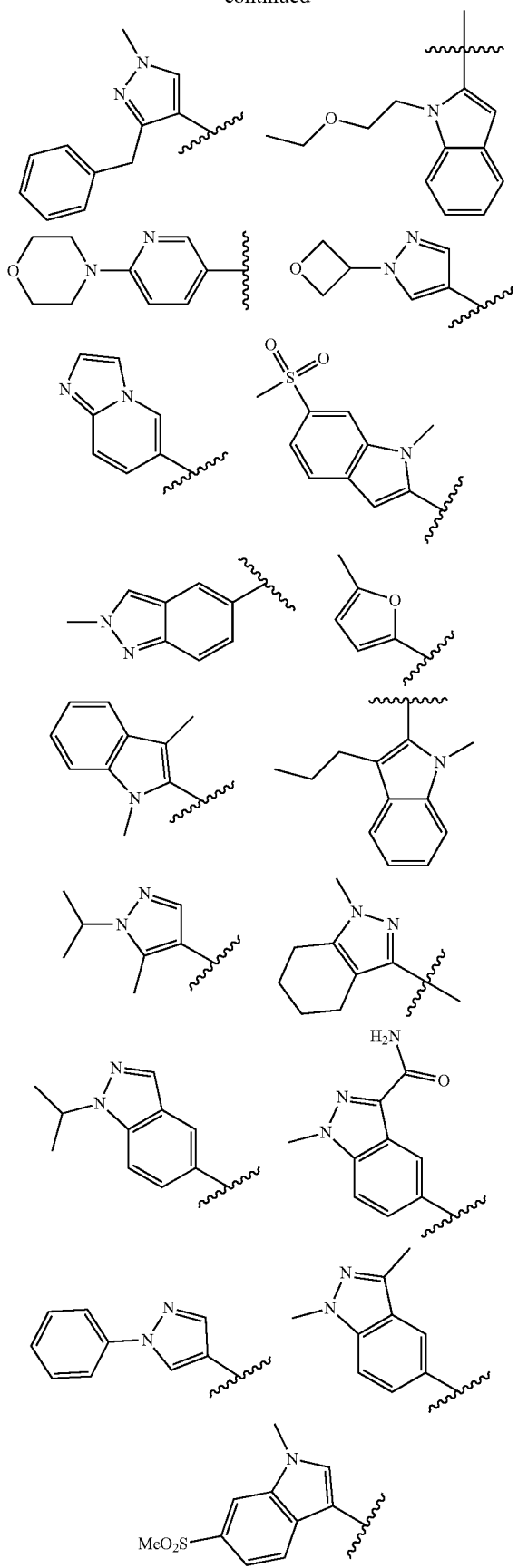
498
-continued
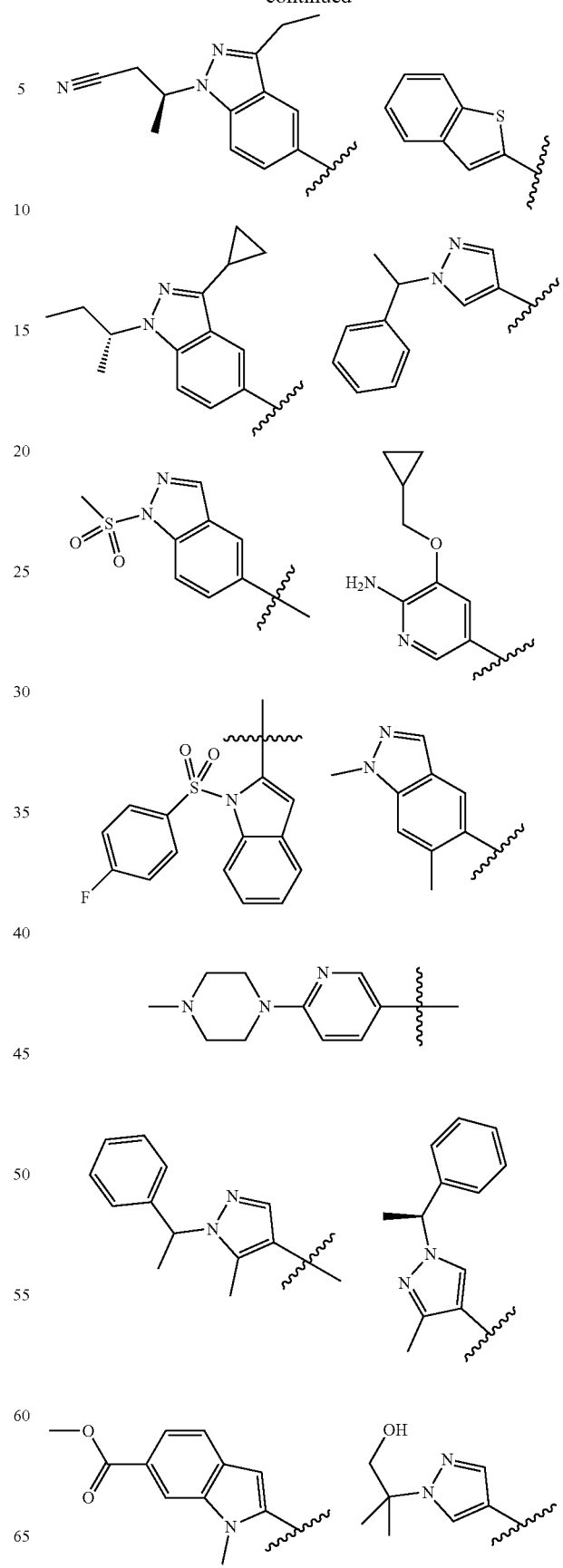

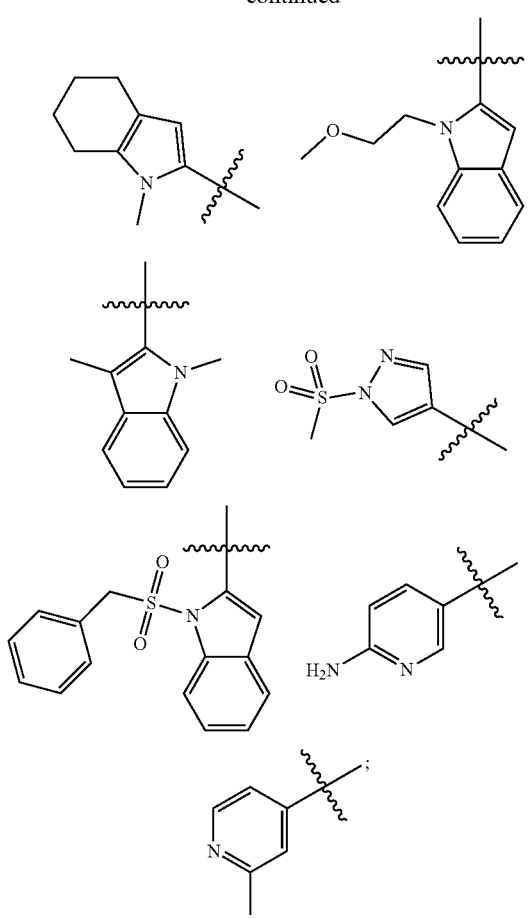
or a salt thereof.
12. The compound of claim 1 which is a compound of formula (If):
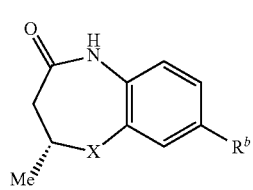
(If)
wherein:
X is NH; and
R$^{b1}$ is
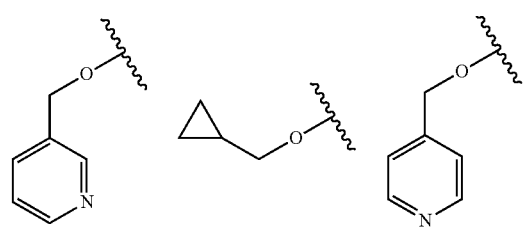
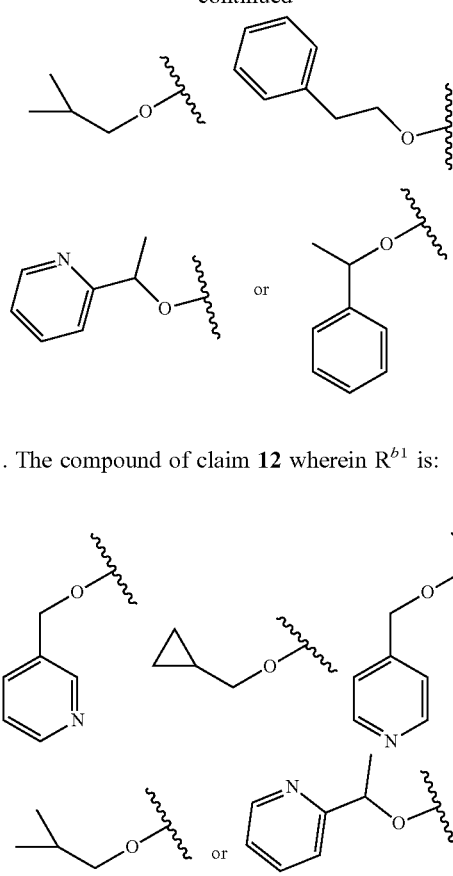
13. The compound of claim 12 wherein R$^{b1}$ is:
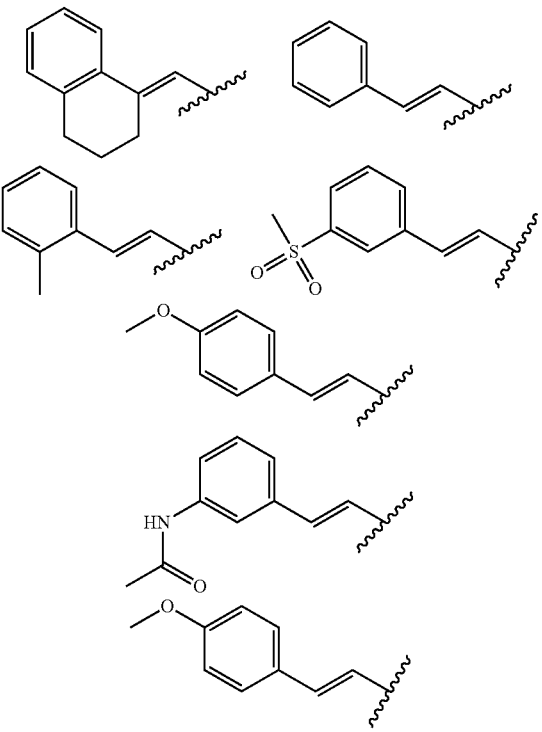
14. The compound of claim 1 wherein R$^b$ is:

501
-continued
502
-continued
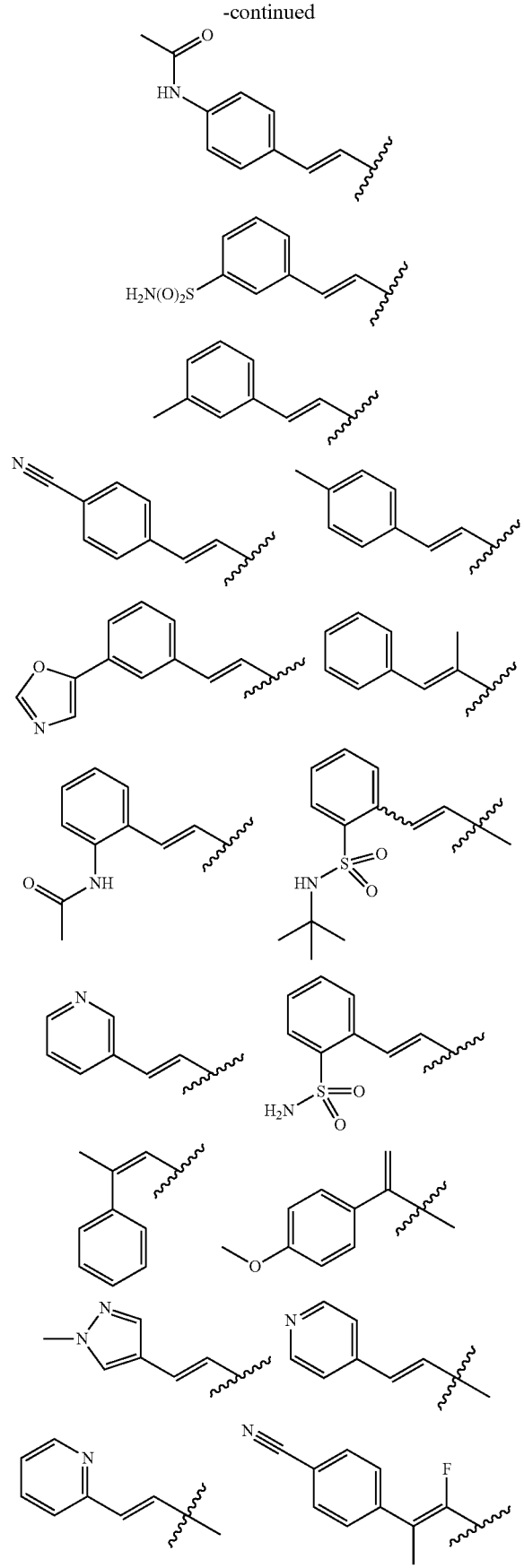
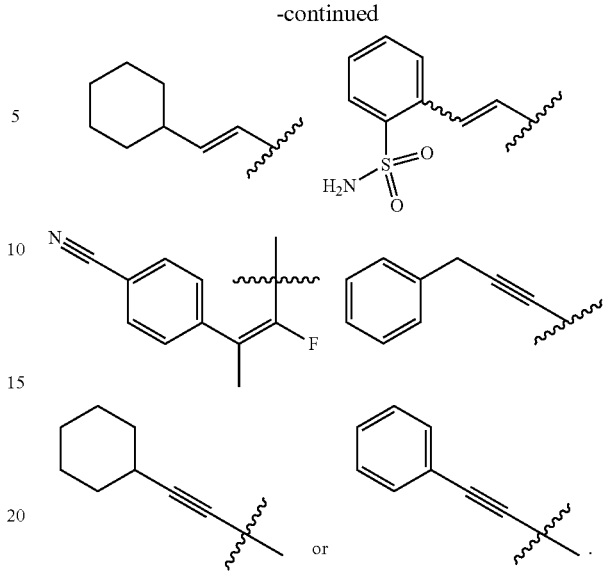
15. A compound selected from the group consisting of:
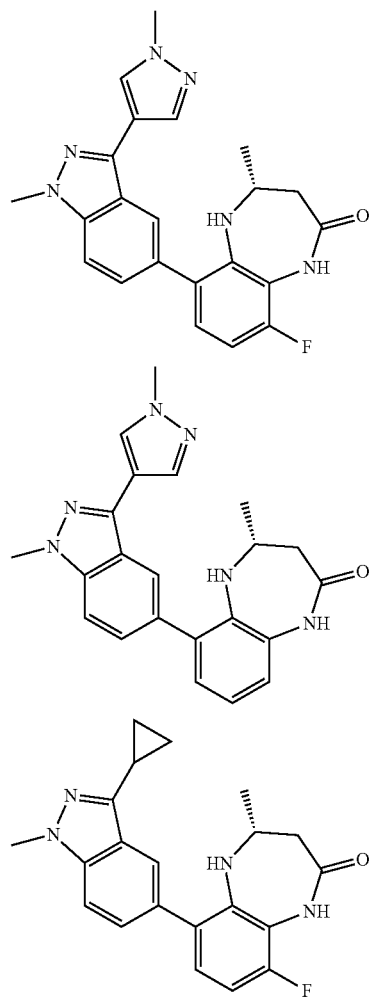

-continued
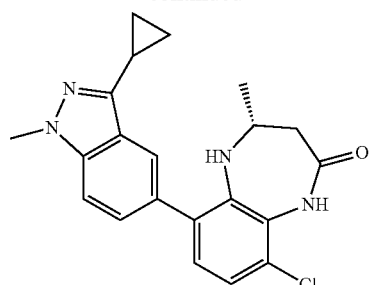
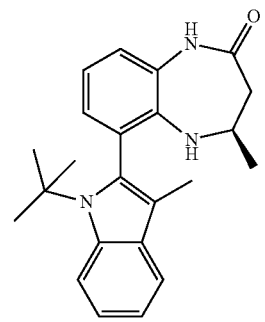
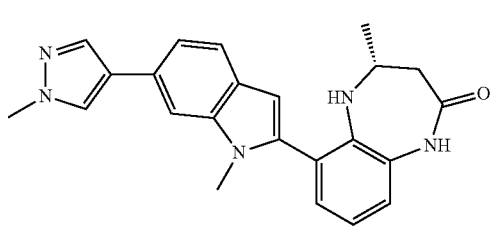
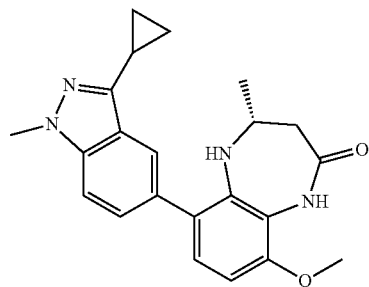
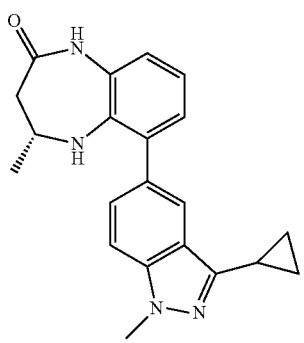
-continued
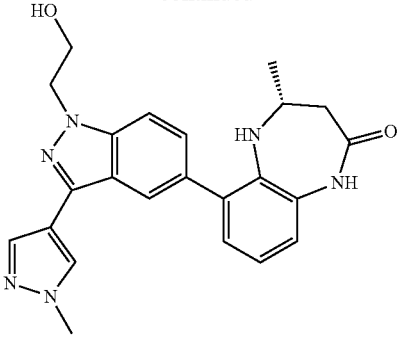
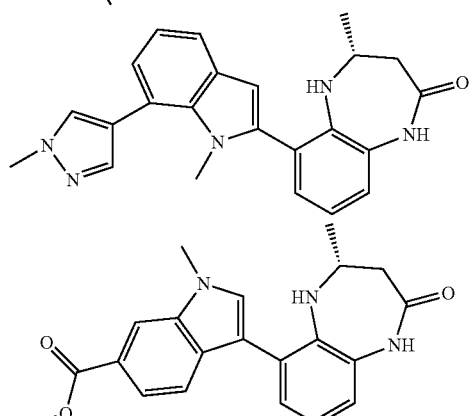
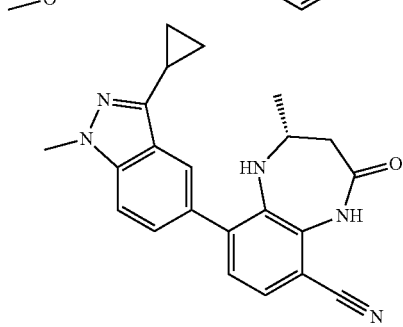
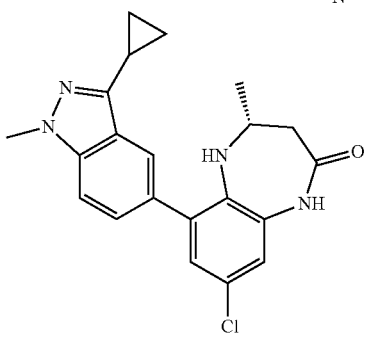
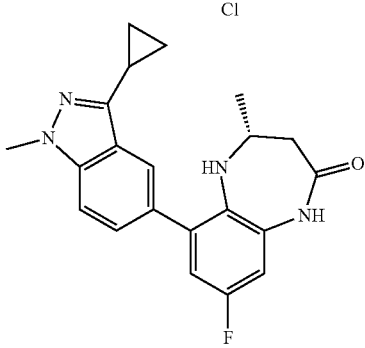

505
-continued
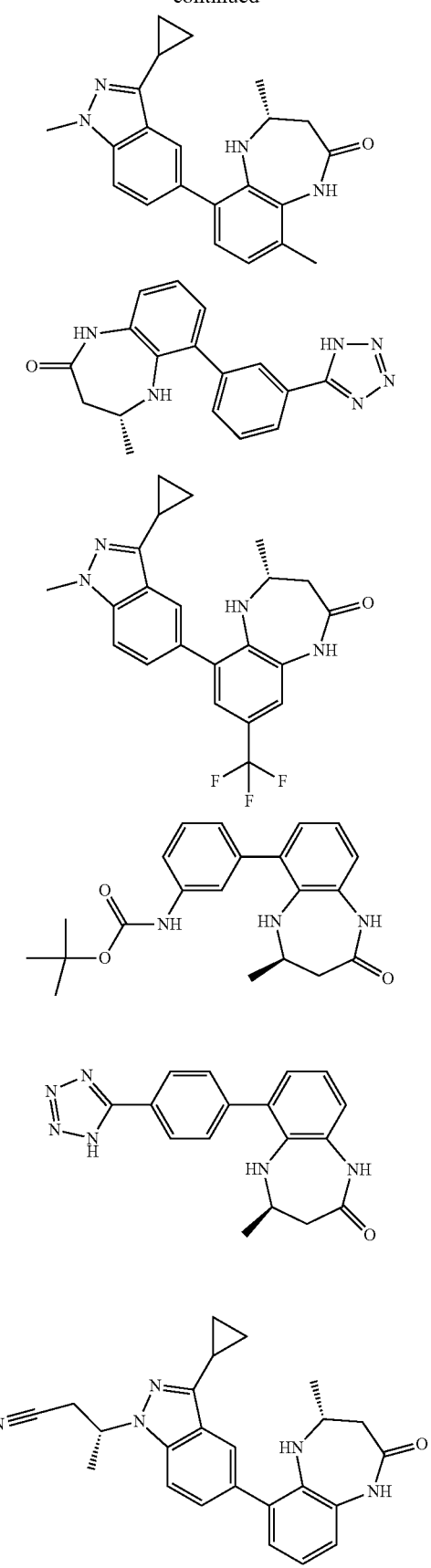
506
-continued
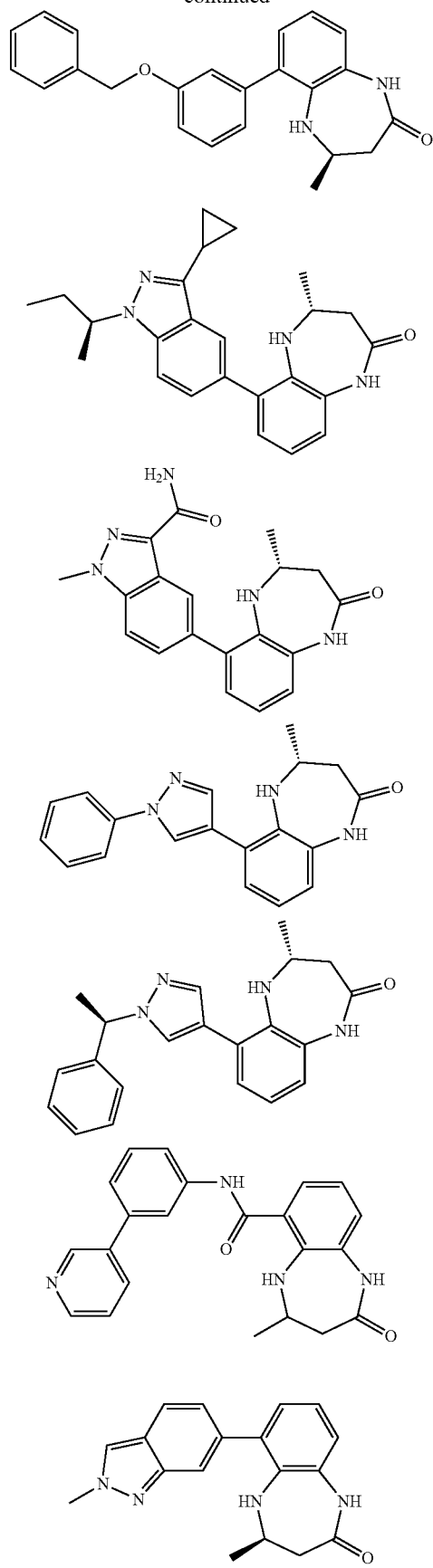

507
-continued
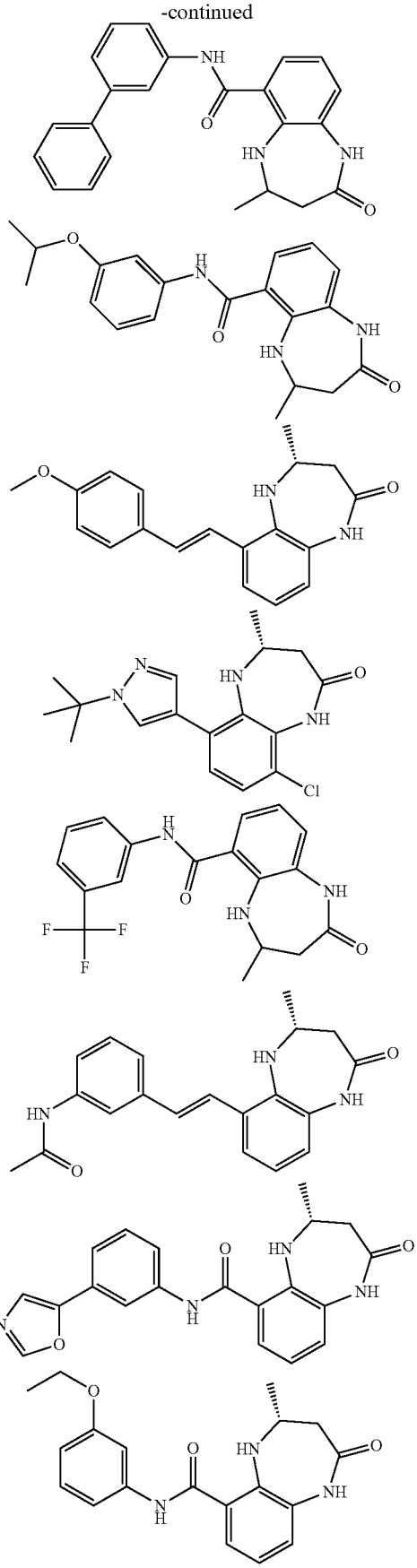
508
-continued
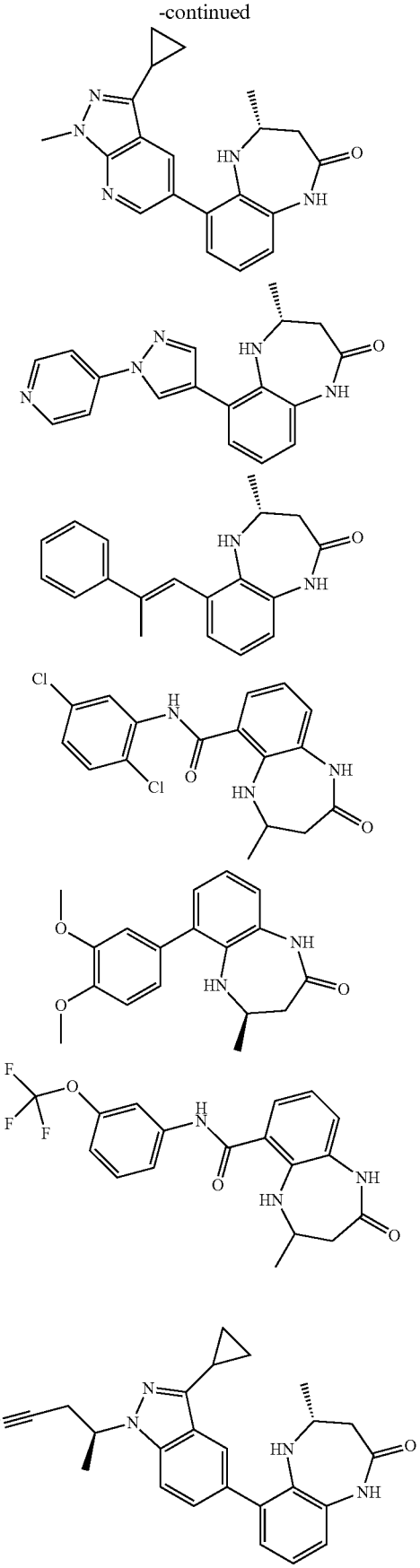

509
-continued
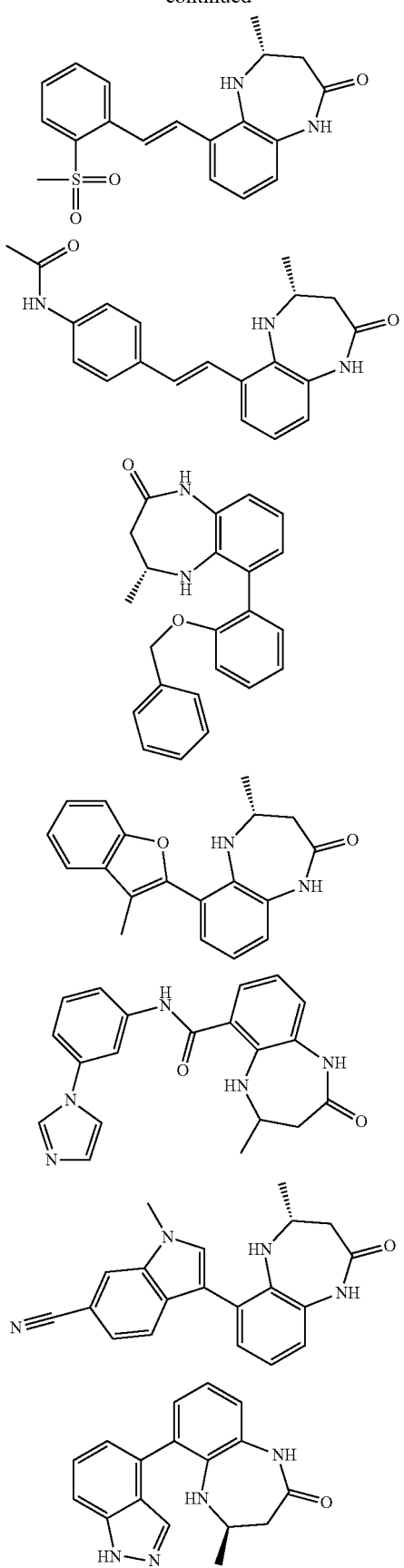
510
-continued
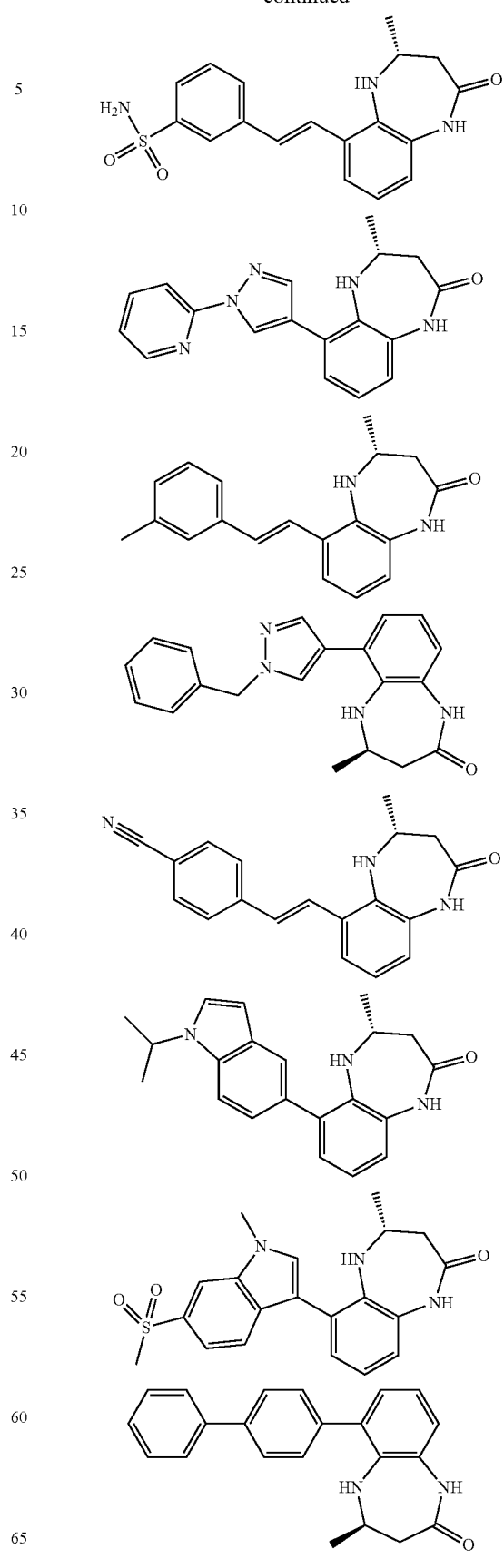

511
-continued
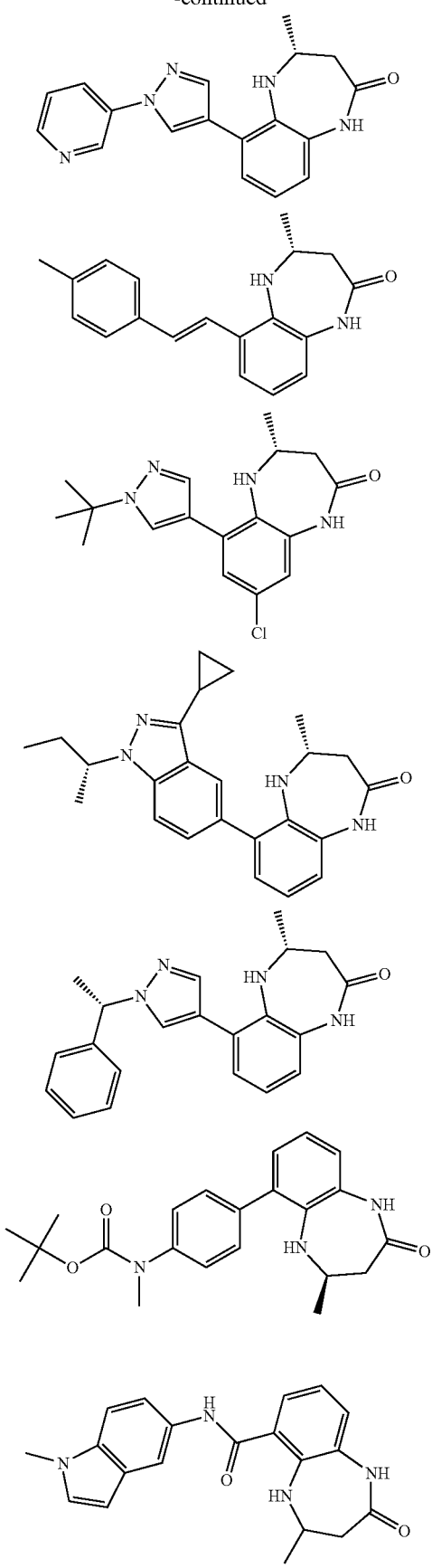
512
-continued
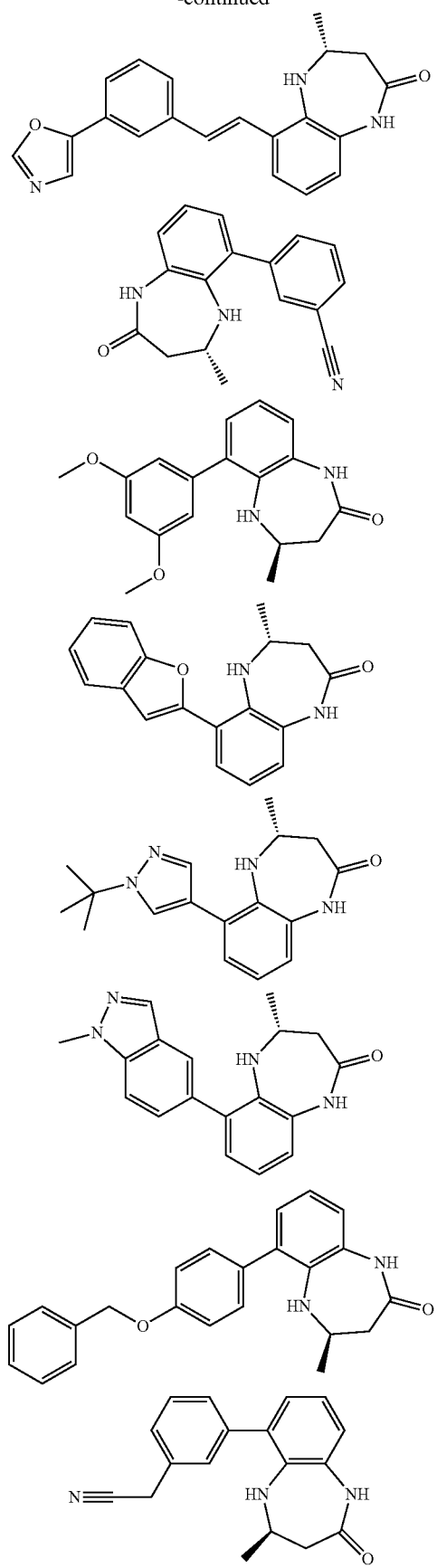

513
-continued
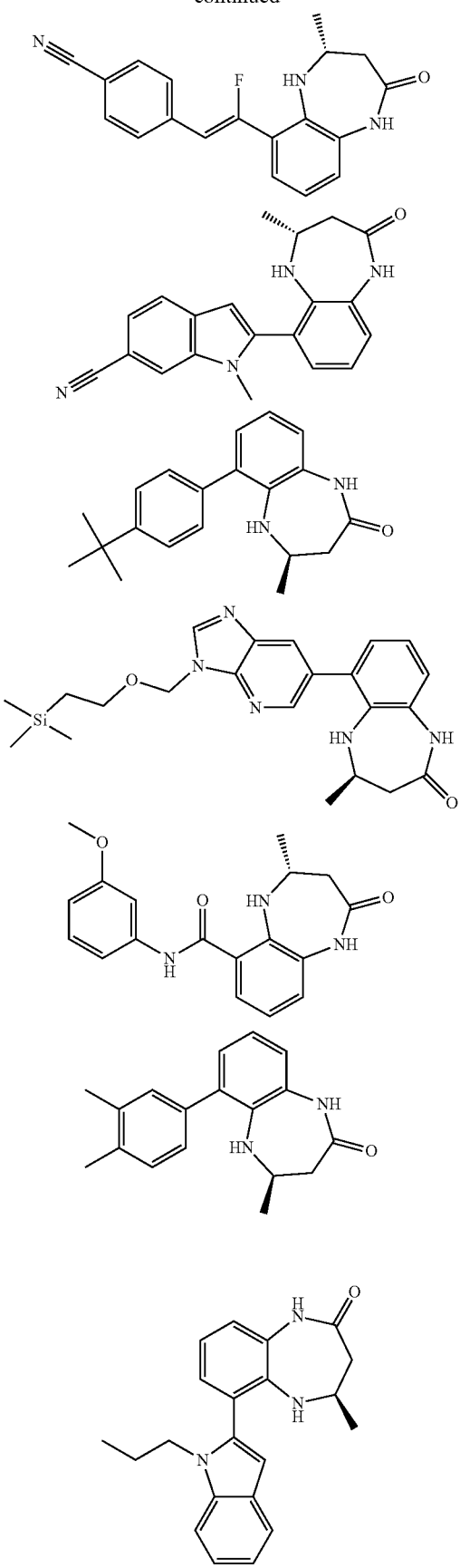
514
-continued
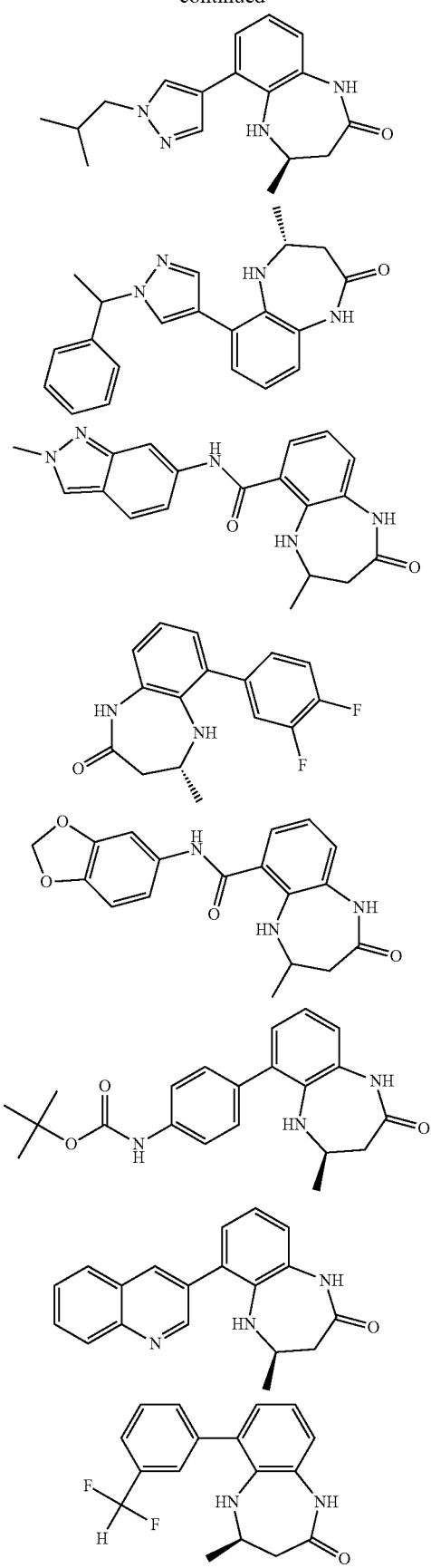

515
-continued
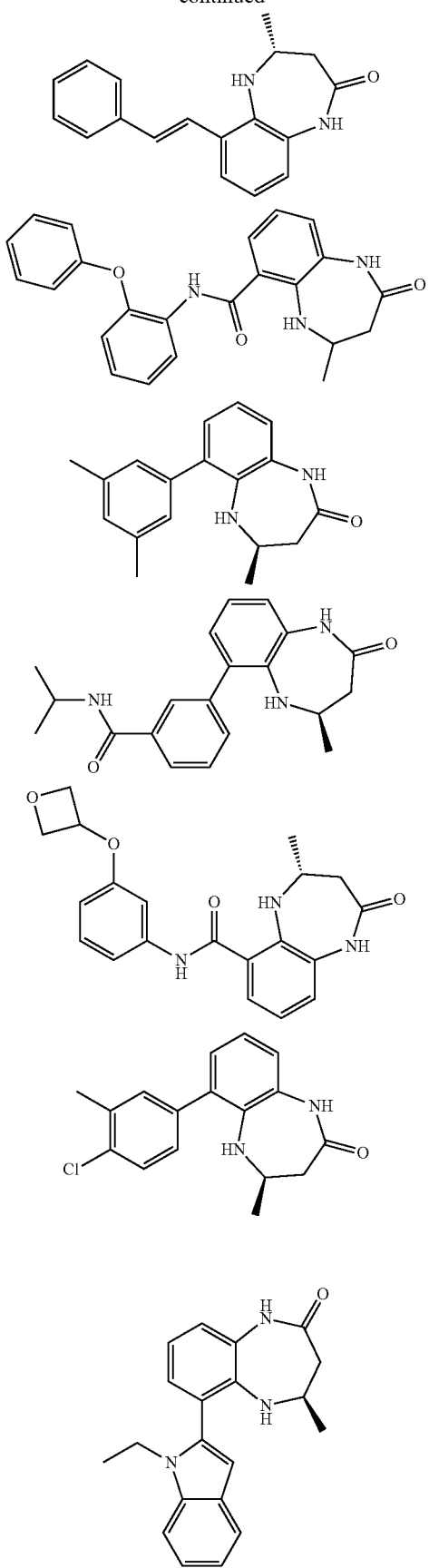
516
-continued
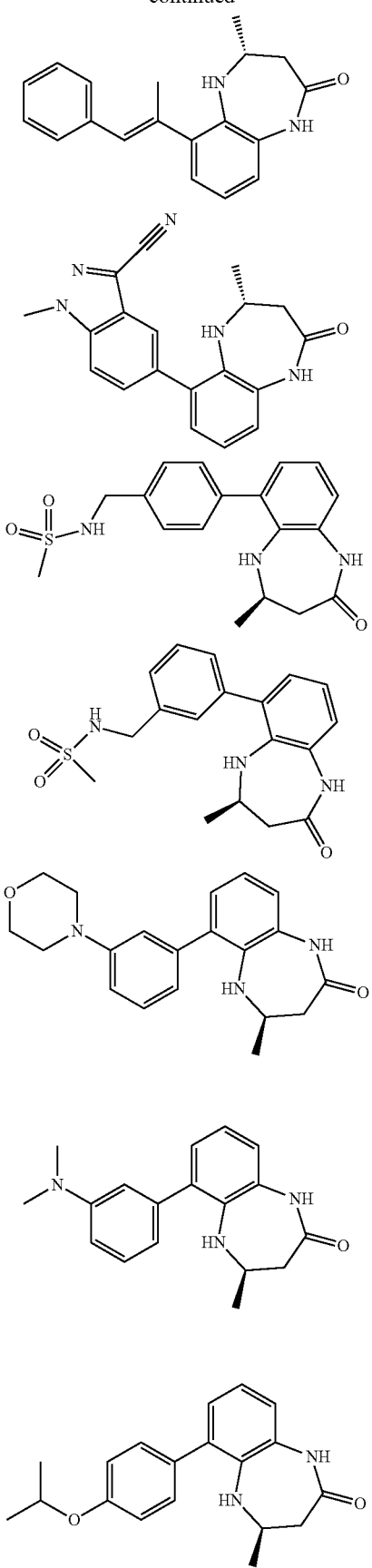

517
-continued
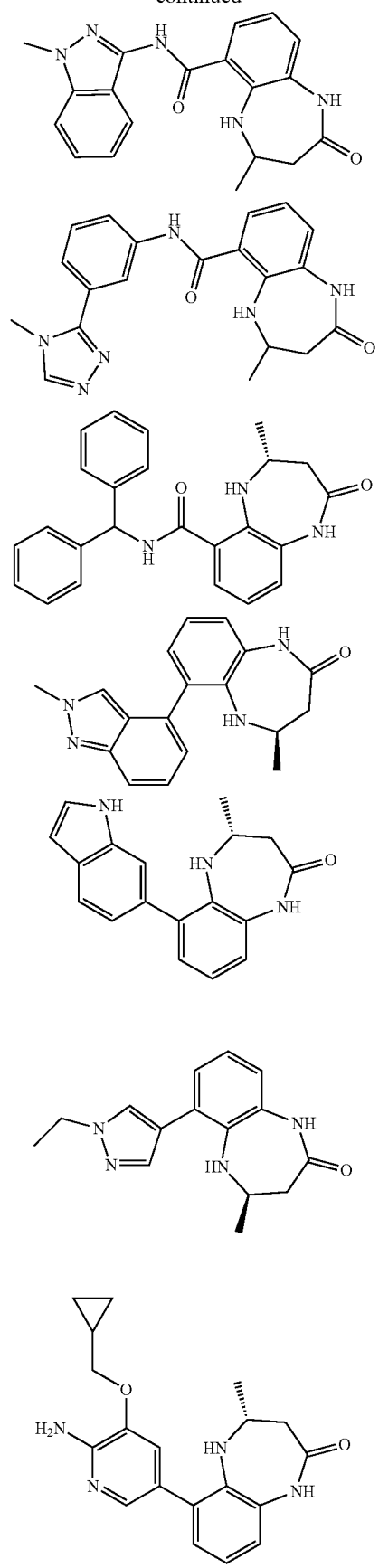
518
-continued
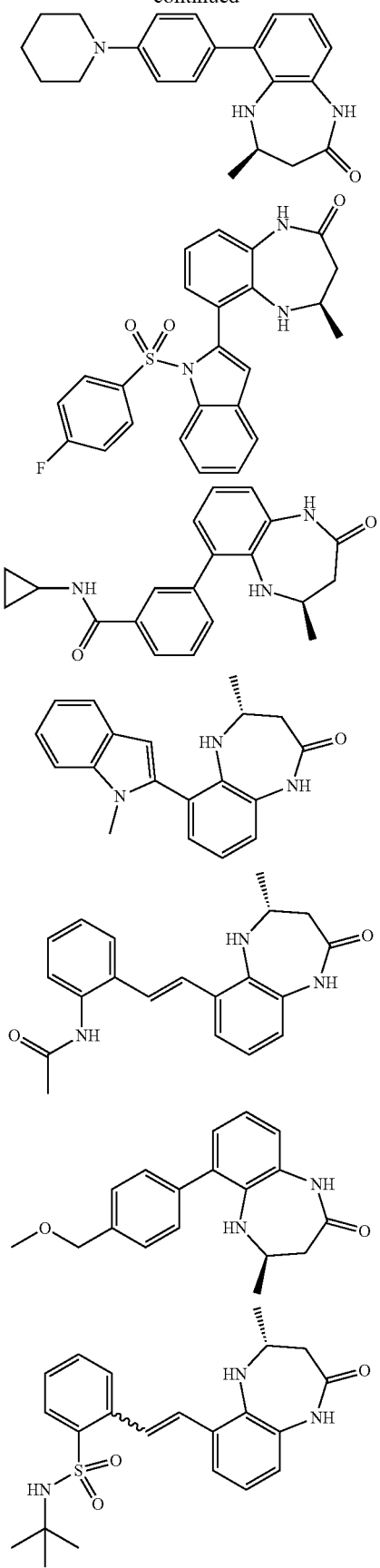

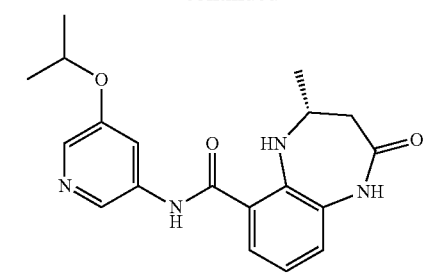
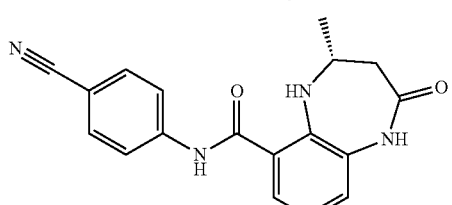
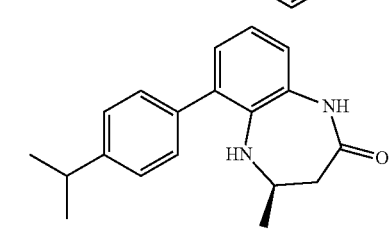
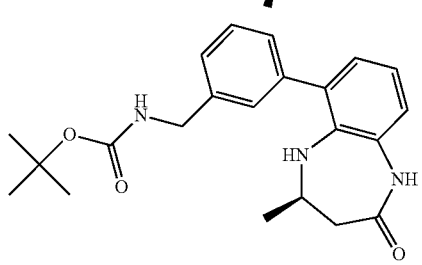
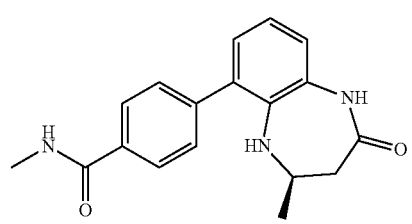
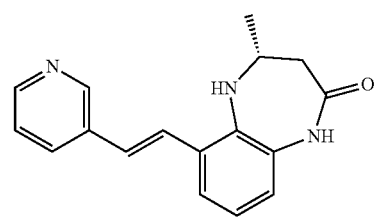
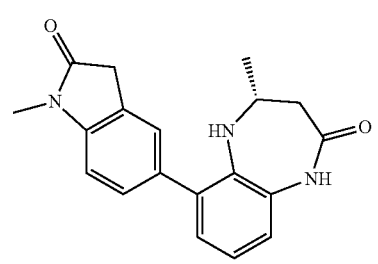
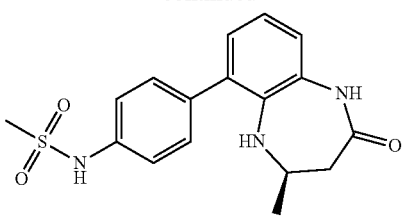 [SMILES: C[C@@H]1CC(=O)Nc2cccc(-c3ccc(NS(C)(=O)=O)cc3)c2N1]
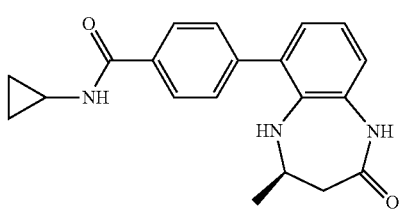
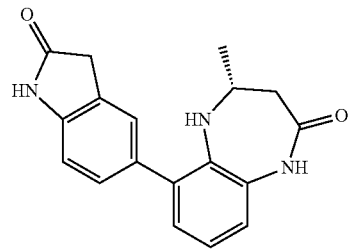
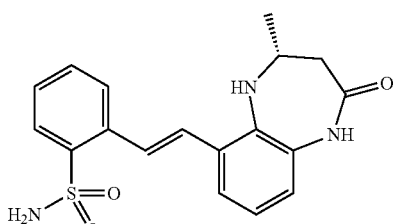
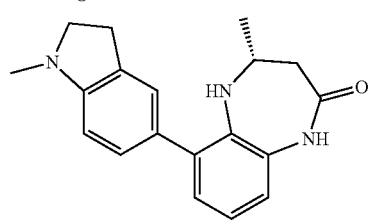
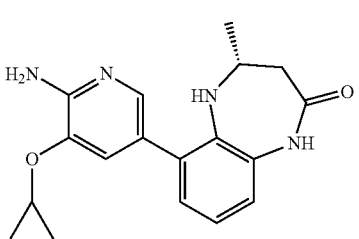
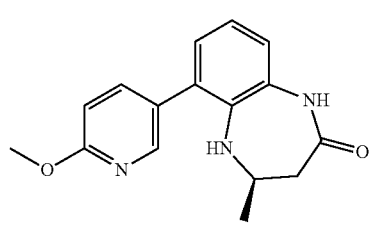 [SMILES: COc1ccc(-c2cccc3c2N[C@H](C)CC(=O)N3)cn1]

521
-continued
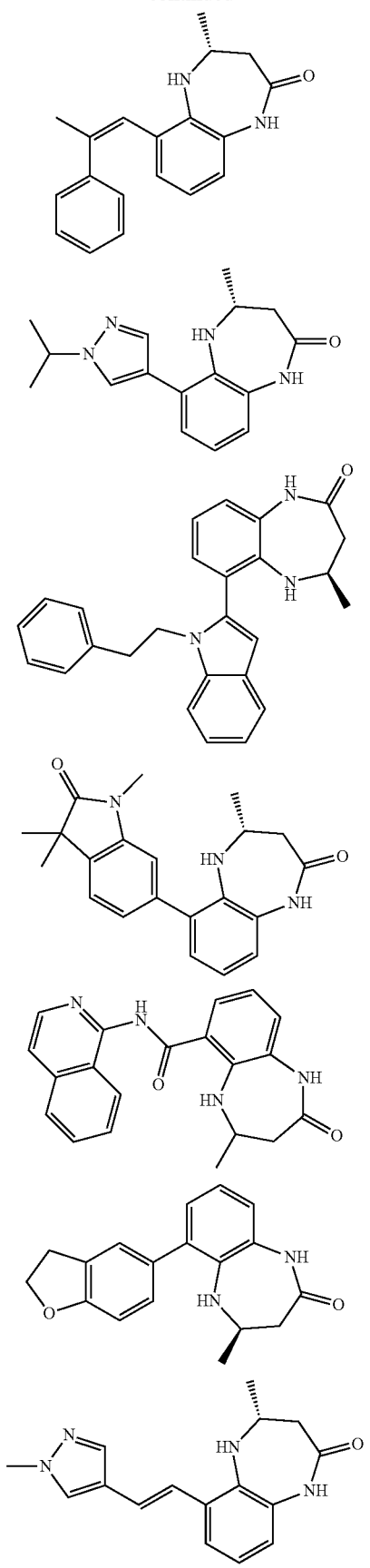
522
-continued
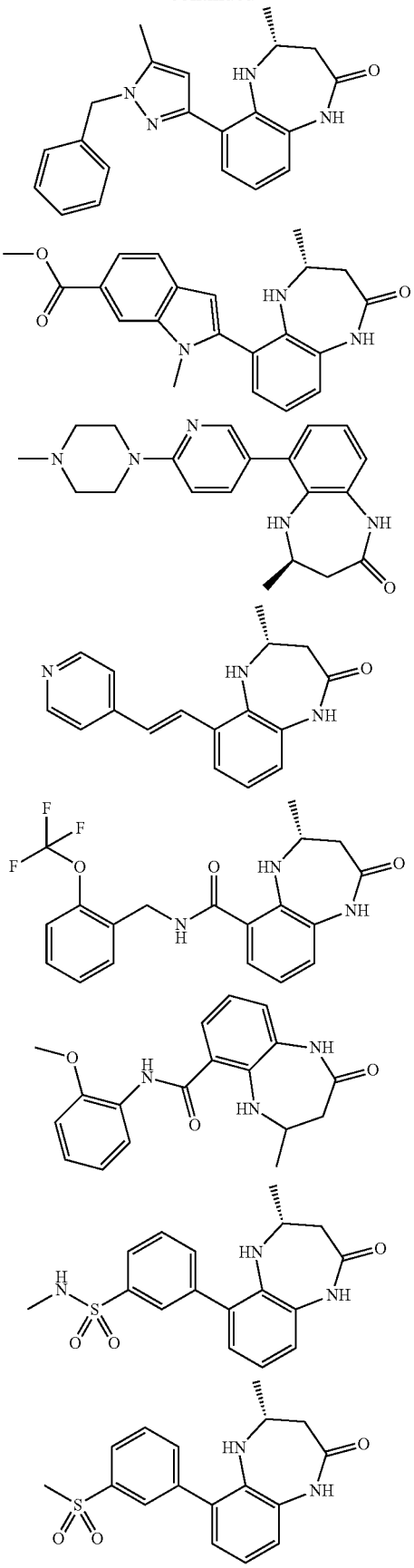

523
-continued
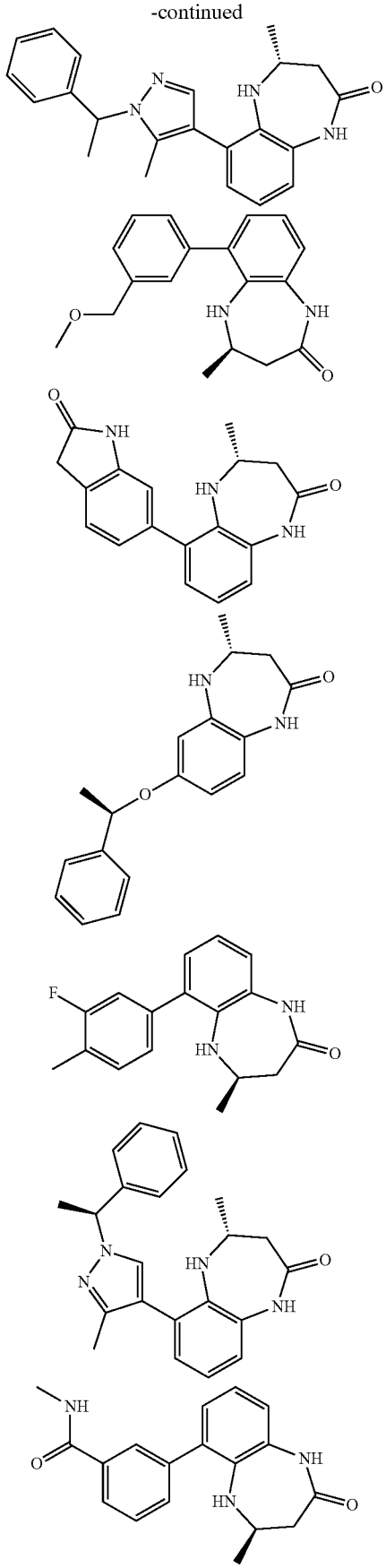
524
-continued
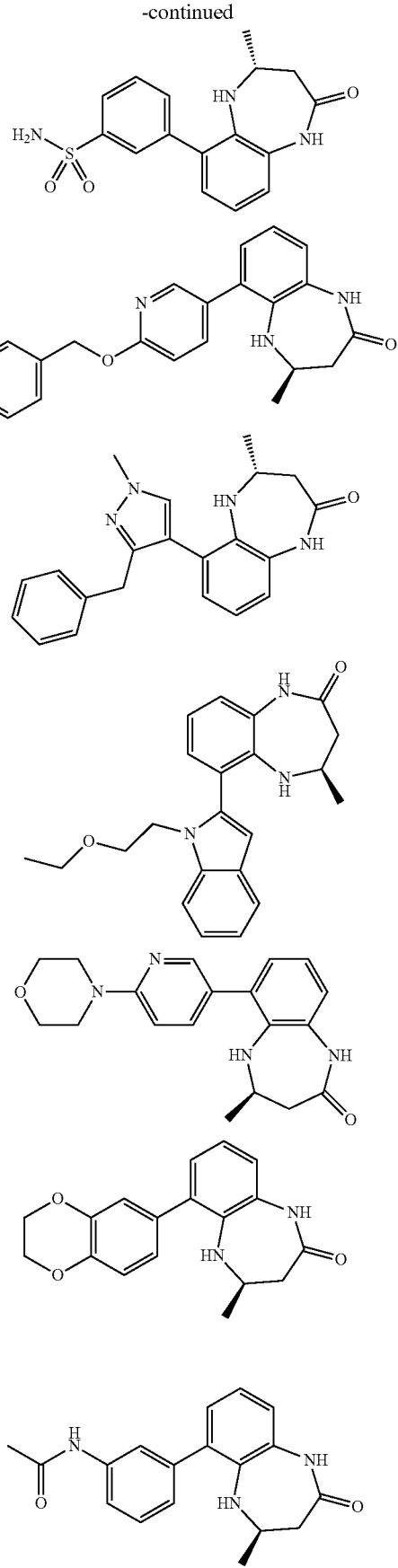

-continued
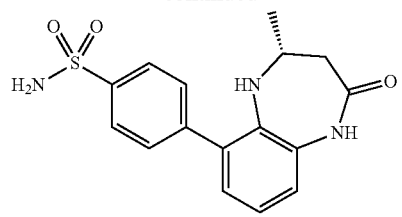
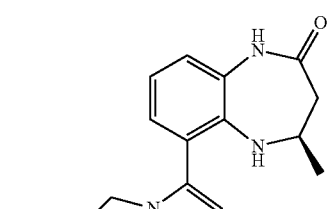
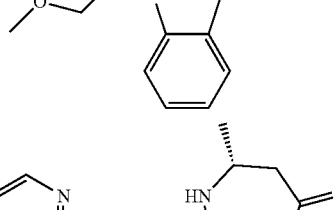
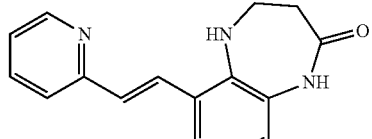
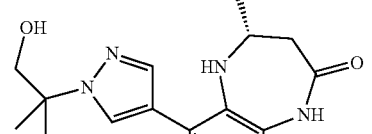
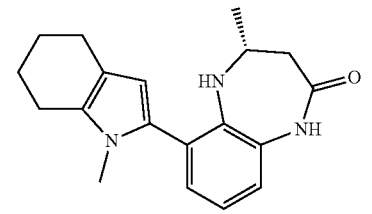
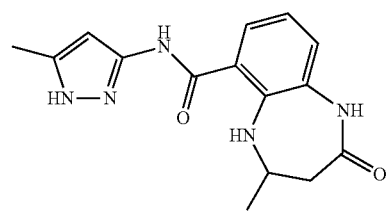
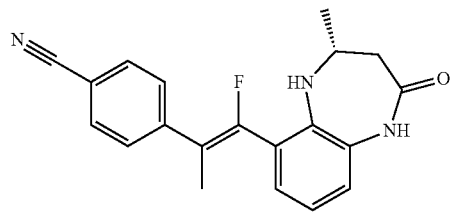
-continued
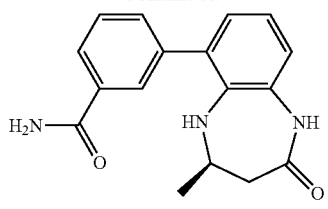
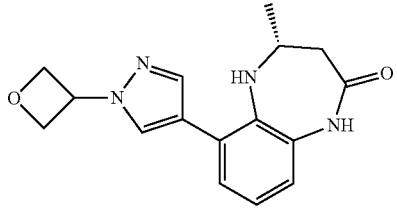
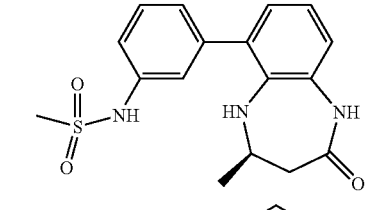
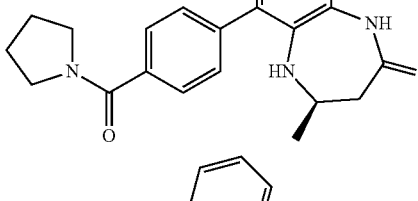
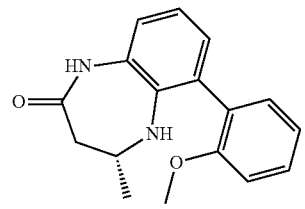
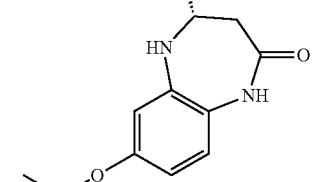
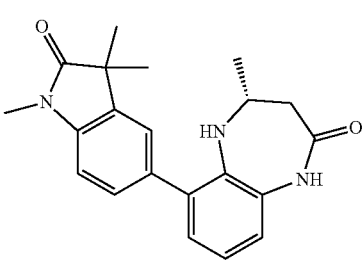

527
-continued
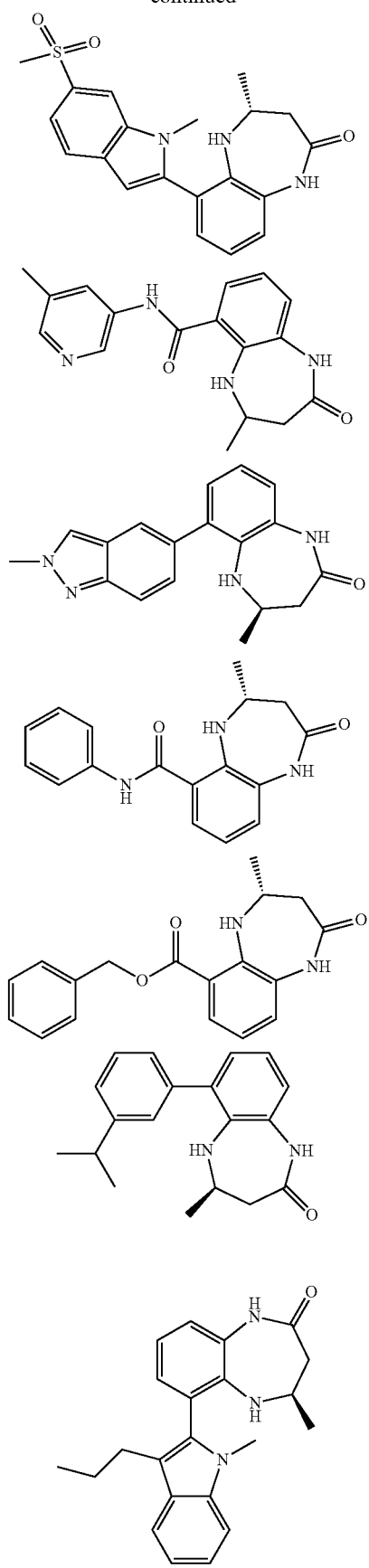
528
-continued
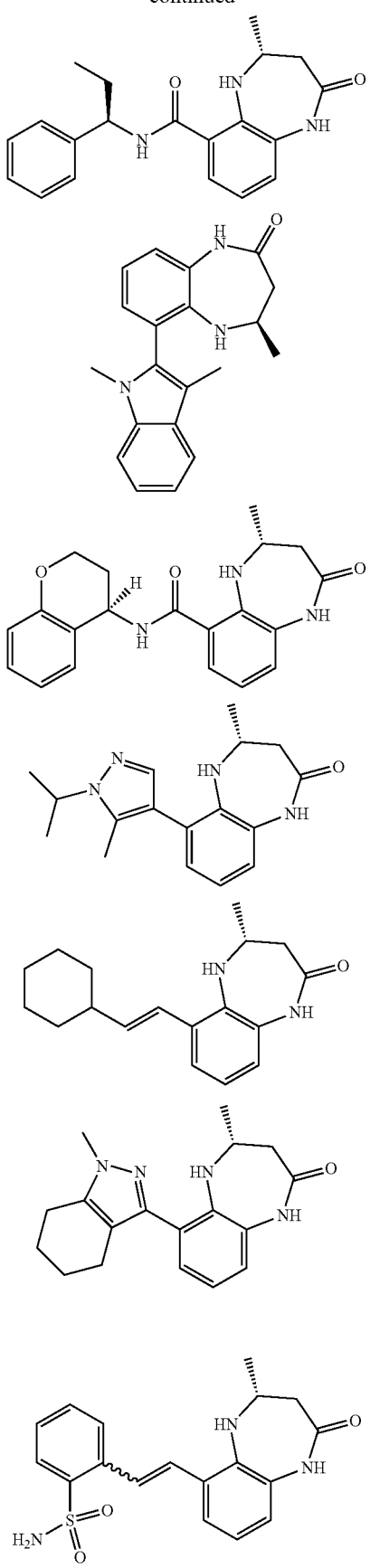

529
-continued
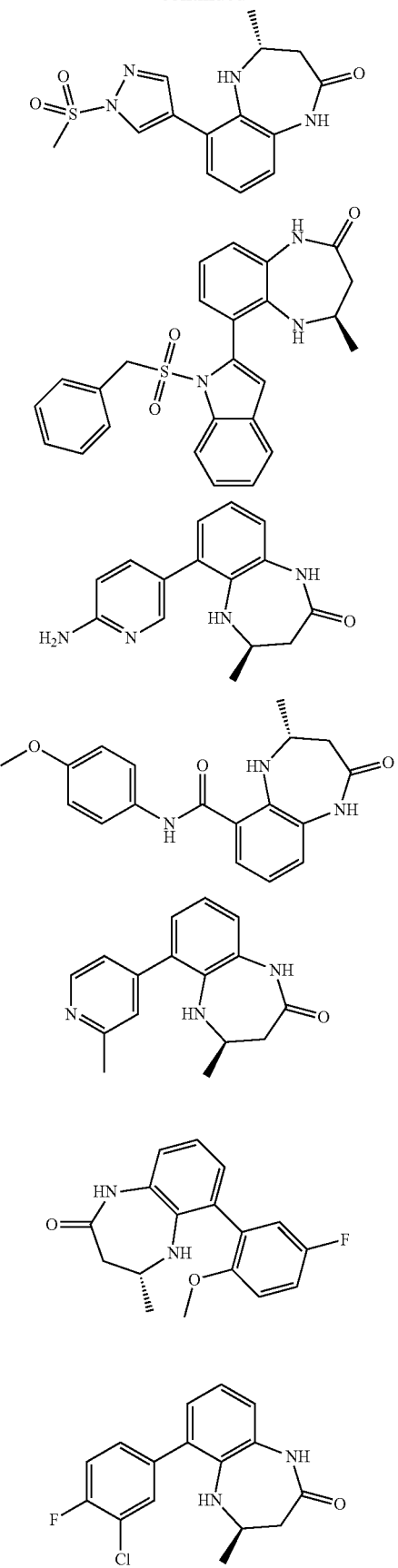
530
-continued
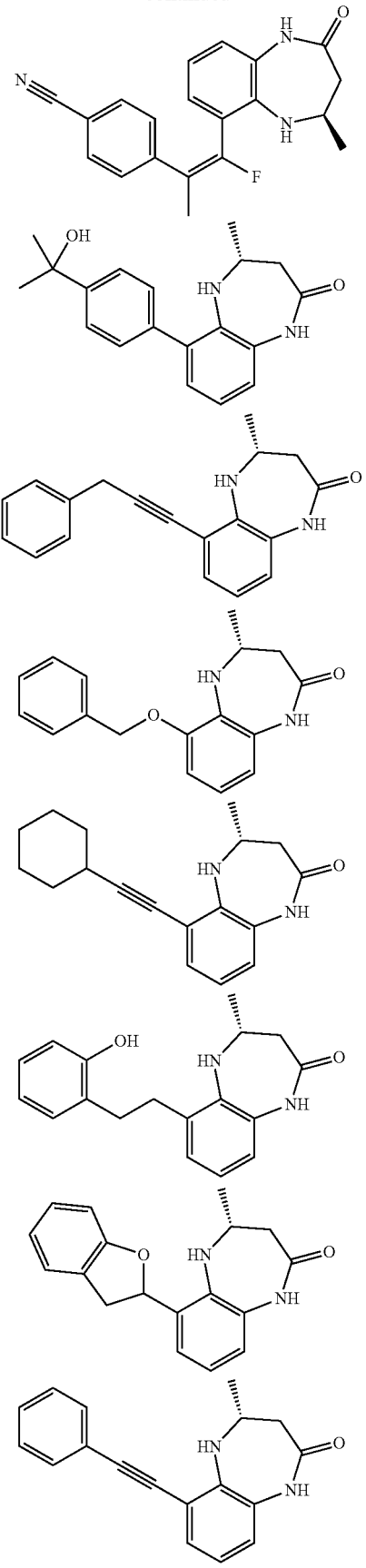

531
-continued
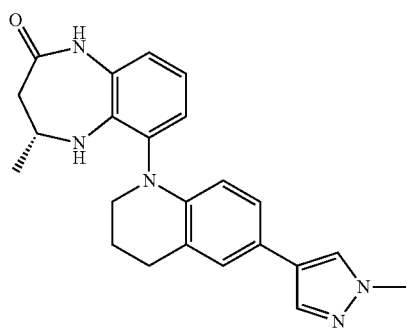
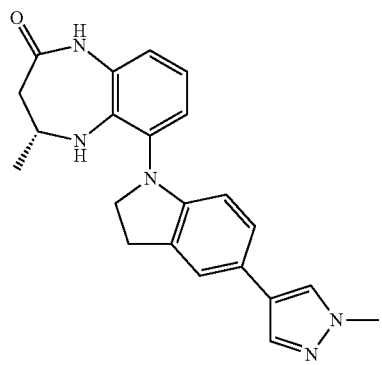
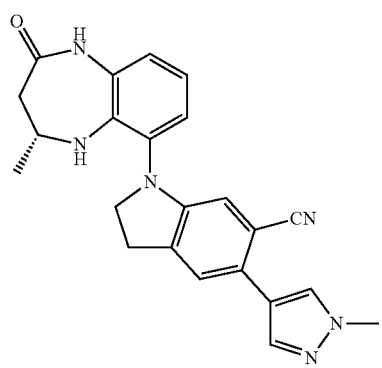
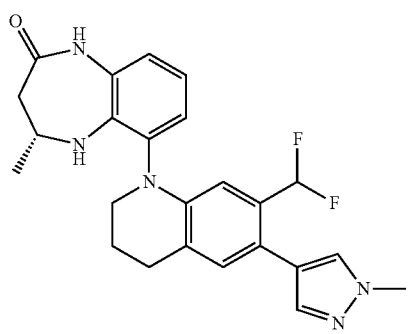
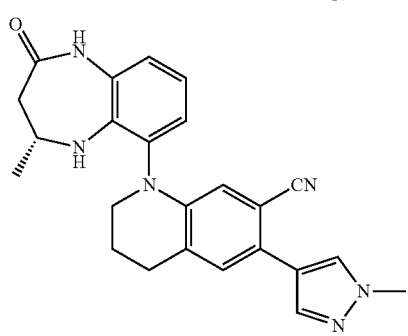
532
-continued
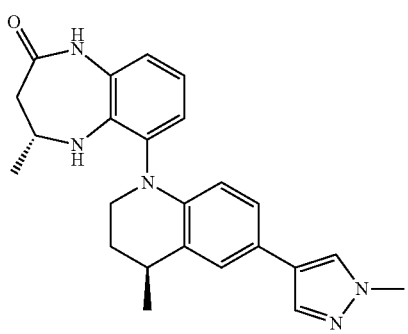
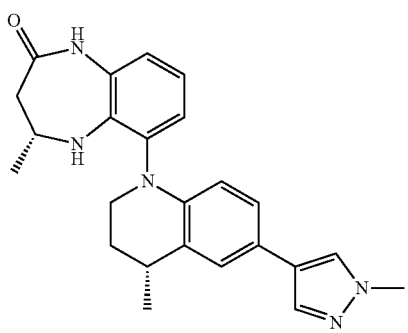
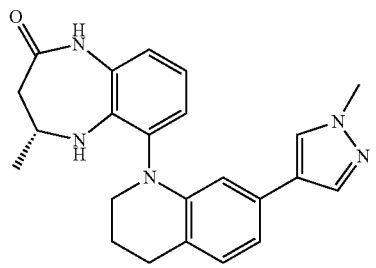
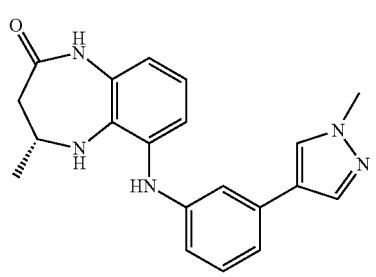
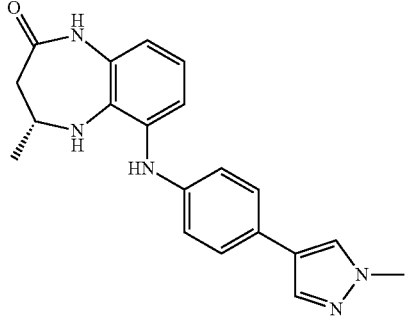

533
-continued
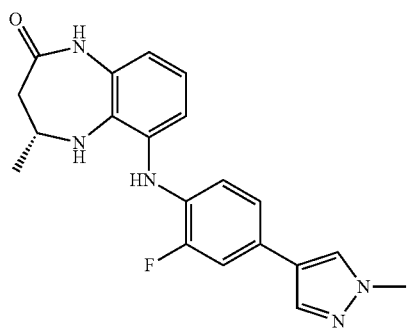
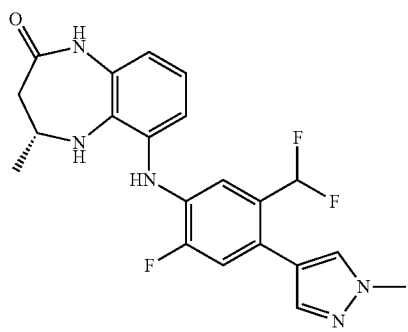
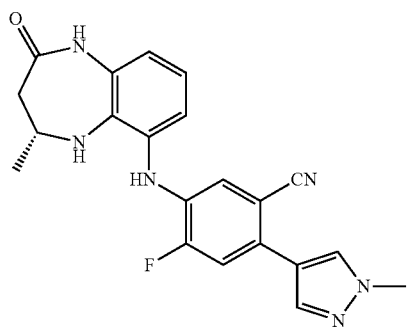
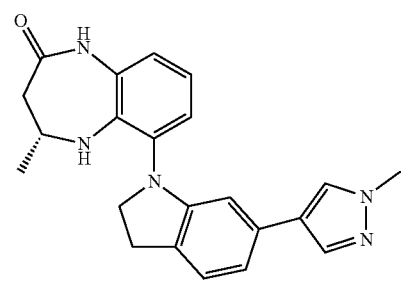
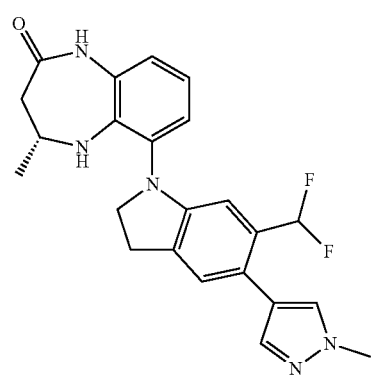
534
-continued
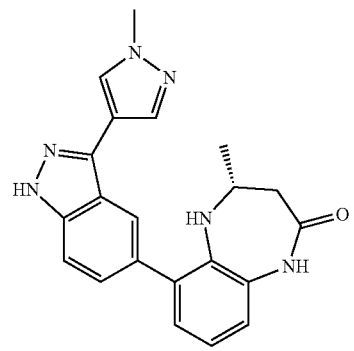
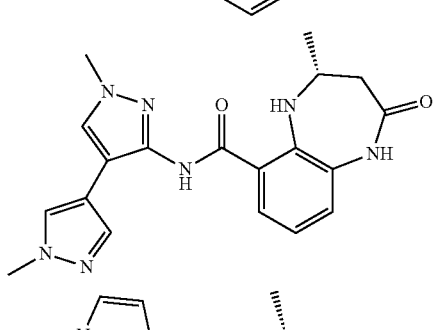
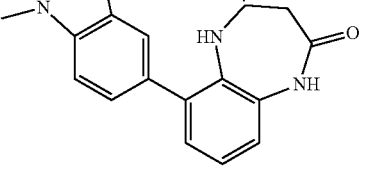
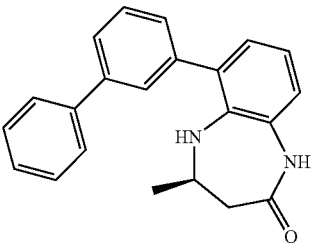
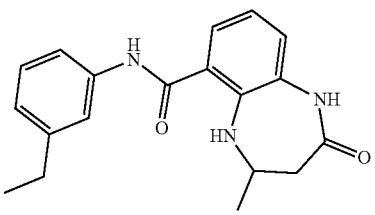
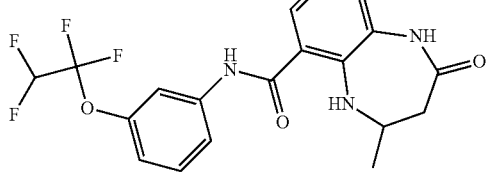
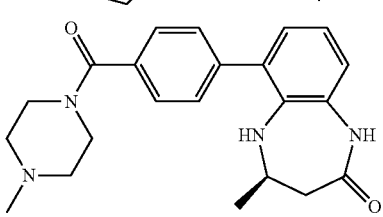

535
-continued
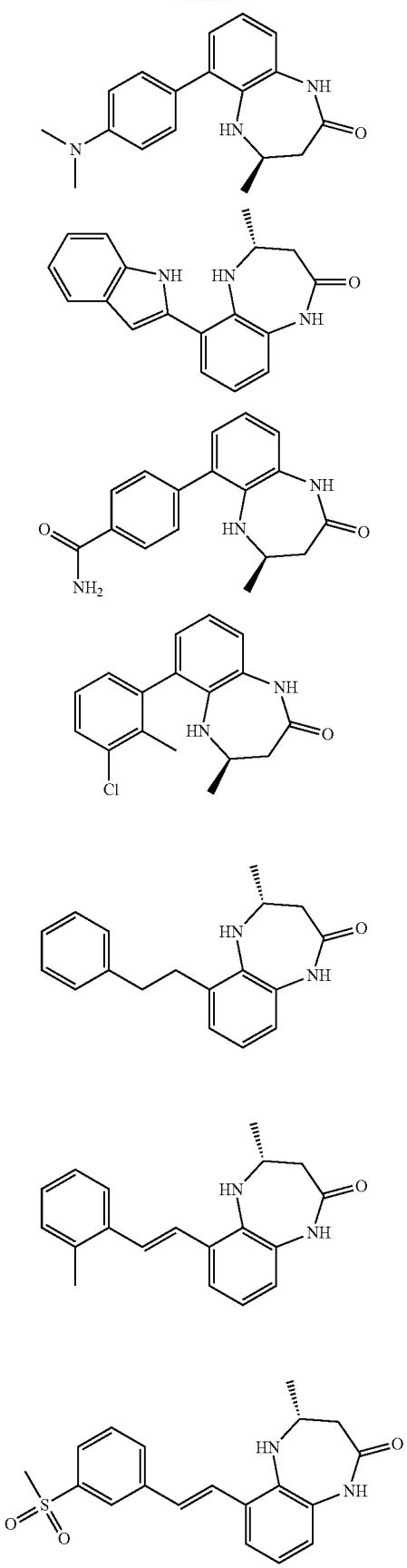
536
-continued
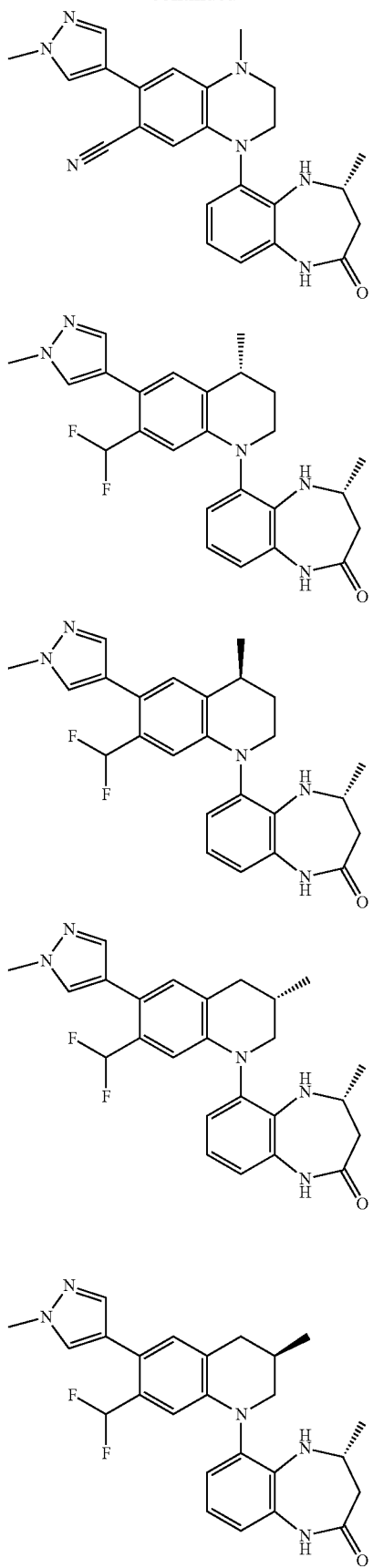

-continued

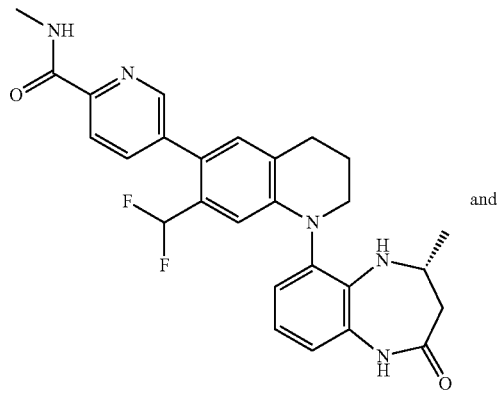

and

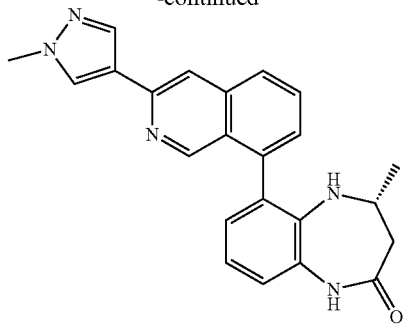

or a salt thereof.

16. A composition comprising a compound of formula (I) as described in claim 1 or a pharmaceutically acceptable salt thereof, and a pharmaceutically acceptable adjuvant, carrier, or vehicle.

17. A method for treating a CBP and/or EP300-mediated disorder in an animal comprising administering a compound of formula (I), or a pharmaceutically acceptable salt thereof as described in claim 1, to the animal, wherein the CBP and/or EP300-mediated disorder is cancer and the cancer is lung cancer, breast cancer, pancreatic cancer, colorectal cancer, or melanoma.

* * * * *

UNITED STATES PATENT AND TRADEMARK OFFICE
CERTIFICATE OF CORRECTION

PATENT NO. : 10,206,931 B2
APPLICATION NO. : 15/482581
DATED : February 19, 2019
INVENTOR(S) : Romero et al.

It is certified that error appears in the above-identified patent and that said Letters Patent is hereby corrected as shown below:

In the Claims

Column 457, Line 38, Claim 1, please delete "—CH=C(Re)$_2$" and insert -- —CH=C(R$^e$)$_2$ --;

Column 457, Line 40, Claim 1, please delete "C$_{2-6}$alkenyl, C$_{2-6}$ alkynyl," and insert -- C$_{2-6}$alkenyl, C$_{2-6}$alkynyl, --;

Column 457, Line 42, Claim 1, please delete "C$_{1-6}$ alkyl, C$_{2-6}$ alkenyl," and insert -- C$_{1-6}$alkyl, C$_{2-6}$alkenyl, --;

Column 457, Line 53, Claim 1, please delete "C$_{1-6}$ alkyl," and insert -- C$_{1-6}$alkyl, --;

Column 457, Line 55, Claim 1, please delete "C$_{1-6}$ alkyl," and insert -- C$_{1-6}$alkyl, --;

Column 457, Line 58, Claim 1, please delete "C$_{1-6}$ alkyl, C$_{2-6}$alkenyl, C$_{2-6}$ alkynyl," and insert -- C$_{1-6}$alkyl, C$_{2-6}$alkenyl, C$_{2-6}$alkynyl, --;

Column 457, Line 60, Claim 1, please delete "C$_{1-6}$ alkyl, C$_{2-6}$ alkenyl," and insert -- C$_{1-6}$alkyl, C$_{2-6}$alkenyl, --;

Column 457, Line 61, Claim 1, please delete "C$_{2-6}$alkynyl, C$_{1-6}$ alkoxy," and insert -- C$_{2-6}$alkynyl, C$_{1-6}$alkoxy, --;

Column 458, Line 1, Claim 1, please delete "C$_{1-3}$ alkyl that" and insert -- C$_{1-3}$alkyl that --;

Column 458, Lines 5-6, Claim 1, please delete "C$_{1-6}$ alkyl, C$_{2-6}$ alkenyl, C$_{2-6}$ alkynyl, and C$_{3-6}$ carbocyclyl" and insert -- C$_{1-6}$alkyl, C$_{2-6}$alkenyl, C$_{2-6}$alkynyl, and C$_{3-6}$carbocyclyl --;

Column 458, Line 10, Claim 1, please delete "C$_1$-C$_6$ alkyl" and insert -- C$_{1-6}$alkyl --;

Signed and Sealed this
Thirtieth Day of August, 2022

*Katherine Kelly Vidal*
Katherine Kelly Vidal
*Director of the United States Patent and Trademark Office*

CERTIFICATE OF CORRECTION (continued)
U.S. Pat. No. 10,206,931 B2

Column 458, Line 11, Claim 1, please delete "$C_1$-$C_6$ alkyl" and insert -- $C_{1-6}$alkyl --;

Column 458, Lines 16-17, Claim 1, please delete "$C_{1-6}$ alkyl, $C_{2-6}$ alkenyl, $C_{2-6}$ alkynyl, and $C_{3-6}$ carbocyclyl" and insert -- $C_{1-6}$alkyl, $C_{2-6}$alkenyl, $C_{2-6}$alkynyl, and $C_{3-6}$carbocyclyl --;

Column 458, Line 28, Claim 1, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

Column 458, Lines 30-31, Claim 1, please delete "$C_{1-6}$ alkyl, $C_{2-6}$ alkenyl, $C_{2-6}$alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 458, Line 38, Claim 1, please delete "$C_{1-3}$ alkyl" and insert -- $C_{1-3}$alkyl --;

Column 458, Line 44, Claim 1, please delete "$C_1$-$C_6$ alkyl" and insert -- $C_{1-6}$alkyl --;

Column 458, Line 45, Claim 1, please delete "$C_1$-$C_6$ alkyl" and insert -- $C_{1-6}$alkyl --;

Column 458, Lines 50-51, Claim 1, please delete "$C_{1-6}$ alkyl, $C_{2-6}$ alkenyl, $C_{2-6}$ alkynyl, and $C_{3-6}$ carbocyclyl" and insert -- $C_{1-6}$alkyl, $C_{2-6}$alkenyl, $C_{2-6}$alkynyl, and $C_{3-6}$carbocyclyl --;

Column 458, Line 53, Claim 1, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

Column 458, Line 55, Claim 1, please delete "$C_{1-6}$ alkyl, $C_{2-6}$ alkenyl" and insert -- $C_{1-6}$alkyl, $C_{2-6}$alkenyl --;

Column 458, Line 63, Claim 1, please delete "$C_{1-3}$ alkyl" and insert -- $C_{1-3}$alkyl --;

Column 459, Line 1, Claim 1, please delete "$C_{1-6}$ alkyl wherein any $C_{1-6}$ alkyl" and insert -- $C_{1-6}$alkyl wherein any $C_{1-6}$alkyl --;

Column 459, Line 5, Claim 1, please delete "oxo, $C_1$-$C_4$ alkyl" and insert -- oxo, $C_{1-4}$alkyl --;

Column 459, Line 7, Claim 1, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

Column 459, Lines 9-10, Claim 1, please delete "$C_{1-6}$ alkyl, $C_{2-6}$ alkenyl, $C_{2-6}$alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 459, Line 17, Claim 1, please delete "and $C_1$-$C_6$ alkyl" and insert -- and $C_{1-6}$alkyl --;

Column 459, Line 18, Claim 1, please delete "and $C_1$-$C_6$ alkyl" and insert -- and $C_{1-6}$alkyl --;

Column 459, Line 27, Claim 1, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

CERTIFICATE OF CORRECTION (continued)
U.S. Pat. No. 10,206,931 B2

Column 459, Lines 29-30, Claim 1, please delete "$C_{1-6}$ alkyl, $C_{2-6}$ alkenyl, $C_{2-6}$alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 459, Line 37, Claim 1, please delete "and $C_1$-$C_6$ alkyl" and insert -- and $C_{1-6}$alkyl --;

Column 459, Line 38, Claim 1, please delete "and $C_1$-$C_6$ alkyl" and insert -- and $C_{1-6}$alkyl --;

Column 459, Lines 44-45, Claim 1, please delete "$C_{1-6}$ alkyl, $C_{2-6}$ alkenyl, $C_{2-6}$ alkynyl, and $C_{3-6}$ carbocyclyl" and insert -- $C_{1-6}$alkyl, $C_{2-6}$alkenyl, $C_{2-6}$alkynyl, and $C_{3-6}$carbocyclyl --;

Column 465, Lines 43-47, Claim 5, please delete " 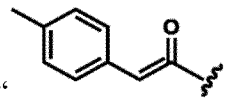 " and insert -- 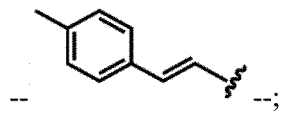 --;

Column 465, Lines 48-58, Claim 5, please delete " 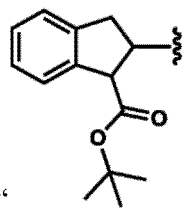 " and insert -- 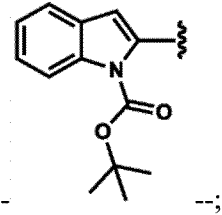 --;

Column 470, Lines 40-48, Claim 5, please delete " 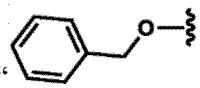 " and insert -- 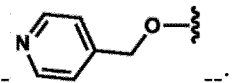 --;

Column 478, Line 6, Claim 6, please delete "—O—C(O)—W," and insert -- —O—C(O)—R$^g$, --;

Column 478, Line 16, Claim 6, please delete "—N(R$^1$)—S(O)—R$^1$, —N(R$^1$)—C(O)—O—R$^1$" and insert -- —N(R$^1$)—S(O)—R$^1$, —N(R$^1$)—C(O)—R$^1$, —N(R$^1$)—C(O)—O—R$^1$ --;

Column 482, Lines 50-58, Claim 7, please delete " 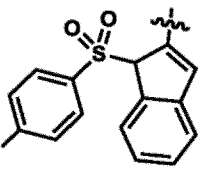 " and insert -- 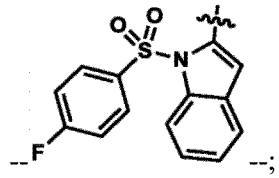 --;

Column 490, Line 3, Claim 8, please delete "R$^d$ is $C_{1-6}$ alkyl" and insert -- R$^d$ is $C_{1-6}$alkyl --;

Column 490, Lines 9-10, Claim 8, please delete "and $C_1$-$C_6$ alkyl, wherein any $C_1$-$C_6$ alkyl" and insert -- and $C_{1-6}$alkyl, wherein any $C_{1-6}$alkyl --;

Column 490, Line 13, Claim 8, please delete "oxo, $C_1$-$C_4$ alkyl" and insert -- oxo, $C_{1-4}$alkyl --;

Column 490, Line 16, Claim 8, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

Column 490, Lines 18-19, Claim 8, please delete "each $C_{1-6}$ alkyl, $C_{2-6}$ alkenyl, $C_{2-6}$alkynyl, $C_{1-6}$ alkoxy" and insert -- each $C_{1-6}$alkyl, $C_{2-6}$alkenyl, $C_{2-6}$alkynyl, $C_{1-6}$alkoxy --;

Column 490, Line 23, Claim 8, please delete "$R^q$ is $C_{1-6}$ alkyl" and insert -- $R^q$ is $C_{1-6}$alkyl --;

Column 492, Line 32, Claim 10, please delete "—S—$R^g$, —O—C(O)—W," and insert -- —S—$R^g$, —O—C(O)—$R^g$, --;

Column 492, Line 36, Claim 10, please delete "and, $C_{1-6}$ alkyl" and insert -- and, $C_{1-6}$alkyl --;

Column 492, Line 38, Claim 10, please delete "and, $C_{1-6}$ alkyl" and insert -- and, $C_{1-6}$alkyl --;

Column 492, Lines 42-43, Claim 10, please delete "—N($R^l$)$_2$, —S(O)$_2$—$R^l$," and insert -- —N($R^l$)$_2$, —O—$R^l$, —S(O)—$R^l$, —S(O)$_2$—$R^l$, --;

Column 492, Line 51, Claim 10, please delete "$C_{1-6}$ alkyl, $C_{2-6}$alkenyl, $C_{2-6}$ alkynyl" and insert -- $C_{1-6}$alkyl, $C_{2-6}$alkenyl, $C_{2-6}$alkynyl --;

Column 492, Lines 53-54, Claim 10, please delete "$C_{1-6}$ alkyl, $C_{2-6}$alkenyl, $C_{2-6}$ alkynyl, $C_{1-6}$ alkoxy" and insert -- $C_{1-6}$alkyl, $C_{2-6}$alkenyl, $C_{2-6}$alkynyl, $C_{1-6}$alkoxy --;

Column 492, Line 59, Claim 10, please delete "and, $C_{1-6}$ alkyl" and insert -- and, $C_{1-6}$alkyl --;

Column 492, Line 60, Claim 10, please delete "and, $C_{1-6}$ alkyl" and insert -- and, $C_{1-6}$alkyl --;

Column 492, Lines 65-66, Claim 10, please delete "$C_{1-6}$ alkyl, $C_{2-6}$ alkenyl, $C_{2-6}$ alkynyl, and $C_{3-6}$ carbocyclyl" and insert -- $C_{1-6}$alkyl, $C_{2-6}$alkenyl, $C_{2-6}$alkynyl, and $C_{3-6}$carbocyclyl --;

Column 499, Lines 45-50, Claim 12, please delete " 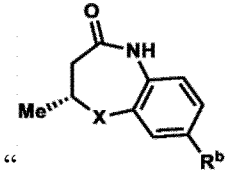 and insert 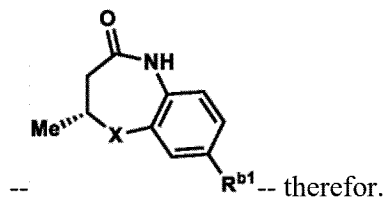 -- therefor.